(12) United States Patent
Chaturvedula et al.

(10) Patent No.: US 7,754,732 B2
(45) Date of Patent: Jul. 13, 2010

(54) SPIROCYCLIC ANTI-MIGRAINE COMPOUNDS

(75) Inventors: Prasad V. Chaturvedula, Cheshire, CT (US); Gene M. Dubowchik, Middlefield, CT (US); Xiang Jun J. Jiang, North Haven, CT (US); John E. Macor, Guilford, CT (US); Graham S. Poindexter, Old Saybrook, CT (US); Shikha Vig, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 227 days.

(21) Appl. No.: 11/620,253

(22) Filed: Jan. 5, 2007

(65) Prior Publication Data

US 2007/0149502 A1 Jun. 28, 2007

Related U.S. Application Data

(60) Division of application No. 10/729,155, filed on Dec. 5, 2003, now Pat. No. 7,220,862, which is a continuation-in-part of application No. 10/445,523, filed on May 27, 2003, now abandoned.

(60) Provisional application No. 60/386,138, filed on Jun. 5, 2002, provisional application No. 60/388,617, filed on Jun. 13, 2002, provisional application No. 60/389,870, filed on Jun. 19, 2002, provisional application No. 60/393,200, filed on Jul. 1, 2002, provisional application No. 60/413,534, filed on Sep. 25, 2002.

(51) Int. Cl.
*C07D 487/10* (2006.01)
*A61K 31/4427* (2006.01)
*A61K 31/496* (2006.01)
*A61K 31/517* (2006.01)
*A61P 11/00* (2006.01)
*A61P 11/06* (2006.01)
*A61P 25/06* (2006.01)
*C07D 487/20* (2006.01)

(52) U.S. Cl. .................. 514/278; 546/18; 546/196; 546/197; 546/198; 546/200; 546/201; 514/345

(58) Field of Classification Search .................. 546/18; 514/278
See application file for complete search history.

(56) References Cited

U.S. PATENT DOCUMENTS

| 5,869,489 | A | 2/1999 | Shah et al. |
| 5,869,498 | A | 2/1999 | Mayer et al. |
| 5,932,737 | A | 8/1999 | Itoh et al. |
| 6,313,097 | B1 | 11/2001 | Eberlein et al. |
| 6,344,449 | B1 | 2/2002 | Rudolf et al. |
| 6,521,609 | B1 | 2/2003 | Doods et al. |
| 6,552,043 | B1 | 4/2003 | Patchett et al. |
| 2001/0036946 | A1 | 11/2001 | Rudolf et al. |
| 2003/0139417 | A1 | 7/2003 | Eberlein et al. |
| 2003/0181462 | A1 | 9/2003 | Doods et al. |
| 2003/0191068 | A1 | 10/2003 | Trunk et al. |
| 2003/0212057 | A1 | 11/2003 | Rudolf et al. |
| 2003/0236282 | A1 | 12/2003 | Hurnaus et al. |
| 2004/0002495 | A1 | 1/2004 | Sher et al. |
| 2004/0014679 | A1 | 1/2004 | Trunk et al. |
| 2004/0039040 | A1 | 2/2004 | Takahashi et al. |
| 2004/0076587 | A1 | 4/2004 | Kruss et al. |
| 2004/0132716 | A1 | 7/2004 | Rudolf et al. |
| 2004/0192729 | A1 | 9/2004 | Rudolf et al. |
| 2004/0214819 | A1 | 10/2004 | Rudolf et al. |
| 2004/0229861 | A1 | 11/2004 | Burgey et al. |
| 2004/0248816 | A1 | 12/2004 | Doods et al. |
| 2005/0032783 | A1 | 2/2005 | Doods et al. |
| 2005/0065094 | A1 | 3/2005 | Davidai |
| 2005/0153959 | A1 | 7/2005 | Luo et al. |
| 2005/0215546 | A1 | 9/2005 | Hurnaus et al. |
| 2005/0215576 | A1 | 9/2005 | Degnan et al. |
| 2005/0227968 | A1 | 10/2005 | Lustenberger et al. |
| 2005/0233980 | A1 | 10/2005 | Doods et al. |
| 2005/0234054 | A1 | 10/2005 | Mueller et al. |
| 2005/0234067 | A1 | 10/2005 | Mueller et al. |

(Continued)

FOREIGN PATENT DOCUMENTS

CA 2 387 613 5/2001

(Continued)

OTHER PUBLICATIONS

U.S. Appl. No. 11/508,568, filed Aug. 23, 2006, Chaturvedula, et al.

(Continued)

*Primary Examiner*—Venkataraman Balasubramanian
(74) *Attorney, Agent, or Firm*—Shah R. Makujina; James Epperson

(57) ABSTRACT

The present invention relates to compounds of Formula (I)

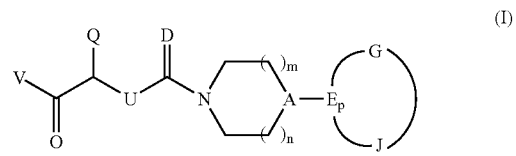

as antagonists of calcitonin gene-related peptide receptors ("CGRP-receptor"), pharmaceutical compositions comprising them, methods for identifying them, methods of treatment using them and their use in therapy for treatment of neurogenic vasodilation, neurogenic inflammation, migraine and other headaches, thermal injury, circulatory shock, flushing associated with menopause, airway inflammatory diseases, such as asthma and chronic obstructive pulmonary disease (COPD), and other conditions the treatment of which can be effected by the antagonism of CGRP-receptors.

32 Claims, 5 Drawing Sheets

U.S. PATENT DOCUMENTS

| | | | |
|---|---|---|---|
| 2005/0250763 | A1 | 11/2005 | Mueller et al. |
| 2005/0256098 | A1 | 11/2005 | Burgey et al. |
| 2005/0256099 | A1 | 11/2005 | Mueller et al. |
| 2005/0272955 | A1 | 12/2005 | Zimmer et al. |
| 2006/0094707 | A1 | 5/2006 | Chaturvedula et al. |
| 2006/0122250 | A1 | 6/2006 | Chaturvedula et al. |
| 2006/0229447 | A1 | 10/2006 | Chaturvedula et al. |

FOREIGN PATENT DOCUMENTS

| | | |
|---|---|---|
| CA | 2 503 455 | 4/2005 |
| EP | 1 227 090 A1 | 7/2002 |
| EP | 1 323 709 | 7/2003 |
| WO | WO 97/09046 | 3/1997 |
| WO | WO 97/42951 | 11/1997 |
| WO | WO 98/09630 | 3/1998 |
| WO | WO 98/11128 | 3/1998 |
| WO | WO 98/44921 | 10/1998 |
| WO | WO 98/44922 | 10/1998 |
| WO | WO 98/45285 | 10/1998 |
| WO | WO 98/56779 | 12/1998 |
| WO | WO 99/52875 | 10/1999 |
| WO | WO 00/18764 | 4/2000 |
| WO | WO 00/55154 | 9/2000 |
| WO | WO 01/32648 | 3/2001 |
| WO | WO 01/25228 | 4/2001 |
| WO | WO 01/32649 | 5/2001 |
| WO | WO 01/49676 | 7/2001 |
| WO | WO 02/10140 | 2/2002 |
| WO | WO 02/22563 | 3/2002 |
| WO | WO 03/027252 | 4/2003 |
| WO | WO 03/070753 | 8/2003 |
| WO | WO 03/076432 | 9/2003 |
| WO | WO2004/002960 A1 | 1/2004 |
| WO | WO 2004/037810 | 5/2004 |
| WO | WO 2004/082602 A2 | 9/2004 |
| WO | WO 2004/082605 A2 | 9/2004 |
| WO | WO 2004/082678 A1 | 9/2004 |
| WO | WO 2004/083187 A1 | 9/2004 |
| WO | WO 2004/087649 A2 | 10/2004 |
| WO | WO 2004/091514 A2 | 10/2004 |
| WO | WO 2004/092166 A2 | 10/2004 |
| WO | WO 2004/092168 A1 | 10/2004 |
| WO | WO 2005/000807 | 1/2005 |
| WO | WO 2005/009962 | 2/2005 |
| WO | WO 2005/013894 | 2/2005 |
| WO | WO 2005/056550 | 6/2005 |
| WO | WO2005/065779 | 7/2005 |
| WO | WO 2005/072308 | 8/2005 |
| WO | WO2005/084672 | 9/2005 |
| WO | WO 2005/092880 | 10/2005 |
| WO | WO 2005/095383 | 10/2005 |
| WO | WO/2005/100343 | 10/2005 |
| WO | WO/2005/100352 | 10/2005 |
| WO | WO/2005/100360 | 10/2005 |
| WO | WO 2005/102322 | 11/2005 |
| WO | WO 2005/103037 | 11/2005 |
| WO | WO/2005/121078 | 12/2005 |
| WO | WO 2006/052378 | 5/2006 |
| WO | WO 2006/060678 | 6/2006 |

OTHER PUBLICATIONS

Amara, S.G., et al., "Alternate RNA processing in calcitonin gene expression generates mRNAs encoding different polypeptide products", *Nature*, 1982, 298:240-244.

Ashina, M., et al., "Evidence for increased plasma levels of calcitonin gene-related peptide in migraine outside of attacks", *Pain*, 2000, 86(1-2):133-138.

Brain, S.D., et al., "CGRP receptors: a headache to study, but will antagonists prove therapeutic in migraine?", *TiPS*, 2002, 23(2): 51-53.

Carlström, A.-S. and Frejd, T., "Palladium-Catalyzed Bis-coupling of Dihaloaromatics with 2-Amidoacrylates", *J. Org. Chem.*, 1991, 56: 1289-1293.

Carlström, A.-S. and Frejd, T., Palladium-Catalyzed Synthesis of Didehydroamino Acid Derivatives, *Synthesis*, 1989, 6, 414-418.

Chu, D.Q., et al., "The calcitonin gene-related peptide (CGRP) antagonist CGRP8-37 blocks vasodilatation in inflamed rat skin: involvement of adrenomedullin in addition to CGRP," *Neuroscience Letters*, 2001, 310:169-172.

De Vries, P., et al., "Pharmacological aspects of experimental headache models in relation to acute antimigraine therapy," *European Journal of Pharmacology*, 1999, 375: 61-74.

Doods, H., et al., "Pharmacological profile of BIBN4096BS, the first selective small molecule CGRP antagonist," *British Journal of Pharmacology*, 2000, 129: 420-423.

Dygos, J.H., "A Convenient Asymmetric Synthesis of the Unnatural Amino Acid 2,6-Dimethyl-L-tyrosine", *Synthesis*, 1992, 741-743.

Edvinsson, L., "Calcitonin Gene-Related Peptide (CGRP) and the Pathophysiology of Headache", *CNS Drugs*, 2001,15(10):745-753.

Escott, K.J., et al., "Effect of a calcitonin gene-related peptide antagonist (CGRP8-37) on skin vasodilatation and oedema induced by stimulation of the rat saphenous nerve", *British Journal of Pharmacology*, 1993, 110, 772-776.

Escott, et al., "Trigeminal ganglion stimulation increases facial skin blood flow in the rat: a major role for calcitonin gene-related peptide", *Brain Research*, 1995, 669:93-99.

Evans, B.N. et al., "CGRP-RCP, a Novel Protein Required for Signal Transduction at Calcitonin Gene-related Peptide and Adrenomedullin Receptors", *J. Biol. Chem.*, 2000, 275(4): 31438-31443.

Gallai, V., et al. "Vasoactive peptide levels in the plasma of young migraine patients with and without aura assessed both interictally and ictally", *Cephalalgia*, 1995;15: 384-390.

Goadsby, P.J., et al., "Vasoactive peptide release in the extracerebral circulation of humans during migraine headache", *Annals of Neurology*, 1990, 28(2):183-187.

Grant, A.D., "Evidence of a role for NK1 and CGRP receptors in mediating neurogenic vasodilatation in the mouse ear", *British Journal of Pharmacology*, 2002, 135: 356-362.

Hall, J.M. and Brain, S.D., "Interaction of amylin with calcitonin gene-related peptide receptors in the microvasculature of the hamster cheek pouch in vivo," *British Journal of Pharmacology*, 1999, 126: 280-284.

Hall, J.M., et al., "Interaction of human adrenomedullin 13-52 with calcitonin gene-related peptide receptors in the microvasculature of the rat and hamster," *British Journal of Pharmacology*, 1995, 114: 592-597.

Juaneda, C. et al. "The molecular pharmacology of CGRP and related peptide receptor subtypes", *TiPS*, 2000, 21: 432-438.

Lassen, L.H. et al. "CGRP may play a causative role in migraine", *Cephalalgia*, 2002, 22(1): 54-61.

Mallee, J.J., et al. "Receptor Activity-modifying Protein 1 Determines the Species Selectivity of Non-peptide CGRP Receptor Antagonist", *J. Biol. Chem.*, 2002, 277(16): 14294-14298.

McLatchie, L.M. et al., "RAMPs regulate the transport and ligand specificity of the calcitonin-receptor-like receptor", *Nature*, 1998, 393: 333-339.

Olesen, J. et al., "Calcitonin Gene-Related Peptide Receptor Antagonist BIBN 4096 BS for the Acute Treatment of Migraine", *New England J. of Medicine*, 2004, 350 (11): 1104-1110.

Pasternak, A., et al., "Potent, orally bioavailable somatostatin agonists: good absorption achieved by urea backbone cyclization", *Bioorganic & Medicinal Chemistry Letters*, Oxford GB, vol. 9, No. 3, Feb. 8, 1999, p. 491-496.

Poyner, D.R. et al., "Pharmacological characterization of a receptor for calcitonin gene-related peptide on rat, L6 myocytes", *British Journal of Pharmacology*, 1992, 105: 441-447.

Rosenfeld, M.G., et al., "Production of a novel neuropeptide encoded by the calcitonin gene via tissue-specific RNA processing", *Nature*, 1983, 304:129-135.

Rudolf, K., et al., "Development of Human Calcitonin Gene-Related Peptide (CGRP) Receptor Antagonists. 1. Potent and Selective Small Molecule CGRP Antagonists. 1-[$N^2$-[3,5-Dibromo-$N$-[[4-(3,4-dihydro-2(1$H$)-oxoquinazolin-3-yl)-1-piperidinyl]carbonyl]-D- tyrosyl] L-lysyl]-4-(4-pyridinyl)piperazine: The First CGRP Antagonist for Clinical Trials in Acute Migraine", *J. Med. Chem.* 2005, 48: 5921-5931.

Shen, Y-T. et al., "Functional Role of α-Calcitonin Gene-Related Peptide in the Regulation of the Cardiovascular System", *J. Pharm. Exp. Ther.*, 2001, 298: 551-558.

Van Valen, F. et al., "Calcitonin gene-related peptide (CGRP) receptors are linked to cyclic adenosine monophosphate production in SK-N-MC human neuroblastoma cells", *Neuroscience Letters*, 1990, 119: 195-198.

Williamson, D.J. and Hargreaves, R.J., "Neurogenic Inflammation in the Context of Migraine", *Microsc. Res. Tech.*, 2001, 53: 167-178.

Williamson, D.J., et al., "Intravital microscope studies on the effects of neurokinin agonists and calcitonin gene-related peptide on dural vessel diameter in the anaesthetized rat," *Cephalalgia*, 1997, 17: 518-524.

Williamson, D.J., et al., "Sumatriptan inhibits neurogenic vasodilation of dural blood vessels in the anaesthetized rat-intravital microscope studies," *Cephalalgia*, 1997, 17: 525-531.

Xin, Z., et al., "Potent, Selective Inhibitors of Protein Tyrosine Phosphatase IB", *Bioorg. Med. Chem. Lett.*, 2003, 13: 1887-1890.

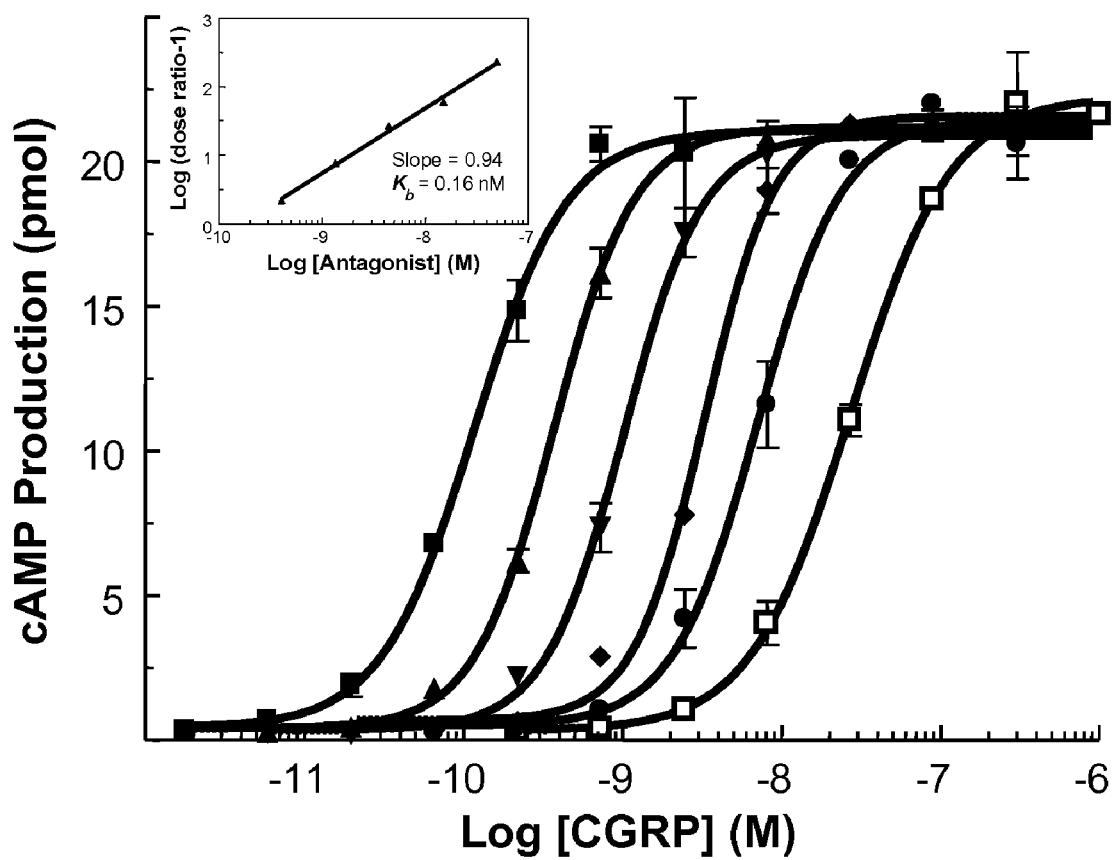
Figure 1. Schild Analysis

Figure 2. Direct Validation of Facial Blood Flow as Surrogate for Intracranial Artery Dilation in the Rat
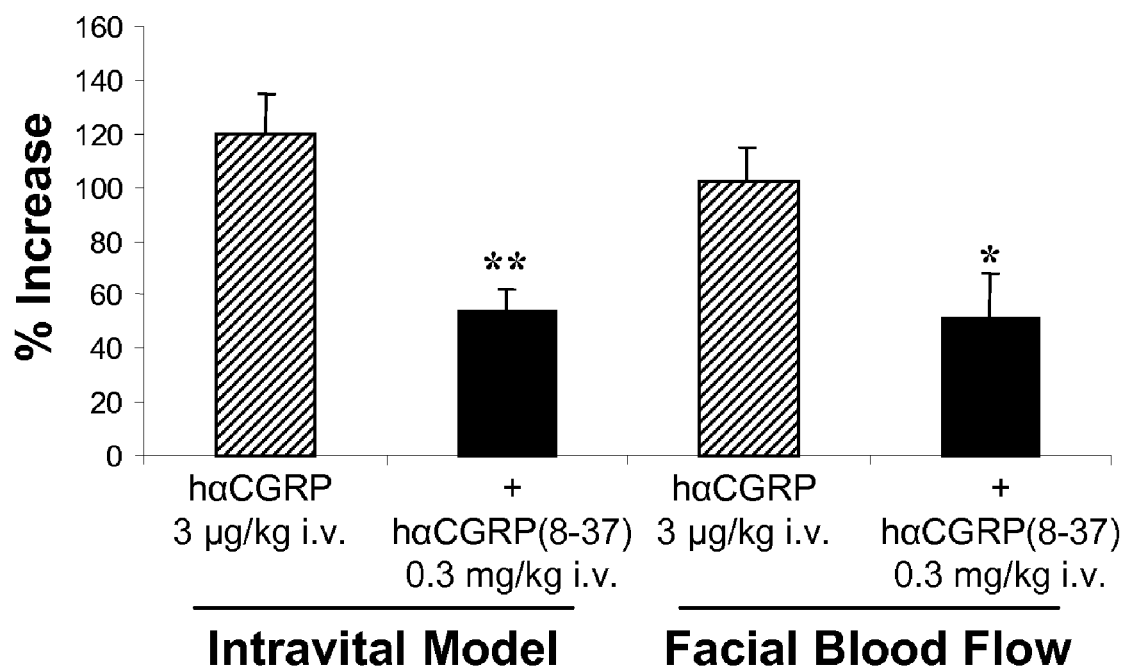

Figure 3. Dose-Response for hαCGRP in Non-Human-Primate Laser Doppler Facial Blood Flow.
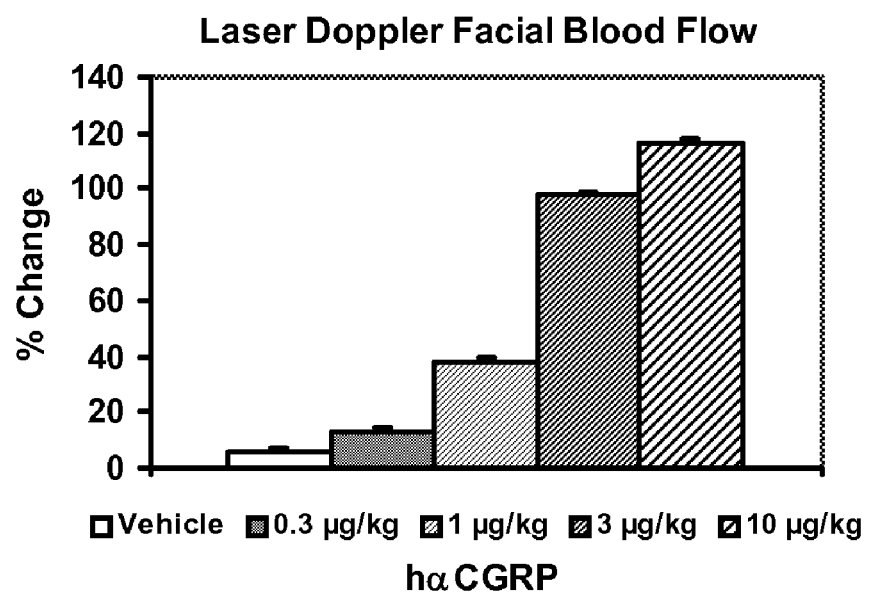

Figure 4. Inhibitition of CGRP-Induced Changes in Non-Human Primate Facial Blood Flow
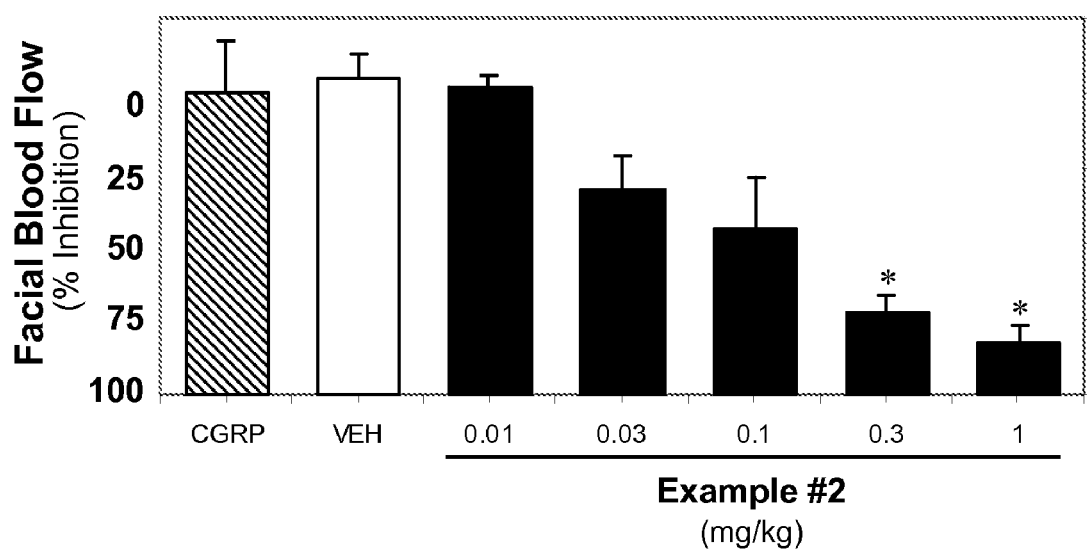

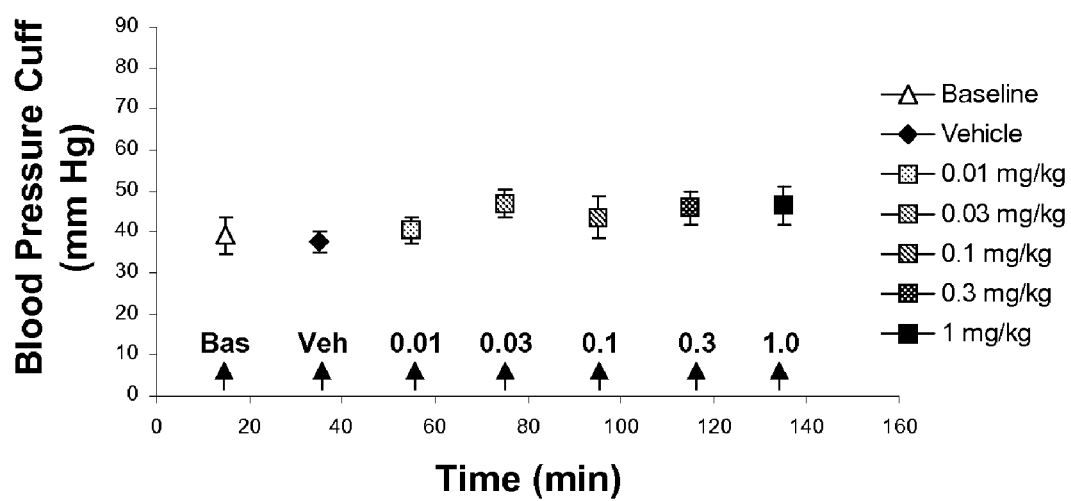
Figure 5. Effect of CGRP Antagonist on Non-Human Primate Blood Pressure.

SPIROCYCLIC ANTI-MIGRAINE COMPOUNDS

CROSS REFERENCE TO RELATED APPLICATIONS

This application is a divisional of Ser. No. 10/729,155, filed Dec. 5, 2003 now U.S. Pat. No. 7,220,862, which is a continuation-in-part of Ser. No. 10/445,523, filed May 27, 2003, now abandoned, which is a nonprovisional application that claims the benefit of U.S. Provisional Application No. 60/386,138 filed Jun. 5, 2002 and U.S. Provisional Application No. 60/388,617 filed Jun. 13, 2002 and U.S. Provisional Application No. 60/389,870 filed Jun. 19, 2002 and U.S. Provisional Application No. 60/393,200 filed Jul. 1, 2002 and U.S. Provisional Application No. 60/413,534 filed Sep. 25, 2002.

FIELD OF THE INVENTION

The present invention relates to novel small molecule antagonists of calcitonin gene-related peptide receptors ("CGRP-receptor"), pharmaceutical compositions comprising them, methods for identifying them, methods of treatment using them and their use in therapy for treatment of neurogenic vasodilation, neurogenic inflammation, migraine, cluster headache and other headaches, thermal injury, circulatory shock, flushing associated with menopause, airway inflammatory diseases, such as asthma and chronic obstructive pulmonary disease (COPD), and other conditions the treatment of which can be effected by the antagonism of CGRP-receptors.

BACKGROUND OF THE INVENTION

Calcitonin gene-related peptide (CGRP) is a naturally occurring 37-amino-acid peptide first identified in 1982 (Amara, S. G. et al, *Science* 1982, 298, 240-244). Two forms of the peptide are expressed ($\alpha$CGRP and $\beta$CGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, *Br J Pharmacol* 1992, 105, 441-7; Van Valen, F. et al, *Neurosci Lett* 1990, 119, 195-8.). Two classes of CGRP receptors, $CGRP_1$ and $CGRP_2$, have been proposed based on the antagonist properties of the peptide fragment CGRP(8-37) and the ability of linear analogues of CGRP to activate $CGRP_2$ receptors (Juaneda, C. et al. *TiPS* 2000, 21, 432-438). However, there is lack of molecular evidence for the $CGRP_2$ receptor (Brain, S. D. et al, *TiPS* 2002, 23, 51-53). The $CGRP_1$ receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., *J Biol Chem.* 2000, 275, 31438-43). RAMP1 is required for transport of CRLR to the plasma membrane and for ligand binding to the CGRP-receptor (McLatchie, L. M. et al, *Nature* 1998, 393, 333-339). RCP is required for signal transduction (Evans B. N. et al., *J Biol Chem.* 2000, 275, 31438-43). There are known species-specific differences in binding of small molecule antagonists to the CGRP-receptor with typically greater affinity seen for antagonism of the human receptor than for other species (Brain, S. D. et al, *TiPS* 2002, 23, 51-53). The amino acid sequence of RAMP1 determines the species selectivity, in particular, the amino acid residue Trp74 is responsible for the phenotype of the human receptor (Mallee et al. *J Biol Chem* 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. *CNS Drugs* 2001; 15(10): 745-53; Williamson, D. J. *Microsc. Res. Tech.* 2001, 53, 167-178; Grant, A. D. *Brit. J. Pharmacol.* 2002, 135, 356-362.). Serum levels of CGRP are elevated during migraine (Goadsby P J, et al. *Ann Neurol* 1990; 28:183-7) and treatment with anti-migraine drugs returns CGRP levels to normal coincident with alleviation of headache (Gallai V. et al. *Cephalalgia* 1995; 15: 384-90). Migraineurs exhibit elevated basal CGRP levels compared to controls (Ashina M, et al., Pain. 2000; 86(1-2):133-8.2000). Intravenous CGRP infusion produces lasting headache in migraineurs (Lassen L H, et al. *Cephalalgia.* 2002 February; 22(1):54-61). Preclinical studies in dog and rat report that systemic CGRP blockade with the peptide antagonist CGRP(8-37) does not alter resting systemic hemodynamics nor regional blood flow (Shen, Y-T. et al, *J Pharmacol Exp Ther* 2001, 298, 551-8). Thus, CGRP-receptor antagonists may present a novel treatment for migraine that avoids the cardiovascular liabilities of active vasoconstriction associated with non-selective $5\text{-HT}_{1B/1D}$ agonists, 'triptans' (e.g., sumatriptan).

There are various in vivo migraine models known in the literature (see De Vries, P. et al, *Eur J Pharmacol* 1999, 375, 61-74). Some electrically stimulate the trigeminal ganglion and measure dilation of the intracranial vessels which they innervate (e.g., Williamson et al. *Cephalalgia* 1997 17:518-24). Since facial arteries are also innervated by the trigeminal nerve, other models study changes in facial blood flow induced by electrical trigeminal activation (e.g., Escott et al. *Brain Res* 1995 669:93). Alternatively, other peripheral nerves (e.g., saphenous) and vascular beds (e.g., abdominal blood flow) are also studied (e.g., Escott et al. *Br J Pharmacol* 1993 110, 772-6;). All models have been shown to be blocked by pretreatment with the peptide antagonist CGPR(8-37) a peptide fragment that is absent the $1^{st}$ seven residues, or by a small molecule CGRP-receptor antagonist. In some instances, exogenous CGRP has been used as a stimulus. However, these models are all invasive terminal procedures, and none have shown the clinically important abortive effect of reversing an established increase in artery dilation or increased blood flow using post-treatment of a CGRP-receptor antagonist. Williamson et al. *Cephalalgia* 1997 17:518-24, and Williamson et al. *Cephalalgia.* 1997 17:525-31: used inter alia i.v. CGRP as a stimulus to increase intracranial dural artery diameter in sodium pentobarb anesthetized rats employing a terminal 'intravital' procedure that involved drilling to thin the skull and the creation of a closed cranial window to visualize dural arteries. The effect was blocked by pretreatment with i.v. CGRP(8-37). Escott et al. Brain Res 1995 669:93; inter alia drilled into the rat skull and used brain electrodes to electrically stimulate the trigeminal ganglion and measured laser Doppler facial blood flow in a terminal procedure in sodium pentobarb anesthetized rats involving neuromuscular blockade, tracheal intubation and artificial ventilation. The effect was blocked by pretreatment with CGRP(8-37). Escott et al. *Br J Pharmacol* 1993 110, 772-6; inter alia used intradermal (i.d.) CGRP as the stimulus to increase blood flow in rat abdominal skin of sodium pentobarb anesthetized animals outfitted with cannulated jugular veins for anesthetic and drug delivery. The effect was blocked by pretreatment with i.v. CGRP(8-37). Chu et al. *Neurosci Lett* 2001 310, 169-72 used inter alia i.d. CGRP as the stimulus in rats and measured laser Doppler changes in blood flow in the skin of the back in a terminal method using sodium pentobarb anesthetized and tracheal cannulated animals; and showed pretreatment blockade by continuous release of CGRP(8-37) from subcutaneously (s.c.) implanted osmotic pumps. Hall et al *Br J Pharmacol* 1995 114, 592-7 and Hall et al *Br J Pharmacol* 1999 126, 280-4 inter alia used topical CGRP to increase hamster cheek pouch arteriole diameter, and i.d. CGRP to increase blood flow in rat dorsal skin of sodium pentobarb anesthetized animals outfitted with cannulated jugular veins for anesthetic and drug delivery. The effect was blocked by pretreatment with i.v. CGRP(8-37). Doods et al. *Br J Pharmacol.* 2000 February; 129(3):420-3 inter alia drilled into the skull of the marmoset (new world monkey) and used brain electrodes to produce electrical stimulation of the trigeminal ganglion and measured facial blood flow in an invasive terminal procedure involving neuromuscular blockade and artificial ventilation of sodium pentobarbital anesthetized primates. Increase in flow was blocked by pre-treatment of a small molecule CGRP antagonist. See also WO 03/272252 Isolated DNA Molecules Encoding Humanized Calcitonin Gene-Related Peptide Receptor, Related Non-Human Transgenic Animals and Assay Methods. Thus the method of the present invention procedure being inter alia a non-invasive survival model in primates measuring exogenous CGRP-induced changes in facial blood flow and demonstrating pre- and post-treatment effects of peptide and small molecule CGRP antagonists in spontaneously breathing isoflurane anesthetized marmosets who recover from the procedure offers significant advantages.

A number of non-peptidic, small molecule CGRP-receptor antagonists have been recently reported. WO 97/09046 and equivalents disclose inter alia quinine and quinidine related compounds which are ligands, in particular antagonists, of CGRP-receptor. WO 98/09630 and WO 98/56779 and equivalents disclose inter alia variously substituted, nitrobenzamide compounds as CGRP-receptor antagonists. WO 01/32649, WO 01/49676, and WO 01/32648 and equivalents disclose inter alia a series of 4-oxobutanamides and related cyclopropane derivatives as CGRP-receptor antagonists. WO 00/18764, WO 98/11128 and WO 00/55154 and equivalents disclose inter alia benzimidazolonyl piperidines as antagonists to CGRP-receptor. Unrelated to CGRP, a series of somatostatin antagonists have been disclosed in WO 99/52875 and WO 01/25228 and equivalents. See also U.S. Pat. No. 6,344, 449, U.S. Pat. No. 6,313,097, U.S. Pat. No. 6,521,609, U.S. Pat. No. 6,552,043, US 20030181462, US 20030191068 and WO 03/076432 and related applications. Thus, novel CGRP-receptor antagonists effective for the treatment of neurogenic inflammation, migraine and other disorders would be greatly advantageous.

SUMMARY OF THE INVENTION

Thus according to a first embodiment of the first aspect of the present invention are provided compounds of Formula (I)

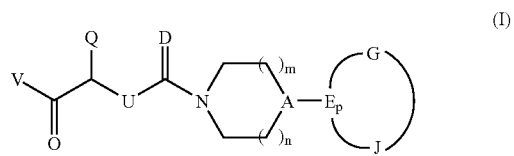

and pharmaceutically acceptable salts and solvates thereof wherein
V is $-N(R^1)(R^2)$ or $OR^4$;
$R^4$ is H, $C_{1-6}$alkyl, $C_{1-4}$ haloalkyl or $(C_{1-4}$alkylene$)_{0-1}R^{4'}$
$R^{4'}$ is $C_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl; and
$R^4$ is optionally substituted with 1 or 2 of the same or different substituents selected from the group consisting of halo, cyano, $C_{1-4}$alkyl, $C_{1-4}$ haloalkyl, $C_{1-4}$alkoxy, hydroxy, amino, $C_{3-7}$cycloalkyl, $C_{1-3}$alkylamino, $C_{1-3}$dialkylamino, $(C_{1-3}$alkyl$)_{0-2}$ureido, phenyl and benzyl; and
$R^{4'}$ optionally contains 1 or 2 carbonyls wherein the carbon atom of said carbonyl is a member of the ring structure of $R^{4'}$;
$R^1$ and $R^2$ are each independently $L^1$, wherein $L^1$ is selected from the group consisting of H, $C_{1-6}$alkyl, $C_{2-6}$alkenyl, $C_{2-6}$alkynyl, $-C_{1-6}$alkylene-amino($C_{1-3}$ alkyl$)_2$, $C_{3-7}$cycloalkyl, phenyl, azetidinyl, adamantyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and
$R^1$ and $R^2$ are each optionally and independently substituted with 1 or 2 of the same or different substituents selected from the group consisting of halo, cyano, $C_{1-4}$alkyl, $C_{1-4}$ haloalkyl, $C_{1-4}$alkoxy, hydroxy, amino, $C_{3-7}$cycloalkyl, $C_{1-3}$alkylamino, $C_{1-3}$dialkylamino, $(C_{1-3}$alkyl$)_{0-2}$ureido, phenyl and benzyl;
$R^1$ and $R^2$ optionally and independently contain 1 or 2 carbonyls wherein the carbon atom of said carbonyl is a member of the heterocycles comprising $R^1$ and $R^2$;
wherein $L^1$ is optionally and independently interrupted from the nitrogen to which it is attached by $L^2$, wherein $L^2$ is independently $C_{1-3}$alkylene or $C_{1-3}$alkylidene; or
$R^1$ and $R^2$ together with the nitrogen to which they are attached form X,
wherein X is azetidinyl, pyrrolyl, pyrrolinyl, pyrrolidinyl, imidazolyl, imidazolidinyl, pyrazolyl, pyrazolidinyl, azepinyl, diazepinyl, piperazinyl, piperidinyl, morpholino or thiomorpholino;
wherein X is optionally substituted with Y, wherein Y is dioxolanyl, $C_{1-9}$alkyl, $C_{2-9}$alkenyl, $C_{2-9}$alkynyl, $C_{1-4}$alkylamino, $C_{1-4}$dialkylamino, $C_{1-4}$alkoxy, C$_{3-7}$cycloalkyl, phenyl, azetidinyl, furanyl, thienyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;

and wherein X and Y are
- optionally interrupted with Z, wherein Z is —NHC(O)O—, —NHC(O)NH—, NC(O)NH$_2$, v-NH—, —C$_{1-3}$alkylene-, —C$_{1-3}$alkylene-, —C$_{1-3}$alkenylene-NHC(O)O—C$_{1-3}$alkylene-; and
- optionally and independently substituted with 1 or 2 of the same or different substituents selected from the group consisting of C$_{1-4}$alkyl, amino, C$_{1-3}$alkylamino, —C$_{1-6}$alkylene-amino (C$_{1-3}$alkyl)$_2$, (C$_{1-3}$alkyl)$_{0-2}$ureido, phenyl and benzyl;
- X and Y optionally and independently contain 1 or 2 carbonyls wherein the carbon atom of said carbonyl is a member of the heterocycles comprising X and Y;
- provided that if X is substituted with Y, and if X and Y are not interrupted with Z, then
- X and Y optionally share one carbon atom and together form a spirocyclic moiety;

Q is Q' or Q";
wherein
Q' is (S$^y$)$_s$R$^3$; and
Q" is NH(S$^y$)$_s$R$^3$, NHC(O)(S$^y$)$_s$R$^3$, NHC(O)O(S$^y$)$_s$R$^3$, NHC(O)NH(S$^y$)$_s$R$^3$, O(S$^y$)$_s$R$^3$, (S$^y$)$_s$NHR$^3$, (S$^y$)$_s$NHC(O)R$^3$, (S$^y$)$_s$NHC(O)OR$^3$, (S$^y$)$_s$NHC(O)NHR$^3$ or (S$^y$)$_s$OR$^3$;
wherein S$^y$ is C$_{1-3}$alkylene or C$_{1-3}$alkylidene and s is 0 or 1;
U is CH$_2$ or NH;
provided that if Q is Q", then U is CH$_2$;
R$^3$ is R$^{3a}$ or R$^{3b}$
wherein
R$^{3a}$ is
(i) a heterocycle having two fused rings with 5 to 7 members in each of said rings, said heterocycle containing one to five of the same or different heteroatoms selected from the group consisting of O, N and S and said heterocycle optionally containing 1 or 2 carbonyls wherein the carbon atom of said carbonyl is a member of said fused rings;
(ii) a 4 to 6 membered heterocycle containing one to three of the same or different heteroatoms selected from the group consisting of O, N and S, optionally containing 1 to 2 carbonyls, wherein the carbon atom of said carbonyl is a member of said 4 to 6 membered heterocycle;
(iii) C$_{3-7}$cycloalkyl;
(iv) carbazolyl, fluorenyl, phenyl, —O-phenyl, —O—C$_{1-4}$alkylene-phenyl, or napthyl; or
(v) C$_{1-8}$alkyl, C$_{2-7}$alkenyl, —C(O)R$^{3'}$, CHC(O)O—R$^{3'}$, CH(CH$_3$)C(O)O—R$^{3'}$, —C(O)O—R$^{3'}$ or C$_{2-7}$alkynyl; and
wherein R$^{3a}$ is optionally substituted with 1 to 3 of the same or different substituents selected from the group consisting of benzyl, phenyl, —O-phenyl, —O—C$_{1-3}$alkylenephenyl, —C$_{1-3}$alkylene-OC(O)-phenyl, cyano, amino, nitro, halo, C$_{1-6}$alkyl, C$_{1-3}$mono-bi-tri-haloalkyl, C$_{1-3}$mono-bi-tri-haloalkyloxy, (C$_{1-3}$alkyl)$_{1-2}$ amine, —OR$^{3'}$, —C(O)R$^{3'}$, —C(O)O—R$^{3'}$, —O—C(O)R$^{3'}$—N(R$^{3'}$)$_2$, —C(O)N(R$^{3'}$)$_2$, —N(R$^{3'}$)C(O)(R$^{3'}$)$_2$, —N(R$^{3'}$)C(O)N(R$^{3'}$)$_2$, —N(R$^{3'}$)C(O)OR$^{3'}$, —O—C(O)N(R$^{3'}$)$_2$, —N(R$^{3'}$)SO$_2$R$^{3'}$, —SO$_2$N(R$^{3'}$)$_2$ and —SO$_2$R$^{3'}$;

R$^{3'}$ is H or —C$_{1-6}$alkyl;
provided that if R$^{3a}$ is, —C(O)R$^{3'}$, CHC(O)O—R$^{3'}$, CH(CH$_3$)C(O)O—R$^{3'}$ or —C(O)O—R$^{3'}$, then said —C(O)R$^{3'}$, CHC(O)O—R$^{3'}$, CH(CH$_3$)C(O)O—R$^{3'}$ or —C(O)O—R$^{3'}$ are unsubstituted;

R$^{3b}$ is R$^{3a}$ but is not phenyl, 1-naphthyl, 2-naphthyl, 1,2,3,4-tetrahydro-1-naphthyl, 1H-indol-3-yl, 1-methyl-1H-indol-3-yl, 1-formyl-1H-indol-3-yl, 1-(1,1-dimethylethoxycarbonyl)-1H-indol-3-yl, 4-imidazolyl, 1-methyl-4-imidazolyl, 2-thienyl, 3-thienyl, thiazolyl, 1H-indazol-3-yl, 1-methyl-1H-indazol-3-yl, benzo[b]fur-3-yl, benzo[b]thien-3-yl, pyridinyl, quinolinyl or isoquinolinyl; optionally substituted in the carbon skeleton with mono-, di- or trisubstituted by fluorine, chlorine or bromine atoms or by branched or unbranched alkyl groups, C$_{3-8}$-cycloalkyl groups, phenylalkyl groups, alkenyl, alkoxy, phenyl, phenylalkoxy, trifluoromethyl, alkoxycarbonylalkyl, carboxyalkyl, alkoxycarbonyl, carboxy, dialkylaminoalkyl, dialkylaminoalkoxy, hydroxy, nitro, amino, acetylamino, propionylamino, benzoyl, benzoylamino, benzoylmethylamino, methylsulphonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulphinyl- or trifluoromethylsulphonyl groups;

wherein said substituents may be the same or different and the above-mentioned benzoyl, benzoylamino- and benzoylmethylamino groups may in turn additionally be substituted in the phenyl moiety by a fluorine, chlorine or bromine atom, or by an alkyl, trifluoromethyl, amino or acetylamino group;

D is O, NCN or NSO$_2$C$_{1-3}$alkyl;
A is C, N or CH;
m and n are independently 0, 1 or 2;
provided that
if m and n are 0, then A is not N;
if m is 2, then n is not 2; or
if n is 2, then m is not 2;
E is N, CH or C;
p is 0 or 1;
if p is 1, then G, J and E together form A$^x$ or A$^y$;
A$^x$ is a fused heterocycle having two fused rings with 5 to 7 members in each of said rings, said heterocycle containing one to four of the same or different heteroatoms selected from the group consisting of O, N and S; and
optionally containing 1 or 2 carbonyls wherein the carbon atom of said carbonyl is a member of said fused heterocycle;

A$^y$ is a 4 to 6 membered heterocycle containing one to three heteroatoms selected from the group consisting of O, N and S; and
optionally containing 1 to 2 carbonyls, wherein the carbon atom of said carbonyl is a member of said 4 to 6 membered heterocycle;
wherein A$^x$ and A$^y$ are optionally substituted with C$_{1-4}$alkyl, C$_{1-4}$alkoxy, C$_{1-4}$ haloalkyl, cyano, $C_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino; or if p is 0 such that G and J are each attached to A, then A is C, and G, J and A together form a spirocyclic ring system with said rings of said system containing A and wherein G, J and A together are GJA' or GJA";

wherein
GJA' is $A^x$ or $A^y$; and
GJA" is $A^x$ or $A^y$;
provided that
$A^x$ is not a 1,3-diaza-fused heterocycle; and
$A^y$ is not a 1,3-diaza-heterocycle;
and further provided that
if Q is Q", then $R^3$ is $R^{3a}$; and
if Q is Q', then
$R^3$ is $R^{3b}$; or
$R^3$ is $R^{3a}$, p is 0 and G, J and A together form GJA".

According to another embodiment of the first aspect of the present invention are provided compounds according to the first embodiment of the first aspect of the present invention wherein Q is Q' and $R^3$ is $R^{3b}$.

According to another embodiment of the first aspect of the present invention are provided compounds according to the first embodiment of the first aspect of the present invention wherein Q is Q', $R^3$ is $R^{3a}$ and p is 0 such that G, J and A together form GJA".

According to another embodiment of the first aspect of the present invention are provided compounds according to the first embodiment of the first aspect of the present invention wherein Q is Q' and Q' is $(S^y)_sR^3$ and s is 0.

According to another embodiment of the first aspect of the present invention are provided compounds according to the first embodiment of the first aspect of the present invention wherein Q is Q' and Q' is $(S^y)_sR^3$, $S^y$ is $C_{1-3}$alkylene and s is 1.

According to another embodiment of the first aspect of the present invention are provided compounds according to the first embodiment of the first aspect of the present invention wherein Q is Q' and Q' is $(S^y)_sR^3$, $S^y$ is $C_{1-3}$alkylidene and s is 1.

According to another embodiment of the first aspect of the present invention are provided compounds according to the first embodiment of the first aspect of the present invention wherein Q is Q' and U is $CH_2$.

According to another embodiment of the first aspect of the present invention are provided compounds according to the first embodiment of the first aspect of the present invention wherein Q is Q', Q' is $(S^y)_sR^3$, s is 0 and U is $CH_2$.

According to another embodiment of the first aspect of the present invention are provided compounds according to the first embodiment of the first aspect of the present invention wherein Q is Q', Q' is $(S^y)_sR^3$, $S^y$ is $C_{1-3}$alkylene, s is 1 and U is $CH_2$.

According to another embodiment of the first aspect of the present invention are provided compounds according to the first embodiment of the first aspect of the present invention wherein Q is Q', Q' is $(S^y)_sR^3$, $S^y$ is $C_{1-3}$ alkylidene, s is 1 and U is $CH_2$.

According to another embodiment of the first aspect of the present invention are provided compounds according to the first embodiment of the first aspect of the present invention wherein Q is Q' and U is NH.

According to another embodiment of the first aspect of the present invention are provided compounds according to the first embodiment of the first aspect of the present invention wherein Q is Q', Q' is $(S^y)_sR^3$, s is 0 and U is NH.

According to another embodiment of the first aspect of the present invention are provided compounds according to the first embodiment of the first aspect of the present invention wherein Q is Q', Q' is $(S^y)_sR^3$, $S^y$ is $C_{1-3}$alkylene, s is 1 and U is NH.

According to another embodiment of the first aspect of the present invention are provided compounds according to the first embodiment of the first aspect of the present invention wherein Q is Q', Q' is $(S^y)_sR^3$, $S^y$ is $C_{1-3}$alkylidene, s is 1 and U is NH.

According to another embodiment of the first aspect of the present invention are provided compounds according to the first embodiment of the first aspect of the present invention wherein Q is Q".

According to another embodiment of the first aspect of the present invention are provided compounds according to the first embodiment of the first aspect of the present invention wherein Q is Q" and Q" is $NH(S^y)_sR^3$.

According to another embodiment of the first aspect of the present invention are provided compounds according to the first embodiment of the first aspect of the present invention wherein Q is Q" and Q" is $NH(S^y)_sR^3$ and s is 0.

According to another embodiment of the first aspect of the present invention are provided compounds according to the first embodiment of the first aspect of the present invention wherein Q is Q" and Q" is $NH(S^y)_sR^3$, $S^y$ is $C_{1-3}$alkylene and s is 1.

According to another embodiment of the first aspect of the present invention are provided compounds according to the first embodiment of the first aspect of the present invention wherein Q is Q" and Q" is $NH(S^y)_sR^3$, $S^y$ is $C_{1-3}$alkylidene and s is 1.

According to another embodiment of the first aspect of the present invention are provided compounds according to the first embodiment of the first aspect of the present invention wherein Q is Q" and Q" is $NHC(O)(S^y)_sR^3$.

According to another embodiment of the first aspect of the present invention are provided compounds according to the first embodiment of the first aspect of the present invention wherein Q is Q" and Q" is $NHC(O)(S^y)_sR^3$ and sm is 0.

According to another embodiment of the first aspect of the present invention are provided compounds according to the first embodiment of the first aspect of the present invention wherein Q is Q" and Q" is $NHC(O)(S^y)_sR^3$, $S^y$ is $C_{1-3}$alkylene and s is 1.

According to another embodiment of the first aspect of the present invention are provided compounds according to the first embodiment of the first aspect of the present invention wherein Q is Q" and Q" is $NHC(O)(S^y)_sR^3$, $S^y$ is $C_{1-3}$alkylidene and s is 1.

According to another embodiment of the first aspect of the present invention are provided compounds according to the first embodiment of the first aspect of the present invention wherein Q is Q" and Q" is $NHC(O)O(S^y)_sR^3$.

According to another embodiment of the first aspect of the present invention are provided compounds according to the first embodiment of the first aspect of the present invention wherein Q is Q" and Q" is $NHC(O)O(S^y)_sR^3$ and s is 0.

According to another embodiment of the first aspect of the present invention are provided compounds according to the first embodiment of the first aspect of the present invention wherein Q is Q" and Q" is $NHC(O)O(S^y)_sR^3$, $S^y$ is $C_{1-3}$alkylene and s is 1.

According to another embodiment of the first aspect of the present invention are provided compounds according to the first embodiment of the first aspect of the present invention wherein Q is Q" and Q" is NHC(O)O(S$^y$)$_s$R$^3$, S$^y$ is C$_{1-3}$alkylidene and s is 1.

According to another embodiment of the first aspect of the present invention are provided compounds according to the first embodiment of the first aspect of the present invention wherein Q is Q" and Q" is NHC(O)NH(S$^y$)$_s$R$^3$.

According to another embodiment of the first aspect of the present invention are provided compounds according to the first embodiment of the first aspect of the present invention wherein Q is Q" and Q" is NHC(O)NH(S$^y$)$_s$R$^3$ and s is 0.

According to another embodiment of the first aspect of the present invention are provided compounds according to the first embodiment of the first aspect of the present invention wherein Q is Q" and Q" is NHC(O)NH(S$^y$)$_s$R$^3$, S$^y$ is C$_{1-3}$alkylene and s is 1.

According to another embodiment of the first aspect of the present invention are provided compounds according to the first embodiment of the first aspect of the present invention wherein Q is Q" and Q" is NHC(O)NH(S$^y$)$_s$R$^3$, S$^y$ is C$_{1-3}$alkylidene and s is 1.

According to another embodiment of the first aspect of the present invention are provided compounds according to the first embodiment of the first aspect of the present invention wherein V is OR$^4$.

According to another embodiment of the first aspect of the present invention are provided compounds according to the first embodiment of the first aspect of the present invention wherein V is OR$^4$ and R$^4$ is C$_{1-6}$alkyl.

According to another embodiment of the first aspect of the present invention are provided compounds according to the first embodiment of the first aspect of the present invention wherein V is —N(R$^1$)(R$^2$).

According to another embodiment of the first aspect of the present invention are provided compounds according to the first embodiment of the first aspect of the present invention wherein V is —N(R$^1$)(R$^2$) or OR$^{4'}$;

R$^4$ is H, C$_{1-6}$alkyl, C$_{1-4}$ haloalkyl, (C$_{1-4}$alkylene)$_{0-1}$R$^{4'}$ R$^{4'}$ is C$_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl; and R$^{4'}$ is optionally substituted with 1 or 2 of the same or different substituents selected from the group consisting of halo, cyano, C$_{1-4}$alkyl, C$_{1-4}$ haloalkyl, C$_{1-4}$alkoxy, hydroxy, amino, C$_{3-7}$cycloalkyl, C$_{1-3}$alkylamino, C$_{1-3}$dialkylamino, (C$_{1-3}$alkyl)$_{0-2}$ureido, phenyl and benzyl;

R$^{4'}$ optionally contains 1 or 2 carbonyls wherein the carbon atom of said carbonyl is a member of the ring structure of R$^{4'}$;

R$^1$ and R$^2$ are each independently L$^1$, wherein L$^1$ is selected from the group consisting of H, C$_{1-6}$alkyl, —C$_{1-6}$alkylene-amino(C$_{1-3}$alkyl)$_2$, C$_{3-7}$cycloalkyl, phenyl, adamantyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and R$^1$ and R$^2$ are each optionally and independently substituted with 1 or 2 of the same or different substituents selected from the group consisting of halo, cyano, C$_{1-4}$alkyl, C$_{1-4}$ haloalkyl, C$_{1-4}$alkoxy, hydroxy, amino, C$_{3-7}$cycloalkyl, C$_{1-3}$alkylamino, C$_{1-3}$dialkylamino, (C$_{1-3}$alkyl)$_{0-2}$ureido, phenyl and benzyl;

R$^1$ and R$^2$ optionally and independently contain 1 or 2 carbonyls wherein the carbon atom of said carbonyl is a member of the heterocycles comprising R$^1$ and R$^2$;

wherein L$^1$ is optionally interrupted from the nitrogen to which it is attached by L$^2$, wherein L$^2$ is C$_{1-3}$alkylene; or R$^1$ and R$^2$ together with the nitrogen to which they are attached form X, wherein X is azetidinyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;

wherein X is optionally substituted with Y, wherein Y is dioxolanyl, C$_{1-4}$alkyl, C$_{1-4}$alkylamino, C$_{1-4}$dialkylamino, C$_{1-4}$alkoxy, C$_{3-7}$cycloalkyl, phenyl, azetidinyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;

and wherein X and Y are optionally interrupted with Z, wherein Z is —NHC(O)O—, —NHC(O)NH—, NC(O)NH$_2$, —NH—, —C$_{1-3}$alkylene-, —C$_{1-3}$alkylene-NHC(O)O—C$_{1-3}$alkylene-; and optionally and independently substituted with 1 or 2 of the same or different substituents selected from the group consisting of C$_{1-4}$alkyl, amino, C$_{1-3}$alkylamino, —C$_{1-6}$alkylene-amino (C$_{1-3}$alkyl)$_2$, (C$_{1-3}$alkyl)$_{0-2}$ureido, phenyl and benzyl;

X and Y optionally and independently contain 1 or 2 carbonyls wherein the carbon atom of said carbonyl is a member of the heterocycles comprising X and Y;

provided that if X is substituted with Y, and if X and Y are not interrupted with Z, then X and Y optionally share one carbon atom and together form a spirocyclic moiety.

According to another embodiment of the first aspect of the present invention are provided compounds according to the first embodiment of the first aspect of the present invention wherein R$^4$ is H, C$_{1-6}$alkyl, C$_{1-4}$ haloalkyl or (C$_{1-4}$alkylene)$_{0-1}$R$^{4'}$; R$^{4'}$ is C$_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl; and R$^{4'}$ is optionally substituted with 1 or 2 of the same or different substituents selected from the group consisting of halo, cyano, C$_{1-4}$alkyl, C$_{1-4}$ haloalkyl, C$_{1-4}$alkoxy, hydroxy, amino, C$_{3-7}$cycloalkyl, C$_{1-3}$alkylamino, C$_{1-3}$dialkylamino, (C$_{1-3}$alkyl)$_{0-2}$ureido, phenyl and benzyl.

According to another embodiment of the first aspect of the present invention are provided compounds according to the first embodiment of the first aspect of the present invention wherein $R^4$ is H, $C_{1-6}$alkyl, $C_{1-4}$ haloalkyl or $(C_{1-4}$alkylene$)_{0-1}R^{4'}$; $R^{4'}$ is $C_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl.

According to another embodiment of the first aspect of the present invention are provided compounds according to the first embodiment of the first aspect of the present invention wherein $R^4$ is H, $C_{1-6}$alkyl or $(C_{1-4}$alkylene$)_{0-1}R^{4'}$; $R^{4'}$ is $C_{3-7}$cycloalkyl.

According to another embodiment of the first aspect of the present invention are provided compounds according to the first embodiment of the first aspect of the present invention wherein V is $-N(R^1)(R^2)$ and
- $R^1$ and $R^2$ are each independently $L^1$, wherein $L^1$ is selected from the group consisting of H, $C_{1-6}$alkyl, $-C_{1-6}$alkylene-amino$(C_{1-3}$alkyl$)_2$, $C_{3-7}$cycloalkyl, phenyl, azetidinyl, adamantyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; or
- $R^1$ and $R^2$ together with the nitrogen to which they are attached form X,
  - wherein X is azetidinyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;
    - wherein X is substituted with Y, wherein Y is dioxolanyl, $C_{1-4}$alkyl, $C_{1-4}$alkoxy, $C_{3-7}$cycloalkyl, phenyl, azetidinyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;
    - and wherein X and Y optionally share one carbon atom and together form a spirocyclic moiety.

According to another embodiment of the first aspect of the present invention are provided compounds according to the first embodiment of the first aspect of the present invention wherein V is $-N(R^1)(R^2)$ and
- $R^1$ and $R^2$ are each independently $L^1$, wherein $L^1$ is selected from the group consisting of H, $C_{1-6}$alkyl, or
- $R^1$ and $R^2$ together with the nitrogen to which they are attached form X,
  - wherein X is piperidinyl or morpholino;
    - wherein X is substituted with Y, wherein Y is dioxolanyl, $C_{1-4}$alkyl or piperidinyl;
    - and wherein X and Y optionally share one carbon atom and together form a spirocyclic moiety.

According to another embodiment of the first aspect of the present invention are provided compounds according to the first embodiment of the first aspect of the present invention wherein V is $-N(R^1)(R^2)$ and wherein $R^1$ and $R^2$ are each independently $L^1$, wherein $L^1$ is selected from the group consisting of H, $C_{1-6}$alkyl.

According to another embodiment of the first aspect of the present invention are provided compounds according to the first embodiment of the first aspect of the present invention wherein V is $-N(R^1)(R^2)$ and wherein
- $R^1$ and $R^2$ together with the nitrogen to which they are attached form X,
  - wherein X is piperidinyl or morpholino;
    - wherein X is substituted with Y, wherein Y is dioxolanyl, $C_{1-4}$alkyl or piperidinyl;
    - and wherein X and Y optionally share one carbon atom and together form a spirocyclic moiety.

According to another embodiment of the first aspect of the present invention are provided compounds according to the first embodiment of the first aspect of the present invention wherein V is $-N(R^1)(R^2)$ and wherein
- $R^1$ and $R^2$ together with the nitrogen to which they are attached form X,
  - wherein X is piperidinyl;
    - wherein X is substituted with Y, wherein Y is piperidinyl.

According to another embodiment of the first aspect of the present invention are provided compounds according to the first embodiment of the first aspect of the present invention wherein V is $-N(R^1)(R^2)$ and wherein
- $R^1$ and $R^2$ together with the nitrogen to which they are attached form X,
  - wherein X is morpholino;
    - wherein X is substituted with Y, wherein Y is $C_{1-4}$alkyl.

According to another embodiment of the first aspect of the present invention are provided compounds according to the first embodiment of the first aspect of the present invention wherein V is $-N(R^1)(R^2)$ and wherein
- $R^1$ and $R^2$ together with the nitrogen to which they are attached form X,
  - wherein X is piperidinyl;
    - wherein X is substituted with Y, wherein Y is $C_{1-4}$alkyl.

According to another embodiment of the first aspect of the present invention are provided compounds according to the first embodiment of the first aspect of the present invention wherein V is $-N(R^1)(R^2)$ and wherein
- $R^1$ and $R^2$ together with the nitrogen to which they are attached form X,
  - wherein X is piperidinyl;
    - wherein X is substituted with Y, wherein Y is dioxolanyl;
    - and wherein X and Y share one carbon atom and together form a spirocyclic moiety.

According to another embodiment of the first aspect of the present invention are provided compounds according to the first embodiment of the first aspect of the present invention wherein X and Y are not interrupted with Z.

According to another embodiment of the first aspect of the present invention are provided compounds according to the first embodiment of the first aspect of the present invention wherein X and Y are not interrupted with Z; and X and Y share one carbon atom and together form a spirocyclic moiety According to another embodiment of the first aspect of the present invention are provided compounds according to the first embodiment of the first aspect of the present invention wherein $R^3$ is $R^{3a}$.

According to another embodiment of the first aspect of the present invention are provided compounds according to the first embodiment of the first aspect of the present invention wherein $R^3$ is $R^{3b}$.

According to another embodiment of the first aspect of the present invention are provided compounds according to the first embodiment of the first aspect of the present invention wherein $R^{3a}$ is a heterocycle having two fused rings with 5 to 7 members in each of said rings, said heterocycle containing one to five of the same or different heteroatoms selected from the group consisting of O, N and S.

According to another embodiment of the first aspect of the present invention are provided compounds according to the first embodiment of the first aspect of the present invention wherein $R^{3a}$ is a heterocycle having two fused rings with 5 to 7 members in each of said rings, said heterocycle containing one to five of the same or different heteroatoms selected from the group consisting of O, N and S and said heterocycle optionally containing 1 or 2 carbonyls wherein the carbon atom of said carbonyl is a member of said fused rings.

According to another embodiment of the first aspect of the present invention are provided compounds according to the first embodiment of the first aspect of the present invention wherein $R^{3a}$ is a heterocycle having two fused rings with 5 to 7 members in each of said rings, said heterocycle containing one to five of the same or different heteroatoms selected from the group consisting of O, N and S and said heterocycle optionally containing 1 or 2 carbonyls wherein the carbon atom of said carbonyl is a member of said fused rings; wherein $R^{3a}$ is optionally substituted with 1 to 3 of the same or different substituents selected from the group consisting of benzyl, phenyl, —O-phenyl, —O—$C_{1-3}$alkylphenyl, —$C_{1-3}$alkylene-OC(O)-phenyl, cyano, amino, nitro, halo, $C_{1-3}$mono-bi-tri-haloalkyl, $C_{1-3}$mono-bi-tri-haloalkyloxy, $C_{1-6}$alkoxy, $(C_{1-3}$alkyl$)_{1-2}$amine, —$OR^{3'}$, —$C(O)R^{3'}$, —$C(O)O$—$R^{3'}$, —$O$—$C(O)R^{3'}$, —$N(R^{3'})_2$, —$C(O)N(R^{3'})_2$, —$N(R^{3'})C(O)(R^{3'})_2$, —$N(R^{3'})C(O)N(R^{3'})_2$, —$N(R^{3'})C(O)OR^{3'}$, —$O$—$C(O)N(R^{3'})_2$, —$N(R^{3'})SO_2R^{3'}$, —$SO_2N(R^{3'})_2$ and —$SO_2R^{3'}$; $R^{3'}$ is H or —$C_{1-6}$alkyl.

According to another embodiment of the first aspect of the present invention are provided compounds according to the first embodiment of the first aspect of the present invention wherein $R^{3a}$ is a 4 to 6 membered heterocycle containing one to three of the same or different heteroatoms selected from the group consisting of O, N and S.

According to another embodiment of the first aspect of the present invention are provided compounds according to the first embodiment of the first aspect of the present invention wherein $R^{3a}$ is a 4 to 6 membered heterocycle containing one to three of the same or different heteroatoms selected from the group consisting of O, N and S, optionally containing 1 to 2 carbonyls, wherein the carbon atom of said carbonyl is a member of said 4 to 6 membered heterocycle.

According to another embodiment of the first aspect of the present invention are provided compounds according to the first embodiment of the first aspect of the present invention wherein $R^{3a}$ is a 4 to 6 membered heterocycle containing one to three of the same or different heteroatoms selected from the group consisting of O, N and S, optionally containing 1 to 2 carbonyls, wherein the carbon atom of said carbonyl is a member of said 4 to 6 membered heterocycle; wherein $R^{3a}$ is optionally substituted with 1 to 3 of the same or different substituents selected from the group consisting of benzyl, phenyl, —O-phenyl, —O—$C_{1-3}$alkylphenyl, —$C_{1-3}$alkylene-OC(O)-phenyl, cyano, amino, nitro, halo, $C_{1-3}$mono-bi-tri-haloalkyl, $C_{1-3}$mono-bi-tri-haloalkyloxy, $C_{1-6}$alkoxy, $(C_{1-3}$ alkyl$)_{1-2}$amine, —$OR^{3'}$, —$C(O)R^{3'}$, —$C(O)O$—$R^{3'}$, —$O$—$C(O)R^{3'}$, —$N(R^{3'})_2$, —$C(O)N(R^{3'})_2$, —$N(R^{3'})C(O)(R^{3'})_2$, —$N(R^{3'})C(O)N(R^{3'})_2$, —$N(R^{3'})C(O)OR^{3'}$, —$O$—$C(O)N(R^{3'})_2$, —$N(R^{3'})SO_2R^{3'}$, —$SO_2N(R^{3'})_2$ and —$SO_2R^{3'}$; $R^{3'}$ is H or —$C_{1-6}$alkyl.

According to another embodiment of the first aspect of the present invention are provided compounds according to the first embodiment of the first aspect of the present invention wherein $R^{3a}$ is $C_{3-7}$cycloalkyl.

According to another embodiment of the first aspect of the present invention are provided compounds according to the first embodiment of the first aspect of the present invention wherein $R^{3a}$ is $C_{3-7}$cycloalkyl; wherein $R^{3a}$ is optionally substituted with 1 to 3 of the same or different substituents selected from the group consisting of benzyl, phenyl, —O-phenyl, —O—$C_{1-3}$alkylphenyl, —$C_{1-3}$alkylene-OC(O)-phenyl, cyano, amino, nitro, halo, $C_{1-3}$mono-bi-tri-haloalkyl, $C_{1-3}$mono-bi-tri-haloalkyloxy, $C_{1-6}$alkoxy, $(C_{1-3}$alkyl$)_{1-2}$amine, —$OR^3$, —$C(O)R^{3'}$, —$C(O)O$—$R^{3'}$, —$O$—$C(O)R^{3'}$, —$N(R^{3'})_2$, —$C(O)N(R^{3'})_2$, —$N(R^{3'})C(O)(R^{3'})_2$, —$N(R^{3'})C(O)N(R^{3'})_2$, —$N(R^{3'})C(O)OR^3$, —$O$—$C(O)N(R^{3'})_2$, —$N(R^{3'})SO_2R^{3'}$, —$SO_2N(R^{3'})_2$ and —$SO_2R^{3'}$; $R^{3'}$ is H or —$C_{1-6}$alkyl.

According to another embodiment of the first aspect of the present invention are provided compounds according to the first embodiment of the first aspect of the present invention wherein $R^{3a}$ is carbazolyl, fluorenyl, phenyl, —O-phenyl, —O—$C_{1-4}$alkylene-phenyl, or napthyl.

According to another embodiment of the first aspect of the present invention are provided compounds according to the first embodiment of the first aspect of the present invention wherein $R^{3a}$ is carbazolyl, fluorenyl, phenyl, —O-phenyl, —O—$C_{1-4}$alkylene-phenyl, or napthyl; wherein $R^{3a}$ is optionally substituted with 1 to 3 of the same or different substituents selected from the group consisting of benzyl, phenyl, —O-phenyl, —O—$C_{1-3}$alkylphenyl, —$C_{1-3}$alkylene-OC(O)-phenyl, cyano, amino, nitro, halo, $C_{1-3}$mono-bi-tri-haloalkyl, $C_{1-3}$mono-bi-tri-haloalkyloxy, $C_{1-6}$alkoxy, $(C_{1-3}$ alkyl$)_{1-2}$amine, —$OR^{3'}$, —$C(O)R^{3'}$, —$C(O)O$—$R^{3'}$, —$O$—$C(O)R^{3'}$, —$N(R^{3'})_2$, —$C(O)N(R^{3'})_2$, —$N(R^{3'})C(O)(R^{3'})_2$, —$N(R^{3'})C(O)N(R^{3'})_2$, —$N(R^{3'})C(O)OR^{3'}$, —$O$—$C(O)N(R^{3'})_2$, —$N(R^{3'})SO_2R^{3'}$, —$SO_2N(R^{3'})_2$ and —$SO_2R^{3'}$; $R^{3'}$ is H or —$C_{1-6}$alkyl.

According to another embodiment of the first aspect of the present invention are provided compounds according to the first embodiment of the first aspect of the present invention wherein $R^{3a}$ is $C_{1-8}$alkyl, $C_{2-7}$alkenyl, —$C(O)R^{3'}$, —$C(O)O$—$R^{3'}$ or $C_{2-7}$alkynyl.

According to another embodiment of the first aspect of the present invention are provided compounds according to the first embodiment of the first aspect of the present invention wherein $R^{3a}$ is $C_{1-8}$alkyl, $C_{2-7}$alkenyl, —$C(O)R^{3'}$, —$C(O)O$—$R^{3'}$ or $C_{2-7}$alkynyl; wherein $R^{3a}$ is optionally substituted with 1 to 3 of the same or different substituents selected from the group consisting of benzyl, phenyl, —O-phenyl, —O—$C_{1-3}$alkylphenyl, —$C_{1-3}$alkylene-OC(O)-phenyl, cyano, amino, nitro, halo, $C_{1-3}$mono-bi-tri-haloalkyl, $C_{1-3}$mono-bi-tri-haloalkyloxy, $C_{1-6}$alkoxy, $(C_{1-3}$alkyl$)_{1-2}$amine, —$OR^{3'}$, —$C(O)R^{3'}$, —$C(O)O$—$R^{3'}$, —$O$—$C(O)R^{3'}$, —$N(R^{3'})_2$, —$C(O)N(R^{3'})_2$, —$N(R^{3'})C(O)(R^{3'})_2$, —$N(R^{3'})C(O)N(R^{3'})_2$, —$N(R^{3'})C(O)OR^{3'}$, —$O$—$C(O)N(R^{3'})_2$, —$N(R^{3'})SO_2R^{3'}$, —$SO_2N(R^{3'})_2$ and —$SO_2R^{3'}$; $R^{3'}$ is H or —$C_{1-6}$alkyl; provided that if $R^{3a}$ is —$C(O)R^{3'}$, CHC(O)O—$R^{3'}$, CH(CH$_3$)C(O)O—$R^{3'}$ or —$C(O)O$—$R^{3'}$, then said —$C(O)R^{3'}$, CHC(O)O—$R^{3'}$, CH(CH$_3$)C(O)O—$R^{3'}$ or —$C(O)O$—$R^{3'}$ are unsubstituted.

According to another embodiment of the first aspect of the present invention are provided compounds according to the first embodiment of the first aspect of the present invention wherein $R^3$ is $R^{3a}$ and $R^{3a}$ is phenyl, hydroxyphenyl, azetidinyl, napthyl, $C_{1-6}$alkyl, $C_{2-6}$alkenyl, $C_{2-6}$alkynyl, dihydroquinolinonyl, hydroquinolinonyl, quinolinyl, dihydroisoquinolinonyl, hydroisoquinolinonyl, isoquinolinyl, dihydroquinazolinonyl, hydroquinazolinonyl, quinazolinyl, dihydroquinoxalinonyl, hydroquinoxalinonyl, quinoxalinyl, benzimidazolyl, indazolyl, dihydrobenzimidazolonyl, hydrobenzimidazolonyl, benzimidazolinyl, dihydro-benzthiazolonyl, hydrobenzthiazolonyl, benzthiazolyl, dihydrobenzoxazolyl, benzotriazolyl, dihydrobenzothiophenonyl, hydrobenzothiophenonyl, benzothienyl, dihydrobenzofuranonyl, hydrobenzofuranonyl, benzofuranyl, benzdioxolanyl, dihydroindolonyl, hydroindolonyl, indolyl, indolizinyl, isoindolyl, indolinyl, indazolyl, pyrazolyl, pyrazolinyl, pyrazolidinyl, furanyl, thienyl, pyrrolyl, pyrrolinyl, pyrrolidinyl, imidazolyl, imidazolinyl, imidazolidinyl, pyridyl, purinyl, carbazolyl, pyrimidinyl, piperidinyl, triazolopyrimidinyl, tetrahydropyrazolopyridinyl, piperazinyl or morpholino; optionally substituted as provided in the first embodiment of the first aspect.

According to another embodiment of the first aspect of the present invention are provided compounds according to the first embodiment of the first aspect of the present invention wherein $R^3$ is $R^{3a}$ and $R^{3a}$ is phenyl, napthyl, indazolyl, benzimidazolinyl, dihydrobenzoxazolyl, benzotriazolyl, benzothienyl, benzdioxolanyl, dihydroindolonyl, indolyl, furanyl, thienyl, pyridyl, purinyl, carbazolyl, piperidinyl, triazolopyrimidinyl, tetrahydropyrazolopyridinyl; optionally substituted as provided in the first embodiment of the first aspect.

According to another embodiment of the first aspect of the present invention are provided compounds according to the first embodiment of the first aspect of the present invention wherein $R^3$ is $R^{3a}$ and $R^{3a}$ is dihydro-benzthiazolonyl, hydrobenzthiazolonyl, benzthiazolyl, dihydrobenzothiophenonyl, hydrobenzothiophenonyl, benzothienyl, dihydrobenzofuranonyl, hydrobenzofuranonyl, benzofuranyl, dihydroindolonyl, hydroindolonyl, indolyl, indolizinyl, isoindolyl, indolinyl or indazolyl; optionally substituted as provided in the first embodiment of the first aspect.

According to another embodiment of the first aspect of the present invention are provided compounds according to the first embodiment of the first aspect of the present invention wherein $R^3$ is $R^{3a}$ and $R^{3a}$ is dihydrobenzoxazolyl, benzotriazolyl, indolyl, halonitrophenyl, halopyrimidine, halopurinyl, $C_{1-3}$alkyl-nitroaminopyrimidine, triazolopyrimidinyl, pyridyl, indazolyl, phenyl or benzdioxolanyl; optionally substituted as provided in the first embodiment of the first aspect.

According to another embodiment of the first aspect of the present invention are provided compounds according to the first embodiment of the first aspect of the present invention wherein $R^3$ is $R^{3a}$ and $R^{3a}$ is naphthyl, phenyl-O-phenyl, or thienyl; optionally substituted as provided in the first embodiment of the first aspect.

According to another embodiment of the first aspect of the present invention are provided compounds according to the first embodiment of the first aspect of the present invention wherein $R^3$ is $R^{3b}$.

According to another embodiment of the first aspect of the present invention are provided compounds according to the first embodiment of the first aspect of the present invention wherein $R^3$ is $R^{3b}$ and $R^{3b}$ is 1H-Indol-5-yl

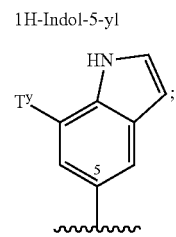

1H-Indazol-5-yl

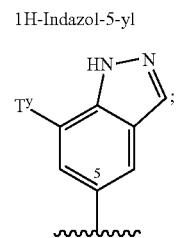

1H-Benzotriazol-5-yl

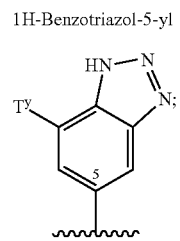

1,3-Dihydro-indol-2-on-5-yl

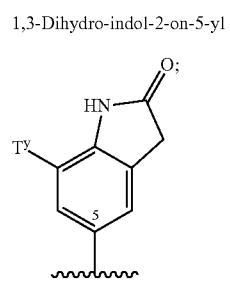

3H-Benzooxazol-2-on-6-yl

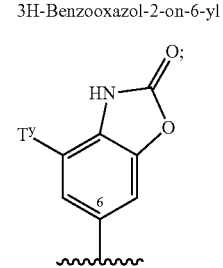

1,3 Dihydro-benzoimidazol-2-on-5-yl

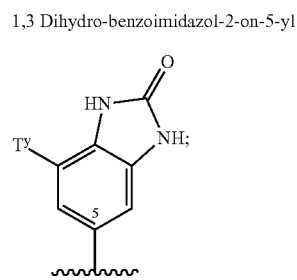

-continued

1-Methyl-1,3-dihydro-benzoimidazol-2-on-6-yl

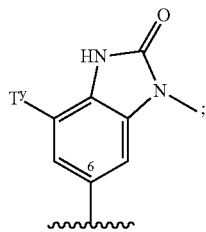

3,4-Dihydro-1H-quinolin-2-on-6-yl

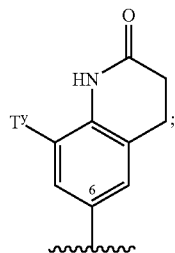

1,4-Dihydro-benzo[d][1,3]oxazin-2-on-6-yl

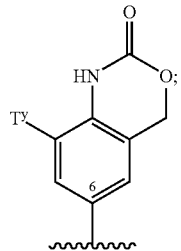

3,4-Dihydro-1H-quinazolin-2-on-6-yl

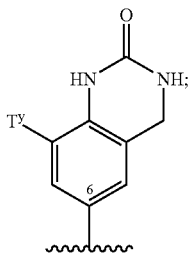

3-Methyl-3,4-dihydro-1H-quinazolin-2-on-6-yl

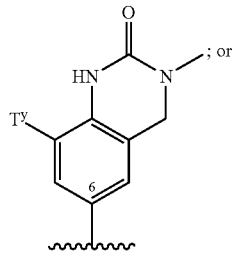

4H-Benzo[1,4]oxazin-3-on-7-yl

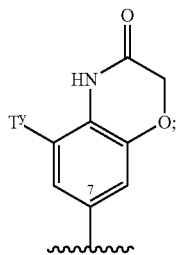

wherein $T^y$ is H, $C_{1-4}$alkyl, F, Cl, Br or nitrile.

According to another embodiment of the first aspect of the present invention are provided compounds according to the first embodiment of the first aspect of the present invention wherein $R^3$ is $R^{3b}$ and $R^{3b}$ is azetidinyl, $C_{1-6}$alkyl, $C_{2-6}$alkenyl, $C_{2-6}$alkynyl, dihydroquinolinonyl, hydroquinolinonyl, dihydroisoquinolinonyl, hydroisoquinolinonyl, dihydroquinazolinonyl, hydroquinazolinonyl, quinazolinyl, dihydroquinoxalinonyl, hydroquinoxalinonyl, quinoxalinyl, benzimidazolyl, 1H-indazol-5-yl, dihydrobenzimidazolonyl, hydrobenzimidazolonyl, benzimidazolinyl, dihydro-benzthiazolonyl, hydrobenzthiazolonyl, benzthiazolyl, dihydrobenzothiophenonyl, hydrobenzothiophenonyl, dihydrobenzofuranonyl, hydrobenzofuranonyl, benzdioxolanyl, dihydrobenzoxazolyl, benzotriazolyl, dihydroindolonyl, hydroindolonyl, indolizinyl, isoindolyl, indolinyl, pyrazolyl, pyrazolinyl, pyrazolidinyl, furanyl, pyrrolyl, pyrrolinyl, pyrrolidinyl, imidazolinyl, imidazolidinyl, purinyl, carbazolyl, pyrimidinyl, piperidinyl, piperazinyl or morpholino; optionally substituted as provided in the first embodiment of the first aspect.

According to another embodiment of the first aspect of the present invention are provided compounds according to the first embodiment of the first aspect of the present invention wherein $R^3$ is $R^{3b}$ and $R^{3b}$ is dihydrobenzimidazolonyl, hydrobenzimidazolonyl, benzimidazolinyl, dihydro-benzthiazolonyl, hydrobenzthiazolonyl, benzthiazolyl, dihydrobenzothiophenonyl, hydrobenzothiophenonyl, dihydrobenzofuranonyl, hydrobenzofuranonyl, 1H-indazol-5-yl, benzdioxolanyl, dihydrobenzoxazolyl, benzotriazolyl, dihydroindolonyl, hydroindolonyl, indolizinyl, isoindolyl, indolinyl, pyrazolyl, pyrazolinyl, pyrazolidinyl, furanyl, pyrrolyl, pyrrolinyl, pyrrolidinyl, imidazolinyl, imidazolidinyl, purinyl, carbazolyl, pyrimidinyl, piperidinyl, piperazinyl or morpholino; optionally substituted as provided in the first embodiment of the first aspect.

According to another embodiment of the first aspect of the present invention are provided compounds according to the first embodiment of the first aspect of the present invention wherein $R^3$ is $R^{3b}$ and $R^{3b}$ is azetidinyl, $C_{1-6}$alkyl, $C_{2-6}$alkenyl, $C_{2-6}$alkynyl, dihydroquinolinonyl, hydroquinolinonyl, dihydroisoquinolinonyl, hydroisoquinolinonyl, dihydroquinazolinonyl, hydroquinazolinonyl, quinazolinyl, dihydroquinoxalinonyl, hydroquinoxalinonyl, quinoxalinyl, benzimidazolyl, 1H-indazol-5-yl, dihydrobenzimidazolonyl, hydrobenzimidazolonyl, benzimidazolinyl, dihydro-benzthiazolonyl, hydrobenzthiazolonyl, benzthiazolyl, dihydrobenzothiophenonyl, hydrobenzothiophenonyl, dihydrobenzofuranonyl, hydrobenzofuranonyl, benzdioxolanyl, dihydrobenzoxazolyl, benzotriazolyl, purinyl, carbazolyl, pyrimidinyl, piperidinyl, piperazinyl or morpholino; optionally substituted as provided in the first embodiment of the first aspect.

According to another embodiment of the first aspect of the present invention are provided compounds according to the first embodiment of the first aspect of the present invention wherein $R^3$ is $R^{3b}$ and $R^{3b}$ is azetidinyl, $C_{1-6}$alkyl, $C_{2-6}$alkenyl, $C_{2-6}$alkynyl, dihydroquinolinonyl, hydroquinolinonyl, dihydroisoquinolinonyl, hydroisoquinolinonyl, dihydroquinazolinonyl, hydroquinazolinonyl, quinazolinyl, dihydroquinoxalinonyl, hydroquinoxalinonyl, quinoxalinyl, benzimidazolyl, benzdioxolanyl, dihydrobenzoxazolyl, benzotriazolyl, dihydroindolonyl, hydroindolonyl, 1H-indazol-5-yl, indolizinyl, isoindolyl, indolinyl, pyrazolyl, pyrazolinyl, pyrazolidinyl, furanyl, pyrrolyl, pyrrolinyl, pyrrolidinyl, imidazolinyl, imidazolidinyl, purinyl, carbazolyl, pyrimidinyl, piperidinyl, piperazinyl or morpholino; optionally substituted as provided in the first embodiment of the first aspect.

According to another embodiment of the first aspect of the present invention are provided compounds according to the first embodiment of the first aspect of the present invention wherein $R^3$ is $R^{3b}$ and $R^{3b}$ is benzdioxolanyl, dihydrobenzoxazolyl, benzotriazolyl, purinyl, carbazolyl; optionally substituted as provided in the first embodiment of the first aspect.

According to another embodiment of the first aspect of the present invention are provided compounds according to the first embodiment of the first aspect of the present invention wherein $R^3$ is $R^{3b}$ and $R^{3b}$ is dihydrobenzoxazolyl, benzotriazolyl, indolyl, halonitrophenyl, halopyrimidinyl, halopurinyl, $C_{1-3}$alkyl-nitroaminopyrimidinyl, triazolopyrimidinyl, pyridyl, 1H-indazol-5-yl, phenyl or benzdioxolanyl.

According to another embodiment of the first aspect of the present invention are provided compounds according to the first embodiment of the first aspect of the present invention wherein Q is Q' and wherein said compounds have an absolute configuration of R.

According to another embodiment of the first aspect of the present invention are provided compounds according to the first embodiment of the first aspect of the present invention wherein Q is Q' and wherein said compounds have an absolute configuration of S.

According to another embodiment of the first aspect of the present invention are provided compounds according to the first embodiment of the first aspect of the present invention wherein Q is Q" and wherein said compounds have an absolute configuration of R.

According to another embodiment of the first aspect of the present invention are provided compounds according to the first embodiment of the first aspect of the present invention wherein Q is Q" and wherein said compounds have an absolute configuration of S.

According to another embodiment of the first aspect of the present invention are provided compounds according to the first embodiment of the first aspect of the present invention wherein m and n are each 1.

According to another embodiment of the first aspect of the present invention are provided compounds according to the first embodiment of the first aspect of the present invention wherein D is O.

According to another embodiment of the first aspect of the present invention are provided compounds according to the first embodiment of the first aspect of the present invention wherein A is C.

According to another embodiment of the first aspect of the present invention are provided compounds according to the first embodiment of the first aspect of the present invention wherein A is CH.

According to another embodiment of the first aspect of the present invention are provided compounds according to the first embodiment of the first aspect of the present invention wherein A is N.

According to another embodiment of the first aspect of the present invention are provided compounds according to the first embodiment of the first aspect of the present invention wherein E is N.

According to another embodiment of the first aspect of the present invention are provided compounds according to the first embodiment of the first aspect of the present invention wherein E is CH.

According to another embodiment of the first aspect of the present invention are provided compounds according to the first embodiment of the first aspect of the present invention wherein E is C.

According to another embodiment of the first aspect of the present invention are provided compounds according to the first embodiment of the first aspect of the present invention wherein said compounds exhibit as described herein a CGRP Binding $IC_{50}$ of less than 10 nM.

According to another embodiment of the first aspect of the present invention are provided compounds according to the first embodiment of the first aspect of the present invention wherein said compounds exhibit as described herein a CGRP Binding $IC_{50}$ of less than 100 nM.

According to another embodiment of the first aspect of the present invention are provided compounds according to the first embodiment of the first aspect of the present invention wherein said compounds exhibit as described herein a CGRP Binding $IC_{50}$ of less than 1000 nM.

According to another embodiment of the first aspect of the present invention are provided compounds according to the first embodiment of the first aspect of the present invention wherein p is 1; and G, J and E together form $A^x$ or $A^y$.

According to another embodiment of the first aspect of the present invention are provided compounds according to the first embodiment of the first aspect of the present invention wherein p is 1; and G, J and E together form A.

According to another embodiment of the first aspect of the present invention are provided compounds according to the first embodiment of the first aspect of the present invention wherein p is 1; and G, J and E together form $A^y$.

According to another embodiment of the first aspect of the present invention are provided compounds according to the first embodiment of the first aspect of the present invention wherein $A^x$ is a fused heterocycle having two fused rings with 5 to 7 members in each of said rings, said heterocycle containing one to four of the same or different heteroatoms selected from the group consisting of O, N and S; and optionally containing 1 or 2 carbonyls wherein the carbon atom of said carbonyl is a member of said fused heterocycle.

According to another embodiment of the first aspect of the present invention are provided compounds according to the first embodiment of the first aspect of the present invention wherein $A^x$ is a fused heterocycle having two fused rings with 5 to 7 members in each of said rings, said heterocycle containing one to four of the same or different heteroatoms selected from the group consisting of O, N and S.

According to another embodiment of the first aspect of the present invention are provided compounds according to the first embodiment of the first aspect of the present invention wherein $A^x$ is a fused heterocycle having two fused rings with 5 to 7 members in each of said rings, said heterocycle containing one to four of the same or different heteroatoms selected from the group consisting of O, N and S and wherein $A^x$ is substituted with phenyl.

According to another embodiment of the first aspect of the present invention are provided compounds according to the first embodiment of the first aspect of the present invention wherein $A^x$ is a fused heterocycle described herein.

According to another embodiment of the first aspect of the present invention are provided compounds according to the first embodiment of the first aspect of the present invention wherein $A^y$ is a 4 to 6 membered heterocycle containing one to three heteroatoms selected from the group consisting of O, N and S; and optionally containing 1 to 2 carbonyls, wherein the carbon atom of said carbonyl is a member of said 4 to 6 membered heterocycle.

According to another embodiment of the first aspect of the present invention are provided compounds according to the first embodiment of the first aspect of the present invention wherein $A^y$ is a 4 to 6 membered heterocycle containing one to three heteroatoms selected from the group consisting of O, N and S.

According to another embodiment of the first aspect of the present invention are provided compounds according to the first embodiment of the first aspect of the present invention wherein $A^y$ is a 4 to 6 membered heterocycle containing one to three heteroatoms selected from the group consisting of O, N and S; and optionally containing 1 to 2 carbonyls, wherein the carbon atom of said carbonyl is a member of said 4 to 6 membered heterocycle; and wherein $A^y$ is substituted with phenyl.

According to another embodiment of the first aspect of the present invention are provided compounds according to the first embodiment of the first aspect of the present invention wherein $A^y$ is a 4 to 6 membered heterocycle described herein.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA' or GJA".

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA'.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA".

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA' and GJA' is $A^x$.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA' and GJA' is $A^y$.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA" and GJA" is $A^x$.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA" and GJA" is $A^y$.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydroquinoxalinonyl, dihydrobenzoxazinyl, hydrobenzoxazinyl, dihydrobenzoxazinonyl, dihydrobenzimidazolonyl, dihydrobenzimidazolyl, dihydro-benzthiazolonyl, dihydrobenzothiazolyl, dihydrobenzothiophenonyl, dihydrobenzofuranonyl, dihydroindolonyl, indolinyl, pyrazolinyl, pyrazolidinyl, pyrrolinyl, pyrrolidinyl, imidazolinyl, imidazolidinyl, piperidinyl, piperazinyl and morpholino; wherein said heterocycle is optionally substituted with $C_{1-4}$alkyl, $C_{1-4}$ alkoxy, $C_{1-4}$ haloalkyl, cyano, $C_{3-7}$cycloalkyl, phenyl, halophenyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydroquinoxalinonyl, dihydrobenzoxazinyl, hydrobenzoxazinyl, dihydrobenzoxazinonyl, dihydrobenzimidazolonyl, dihydrobenzimidazolyl, dihydro-benzthiazolonyl, dihydrobenzothiazolyl, dihydrobenzothiophenonyl, dihydrobenzofuranonyl, dihydroindolonyl, indolinyl, pyrazolinyl, pyrazolidinyl, pyrrolinyl, pyrrolidinyl, imidazolinyl, imidazolidinyl, piperidinyl, piperazinyl and morpholino; wherein said heterocycle is optionally substituted with $C_{1-4}$alkyl, $C_{1-4}$ alkoxy, $C_{1-4}$ haloalkyl, cyano, $C_{3-7}$cycloalkyl, phenyl, halophenyl, furanyl, pyrazolyl, pyrazolinyl, pyrazolidinyl, pyridyl, pyrimidinyl, piperidinyl, piperazinyl or morpholino.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydrobenzofuranonyl, dihydroindolonyl, indolinyl, pyrazolinyl, pyrazolidinyl, pyrrolinyl, pyrrolidinyl, imidazolinyl, imidazolidinyl, piperidinyl, piperazinyl and morpholino; wherein said heterocycle is optionally substituted with $C_{1-4}$alkyl, $C_{1-4}$ alkoxy, $C_{1-4}$ haloalkyl, cyano, $C_{3-7}$cycloalkyl, phenyl, halophenyl, piperazinyl or morpholino.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydroquinoxalinonyl, dihydrobenzoxazinyl, hydrobenzoxazinyl, dihydrobenzoxazinonyl, dihydrobenzimidazolonyl, dihydrobenzimidazolyl, dihydro-benzthiazolonyl, dihydrobenzothiazolyl, dihydrobenzothiophenonyl, dihydrobenzofuranonyl, dihydroindolonyl, indolinyl, pyrazolinyl, pyrazolidinyl, pyrrolinyl, pyrrolidinyl, imidazolinyl, imidazolidinyl, piperidinyl, piperazinyl and morpholino.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydroquinoxalinonyl, dihydrobenzoxazinyl, hydrobenzoxazinyl and dihydrobenzoxazinonyl.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydroquinoxalinonyl and dihydrobenzoxazinyl.

According to various embodiments of a second aspect of the present invention are provided pharmaceutical compositions comprising compounds of Formula (I) as defined herein.

According to various embodiments of a third aspect of the present invention are provided methods of treating inflammation (particularly neurogenic inflammation), headache (particularly migraine), pain, thermal injury, circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising compounds of Formula (I) as defined herein.

According to various embodiments of a fourth aspect of the present invention are uses of the compounds of the present invention selected from the group consisting of (a) immune regulation in gut mucosa (b) protective effect against cardiac anaphylaxis (c) stimulating or preventing interleukin-1b(IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, Stefanie; Knauer, Jens; Haberberger, Rainer; Goeke, Burkhard; Voigt, Karlheinz; McGregor, Gerard Patrick. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, Wei-Qing; Du, Yan-Hua; Hu, Chang-Ping; Ye, Feng; Tan, Gui-Shan; Deng, Han-Wu; Li, Yuan-Jian. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1. Lian, Kai; Du, Jingyuan; Rao, Zhenyu; Luo, Huaican. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokinin 1receptors by rat spinal neurons. Seybold V S, McCarson K E, Mermelstein P G, Groth R D, Abrahams L G. J. Neurosci. 2003 23 (5): 1816-1824. Department of Neuroscience, University of Minnesota, Minneapolis, Minn. 55455, and Department of Pharmacology, Toxicology, and Therapeutics, University of Kansas Medical Center, Kansas City, Kans. 66160 (e) Attenuation of antigen-induced airway hyperresponsiveness in CGRP-deficient mice. Aoki-Nagase, Tomoko; Nagase, Takahide; Oh-Hashi, Yoshio; Shindo, Takayuki; Kurihara, Yukiko; Yamaguchi, Yasuhiro; Yamamoto, Hiroshi; Tomita, Tetsuji; Ohga, Eijiro; Nagai, Ryozo; Kurihara, Hiroki; Ouchi, Yasuyoshi. Department of Geriatric Medicine, Graduate School of Medicine, University of Tokyo, Tokyo, Japan. American Journal of Physiology (2002), 283(5,Pt. 1), L963-L970; (f) Calcitonin gene-related peptide as inflammatory mediator. Springer, Jochen; Geppetti, Pierangelo; Fischer, Axel; Groneberg, David A. Charite Campus-Virchow, Department of Pediatric Pneumology and Immunology, Division of Allergy Research, Humboldt-University Berlin, Berlin, Germany. Pulmonary Pharmacology & Therapeutics (2003), 16(3), 121-130; and (g) Pharmacological targets for the inhibition of neurogenic inflammation. Helyes, Zsuzsanna; Pinter, Erika; Nemeth, Jozsef, Szolcsanyi, Janos. Department of Pharmacology and Pharmacotherapy, Faculty of Medicine, University of Pecs, Pecs, Hung. Current Medicinal Chemistry: Anti-Inflammatory & Anti-Allergy Agents (2003), 2(2), 191-218 all incorporated by reference herein.

According to various embodiments of a fifth aspect of the present invention are provided combinations of the compounds of the present invention with one or more agents selected from the group consisting of COX-2 inhibitors, NSAIDS, aspirin, acetaminophen, triptans, ergotamine and caffeine for the treatment of migraine.

According to a sixth aspect of the present invention are provided in vivo non-terminal methods of identifying anti-migraine compounds.

According to the first embodiment of the sixth aspect of the present invention is provided an in vivo non-terminal method of identifying anti-migraine compounds comprising administering a CGRP-receptor agonist to a mammal in an amount capable of inducing an increase in blood flow, followed by administering a test compound in an amount capable of reversing said CGRP-induced increase in blood flow, wherein said mammal is a transgenic mammal with humanized RAMP1 having Trp74 or a mammal endogenously expressing RAMP1 having Trp74.

According to another embodiment of the sixth aspect of the present invention is provided an in vivo non-terminal method of identifying anti-migraine compounds comprising administering to a mammal a test compound prior to the delivery of a CGRP-receptor agonist wherein said CGRP-receptor agonist is administered in an amount capable of inducing an increase in blood flow and wherein said test compound is administered in an amount capable of suppressing said CGRP-induced increase in blood flow, wherein said mammal is a transgenic mammal with humanized RAMP1 having Trp74 or a mammal endogenously expressing RAMP1 having Trp74.

According to another embodiment of the sixth aspect of the present invention is provided an in vivo non-terminal method of identifying anti-migraine compounds comprising administering to a mammal a CGRP-receptor agonist in an amount capable of inducing an increase in peripheral artery diameter, followed by administering a test compound in an amount capable of reversing said CGRP-induced increase in peripheral artery diameter, wherein said mammal is a transgenic mammal with humanized RAMP1 having Trp74 or a mammal endogenously expressing RAMP1 having Trp74.

According to another embodiment of the sixth aspect of the present invention is provided an in vivo non-terminal method of identifying anti-migraine compounds comprising administering to a mammal a test compound prior to the delivery of a CGRP-receptor agonist wherein said CGRP-receptor agonist is administered in an amount capable of inducing an increase in peripheral artery diameter and wherein said test compound is administered in an amount capable of suppressing said CGRP-induced increase in peripheral artery diameter, wherein said mammal is a transgenic mammal with humanized RAMP1 having Trp74 or a mammal endogenously expressing RAMP1 having Trp74.

According to other embodiments of the sixth aspect of the present invention are provided in vivo non-terminal methods of identifying anti-migraine compounds as described herein wherein said blood flow is facial blood flow.

According to other embodiments of the sixth aspect of the present invention are provided in vivo non-terminal methods of identifying anti-migraine compounds as described herein wherein said mammal endogenously expressing RAMP1 having Trp74 is a non-human primate.

According to other embodiments of the sixth aspect of the present invention are provided in vivo non-terminal methods of identifying anti-migraine compounds as described herein wherein said mammal endogenously expressing RAMP1 having Trp74 is man.

According to other embodiments of the sixth aspect of the present invention are provided in vivo non-terminal methods of identifying anti-migraine compounds as described herein wherein said mammal endogenously expressing RAMP1 having Trp74 is a non-human primate and said non-human primate is a marmoset.

According to other embodiments of the sixth aspect of the present invention are provided in vivo non-terminal methods of identifying anti-migraine compounds as described herein wherein said anti-migraine compounds are CGRP-receptor antagonists.

Other embodiments of the present invention may comprise a suitable combination of two or more of the embodiments and/or aspects disclosed herein.

Yet other embodiments of the present invention may comprise a suitable subset of an embodiment and/or aspect disclosed herein.

Still yet other embodiments and aspects of the invention will be apparent according to the description provided below.

BRIEF DESCRIPTION OF THE FIGURES

FIG. 1. Schild Analysis.

Dose response of CGRP stimulated cAMP production in the absence (filled squares) and presence (all others) of increasing concentrations (left-to-right) of the CGRP antagonist Example 2. Inset is Schild plot of log dose ratio minus 1 (Y-axis) against log concentration of the antagonist Example 2 (X-axis): Slope=0.94, $K_b$=0.16 nM.

FIG. 2. Direct Validation of Facial Blood Flow as Surrogate for Intracranial Artery Dilation in the Rat.

Intravenous delivery of i.v. hαCGRP induces comparable percent increases (100-120% of baseline) in rat middle meningeal artery diameter and rat facial blood flow (left and right striped bars, respectively). Pretreatment with the peptide antagonist CGRP(8-37) produces a 50% inhibition of subsequent i.v. hαCGRP administration for both measures (filled bars). Intracranial artery diameter and facial blood flow were measured concurrently in each animal (n=5 rats). Data are mean±sem*p<0.05, **p<0.01 vs corresponding hαCGRP alone.

FIG. 3. Dose-Response for hαCGRP in Non-Human-Primate Laser Doppler Facial Blood Flow.

Delivery of hαCGRP induces dose-dependent increase in laser Doppler facial blood flow in non-human primates (e.g., common marmoset). Animals (n=6) received increasing doses of hαCGRP at 30 min intervals. Data are peak % change from baseline±sem, with each animal serving as its own control.

FIG. 4. Inhibition of CGRP-Induced Changes in Non-Human Primate Facial Blood Flow.

The novel CGRP antagonist Example 2 (filled bars) delivered prior to hαCGRP (striped bar), dose-dependently inhibits the CGRP-induced increase in laser Doppler facial blood flow. Vehicle (open bar) was without effect. Data are mean±sem (n=5-6 primates per group). *p<0.05 compared CGRP alone.

FIG. 5. Effect of CGRP Antagonist on Non-Human Primate Blood Pressure.

In contrast to the dose-dependent inhibition of primate facial blood flow (see FIG. 4), Example 2 has negligible effect on blood pressure (parallel studies in separate animals, n=6). Animals received repeat doses of Example 2 at 20 min intervals. BP data are mean±sem over 20 min period measured by arm cuff

DETAILED DESCRIPTION OF THE INVENTION

The description of the invention herein should be construed in congruity with the laws and principals of chemical bonding. For example, it may be necessary to remove a hydrogen atom in order accommodate a substitutent at any given location.

As used herein, "heterocyclic" or "heterocycle" includes cyclic moieties containing one or more heteroatoms, (e.g., O, N or S) said heterocycles include those that are aromatic and those that are not, i.e., "alicyclic", unless otherwise specified.

As used herein, the term "fused bicyclic system" when describing for example a 5.6-fused bicyclic system containing 1 to 4 nitrogen atoms includes aromatic and alicyclic systems, e.g. indolizine, indole, isoindole, 3H-indole, indoline, indazole or benzimidazole.

If a substitutent is named generically, then any and all species of that genus comprise that aspect of the invention. For example, a substituent generically named as "pyrrolonyl" (the radical of "pyrrolone", a pyrrole having a carbonyl) includes pyrrol-2-onyls wherein the carbonyl is adjacent to the nitrogen and pyrrol-3-onyls wherein the carbonyl and nitrogen have an intervening methylene.

Similarly, the present invention comprises that a substituent may be attached at any and all suitable points of attachment on said substituent unless otherwise specified.

However, it is also understood that the compounds encompassed by the present invention are those that are chemically stable, i.e., heteroalicyclic substituents of the present invention should not be attached in such a way that a heteroatom in said heteroalicyclic substituent is alpha to a point of attachment wherein said point of attachment is also a heteroatom.

An embodiment or aspect which depends from another embodiment or aspect, will describe only the variables having values or provisos that differ from the embodiment or aspect from which it depends. If for example a dependent embodiment only addresses $R^2$, then the variables and provisos not related to $R^2$ should reflect that of the embodiment from which it depends.

If a variable is quantified with a value of zero, then a bond attaching said variable should no longer be represented.

As used herein, "alkylene" means a divalent alkane, i.e., an alkane having two hydrogen atoms removed from said alkane (said hydrogen removed from two different carbon atoms when said alkane contains more than one carbon atom), e.g.,

—$CH_2CH_2CH_2$—.

As used herein, "alkylidene" means an alkane having two hydrogen atoms removed from one carbon atom in said alkane, e.g.,

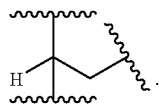

It should be understood that the alternating double bond designations in the six-membered ring of the 5,6-membered fused structure represented in Formula (I) are relative and represent the delocalized π orbital electrons of said ring.

As used herein, "aryl" or "ar-" includes phenyl or napthyl.

As used herein, "heterocyclic" or "heterocyclo" includes both heteroaryl and heteroalicyclic.

As used herein, "halo" or "halogen" includes fluoro, chloro, bromo and iodo and further means one or more of the same or different halogens may be substituted on a respective moiety.

Unless specified otherwise, acyclic hydrocarbons such as alkyl, alkoxy, alkenyl and alkynyl may be branched or straight chained.

It is to be understood that the present invention may include any and all possible stereoisomers, geometric isomers, diastereoisomers, enantiomers, anomers and optical isomers, unless a particular description specifies otherwise.

As used herein, "Trp74", means that the $74^{th}$ residue in RAMP1 is tryptophan (Mallee et al. *J Biol Chem* 2002, 277, 14294-8) incorporated by reference herein.

As used herein "anti-migraine compound" includes any compound, peptide or peptide fragment (modified or unmodified) capable of reversing or attenuating CGRP-receptor mediated vasodilation, (e.g., CGRP-receptor antagonists).

As used herein "test compound" includes any compound, peptide or peptide fragment (modified or unmodified) being tested to determine if it is capable of reversing or attenuating CGRP-receptor mediated vasodilation, (e.g. putative CGRP-receptor antagonists).

As used herein, "CGRP-receptor agonist" includes any compound, peptide or peptide fragment (modified or unmodified) capable of inducing CGRP-receptor mediated vasodilation particularly by example αCGRP or βCGRP; other members of the calcitonin family, e.g., adrenomedullin; N-terminal CGRP fragments, e.g., CGRP(1-12) CGRP(1-15) and CGRP(1-22); C-terminal amide (NH2) versions of CGRP e.g., CGRP(1-8+NH2), CGRP(1-13+NH2) or CGRP (1-14+NH2); and non-naturally occurring CGRP analogues e.g., [Ala$^1$ ψ(CH2NH)Cys$^2$]hCGRP which contains a pseudopeptide bond between Ala$^1$ and Cys$^2$. See Maggi C A, Rovero P, Giuliani S, Evangelista S, Regoli D, Meli A. Biological activity of N-terminal fragments of calcitonin gene-related peptide. Eur J Pharmacol. 1990 Apr. 10; 179(1-2): 217-9; Qing X, Wimalawansa S J, Keith I M. Specific N-terminal CGRP fragments mitigate chronic hypoxic pulmonary hypertension in rats. Regul Pept. 2003 Jan. 31; 110 (2):93-9; and Dennis T, Fournier A, St Pierre S, Quirion R. Structure-activity profile of calcitonin gene-related peptide in peripheral and brain tissues. Evidence for receptor multiplicity. J Pharmacol Exp Ther. 1989 November; 251(2):718-25 incorporated by reference herein.

The compounds of this invention may exist in the form of pharmaceutically acceptable salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group may exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. In the case of a sublingual formulation a saccharin salt or maleate salt may be of particular benefit. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

While dosing from 0.01 mg/kg to 30 mg/kg is envisaged for compounds of the present invention, the dosage and dosage regimen and scheduling of a compounds of the present invention must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

Synthesis

Compounds of the present invention may be synthesized according to the general schemas provided below. Variables provided in the schema below are defined in accordance with the description of compounds of the above Formula unless otherwise specified. The compounds of the present invention may be prepared according to Scheme 1 or Scheme 2. It may also be possible to use variations of said schemes to prepare the compounds of the present inventions, said variations known to those of ordinary skill in the art.

VI compound. The Formula VI compound is converted to a free acid compound of Formula VII which is then coupled with an amine of Formula $HNR^1R^2$ to generate a Formula I compound.

Scheme 1. Synthesis of Formula I Compounds

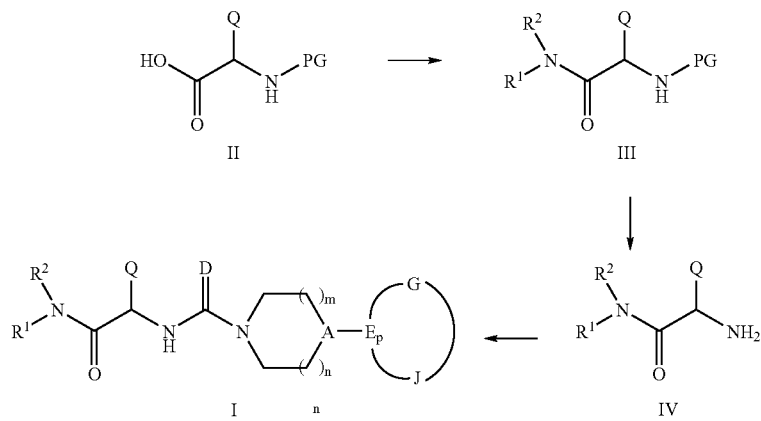

The synthesis described in Scheme 1 begins with a compound of Formula II, which is an amino acid with a protected amino terminus. Common amino protecting groups (PG) include BOC, CBZ, and FMOC and their addition and removal are well known in the field. The carboxylic acid moiety of a Formula II compound is coupled with an amine of formula $HNR^1R^2$ using standard peptide coupling reagents to form an amide of Formula III. The amino protecting group is removed resulting in a Formula IV compound. This compound is then coupled with an amine of Formula V (see below) in a mixed urea or urea isostere reaction, generating a Formula I compound. Mixed urea formation is conveniently carried using phosgene, disuccinimidyl carbonate, carbonyl diimidazole or other equivalents. Formation of urea isosteres, such as cyanoguanidines and sulfonylguanidines, are known in the literature.

Scheme 3. Synthesis of Formula I Compounds

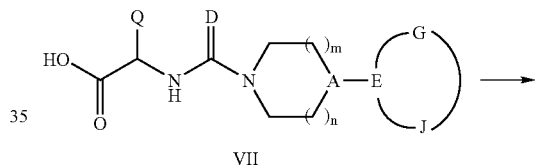

Scheme 2. Synthesis of Formula I Compounds

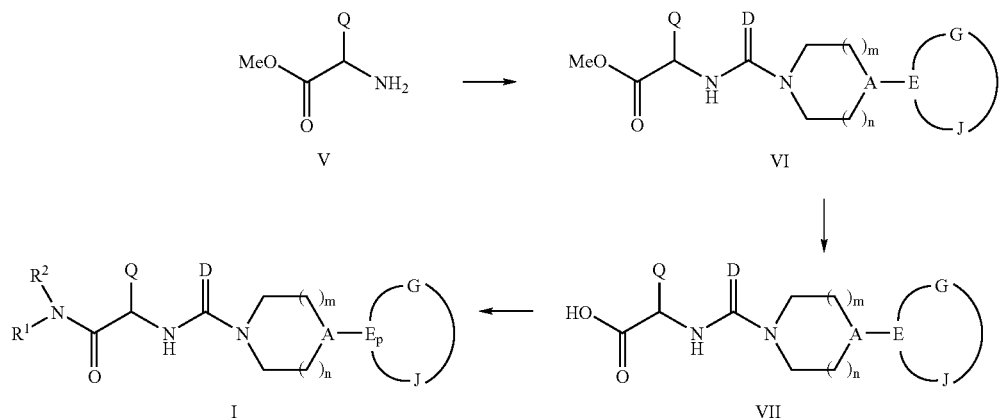

The synthesis described by Scheme 2 begins with a compound of Formula V, which is an amino acid with a protected carboxylate terminus. The protection is generally a methyl ester, but other protecting groups such as ethyl, t-butyl, and benzyl esters may also be used. The Formula V compound is coupled with an amine of Formula VIII (see below) in a mixed urea or urea isostere reaction, as above, to generate a Formula -continued

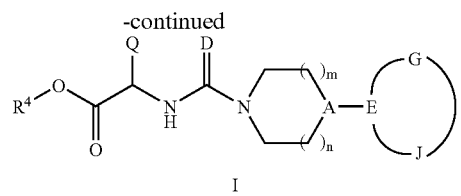

The synthesis described by Scheme 3 begins with a compound of Formula VII from Scheme 2. The Formula V compound is coupled with an alcohol, $R^4$—OH. Such ester-forming reactions are well known in the art and can be carried out, for example, with carbodiimide coupling agents such as N,N-dicyclohexylcarbodiimide. In addition, it is often advantageous, especially for esters of secondary and tertiary alcohols, to include additives that accelerate acylations such as 4-dimethylaminopyridine.

Preparation of $HNR^1R^2$ and Formula VIII Amines

Formula VIII and $HNR^1R^2$ amines are commercially available, made by literature methods or described herein.

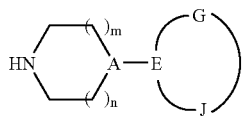

VIII

Preparation of Formula II and Formula V Amino Acids

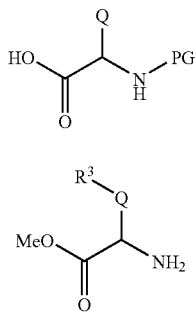

II

V

Formula II and Formula V amino acids may be commercially available or made as described in Scheme 4.

Scheme 4. Synthesis of Formula II and Formula V Compounds

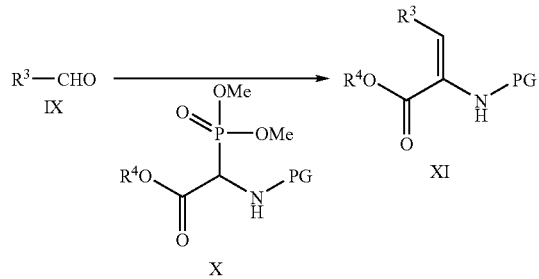

-continued

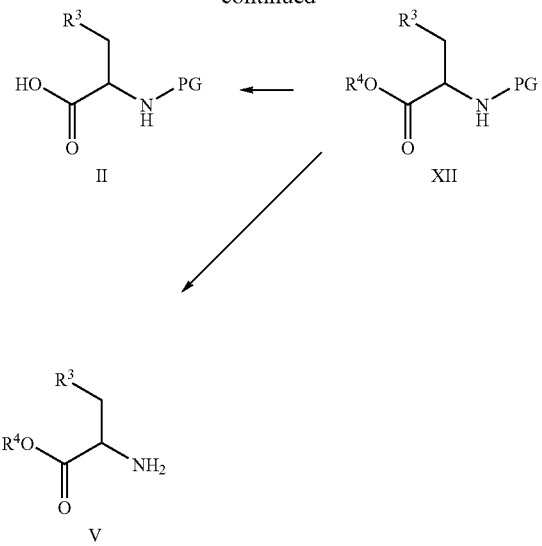

The synthesis described in Scheme 4 begins with an aldehyde of Formula IX, which is reacted with a glycine phosphonate of Formula X in a Wadsworth-Emmons coupling reaction. The compound of Formula X is deprotonated with a base such as diazabicycloundecene or tetramethylguanidine or other organic or inorganic bases well known in the art. The double bond of the resulting Formula XI compound is reduced to give compounds of Formula XII. Reduction can be carried out to give either a racemate or by use of a stereoselective catalyst to give either enantiomer of Formula XII. Such reductions can result from transfer hydrogenation from hydrogen donors such as formic acid or cyclohexadiene, or hydrogenation using gaseous hydrogen, both in the presence of a suitable catalyst. Compounds of Formula II are prepared by acid or base hydrolysis of the ester. Compounds of Formula V are prepared by removal of the protecting group (PG) using methods well known in the art.

Other amino acid derivatives of Formula XII may be prepared as shown in Scheme 5.

Scheme 5. Synthesis of Formula XII

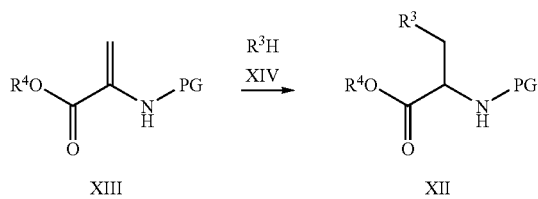

XIII

XII

Where, for the purposes of Scheme 5, compounds of Formula XIV are nucleophilic compounds such as amines or alcohols that are able to participate in a Michael Reaction with a compound of Formula XIII as shown.

Other compounds of Formula I may be prepared according to Scheme 6 or Scheme 7. It may also be possible to use variations of said schemes to prepare the compounds of the present inventions, said variations known to those of ordinary skill in the art.

Scheme 5. Synthesis of Formula I Compounds

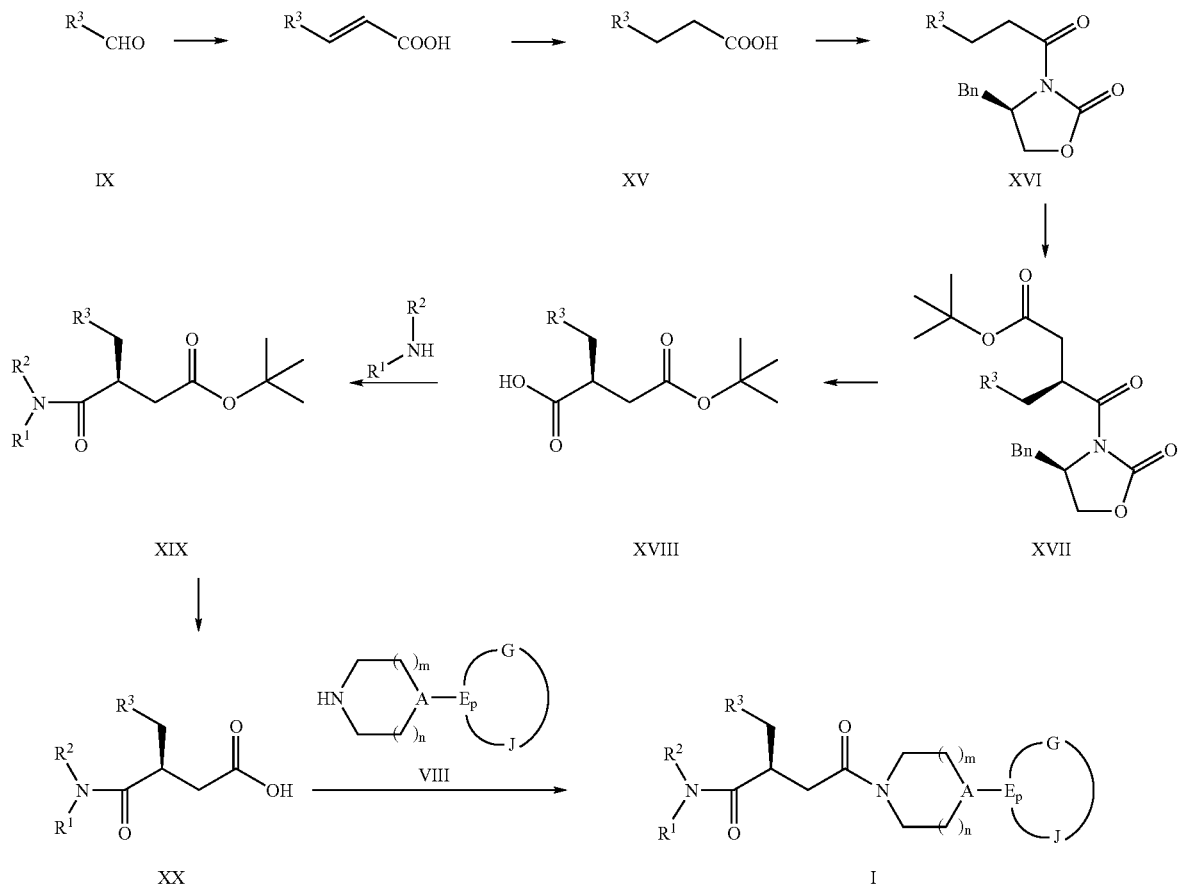

The synthesis described in Scheme 6 begins with commercially available or synthesized aldehydes. The two-carbon homologation and double-bond reduction which are well-known in the literature and lead to compounds of Formula XV. Some Formula XV compounds are also commercially available and others may be prepared by other methods well known in the art. Preparation of compounds of Formula XVI and XVII are known in the literature as substrates and products of the Evans chiral asymmetric synthesis. Hydrolysis leads to compounds of Formula XVIII. As with compounds of Formula VII in Scheme 2, these carboxylic acids can react with amines of formula $R^1R^2NH$ to afford compounds of Formula XIX using well known amide coupling protocols. Hydrolysis of the tert-butyl ester leads to compounds of Formula XX, which can be further coupled with compounds of Formula VIII to afford Formula I compounds.

Scheme 7. Synthesis of Formula I Compounds

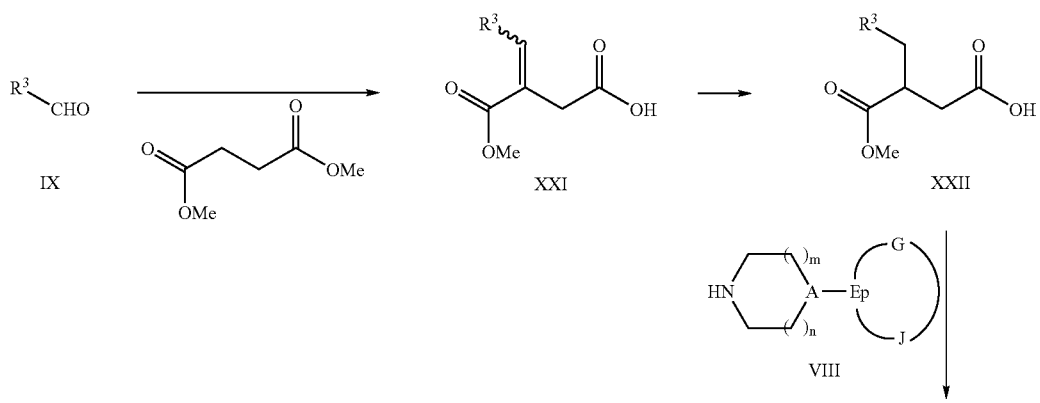

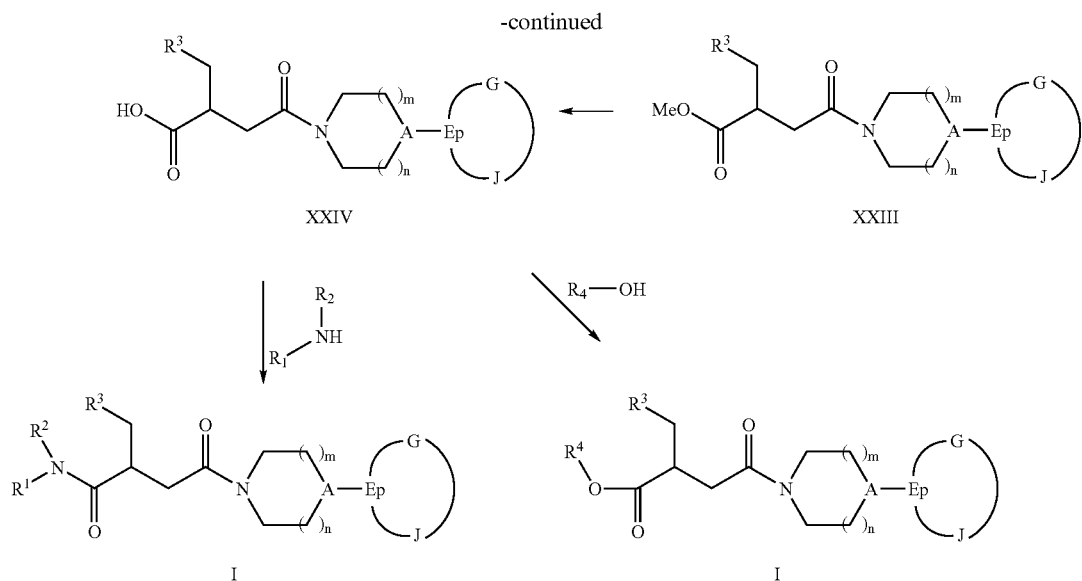

Scheme 7 also starts with commercially available or synthesized aldehydes. These are reacted with dimethyl succinate in the presence of bases to give compounds of Formula XXI. The double bond of the Formula XXI compound is reduced to give compounds of Formula XXII. Reduction can be carried out to give either a racemate or by use of a stereoselective catalyst to give either enantiomer of Formula XXII. Such reductions can result from transfer hydrogenation from hydrogen donors such as formic acid or cyclohexadiene, or hydrogenation using gaseous hydrogen, both in the presence of a suitable catalyst. Amide coupling with amines of Formula VIII lead to compounds of Formula XXIII using well known amide synthesis protocols. Hydrolysis of methyl ester leads to Formula XXIV compounds, which are further coupled with various amines or alcohols to give amides of Formula I and esters of Formula I, respectively.

Compounds of Formula I may also be prepared according to Scheme 8.

Scheme 8. Synthesis of Formula I Compounds

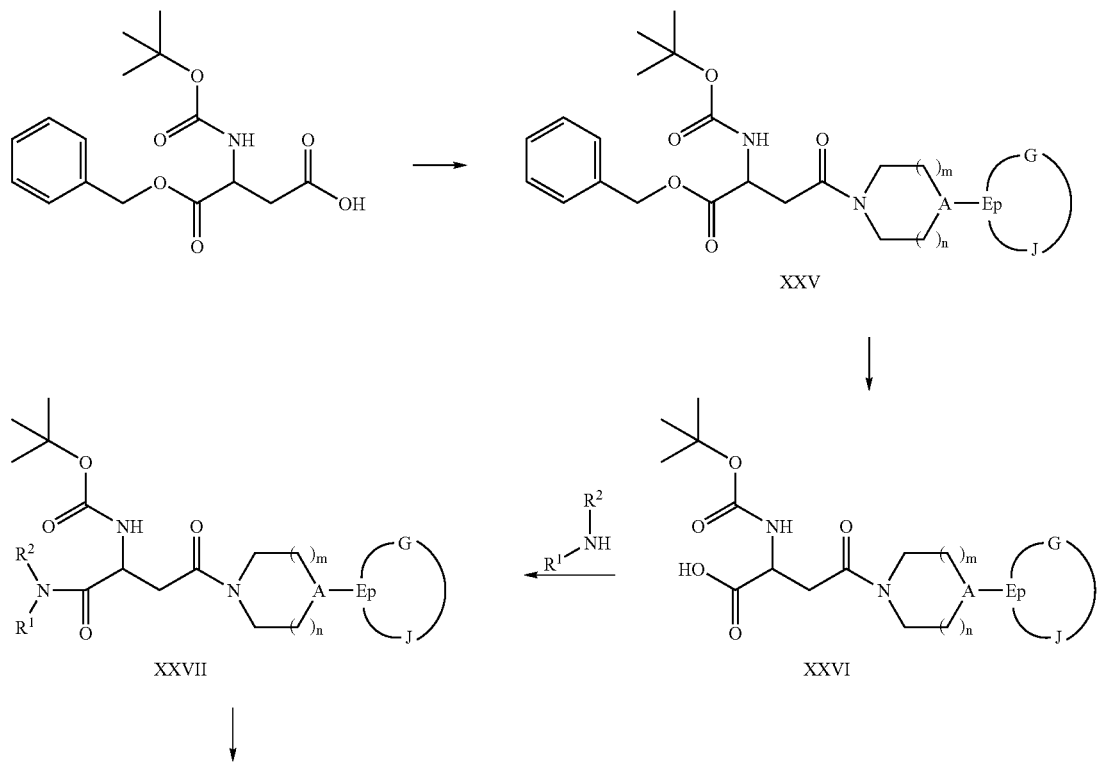

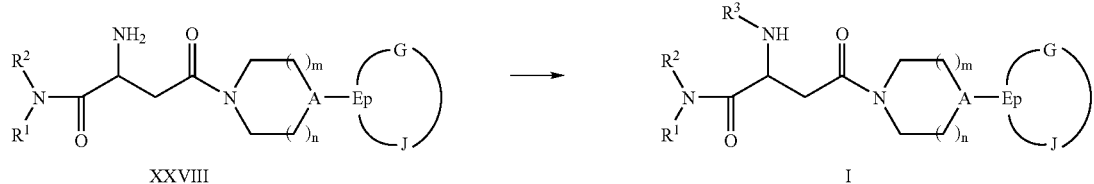

The synthesis described in Scheme 8 begins with a commercially available N-tert-butyloxycarbonyl-L-aspartic acid benzyl ester. Differently protected aspartic acid derivatives may also be used for synthetic convenience. The beta carboxyl group is coupled with amines of Formula VIII using standard peptide coupling protocols. The alpha-carboxyl protecting group of the Formula XXV compound is removed by hydrogenolysis giving compounds of Formula XXVI. These are further coupled with amines of the formula $HNR^1R^2$ to give compounds of formula XXVII. The amino protecting group is removed by treatment with strong acids such as trifluoroacetic acid or hydrogen chloride in organic solvents. The resulting compounds of Formula XXVIII are then reacted with a variety of electrophilic reagents to generate Formula I compounds. For example, they can be coupled with halo-aromatic compounds using known methods involving heating at various temperatures or by catalysis with transition metals such as palladium or copper, either in stoichiometric amounts or as catalysts. They can also react with various aldehydes or ketones under reductive alkylation conditions, well described in the art. They can also react with isocyanates, acyl chlorides, or carbamoyl chlorides to generate urea, amide or carbamate derivatives, respectively. It is understood that the sequence of the modifications described above can be changed depending on the selection of protecting groups and the order of their removal.

Compounds of Formula I may also be prepared according to Scheme 9.

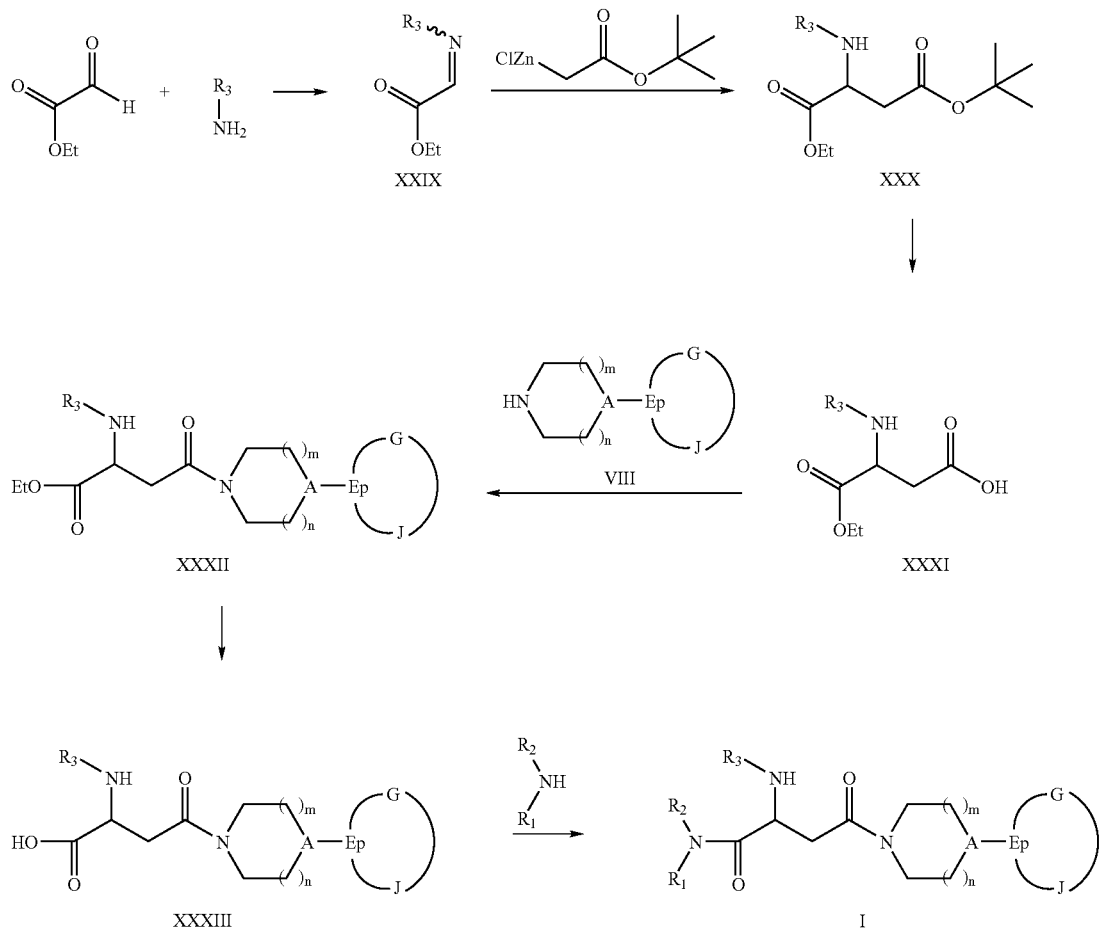

The synthesis described in Scheme 9 begins with an imine of Formula XXIX, prepared by condensation of ethyl glyoxalate and amines of formula $R^3$—$NH_2$. These are reacted with 2-tert-butoxy-2-oxoethylzinc chloride to give compounds of Formula XXX. Treatment with strong acids removes the tert-butyl ester protecting group to give free acids of Formula XXXI which are coupled to amines of Formula VIII to yield compounds of Formula XXXII. The ethyl ester is hydrolyzed with a metal hydroxide salt or aqueous base to give free alpha-acids of Formula XXXIII. These, in turn are coupled with amines of the formula $HNR^1R^2$ to give compounds of formula I.

Ureidoamide Intermediates and Examples

General. $^1H$- and $^{13}C$-NMR spectra were run on a Bruker 500 or 300 MHz instrument and chemical shifts were reported in ppm (δ) with reference to tetramethylsilane (δ=0.0). All evaporations were carried out under reduced pressure. Unless otherwise stated, LC/MS analyses were carried out on a Shimadzu instrument using a YMC C18 column (3×50 mm) employing a 2 min linear gradient of 0% to 100% solvent B in A in a 3 min run. For LC/MS and for Shimadzu Preparative HPLC system, Solvent A-was: 10% methanol/ 90% water/0.1% trifluoroacetic acid, and solvent B was 90% methanol/10% water/0.1% trifluoroacetic acid with a UV detector set at 220 nm.

1-Benzyl-2',3'-dihydro-2'-oxospiro-[piperidine-4,4'(1'H)-quinazoline

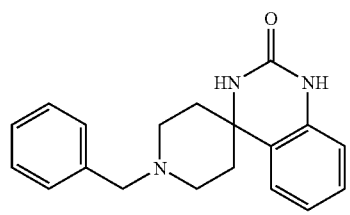

Polyphosphoric acid (113 g) was heated to 100-110° C. and stirred while 1-benzyl-piperidin-4-one (9.27 ml, 50 mmol) was added. Immediately afterwards, phenyl urea (9.55 g, 70. mmol) was added in portions small enough to avoid excessive foaming. The mixture was heated at 150-160° C. overnight. Water (200 mL) was then added slowly to the mixture which had been allowed to cool to 100-110° C. (at lower temperatures the mixture becomes too viscous to stir). The resulting solution was neutralized with 10N NaOH to ca. pH 8, and then extracted with chloroform. The organic phase was dried over magnesium sulfate and then concentrated to give the crude product which was purified by flash column chromatography on silica gel (6:4 ethyl acetate/hexanes) to give the desired product (9.0 g, 58%). Mass spec.: 308.25 (MH)⁺.

2',3'-dihydro-2'-oxospiro-[piperidine-4,4'(1'H)-quinazoline

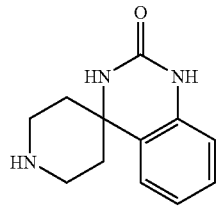

To a solution of 1-benzyl-2',3'-dihydro-2'-oxospiro-[piperidine-4,4'(1'H)-quinazoline (1.00 g) in degassed methanol (50 ml) and 6N hydrochloric acid (2.0 ml) was added 10% palladized charcoal (150 mg). The mixture was shaken on a Parr apparatus under an atmosphere of hydrogen at 60 psi overnight. LC/MS showed incomplete reaction. More 10% palladized charcoal (200 mg) was added, and the mixture was shaken for 2 more days. At that point, all starting material was consumed. The mixture was filtered and the filtrate concentrated to give 531 mg of the desired compound (64%). Mass spec.: 218.12 (MH)⁺.

4-Amino-4-cyano-piperidine-1-carboxylic acid tert-butyl ester

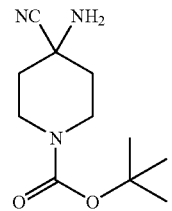

To a well stirred solution of 4-oxo-piperidine-1-carboxylic acid tert-butyl ester (9.0 g, 45.3 mmol) in methanol was added ammonium chloride (2.66 g, 49.8 mmol) at room temperature and stirred for 1 h. Sodium cyanide (2.44 g, 49.8 mmol) was added and stirring was continued for additional 16 h. The reaction mixture was quenched with 5% aqueous sodium hydrogencarbonate (50 mL), diluted with water, and the methanol removed by rotary evaporation. The cyanoimine was extracted with methylene chloride (3×100 mL), dried over sodium sulfate, and the solvents evaporated to give the desired compound as an oil in 91% yield. $^1H$-NMR (300 MHz, CDCl₃): δ 3.95-3.90 (m, 1H), 3.80-3.71 (m, 1H), 3.42-3.06 (m, 2H), 2.04-1.94 (m, 1H), 1.71-1.50 (m, 3H). Mass spec.: 226 (MH)⁺.

2-Phenyl-1,3,8-triaza-spiro[4.5]dec-1-en-4-one, hydrochloride

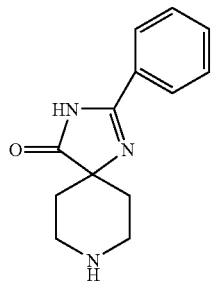

To a solution of 4-amino-4-cyano-piperidine-1-carboxylic acid tert-butyl ester (1.0 g, 4.44 mmol) in methylene chloride (30 mL) was added triethylamine (1.24 mL, 8.88 mol), followed by benzoyl chloride (936 mg, 6.66 mmol). After 30 min, 4-(dimethylamino)pyridine (40 mg, 0.33 mmol) was added and stirring continued for additional 12 h. The reaction mixture was then quenched with 1M sodium hydroxide (10 mL), diluted with ethyl acetate (100 mL), and separated. The organic layer was washed sequentially with 1M sodium hydroxide (40 mL), aqueous sodium hydrogencarbonate (50 mL), and brine (50 mL) then dried over sodium sulfate. The desired product, 4-benzoylamino-4-cyano-piperidine-1-carboxylic acid tert-butyl ester was obtained in 90% yield through crystallization using 30% ethyl acetate in hexane as a solvent.

To a solution of 4-benzoylamino-4-cyano-piperidine-1-carboxylic acid tert-butyl ester (1.3 g, 4 mmol) in ethanol (10 mL) was added 6M sodium hydroxide (1.5 mL) followed by 30% hydrogen peroxide. The reaction mixture was then refluxed for 3 h. The reaction mixture was then diluted with water (30 mL), and the ethanol removed. The residue was diluted with ethyl acetate (100 mL). The organic phase was washed with brine (30 mL) and dried over sodium sulfate. The desired product, 4-oxo-2-phenyl-1,3,8-triaza-spiro[4.5]dec-1-ene-8-carboxylic acid tert-butyl ester was obtained in 80% yield through crystallization from 30% ethyl acetate in hexane. The tert-butyl ester was then dissolved in methylene chloride (5 mL) and a saturated solution of hydrogen chloride in dioxane (25 mL) was added. After 2 h, the solvent was removed to give 2-phenyl-1,3,8-triaza-spiro[4.5]dec-1-en-4-one, hydrochloride as white powder in 95% yield. $^{1}$H-NMR (500 MHz, CD$_{3}$OD): δ 8.23-8.21 (m, 2H), 7.96-7.92 (m, 1H), 7.79-7.76 (m, 2H), 3.68-3.64 (m, 3H), 3.31-3.30 (m, 1H), 2.47-2.44 (m, 4H). Mass spec.: 230 (MH)$^{+}$.

5-Formyl-indazole-1-carboxylic acid tert-butyl ester

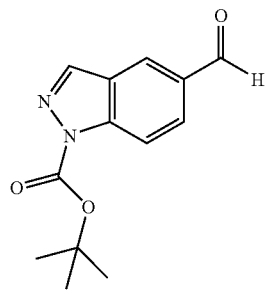

A methylene chloride (2 mL) solution of di-tert-butyldicarbonate (388 mg, 1.78 mmol) was added dropwise at room temperature to a solution of 1H-indazole-5-carbaldehyde (273 mg, 1.87 mmol), 4-dimethylaminopyridine (114 mg, 0.94 mmol), and triethylamine (0.26 mL, 1.87 mmol) in methylene chloride (10 mL). The resulting bright yellow solution was stirred at room temperature for 16 h. Solvents were removed in vacuo and the residue was subjected to flash chromatography with silica gel (25 g) and ethyl acetate/hexanes (1:1) containing 1% triethylamine as eluent to afford the title compound as a brownish yellow liquid (414 mg, 90%). $^{1}$H-NMR (CDCl$_{3}$, 500 MHz) δ 10.08 (s, 1H), 8.38 (s, 1H), 8.34 (s, 1H), 8.25 (d, J=8.5 Hz, 1H), 8.04 (d, J=8.8 Hz, 1H), 1.71 (s, 9H). $^{13}$CNMR (CDCl$_{3}$, 125 MHz) δ 191.8, 149.0, 142.5, 140.6, 133.0, 128.3, 126.4, 125.8, 115.3, 85.7, 27.8.

5-(2-Benzyloxycarbonylamino-2-methoxycarbonyl-vinyl)-indazole-1-carboxylic acid tert-butyl ester

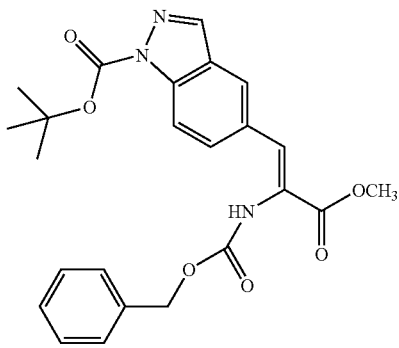

A solution of N-(benzyloxycarbonyl)-α-phosphonoglycine trimethyl ester (5.50 g, 16.6 mmol) and tetramethylguanidine (1.99 mL, 15.9 mmol) in anhydrous tetrahydrofuran (50 mL) was stirred at −78° C. for 20 min. To this was added a solution of 5-formyl-indazole-1-carboxylic acid tert-butyl ester (3.72 g, 15.1 mmol) in tetrahydrofuran (25 mL) slowly via syringe over 10 min. The reaction mixture was stirred at −78° C. for 4 h and then allowed to warm to room temperature overnight. The solvent was evaporated and the resulting residue subjected to flash column chromatography on silica gel (1:2 ethyl acetate/hexane) giving the title compound as a white foam (5.77 g, 85%). $^{1}$H-NMR (CDCl$_{3}$, 500 MHz) δ 8.09 (d, J=9.0 Hz, 1H), 8.08 (s, 1H), 7.84 (s, 1H), 7.67 (d, J=9.0 Hz, 1H), 7.47 (s, 1H), 7.30 (br s, 5H), 6.43 (br s, 1H), 5.09 (s, 2H), 3.84 (s, 3H), 1.72 (s, 9H). Mass spec.: 452 (MH)$^{+}$.

(±)-5-(2-Amino-2-methoxycarbonyl-ethyl)-indazole-1-carboxylic acid tert-butyl ester

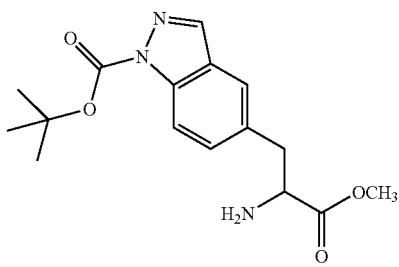

A mixture of 5-(2-benzyloxycarbonylamino-2-methoxycarbonyl-vinyl)-indazole-1-carboxylic acid tert-butyl ester (524 mg, 1.16 mmol) and 10% palladium on carbon (60 mg) in methanol (20 mL) was shaken for 4.5 h under 50 psi hydrogen gas using a Parr hydrogenator. The reaction mixture was evacuated and purged with nitrogen. Then, the reaction mixture was filtered through a pad of celite and the pad was rinsed with several portions of methanol. The methanol filtrate was evaporated to give the title compound (351 mg, 95%). $^1$H-NMR (CDCl$_3$, 500 MHz) δ 8.12-8.10 (m, 2H), 7.55 (br s, 1H), 7.37 (dd, J=8.9, 1.5 Hz, 1H), 3.77-3.75 (m, 1H), 3.70 (s, 3H), 3.19 (dd, J=13.7, 5.5 Hz, 1H), 2.99 (dd, J=13.7, 8.0 Hz, 1H), 1.72 (s, 9H). Mass spec.: 320 (MH)$^+$.

(±)-5-(2-Methoxycarbonyl-2-{[4-(2-oxo-1,4-dihydro-2H-quinazolin-3-yl)-piperidine-1-carbonyl]-amino}-ethyl)-indazole-1-carboxylic acid tert-butyl ester

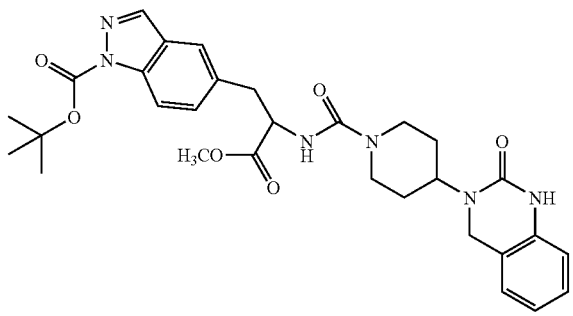

A solution of 5-(2-amino-2-methoxycarbonyl-ethyl)-indazole-1-carboxylic acid tert-butyl ester (307 mg, 0.96 mmol), N,N-disuccinimidyl carbonate (246 mg, 0.961 mmol), and N,N-diisopropylethylamine (0.67 mL, 3.84 mmol) in methylene chloride was stirred for 30 min at room temperature. 3-piperidin-4-yl-3,4-dihydro-1H-quinazolin-2-one (238 mg, 1.03 mmol) was added and the reaction mixture was stirred at room temperature for 16 h. The solvent was evaporated and the residue subjected to flash chromatography using methylene chloride/methanol/triethylamine (93:5:2) as eluent, giving the product (259 mg, 47%). $^1$H-NMR (CDCl$_3$, 300 MHz) δ 8.13-8.10 (m, 2H), 7.48 (br s, 1H), 7.31 (dd, J=8.8, 1.6 Hz, 1H), 7.16 (t, J=8.0 Hz, 1H), 7.05 (d, J=7.0 Hz, 1H), 6.94 (t, J=7.7 Hz, 1H), 6.82 (s, 1H), 6.66 (d, J=8.0 Hz, 1H), 4.98 (d, J=7.7 Hz, 1H), 4.87-4.81 (m, 1H), 4.58-4.49 (m, 1H), 4.26 (s, 2H), 4.05-3.97 (m, 2H), 3.74-3.67 (m, 4H), 3.29-3.23 (m, 2H), 2.93-2.84 (m, 2H), 1.76-1.62 (m, 1H), 1.70 (s, 9H), 1.48-1.42 (m, 1H). Mass spec.: 577 (MH)$^+$.

2-Trimethylsilanyl-ethanesulfonyl chloride

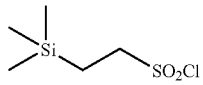

Sulfuryl chloride (43 ml, 539 mmol) was added in 3 min to a clear solution of triphenylphosphine (129 g, 490 mmol) in methylene chloride (200 mL) at 0° C. in a flame-dried three-neck round bottom flask. After stirring at 0° C. for 5 min, the ice-water bath was removed and sodium 2-trimethylsilylethanesulfonate (50 g, 245 mmol) was added in portions over 10 min. The resulting white suspension was stirred at room temperature for 16 h, then it was filtered through a pad of celite. The filtrate was concentrated to ca 50 mL, ethyl acetate/hexanes (1:3, 1000 mL) and celite (40 g) were added. The mixture was stirred at room temperature for 15 min and filtered through a pad of celite. Solvents were removed in vacuo and the residue was loaded onto a pre-wetted column with silica gel (300 mL) using 1:3 ethyl acetate/hexanes as the eluent. Solvents were removed and the title compound was obtained as a light tan liquid (41.9 g, 85%). If not used immediately, the final product should be stored under nitrogen in the freezer or refrigerator to minimize decomposition. $^1$H-NMR (CDCl$_3$, 500 MHz) δ 3.61-3.57 (m, 2H), 1.32-1.27 (m, 2H), 0.10 (s, 9H).

1-(2-Trimethylsilanyl-ethanesulfonyl)-1H-indole-5-carboxylic acid ethyl ester

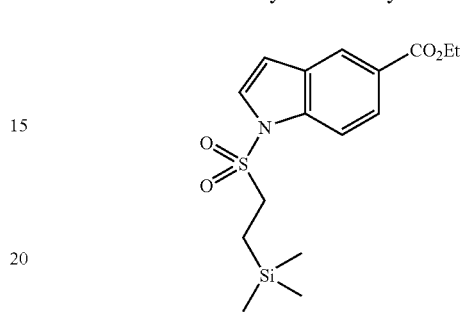

A solution of 1H-indole-5-carboxylic acid ethyl ester (10.31 g, 58.8 mmol) in dimethylformamide (50 mL) was added dropwise at 0° C. to a mixture of sodium hydride (1.83 g, 76.4 mmol) in dimethylformamide (150 mL). The resulting mixture was stirred at 0° C. for 30 min, then a solution of 2-trimethylsilanyl-ethanesulfonyl chloride (17.7 g, 88.2 mmol) in dimethylformamide (100 mL) was added slowly at 0° C. to the above mixture. After 2 h, sat. aqueous ammonium chloride (200 mL) was added, and the mixture was extracted with ethyl acetate (300 mL). After separation, the aqueous layer was extracted with ethyl acetate (2×150 mL). The combined organic layers were washed with brine (3×150 mL), and dried over anhydrous sodium sulfate. Solvents were removed in vacuo and the residue was subjected to flash chromatography on silica gel using 1:1.5 methylene chloride/hexanes as eluent to afford the title compound as a white solid (15.8 g, 79%). $^1$H-NMR (CDCl$_3$, 500 MHz) δ 8.36 (d, J=1.5 Hz, 1H), 8.03 (dd, J=9.0, 2.0 Hz, 1H), 7.92 (d, J=8.5 Hz, 1H), 7.50 (d, J=3.5 Hz, 1H), 6.75 (d, J=3.5 Hz, 1H), 3.94 (s, 3H), 3.21-3.18 (m, 2H), 0.84-0.80 (m, 2H), −0.06 (s, 9H). $^{13}$C-NMR (CDCl$_3$, 125 MHz) δ 167.3, 137.7, 130.3, 128.3, 125.9, 125.5, 124.0, 112.8, 108.3, 52.2, 51.2, 10.1, −2.1. Mass spec. 354.12 (MH)$^+$.

Similarly Prepared:

1-(2-Trimethylsilanyl-ethanesulfonyl)-1H-indazole-5-carboxylic acid ethyl ester

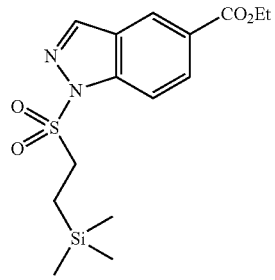

$^1$H-NMR (CDCl$_3$, 500 MHz) δ 8.51 (s, 1H), 8.34 (s, 1H), 8.21 (dd, J=8.9, 1.5 Hz, 1H), 8.12 (d, J=9.2 Hz, 1H), 3.96 (s, 3H), 3.42-3.39 (m, 2H), 0.86-0.82 (m, 2H), −0.02 (s, 9H).

$^{13}$C-NMR (CDCl$_3$, 125 MHz) δ 166.4, 143.1, 141.2, 130.1, 126.5, 125.0, 124.2, 112.9, 52.5, 51.3, 9.8, −2.1. Mass spec. 355.13 (MH)$^+$.

[1-(2-Trimethylsilanyl-ethanesulfonyl)-1H-indol-5-yl]-methanol

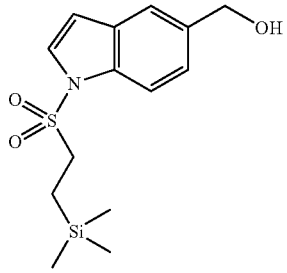

A solution of diisobutylaluminum hydride (82.9 mL, 1M in toluene, 82.9 mmol) was added slowly at 0° C. to the solution of 1-(2-trimethylsilanyl-ethanesulfonyl)-1H-indole-5-carboxylic acid ethyl ester (8.81 g, 25.9 mmol) in toluene (200 mL). After it was stirred at 0° C. for 45 min, the reaction was quenched by the addition of methanol (26 mL), pulverized sodium sulfate decahydrate (194 g) and celite (26 mL). The mixture was warmed up to room temperature in 1 h and filtered through a pad of celite. Solvents were removed in vacuo to afford the title compound as a very viscous liquid, which solidified upon cooling. A white solid (8.08 g, 100% yield). $^1$H-NMR (CDCl$_3$, 500 MHz) δ 7.87 (d, J=8.5 Hz, 1H), 7.62 (s, 1H), 7.44 (d, J=3.7 Hz, 1H), 7.35 (dd, J=8.6, 1.5 Hz, 1H), 6.66 (d, J=3.7 Hz, 1H), 4.79 (s, 2H), 3.18-3.14 (m, 2H), 1.73 (s, 1H), 0.85-0.82 (m, 2H), −0.06 (s, 9H). Mass spec. 312.14 (MH)$^+$.

[1-(2-Trimethylsilanyl-ethanesulfonyl)-1H-indazol-5-yl]-methanol

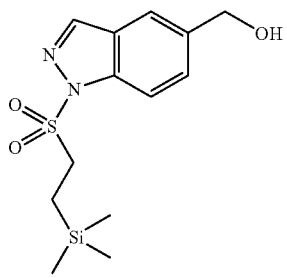

A solution of 1-(2-trimethylsilanyl-ethanesulfonyl)-1H-indazole-5-carboxylic acid ethyl ester (azeotropically dried with toluene (2×), 5.77 g, 16.9 mmol) in tetrahydrofuran (50 mL) was added at 0° C. to a mixture of lithium borohydride (3.68 g, 169 mmol) in tetrahydrofuran (100 mL). The mixture was warmed up to room temperature and stirred for 14 h. It was cooled to 0° C. and lithium borohydride (3.5 g) was added. The mixture was warmed up to room temperature and stirred for 14 h. It was re-cooled to 0° C. and sat. aqueous ammonium chloride (25 mL) was added slowly. The resulted white suspension was filtered through a pad of celite, solvents were removed and the residue was subjected to flash chromatography using ethyl acetate/hexanes (1:1.5) with 1% triethylamine to afford the title compound as a white solid (3.8 g, 72%). $^1$H-NMR (CD$_3$OD, 500 MHz) δ 8.41 (s, 1H), 8.04 (d, J=8.5 Hz, 1H), 7.85 (s, 1H), 7.61 (dd, J=8.5, 1.2 Hz, 1H), 4.76 (s, 2H), 3.49-3.46 (m, 2H), 0.76-0.72 (m, 2H), −0.03 (s, 9H); $^{13}$C-NMR (CD$_3$OD, 125 MHz) δ 141.2, 140.9, 138.3, 129.2, 125.8, 119.6, 112.7, 63.8, 50.8, 9.9, −3.2. Mass spec. 313.12 (MH)$^+$.

1-(2-Trimethylsilanyl-ethanesulfonyl)-1H-indole-5-carbaldehyde

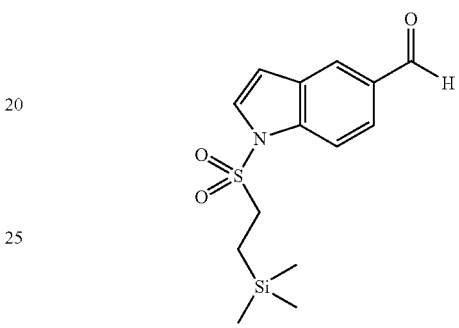

A solution of [1-(2-trimethylsilanyl-ethanesulfonyl)-1H-indol-5-yl]-methanol (2.1 g, 6.74 mmol) in methylene chloride (30 mL) was added at 0° C. to a mixture of activated manganese dioxide (22 g, azeotropically dried with toluene (2×)) and methylene chloride (70 mL) in a 500 mL round bottom flask. The reaction mixture was stirred at 0° C. for 30 min and filtered through a pad of celite. Solvents were removed in vacuo to afford the title compound as a white solid (1.8 g, 80%). $^1$H-NMR (CDCl$_3$, 500 MHz) δ 10.06 (s, 1H), 8.15 (s, 1H), 8.01 (d, J=8.6 Hz, 1H), 7.87 (dd, J=8.6, 1.5 Hz, 1H), 7.54 (d, J=3.4 Hz, 1H), 6.80 (d, J=3.6 Hz, 1H), 3.24-3.20 (m, 2H), 0.86-0.82 (m, 2H), −0.06 (s, 9H). $^{13}$C-NMR (CDCl$_3$, 125 MHz) δ 191.9, 138.5, 132.3, 130.7, 128.8, 125.3, 125.1, 1134.6, 108.4, 51.4, 10.2, −2.1. Mass spec. 310.12 (MH)$^+$.

Similarly Prepared:

1-(2-Trimethylsilanyl-ethanesulfonyl)-1H-indazole-5-carbaldehyde

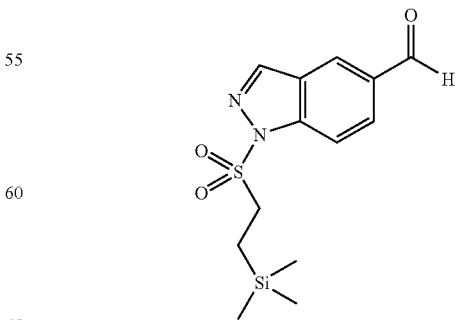

Mass spec. 311.10 (MH)$^+$.

2-Benzyloxycarbonylamino-3-[1-(2-trimethylsilanyl-ethanesulfonyl)-1H-indol-5-yl]-acrylic acid methyl ester

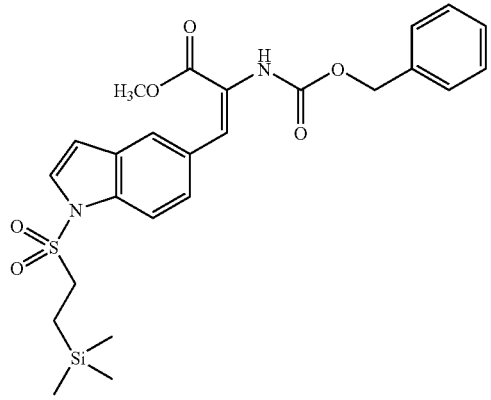

1,1,3,3-Tetramethylguanidine (0.68 mL, 5.43 mmol) was added at room temperature to a solution of N-(benzyloxycarbonyl)-α-phophonoglycine trimethyl ester (1.88 g, 5.69 mmol) in tetrahydrofuran (40 mL). The mixture was stirred at room temperature for 15 min and cooled to −78° C., and a solution of 1-(2-trimethylsilanyl-ethanesulfonyl)-1H-indole-5-carbaldehyde (1.6 g, 5.17 mmol) in tetrahydrofuran (15 mL) was added slowly. The resulting reaction mixture was stirred at −78° C. for 2 h and then warmed to room temperature in 3 h. Solvents were removed in vacuo and the residue was subjected to flash chromatography on silica gel using methylene chloride/hexanes (1:1.5) with 1% triethylamine as eluent to afford the title compound as a 92:8 Z/E mixture (determined by integration of $CO_2CH_3$, for Z isomer at 3.79 ppm, and E isomer at 3.65 ppm). For the Z isomer: $^1$H-NMR (CD$_3$CN, 500 MHz) δ 7.96 (s, 1H), 7.91 (d, J=8.5 Hz, 1H), 7.66 (d, J=8.5 Hz, 1H), 7.56 (d, J=3.7 Hz, 1H), 7.51 (s, 1H), 7.43-7.35 (m, 5H), 7.67 (d, J=3.7 Hz, 1H), 5.16 (s, 2H), 3.79 (s, 3H), 3.42-3.38 (m, 2H), 0.87-0.83 (m, 2H), −0.04 (s, 9H). Mass spec. 515.20 (MH)$^+$.

Similarly Prepared:

2-Benzyloxycarbonylamino-3-[1-(2-trimethylsilanyl-ethanesulfonyl)-1H-indazol-5-yl]-acrylic acid methyl ester

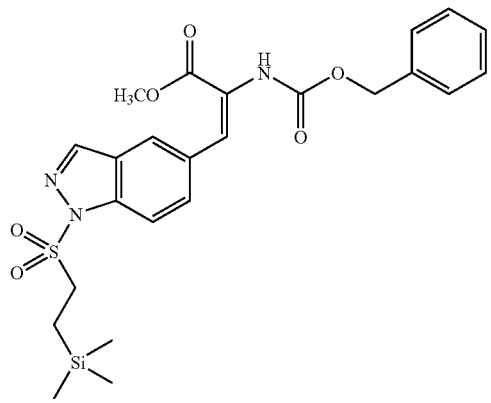

Flash chromatography on silica gel using methylene chloride containing 1% triethylamine as eluent afforded the title compound as a 95:5 Z/E mixture (determined by the integration of —CH═C(CO$_2$Me)(NHCBz), 3.72 g, 92%). For the Z isomer: $^1$H-NMR (CD$_3$CN, 500 MHz) δ 8.39 (s, 1H), 8.12 (s, 1H), 8.03 (d, J=8.8 Hz, 1H), 7.84 (dd, J=8.8, 1.2 Hz, 1H), 7.51 (s, 1H), 7.43-7.35 (m, 5H), 5.14 (s, 2H), 3.81 (s, 3H), 3.51-3.47 (m, 2H), 0.83-0.79 (m, 2H), −0.02 (s, 9H). Mass spec. 516.18 (MH)$^+$.

(±)-2-Amino-3-[1-(2-trimethylsilanyl-ethanesulfonyl)-1H-indol-5-yl]-propionic acid methyl ester

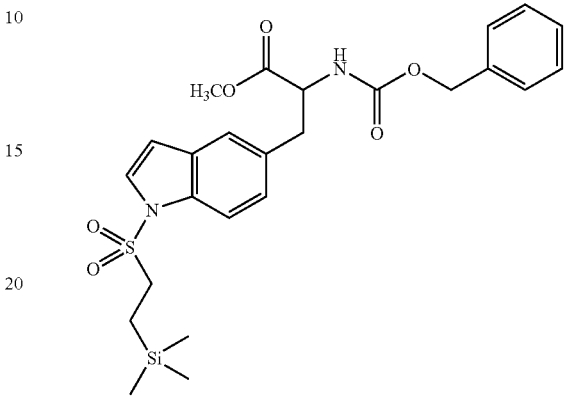

To a flame dried 500 mL of round bottom flask was added 2-benzyloxycarbonylamino-3-[1-(2-trimethylsilanyl-ethanesulfonyl)-1H-indol-5-yl]-acrylic acid methyl ester (2.24 h, 4.36 mmol), methanol (100 mL) and 10% palladium on charcoal (0.52 g). The mixture was degassed and purged with hydrogen five times. It was stirred at room temperature for 1 h and filtered through a pad of celite. Solvents were removed and the residue was subjected to flash chromatography using ethyl acetate/hexanes (1:1 and 2:1) containing 1% triethylamine to afford the tile compound as a colorless viscous liquid (1.27 g, 76%), which solidified upon cooling. $^1$H-NMR (CD$_3$CN, 500 MHz) δ 7.82 (d, J=8.2 Hz, 1H), 7.51-7.49 (m, 2H), 7.22 (dd, J=8.6, 1.5 Hz, 1H), 6.72 (d, J=3.7 Hz, 1H), 3.70 (dd, J=7.3, 6.1 Hz, 1H), 3.65 (s, 3H), 3.38-3.34 (m, 2H), 3.08 (dd, J=13.4, 5.8 Hz, 1H), 2.95 (dd, J=13.4, 7.3 Hz, 1H), 0.82-0.79 (m, 2H), −0.05 (s, 9H). $^{13}$C-NMR(CDCl$_3$, 125 MHz) δ 176.0, 134.4, 133.4, 131.1, 127.9, 126.4, 122.4, 113.1, 107.7, 56.6, 51.7, 50.8, 41.3, 10.1, −2.7. Mass spec. 383.16 (MH)$^+$.

Similarly Prepared:

(±)-2-Amino-3-[1-(2-trimethylsilanyl-ethanesulfonyl)-1H-indazol-5-yl]-propionic acid methyl ester

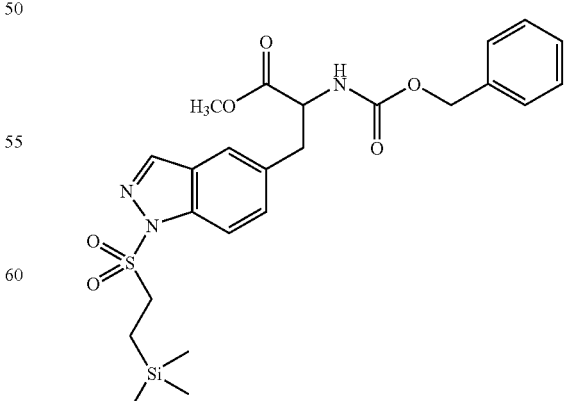

$^1$H-NMR (CD$_3$CN, 500 MHz) δ 8.34 (s, 1H), 7.98 (d, J=8.6 Hz, 1H), 7.69 (s, 1H), 7.46 (dd, J=8.6, 1.5 Hz, 1H), 3.71 (dd,

J=7.3, 5.8 Hz, 1H), 3.65 (s, 3H), 3.48-3.44 (m, 2H), 3.12 (dd, J=13.7, 5.8 Hz, 1H), 2.97 (dd, J=13.7, 7.6 Hz, 1H), 0.83-0.79 (m, 2H), −0.02 (s, 9H). $^{13}$C-NMR (CDCl$_3$, 125 MHz) δ 175.9, 141.1, 140.5, 134.6, 131.5, 126.0, 122.2, 112.7, 56.4, 51.8, 51.1, 40.9, 9.8, −2.6. Mass spec. 384.15 (MH)$^+$.

(R)-2-Benzyloxycarbonylamino-3-[1-(2-trimethylsilanyl-ethanesulfonyl)-1H-indazol-5-yl]-propionic acid methyl ester

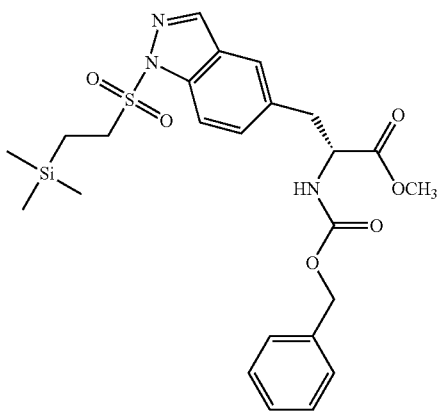

In a glove bag that was subjected to 3 vacuum/nitrogen purge cycles, an AIRFREE® (Schlenk) reaction flask equipped with stir bar was charged with (−)-1,2-bis((2R,5R)-2,5-diethylphospholano)benzene(cyclooctadiene) rhodium (I) trifluoromethylsulfonate (123 mg, 0.17 mmol, 5 mol %), sealed with a rubber septum, and removed from the glove bag. The 2-benzyloxycarbonylamino-3-[1-(2-trimethylsilanyl-ethanesulfonyl)-1H-indazol-5-yl]-acrylic acid methyl ester (1.75 g, 3.40 mmol) was weighed into a second AIRFREE® (Schlenk) reaction flask equipped with stir bar and sealed with a rubber septum. After 3 vacuum/nitrogen purge cycles, it was dissolved in a mixture of anhydrous methanol (75 mL) and anhydrous methylene chloride (15 mL). Both solvents were deoxygenated prior to addition by sparging with nitrogen for at least 1 h. Once in solution, the mixture was again subjected to 3 vacuum/nitrogen purge cycles. The dehydroamino acid solution was introduced into the AIRFREE® (Schlenk) reaction flask containing the catalyst via cannula. The reaction mixture was subjected to 5 vacuum/hydrogen purge cycles before opening the flask to 1 atm. of hydrogen (balloon). After 16 h, the reaction mixture was purged with 3 vacuum/nitrogen purge cycles. The solvent was evaporated and the residue was subjected to column chromatography (gradient 1:4 ethyl acetate/hexanes to 1:2 ethyl acetate/hexanes) to give 1.5 g (85%) of the title compound as a white solid with 98.4% ee as determined by HPLC analysis using a Chirocel OD column with 80% hexane/20% ethanol as eluent (retention times: 13.9 min for title compound and 11.2 min for S-enantiomer). $^1$H-NMR (CDCl$_3$, 300 MHz) δ 8.17 (s, 1H), 7.98 (d, J=8.8 Hz, 1H), 7.47 (s, 1H), 7.35-7.25 (m, 6H), 5.29-5.24 (m, 1H), 5.08 (dd, J=19.0, 12.1 Hz, 2H), 4.73-4.67 (m, 1H), 3.73 (s, 3H), 3.38-3.32 (m, 2H), 3.29 (dd, J=14.2, 5.6 Hz, 1H), 3.19 (dd, J=13.9, 5.6 Hz, 1H), 0.91-0.85 (m, 2H), −0.02 (s, 9H). Mass spec.: 518 (MH)$^+$.

(R)-2-Amino-3-[1-(2-trimethylsilanyl-ethanesulfonyl)-1H-indazol-5-yl]-propionic acid methyl ester

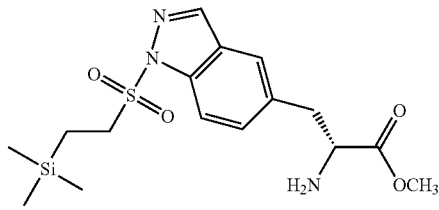

A mixture of (R)-2-Benzyloxycarbonylamino-3-[1-(2-trimethylsilanyl-ethanesulfonyl)-1H-indazol-5-yl]-propionic acid methyl ester (1.24 g, 2.40 mmol) and 10% palladium on carbon (124 mg) in methanol (50 mL) was agitated for 2 h under 50 psi hydrogen using a Parr hydrogenator. The reaction mixture was purged with 3 vacuum/nitrogen purge cycles. The reaction mixture was then filtered through a pad of celite and the pad was rinsed with several portions of methanol. The methanol filtrate was evaporated to give 879 mg (96%) of the title compound as a sticky gum. $^1$H-NMR (CDCl$_3$, 300 MHz) δ 8.21 (s, 1H), 8.02 (d, J=8.8 Hz, 1H), 7.59 (s, 1H), 7.38 (d, J=8.8 Hz, 1H), 3.72 (s, 3H), 3.38-3.32 (m, 2H), 3.21 (dd, J=13.9, 5.1 Hz, 1H), 2.98 (dd, J=13.9, 7.9 Hz, 1H), 0.91-0.85 (m, 2H), −0.02 (s, 9H). Mass spec.: 384 (MH)$^+$ 7-Methyl-2-(2-trimethylsilanyl-ethanesulfonyl)-2H-indazole-5-carbaldehyde

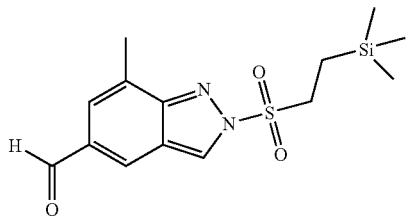

To a suspension of 7-methylindazole 5-aldehyde (3.0 g, 18.7 mmol) in methylene chloride (150 mL) was added triethylamine (7.83 mL, 56.2 mL, 3 equiv) followed by dropwise addition of neat 2-trimethylsilanyl-ethanesulfonyl chloride (5.60 g, 28.1 mmol, 1.5 equiv). The mixture gradually became homogeneous and was allowed to stir at room temperature for 16 h. The solution was concentrated to a minimum amount of methylene chloride and then subjected to flash column chromatography on silica gel (1:4 ethyl acetate/hexanes) to give 4.7 g (77%) of the product as a pale yellow solid. $^1$H-NMR (CDCl$_3$, 300 MHz) δ 9.98 (s, 1H), 8.77 (s, 1H), 8.09 (s, 1H), 7.64 (s, 1H), 3.64-3.58 (m, 2H), 2.65 (s, 3H), 0.88-0.82 (m, 2H), 0.01 (s, 9H).

2-Benzyloxycarbonylamino-3-[7-methyl-2-(2-trimethylsilanyl-ethanesulfonyl)-2H-indazol-5-yl]-acrylic acid methyl ester

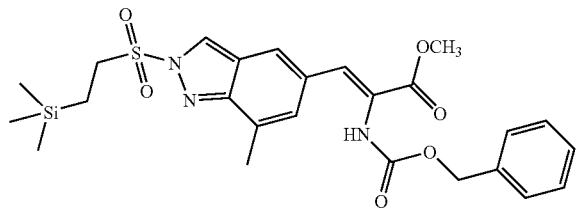

To a solution of N-(benzyloxycarbonyl)-α-phosphonoglycine trimethyl ester (4.93 g, 14.9 mmol, 1.1 equiv) in anhydrous tetrahydrofuran (75 mL) was added tetramethylguanidine (1.78 mL, 1.05 equiv). The mixture was stirred at room temperature under nitrogen for 5 min and was then cooled to −78° C. After stirring for 15 min at −78° C., a solution of 7-methyl-2-(2-trimethylsilanyl-ethanesulfonyl)-2H-indazole-5-carbaldehyde in tetrahydrofuran (25 mL) was added. The reaction mixture was allowed to slowly warm to room temperature overnight. Although the reaction was incomplete, the solvent was evaporated. The resulting residue was dissolved in ethyl acetate and washed with 1M sulfuric acid. The organic layer was separated, dried over magnesium sulfate, filtered and evaporated. Flash column chromatography (1:4 ethyl acetate/hexanes) gave 2.66 g (37%) of the product as white glass foam. $^1$H-NMR (CDCl$_3$, 300 MHz) δ 8.48 (s, 1H), 7.62 (s, 1H), 7.38-7.25 (m, 7H), 6.48 (bs, 1H), 5.10 (s, 2H), 3.83 (s, 3H), 3.58-3.52 (m, 2H), 2.51 (s, 3H), 0.89-0.83 (m, 2H), 0.02 (s, 9H). Mass spec.: 530 (MH)$^+$.

(R)-2-Benzyloxycarbonylamino-3-[7-methyl-2-(2-trimethylsilanyl-ethanesulfonyl)-2H-indazol-5-yl]-propionic acid methyl ester

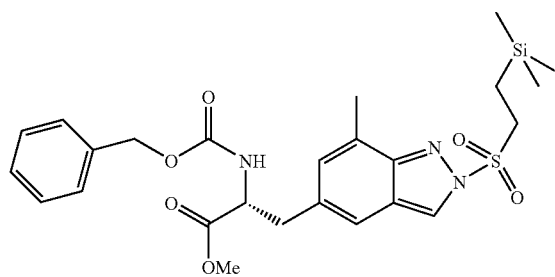

In a glove bag that was subjected to 3 vacuum/nitrogen purge cycles, an AIRFREE® (Schlenk) reaction flask equipped with stir bar was charged with (−)-1,2-bis((2R,5R)-2,5-diethylphospholano)benzene(cyclooctadiene) rhodium (I) trifluoromethylsulfonate (259 mg, 0.36 mmol, 9 mol-%), sealed with a rubber septum, and removed from the glove bag. The 2-benzyloxycarbonylamino-3-[7-methyl-2-(2-trimethylsilanyl-ethanesulfonyl)-2H-indazol-5-yl]-acrylic acid methyl ester (2.03 g, 3.83 mmol) was weighed into a second AIRFREE® (Schlenk) reaction flask equipped with stir bar and sealed with a rubber septum. After 3 vacuum/nitrogen purge cycles, it was dissolved in anhydrous methanol (80 mL, deoxygenated prior to addition by sparging with nitrogen for at least 1 h). Once in solution, it was again subjected to 3 vacuum/nitrogen purge cycles. The dehydroamino acid solution was transferred via cannula to the AIRFREE® (Schlenk) reaction flask containing the catalyst. The reaction mixture was purged with 5 vacuum/hydrogen purge cycles before opening the flask to a balloon of hydrogen (1 atm). After 2.5 h, the reaction mixture was purged with 3 vacuum/nitrogen purge cycles. The solvent was evaporated and the residue was subjected to column chromatography (gradient 1:4 ethyl acetate/hexanes to 1:2 ethyl acetate/hexanes) to give 1.4 g (68%; ee=99.2%) of the title compound as a white solid. $^1$H-NMR (CDCl$_3$, 300 MHz) δ 8.43 (s, 1H), 7.34 (s, 5H), 7.19 (s, 1H), 6.87 (s, 1H), 5.24 (d, J=8.1 Hz, 1H), 5.08 (dd, J=18.3, 12.1 Hz, 2H), 4.67 (dd, J=13.9, 6.2 Hz, 1H), 3.73 (s, 3H), 3.57-3.51 (m, 2H), 3.16 (dd, J=14.0, 5.9 Hz, 1H). 3.06 (dd, J=13.9, 6.6 Hz, 1H), 2.55 (s, 3H), 0.89-0.83 (m, 2H), 0.01 (s, 9H). $^{13}$C-NMR (CDCl$_3$, 75 MHz) δ 172.0, 155.7, 151.7, 136.2, 132.2, 129.8, 129.5, 128.6, 128.4, 128.2, 125.1, 121.1, 118.1, 67.1, 54.7, 52.5, 51.1, 38.6, 17.1, 9.7, −2.0. Mass spec.: 532 (MH)$^+$.

(R)-2-Amino-3-[7-methyl-2-(2-trimethylsilanyl-ethanesulfonyl)-2H-indazol-5-yl]-propionic acid methyl ester

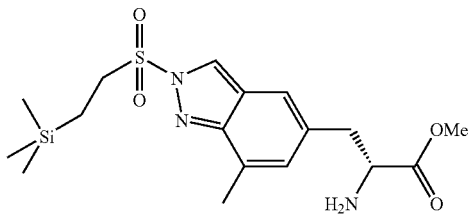

2-Benzyloxycarbonylamino-3-[7-methyl-2-(2-trimethylsilanyl-ethanesulfonyl)-2H-indazol-5-yl]-propionic acid methyl ester, (1.35 g, 2.54 mmol) and 10% palladium on carbon (135 mg) in methanol (40 mL) were agitated for 3.0 h under 55 psi hydrogen using a Parr apparatus. The reaction mixture was purged with 3 vacuum/nitrogen purge cycles. The reaction mixture was then filtered through a pad of celite and the pad was rinsed with several portions of methanol. The methanol filtrate was evaporated to give the title compound (1.01 g, quantitative yield) as a sticky gum. $^1$H-NMR (CDCl$_3$, 300 MHz) δ 8.45 (s, 1H), 7.29 (s, 1H), 6.97 (s, 1H), 3.79-3.73 (m, 1H), 3.73 (s, 3H), 3.56-3.50 (m, 2H), 5.12 (dd, J=13.5, 5.12 Hz, 1H), 4.85 (dd, J=13.5, 8.1 Hz, 1H), 2.58 (s, 3H), 0.87-0.81 (m, 2H), 0.01 (s, 9H). $^{13}$C-NMR (CDCl$_3$, 75 MHz) δ 175.5, 151.8, 133.7, 129.9, 129.4, 125.0, 121.3, 117.9, 55.5, 52.1, 51.1, 41.4, 17.1, 9.8, −2.1. Mass spec.: 398 (MH)$^+$.

(R)-3-[7-Methyl-2-(2-trimethylsilanyl-ethanesulfonyl)-2H-indazol-5-yl]-2-{[4-(2-oxo-1,4-dihydro-2H-quinazolin-3-yl)-piperidine-1-carbonyl]-amino}-propionic acid methyl ester

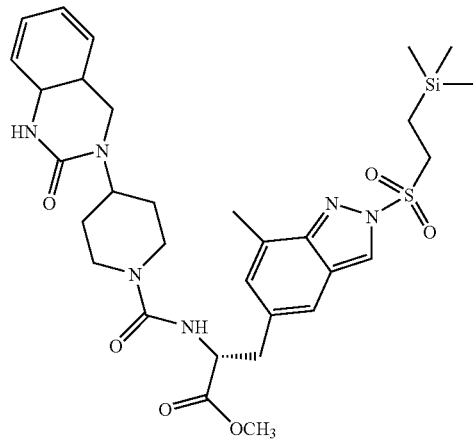

A mixture of 2-amino-3-[7-methyl-2-(2-trimethylsilanyl-ethanesulfonyl)-2H-indazol-5-yl]-propionic acid methyl ester (500 mg, 1.26 mmol), N,N-diisopropylethylamine (0.66 mL, 3.77 mmol) and disuccinimidylcarbonate (322 mg, 1.26 mmol) were stirred together in methylene chloride (20 mL) for 30 min at room temperature. Then, 3-piperidin-4-yl-3,4-dihydro-1H-quinazolin-2-one (444 mg, 1.35 mmol) was added and the reaction mixture was allowed to stir overnight at room temperature. The solvent was evaporated and the residue was subjected to flash column chromatography (1:4 acetone/ethyl acetate) to give 490 mg (60% yield) of the title compound as a white solid. $^1$H-NMR (CDCl$_3$, 300 MHz) δ 8.47 (s, 1H), 7.23 (s, 1H), 7.19-7.14 (m, 1H), 7.04 (d, J=7.3 Hz, 1H), 6.97-6.93 (m, 2H), 6.77 (s, 1H), 6.65 (d, J=7.7 Hz, 1H), 4.99 (d, J=7.3 Hz, 1H), 4.81 (dd, J=13.5, 6.2 Hz, 1H), 4.58-4.46 (m, 1H), 4.27 (s, 2H), 4.10-3.98 (m, 2H), 3.73 (s, 2H), 3.57-3.51 (m, 2H), 3.14-3.11 (m, 2H), 2.95-2.83 (m, 2H), 2.58 (s, 3H), 1.77-1.65 (m, 4H), 0.92-0.84 (m, 2H), −0.01 (s, 9H). Mass spec.: 655 (MH)$^+$.

Similarly Prepared:

(±)-2-{[4-(2-Oxo-1,4-dihydro-2H-quinazolin-3-yl)-piperidine-1-carbonyl]-amino}-3-[1-(2-trimethylsilanyl-ethanesulfonyl)-1H-indol-5-yl]-propionic acid methyl ester

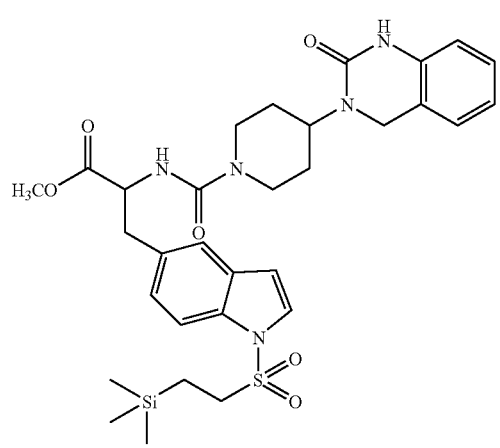

$^1$H-NMR (CD$_3$OD, 500 MHz) δ 7.85 (d, J=8.2 Hz, 1H), 7.55 (s, 1H), 7.51 (d, J=3.7 Hz, 1H), 7.27 (dd, J=8.6, 1.5 Hz, 1H), 7.16 (t, J=7.6 Hz, 1H), 7.10 (d, J=7.6 Hz, 1H), 6.95 (t, J=7.6 Hz, 1H), 6.79 (d, J=8.0 Hz, 1H), 6.73 (d, J=3.7 Hz, 1H), 4.44-4.38 (m, 1H), 4.26 (s, 2H), 4.13-4.08 (m, 2H), 3.73 (s, 3H), 3.34-3.29 (m, 4H), 3.13 (dd, J=13.5, 9.4 Hz, 1H), 2.89-2.79 (m, 2H), 1.76-1.70 (m, 1H), 1.63-1.59 (m, 3H), 0.76-0.72 (m, 2H), −0.07 (s, 9H); Mass spec.: 640.40 (MH)$^+$.

(R)-2-{[4-(2-Oxo-1,4-dihydro-2H-quinazolin-3-yl)-piperidine-1-carbonyl]-amino}-3-[1-(2-trimethylsilanyl-ethanesulfonyl)-1H-indazol-5-yl]-propionic acid methyl ester

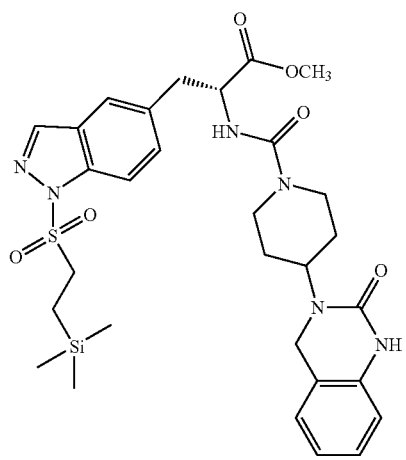

A solution of (R)-2-Amino-3-[1-(2-trimethylsilanyl-ethanesulfonyl)-1H-indazol-5-yl]-propionic acid methyl ester (764 mg, 1.99 mmol), N,N-diisopropylethylamine (1.10 mL, 5.97 mmol) and disuccinimidylcarbonate (509 mg, 1.99 mmol) in methylene chloride (20 mL) was stirred for 40 min at room temperature. Then, 3-piperidin-4-yl-3,4-dihydro-1H-quinazolin-2-one (70% pure, 703 mg, 2.13 mmol) was added and the reaction mixture was allowed to stir overnight at room temperature. The solvent was evaporated in vacuo and the residue was subjected to flash column chromatography (1:4 acetone/ethyl acetate) to give 1.15 g (90%) of the title compound. $^1$H-NMR (CDCl$_3$, 300 MHz) δ 8.21 (s, 1H), 8.01 (d, J=8.5 Hz, 1H), 7.53 (s, 1H), 7.32 (d, J=8.5 Hz, 1H), 7.16 (t, J=7.8 Hz, 1H), 7.06 (d, J=7.6 Hz, 1H), 6.95 (d, J=7.6 Hz, 1H)1, 6.76 (s, 1H), 6.65 (d, J=7.9 Hz, 1H), 5.01 (d, J=7.6 Hz, 1H), 4.84 (dd, J=13.1, 6.0 Hz, 1H), 4.56-4.49 (m, 1H), 4.28 (s, 2H), 4.13-3.98 (m, 2H), 3.73 (s, 3H), 3.39-3.35 (m, 2H), 3.28 (dd, J=14.0, 6.1 Hz, 1H), 3.24 (dd, J=13.7, 5.8 Hz, 1H), 2.94-2.87 (m, 2H), 1.75-1.67 (m, 4H), 0.91-0.87 (m, 2H), −0.02 (s, 9H). Mass spec.: 641 (MH)$^+$.

Similarly Prepared:

(±)-2-{[4-(2-Oxo-2,3-dihydro-benzoimidazol-1-yl)-piperidine-1-carbonyl]-amino}-3-[1-(2-trimethylsilanyl-ethanesulfonyl)-1H-indol-5-yl]-propionic acid methyl ester

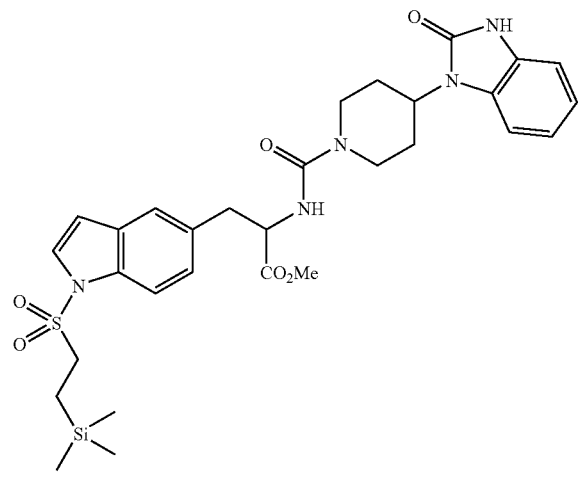

¹H-NMR (CD₃CN, 500 MHz) δ 9.78 (s, 1H), 7.86 (d, J=8.5 Hz, 1H), 7.56 (s, 1H), 7.49 (d, J=3.7 Hz, 1H), 7.28 (dd, J=8.5, 1.5 Hz, 1H), 7.10-7.08 (m, 1H), 7.05-7.03 (m, 1H), 6.99-6.97 (m, 2H), 6.70 (d, J=3.7 Hz, 1H), 5.91 (d J=7.9 Hz, 1H), 4.66 (q, J=8.2 Hz, 1H), 4.45-4.39 (m, 1H), 4.14 (br s, 1 h), 3.68 (s, 3H), 3.36-3.32 (m, 2H), 3.27 (dd, J=14.0, 5.5 Hz, 1H), 3.18 (dd, J=13.7, 8.5 Hz, 1H), 2.90-2.84 (m, 2H), 2.55 (br s, 1H), 2.36-2.21 (m, 2H), 1.74-1.70 (m, 2H), 0.82-0.78 (m, 2H), −0.09 (s, 9H). Mass spec. 626.26 (MH)⁺.

(±)-2-{[4-(2-Oxo-2,3-dihydro-benzoimidazol-1-yl)-piperidine-1-carbonyl]-amino}-3-[1-(2-trimethylsilanyl-ethanesulfonyl)-1H-indazol-5-yl]-propionic acid methyl ester

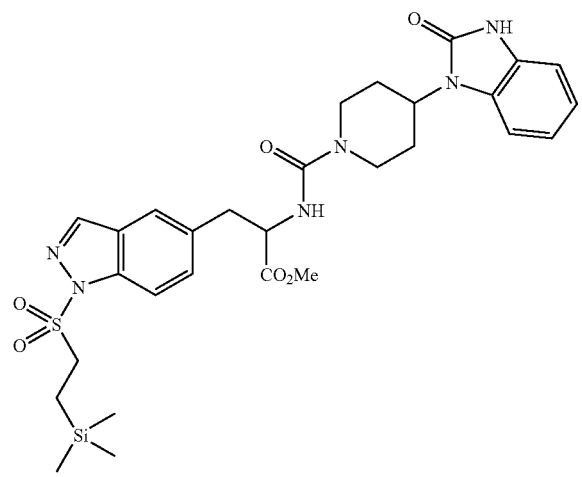

¹H-NMR (CD₃CN, 500 MHz) δ 9.61 (br s, 1H), 8.35 (s, 1H), 8.00 (d, J=8.5 Hz, 1H), 7.74 (s, 1H), 7.51 (dd, J=8.8, 1.5 Hz, 1H), 7.10-7.06 (m, 1H), 7.05-7.02 (m, 1H), 7.00-6.97 (m, 2H), 5.90n(d, J=7.9 Hz, 1H), 4.67 4.62 (m, 1H), 4.42-4.36 (m, 1H), 4.13-4.07 (br s, 1H), 3.68 (s, 3H), 3.45-3.42 (m, 2H), 3.30 (dd, J=14.0, 5.8 Hz, 1H), 3.20 (dd, J=13.7, 8.8 Hz, 1H), 2.89-2.84 (m, 2H), 2.52 (br s, 1H), 2.33-2.23 (m, 2H), 1.72-1.69 (m, 2H), 0.80-0.76 (m, 2H), −0.07 (s, 9H). Mass spec. 627.25 (MH)⁺.

(±)-2-{[4-(2-Oxo-1,4-dihydro-2H-quinazolin-3-yl)-piperidine-1-carbonyl]-amino}-3-[1-(2-trimethylsilanyl-ethanesulfonyl)-1H-indol-5-yl]-propionic acid methyl ester

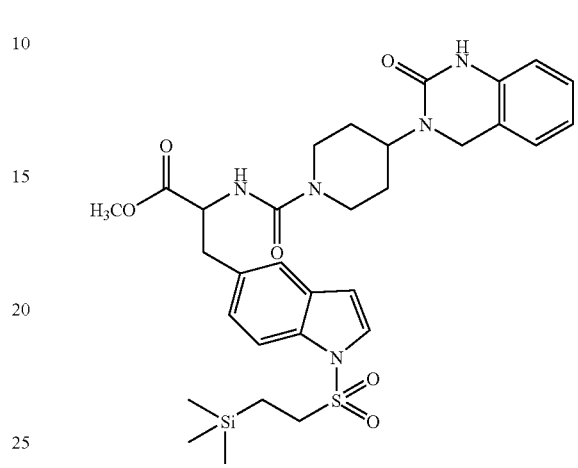

¹H-NMR (CD₃OD, 500 MHz) δ 7.85 (d, J=8.2 Hz, 1H), 7.55 (s, 1H), 7.51 (d, J=3.7 Hz, 1H), 7.27 (dd, J=8.6, 1.5 Hz, 1H), 7.16 (t, J=7.6 Hz, 1H), 7.10 (d, J=7.6 Hz, 1H), 6.95 (t, J=7.6 Hz, 1H), 6.79 (d, J=8.0 Hz, 1H), 6.73 (d, J=3.7 Hz, 1H), 4.44-4.38 (m, 1H), 4.26 (s, 2H), 4.13-4.08 (m, 2H), 3.73 (s, 3H), 3.34-3.29 (m, 4H), 3.13 (dd, J=13.5, 9.4 Hz, 1H), 2.89-2.79 (m, 2H), 1.76-1.70 (m, 1H), 1.63-1.59 (m, 3H), 0.76-0.72 (m, 2H), −0.07 (s, 9H). Mass spec. 640.40 (MH)⁺.

(±)-2-{[4-(2-Oxo-1,4-dihydro-2H-quinazolin-3-yl)-piperidine-1-carbonyl]-amino}-3-[1-(2-trimethylsilanyl-ethanesulfonyl)-1H-indazol-5-yl]-propionic acid methyl ester

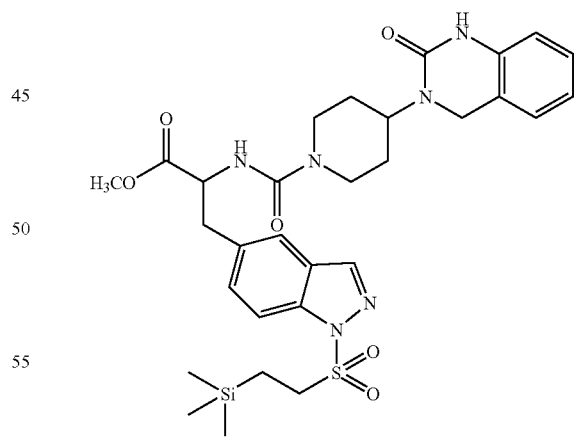

¹H-NMR (CD₃OD, 500 MHz) δ 8.39 (d, J=0.5 Hz, 1H), 8.02 (d, J=8.5 Hz, 1H), 7.75 (s, 1H), 7.52 (dd, J=8.5, 1.5 Hz, 1H), 7.14-7.10 (m, 2H), 6.94 (t, J=7.5 Hz, 1H), 6.78 (d, J=7.5 Hz, 1H), 4.63-4.60 (m, 1 h), 4.43-4.37 (m, 1H), 4.27 (s, 2H), 4.11 (br s, 1H), 4.08 (br s, 1H), 3.71 (s, 3H), 3.47-3.43 (m, 2H), 3.37-3.33 (m, 1H), 3.18 (dd, j=13.5, 10.0 Hz, 1H), 2.87-2.79 (m, 2H), 1.73-1.59 (m, 4H), 0.80-0.75 (m, 2H), −0.05 (s, 9H); ¹³C-NMR (CD₃OD, 125 MHz) δ 173.7, 155.5, 158.1, 141.0, 140.6, 137.2, 134.4, 131.3, 128.2, 126.1, 125.8, 122.2, 121.9, 118.3, 113.4, 112.6, 55.9, 52.1, 51.7, 50.8, 48.9, 48.6, 48.4, 48.2, 48.0, 47.9, 47.7, 47.5, 43.8, 43.7, 43.1, 37.2, 28.5, 9.8, −3.2. Mass spec.: 641.40 (MH)+.

Example 1

(±)-3-(1H-Indazol-5-yl)-2-{[4-(2-oxo-1,4-dihydro-2H-quinazolin-3-yl)-piperidine-1-carbonyl]-amino}-propionic acid

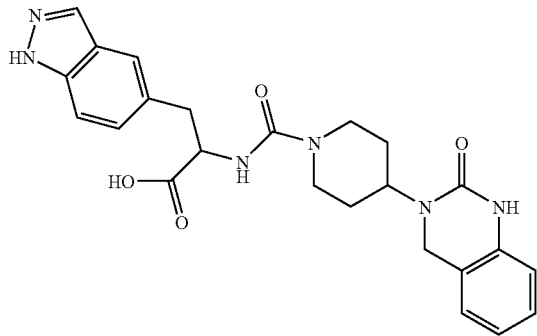

A solution of 5-(2-methoxycarbonyl-2-{[4-(2-oxo-1,4-dihydro-2H-quinazolin-3-yl)-piperidine-1-carbonyl]-amino}-ethyl)-indazole-1-carboxylic acid tert-butyl ester (168 mg, 0.29 mmol) was dissolved in tetrahydrofuran (5 mL) in methanol (5 mL) was cooled to 0° C. A solution of lithium hydroxide monohydrate (49 mg, 2.04 mmol) in water (5 mL) was added. The reaction mixture was stirred at 0° C. for 6 h and then placed in the freezer for a further 16 h. The solvents were removed in vacuo and the residue dissolved in water (15 mL). The pH of the aqueous solution was adjusted to ca. 1 with 1N hydrochloric acid. The resulting white solid precipitated was collected by filtration. The solid was dried under vacuum to give the title compound (108 mg, 80%). $^1$H-NMR (DMSO-d$_6$, 300 MHz) δ 12.94 (bs, 1H), 9.19 (s, 1H), 8.01 (s, 1H), 7.61 (s, 1H), 7.46 (d, J=8.4 Hz, 1H), 7.28 (dd, J=8.5, 1.5 Hz, 1H), 7.13-7.06 (m, 2H), 6.86 (t, J=7.0 Hz, 1H), 6.76-6.72 (m, 2H), 4.32-4.24 (m, 2H), 4.09-4.02 (m, 4H), 3.17-2.97 (m, 2H), 2.72-2.59 (m, 2H), 1.57-1.35 (m, 4H). IR (KBr, cm$^{-1}$) 3424, 2963, 2930, 1660, 1628, 1505, 1474, 1446, 753. Mass spec.: 463 (MH)+.

(R)-2-{[4-(2-Oxo-1,4-dihydro-2H-quinazolin-3-yl)-piperidine-1-carbonyl]-amino}-3-[1-(2-trimethylsilanyl-ethanesulfonyl)-1H-indazol-5-yl]-propionic acid

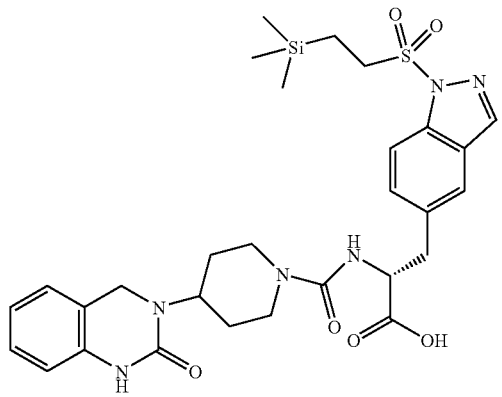

A solution of (R)-2-{[4-(2-Oxo-1,4-dihydro-2H-quinazolin-3-yl)-piperidine-1-carbonyl]-amino}-3-[1-(2-trimethyl-silanyl-ethanesulfonyl)-1H-indazol-5-yl]-propionic acid methyl ester (775 mg, 1.21 mmol) in tetrahydrofuran (9 mL) and methanol (3 mL) was cooled to 0° C. A solution of lithium hydroxide monohydrate (115 mg, 4.84 mmol) in water (3 mL) was added. The reaction mixture was stirred at 0° C. for 2 h and then placed in the freezer at −15° C. for 16 h. While cooling the reaction mixture with an ice bath, the pH was increased to ca. 7 by addition of 1N hydrochloric acid (3.8 mL). Organic solvents were removed under vacuum. The resulting aqueous solution was extracted with ethyl acetate after addition of more 1N hydrochloric acid (0.5 mL). The combined extracts were dried over magnesium sulfate, filtered and evaporated to give 684 mg (90%) of the title compound as a white solid. $^1$H-NMR (DMSO-d$_6$, 300 MHz) δ 9.21 (s, 1H), 8.58 (s, 1H), 7.90 (d, J=8.4 Hz, 1H), 7.78 (s, 1H), 7.56 (d, J=8.1 Hz, 1H), 7.13-7.09 (m, 2H), 6.88-6.83 (m, 1H), 6.76-6.74 (m, 2H), 4.33-4.27 (m, 2H), 4.18 (s, 2H), 4.09-3.96 (m, 3H), 3.57-3.51 (m, 2H), 3.25-3.04 (m, 2H), 2.74-2.60 (m, 2H), 1.54-1.43 (m, 4H), 0.70-0.64 (m, 2H), −0.08 (s, 9H). Mass spec.: 627 (MH)+.

Similarly Prepared:

(±)-2-{[4-(2-Oxo-2,3-dihydro-benzoimidazol-1-yl)-piperidine-1-carbonyl]-amino}-3-[1-(2-trimethylsilanyl-ethanesulfonyl)-1H-indol-5-yl]-propionic acid

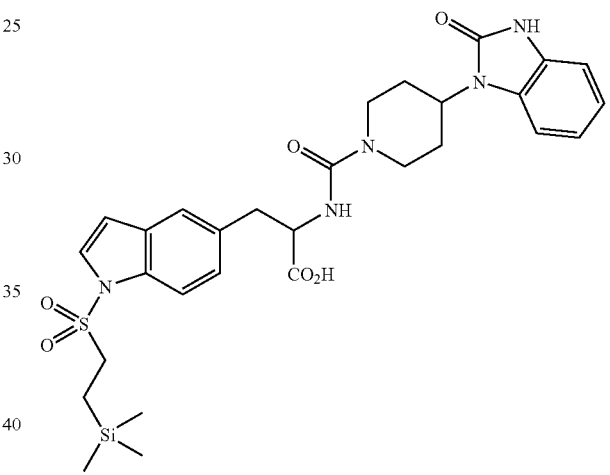

Mass spec. 612.25 (MH)+.

(±)-2-{[4-(2-Oxo-2,3-dihydro-benzoimidazol-1-yl)-piperidine-1-carbonyl]-amino}-3-[1-(2-trimethylsilanyl-ethanesulfonyl)-1H-indazol-5-yl]-propionic acid

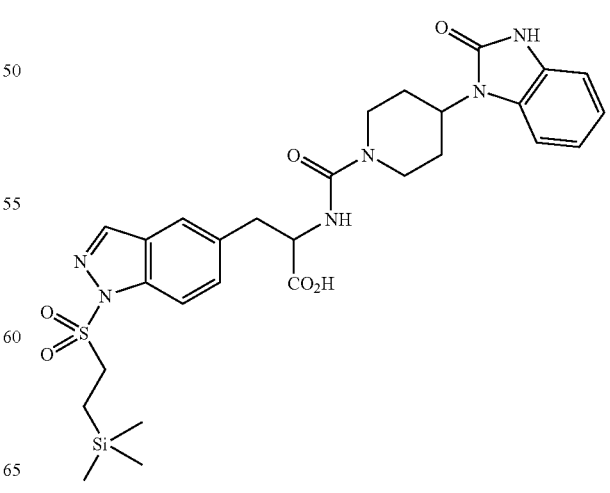

Mass spec. 613.26 (MH)+.

(±)-2-{[4-(2-Oxo-1,4-dihydro-2H-quinazolin-3-yl)-piperidine-1-carbonyl]-amino}-3-[1-(2-trimethylsilanyl-ethanesulfonyl)-1H-indazol-5-yl]-propionic acid

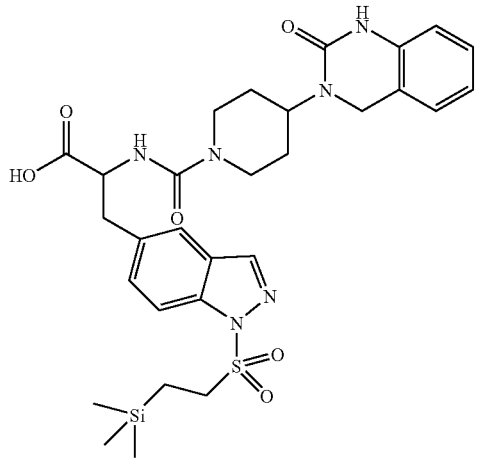

$^1$H-NMR (CD$_3$CN, 500 MHz) δ 8.37 (s, 1H), 8.08 (s, 1H), 8.01 (d, J=8.5 Hz, 1H), 7.77 (s, 1H), 7.53 (dd, J=8.5, 1.5 Hz, 1H), 7.19 (t, J=7.3 Hz, 1H), 7.14 (d, J=7.3 Hz, 1H), 6.98 (td, j=7.6, 1.2 Hz, 1H), 6.79 (d, j=8.0 Hz, 1H), 6.28 (br s, 3H), 4.54-4.49 (m, 1H), 4.37-4.32 (m, 1H), 4.30 (s, 2H), 3.98-3.92 (m, 2H), 3.45-3.41 (m, 2H), 3.37 (dd, j=14.0, 4.9 Hz, 1H), 3.20 (dd, J=14.0, 9.7 Hz, 1H), 2.84-2.77 (m, 2H), 1.65-1.57 (m, 4H), 0.79-0.76 (m, 2H), −0.05 (s, 9H). Mass spec.: 627.30 (MH)$^+$.

(R)-4-(2-Oxo-1,4-dihydro-2H-quinazolin-3-yl)-piperidine-1-carboxylic acid {2-[1,4']bipiperidinyl-1'-yl-2-oxo-1-[1-(2-trimethylsilanyl-ethanesulfonyl)-1H-indazol-5-ylmethyl]-ethyl}-amide

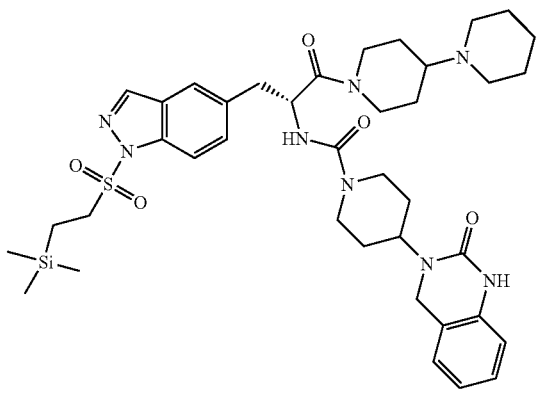

To a solution of (R)-2-{[4-(2-oxo-1,4-dihydro-2H-quinazolin-3-yl)-piperidine-1-carbonyl]-amino}-3-[1-(2-trimethylsilanyl-ethanesulfonyl)-1H-indazol-5-yl]-propionic acid (554 mg, 0.88 mmol) and N,N-diisopropylethylamine (0.62 mL, 3.54 mmol) in methylene chloride (20 mL) was added a solution of 4-piperidinopiperidine (164 mg, 0.97 mmol) and PyBOP® (460 mg, 0.88 mmol) in methylene chloride (15 mL). The reaction mixture was stirred for 16 h at room temperature. It was then concentrated to approximately 2 mL and subjected to flash column chromatography using methylene chloride/methanol/triethylamine (94:5:1) as eluent to give 599 mg (87%) of the title compound as a white solid. $^1$H-NMR (CD$_3$CN, 300 MHz) δ 8.37 (s, 0.5H), 8.36 (s, 0.5H), 8.02-7.96 (m, 1H), 7.74 (s, 0.5H), 7.71 (s, 0.5H), 7.55-7.46 (m, 1H), 7.21-7.12 (m, 2H), 6.97-6.92 (m, 1H), 6.79 (d, J=8.1 Hz, 1H), 5.71 (t, J=8.1 Hz, 1H), 5.00 (dd, J=15.0, 8.1 Hz, 1H), 4.63-4.51 (m, 1H), 4.39-4.29 (m, 1H), 4.29 (s, 2H), 4.10-3.96 (m, 3H), 3.46-3.40 (m, 2H), 2.92-2.70 (m, 8H), 2.58-2.37 (m, 5H), 1.74-1.40 (m, 13H), 0.80-0.74 (m, 2H), −0.04 (s, 9H). Mass spec.: 778 (MH)$^+$.

Similarly Prepared:

(±)-4-(2-Oxo-2,3-dihydro-benzoimidazol-1-yl)-piperidine-1-carboxylic acid {2-[1,4']bipiperidinyl-1'-yl-2-oxo-1-[1-(2-trimethylsilanyl-ethanesulfonyl)-1H-indol-5-ylmethyl]-ethyl}-amide

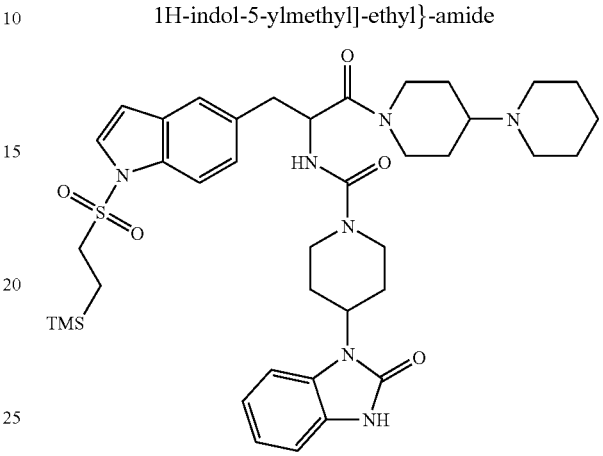

$^1$H-NMR (CD$_3$CN, 500 MHz) δ 9.42 (br s, 1H), 7.80 (d, J=8.5 Hz, 0.6H), 7.78 (d, J=8.2 Hz, 0.4H), 7.50 (s, 1H), 7.43 (t, J=3.0 Hz, 1H), 7.27 (d, J=8.5 Hz, 0.6H), 7.23 (d, J=8.5 Hz, 0.4H), 7.10-7.07 (m, 1H), 7.02-6.95 (m, 3H), 6.69 (s, 0.4H), 6.68 (s, 0.6H), 5.88 (d, J=8.5 Hz, 0.6H), 5.85 (d, J=8.4 Hz, 0.4H), 5.04-4.98 (m, 1H), 4.49 (s, 0.4H), 4.46 (s, 0.6H), 4.36-4.30 (m, 1H), 4.11-4.07 (m, 1H), 3.97-3.91 (m, 1H), 3.31-3.28 (m, 2H), 3.11-3.05 (m, 6H), 2.87-2.80 (m, 2H), 2.43-2.07 (m, 8H), 1.78-1.74 (m, 4H), 1.71-1.65 (m, 2H), 1.46-1.40 (m, 2H), 1.37-1.31 (m, 2H), 0.80-74 (m, 2H), −0.10 (s, 9H). LC/MS: t$_R$=2.47 min, 762.37 (MH)$^+$.

(±)-4-(2-Oxo-2,3-dihydro-benzoimidazol-1-yl)-piperidine-1-carboxylic acid {2-[1,4']bipiperidinyl-1'-yl-2-oxo-1-[1-(2-trimethylsilanyl-ethanesulfonyl)-1H-indazol-5-ylmethyl]-ethyl}-amide

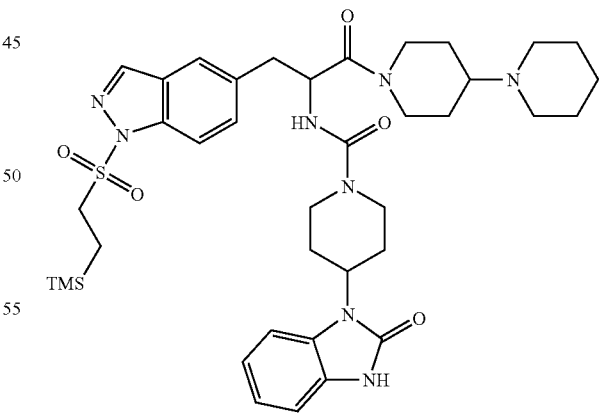

$^1$H-NMR (CD$_3$CN, 500 MHz) δ 9.67 (s, 1H), 8.32 (s, 1H), 7.96 (d, J=8.7 Hz, 0.55H), 7.93 (d, J=8.6 Hz, 0.45H), 7.70 (s, 1H), 7.51 (d, J=8.6 Hz, 0.55H), 7.47 (d, J=8.8 Hz, 0.45H), 7.08-7.05 (m, 1H), 7.03-6.99 (m, 1H), 6.98-6.94 (m, 2H), 6.01 (d, J=7.9 Hz, 0.45H), 5.96 (d, J=7.9 Hz, 0.55 h), 5.05-5.00 (m, 1H), 4.49-4.46 (m, 1H), 4.35-4.29 (m, 1H), 4.10-4.05 (m, 1H), 4.00-3.93 (m, 1H), 3.40-3.36 (m, 2H), 3.17-3.30 (m, 6H), 2.91-2.71 (m, 2H), 2.52-2.13 (m, 8H), 1.76 9br s, 4H), 1.69-1.65 (m, 2H), 1.44-1.41 (m, 2H), 1.34-1.30 (m, 2H), 0.77-0.71 (m, 2H), −0.08 (s, 9H). LC/MS: $t_R$=2.35 min, 763.35 (MH)$^+$.

(±)-4-(2-Oxo-1,4-dihydro-2H-quinazolin-3-yl)-piperidine-1-carboxylic acid {2-[1,4']bipiperidinyl-1'-yl-2-oxo-1-[1-(2-trimethylsilanyl-ethanesulfonyl)-1H-indol-5-ylmethyl]-ethyl}-amide

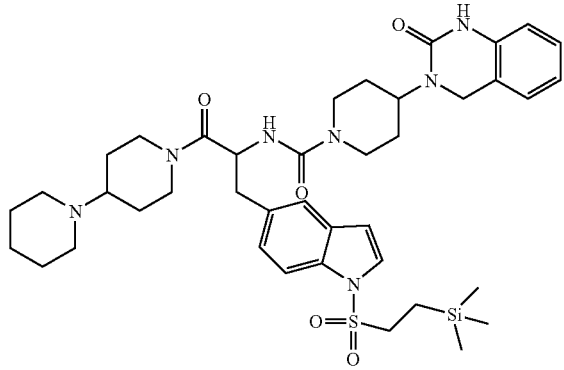

$^1$H-NMR (CD$_3$CN, 500 MHz) δ 8.17 (s, 0.6H), 8.16 (s, 0.4H), 7.84 (d, J=8.5 Hz, 0.6H), 7.81 (d, J=8.5 Hz, 0.4H), 7.54 (s, 0.4H), 7.53 (s, 0.6H), 7.48 (t, J=4.1 Hz, 1H), 7.31 (dd, J=8.5, 1.5 Hz, 0.6H), 7.28 (dd, J=8.5, 1.5 Hz, 0.4H), 7.18 (t, j=7.4 Hz, 1H), 7.09-7.06 (m, 1H), 6.93 (t, J=7.3 Hz, 1H), 6.83 (d, J=7.9 Hz, 1H), 6.72 (d, J=3.6 Hz, 1H), 6.09 (d, J=8.2 Hz, 1H), 5.05-4.99 (m, 1H), 4.53-4.50 (m, 1H), 4.40-4.34 (m, 1H), 4.26 (s, 1.2H)<4.24 (s, 0.8H), 3.99-3.94 (m, 1H), 3.35-3.30 (m, 2H), 3.15-3.07 (m, 3H), 3.08-3.03 (m, 1H), 2.81-2.73 (m, 3H), 2.55-2.37 (m, 6H), 2.21-2.16 (m, 1H), 2.13-2.08 (m, 1H), 1.69-1.57 (m, 4H), 1.51-1.45 (m, 4H), 1.41-1.35 (m, 4H), 0.83-0.74 (m, 2H), −0.06 (s, 9H). Mass spec.: 776.44 (MH)$^+$.

(±)-4-(2-Oxo-1,4-dihydro-2H-quinazolin-3-yl)-piperidine-1-carboxylic acid {2-[1,4']bipiperidinyl-1'-yl-2-oxo-1-[1-(2-trimethylsilanyl-ethanesulfonyl)-1H-indazol-5-ylmethyl]-ethyl}-amide

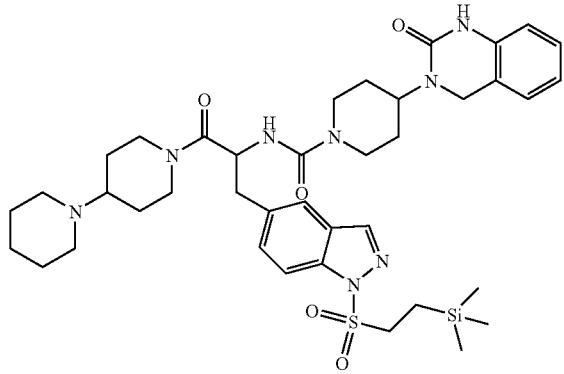

Purified by silica gel chromatography using methylene chloride:methanol/triethylamine (90:10:0.5) as eluent. $^1$H-NMR (CD$_3$CN, 500 MHz) δ 8.36 (s, 1H), 8.04 (s, 1H), 8.01 (d, J=8.8 Hz, 0.6H), 7.97 (dd, J=8.8 Hz, 0.4H), 7.74 (s, 1H), 7.54 (dd, J=8.5, 1.5 Hz, 0.6H), 7.51 (dd, J=8.5, 1.5 Hz, 0.4H), 7.18 (t, J=7.4 Hz, 1H), 7.11 (t, J=7.3 Hz, 1H), 6.94 (t, J=7.3 Hz, 1H), 6.83 (d, J=7.9 Hz, 1H), 6.05 (d, J=8.5 Hz, 0.4H), 6.02 (d, J=8.5 Hz, 0.6H), 5.06-5.01 (m, 1H), 4.52-4.50 (m, 1H), 4.39-4.34 (m, 1H), 4.27 (s, 1.2H), 4.25 (s, 0.8H), 4.00-3.97 (m, 2H), 3.45-3.40 (m, 2H), 3.20-3.08 (m, 2H), 2.81-2.74 (m, 2H), 2.56-2.39 (m, 8H), 2.27-2.24 (m, 1H), 2.20-2.16 (m, 1H), 1.68-1.57 (m, 4H), 1.52-1.45 (m, 4H), 1.41-1.34 (m, 4H), 1.06-1.01 (m, 1H), 0.80 0.75 (m, 2H), −0.07 (s, 9H). Mass spec.: 777.40 (MH)$^+$.

(±)-4-(2-Oxo-2,3-dihydro-benzoimidazol-1-yl)-piperidine-1-carboxylic acid {2-(4-isobutyl-piperazin-1-yl)-2-oxo-1-[1-(2-trimethylsilanyl-ethanesulfonyl)-1H-indol-5-ylmethyl]-ethyl}-amide

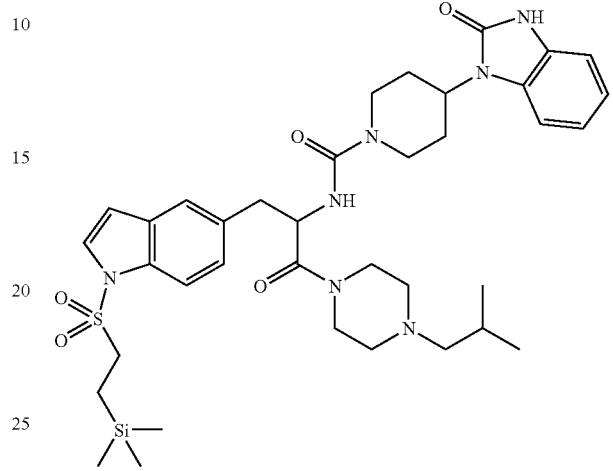

$^1$H-NMR (CD$_3$CN, 500 MHz) δ 9.75 (s, 1H), 7.82 (d, J=8.2 Hz, 1H), 7.54 (s, 1H), 7.48 (d, J=3.6 Hz, 1H), 7.28 (d, J=8.5 Hz, 1H), 7.12-7.09 (m, 1H), 7.04-7.02 (m, 1H), 7.00-6.97 (m, 2H), 6.72 (d, J=3.7 Hz, 1H), 5.97 (d, J=8.2 Hz, 1H), 5.01 (dd, J=14.6, 7.2 Hz, 1H), 4.40-4.34 (m, 1H), 4.15-4.08 (m, 2H), 3.58-3.54 (m, 1H), 3.50-3.45 (m, 2H), 3.39-3.35 (m, 1H), 3.36-3.32 (m, 2H), 3.14-3.10 (m, 8H), 2.89-2.83 (m, 2H), 2.34-2.23 (m, 4H), 2.17-2.13 (m, 1H), 0.85 (d, J=6.7 Hz, 6H), 0.83-0.80 (m, 2H), −0.06 (s, 9H). Mass spec.: 736.40 (MH)$^+$.

(±)-4-(2-Oxo-2,3-dihydro-benzoimidazol-1-yl)-piperidine-1-carboxylic acid {2-(1,4-dioxa-8-aza-spiro[4.5]dec-8-yl)-2-oxo-1-[1-(2-trimethylsilanyl-ethanesulfonyl)-1H-indol-5-ylmethyl]-ethyl}-amide

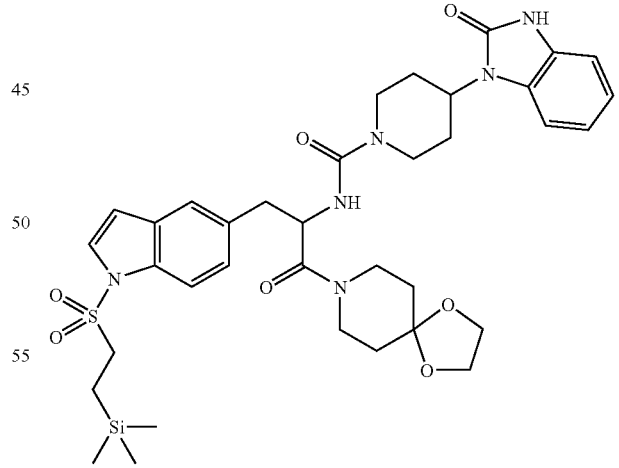

$^1$H-NMR (CD$_3$CN, 500 MHz) δ 9.27 (s, 1H), 7.82 (d, J=8.5 Hz, 1H), 7.55 (s, 1H), 7.48 (d, J=3.6 Hz, 1H), 7.28 (dd, J=8.5, 1.5 Hz, 1H), 7.13-7.10 (m, 1H), 7.06-7.03 (m, 1H), 7.01-6.98 (m, 2H), 6.72 (d, J=3.6 Hz, 1H), 5.95 (d, J=8.0 Hz, 1H), 5.05 (dd, J=15.0, 7.3 Hz, 1H), 4.41-4.34 (m, 1H), 4.14-4.08 (m, 2H), 3.90-3.86 (m, 3H), 3.68-3.64 (m, 1H), 3.60-3.56 (m, 2H), 3.45-3.40 (m, 1H), 3.35-3.31 (m, 2H), 3.15 (dd, J=13.4, 7.1 Hz, 1H), 3.05 (dd, J=13.4, 7.0 Hz, 1H), 2.89-2.83 (m, 2H), 2.34-2.19 (m, 3H), 1.73-1.70 (m, 2H), 1.64-1.56 (m, 2H), 1.53-1.49 (m, 1H), 1.29-1.26 (m, 1H), 0.84-0.80 (m, 2H), −0.05 (s, 9H). Mass spec.: 737.37 (MH)+.

(±)-4-(2-Oxo-2,3-dihydro-benzoimidazol-1-yl)-piperidine-1'-carboxylic acid {2-(4-isobutyl-piperazin-1-yl)-2-oxo-1'-[1-(2-trimethylsilanyl-ethanesulfonyl)-1H-indazol-5-ylmethyl]-ethyl}-amide

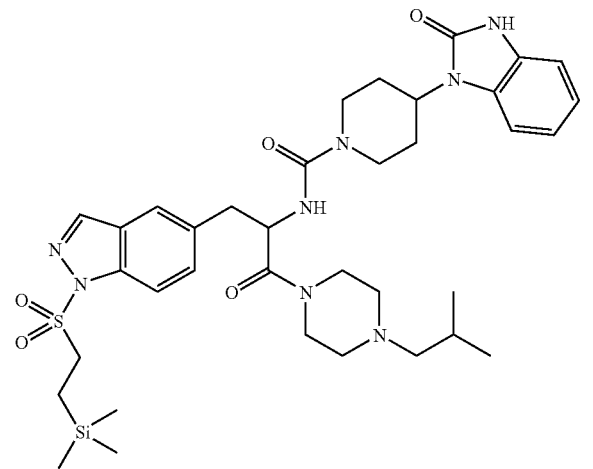

$^1$H-NMR (CD$_3$CN, 500 MHz) δ 9.84 (s, 1H), 8.37 (s, 1H), 7.98 (d, J=8.5 Hz, 1H), 7.74 (s, 1H), 7.52 (dd, J=8.8, 1.5 Hz, 1H), 7.11-7.09 (m, 1H), 7.06-7.03 (m, 1H), 7.02-6.98 (m, 2H), 5.97 (d, J=8.2 Hz, 1H), 5.02 (dd, J=14.3, 7.3 hz, 1H), 4.39-4.33 (m, 1H), 4.14-4.07 (m, 2H), 3.53-3.50 (m, 3H), 3.46-3.42 (m, 2H), 3.45-3.39 (m, 1H), 3.20-3.06 (m, 5H), 2.89-2.83 (m, 2H), 2.30-2.27 (m, 4H), 2.21-2.17 (m, 1H), 1.74-1.70 (m, 3H), 0.86 (d, J=6.7 Hz, 6H), 0.81-0.77 (m, 2H), −0.04 (s, 9H). Mass spec.: 737.40 (MH)+.

(±)-4-(2-Oxo-2,3-dihydro-benzoimidazol-1-yl)-piperidine-1-carboxylic acid {2-(1,4-dioxa-8-aza-spiro[4.5]dec-8-yl)-2-oxo-1-[1-(2-trimethylsilanyl-ethanesulfonyl)-1H-indazol-5-ylmethyl]-ethyl}-amide

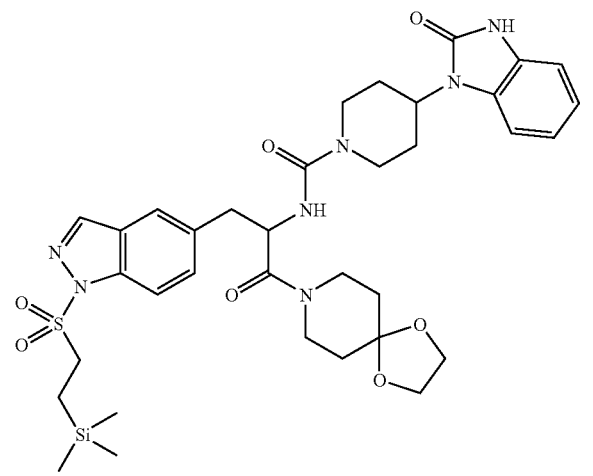

$^1$H-NMR (CD$_3$CN, 500 MHz) δ 9.34 (s, 1H), 8.36 (s, 1H), 7.97 (d, J=8.5 Hz, 1H), 7.74 (s, 1H), 7.52 (dd, J=8.5, 1.5 Hz, 1H), 7.11-7.08 (m, 1H), 7.06-7.03 (m, 1H), 7.02-6.98 (m, 2H), 5.98 (d, J=8.2 Hz, 1H), 5.06 (dd, J=14.6, 7.3 Hz, 1H), 4.39-4.32 (m, 1H), 4.13-4.03 (m, 2H), 3.92-3.88 (m, 2H), 3.71-3.66 (m, 1H), 3.63-3.53 (m, 2H), 3.48-3.45 (m, 1H), 3.44-3.40 (m, 2H), 3.19 (dd, j=13.4, 6.5 Hz, 1H), 3.08 (dd, J=13.7, 7.3 Hz, 1H), 2.85 (t, J=12.8 Hz, 2H), 2.32-2.20 (m, 4H), 1.73-1.70 (m, 2H), 1.67-1.51 (m, 3H), 1.38-1.33 (m, 1H), 0.81-0.77 (m, 2H), −0.04 (s, 9H). Mass spec.: 738.32 (MH)+.

Example 2

(R)-4-(2-Oxo-1,4-dihydro-2H-quinazolin-3-yl)-piperidine-1-carboxylic acid [2-[1,4']bipiperidinyl-1'-yl-1-(1H-indazol-5-ylmethyl)-2-oxo-ethyl]-amide

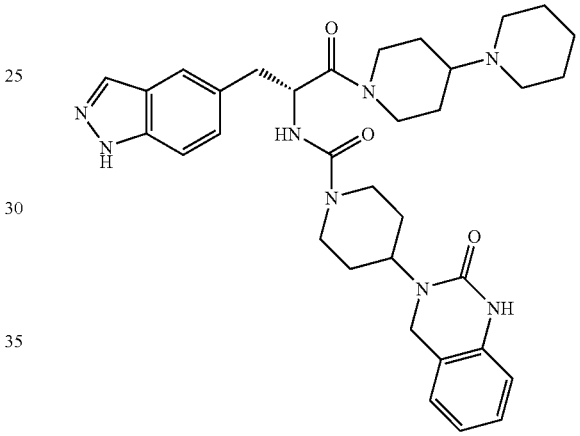

A solution of (R)-4-(2-Oxo-1,4-dihydro-2H-quinazolin-3-yl)-piperidine-1-carboxylic acid {2-[1,4']bipiperidinyl-1'-yl-2-oxo-1-[1-(2-trimethylsilanyl-ethanesulfonyl)-1H-indazol-5-ylmethyl]-ethyl}-amide (568 mg, 0.73 mmol) and cesium fluoride (1.11 g, 7.31 mmol) was heated at 80° C. in acetonitrile (50 mL) for 4.5 h. The reaction mixture was concentrated and the residue was subjected to flash column chromatography (methylene chloride/methanol/triethylamine, 94:5:1) to give 280 mg (63% yield) of the title compound as a white solid with 98.2% ee as determined by HPLC analysis using a Chirocel OD column with 20% B (A=ethanol, B=0.05% diethylamine in hexanes) as eluent (Retention times: 9.51 min for title compound and 15.9 min for S-enantiomer). $^1$H-NMR (CD$_3$OD, 500 MHz) δ 8.04 (s, 0.75H), 8.03 (s, 0.25H), 7.67 (s, 0.75H), 7.65 (s, 0.25H), 7.56 (d, J=8.5 Hz, 0.75H), 7.51 (d, J=8.5 Hz, 0.25H), 7.41 (d, J=8.5 Hz, 0.75H), 7.31 (d, J=8.5 Hz, 0.25H), 7.19-7.12 (m, 2H), 6.97-6.94 (m, 1H), 6.80 (d, J=7.9 Hz, 1H), 5.08-5.05 (m, 1H), 4.60-4.53 (m, 1H), 4.48-4.40 (m, 1H), 4.37 (s, 1.5H), 4.26 (s, 0.5H), 4.24-4.14 (m, 2H), 4.06-3.97 (m, 1H), 3.15 (d, J=7.9 Hz, 1.5H), 3.12-3.05 (m, 0.5H), 2.94-2.86 (m, 3H), 2.57-2.51 (m, 1.5H), 2.47-2.42 (m, 1H), 2.37-2.33 (m, 0.75H), 2.03-2.02 (m, 1.5H), 1.87-1.75 (m, 3.75H), 1.73-1.68 (m, 2H), 1.67-1.54 (m, 3H), 1.53-1.44 (m, 4H), 1.43-1.34 (m, 2H), 1.30-1.26 (m, 1H), 0.83-0.77 (m, 0.75H), −0.16 to −0.24 (m, 0.75H). Mass spec.: 613 (MH)+.

Similarly Prepared:

Example 3

(±)-4-(2-Oxo-2,3-dihydro-benzoimidazol-1-yl)-piperidine-1-carboxylic acid [2-[1,4']bipiperidinyl-1'-yl-1-(1H-indol-5-ylmethyl)-2-oxo-ethyl]-amide

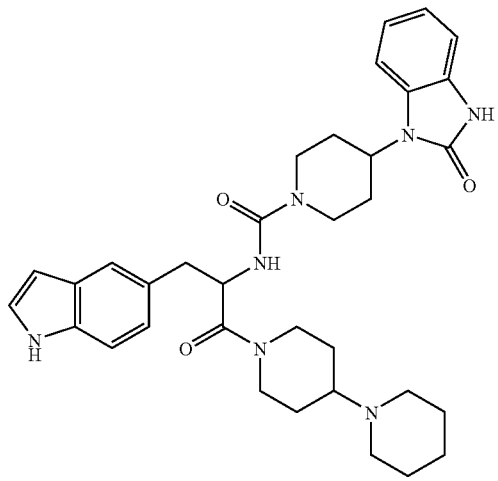

$^1$H-NMR (DMSO-d$_6$, 500 MHz) δ 10.99 (s, 0.6H), 10.96 (s, 0.4H), 10.85 (s, 1H), 7.41 (s, 0.4H), 7.36 (s, 0.6H), 7.33 (d, J=8.0 Hz, 0.6H), 7.29-7.26 (m, 1H), 7.16-7.14 (m, 1H), 7.10 (d, J=7.6 Hz, 0.4H), 7.02-6.96 (m, 4H), 6.81 (br s, 1H), 6.37-6.35 (m, 1H), 4.86 (q, J=8.0 Hz, 0.6H), 4.80 (q, J=7.5 Hz, 0.4H), 4.45 (br s, 1H), 4.38-4.32 (m, 1H), 4.21-4.16 (m, 1H), 3.98 (br s, 1H), 3.18 (d, J=5.2 Hz, 0.6H), 3.04-2.92 (m, 2.4H), 2.82-2.74 (m, 4H), 2.37-2.33 (m, 2H), 2.25-2.08 (m, 4H), 2.04-1.90 (m, 2H), 1.47-1.24 (m, 10H), 0.75-0.71 (m, 1H). LC/MS: t$_R$=1.90 min, 598.42 (MH)$^+$.

Example 4

(±)-4-(2-Oxo-2,3-dihydro-benzoimidazol-1-yl)-piperidine-1-carboxylic acid[2-[1,4']bipiperidinyl-1'-yl-1-(1H-indazol-5-ylmethyl)-2-oxo-ethyl]-amide

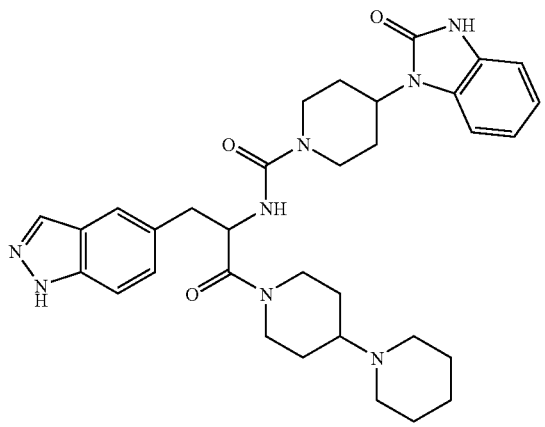

$^1$H-NMR (DMSO-d$_6$, 500 MHz) δ 10.70 (s, 1H), 8.22 (d, J=8.2 Hz, 0.6H), 8.11 (s, 0.4H), 8.00 (s, 0.6H), 7.89 (d, J=9.1 Hz, 0.4H), 7.62-7.57 (m, 1H), 7.50-7.43 (m, 1H), 7.30-7.26 (m, 1H), 7.14-7.08 (m, 1H), 6.99-6.95 (m, 2H), 6.85 (br s, 1H), 4.89-4.80 (m, 1H), 4.45-4.31 (m, 2H), 4.18-4.00 (m, 2H), 3.26-3.16 (m, 1H), 3.09-2.96 (m, 2H), 2.82-2.73 (m, 4H), 2.38-2.34 (m, 2H), 2.24-2.08 (m, 4H), 2.03-1.88 (m, 2H), 1.47-1.22 (m, 10H), 0.90-0.84 (m, 1H). LC/MS: t$_R$=1.73 min, 599.32 (MH)$^+$.

Example 5

(±)-4-(2-Oxo-1,4-dihydro-2H-quinazolin-3-yl)-piperidine-1-carboxylic acid[2-[1,4']bipiperidinyl-1'-yl-1-(1H-indol-5-ylmethyl)-2-oxo-ethyl]-amide

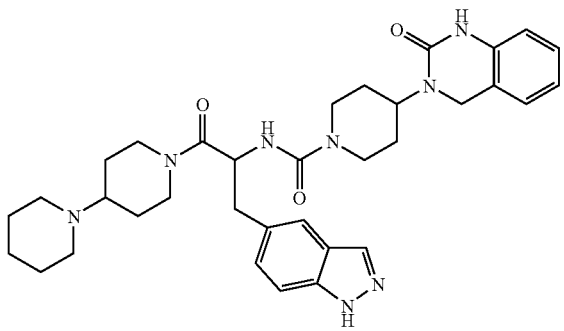

A mixture of 4-(2-Oxo-1,4-dihydro-2H-quinazolin-3-yl)-piperidine-1-carboxylic acid {2-[1,4']bipiperidinyl-1'-yl-2-oxo-1-[1-(2-trimethylsilanyl-ethanesulfonyl)-1H-indol-5-ylmethyl]-ethyl}-amide (52 mg, 0.067 mmol), cesium fluoride (51 mg, 0.33 mmol) in acetonitrile (5 mL) was heated at 80° C. for 4 h. The solvents were removed in vacuo and the residue was subjected to chromatography on silica gel using methylene chloride/methanol/triethylamine (93:5:2) as eluent to afford the title compound as a white solid (70% yield). $^1$H-NMR (CD$_3$CN, 500 MHz) δ 9.30 (s, 1H), 7.48 (s, 1H), 7.42 (s, 1H), 7.39 (d, J=8.2 Hz, 0.6H), 7.36 (d, J=8.2 Hz, 0.4H), 7.24-7.21 (m, 1H), 7.19 (t, J=7.9 Hz, 1H), 7.12-7.09 (m, 1H), 7.06 (d, J=8.2 Hz, 0.6H), 7.02 (d, J=8.2 Hz, 0.4H), 6.95 (t, J=7.4 Hz, 1, 4.04-3.93 (m, 1H), 3.07-3.02 (m, 1.6H), 2.95 (dd, J=13.7, 7.1 Hz, 0.4H), 2.85-2.72 (m, 3H), 2.56-2.37 (m, 3H), 2.42-2.37 (m, 1H), 1.99-1.95 (m, 7H), 1.76-1.51 (m, 8H), 1.45-1.40 (m, 3H). LC/MS: t$_R$=1.91 min, 612.44 (MH)$^+$.

Example 6

(±)-4-(2-Oxo-1,4-dihydro-2H-quinazolin-3-yl)-piperidine-1-carboxylic acid[2-[1,4']bipiperidinyl-1'-yl-1-(1H-indazol-5-ylmethyl)-2-oxo-ethyl]-amide Purified by silica gel chromatography using methylene chloride:methanol:triethylamine (93:5:2) as eluent to afford the title compound as a white solid (90% yield). $^1$H-NMR (CD$_3$OD, 500 MHz) δ 8.04 (s, 0.7H), 8.02 (s, 0.3H), 7.67 (s, 0.7H), 7.65 (s, 0.3H), 7.56 (d, J=8.5 Hz, 0.7H), 7.51 (d, J=8.5 Hz, 0.3H), 7.40 (d, J=8.5 Hz, 0.7H), 7.33 (d, J=8.5 Hz, 0.3H), 7.19-7.12 (m, 2H), 6.97-6.94 (m, 1H), 6.80 (d, J=8.0 Hz, 1H), 5.08-5.05 (m, 1H), 4.59-4.54 (m, 1H), 4.48-4.42 (m, 1H), 4.37 (s, 1H), 4.27-4.20 (m, 2H), 4.04 (d, J=13.4 Hz, 0.3H), 3.99 (d, J=13.4 Hz, 0.7H), 3.19-3.08 (m, 2H), 2.94-2.86 (m, 3H), 2.57 (br s, 2H), 2.51-2.36 (m, 2H), 2.07-2.05 (m 1H), 1.90-1.31 (m, 16H). LC/MS: $t_R$=1.85 min, 613.44 (MH)$^+$.
The (R)-enantiomer, whose discrete synthesis is described above (Example 1), was obtained by chiral separation of the racemate by employing the following conditions: Chiracel OD prep column, 50×500 mm, 20 um; A=EtOH, B=0.05% diethylamine/hexane; 20% B @ 65 ml/min for 45 min; retention times: 20.5 min for R and 32.8 min for S enantiomers.

Example 7

(±)-4-(2-Oxo-2,3-dihydro-benzoimidazol-1-yl)-piperidine-1-carboxylic acid [1-(1H-indol-5-ylmethyl)-2-(4-isobutyl-piperazin-1-yl)-2-oxo-ethyl]-amide

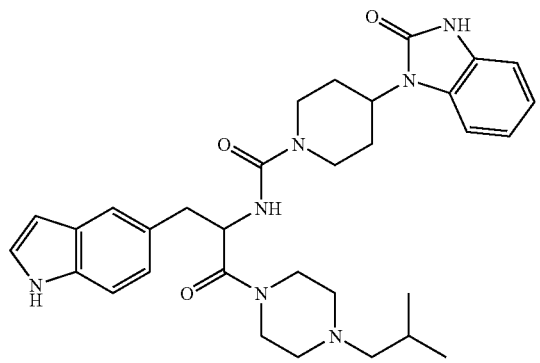

LC/MS: $t_R$=2.05 min, 572.31 (MH)$^+$.

Example 8

(±)-4-(2-Oxo-2,3-dihydro-benzoimidazol-1-yl)-piperidine-1-carboxylic acid [2-(1,4-dioxa-8-aza-spiro[4.5]dec-8-yl)-1-(1H-indol-5-ylmethyl)-2-oxo-ethyl]-amide

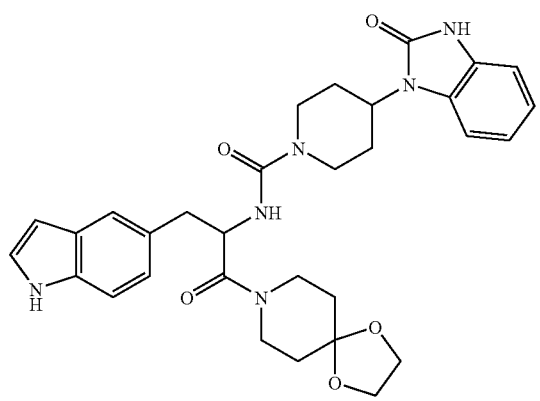

LC/MS: $t_R$=2.35 min, 573.26 (MH)$^+$.

Example 9

(±)-4-(2-Oxo-2,3-dihydro-benzoimidazol-1-yl)-piperidine-1-carboxylic acid [1-(1H-indazol-5-ylmethyl)-2-(4-isobutyl-piperazin-1-yl)-2-oxo-ethyl]-amide

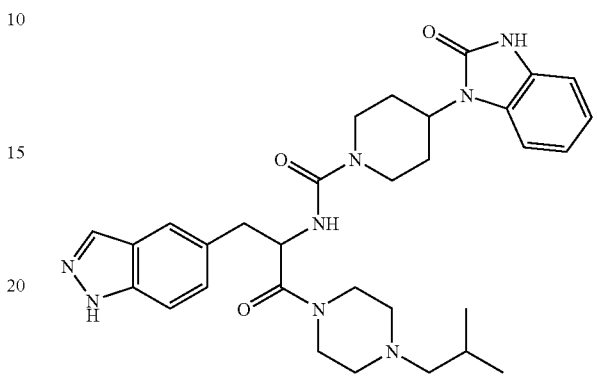

LC/MS: $t_R$=1.86 min, 573.28 (MH)$^+$.

Example 10

(±)-4-(2-Oxo-2,3-dihydro-benzoimidazol-1-yl)-piperidine-1-carboxylic acid [2-(1,4-dioxa-8-aza-spiro[4.5]dec-8-yl)-1-(1H-indazol-5-ylmethyl)-2-oxo-ethyl]-amide

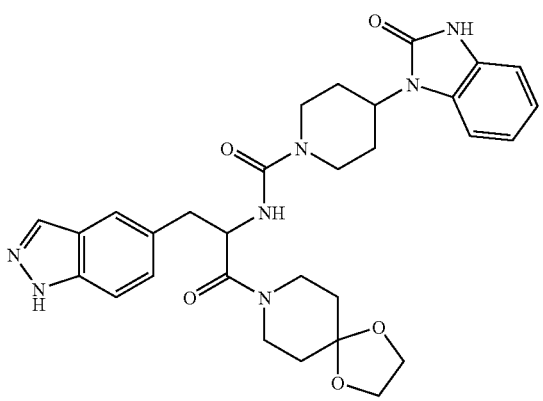

LC/MS: $t_R$=2.18 min, 574.23 (MH)$^+$.

Example 11

(±)-4-(2-Oxo-1,4-dihydro-2H-quinazolin-3-yl)-piperidine-1-carboxylic acid [2-(1,4-dioxa-8-aza-spiro[4.5]dec-8-yl)-1-(1H-indazol-5-ylmethyl)-2-oxo-ethyl]-amide

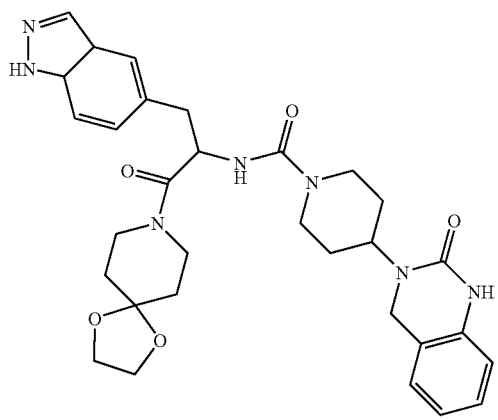

To a solution of the 3-(1H-indazol-5-yl)-2-{[4-(2-oxo-1,4-dihydro-2H-quinazolin-3-yl)-piperidine-1-carbonyl]-amino}-propionic acid (95 mg, 0.21 mmol) and N,N-diisopropylethylamine (0.14 mL, 0.82 mmol) in dimethylformamide (5 mL) was added a solution of 1,4-dioxa-8-azaspiro[4,5]decane (32 mg, 0.23 mmol) and PyBOP® (107 mg, 0.21 mmol) in methylene chloride (5 mL). The reaction mixture was stirred for 16 h at room temperature. All solvent was removed using high vacuum. The residue was subjected to flash column chromatography using methylene chloride/methanol/triethylamine (93:5:2) to give the title compound as a white solid (67 mg, 56% yield). $^1$H-NMR (CDCl$_3$, 500 MHz) δ 10.52 (s, 1H), 7.97 (s, 1H), 7.54 (s, 1H), 7.37 (d, J=8.6 Hz, 1H), 7.20 (d, J=10.7 Hz, 1H), 7.16 (t, J=7.2 Hz, 1H), 7.04 (d, J=7.6 Hz, 1H), 7.01 (s, 1H), 6.94 (t, J=8.6 Hz, 1H), 6.67 (d, J=7.6 Hz, 1H), 5.64 (d, J=7.9 Hz, 1H), 5.16 (dd, J=15.0, 6.7 Hz, 1H), 4.56-4.49 (m, 1H), 4.25 (s, 2H), 4.11 (br t, J=15.6 Hz, 2H), 3.92-3.84 (m, 4H), 3.73-3.69 (m, 1H), 3.60-3.56 (m, 1H), 3.48-3.43 (m, 1H), 3.22-3.17 (m, 1H), 3.11 (d, J=6.7 Hz, 2H), 2.90-2.85 (m, 2H), 2.68-2.60 (m, 4H), 1.67-1.61 (m, 2H), 1.54-1.49 (m, 2H). Mass spec.: 588 (MH)$^+$.

4-Bromo-2,6-dimethylphenyldiazo-t-butyl sulfide

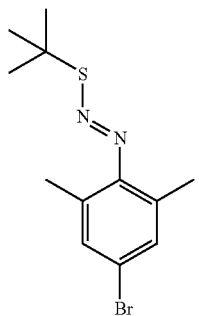

4-Bromo-2,6-dimethylaniline (20.00 g, 100 mmol) was ground to a powder with a mortar and pestle and then suspended in 24% hydrochloric acid (41 mL). The stirred mixture was cooled to −20° C. and treated with sodium nitrite (7.24 g, 1.05 equiv) in water (16 mL), dropwise over 40 min while the temperature was maintained below −5° C. After a further 30 min at −5° C. to −20° C., the mixture was buffered to ca. pH 5 with solid sodium acetate. This mixture (kept at ca. −10° C.) was added in portions to a stirred solution of t-butyl thiol (11.3 mL, 1 equiv) in ethanol (100 mL) at 0° C. over ca. 10 min. Following addition, the mixture was stirred at 0° C. for 30 min and then crushed ice (ca. 150 mL) was added. The mixture was stored in the refrigerator overnight. The resulting light-brown solid was collected by filtration, washed with water, and dried under high vacuum for several h.

(26.90 g, 89%). The compound appeared to be stable as a solid but underwent significant decomposition when recrystallization from ethanol was attempted.
$^1$H-NMR (CDCl$_3$, 500 MHz) δ 1.58 (9H, s), 1.99 (6H, s), 7.21 (2H, s). Mass spec.: 303.05 (MH)$^+$.

5-Bromo-7-methylindazole

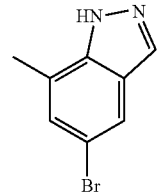

Into a flame-dried round bottom flask, 4-bromo-2,6-dimethylphenyldiazo-t-butyl sulfide (12.50 g, 41.5 mmol) and potassium t-butoxide (46.56 g, 10 equiv) were combined. A stir bar was added and the mixture placed under nitrogen. To this was added dry DMSO (120 mL). The mixture was stirred vigorously overnight at rt. The reaction mixture was then carefully poured into a mixture of crushed ice (400 mL) and 10% hydrochloric acid (200 mL). The resulting suspension was left to stand at 4° C. overnight and the solid was collected by filtration and washed with water. The crude solid was dissolved in 5:1 methylene chloride/methanol and the solution dried over magnesium sulfate and evaporated to give the product as an off-white solid (7.60 g, 87%). $^1$H-NMR (CDCl$_3$/CD$_3$OD, 500 MHz) δ 2.51 (3H, s), 7.22 (1H, s), 7.69 (1H, s), 7.94 (1H, s). Mass spec.: 211.03 (MH)$^+$.

7-methylindazole-5-carboxaldehyde

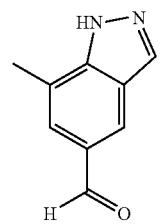

5-Bromo-7-methylindazole (6.10 g, 28.9 mmol) and sodium hydride (60% in mineral oil, 1.27 g, 1.1 equiv) were weighed into a flame-dried round-bottom flask containing a magnetic stir bar. Under a nitrogen atmosphere at room temperature, dry tetrahydrofuran (30 mL) was added. The mixture was stirred at room temperature for 15 min, during which time it became homogeneous. The stirred mixture was cooled to −70° C. and a solution of sec-butyllithium in cyclohexane (1.4M, 45 mL, 2.2 equiv) was added over several minutes.

After 1 h at −70° C., dimethylformamide (10 mL) was added over several minutes. The mixture was allowed to warm to room temperature and was stirred overnight. It was then cooled to 0° C. and carefully treated with 1N hydrochloric acid (60 mL). After a few minutes, solid sodium bicarbonate was added to basify the mixture to pH 9-10. The layers were separated and the aqueous phase washed twice with ethyl acetate. The combined organic phases were extracted with 0.8M sodium hydrogen sulfate (3×125 mL). The combined aqueous phases were washed with ethyl acetate (100 mL) and then the pH was adjusted to ca. 10 with solid sodium hydroxide. The resulting suspension was extracted with ethyl acetate (3×150 mL). The combined organic phases were washed with brine, dried (magnesium sulfate) and evaporated to give the product as a light-tan solid (3.01 g, 65%). $^1$H-NMR (CDCl$_3$, 500 MHz) δ 2.63 (3H, s), 7.73 (1H, s), 8.12 (1H, s), 8.25 (1H, s), 10.03 (1H, s). Mass spec.: 161.06 (MH)$^+$.

2-Benzyloxycarbonylamino-3-(7-methyl-1H-indazol-5-yl)-acrylic acid methyl ester

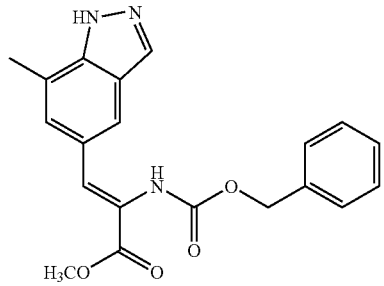

A stirred solution of N-benzyloxycarbonyl-α-phosphonoglycine trimethyl ester (5.51 g, 1.2 equiv.) in tetrahydrofuran (30 mL) at room temperature was treated with tetramethylguanidine (1.91 mL, 1.1 equiv). After 10 min, 7-methylindazole-5-carboxaldehyde (2.22 g, 13.86 mmol) in tetrahydrofuran (20 mL) was added. Disappearance of starting material was monitored by TLC and LC/MS. After 5 days at room temperature, the solvent was evaporated and the residue dissolved in ethyl acetate. The solution was washed with 2% phosphoric acid and brine, dried (magnesium sulfate) and evaporated. The residue was purified by flash chromatography on silica gel, eluting with 1) 1:1 and 2) 2:1 ethyl acetate/hexane, to give the product as a colorless foam (4.93 g, 97%). $^1$H-NMR (CDCl$_3$, 500 MHz) δ 2.43 (3H, s), 3.80 (3H, s), 5.12 (2H, s), 6.66 (1H, s), 7.28 (5H, brs), 7.33 (1H, s), 7.47 (1H, s), 7.74 (1H, s), 7.96 (1H, s). Mass spec.: 366.16 (MH)$^+$.

(±)-2-Amino-3-(7-methyl-1H-indazol-5-yl)-propionic acid methyl ester

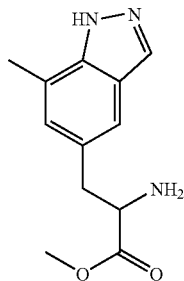

A solution of 2-benzyloxycarbonylamino-3-(7-methyl-1H-indazol-5-yl)-acrylic acid methyl ester (4.93 g, 13.49 mmol) in methanol (125 mL) was degassed by bubbling nitrogen through it for 30 min and then 10% palladium on charcoal (0.6 g) was carefully added. The mixture was hydrogenated at 40 psi in a Parr shaker apparatus overnight. The catalyst was removed by filtration through a pad of celite and the filtrate was concentrated in vacuo to give the product as a colorless foam (3.62 g, quant.). $^1$H-NMR (CD$_3$OD, 500 MHz) δ 2.45 (3H, s), 2.99 (1H, Abq), 3.22 (1H, Abq), 3.74 (3H, s), 3.89 (1H, m), 6.91 (1H, s), 7.31 (1H, s), 7.73 (1H, s). Mass spec.: 234.11 (MH)$^+$.

Example 12

(±)-3-(7-Methyl-1H-indazol-5-yl)-2-{[4-(2-oxo-1,4-dihydro-2H-quinazolin-3-yl)-piperidine-1-carbonyl]-amino}-propionic acid methyl ester

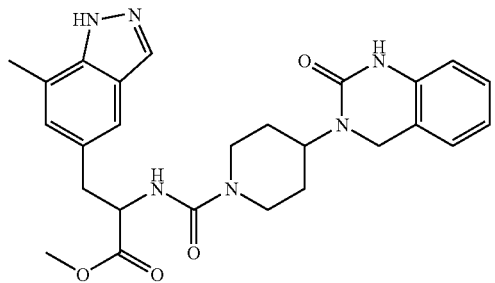

A stirred solution of (±)-2-amino-3-(7-methyl-1H-indazol-5-yl)-propionic acid methyl ester (162.9 mg, 0.698 mmol) in methylene chloride (3 mL) at room temperature was treated with carbonyl diimidazole (113.2 mg, 1 equiv). After 1.5 h at room temperature, 3-piperidin-4-yl-3,4-dihydro-1H-quinazolin-2-one (161.5 mg, 1 equiv.) was added. The mixture was stirred at room temperature overnight. A white precipitate had formed that was shown to be the desired product. The solvent was evaporated and the residue triturated with methylene chloride. The product was collected by filtration, washed with methylene chloride and dried in vacuo to give a white solid (241.5 mg, 71%). Some product remained in the mother liquors. $^1$H-NMR (dimethylformamide-d$_7$, 500 MHz) δ 1.75 (4H, m), 2.78 (3H, s), 2.7-3.1 (4H, m), 3.35 (2H, m), 3.86 (3H, s), 4.44 (2H, s), 4.57 (1H, m), 4.72 (1H, m), 7.11 (3H, m), 7.31 (1H, s), 7.34 (2H, m), 7.72 (1H, s), 9.34 (1H, s). Mass spec.: 491.13 (MH)$^+$.

Similarly Prepared:

Example 13

3-(7-Methyl-1H-indazol-5-yl)-2-[2',3'-dihydro-2'-oxospiro-(piperidine-4,4'-(1H)-quinazoline)carbonyl amino]-propionic acid methyl ester

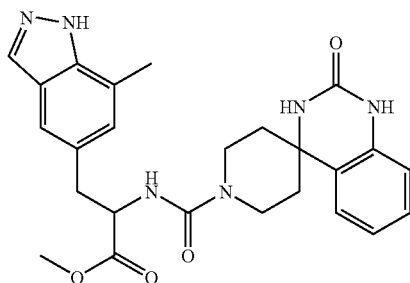

$^1$H-NMR (DMSO-d$_6$) δ 1.59 (4H, m), 2.46 (3H, s), 3.00-3.08 (4H, m), 3.6 (3H, s), 3.78-3.81 (2H, m), 4.30-4.32 (1H, m), 6.78-6.88 (4H, m), 7.03 (1H, s), 7.10 (1H, m), 7.13 (1H, s), 7.41 (1H, s), 7.96 (1H, s), 9.12 (1H, s). Mass spec.: 477.11 (MH)$^+$.

Example 14

3-(7-Methyl-1H-indazol-5-yl)-2-(1,2-dihydro-2-oxospiro-4H-3,1-dihydro-benzoxazine-4'4-piperidine-carbonylamino)-propionic acid methyl ester

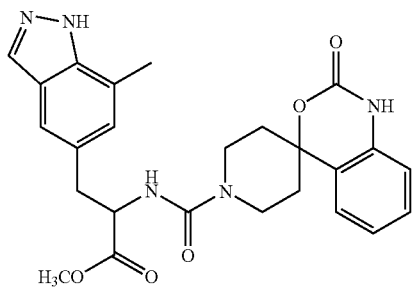

Mass spec.: 478.15 (MH)$^+$.

3-(7-Methyl-1H-indazol-5-yl)-2{3',4'-dihydro-2'-oxospiro-(piperidine-4,4'-(1H)-quinolinecarbonyl amino}-propionic acid methyl ester

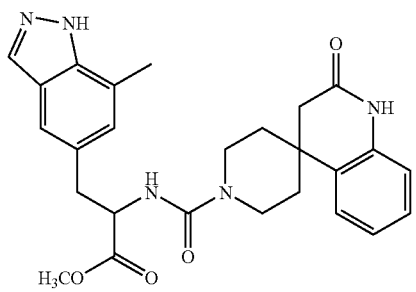

$^1$H-NMR (DMSO-d$_6$) δ 1.42-1.56 (4H, m), 2.47 (3H, s), 2.50-2.54 (1H, d), 2.60-2.64 (1H, d), 2.98-3.06 4H, m), 3.60 (3H, s) 3.80 (2H, m), 4.30 (1H, m), 6.86 (2H, d), 6.95 (2H, m), 7.15 (1H, m), 7.40 (1H, s), 7.95 (1H, s), 8.32 (1H, s), 10.14 (1H, s), 13.05 (1H, s). Mass spec.: 476.17 (MH)$^+$.

3-(7-Methyl-1H-indazol-5-yl)-2-[2'-phenyl-1',3',8'-triaza-spiro(4',5')deo-1-ene-8-carbonyl amino]-propionic acid methyl ester

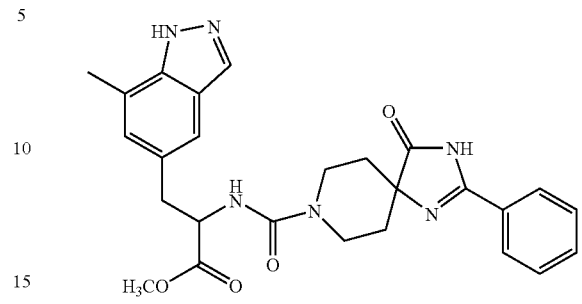

$^1$H-NMR (DMSO-d$_6$) δ 1.50 (2H, m), 1.68 (2H, m), 2.46 (3H, s was overlapped with DMSO), 3.05 (2H, m), 3.30 (2H, m), 3.60 (3H, s), 3.86 (2H, m), 4.28 (1H, m), 6.98 (1H, d), 7.04 (1H, s), 7.40 (1H, s), 7.58 (2H, m), 7.65 (1H, m), 8.00 (1H, s), 8.04 (2H, m). Mass spec.: 489.15 (MH)$^+$.

Example 15

(±)-3-(7-Methyl-1H-indazol-5-yl)-2-{[4-(2-oxo-1,4-dihydro-2H-quinazolin-3-yl)-piperidine-1-carbonyl]-amino}-propionic acid

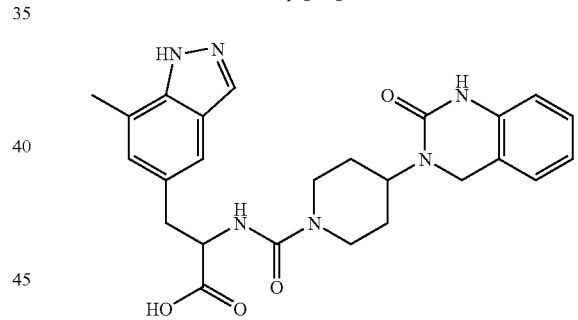

A suspension of (±)-3-(7-methyl-1H-indazol-5-yl)-2-{[4-(2-oxo-1,4-dihydro-2H-quinazolin-3-yl)-piperidine-1-carbonyl]-amino}-propionic acid methyl ester (240.0 mg, 0.489 mmol) in 1:1 tetrahydrofuran/methanol (20 mL) at room temperature was treated with a solution of lithium hydroxide (140.5 mg, 7 equiv) in water (10 mL). Within 1 min, the mixture became homogeneous and it was left to stand at 4° C. overnight. The solvents were evaporated at ca. 30° C. and the pH was adjusted to ca. 1 with 1N hydrochloric acid. The resulting white suspension was stored at 4° C. for several hours and the product was collected by filtration, washed with a small amount of water, and dried in vacuo (169.0 mg, 73%). Solid sodium chloride was added to the filtrate resulting in precipitation of more product (5.2 mg, total yield 75%). $^1$H-NMR (CD$_3$OD, 500 MHz) δ 1.2-1.7 (4H, m), 2.58 (3H, s), 2.5-3.2 (4H, m), 3.35 (2H, m), 4.15 (2H, m), 4.36 (1H, m), 4.60 (1H, m), 6.79 (1H, d), 6.96 (1H, t), 7.18 (3H, m), 7.49 (1H, s), 8.00 (1H, s). Mass spec.: 477.13 (MH)$^+$.

Similarly Prepared:

3-(7-Methyl-1H-indazol-5-yl)-2-[2',3'-dihydro-2'-oxospiro-(piperidine-4,4'-(1H)-quinazolinecarbonyl amino]-propionic acid

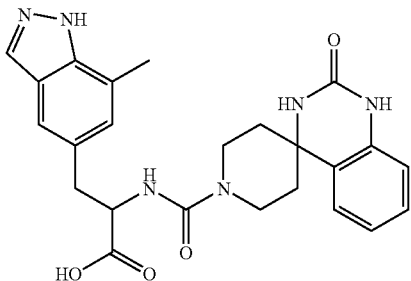

$^1$H-NMR (DMSO-d$_6$) δ 1.58 (4H, m), 2.46 (3H, s), 3.00-3.23 (3H, m), 3.78-3.91 (3H, m), 3.88 (2H, m) 4.28 (1H, s), 6.70 (1H, d), 6.75-6.85 (3H, m), 7.04 (1H, d), 7.11 (1H, m) 7.18 (1H, s), 7.96 (1H, s), 13.02 (1H, m). Mass spec.: 463.09 (MH)$^+$.

3-(7-Methyl-1H-indazol-5-yl)-2-(1,2-dihydro-2-oxospiro-4H-3,1-dihydro-benzoxazine-4'4-piperidine-carbonylamino)-propionic acid methyl ester

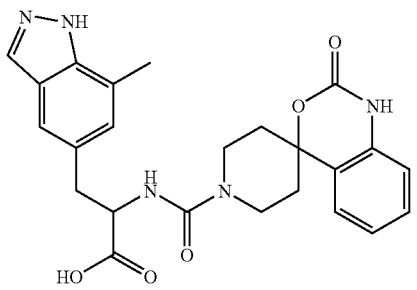

$^1$H-NMR (DMSO-d$_6$) δ 1.63-1.98 (4H, m), 2.46 (3H, s, 7-Me was overlapped with DMSO), 2.98-3.32 (4H, m), 3.90 (2H, m), 4.28 (1H, m), 6.78 (1H, d), 6.87 (2H, m), 6.96 (1H, m), 7.05 (1H, s), 7.24 (1H, m), 7.41 (1H, s), 7.96 (1H, s), 10.22 (1H, s) 12.42 (1H, br.) 13.02 (1H, m). Mass spec.: 464.07 (MH)$^+$.

3-(7-Methyl-1H-indazol-5-yl)-2{3',4'-dihydro-2'-oxospiro-(piperidine-4,4'-(1H)-quinoline-carbonyl amino}-propionic acid

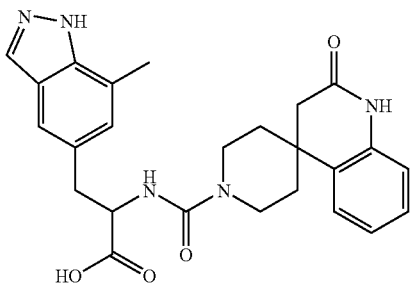

$^1$H-NMR (DMSO-d$_6$) δ 1.39-1.45 (2H, m), 1.53-1.56 (2H, m), 2.46 (3H, s), 2.50-2.54 (1H, d), 2.60-2.63 (1H, d), 2.88-3.00 (3H, m), 3.09-3.11 (1H, m), 3.78-3.81 (2H, m), 4.27 (1H, m), 6.69-6.70 (1H, d), 6.86-6.87 (1H, d), 6.93-6.94 (1H, m) 6.99-7.00 (1H, m), 7.05 (1H, m), 7.41 (1H, s), 7.95 (1H, s), 10.13 (1H, s), 12.50 (1H, m), 13.03 (1H, m). Mass spec.: 462 (MH)$^+$.

3-(7-Methyl-1H-indazol-5-yl)-2-[2'-phenyl-1',3',8'-triaza-spiro(4',5')deo-1-ene-8-carbonyl amino]-propionic acid

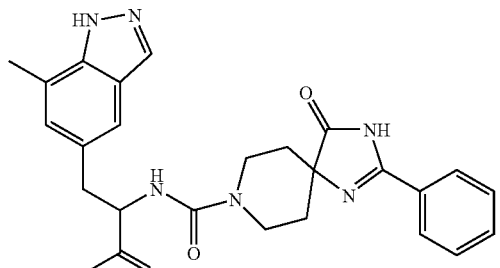

$^1$H-NMR (DMSO-d$_6$) δ 1.36 (2H, m), 1.63 (2H, m), 2.46 (3H, s was overlapped with DMSO), 2.98-3.03 (2H, m), 3.09-3.11 (2H, m), 3.86 (2H, m), 4.21 (1H, m), 6.69 (1H, m), 7.04 (1H, s), 7.40 (1H, s), 7.52-7.58 (3H, m), 7.99 (3H, m), 11.55 (1H, m), 13.00 (1H, m). Mass spec.: 475.08 (MH)$^+$.

Example 16

(±)-4-(2-Oxo-1,4-dihydro-2H-quinazolin-3-yl)-piperidine-1-carboxylic acid[2-[1,4']bipiperidinyl-1'-yl-1-(7-methyl-1H-indazol-5-ylmethyl)-2-oxo-ethyl]-amide

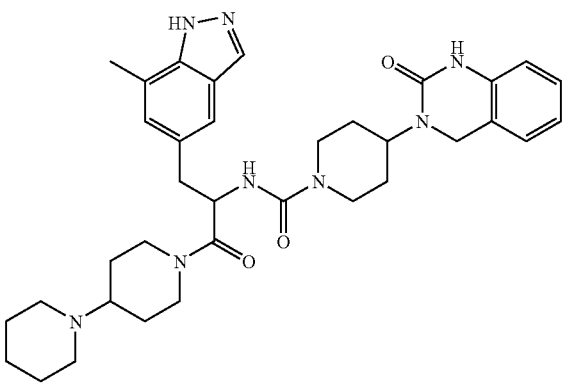

A stirred solution of (±)-3-(7-methyl-1H-indazol-5-yl)-2-{[4-(2-oxo-1,4-dihydro-2H-quinazolin-3-yl)-piperidine-1-carbonyl]-amino}-propionic acid (65.7 mg, 0.138 mmol) in 2:1 dimethylformamide/methylene chloride (1.5 mL) at 0° C. was treated with 4-(1-piperidyl)-piperidine (46.5 mg, 2 equiv), diisopropylethylamine (0.048 mL, 2 equiv) and PyBOP® (75.5 mg, 1.05 equiv). The ice bath was allowed to melt and the mixture was stirred at room temperature overnight. The solvents were removed under high vacuum and the residue was purified by flash chromatography on silica gel, eluting with 18:1 methylene chloride/methanol containing 1% triethylamine, to give the product as a pale-yellow solid (80.4 mg, 93%). $^1$H-NMR (CD$_3$OD, 500 MHz) δ −0.28 (1H, m), 0.75 (1H, m), 1.2-2.0 (12H, m), 2.08 (2H, m), 2.4-2.5 (3H, m), 2.59 (3H, s), 2.68 (2H, m), 2.90 (4H, m), 3.08 (4H, m), 3.9-5.1 (4H, several m), 6.81 (1H, d), 6.96 (1H, t), 7.16 (3H, m), 7.49 (1H, s), 8.03 (1H, s). Mass spec.: 627.29 (MH)$^+$.

Similarly Prepared:

Example 17

(±)-4-(2-Oxo-1,4-dihydro-2H-quinazolin-3-yl)-piperidine-1-carboxylic acid [1-(7-methyl-1H-indazol-5-ylmethyl)-2-oxo-2-piperidin-1-yl-ethyl]-amide

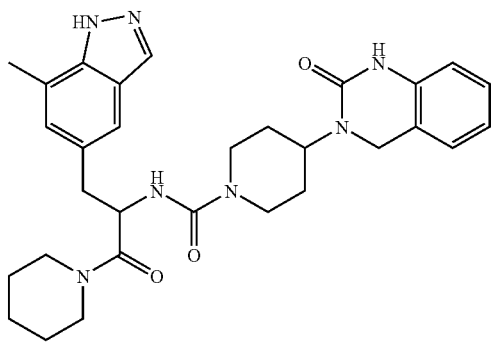

¹H-NMR (CD₃OD, 500 MHz) δ 0.87 (1H, m), 1.33 (1H, m), 1.47 (2H, m), 1.80 (6H, m), 2.57 (3H, s), 2.89 (2H, m), 3.06 (2H, m), 3.18 (4H, m), 3.40 (2H, m), 3.61 (1H, m), 4.16 (1H, m), 4.28 (1H, Abq), 4.43 (1H, m), 5.02 (1H, m), 6.51 (1H, d), 6.79 (1H, d), 6.96 (1H, t), 7.11 (1H, d), 7.15 (1H, t), 7.48 (1H, s), 8.01 (1H, s). Mass spec.: 544.24 (MH)⁺.

Example 18

(±)-4-(2-Oxo-1,4-dihydro-2H-quinazolin-3-yl)-piperidine-1-carboxylic acid [1-dimethylcarbamoyl-2-(7-methyl-1H-indazol-5-yl)-ethyl]-amide

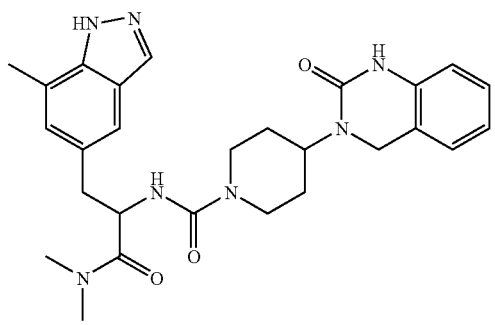

¹H-NMR (CD₃OD, 500 MHz) δ 1.12 (2H, d), 1.64 (2H, m), 2.57 (3H, s), 2.74 (1H, m), 2.87 (3H, s), 2.89 (3H, s), 2.86 (2H, m), 3.07 (2H, m), 3.20 (1H, m), 4.17 (1H, m), 4.25 (1H, Abq), 4.43 (1H, m), 4.97 (1H, m), 6.79 (1H, d), 6.95 (1H, t), 7.0-7.4 (3H, m), 7.48 (1H, d), 8.01 (1H, s). Mass spec.: 504.15 (MH)⁺.

Example 19

(±)-4-(2-Oxo-1,4-dihydro-2H-quinazolin-3-yl)-piperidine-1-carboxylic acid [1-(7-methyl-1H-indazol-5-ylmethyl)-2-(4-methyl-piperazin-1-yl)-2-oxo-ethyl]-amide

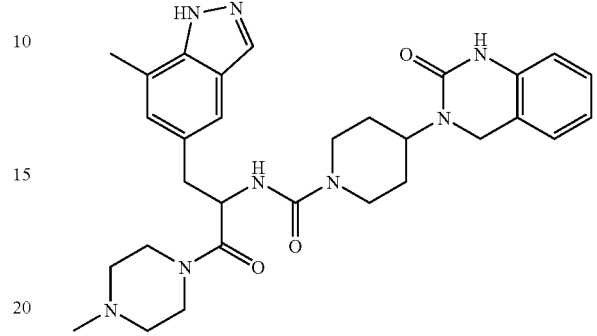

¹H-NMR (CD₃OD, 500 MHz) δ 1.30 (2H, m), 1.66 (2H, m), 1.78 (1H, m), 1.90 (1H, m), 2.00 (3H, s), 2.19 (1H, m), 2.35 (1H, m), 2.58 (3H, s), 2.88 (2H, m), 3.09 (2H, d), 3.10-3.45 (3H, m), 3.66 (1H, m), 4.19 (2H, d), 4.20 (2H, s), 4.43 (1H, m), 4.98 (1H, t), 6.80 (1H, d), 6.95 (1H, t), 7.11 (2H, m), 7.16 (1H, t), 7.47 (1H, s), 8.02 (1H, s). Mass spec.: 559.23 (MH)⁺.

Example 20

(±)-4-(2-Oxo-1,4-dihydro-2H-quinazolin-3-yl)-piperidine-1-carboxylic acid [1-(7-methyl-1H-indazol-5-ylmethyl)-2-oxo-2-pyrrolidin-1-yl-ethyl]-amide

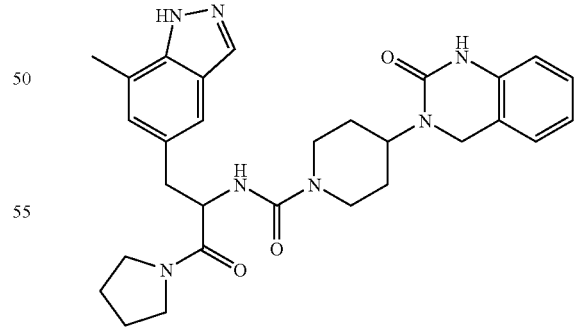

¹H-NMR (CD₃OD, 500 MHz) δ 1.40-1.90 (5H, m), 2.02 (3H, brs), 2.57 (3H, s), 2.86 (1H, m), 2.89 (2H, q), 309 (2H, m), 3.16 (1H, m), 3.25 (2H, m), 3.40 (1H, m), 3.56 (1H, m), 4.17 (2H, d), 4.27 (2H, s), 4.40 (1H, m), 4.69 (1H, t), 6.80 (1H, d), 6.95 (1H, t), 7.10 (1H, s), 7.16 (1H, m), 7.48 (1H, s), 7.53 (1H, m), 8.01 (1H, s). Mass spec.: 530.19 (MH)⁺.

Example 21

(±)-4-(2-Oxo-1,4-dihydro-2H-quinazolin-3-yl)-piperidine-1-carboxylic acid [1-(7-methyl-1H-indazol-5-ylmethyl)-2-oxo-2-(4-pyridin-4-yl-piperazin-1-yl)-ethyl]-amide

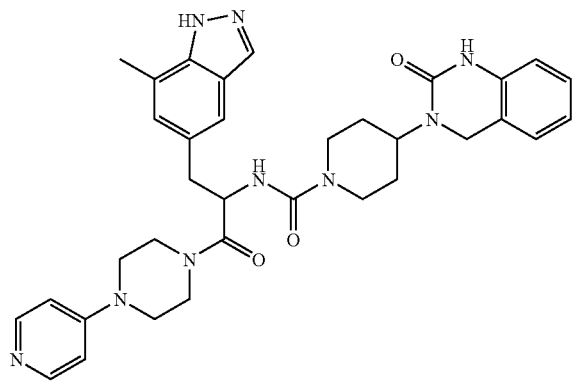

$^1$H-NMR (CD$_3$OD, 500 MHz) δ 1.38 (1H, t), 1.68 (2H, m), 1.81 (1H, m), 2.30 (1H, m), 2.53 (3H, s), 2.95 (4H, m), 3.13 (2H, d), 3.22 (1H, m), 3.35-3.65 (4H, m), 3.79 (1H, m), 4.18 (2H, d), 4.31 (2H, s), 4.42 (1H, m), 4.99 (1H, t), 6.64 (2H, d), 6.80 (1H, d), 6.89 (1H, m), 6.96 (1H, t), 7.14 (3H, m), 7.51 (1H, s), 7.99 (1H, s), 8.10 (2H, d), 8.16 (1H, m). Mass spec.: 622.26 (MH)$^+$.

Example 22

(±)-4-(2-Oxo-1,4-dihydro-2H-quinazolin-3-yl)-piperidine-1-carboxylic acid [1-(7-methyl-1H-indazol-5-ylmethyl)-2-oxo-2-(4-pyridin-2-yl-piperazin-1-yl)-ethyl]-amide

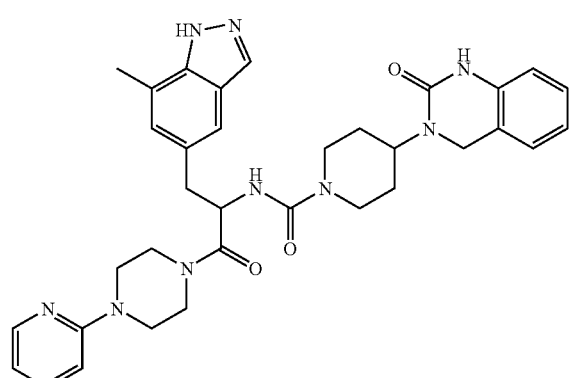

$^1$H-NMR (CD$_3$OD, 500 MHz) δ 1.27 (1H, m), 1.38 (1H, m), 1.67 (2H, m), 1.84 (1H, m), 2.54 (3H, s), 2.65 (1H, m), 2.88 (2H, m), 3.15 (4H, m), 3.35 (1H, m), 3.58 (3H, m), 3.77 (1H, m), 4.18 (2H, d), 4.30 (2H, s), 4.42 (1H, m), 5.01 (1H, t), 6.62 (1H, d), 6.70 (1H, t), 6.80 (1H, d), 6.95 (1H, t), 7.10 3H, m), 7.50 (1H, s), 7.54 (1H, t), 7.99 (1H, 7). Mass spec.: 622.25 (MH)$^+$.

Example 23

(±)-1-(7-Methyl-1H-indazol-5-ylmethyl)-2-[1,4-bipiperidin]-1-yl-2-oxoethyl]-2',3'-dihydro-2'-oxospiro-[piperidine-4,4'-(1H)-quinazoline]-1-carboxamide

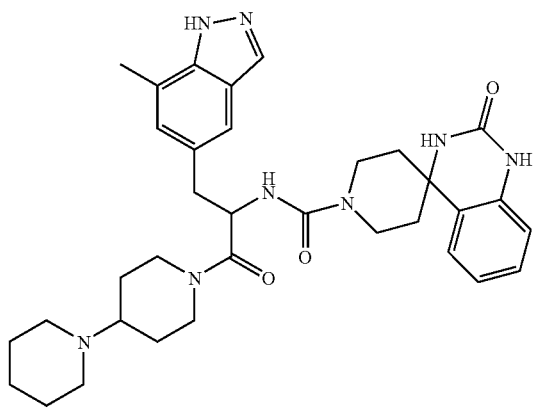

$^1$H-NMR (DMSO-d$_6$, 500 MHz) δ 1.2-1.73 (14H, m), 2.46 (3H, s), 2.75-3.24 (12H, m), 3.87 (2H, m), 4.45 (1H, m), 4.78-4.85 (1H, m), 6.80 (1H, m), 6.86 (1H, m), 7.05 (1H, m), 7.12 (1H, m), 7.21 (1H, m), 7.27 (2H, m), 7.98 (1H, m), 9.23 (1H, m). Mass spec.: 613.25 (MH)$^+$

Example 24

(±)-1-(7-Methyl-1H-indazol-5-ylmethyl)-2-(1-piperidinyl)-2-oxoethyl]-2',3'-dihydro-2'-oxospiro-[piperidine-4,4'-(1H)-quinazoline]-1-carboxamide

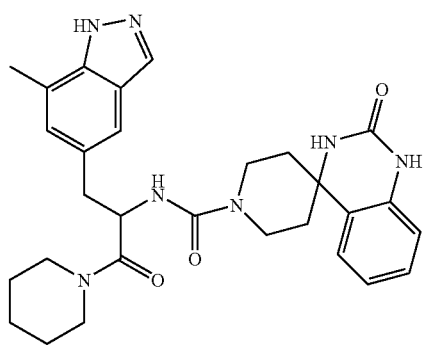

$^1$H-NMR (CD$_3$OD, 500 MHz) δ 0.87 (1H, m), 1.28-1.47 (5H, m), 1.74-1.85 (4H, m), 2.53 (3H, s), 3.02-3.38 (8H, m), 3.92 (2H, m), 5.02 (1H, m), 6.82 (1H, d), 6.99 (1H, d), 7.04-7.09 (2H, m), 7.17 (1H, m), 7.32 (2H, s), 7.45 (1H, s), 7.96 (1H, s). Mass spec.: 530.17 (MH)$^+$.

Example 25

(±)-1-(7-Methyl-1H-indazol-5-ylmethyl)-2-[1,4-bipiperidin]-1-yl-2-oxoethyl]-1',2'-dihydro-2'-oxospiro-[4H-3',1-benzoxazine-4,4'-piperidine]-1-carboxamide

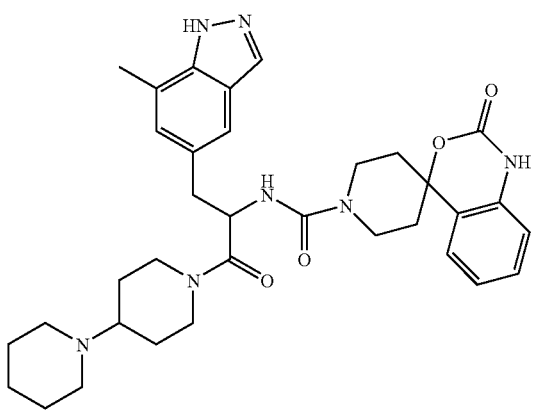

¹H-(DMSO-d₆, 500 MHz) δ 1.88 (14H, m), 2.64 (3H, s), 2.78 (12H, m), 4.0 (2H, m), 4.4 (1H, m), 4.85 (1H, m), 6.80-6.88 (2H, m), 7.03 (2H, m), 7.11 (1H, m), 7.23 (1H, m), 7.36 (2H, m), 7.97 (1H, m). Mass spec.: 614.73 (MH)⁺.

Example 27

(±)-[1-Dimethylcarbamoyl-2-(7-methyl-1H-indazol-5-yl)-ethyl]-1',2'-dihydro-2'-oxospiro-[4H-3',1-benzoxazine-4,4'-piperidine]-1-carboxamide

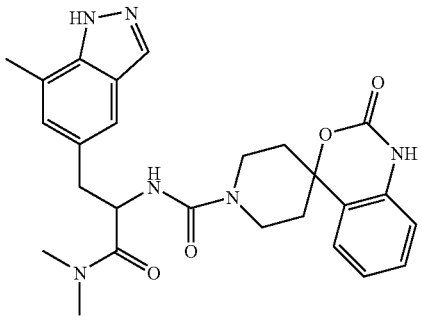

¹H-NMR (DMSO-d₆, 500 MHz) δ 1.68-1.88 (4H, m), 2.47 (3H, m), 2.79 (6H, s), 2.89-3.04 (4H, m), 3.96 (2H, d), 4.75 (1H, m), 6.81 (1H, d), 6.88 (1H, m), 6.93 (1H, m), 6.98 (1H, m), 7.05 (1H, s), 7.24 (1H, m), 7.43 (1H, s), 7.97 (1H, m), 8.32 (1H, s). Mass spec.: 491.14 (MH)⁺.

Example 26

(±)-1-(7-Methyl-1H-indazol-5-ylmethyl)-2-(1-piperidinyl)-2-oxoethyl]-1',2'-dihydro-2'-oxospiro-[4H-3',1-benzoxazine-4,4'-piperidine]-1-carboxamide

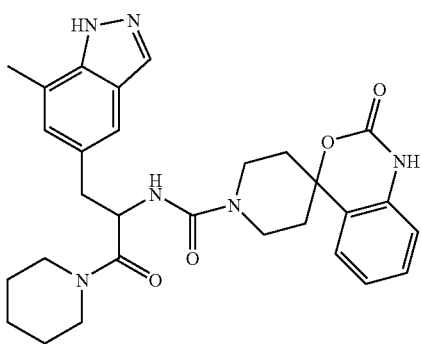

¹H-NMR (DMSO-d₆, 500 MHz) δ 1.15-1.91 (10H, m), 2.47 (3H, s), 2.95-3.05 (6H, m) 3.40 (4H, m) 3.95 (2H, d), 4.81 (1H, m), 6.81 (1H, d), 6.88 (1H, d), 6.94 (1H, m), 6.99 (1H, m), 7.04 (1H, s), 7.24 (1H, m), 7.37 (1H, s), 7.96 (1H, s). Mass spec.: 531.23 (MH)⁺.

Example 28

(±)-[1-(2-adamantyl-carbamoyl)-2-(7-methyl-1H-indazol-5-yl)-ethyl]-1',2'-dihydro-2'-oxospiro-[4H-3',1-benzoxazine-4,4'-piperidine]-1-carboxamide

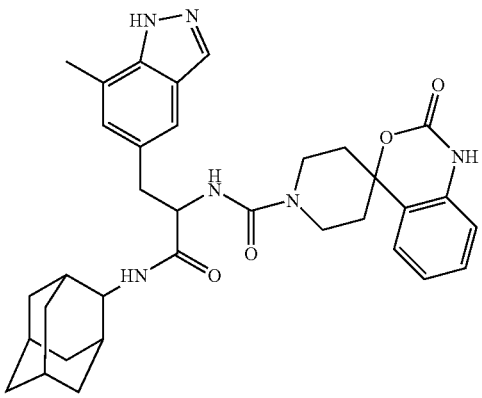

¹H-NMR (DMSO-d₆, 500 MHz) δ 1.40-1.95 (15H, m), 2.46 (3H, m), 2.89-3.07 (4H, m), 3.81 (1H, m), 3.90 (2H, m), 4.48 (1H, m), 6.74 (2H, m), 6.86 (1H, d), 6.97 (1H, m), 7.11 (1H, s), 7.24 (1H, m), 7.36 (1H, s), 7.44 (1H, s), 7.96 (1H, s). Mass Spec.: 597.27 (MH)⁺.

Example 29

(±)-1',2'-Dihydro-2'-oxospiro-[4H-3',1-benzoxazine-4,4'-piperidine-1-carboxylic acid [1-(7-methyl-1H-indazol-5-ylmethyl)-2-oxo-2-(4-pyridin-4-yl-piperazin-1-yl)-ethyl]-amide

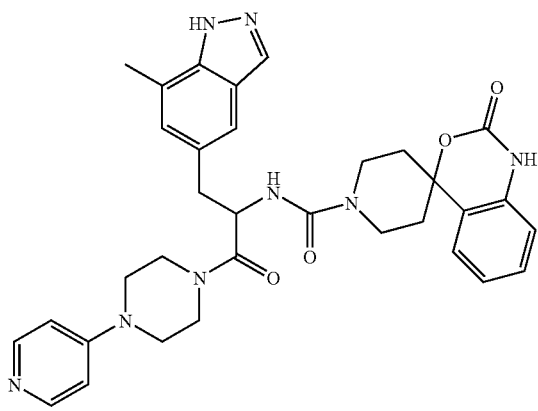

LC/MS: $t_R$=1.56 min, 609.14 (MH)$^+$.

Example 30

(±)-1',2'-Dihydro-2'-oxospiro-[4H-3',1-benzoxazine-4,4'-piperidine-1-carboxylic acid {2-(7-methyl-1H-indazol-5-yl)-1-[(pyridin-4-ylmethyl)-carbamoyl]-ethyl}-amide

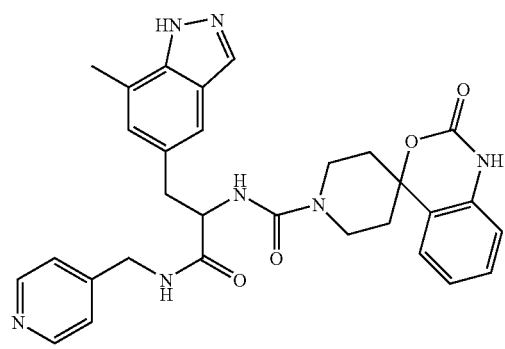

LC/MS: $t_R$=1.49 min, 553.12 (MH)$^+$.

Example 31

(±)-1-(7-Methyl-1H-indazol-5-ylmethyl)-2-[1,4-bipiperidin]-1-yl-2-oxoethyl]3',4'-dihydro-2'-oxospiro-[piperidine-4,4'-(1H)-quinoline]-1-carboxamide

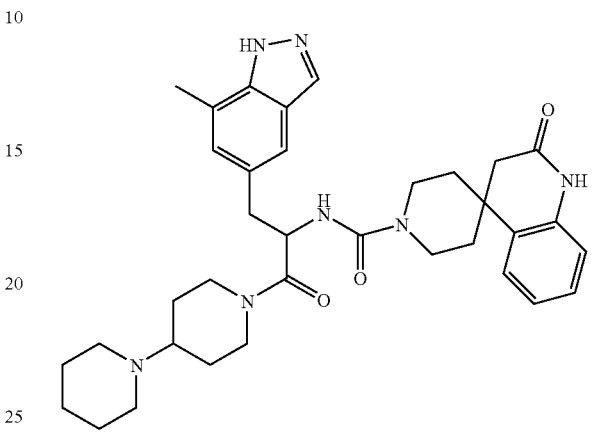

$^1$H-NMR (DMSO-d$_6$, 500 MHz) δ 1.20-2.00 (14H, m), 2.46 (3H, s), 2.38-3.03 (12H, m), 3.87 (2H, m), 4.34 (1H, m), 4.76-4.87 (1H, m), 6.65 (1H, m), 6.82-7.64 (3H, m), 7.13-7.23 (2H, m), 7.36 (3h, m), 7.96 (1H, s). Mass spec.: 612.32 (MH)$^+$.

Example 32

(±)-1-(7-Methyl-1H-indazol-5-ylmethyl)-2-[1-piperidinyl]-2-oxoethyl]3',4'-dihydro-2'-oxospiro-[piperidine-4,4'-(1H)-quinoline]-1-carboxamide

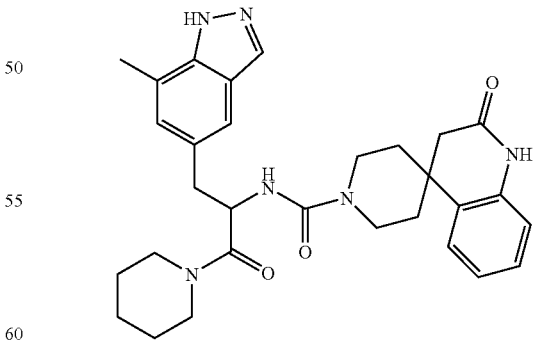

$^1$H-NMR (DMSO-d$_6$, 500 MHz) δ 1.10-1.68 (10H, m), 2.46 (3H, s), 2.50-2.60 (2H, m), 2.82-2.97 (4H, m), 3.39 (2H, m), 3.85 (2H, m), 4.80 (1H, m), 6.68 (1H, m), 6.87 (1H, d), 6.94 (1H, m), 7.03 (1H, s), 7.06 (1H, m), 7.15 (1H, m), 7.37 (1H, s), 7.40 (1H, s), 7.96 (1H, s). Mass spec.: 529.25 (MH)$^+$.

Example 33

(±)-[1-Dimethylcarbmoyl-2-(7-methyl-1H-indazol-5-yl)-ethy]1-3',4'-dihydro-2'-oxospiro-[piperidine-4,4'-(1H)-quinoline]-1-carboxamide

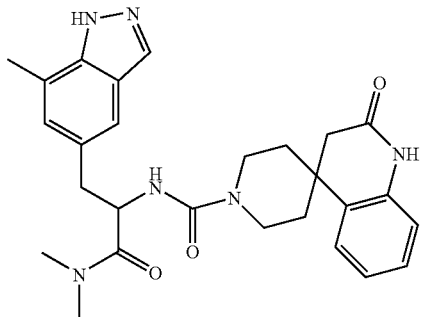

$^1$H-NMR (DMSO-d$_6$, 500 MHz) δ 1.43 (2H, m), 1.56 (2H, m), 2.46 (3H, s), 2.56 (2H, m), 2.79 (3H, s), 2.90 (5H, m), 3.84 (2H, m), 4.73 1H, m), 6.69 (1H, d), 2.69 (1H, d), 6.94 (1H, m), 7.05 (2H, m), 7.14 (1H, m), 7.37 (1H, s), 7.42 (1H, s), 7.96 (1H, s). Mass spec.: 489.2 (MH)$^+$.

Example 34

(±)-4-Oxo-2-phenyl-1,3,8-triaza-spiro[4,5]dec-1-ene-8-carboxylic acid {1-(7-methyl-1H-indazol-5-yl methyl)-2-[1,4]bipiperidinyl-1'-yl-2-oxo-ethyl}-amide

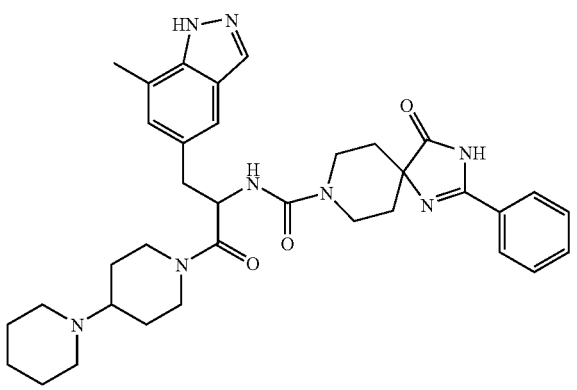

$^1$H-NMR (DMSO-d$_6$, 500 MHz) δ 1.34-2.00 (14H, m), 2.48 (3H, s overlapped with DMSO), 2.70-3.30 (12H, m), 3.90 (2H, m), 4.40 (1H, m), 4.82 (1H, m), 6.82 (1H, m), 7.04 (1H, s), 7.37 (2H, m), 7.56 (3H, m), 7.98 (3H, m). Mass spec.: 625.29 (MH)$^+$.

Example 35

(±)-4-Oxo-2-phenyl-1,3,8-triaza-spiro[4,5]dec-1-ene-8-carboxylic acid {1-(7-methyl-1H-indazol-5-yl methyl)-2-[1-piperidinylyl]-2-oxo-ethyl}-amide

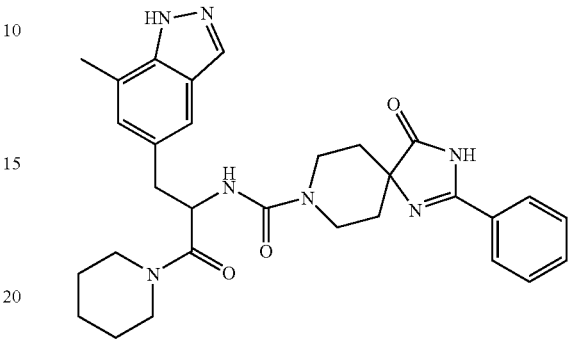

$^1$H-NMR (DMSO-d$_6$, 500 MHz) δ 1.10-1.62 (6H, m), 1.73 (4H, m), 2.48 (3H, s), 3.00 (6H, m), 3.39 (2H, m), 3.93 (2H, m), 4.82 (1H, m), 6.78 (1H, m), 7.05 (1H, s), 7.37 (2H, s), 7.40 (1H, s), 7.53 (2H, m), 7.98 (2H, m). Mass spec.: 543.26 (MH)$^+$.

Example 36

(±)-4-Oxo-2-phenyl-1,3,8-triaza-spiro[4,5]dec-1-ene-8-carboxylic acid[1-dimethylcarbamoyl-2-(7-methyl-1H-indazol-5-yl)-ethyl]amide

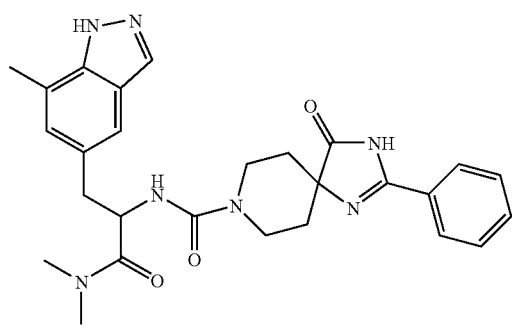

$^1$H-NMR (DMSO-d$_6$, 500 MHz) δ 1.28-1.61 (4H, m), 2.78 (4H, m), 2.90 (6H, m), 3.94 (2H, m), 4.74 (1H, m), 6.77 (1H, m), 7.05 (1H, s), 7.37 (4H, s), 7.42 (1H, m), 7.52 (2H, m), 7.98 (2H, m). Mass spec.: 502.21 (MH)$^+$.

Example 37

4-(2-Oxo-1,4-dihydro-2H-quinazolin-3-yl)-piperidine-1-carboxylic acid {1-(1H-indazol-5-ylmethyl)-2-oxo-2-[4-(2-oxo-1,4-dihydro-2H-quinazolin-3-yl)-piperidin-1-yl]-ethyl}-amide

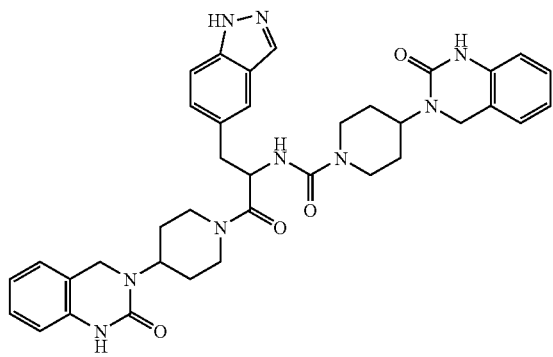

LC/MS: $t_R$=1.51 min, 674 (MH)⁻

Example 38

4-(3-(1H-Indazol-5-yl)-2-{[4-(2-oxo-1,4-dihydro-2H-quinazolin-3-yl)-piperidine-1-carbonyl]-amino}-propionyl)-piperazine-1-carboxylic acid benzyl ester

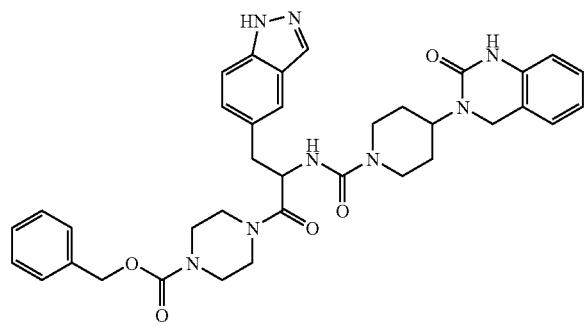

LC/MS: $t_R$=1.74 min, 665 (MH)⁺.

Example 39

4-(2-Oxo-1,4-dihydro-2H-quinazolin-3-yl)-piperidine-1-carboxylic acid [1-(1H-indazol-5-ylmethyl)-2-oxo-2-piperazin-1-yl-ethyl]-amide

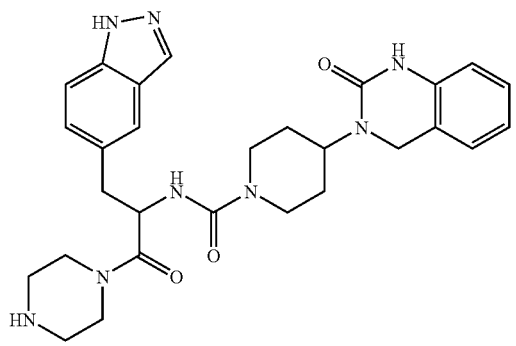

To a degassed solution of 4-(3-(1H-indazol-5-yl)-2-{[4-(2-oxo-1,4-dihydro-2H-quinazolin-3-yl)-piperidine-1-carbonyl]-amino}-propionyl)-piperazine-1-carboxylic acid benzyl ester (280 mg, 0.42 mmol) in methanol (50 ml) was added 10% palladized charcoal (50 mg). The mixture was shaken in a Parr apparatus under an atmosphere of hydrogen at 50 psi for 3 h. The mixture was filtered through celite. The filtrate was concentrated under reduced pressure to give the desired product in 91% yield. LC/MS: $t_R$=1.22 min, 531 (MH)⁺.

Example 40a 4-(2-Oxo-1,4-dihydro-2H-quinazolin-3-yl)-piperidine-1-carboxylic acid {1-(1H-indazol-5-ylmethyl)-2-[4-(2-methyl-butyl)-piperazin-1-yl]-2-oxo-ethyl}-amide

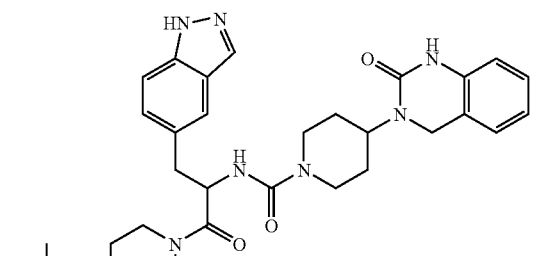

A stirred solution of 4-(2-oxo-1,4-dihydro-2H-quinazolin-3-yl)-piperidine-1-carboxylic acid [1-(1H-indazol-5-ylmethyl)-2-oxo-2-piperazin-1-yl-ethyl]-amide (100 mg, 0.188 mmol) in methanol (25 mL) was treated with 2-methyl-butyraldehyde (0.03 ml, 0.376 mmol). After 1 h at room temperature, sodium triacetoxyborohydride (80 mg, 0.316 mmol) was added. The mixture was allowed to stir overnight. The solution was filtered through an SCX cartridge. The cartridge was eluted first with methanol and then with a 1M solution of ammonia in methanol. The solvent was removed in vacuo to give the desired product in 50% yield. LC/MS: $t_R$=1.31 min, 601(MH)⁺.

General Experimental Procedure for the Preparation of Examples 40b-40k.

The appropriate aldehyde (0.04 mmol) was added to a solution of Example 39 piperazine (0.02 mmol) in methanol (2.0 mL) and the resulting solution was shaken at room temperature for 1 h. Sodium triacetoxyborohydride (0.2 mmol) was then added and the solution allowed stir overnight at room temperature. The solution was then filtered through a SCX cartridge and the cartridge washed with methanol and an ammonia/methanol solution. The ammonia/methanol solution was concentrated in vacuo and the crude products were purified by preparative HPLC to the afford the products listed in Table 1.

TABLE 1

Examples 40b-40k.

| Example No. | Structure | HPLC Retention time (min) | Mass spec (MH)+ |
|---|---|---|---|
| 40b | 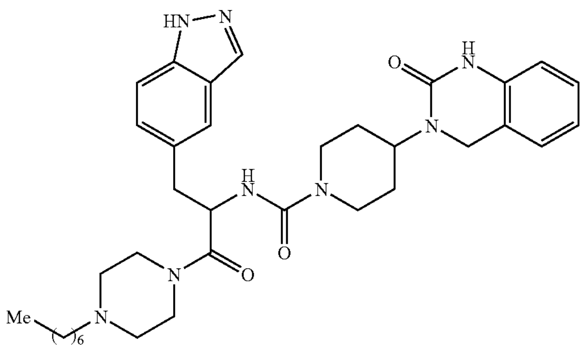 | 2.62 | 629 |
| 40c | 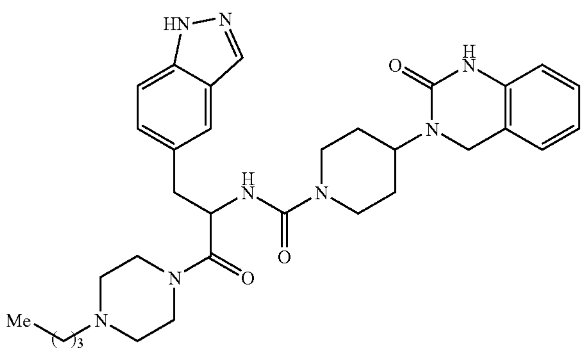 | 1.41 | 587 |
| 40d | 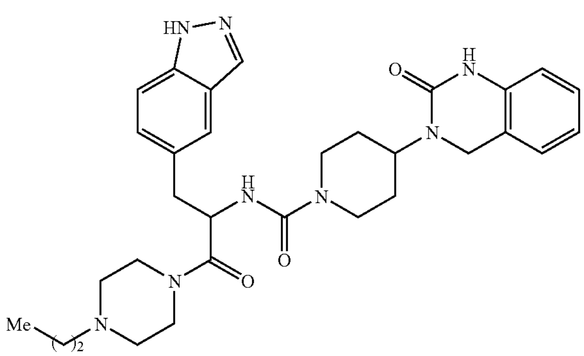 | 1.27 | 573 |
| 40e | 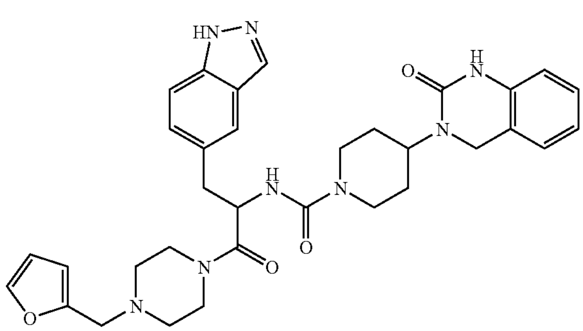 | 1.74 | 611 |

TABLE 1-continued
Examples 40b-40k.
| Example No. | Structure | HPLC Retention time (min) | Mass spec (MH)+ |
|---|---|---|---|
| 40f | 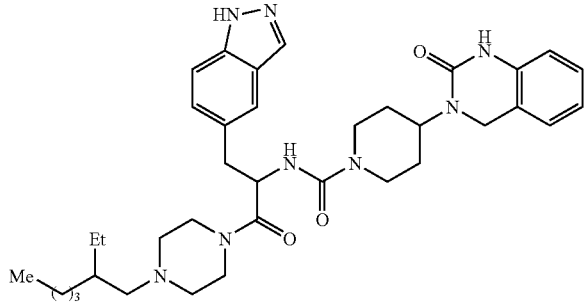 | 1.89 | 643 |
| 40g | 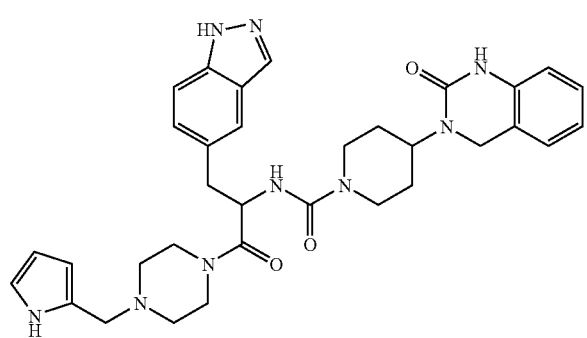 | 1.48 | 610 |
| 40h | 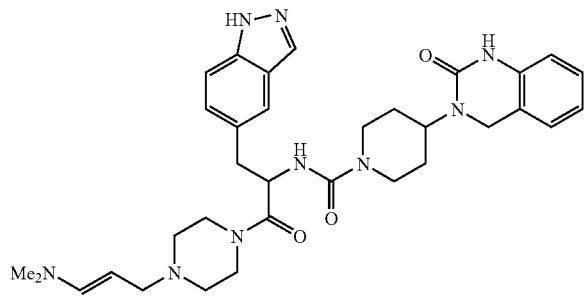 | 2.19 | 614 |
| 40i | 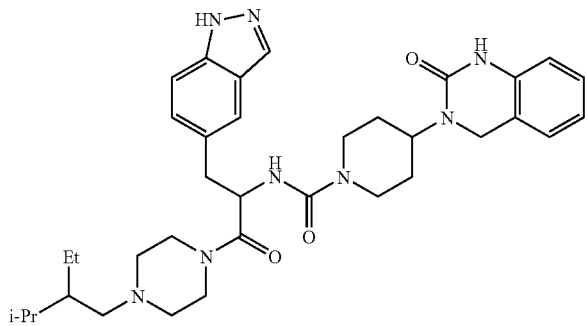 | 2.36 | 629 |

TABLE 1-continued

Examples 40b-40k.

| Example No. | Structure | HPLC Retention time (min) | Mass spec (MH)+ |
|---|---|---|---|
| 40j | 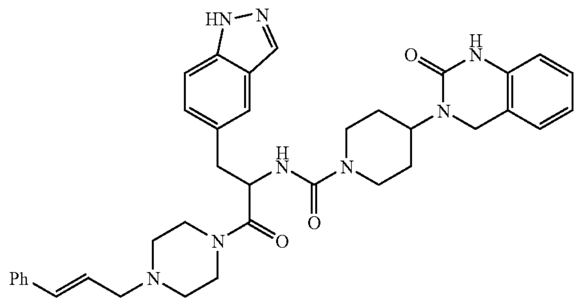 | 1.66 | 647 |
| 40k | 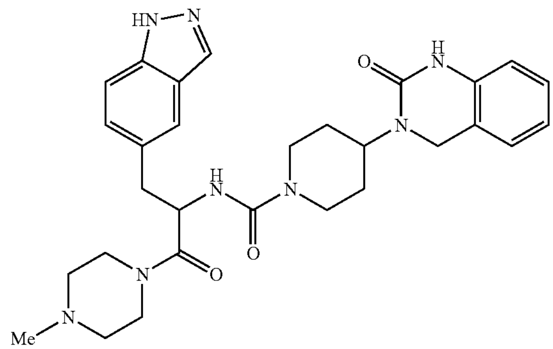 | 2.61 | 545 |

Example 41a 3-(7-Methyl-1H-indazol-5-yl)-2-{[4-(2-oxo-1,4-dihydro-2H-quinazolin-3-yl)-piperidine-1-carbonyl]-amino}-propionic acid cyclohexyl ester

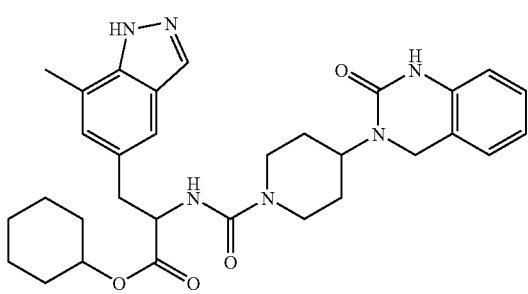

To a stirred solution of (±)-2-amino-3-(7-methyl-1H-indazol-5-yl)-propionic acid (20 mg, 0.042 mmoles), 4-(dimethylamino)pyridine (2.5 mg, 0.02 mmoles), and 1-[3-(dimethylamino)propyl]-3-ethylcarbodimide hydrochloride (33 mg, 0.17 mmoles) in methylene chloride (2 mL) and dimethylformamide (1 mL), was added cyclohexanol (13.3 μL, 0.126 mmoles). The reaction mixture was stirred at 50-55° C. for 4 h. The solvent was removed under reduced pressure, the residue purified by preparative TLC on silica gel (9:1 chloroform/methanol) to give the desired product as white solid (9.4 mg, 40%).

$^1$H-NMR (CD$_3$OD, 500 MHz) δ 1.32-1.87 (14H, m), 2.57 (3H, s), 2.86 (2H, m), 3.11-3.26 (2H, m), 4.13-4.22 (3H, m), 4.46 (1H, m), 4.55 (1H, m), 4.80 (1H, m), 6.79 (1H, d), 6.97 (1H, m), 7.08-7.18 (2H, m), 7.35 (1H, s), 7.47 (1H, s), 8.01-8.02 (1H, m). Mass spec.: 559.22 (MH)+.

Similarly Prepared:

Example 41b 3-(7-Methyl-1H-indazol-5-yl)-2-{[4-(2-oxo-1,4-dihydro-2H-quinazolin-3-yl)-piperidine-1-carbonyl]-amino}-propionic acid 1-benzyl-piperidin-4-yl ester

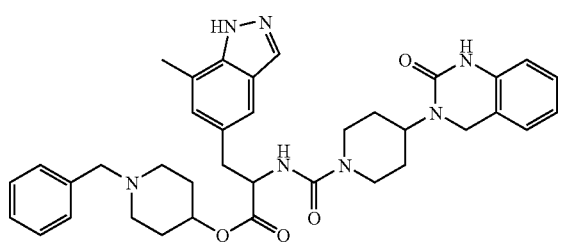

LC/MS: t$_R$=1.76 min, 650.30 (MH)+.

Example 41c 3-(7-Methyl-1H-indazol-5-yl)-2-{[4-(2-oxo-1,4-dihydro-2H-quinazolin-3-yl)-piperidine-1-carbonyl]-amino}-propionic acid 1-methyl-piperidin-4-yl ester

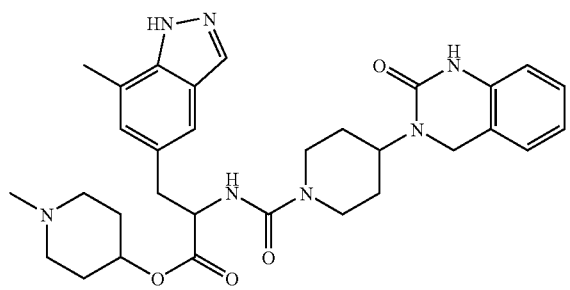

LC/MS: $t_R$=1.59 min, 574.27 (MH)$^+$.

Example 41d 3-(7-Methyl-1H-indazol-5-yl)-2-{[4-(2-oxo-1,4-dihydro-2H-quinazolin-3-yl)-piperidine-1-carbonyl]-amino}-propionic acid 4-phenyl-cyclohexyl ester

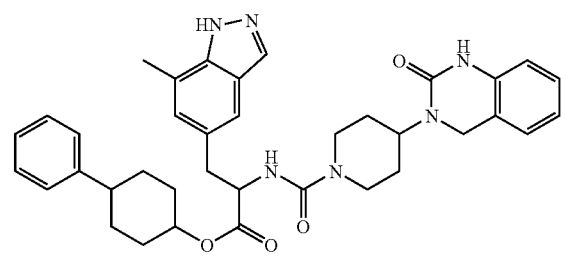

LC/MS: $t_R$=2.69 min, 635.29 (MH)$^+$.

Example 41e 3-(7-Methyl-1H-indazol-5-yl)-2-{[4-(2-oxo-1,4-dihydro-2H-quinazolin-3-yl)-piperidine-1-carbonyl]-amino}-propionic acid (R)-1-pyridin-4-yl-ethyl ester

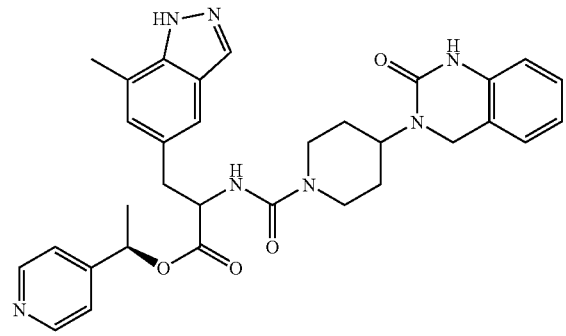

LC/MS: $t_R$=1.66 min, 582.22 (MH)$^+$.

Example 41f 3-(7-Methyl-1H-indazol-5-yl)-2-{[4-(2-oxo-1,4-dihydro-2H-quinazolin-3-yl)-piperidine-1-carbonyl]-amino}-propionic acid (S)-1-pyridin-4-yl-ethyl ester

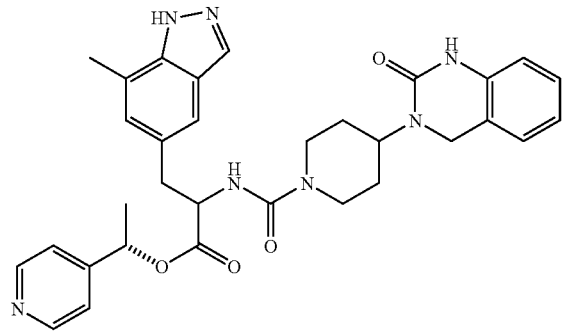

LC/MS: $t_R$=1.65 min, 582.23 (MH)$^+$.

4-Bromo-2-chloro-6-methylphenyldiazo-t-butyl sulfide

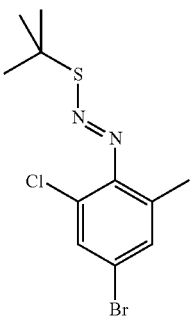

4-Bromo-2-chloro-6-methylaniline (4.0 g, 18.3 mmol) was suspended in 24% hydrochloric acid (5 mL). The stirred mixture was cooled to –20° C. and treated with sodium nitrite (1.32 g, 1.05 equiv.) in water (2 mL), dropwise over 10 min while the temperature was maintained below –5° C. After a further 30 min at –5° C. to –20° C., the mixture was buffered to ca. pH 5 with solid sodium acetate. This mixture (kept at ca. –10° C.) was added in portions to a stirred solution of t-butyl thiol (2.06 mL, 1 equiv.) in ethanol (18.5 mL) at 0° C. over ca. 10 min. Following addition, the mixture was stirred at 0° C. for 30 min and then crushed ice (ca. 50 mL) was added. The mixture was stored in the refrigerator overnight. The resulting light-brown solid was collected by filtration, washed with water, and dried under high vacuum for several hours (4.60 g, 78%). Mass spec.: 323.03 (MH)$^+$.

5-Bromo-7-chloroindazole

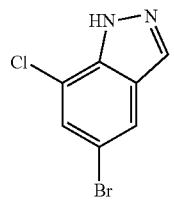

Into a flame-dried round bottom flask, 4-bromo-2,-chloro-6-methylphenyldiazo-t-butyl sulfide (4.60 g, 14.4 mmol) and potassium t-butoxide (16.1 g, 10 equiv) were combined. A stir bar was added and the mixture placed under nitrogen. To this was added dry DMSO (50 mL). The mixture was stirred vigorously for 10 min at room temperature. The reaction mixture was then carefully poured into a mixture of crushed ice (150 mL) and 10% hydrochloric acid (74 mL). The resulting suspension was left to stand at 4° C. overnight and the solid was collected by filtration and washed with water. The solid was collected and dried in vacuo to give 2.86 g (86%) as a beige solid. $^1$H-NMR (CDCl$_3$, 500 MHz) δ 7.52 (d, J=1.5, 1H), 7.82 (d, J=1.5, 1H), 8.08 (s, 1H). Mass spec.: 230.90 (MH)$^+$.

7-Chloroindazole-5-carboxaldehyde

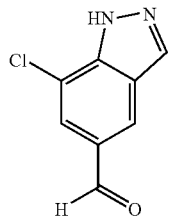

5-Bromo-7-chloroindazole (2.0 g, 8.7 mmol) and sodium hydride (221 mg, 1.1 equiv) were weighed into a flame-dried round-bottom flask containing a magnetic stir bar. Under a nitrogen atmosphere at room temperature, dry tetrahydrofuran (30 mL) was added. The mixture was stirred at room temperature for 15 min, during which time it became homogeneous. The stirred mixture was cooled to −78° C. and a solution of tert-butyllithium in pentane (1.7 M, 10.5 mL, 2.0 equiv) was added over several minutes. After 30 min at −78° C., the reaction was gradually warmed to −50° C., kept there for 15 min, and recooled to −78° C. Dimethylformamide (2.8 mL) was slowly added and the mixture allowed to warm to −50° C. The solution was quickly transferred to a separatory funnel containing diethyl ether and water. The aqueous was made acidic by the addition of 1 M potassium hydrogen sulfate and neutralized by the addition of sodium bicarbonate. The aqueous was extracted with diethyl ether (3×) which was washed with water, then brine, dried over magnesium sulfate, and concentrated to give 1.7 g (100%) of nearly pure material. An analytically pure sample was obtained by recrystallization from hot methanol. $^1$H-NMR (CDCl$_3$, 500 MHz) δ 7.97 (s, 1H), 8.20 (s, 1H), 8.30 (s, 1H), 10.02 (s, 1H). Mass spec.: 181.09 (MH)$^+$.

2-Benzyloxycarbonylamino-3-(7-chloro-1H-indazol-5-yl)-acrylic acid methyl ester

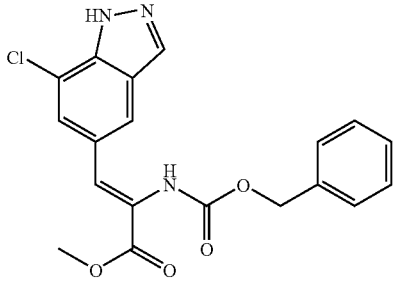

A stirred suspension of potassium tert-butoxide (375 mg, 1.2 equiv.) in methylene chloride (20 mL) was cooled to −20° C. and treated with a solution of N-benzyloxycarbonyl-α-phosphonoglycine trimethyl ester (1.11 g, 1.2 equiv.) in methylene chloride (5 mL). After 10 min, 7-chloroindazole-5-carboxaldehyde (0.50 g, 2.79 mmol) in methylene chloride (5 mL) was added. The reaction was allowed to gradually warm to room temperature and was stirred for 3 days. The reaction was poured into a separatory funnel containing water and diethyl ether. The aqueous was extracted with diethyl ether (3×) which was washed with brine, dried over magnesium sulfate, and concentrated. Column chromatography gave 0.40 g (37%) of product along with 0.20 g (40%) of starting material. $^1$H-NMR (CDCl$_3$, 500 MHz) δ 3.64 (s, 3H), 5.11 (s, 2H), 6.44 (bs, 1H), 7.30 (bs, 5H), 7.43 (s, 1H), 7.62 (s, 1H), 7.80 (s, 1H), 8.07 (s, 1H). Mass spec.: 386.16 (MH)$^+$.

(±)-2-Amino-3-(7-chloro-1H-indazol-5-yl)-propionic acid methyl ester

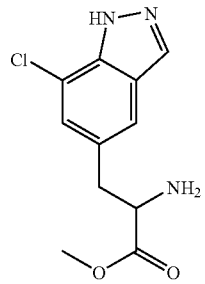

A solution of 2-benzyloxycarbonylamino-3-(7-chloro-1H-indazol-5-yl)-acrylic acid methyl ester (300 mg, 0.78 mmol) in methanol (10 mL) was treated with trifluoroacetic acid (0.2 mL), flushed with nitrogen, and treated with 10% palladium on charcoal (30 mg). The flask was flushed with hydrogen and allowed to stir under an atmosphere of hydrogen. After 4 days, all starting material had been consumed. The reaction was flushed with nitrogen, filtered through celite, and concentrated. Column chromatography gave 78 mg (40%).

$^1$H-NMR (CDCl$_3$, 500 MHz) δ 1.31 (bs, 3H), 2.95 (dd, J=13.7, 7.9, 1H), 3.18 (dd, J=13.7, 5.2, 1H), 3.48 (s, 3H), 3.78 (dd, J=7.9, 5.2, 1H), 7.23 (s, 1H), 7.46 (s, 1H), 8.00 (s, 1H). Mass spec.: 254.06 (MH)$^+$.

Example 42

(±)-3-(7-Chloro-1H-indazol-5-yl)-2-{[4-(2-oxo-1,4-dihydro-2H-quinazolin-3-yl)-piperidine-1-carbonyl]-amino}-propionic acid methyl ester

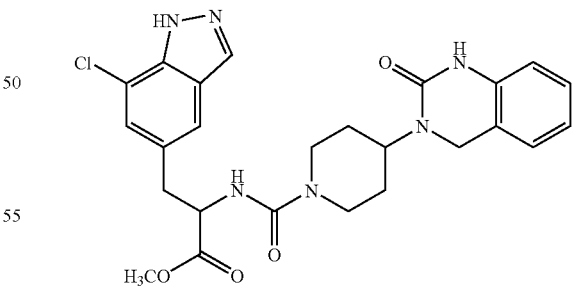

A stirred solution of (±)-2-amino-3-(7-chloro-1H-indazol-5-yl)-propionic acid methyl ester (78 mg, 0.31 mmol) in tetrahydrofuran (2 mL) at 0° C. was treated with carbonyl diimidazole (50 mg, 1 equiv). The reaction was stirred for 5 min, warmed to room temperature, stirred 10 min, and treated with 3-piperidin-4-yl-3,4-dihydro-1H-quinazolin-2-one (78 mg, 1.1 equiv). The mixture was stirred at room temperature overnight. The solvent was evaporated and the residue purified by column chromatography to give 148 mg (94%) as a white powder. $^1$H-NMR (DMSO-$d_6$, 500 MHz) δ 1.46 (m, 4H), 2.55-2.80 (m, 2H), 3.05 (dd, J=13.7, 10.7, 1H), 3.15 (m, 1H), 3.62 (s, 3H), 4.04 (d, J=13.4, 2H), 4.11 (s, 2H), 4.22-4.39 (m, 2H), 6.76 (d, J=7.9, 1H), 6.87 (dd, J=7.3, 7.3, 1H), 6.90 (d, J=8.2, 1H), 7.08 (d, J=7.6, 1H), 7.12 (dd, J=7.6, 7.6, 1H), 7.40 (s, 1H), 7.60 (s, 1H), 8.15 (s, 1H), 9.18 (s, 1H), 13.48 (s, 1H). Mass spec.: 511.18 (MH)$^+$.

Example 43

(±)-4-(2-Oxo-1,4-dihydro-2H-quinazolin-3-yl)-piperidine-1-carboxylic acid[2-[1,4']bipiperidinyl-1'-yl-1-(7-chloro-1H-indazol-5-ylmethyl)-2-oxo-ethyl]-amide

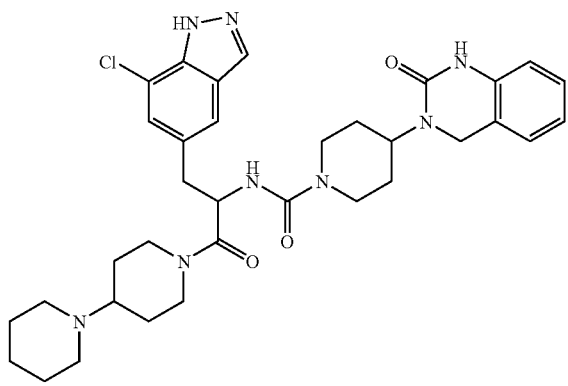

A suspension of (±)-3-(7-chloro-1H-indazol-5-yl)-2-{[4-(2-oxo-1,4-dihydro-2H-quinazolin-3-yl)-piperidine-1-carbonyl]-amino}-propionic acid methyl ester (15 mg, 0.029 mmol) in 1:1 tetrahydrofuran/methanol (1 mL) at room temperature was treated with a solution of lithium hydroxide (3.0 mg, 2.5 equiv) in water (0.25 mL), and the resulting solution was stirred for 1.5 h. The solution was cooled to 0° C., treated with aqueous 1 M potassium hydrogen sulfate (60 μL, 2.0 equiv), and concentrated to give the crude acid which was immediately used without purification. The crude acid was dissolved in dimethylformamide (0.3 mL) and sequentially treated with methylene chloride (0.15 mL), 4-piperidyl-piperidine (10.1 mg, 2 equiv), diisopropylethylamine (10 μL, 2 equiv), and PyBOP® (16.5 mg, 1.1 equiv). The solution was stirred 30 min and concentrated. The product was purified by column chromatography to give 14.7 mg (77%, 2 steps). $^1$H-NMR (CDCl$_3$, 500 MHz) δ 1.30-1.60 (m, 8H), 1.65-1.88 (m, 5H), 2.14 (m, 1H), 2.23 (m, 1H), 2.30-2.70 (m, 7H), 2.80-3.20 (m, 5H), 3.94 (d, J=13.4, 13.1, 1H), 4.10-4.30 (m, 4H), 4.55 (m, 1H), 4.62 (dd, J=13.1, 12.8, 1H), 5.19 (m, 1H), 5.91 (dd, J=30.2, 22.3, 1H), 6.70 (d, J=7.6, 1H), 6.92 (dd, J=7.6, 7.3, 1H), 7.01 (dd, J, 7.9, 7.6, 1H), 7.13 (s, 0.4H), 7.15 (dd, J=7.9, 7.6, 1H), 7.24 (s, 0.6H), 7.33 (s, 0.4H), 7.43 (s, 0.6H), 7.49 (bs, 1H), 7.91 (s, 0.4H), 7.95 (s, 0.6H), 11.25 (bd, J=50.7, 1H). Mass spec.: 647.37 (MH)$^+$.

4-Bromo-2-ethyl-6-methyl-phenylamine

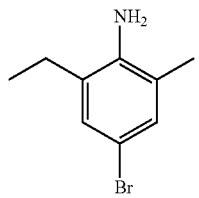

2-Ethyl-6-methyl-phenylamine (14 mL, 100 mmol) was dissolved in concentrated hydrochloric acid (30 mL) and water (220 mL) and cooled to 0° C. To this was added bromine (5.1 mL, 1 equiv.) dropwise. There was rapid formation of a white precipitate. The precipitate was filtered and washed with diethyl ether. The precipitate was suspended in water and neutralized with aqueous potassium carbonate. An oil formed which was extracted into diethyl ether. The ethereal was dried over potassium carbonate, filtered, and concentrated to give 7.0 g (33%) as a purple oil which was used without purification. Mass spec.: 214.01 (MH)$^+$.

4-Bromo-2-ethyl-6-methylphenyldiazo-t-butyl sulfide

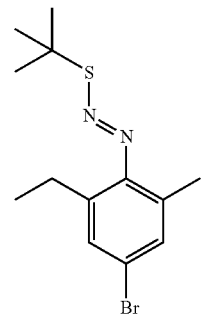

4-Bromo-2-ethyl-6-methylaniline (7.0 g, 33 mmol) was suspended in 7.8 M hydrochloric acid (30 mL). The stirred mixture was cooled to −20° C. and treated with sodium nitrite (2.27 g, 1.05 equiv.) in water (5 mL), dropwise over 10 min while the temperature was maintained below −5° C. After a further 30 min at −5° C. to −20° C., the mixture was buffered to ca. pH 5 with solid sodium acetate. This mixture (kept at ca. −10° C.) was added in portions to a stirred solution of t-butyl thiol (3.7 mL, 1 equiv.) in ethanol (50 mL) at 0° C. over ca. 10 min. Following addition, the mixture was stirred at 0° C. for 30 min and then crushed ice (ca. 50 mL) was added. The mixture was stored in the refrigerator for 2 h. The resulting light-brown solid was collected by filtration, washed with water, and dried under high vacuum for several hours (9.47 g, 92%). Mass spec.: 315.05 (MH)$^+$.

5-Bromo-7-ethyl-1H-indazole

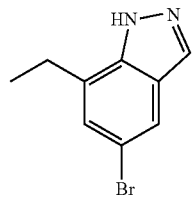

To a stirred solution of potassium t-butoxide (33.6 g, 10 equiv.) in DMSO (200 mL) was added a solution of 4-bromo-2-ethyl-6-methylphenyldiazo-t-butyl sulfide (9.4 g, 30 mmol) in DMSO (100 mL) via cannula. The mixture was stirred vigorously for 1 h. The reaction mixture was then carefully poured into a mixture of crushed ice (500 mL), concentrated hydrochloric acid (25 mL), and water (100 mL). The resulting precipitate was filtered, washed with water, dissolved in methanol, and concentrated to give 5.7 g (85%) as a tan solid. $^1$H-NMR (CDCl$_3$, 500 MHz) δ 1.39 (t, J=7.6, 3H), 2.92 (q, J=7.6, 2H), 7.30 (s, 1H), 7.75 (s, 1H), 8.04 (s, 1H). Mass spec.: 225.00 (MH)+.

7-Ethyl-1H-indazole-5-carbaldehyde

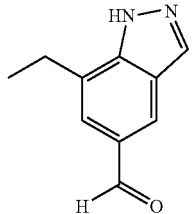

5-Bromo-7-ethyl-1H-indazole (2.0 g, 8.9 mmol) and sodium hydride (226 mg, 1.1 equiv.) were weighed into a flame-dried round-bottom flask containing a magnetic stir bar. Under a nitrogen atmosphere at room temperature, dry tetrahydrofuran (60 mL) was added. The mixture was stirred at room temperature for 15 min. The stirred mixture was cooled to −78° C. and a solution of tert-butyllithium in pentane (1.7 M, 10.5 mL, 2.0 equiv.) was added over several minutes. After 15 min at −78° C., the reaction was gradually warmed to −50° C., and recooled to −78° C. Dimethylformamide (2.8 mL) was slowly added and the mixture allowed to warm to −50° C. The solution was quickly transferred to a stirred solution of water 300 mL and 1 M potassium hydrogen sulfate (25 mL). The resulting suspension was extracted with diethyl ether, washed with water, then brine, dried over magnesium sulfate, and concentrated. Column chromatography gave 160 mg (10%) as a white solid. $^1$H-NMR (CD$_3$OD, 500 MHz) δ 1.38 (t, J=7.6, 3H), 2.98 (q, J=7.6, 2H), 7.71 (s, 1H), 8.22 (s, 1H), 8.24 (s, 1H), 9.96 (s, 1H). Mass spec.: 175.08 (MH)+.

2-Benzyloxycarbonylamino-3-(7-ethyl-1H-indazol-5-yl)-acrylic acid methyl ester

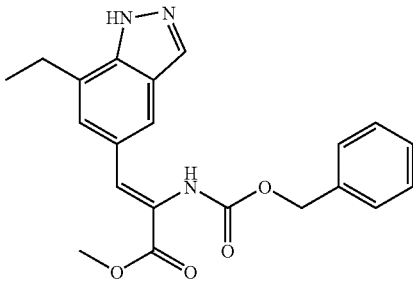

To a stirred solution of N-benzyloxycarbonyl-α-phosphonoglycine trimethyl ester (0.61 g, 2.0 equiv.) and 7-ethyl-1H-indazole-5-carbaldehyde (160 mg, 0.92 mmol) in tetrahydrofuran (5 mL) at 0° C. was added tetramethylguanidine (0.22 mL, 1.9 equiv.). The reaction was allowed to slowly warm to room temperature overnight. The reaction was concentrated, dissolved in diethyl ether, washed with water, then brine, dried (magnesium sulfate), and concentrated. The residue was purified by column chromatography to give 333 mg (95%) as an oil. $^1$H-NMR (CDCl$_3$, 500 MHz) δ 1.33 (t, J=7.6, 3H), 2.86 (q, J=7.3, 2H), 3.83 (s, 3H), 5.11 (s, 2H), 6.39 (bs, 1H), 7.29 (bs, 5H), 7.43 (s, 1H), 7.50 (s, 1H), 7.78 (s, 1H), 8.04 (s, 1H). Mass spec.: 380.17 (MH)+.

(±)-2-Amino-3-(7-ethyl-1H-indazol-5-yl)-propionic acid methyl ester

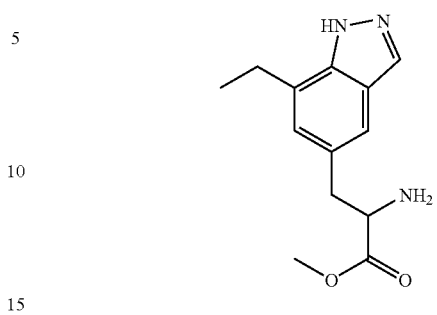

To a solution of 2-benzyloxycarbonylamino-3-(7-ethyl-1H-indazol-5-yl)-acrylic acid methyl ester (330 mg, 0.78 mmol) in methanol (5 mL) under nitrogen was added palladium on charcoal (10%, 33 mg). The flask was flushed with hydrogen and allowed to stir under an atmosphere of hydrogen overnight. The reaction was flushed with nitrogen, filtered through celite, and concentrated to give 210 mg (98%) which was used without purification. $^1$H-NMR (CDCl$_3$, 500 MHz) δ 1.34 (t, J=7.6, 3H), 2.85 (q, J=7.6, 2H), 2.96 (dd, J=13.7, 7.6, 1H), 3.19 (dd, J=13.7, 8.6, 1H), 3.48 (s, 2H), 3.73 (s, 3H), 3.80 (dd, J=7.6, 5.2, 1H), 6.99 (s, 1H), 7.38 (s, 1H), 7.97 (s, 1H). Mass spec.: 248.15 (MH)+.

Example 44

(±)-3-(7-Ethyl-1H-indazol-5-yl)-2-{[4-(2-oxo-1,4-dihydro-2H-quinazolin-3-yl)-piperidine-1-carbonyl]-amino}-propionic acid methyl ester

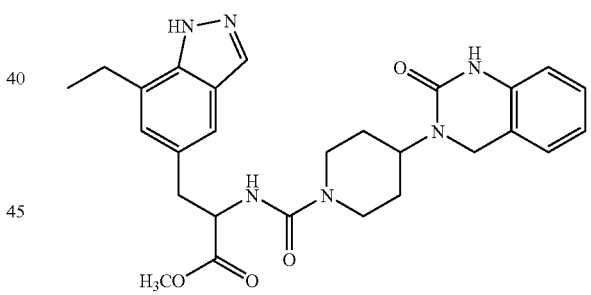

A stirred solution of (±)-2-amino-3-(7-ethyl-1H-indazol-5-yl)-propionic acid methyl ester (100 mg, 0.41 mmol) in tetrahydrofuran (2 mL) at 0° C. was treated with carbonyl diimidazole (66 mg, 1 equiv). The reaction was stirred for 5 min, warmed to room temperature, stirred for 15 min, and then treated with 3-piperidin-4-yl-3,4-dihydro-1H-quinazolin-2-one (103 mg, 1.1 equiv). The mixture was stirred at room temperature overnight. The solvent was evaporated and the residue purified by column chromatography to give 188 mg (92%) as a white solid. $^1$H-NMR (CDCl$_3$, 500 MHz) δ 1.36 (t, J=7.6, 3H), 1.69 (m, 4H), 2.86 (m, 2H), 2.90 (q, J=7.6, 2H), 3.22 (dd, J=5.5, 4.9, 2H), 3.75 (s, 3H), 4.03 (dd, J=44.0, 13.7, 2H), 4.26 (s, 2H), 4.51 (m, 1H), 4.84 (m, 1H), 5.02 (m, 1H), 6.70 (d, J=7.9, 1H), 6.90-7.05 (m, 4H), 7.16 (dd, J=7.6, 7.6, 1H), 7.34 (s, 1H), 8.03 (s, 1H). Mass spec.: 505.29 (MH)+.

Example 45

(±)-4-(2-Oxo-1,4-dihydro-2H-quinazolin-3-yl)-piperidine-1-carboxylic acid[2-[1,4']bipiperidinyl-1'-yl-1-(7-ethyl-1H-indazol-5-ylmethyl)-2-oxo-ethyl]-amide

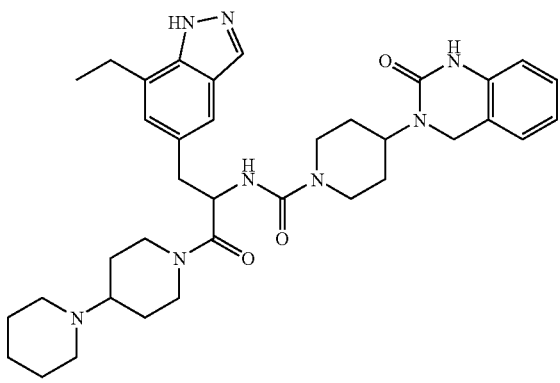

To a solution of (±)-3-(7-ethyl-1H-indazol-5-yl)-2-{[4-(2-oxo-1,4-dihydro-2H-quinazolin-3-yl)-piperidine-1-carbonyl]-amino}-propionic acid methyl ester (15 mg, 0.03 mmol) in methanol (0.6 mL) was added a solution of lithium hydroxide monohydrate (3.0 mg, 2.5 equiv) in water (0.1 mL), and the resulting solution was stirred for 6 h. The solution was cooled to 0° C., treated with aqueous 1 M potassium hydrogen sulfate (60 µL, 2.0 equiv), and concentrated to give the crude acid which was immediately used without purification. The crude acid was dissolved in dimethylformamide (0.4 mL), cooled to 0° C., and sequentially treated with methylene chloride (0.2 mL), 4-piperidyl-piperidine (11 mg, 2.2 equiv), diisopropylethylamine (12 µL, 2.3 equiv.), and PyBOP® (19 mg, 1.2 equiv). The solution was stirred for 15 min at 0° C., warmed to room temperature, stirred 1.5 h, and concentrated. The product was purified by column chromatography to give 14.5 mg (76%, 2 steps). $^1$H-NMR (CDCl$_3$, 500 MHz) δ 1.28-1.48 (m, 10H), 1.52 (m, 2H), 1.60-1.82 (m, 6H), 1.95 (m, 1.4H), 2.06 (m, 1.6H), 2.20-2.50 (m, 5H), 2.77-2.93 (m, 5H), 2.96-3.17 (m, 2H), 3.76 (d, J=13.4, 0.4H), 3.86 (d, J=13.7, 0.6H), 4.10-4.20 (m, 2H), 4.26 (s, 2H), 4.57 (m, 2H), 5.10-5.24 (m, 1H), 5.67 (d, J=8.2, 0.6H), 5.74 (d, J=7.9, 0.4H), 6.67 (d, J=7.9, 1H), 5.67 (d, J=8.2, 0.6H), 5.74 (d, J=7.9, 0.4H), 6.67 (d, J=7.9, 1H), 6.93 (dd, J=7.6, 7.3, 1H), 6.96 (s, 0.4H), 7.03 (dd, J=7.0, 6.7, 1H), 7.09 (m, 1.6H), 7.15 (dd, J=7.0, 6.7, 1H), 7.31 (s, 0.4H), 7.38 (s, 0.6H), 7.94 (s, 0.4H), 7.95 (s, 0.6H). Mass spec.: 641.50 (MH)$^+$.

(3,4-Dinitro-phenyl)-methanol

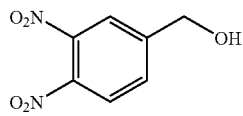

Borane-tetrahydrofuran complex (1M in tetrahydrofuran, 800 mL, 800 mmol) was added at −20° C. over 45 min to a solution of 3,4-dinitrobenzoic acid (93.5 g, 441 mmol) in tetrahydrofuran (300 mL). The resulting mixture was stirred at −20° C. for 1 h and then warmed to room temperature and stirred overnight. It was quenched by the addition of 32 mL of 1:1 acetic acid/water. Solvents were removed in vacuo and the residue was poured into an ice-cold 1000 mL of sat. sodium bicarbonate with vigorous stirring over 15 min. The mixture was extracted with ethyl acetate (3×500 mL). The combined organic layers were washed with sat. sodium bicarbonate, brine and dried over sodium sulfate. After filtration, solvents were removed to afford the title compound as a light yellow solid (100%). $^1$H-NMR (CDCl$_3$, 500 MHz) δ 7.91 (d, J=8.0 Hz, 1H), 7.89 (s, 1H), 7.71 (dd, J=8.5, 1.0 Hz, 1H), 4.87 (s, 2H), 2.30 (s, 1H).

3,4-Dinitro-benzaldehyde

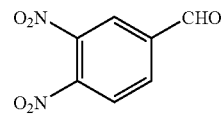

A solution of (3,4-dinitro-phenyl)-methanol (95.3 g, 481 mmol) in methylene chloride (500 mL) was added all at once to a suspension of pyridinium chlorochromate (156 g, 722 mmol) in methylene chloride (900 mL). The mixture was stirred at room temperature for 1.5 h and then ether (1500 mL) was added. The supernatant was decanted from the resulting black gum, and the insoluble residue was washed thoroughly with methylene chloride (3×250 mL). The combined organic solution were filtered through a pad of florisil to afford a light bright yellow clear solution. Solvents were removed in vacuo and the residue was purified by silica gel chromatography using methylene chloride as eluent to afford the title compound as a yellow solid (71%). $^1$H-NMR (CDCl$_3$, 300 MHz) δ 8.45 (d, J=1.5 Hz, 1H), 8.28 (dd, J=8.1, 1.5 Hz, 1H), 8.07 (d, J=8.1 Hz, 1H). $^{13}$CNMR (CD$_3$OD, 125 MHz) δ 187.7, 139.2, 134.2, 126.2, 125.7.

2-Benzyloxycarbonylamino-3-(3,4-dinitro-phenyl)-acrylic acid methyl ester

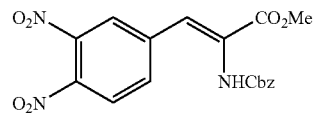

1,1,3,3-Tetramethylguanidine (41.2 mL, 329 mmol) was added at room temperature to a solution of N-(benzyloxycarbonyl)-alpha-phophonoglycine trimethyl ester (114.1 g, 344 mmol) in tetrahydrofuran (800 mL). The mixture was stirred at room temperature for 15 min and cooled to −78° C. A solution 3,4-dinitro-benzaldehyde (61.4 g, 313 mmol) in tetrahydrofuran (200 mL) was slowly added via cannula. The resulting mixture was stirred at −78° C. for 2 h and then allowed to warm to room temperature overnight. Solvents were removed in vacuo, and the yellow residue was dissolved in 4.5 L of ethyl acetate. The solution was washed with 1.5 L of 1N sulfuric acid, water twice, brine and dried over sodium sulfate. After filtration, solvents were removed in vacuo and the residue was crystallized from ethyl acetate (20 g crude product/100 mL of ethyl acetate). The yellow crystals were collected and further purified by chromatography on silica gel using methylene chloride as eluent. The title compound was obtained a s yellow crystals (77%). $^1$H-NMR (CDCl$_3$, 500 MHz) δ 7.85 (d, J=1.5 Hz, 1H), 7.74 (d, J=8.0 Hz, 1H), 7.62 (dd, J=8.5, 1.5 Hz, 1H), 7.35-7.34 (m, 3H), 7.34 (br s, 2H), 7.23 (s, 1H), 6.95 (br s, 1H), 5.07 (s, 2H), 3.90 (s, 3H).

Similarly Prepared:

2-Benzyloxycarbonylamino-3-(3-hydroxy-4-nitro-phenyl)-acrylic acid methyl ester

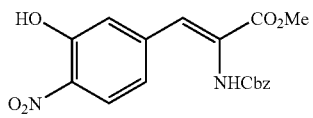

$^1$H-NMR (CDCl$_3$, 500 MHz) δ 7.93 (d, J=9.0 Hz, 1H), 7.32 (br s, sH), 7.28 (br s, 2H), 7.17 (s, 1H), 7.16 (d, J=2.0 Hz, 1H), 7.01 (dd, J=9.0, 2.0 Hz, 1H), 6.74 (br s, 1H), 5.06 (s, 2H), 3.86 (s, 3H).

(R)-2-Benzyloxycarbonylamino-3-(3,4-dinitro-phenyl)-propionic acid methyl ester

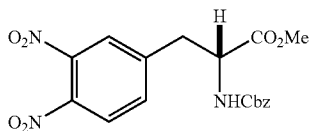

An oven-dried 500 mL Schlenk flask was put into a glove-bag filled with nitrogen. After the glove-bag was evacuated and filled with nitrogen (3×), the flask was sealed and taken out of the glove-bag and weighed. It was put back into the glove-bag and evacuated and filled with nitrogen (3×), then it was charged with (−)-1,2-bis((2R,5R)-2,5-diethylphospholano)benzene(cyclooctadienene)rhodium (I) trifluoromethanesulfonate. The flask was sealed and taken out of the glove-bag and weighed (784 mg, 1.08 mmol). 2-Benzyloxycarbonylamino-3-(3,4-dinitro-phenyl)-acrylic acid methyl ester (8.72 g, 21.7 mmol) was added to another 500 mL of Schlenk flask and was evacuated and filled with nitrogen (3×). Methylene chloride (350 mL, degassed with nitrogen for 2 h) was added and the resulting solution was transferred to the catalyst flask via cannula. The flask was purged and filled with hydrogen (4×) and the mixture was stirred at room temperature for 4 h. The solvents were removed in vacuo and the residue was purified by silica gel chromatography using ethyl acetate/hexanes (1:1) as eluent to afford the title compound as a light tan gummy solid (99% yield and 99.2% ee determined by HPLC analysis using the following conditions: Chiralpak AD column (4.6×250 mm, 10 um; A=ethanol, B=hexane; 40% B @ 1.0 mL/min for 14 min; retention times: 10.9 min for R enatiomer and 6.9 min for S enatiomer). $^1$H-NMR (CDCl$_3$, 500 MHz) δ 7.80 (d, J=8.0 Hz, 1H), 7.63 (s, 1H), 7.45 (d, J=8.0 Hz, 1H), 7.38-7.31 (m, 5H), 5.37 (d, J=6.0 Hz, 1H), 5.13-5.05 (m, 2H), 4.68 (d, J=6.0 Hz, 1H), 3.71 (s, 3H), 3.36 (dd, J=13.5, 5.0 Hz, 1H), 3.17 (dd, J=13.5, 6.0 Hz, 1H).

Similarly Prepared:

(R)-2-Benzyloxycarbonylamino-3-(3-hydroxy-4-nitro-phenyl)-propionic acid methyl ester

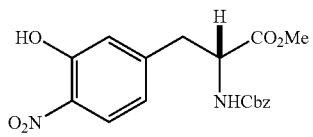

$^1$H-NMR (CDCl$_3$, 500 MHz) δ 7.97 (d, J=9.0 Hz, 1H), 7.36-7.30 (m, 5H), 6.90 (s, 1H), 6.71 (d, J=8.5 Hz, 1H), 5.29 (d, j=7.0 Hz, 1H), 5.11 (d, J=12.5 Hz, 1H), 5.07 (d, J=12.0 Hz, 1H), 4.68 (dd, j=13.0, 6.0 Hz, 1H), 3.74 (s, 3H), 3.20 (dd, j=13.5, 5.0 Hz, 1H), 3.05 (dd, J=13.5, 6.0 Hz, 1H).

(R)-2-Benzyloxycarbonylamino-3-(3,4-diamino-phenyl)-propionic acid methyl ester

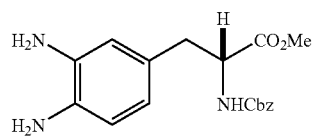

Solid ammonium formate (2.27 g, 36 mmol) was added in small portions at 0° C. to a methanol (50 mL, degassed with nitrogen for 2 h) suspension of (R)-2-benzyloxycarbonylamino-3-(3,4-dinitro-phenyl)-propionic acid methyl ester (1.45 g, 3.6 mmol) and zinc powder (1.41 g, 21.6 mmol). The resulting mixture was stirred at room temperature overnight. The solvents were removed in vacuo and then toluene (30 mL, degassed) and ethyl acetate (30 mL, degassed) were added, followed by acetic acid (3 mL). The mixture was further diluted until all organic solids dissolved, then it was washed with water, brine and dried over sodium sulfate. After filtration, solvents were removed in vacuo to afford the title compound containing 1 equivalent of acetic acid as a reddish gummy solid (85%). Mass Spec.: 344.18 (MH)$^+$.

(R)-2-Benzyloxycarbonylamino-3-(2-methyl-1H-benzoimidazol-5-yl)-propionic acid methyl ester

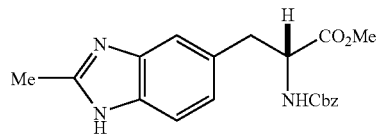

A solution of (R)-2-benzyloxycarbonylamino-3-(3,4-diamino-phenyl)-propionic acid methyl ester-acetic acid (640 mg) in acetic acid (8 mL) was heated at 130° C. for 4 h. The mixture was then poured into water and cooled to 0° C. The pH was adjusted to 8 by gradual addition of solid sodium bicarbonate. The mixture was then extracted with ethyl acetate (3×100 mL), and the combined organic layers were washed with water, brine and dried over sodium sulfate. After filtration, solvents were removed to afford the title compound as a brownish foamy solid (95%). $^1$H-NMR (CDCl$_3$, 500 MHz) δ 7.39 (d, J=8.5 Hz, 1H), 7.35 (s, 1H), 7.26-7.22 (m, 5H), 7.06 (d, J=8.0 Hz, 1H), 5.03 (d, J=12.5 Hz, 1H), 4.99 (d, J=13.0 hz, 1H), 4.51 (dd, J=8.5, 5.5 Hz, 1H), 3.70 (s, 3H), 3.27 (dd, J=13.5, 5.0 Hz, 1H), 3.03 (dd, J=14.0, 9.0 Hz, 1H), 2.55 (s, 3H). Mass spec.: 368.19 (MH)$^+$.

(R)-2-Benzyloxycarbonylamino-3-[2-methyl-3-(2-trimethylsilanyl-ethanesulfonyl)-3H-benzoimidazol-5-yl]-propionic acid methyl ester and (R)-2-Benzyloxycarbonylamino-3-[2-methyl-1-(2-trimethylsilanyl-ethanesulfonyl)-1H-benzoimidazol-5-yl]-propionic acid methyl ester

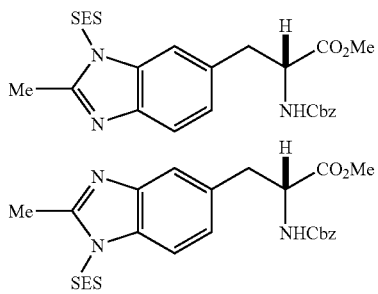

To a suspension of (R)-2-benzyloxycarbonylamino-3-(2-methyl-1H-benzoimidazol-5-yl)-propionic acid methyl ester (533 mg, 1.96 mmol), and sodium carbonate in acetonitrile (20 mL) was added neat 2-trimethylsilanyl-ethanesulfonyl chloride all at once. The mixture was stirred at room temperature overnight. Solvents were removed and the residue was purified by chromatography on silica gel using ethyl acetate/hexanes (1:2) as eluent to afford the title compound as a waxy solid (1:1 mixture of N1 and N3 isomers, 66%).

$^1$H-NMR (CDCl$_3$, 500 MHz) δ 7.68 (d, J=8.5 hz, 0.5H), 7.55 (d, J=8.5 Hz, 0.5H), 7.53 (s, 0.5H), 7.41 (s, 0.5H), 7.34-7.29 (m, 5H), 7.06-7.04 (m, 1H), 5.22 (d, J=8.0 Hz, 0.5H), 5.17 (d, J=7.5 Hz, 0.5H), 5.11-5.07 (m, 2H), 4.72-4.69 (m, 1H), 3.75 (s, 1.5H), 3.72 (s, 1.5H), 3.24-3.17 (m, 2H), 2.79 (s, 3H), 0.92-0.83 (m, 2H), −0.02 (s, 4.5H), −0.05 (s, 4.5H). Mass spec.: 532.26 (MH)$^+$.

(R)-2-Amino-3-[2-methyl-1-(2-trimethylsilanyl-ethanesulfonyl)-1H-benzoimidazol-5-yl]-propionic acid methyl ester and (R)-2-Amino-3-[2-methyl-3-(2-trimethylsilanyl-ethanesulfonyl)-3H-benzoimidazol-5-yl]-propionic acid methyl ester

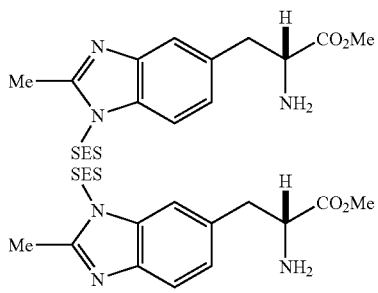

A methanol (50 mL) suspension of (R)-2-benzyloxycarbonylamino-3-[2-methyl-3-(2-trimethylsilanyl-ethanesulfonyl)-3H-benzoimidazol-5-yl]-propionic acid methyl ester and (R)-2-Benzyloxycarbonylamino-3-[2-methyl-1-(2-trimethylsilanyl-ethanesulfonyl)-1H-benzoimidazol-5-yl]-propionic acid methyl ester (1:1 mixture, 600 mg), and 10% palladium on charcoal (180 mg) was agitated on a Parr apparatus overnight under 40 psi of hydrogen at room temperature. After replacing the hydrogen atmosphere with nitrogen, the mixture was filtered through a pad of celite. Solvents were removed in vacuo to afford the title compound as a tan solid (80%). $^1$H-NMR (CD$_3$OD, 500 MHz) δ 7.81 (d, J=8.5, 0.5 Hz, 0.5H), 7.70 (s, 0.5H), 7.58 (d, J=8.5 Hz, 0.5H), 7.49 (s, 0.5H), 7.25 (d, J=9.0 Hz, 1H), 3.89 (dd, J=14.0, 6.5 Hz, 1H), 3.75 (s, 1.5H), 3.72 (s, 1.5H), 3.55-3.51 (m, 2H), 3.18 (d, J=6.0 Hz, 1H), 3.22-3.18 (m, 0.5H), 3.14-3.09 (m, 0.5H), 2.81 (s, 1.5H), 2.80 (s, 1.5H), 0.92-0.88 (m, 2H), 0.02 (s, 4.5H), 0.01 (s, 4.5H); $^{13}$CNMR (CD$_3$OD, 125 MHz) δ 174.3, 174.1, 153.5, 153.3, 141.7, 140.6, 133.9, 133.82, 133.78, 132.7, 126.5, 126.3, 119.7, 119.0, 114.1, 113.4, 55.6, 51.8, 51.7, 51.6, 40.2, 39.8, 15.83, 15.77, 9.9, −3.07, −3.11. Mass spec.: 398.20 (MH)$^+$.

(R)-3-[2-Methyl-1-(2-trimethylsilanyl-ethanesulfonyl)-1H-benzoimidazol-5-yl]-2-{[4-(2-oxo-1,4-dihydro-2H-quinazolin-3-yl)-piperidine-1-carbonyl]-amino}-propionic acid methyl ester and (R)-3-[2-Methyl-3-(2-trimethylsilanyl-ethanesulfonyl)-3H-benzoimidazol-5-yl]-2-{[4-(2-oxo-1,4-dihydro-2H-quinazolin-3-yl)-piperidine-1-carbonyl]-amino}-propionic acid methyl ester

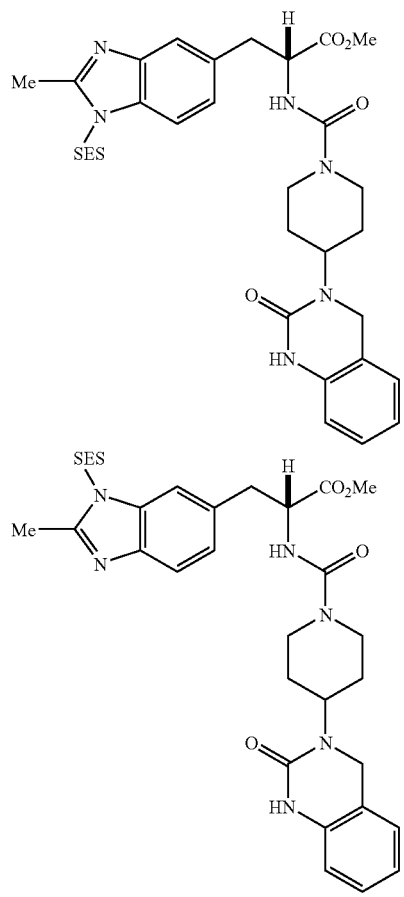

Prepared as described above for (R)-2-{[4-(2-oxo-1,4-dihydro-2H-quinazolin-3-yl)-piperidine-1-carbonyl]-amino}-3-[1-(2-trimethylsilanyl-ethanesulfonyl)-1H-indazol-5-yl]-propionic acid methyl ester. Purified by silica gel chromatography using ethyl acetate with 1% triethylamine as eluent to afford the title compound as an off-white solid (87%). $^1$H-NMR (CD$_3$OD, 500 MHz) δ 7.82 (d, J=8.5 Hz, 0.5H), 7.80 (s, 0.5H), 7.59 (d, J=8.0 Hz, 0.5H), 7.55 (s, 0.5H), 7.33-7.30 (m, 1H), 7.16 (t, J=8.0 Hz, 1H), 7.12 (t, J=7.5 Hz, 1H), 6.95 (t, J=7.5 Hz, 1H), 6.79 (d, J=7.5 Hz, 1H), 4.60-4.55 (m, 1H), 4.45-4.40 (m, 1H), 4.29-4.27 (m, 2H), 4.15-4.10 (m, 2H), 3.77 (s, 1.5H), 3.74 (s, 1.5H), 3.56-3.51 (m, 2H), 3.35-3.31 (m, 2H), 3.21-3.15 (m, 1H), 2.91-2.80 (m, 2H), 2.78 (s, 1.5H), 2.77 (s, 1.5H), 1.76-1.73 (m, 1H), 1.66-1.61 (m, 2H), 0.92-0.87 (m, 2H), 0.009 (s, 4.5H), −0.007 (s, 4.5H). $^{13}$CNMR (CD$_3$OD, 125 MHz) 173.8, 173.7, 158.2, 158.1, 155.6, 153.4, 153.2, 141.6, 140.3, 137.2, 135.3, 135.1, 133.7, 132.5, 128.2, 126.4, 126.3, 125.7, 122.13, 122.10, 119.6, 118.8, 118.4, 114.0, 113.4, 113.2, 57.3, 56.2, 51.9, 51.7, 51.5, 43.8, 43.7, 42.9, 37.6, 37.2, 28.4, 17.4, 15.7, 15.6, 9.9, −3.1, −3.2. Mass spec.: 655.36 (MH)$^+$.

(R)-3-(2-Methyl-1H-benzoimidazol-5-yl)-2-{[4-(2-oxo-1,4-dihydro-2H-quinazolin-3-yl)-piperidine-1-carbonyl]-amino}-propionic acid

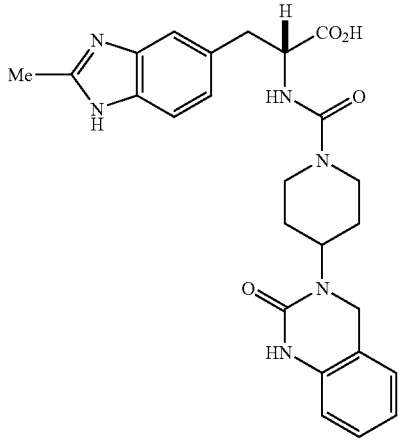

The 1:1 mixture of (R)-3-[2-Methyl-1-(2-trimethylsilanyl-ethanesulfonyl)-1H-benzoimidazol-5-yl]-2-{[4-(2-oxo-1,4-dihydro-2H-quinazolin-3-yl)-piperidine-1-carbonyl]-amino}-propionic acid methyl ester and (R)-3-[2-Methyl-3-(2-trimethylsilanyl-ethanesulfonyl)-3H-benzoimidazol-5-yl]-2-{[4-(2-oxo-1,4-dihydro-2H-quinazolin-3-yl)-piperidine-1-carbonyl]-amino}-propionic acid methyl ester was treated as described above for (R)-2-{[4-(2-oxo-1,4-dihydro-2H-quinazolin-3-yl)-piperidine-1-carbonyl]-amino}-3-[1-(2-trimethylsilanyl-ethanesulfonyl)-1H-indazol-5-yl]-propionic acid. The hydrolysis conditions (lithium hydroxide/methanol-tetrahydrofuran-water (1:1:1) at −15° C. overnight were used. The title compound was obtained as a white solid (25%). Mass spec.: 477.24 (MH)$^+$.

Example 46

(R)-4-(2-Oxo-1,4-dihydro-2H-quinazolin-3-yl)-piperidine-1-carboxylic acid[2-[1,4']bipiperidinyl-1'-yl-1-(2-methyl-1H-benzoimidazol-5-ylmethyl)-2-oxo-ethyl]-amide

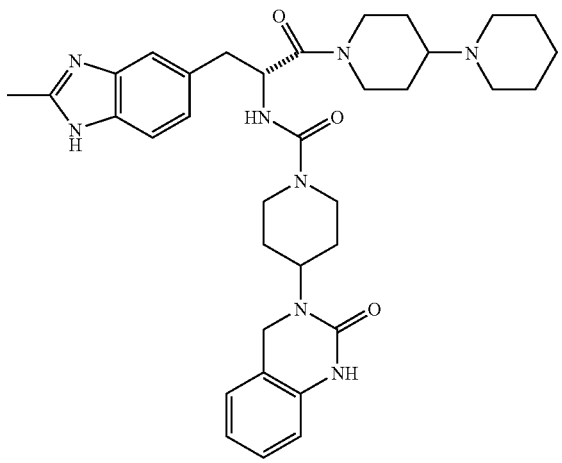

Prepared as described above for (R)-4-(2-oxo-1,4-dihydro-2H-quinazolin-3-yl)-piperidine-1-carboxylic acid {2-[1,4']bipiperidinyl-1'-yl-2-oxo-1-[1-(2-trimethylsilanyl-ethanesulfonyl)-1H-indazol-5-ylmethyl]-ethyl}-amide. Purified by silica gel chromatography using methylene chloride:methanol:triethylamine (93:5:2) as eluent to give a white solid. This was dissolved in ethyl acetate (60 mL) and washed with a 1:1 sat. sodium bicarbonate/brine twice and dried over sodium sulfate. After filtration, solvents were removed to afford the title compound as a white solid (11% yield). LC/MS: t$_R$=1.59 min, 627.34 (MH)$^+$.

(R)-3-(4-Amino-3-hydroxy-phenyl)-2-benzyloxycarbonylamino-propionic acid methyl ester hydrochloride

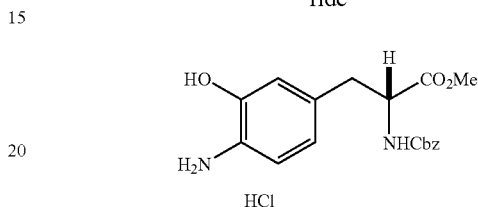

Powdered iron (3.7 g, 66.4 mmol) and ammonium chloride (5.9 g, 111 mmol) were added at 0° C. to a solution of (R)-2-benzyloxycarbonylamino-3-(3hydroxy-4-nitro-phenyl)-propionic acid methyl ester (2.07 g, 5.53 mmol) in degassed 1:1 methanol/water (400 mL). The resulting mixture was stirred at room temperature for 48 h. Trifluoroacetic acid (7 mL) was added, and the mixture was swirled until it was a clear dark red solution containing a suspension of unreacted iron powder. The mixture was filtered and the filtrate was concentrated in vacuo. The residue was extracted with ethyl acetate (2×150 mL), the combined organic layers were washed with brine and dried over sodium sulfate. After filtration, hydrochloric acid (4.2 mL, 4M in dioxane) was added. Solvents were removed in vacuo, and the title compound was obtained as a tan foamy solid (80%). $^1$H-NMR (CD$_3$OD, 500 MHz) δ 7.34-7.28 (m, 5H), 7.20 (d, J=8.0 hz, 1H), 6.88 (s, 1H), 6.78 (d, J=7.5 Hz, 1H), 5.05-5.00 (m, 2H), 4.42 (dd, J=8.5, 5.0 Hz, 1H), 3.70 (s, 3H), 3.65 (s, 1H), 3.33 (br s, 2H), 3.11 (dd, J=14.0, 5.0 hz, 1H), 2.90 (dd, J=13.5, 9.0 Hz, 1H). $^{13}$CNMR (CD$_3$OD, 125 MHz) 172.5, 157.4, 151.2, 140.2, 137.0, 128.5, 128.0, 127.7, 123.8, 120.9, 117.0, 116.9, 67.2, 55.7, 52.0, 37.2. Mass spec.: 345.20 (MH)$^+$.

(R)-2-Benzyloxycarbonylamino-3-(2-oxo-2,3-dihydro-benzooxazol-6-yl)-propionic acid methyl ester

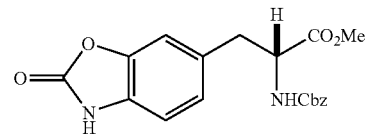

A methylene chloride (15 mL) solution of carbonyl diimidazole (498 mg, 3.07 mmol) was added at 0° C. to a solution of (R)-3-(4-amino-3-hydroxy-phenyl)-2-benzyloxycarbonylamino-propionic acid methyl ester (1.17 g, 3.07 mmol), diisopropylethylamine (1.60 mL, 9.21 mmol), and methylene chloride (85 mL). The mixture was stirred at 0° C. for 4 h. The solvents were removed in vacuo and the residue was purified by silica gel chromatography using ethyl acetate/hexanes as eluent to afford the title compound as a white solid (51%). $^1$H-NMR (CDCl$_3$, 500 MHz) δ 9.07 (s, 1H), 7.37-7.29 (m, 5H), 6.96 (s, 1H), 6.90 (d, J=8.0 Hz, 1H), 6.87 (d, J=8.0 Hz, 1H), 5.36 (d, J=8.0 Hz, 1H), 5.11 (d, J=12.0 Hz, 1H), 5.07 (d, J=12.5 Hz, 1H), 4.65 (dd, J=13.5, 5.5 Hz, 1H), 3.74 (s, 3H), 3.17 (dd, J=14.0, 5.5 Hz, 1H), 3.07 (dd, J=14.0, 6.0 Hz, 1H). $^{13}$CNMR (CDCl$_3$, 125 MHz) δ 171.9, 155.7, 155.5, 144.1, 136.2, 130.8, 128.6, 128.42, 128.38, 128.2, 125.1, 111.1, 109.8, 67.2, 55.1, 52.6, 38.3. Mass spec.: 371.18 (MH)$^+$.

(R)-2-Amino-3-(2-oxo-2,3-dihydro-benzooxazol-6-yl)-propionic acid methyl ester

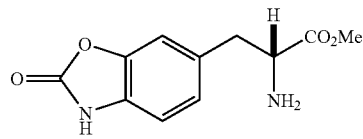

A solution of (R)-2-benzyloxycarbonylamino-3-(2-oxo-2,3-dihydro-benzooxazol-6-yl)-propionic acid methyl ester (310 mg) in 4.4% formic acid in methanol (20 ml, freshly prepared in degassed methanol) was added via cannula to a suspension of 10% palladium on charcoal in 4.4% formic acid in methanol (20 ml, freshly prepared in degassed methanol). The resulting mixture was stirred at room temperature for 4 h. After filtration through a pad of celite, the solvents were removed in vacuo giving a tan solid. The solid was dissolved in a mixture of ethyl acetate (50 mL), toluene (10 mL) and ethanol (40 ml), and solid sodium bicarbonate (3.1 g) was added. The mixture was stirred at room temperature for 2 h and filtered. Solvents were removed in vacuo to afford the title compound.
$^1$H-NMR (CD$_3$OD, 500 MHz) δ 8.41 (br s, 2H), 7.17 (s, 1H), 7.09 (br s, 2H), 4.32 (s, 1H), 3.83 (s, 3H), 3.33 (s, 1H), 3.30 (s, 1H), 3.22 (s, 1H). Mass spec.: 237.20 (MH)$^+$.

(R)-3-(2-Oxo-2,3-dihydro-benzooxazol-6-yl)-2-{[4-(2-oxo-1,4-dihydro-2H-quinazolin-3-yl)-piperidine-1-carbonyl]-amino}-propionic acid methyl ester

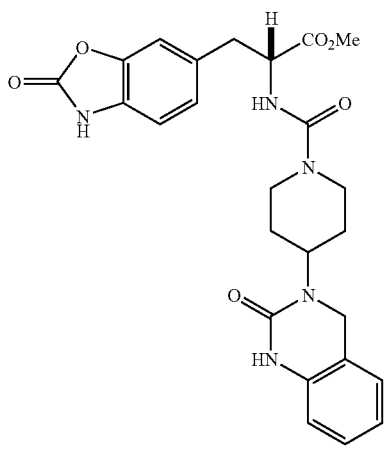

Prepared as described above for (R)-2-{[4-(2-oxo-1,4-dihydro-2H-quinazolin-3-yl)-piperidine-1-carbonyl]-amino}-3-[1-(2-trimethylsilanyl-ethanesulfonyl)-1H-indazol-5-yl]-propionic acid methyl ester. Purified by silica gel chromatography using methylene chloride:methanol:triethylamine (93:5:2) as eluent to afford the title compound as a white solid (33%). $^1$H-NMR (CD$_3$OD, 500 MHz) δ 7.17-7.13 (m, 3H), 7.08 (d, J=7.9 hz, 1H), 7.03 (d, J=8.0 Hz, 1H), 6.95 (t, J=7.0 Hz, 1H), 6.79 (d, J=8.0 Hz, 1H), 4.55-4.51 (m, 1H), 4.44-4.41 (m, 1H), 4.33 (s, 2H), 4.14-4.10 (m, 2H), 3.74 (s, 3H), 3.33 (br s, 2H), 3.23 (dd, j=13.7, 5.2 Hz, 1H), 3.03 (dd, J=14.0, 9.7 Hz, 1H), 2.92-2.82 (m, 2H), 1.79-1.63 (m, 4H). $^{13}$CNMR (CD$_3$OD, 125 MHz) 173.8, 158.2, 156.2, 155.6, 144.4, 137.1, 132.7, 129.3, 128.2, 125.7, 125.0, 122.2, 118.4, 113.4, 110.6, 109.6, 56.2, 52.0, 51.7, 43.8, 42.9, 37.3, 28.4. Mass spec.: 494.30 (MH)$^+$.

(R)-3-(2-Oxo-2,3-dihydro-benzooxazol-6-yl)-2-{[4-(2-oxo-1,4-dihydro-2H-quinazolin-3-yl)-piperidine-1-carbonyl]-amino}-propionic acid

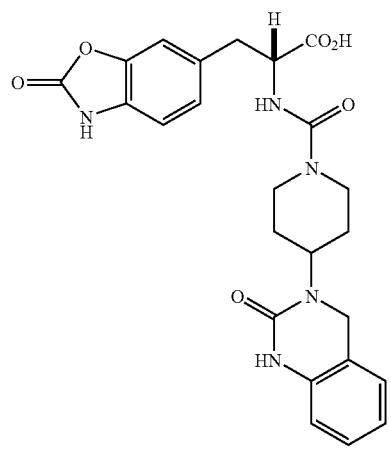

Prepared as described above for (R)-2-{[4-(2-oxo-1,4-dihydro-2H-quinazolin-3-yl)-piperidine-1-carbonyl]-amino}-3-[1-(2-trimethylsilanyl-ethanesulfonyl)-1H-indazol-5-yl]-propionic acid. The hydrolysis conditions (lithium hydroxide/methanol-tetrahydrofuran-water (1:1:1) at −15° C. overnight were used. The title compound was obtained as a white solid (95%). Mass spec.: 480.30 (MH)$^+$.

Example 47

(R)-4-(2-Oxo-1,4-dihydro-2H-quinazolin-3-yl)-piperidine-1-carboxylic acid[2-[1,4']bipiperidinyl-1'-yl-2-oxo-1-(2-oxo-2,3-dihydro-benzooxazol-6-ylmethyl)-ethyl]-amide

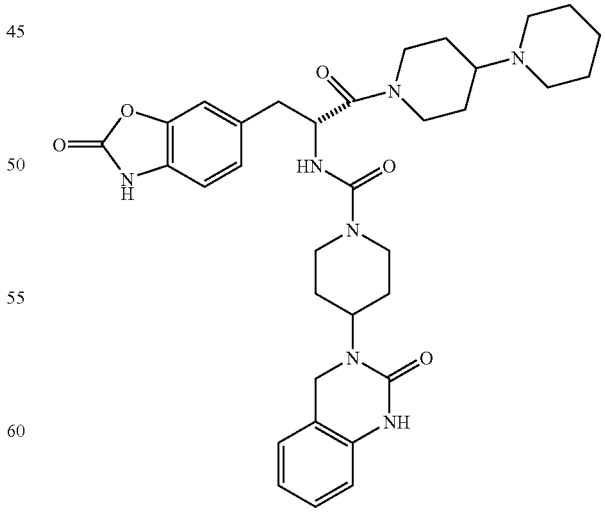

Prepared as described above for (R)-4-(2-oxo-1,4-dihydro-2H-quinazolin-3-yl)-piperidine-1-carboxylic acid {2-[1,4']bipiperidinyl-1'-yl-2-oxo-1-[1-(2-trimethylsilanylethanesulfonyl)-1H-indazol-5-ylmethyl]-ethyl}-amide. The crude product was purified by silica gel chromatography using methylene chloride:methanol:triethylamine (93:5:2) as eluent to give a white solid. This was dissolved in ethyl acetate (60 mL) and washed with a 1:1 sat. sodium bicarbonate/brine twice and dried over sodium sulfate. After filtration, solvents were removed to afford the title compound as a white solid (70%). $^1$H-NMR (CD$_3$OD, 500 MHz) δ 7.20-7.14 (m 4H), 7.08 (d, J=9.0 Hz, 1H), 6.96 (td, J=7.5, 1.0 Hz, 1H), 6.79 (d, J=8.0 Hz, 1H), 4.99-4.94 (m, 1H), 4.61-4.58 (m, 1H), 4.47-4.43 (m, 1H), 4.39 (s, 1H), 4.23-4.16 (m, 2H), 4.08-4.04 (m, 1H), 3.06-2.88 (m, 5H), 2.74-2.69 (m, 2H), 2.59-2.52 (m, 2H), 2.41-2.33 (m, 2H), 1.96-1.89 (m, 1H), 1.88-1.47 (m, 16H). LC/MS: t$_R$=1.86 min, 630.31 (MH)$^+$.

(R)-3-(1H-Benzotriazol-5-yl)-2-benzyloxycarbonylamino-propionic acid methyl ester

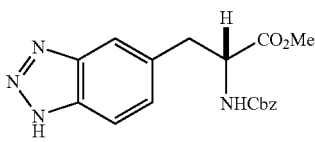

To a solution of (R)-2-benzyloxycarbonylamino-3-(3,4-diamino-phenyl)-propionic acid methyl ester mono acetate (2.68 g, 6.65 mmol) in acetic acid (30 mL) and water (40 mL), at room temperature was added a solution of sodium nitrite (0.46 g, 6.65 mmol) in water (8 mL), dropwise over several minutes. The resulting mixture was stirred at room temperature for 20 min, then cooled to 0° C., concentrated ammonium hydroxide was added to adjust pH to 11. The mixture was extracted with ethyl acetate twice in the presence of solid sodium chloride, and the organic layers were dried over sodium sulfate. After filtration, solvents were removed in vacuo and the residue was purified by chromatography on silica gel using ethyl acetate/hexanes (6:4) as eluent to afford the title compound as a tan solid (94% yield). $^1$H-NMR (CD$_3$OD, 500 MHz) δ 7.75 (d, J=8.5 Hz, 1H), 7.58 (s, 1H), 7.31-7.25 (m, 5H), 7.18 (d, J=8.5 Hz, 1H), 5.39 (d, J=8.0 Hz, 1H), 5.10 (d, J=12.0 Hz, 1H), 5.05 (d, J=12.0 Hz, 1H), 4.74 (dd, j=13.5, 6.0 Hz, 1H), 3.73 (s, 3H), 3.34 (dd, J=14.0, 5.5 Hz, 1H), 3.22 (dd, J=13.5, 6.0 Hz, 1H). $^{13}$CNMR (CD$_3$OD, 125 MHz) δ 172.1, 156.0, 136.1, 128.6, 128.3, 128.1, 67.2, 55.2, 52.7, 38.5. Mass spec. 355.18 (MH)$^+$.

(R)-2-Amino-3-(1H-benzotriazol-5-yl)-propionic acid methyl ester

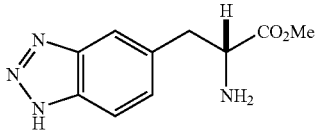

Prepared as described above for (R)-2-amino-3-(2-oxo-2, 3-dihydro-benzooxazol-6-yl)-propionic acid methyl ester. $^1$H-NMR (CD$_3$OD, 500 MHz) δ 8.38 (br s, 2H), 7.89 (d, J=7.5 Hz, 1H), 7.81 (s, 1H), 7.40 (d, J=7.5 Hz, 1H), 4.44 (s, 1H), 3.81 (s, 3H), 3.48-3.45 (m, 1H), 3.40-3.37 (m, 1H), 3.33 (br s, 1H). $^{13}$CNMR (CD$_3$OD, 125 MHz) δ 169.8, 139.4, 138.9, 133.0, 127.6, 115.52, 115.47, 54.3, 52.6, 36.7. Mass spec. 221.15 (MH)$^+$.

Example 48

(R)-3-(1H-Benzotriazol-5-yl)-2-{[4-(2-oxo-1,4-dihydro-2H-quinazolin-3-yl)-piperidine-1-carbonyl]-amino}-propionic acid methyl ester

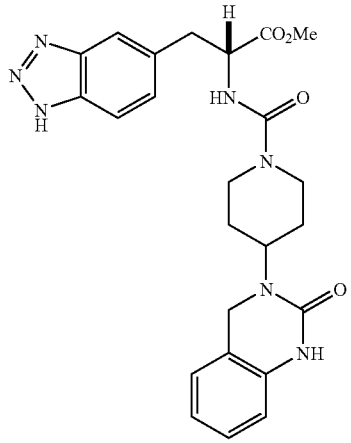

Prepared as described above for (R)-2-{[4-(2-oxo-1,4-dihydro-2H-quinazolin-3-yl)-piperidine-1-carbonyl]-amino}-3-[1-(2-trimethylsilanyl-ethanesulfonyl)-1H-indazol-5-yl]-propionic acid methyl ester except that carbonyl diimidazole was used in place of N,N-disuccinimidyl carbonate (DSC). $^1$H-NMR (CD$_3$OD, 300 MHz) δ 7.82 (d, J=8.4 Hz, 1H), 7.24 (s, 1H), 7.39 (dd, J=8.7, 1.2 Hz, 1H), 7.15-7.08 (m, 2H), 6.94 (td, J=7.5, 0.9 Hz, 1H), 6.75 (d, J=7.8 Hz, 1H), 4.67-4.60 (m, 1H), 4.39-4.31 (m, 1H), 4.15 (s, 2H), 4.08-4.03 (m, 2H), 3.72 (s, 3H), 3.38 (dd, J=13.9, 5.5 Hz, 1H), 3.32-3.29 (m, 1H), 3.17 (dd, J=13.9, 10.3 Hz, 1H), 2.87-2.71 (m, 2H), 1.64-1.48 (m, 4H). Mass spec. 478.30 (MH)$^+$.

Example 49

(R)-4-(2-Oxo-1,4-dihydro-2H-quinazolin-3-yl)-piperidine-1-carboxylic acid [1-(1H-benzotriazol-5-ylmethyl)-2-[1,4']bipiperidinyl-1'-yl-2-oxo-ethyl]-amide

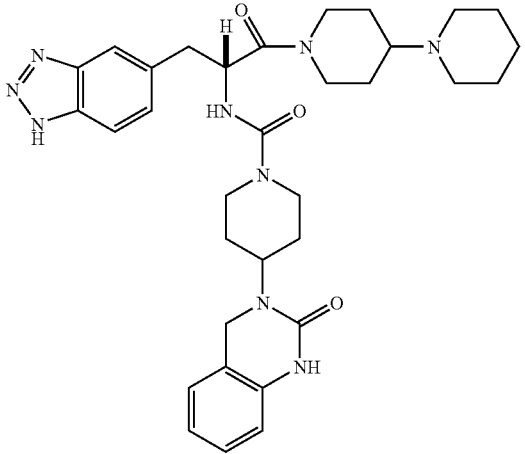

Prepared as described above for (R)-4-(2-oxo-1,4-dihydro-2H-quinazolin-3-yl)-piperidine-1-carboxylic acid {2-[1, 4']bipiperidinyl-1'-yl-2-oxo-1-[1-(2-trimethylsilanylethanesulfonyl)-1H-indazol-5-ylmethyl]-ethyl}-amide. Purified by silica gel chromatography using methylene chloride/methanol/triethylamine (93:5:2) as eluent. ¹H-NMR (CD₃OD, 500 MHz) δ 7.83 d, J=8.2 Hz, 0.75H), 7.79 (d, J=8.5 Hz, 0.25H), 7.71 (s, 0.25H), 7.69 (s, 0.75H), 7.33 (d, J=9.2 Hz, 1H), 7.16-7.12 (m, 2H), 6.96-6.91 (m, 1H), 6.78 (d, J=8.0 Hz, 0.75H), 6.77 (d, J=8.0 Hz, 0.25H), 5.07-5.03 (m, 1H), 4.58-4.55 (m, 1H), 4.45-4.40 (m, 1H), 4.34 (s, 1.25H), 4.24 (s, 0.75H), 4.20-4.05 (m, 2.25H), 4.00-3.96 (m, 0.75H), 3.24-3.09 (m, 2H), 2.91-2.78 (m, 4H), 2.64-2.61 (m, 2H), 2.56-2.42 (m, 2H), 2.15-2.10 (m, 1.25H), 2.02-1.98 (m, 1.75H), 1.95-1.90 (m, 1H), 1.68-1.60 (m, 8H), 1.54-1.46 (m, 6H). LC/MS: $t_R$=1.86 min, 614.28 (MH)⁺.

(R)-2-Benzyloxycarbonylamino-3-(2-oxo-2,3-dihydro-1H-indol-5-yl)-propionic acid methyl ester

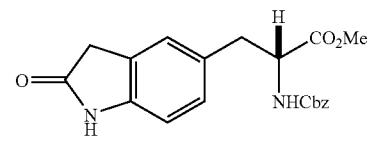

PyHBr₃ (1.28 g, 4.02 mmol) was added in small portions over 30 min to a solution of (R)-2-benzyloxycarbonylamino-3-(1H-indol-5-yl)-propionic acid methyl ester (0.47 g, 1.34 mmol) in t-butanol (10 mL) while the reaction temperature was maintained between 25-30° C. The resulting mixture was stirred at room temperature for 3.5 h. The solvent was removed in vacuo, and the residue was extracted with ethyl acetate (2×). The combined organic phases were washed with brine and dried over sodium sulfate. After filtration, solvents were removed and the residue was azeotropically dried with anhydrous ethanol. The residue was dissolved in glacial acetic acid (10 mL) and zinc powder (0.88 g, 13.4 mmol) was added. The mixture was stirred at room temperature overnight. After the acetic acid was removed in vacuo, the residue was purified by flash chromatography on silica gel using ethyl acetate/hexanes [(1:3) first and then (3:2)] as eluent to afford the title compound as a white solid (41% for 2 steps).

¹H-NMR (CDCl₃, 500 MHz) δ 8.03 (s, 1H), 7.36-7.31 (m, 5H), 6.94 (s, 1H), 6.91 (d, J=8.0 Hz, 1H), 6.73 (d, J=7.5 Hz, 1H), 5.26 (d, J=8.0 Hz, 1H), 5.11 (d, J=12.0 Hz, 1H), 5.05 (d, j=12.5 Hz, 1H), 4.61 (dd, J=13.5, 6.0 hz, 1H), 3.72 (s, 3H), 3.45 (s, 2H), 3.10 (dd, J=14.0, 5.5 Hz, 1H), 3.00 (dd, J=14.0, 6.0 Hz, 1H). ¹³CNMR (CDCl₃, 125 MHz) δ 177.7, 172.2, 155.7, 141.7, 136.3, 129.8, 128.9, 128.6, 128.3, 128.2, 125.8, 125.6, 109.8, 67.1, 55.1, 52.5, 38.0, 36. Mass spec. 369.20 (MH)⁺.

(R)-2-Amino-3-(2-oxo-2,3-dihydro-1H-indol-5-yl)-propionic acid methyl ester

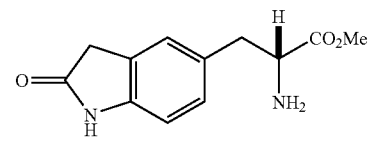

Prepared as described above for (R)-2-amino-3-(2-oxo-2,3-dihydro-benzooxazol-6-yl)-propionic acid methyl ester. ¹H-NMR (CD₃OD, 500 MHz) δ 8.48 (br s, 2H), 7.16 (s, 1H), 7.10 (s, 1H), 6.89 (s, 1H), 4.21 (s, 1H), 3.81 (s, 3H), 3.54 (s, 1H), 3.33 (s, 2H), 3.20 (s, 1H), 3.12 (s, 1H). ¹³CNMR (CD₃OD, 125 MHz) δ 178.9, 170.7, 143.3, 129.0, 128.6, 126.9, 125.6, 110.0, 57.3, 54.6, 52.3, 37.0. Mass spec. 235.30 (MH)⁺.

(R)-3-(2-Oxo-2,3-dihydro-1H-indol-5-yl)-2-{[4-(2-oxo-1,4-dihydro-2H-quinazolin-3-yl)-piperidine-1-carbonyl]-amino}-propionic acid methyl ester

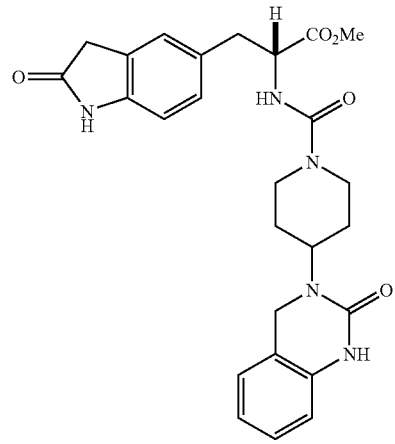

A solution of phosgene in toluene (2M, 0.158 mL, 0.30 mmol) was added to a vigorously stirred mixture of (R)-2-amino-3-(2-oxo-2,3-dihydro-1H-indol-5-yl)-propionic acid methyl ester (70 mg, 0.25 mmol) in methylene chloride (15 mL) and saturated sodium bicarbonate (7.5 mL). After the mixture was stirred at room temperature for 30 min, 3-piperidin-4-yl-3,4-dihydro-1H-quinazolin-2-one (58 mg, 0.25 mmol) was added. The resulting mixture was stirred at room temperature for 1.5 h, diluted with ethyl acetate, and washed with 0.25 N hydrochloric acid that had been saturated with solid sodium chloride. The organic layers were dried over sodium sulfate. After filtration, solvents were removed to afford the title compound as a tan viscous oil. LC/MS: $t_R$=2.01 min, 492.10 (MH)⁺.

Example 50

(R)-4-(2-Oxo-1,4-dihydro-2H-quinazolin-3-yl)-piperidine-1-carboxylic acid[2-[1,4']bipiperidinyl-1'-yl-2-oxo-1-(2-oxo-2,3-dihydro-1H-indol-5-ylmethyl)-ethyl]-amide

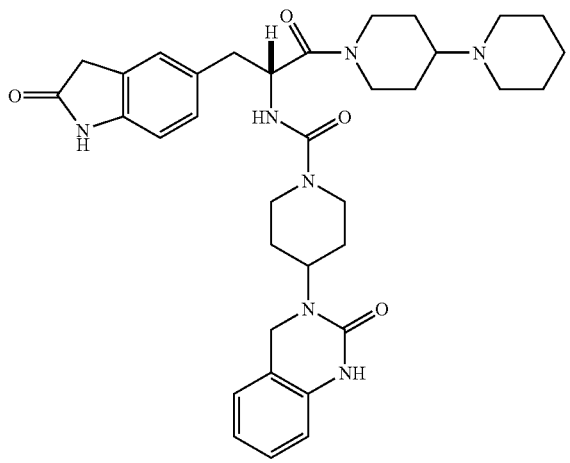

Prepared as described above for (R)-4-(2-oxo-1,4-dihydro-2H-quinazolin-3-yl)-piperidine-1-carboxylic acid {2-[1,4']bipiperidinyl-1'-yl-2-oxo-1-[1-(2-trimethylsilanylethanesulfonyl)-1H-indazol-5-ylmethyl]-ethyl}-amide. Purified by flash chromatography on silica gel using methylene chloride/methanol/triethylamine (93:5:2) as eluent. ¹H-NMR (CD₃OD, 500 MHz) δ 7.20-7.09 (m, 4H), 6.97 (t, J=7.3 Hz, 1H), 6.88 (d, J=7.9 Hz, 0.65H), 6.84 (d, J=7.6 Hz, 0.35H), 6.80 (d, J=7.7 Hz, 1H), 5.51 (s, 0.65H), 5.23 (s, 0.35H), 4.99-4.95 (m, 0.65H), 4.92-4.88 (m, 0.35H), 4.60-4.56 (m, 1.65H), 4.46-4.41 (m, 1.35H), 4.39 (s, 1.3H), 4.36 (s, 0.7H), 4.24-4.17 (m, 2H), 4.05-4.02 (m, 1H), 3.65-3.61 (m, 2H), 3.52-3.47 (m, 1H), 3.20-3.16 (m, 1H), 3.00-2.88 (m, 2H), 2.70-2.64 (m, 2H), 2.53-2.46 (m, 2H), 2.40-2.34 (m, 2H), 1.94-1.46 (m, 15H), 1.39-1.36 (m, 2H). LC/MS: $t_R$=1.83 min, 628.40 (MH)⁺.

2-(Di-tert-butoxycarbonylamino)-acrylic acid methyl ester

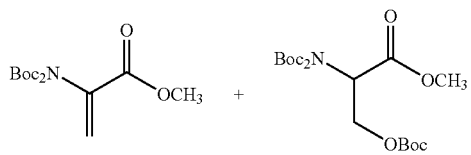

To a solution of 2-tert-butoxycarbonylamino-3-hydroxy-propionic acid methyl ester (10.0 g, 39 mmol) and di-tert-butyl-dicarbonate (21.8 g, 2.6 equiv.) in acetonitrile (40 mL) was added 4-dimethylaminopyridine (0.48 g, 0.1 equiv) at room temperature. The solution was stirred overnight and concentrated. The residue was dissolved in diethyl ether, washed sequentially with 1 M potassium hydrogen sulfate (2×), saturated sodium bicarbonate, brine, dried over magnesium sulfate, and concentrated to give 15.6 g (quant.) as an oil. Inspection of the ¹H NMR showed a mixture of the title compound and 2-(di-tert-butoxycarbonylamino)-3-tert-butoxycarbonyloxy-propionic acid methyl ester. As it was later found that both react with secondary amines to give the same products, the mixture was used without separation. 2-(Di-tert-butoxycarbonylamino)-acrylic acid methyl ester: ¹H-NMR (CDCl₃) δ 1.45 (s, 18H), 3.78 (s, 3H), 5.63 (s, 1H), 6.33 (s, 1H). Mass spec.: 324.14 (M+Na)⁺. 2-(Di-tert-butoxycarbonylamino)-3-tert-butoxycarbonyloxy-propionic acid methyl ester: ¹H-NMR (CDCl₃, 500 MHz) δ 1.46 (s, 9H), 1.49 (s, 18H), 3.72 (s, 3H), 4.42 (dd, J=11.6, 9.2, 1H), 4.75 (dd, J=11.3, 4.6, 1H), 5.30 (dd, J=9.2, 4.6, 1H). Mass spec.: 442.21 (M+Na)⁺.

(±)-3-(4-Benzyloxy-2-oxo-2H-pyridin-1-yl)-2-(di-tert-butoxycarbonylamino)-propionic acid methyl ester

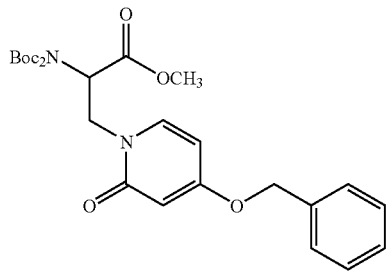

To a solution of 2-(di-tert-butoxycarbonylamino)-acrylic acid methyl ester (900 mg, 3.0 mmol), and 4-benzyloxy-1H-pyridin-2-one (630 mg, 1.03 equiv) in acetonitrile (2.5 mL) was added cesium carbonate (100 mg, 0.10 equiv). The resulting suspension was heated to 80° C. via microwave for 2 h. The reaction was concentrated, dissolved in water, and extracted with methylene chloride (3×). The combined organic phases were washed with brine, dried over magnesium sulfate, and concentrated to give 1.47 g (97%) which was used without purification. Mass spec.: 503.56 (MH)⁺.

(±)-4-Benzyloxy-1-[3-[1,4']bipiperidinyl-1'-yl-2-(di-tert-butoxycarbonylamino)-3-oxo-propyl]-1H-pyridin-2-one

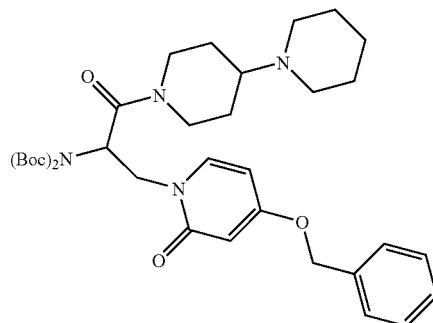

To a stirred solution of 3-(4-benzyloxy-2-oxo-2H-pyridin-1-yl)-2-(di-tert-butoxycarbonylamino)-propionic acid methyl ester (1.47 g, 2.9 mmol) in methanol (17 mL) was added a solution of lithium hydroxide monohydrate (0.50 g, 4 equiv) in water (2.85 mL). The reaction mixture was stirred for 3 h at room temperature, cooled to 0° C., treated with concentrated hydrochloric acid (0.99 mL), and concentrated to afford the crude acid, half of which was taken on in the following step. The crude acid was dissolved in methylene chloride (6 mL), cooled to 0° C. and treated sequentially with 4-piperidyl-piperidine (0.25 g, 1 equiv), triethylamine (0.31 mL, 2.5 equiv), and bis-2-oxo-3-oxazolidinyl)phosphinic chloride (0.38 g, 1 equiv). The reaction was allowed to warm to room temperature and stirred overnight. The reaction was concentrated, and purified by Prep HPLC to afford 489 mg (52%, 2 steps). Mass spec.: 639.41 (MH)⁺.

Example 51

(±)-4-(2-Oxo-1,4-dihydro-2H-quinazolin-3-yl)-piperidine-1-carboxylic acid [1-(4-benzyloxy-2-oxo-2H pyridin-1-ylmethyl)-2-[1,4']bipiperidinyl-1'-yl-2-oxo-ethyl]-amide

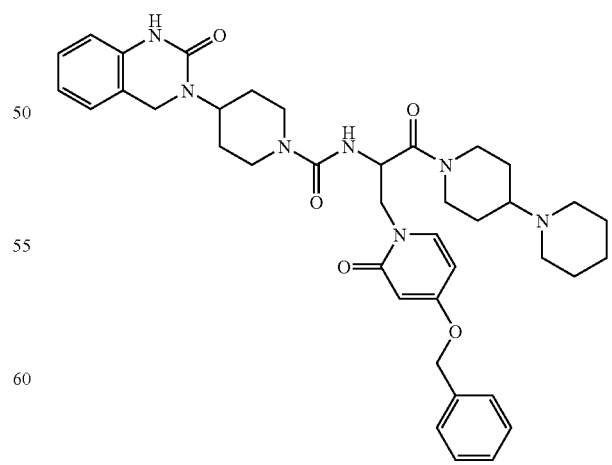

To a stirred solution of 4-benzyloxy-1-[3-[1,4']bipiperidinyl-1'-yl-2-(di-tert-butoxycarbonylamino)-3-oxo-propyl]-1H-pyridin-2-one in methylene chloride (3 mL) was added trifluoroacetic acid (1 mL) at 0° C. After 2 h, the reaction was concentrated to afford the crude amine (151 mg, 97%) as its trifluoroacetic acid salt [Mass spec.: 439.61 (MH)+] which was split into two portions, using half in the following procedure. To a solution of the crude amine (75 mg, 0.11 mmol) and diisopropylethylamine (80 μL, 4 equiv) in methylene chloride (3 mL) at 0° C. was added carbonyl diimidazole (29 mg, 1.6 equiv, in 2 portions). After stirring for 10 min, the solution was treated with 3-piperidin-4-yl-3,4-dihydro-1H-quinazolin-2-acetic acid (40 mg, 1.15 equiv). The reaction was warmed to room temperature and stirred overnight. The reaction was concentrated and purified by prep TLC to give 40.8 mg (53%). $^1$H-NMR (CD$_3$OD, 500 MHz) δ 1.25-1.56 (m, 4H), 1.56-1.84 (m, 9H), 1.90-2.08 (m, 2H), 2.60-2.95 (m, 8H), 3.11 (dd, J=24.1, 12.8, 1H), 3.89 (ddd, J=22.0, 13.2, 9.2, 1H), 4.10 (dd, J=14.3, 14.1, 2H), 4.27-4.54 (m, 5H), 4.60 (bd, J=11.9, 1H), 5.08 (dd, J=13.2, 12.2, 2H), 5.26 (ddd, J=9.4, 9.4, 4.8, 1H), 6.05 (dd, J=13.7, 2.7, 1H), 6.16 (m, 1H), 6.77 (d, J=8.0, 1H), 6.84 (ddd, J=7.6, 7.6, 2.1, 1H), 7.04 (d, J=7.6, 1H), 7.12 (dd, J=7.6, 7.4, 1H), 7.28-7.43 (m, 5H), 7.48 (d, J=7.6, 1H). Mass spec.: 696.85 (MH)+.

Example 52

(±)-4-(2-Oxo-1,4-dihydro-2H-quinazolin-3-yl)-piperidine-1-carboxylic acid[2-[1,4']bipiperidinyl-1'-yl-1-(4-hydroxy-2-oxo-2H-pyridin-1-ylmethyl)-2-oxo-ethyl]-amide

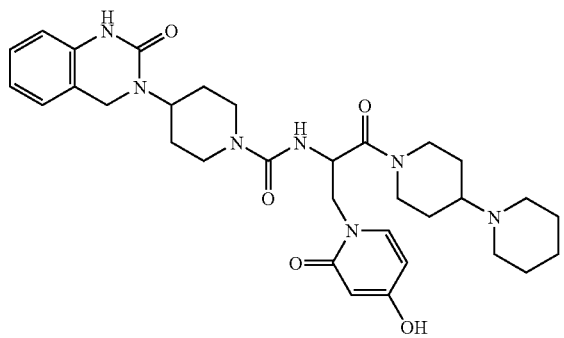

A stirred solution of 4-(2-oxo-1,4-dihydro-2H-quinazolin-3-yl)-piperidine-1-carboxylic acid [1-(4-benzyloxy-2-oxo-2H-pyridin-1-ylmethyl)-2-[1,4']bipiperidinyl-1'-yl-2-oxo-ethyl]-amide (29 mg) and 10% palladium on charcoal (5 mg) in methanol (1 mL) was placed under an atmosphere of hydrogen. After 1 h at room temperature, the reaction was flushed with nitrogen, filtered through celite, and concentrated to give the product. $^1$H-NMR (CD$_3$OD, 500 MHz) δ 1.40-1.85 (m, 12H), 2.04 (dd, J=27.4, 17.0, 2H), 2.66 (dd, J=21.1, 11.0, 1H), 2.80-3.19 (m, 8H), 3.95 (ddd, J=49.8, 12.5, 7.9, 1H), 4.07-4.28 (m, 3H), 4.34 (bs, 2H), 4.36-4.59 (m, 2H), 4.63 (bd, J=12.8, 1H), 5.20 (m, 1H), 5.75 (dd, J=7.3, 2.1, 1H), 5.97 (dd, J=8.9, 7.6, 1H), 6.78 (d, J=7.6, 1H), 6.93 (d, J=7.6, 7.3, 1H), 7.08-7.18 (m, 2H), 7.33 (dd, J=18.3, 11.0, 1H). Mass spec.: 606.32 (MH)+.

(±)-2-(Di-tert-butoxycarbonylamino)-3-(4-hydroxy-piperidin-1-yl)-propionic acid methyl ester

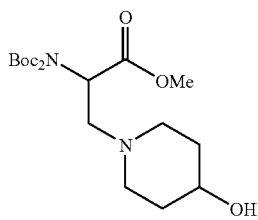

To a solution of 2-(di-tert-butoxycarbonylamino)-acrylic acid methyl ester (1.0 g, 3.0 mmol) in acetonitrile (10 mL) was added piperidin-4-ol (0.33 g, 1.1 equiv). A gentle stream of nitrogen was placed over the reaction while it stirred overnight. The crude oil which resulted was dissolved in ethyl acetate, washed with water, then brine, dried over magnesium sulfate, and concentrated to give 1.38 g (quant.) as an oil which was used without purification. Mass spec.: 403.42 (MH)+.

(±)-1-[1,4']Bipiperidinyl-1'-yl-2-(di-tert-butoxycarbonylamino)-3-(4-hydroxy-piperidin-1-yl)-propan-1-one

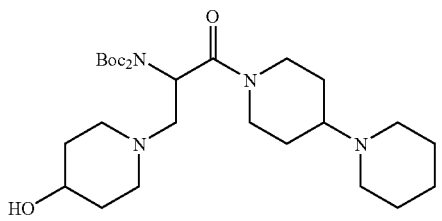

To a solution of 2-(di-tert-butoxycarbonylamino)-3-(4-hydroxy-piperidin-1-yl)-propionic acid methyl ester (1.0 g, 2.5 mmol) in methanol (6 mL) was added a solution of lithium hydroxide monohydrate (400 mg, 3.9 equiv) in water (1 mL). The reaction was stirred 6 h, cooled to 0° C., neutralized with concentrated hydrochloric acid, and concentrated. The crude acid was used without purification. The crude acid was suspended in methylene chloride (25 mL), treated with a few drops of methanol to aid in dissolving the acid, and cooled to 0° C. The resulting suspension was treated sequentially with 4-piperidyl-piperidine (0.53 g, 1.25 equiv), triethylamine (0.70 mL, 2. equiv), and bis-2-oxo-3-oxazolidinyl)phosphinic chloride (0.80 g, 1.25 equiv). The reaction was allowed to warm to room temperature overnight. The reaction was concentrated and then purified by Prep HPLC to afford 310 mg (23%, 2 steps). Mass spec.: 539.49 (MH)+.

(±)-2-Amino-1-[1,4']bipiperidinyl-1'-yl-3-(4-hydroxy-piperidin-1-yl)-propan-1-one

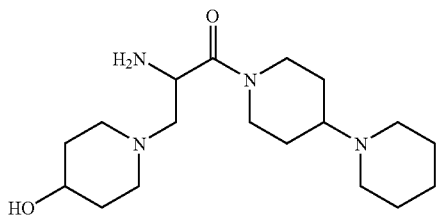

To a solution of 1-[1,4']bipiperidinyl-1'-yl-2-(di-tert-butoxycarbonylamino)-3-(4-hydroxy-piperidin-1-yl)-propan-1-one (310 mg, 0.58 mmol) in methylene chloride (5 mL) at 0° C. was added trifluoroacetic acid (2.0 mL). The ice bath was removed and the reaction stirred for 30 min. The reaction was concentrated to afford the product as its trifluoroacetic acid salt (400 mg, quant.) which was used without purification. Mass spec.: 339.46 (MH)+.-

(±)-[2-[1,4']Bipiperidinyl-1'-yl-1-(4-hydroxy-piperidin-1-ylmethyl)-2-oxo-ethyl]-carbamic acid tert-butyl ester

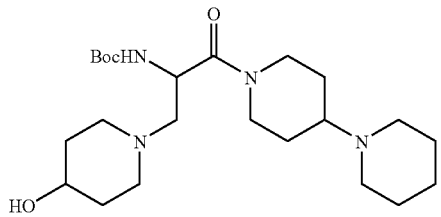

To a solution 2-amino-1-[1,4']bipiperidinyl-1'-yl-3-(4-hydroxy-piperidin-1-yl)-propan-1-one (trifluoroacetic acid salt, 300 mg, 0.58 mmol) and diisopropylethylamine (0.30 mL, 4 equiv) in tetrahydrofuran (5 mL) was added di-tert-butyl-dicarbonate (128 mg, 1 equiv). The resulting solution was stirred at room temperature for 1 h, and concentrated. The residue was dissolved in ethyl acetate, washed with water, then brine, dried over magnesium sulfate, and concentrated to afford to 248 mg (98%) which was used without purification. Mass spec.: 439.65 (MH)$^+$.

(±)-[2-[1,4']Bipiperidinyl-1'-yl-2-oxo-1-(4-oxo-piperidin-1-ylmethyl)-ethyl]-carbamic acid tert-butyl ester

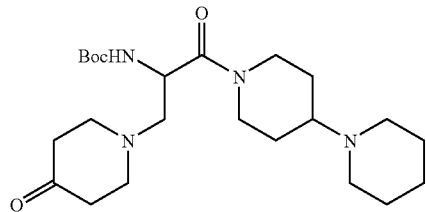

To a solution of 1-[1,4']bipiperidinyl-1'-yl-2-(di-tert-butoxycarbonylamino)-3-(4-hydroxy-piperidin-1-yl)-propan-1-one (200 mg, 0.37 mmol) in methylene chloride (4 mL) was added Dess-Martin periodinane (316 mg, 2 equiv) in two portions. After 1 h, the reaction was quenched by the addition of saturated sodium bicarbonate, and extracted into methylene chloride (3×). The combined organic phases were washed with brine, dried over magnesium sulfate, and concentrated to give 187 mg (94%) which was used without purification. Mass spec.: 437.63 (MH)$^+$.

(±)-1-(2-Amino-3-[1,4']bipiperidinyl-1'-yl-3-oxo-propyl)-piperidin-4-one

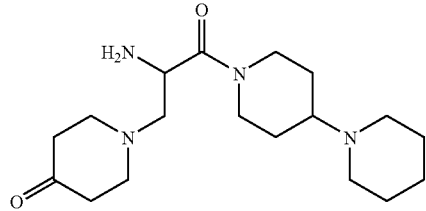

To a solution of [2-[1,4']bipiperidinyl-1'-yl-2-oxo-1-(4-oxo-piperidin-1-ylmethyl)-ethyl]-carbamic acid tert-butyl ester (100 mg, 0.23 mmol) in methylene chloride (5 mL) at 0° C. was added trifluoroacetic acid. The ice bath was removed, stirring continued for 1 h, and the reaction concentrated to give 150 mg (96%) as its trifluoroacetic acid salt which was used without purification. Mass spec.: 337.64 (MH)$^+$.

Example 53

(±)-4-(2-Oxo-1,4-dihydro-2H-quinazolin-3-yl)-piperidine-1-carboxylic acid[2-[1,4']bipiperidinyl-1'-yl-1-(4-hydroxy-piperidin-1-ylmethyl)-2-oxo-ethyl]-amide

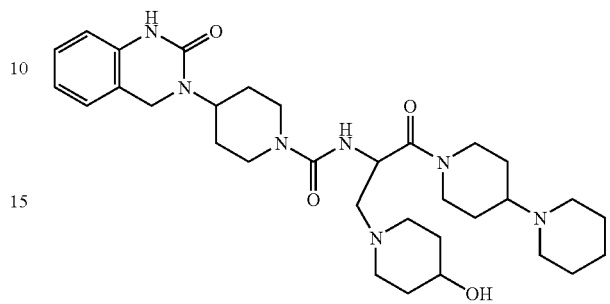

To a solution of 4-(2-oxo-1,4-dihydro-2H-quinazolin-3-yl)-piperidine-1-carboxylic acid[2-[1,4']bipiperidinyl-1'-yl-1-(4-hydroxy-piperidin-1-ylmethyl)-2-oxo-ethyl]-amide (3 trifluoroacetic acid salt, 200 mg, 0.39 mmol) in methylene chloride (5 mL) at 0° C. was added diisopropylethylamine (0.27 mL, 3.9 equiv), and carbonyl diimidazole (63 mg, 1 equiv). After stirring for 15 min, the solution was treated with 3-piperidin-4-yl-3,4-dihydro-1H-quinazolin-2-one (acetic acid salt, 142 mg, 1.25 equiv). The solution was warmed to room temperature and stirred overnight. The reaction was concentrated and purified by Prep TLC to give 130 mg (56%) as an oil. LC/MS: $t_R$=1.17 min, 596.44 (MH)$^+$.

3-Dimethylaminomethylene-4-oxo-piperidine-1-carboxylic acid tert-butyl ester

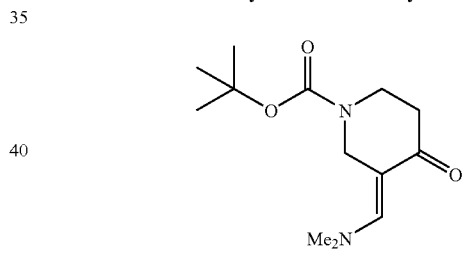

4-Oxo-piperidine-1-carboxylic acid tert-butyl ester (10 g, 50 mmol) was dissolved in dimethyl formamide dimethylacetal (50 mL) and heated to reflux for 1.25 h. The solution was cooled, concentrated, and purified by flash chromatography to give 2.55 g (19%). Mass spec.: 255.16 (MH)$^+$.

1,4,6,7-Tetrahydro-pyrazolo[4,3-c]pyridine-5-carboxylic acid tert-butyl ester

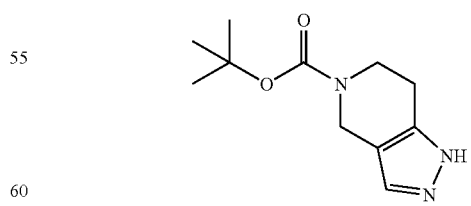

To a solution of 3-dimethylaminomethylene-4-oxo-piperidine-1-carboxylic acid tert-butyl ester (2.55 g, 10 mmol) in methanol (50 mL) was added hydrazine hydrate (0.61 mL, 1.25 equiv). The solution was heated to reflux, immediately allowed to cool to room temperature, and concentrated to give 1.4 g (63%) which was used without purification. Mass spec.: 224.11 (MH)$^+$.

4,5,6,7-Tetrahydro-1H-pyrazolo[4,3-c]pyridine

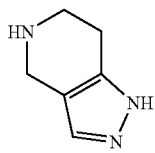

1,4,6,7-Tetrahydro-pyrazolo[4,3-c]pyridine-5-carboxylic acid tert-butyl ester (0.70 g, 3.1 mmol) was dissolved in trifluoroacetic acid (10 mL) at 0° C., stirred for 1 h, and was concentrated. The residue was dissolved in ethanol and treated with concentrated hydrochloric acid (1 mL). The bis-hydrochloride salt precipitated out as a white solid which was filtered to give 510 mg (83%). The free base was prepared as needed by dissolving the salt in water, loading it onto an SCX column, flushing with methanol, and then eluting with 2 M ammonia in methanol.

(±)-2-(Di-tert-butoxycarbonylamino)-3-(1,4,6,7-tetrahydro-pyrazolo[4,3-c]pyridin-5-yl)-propionic acid methyl ester

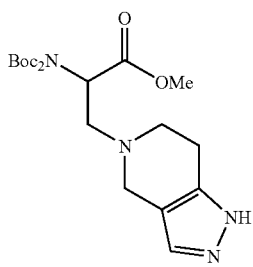

To a solution of 4,5,6,7-tetrahydro-1H-pyrazolo[4,3-c]pyridine (160 mg) in 2.5 mL methanol was added 2-(di-tert-butoxycarbonylamino)-acrylic acid methyl ester (400 mg). The reaction was concentrated to approximately 1.5 mL by application of a gentle stream of nitrogen. The solution was stirred at room temperature overnight. The reaction was concentrated, dissolved in ethyl acetate, washed with brine, dried over magnesium sulfate, and concentrated. The resulting residue was pure enough to use without purification. $^1$H-NMR (CDCl$_3$, 500 MHz) δ 1.44 (s, 9H), 2.73 (m, 3H), 2.91 (m, 1H), 3.06 (dd, J=13.4, 8.6, 1H), 3.22 (dd, J=13.4, 8.2, 1H), 3.54 (d, J=13.4, 1H), 3.63 (d, J=13.4, 1H), 3.71 (s, 3H), 5.11 (dd, J=8.5, 5.2, 1H), 7.25 (s, 1H). Mass spec.: 425.23 (MH)$^+$.

(±)-2-Amino-3-(1,4,6,7-tetrahydro-pyrazolo[4,3-c]pyridin-5-yl)-propionic acid methyl ester

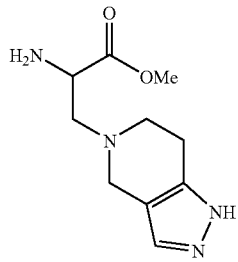

To a solution of 2-(di-tert-butoxycarbonylamino)-3-(1,4,6,7-tetrahydro-pyrazolo[4,3-c]pyridin-5-yl)-propionic acid methyl ester (0.55 g, 1 equiv.) in methylene chloride (5 mL, 0° C.) was added trifluoroacetic acid (1.5 mL). The ice bath was removed and stirring continued for 2 h. The solution was concentrated, redissolved in methanol, and passed onto a column of strong cation exchange resin. After flushing with methanol, the product was removed from the column by eluting with 2 M ammonia in methanol to afford the product as its free base (275 mg, 95%). $^1$H-NMR (CDCl$_3$, 500 MHz) δ 2.71 (dd, J=12.8, 8.6, 1H), 2.74-2.91 (m, 6H), 3.48 (s, 2H), 3.54 (d, J=13.4, 1H), 3.62 (d, J=13.4, 1H), 3.69 (dd, J=8.2, 4.9, 1H), 3.73 (s, 3H), 7.27 (s, 1H). Mass spec.: 225.16 (MH)$^+$.

3,3-Dimethyl-4-oxo-piperidine-1-carboxylic acid tert-butyl ester

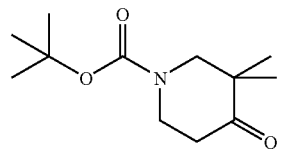

To a solution of 4-oxo-piperidine-1-carboxylic acid tert-butyl ester (16 g, 80 mmol) in tetrahydrofuran (400 mL) at 0° C. was added sodium hydride (4.1 g, 2.1 equiv) in 4 portions. To this was added iodomethane (12.5 mL, 2.5 equiv) dropwise. The reaction was allowed to gradually warm to room temperature and stirred overnight. The reaction was concentrated, dissolved in diethyl ether, washed with brine, dried over magnesium sulfate, and concentrated. The product was crystallized from hot pentane (2×) to give 5.9 g (32%). $^1$H-NMR (CDCl$_3$, 500 MHz) δ 1.09 (s, 6H), 1.47 (s, 9H), 2.47 (dd, J=6.4, 6.4, 2H), 3.41 (m, 2H), 3.70 (m, 2H). Mass spec.: 250.12 (M+Na)$^+$.

5-Dimethylaminomethylene-3,3-dimethyl-4-oxo-piperidine-1-carboxylic acid tert-butyl ester

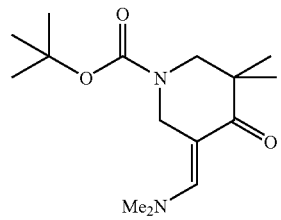

3,3-Dimethyl-4-oxo-piperidine-1-carboxylic acid tert-butyl ester (5 g, 22 mmol) was dissolved in dimethyl formamide dimethylacetal (25 mL) and heated at reflux for 2 h. The reaction mixture was then heated to 130° C. for 1 h via microwave, and concentrated to give 6.43 g (quant.) as an oil which used without purification. $^1$H-NMR (CDCl$_3$, 500 MHz) δ 1.07 (s, 6H), 1.45 (s, 9H), 3.06 (s, 6H), 3.37 (m, 2H), 4.57 (m, 2H), 7.41 (bs, 1H).

7,7-Dimethyl-1,4,6,7-tetrahydro-pyrazolo[4,3-c]pyridine-5-carboxylic acid tert-butyl ester

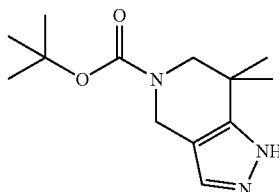

To a solution of 5-dimethylaminomethylene-3,3-dimethyl-4-oxo-piperidine-1-carboxylic acid tert-butyl ester (6.35 g, 22 mmol) in methanol (15 mL) was added hydrazine hydrate (1.2 mL, 1.1 equiv). The solution was stirred at room temperature overnight and concentrated to give 5.3 g (94%) which was used without purification. Mass spec.: 252.19 (MH)$^+$.

7,7-Dimethyl-4,5,6,7-tetrahydro-1H-pyrazolo[4,3-c]pyridine

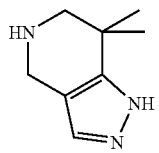

To a solution of 7,7-dimethyl-1,4,6,7-tetrahydro-pyrazolo[4,3-c]pyridine-5-carboxylic acid tert-butyl ester (5.3 g, 21 mmol) in methylene chloride (10 mL) at 0° C. was added trifluoroacetic acid (5 mL). The reaction was allowed to warm to room temperature, stirred 15 min, and treated with additional trifluoroacetic acid (5 mL). After 1 h, the reaction was concentrated, dissolved in ethanol (10 mL), cooled to 0° C., treated with concentrated hydrochloric acid (3 mL), and concentrated. The resulting solid was triturated with ethanol, and filtered to give 3.02 g (64%) as its bis-hydrochloride salt. The free base was prepared as needed by dissolving the salt in water, loading it onto an SCX column, flushing with methanol, and then eluting with 2M ammonia in methanol. $^1$H-NMR (D$_2$O, 500 MHz) δ 1.49 (s, 6H), 3.46 (s, 2H), 4.39 (s, 2H), 7.86 (s, 1H). Mass spec.: 152.14 (MH)$^+$.

(±)-2-(Di-tert-butoxycarbonylamino)-3-(7,7-dimethyl-1,4,6,7-tetrahydro-pyrazolo[4,3-c]pyridin-5-yl)-propionic acid methyl ester

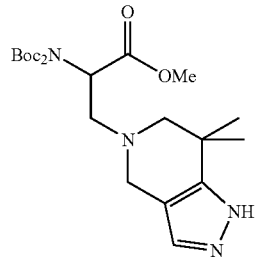

To a solution of 7,7-dimethyl-4,5,6,7-tetrahydro-1H-pyrazolo[4,3-c]pyridine (160 mg) in methanol (3 mL) was added 2-(di-tert-butoxycarbonylamino)-acrylic acid methyl ester (331 mg). A gentle stream of nitrogen was applied and the reaction stirred overnight. In the morning, the volume was greatly reduced. The last traces of solvent were removed under high vacuum to give 490 mg (quant.) which was used without purification. $^1$H-NMR (CDCl$_3$, 500 MHz) δ 1.24 (s, 3H), 1.26 (s, 3H), 1.38 (s, 18H), 2.33 (d, J=11.3, 1H), 2.57 (d, J=11.3, 1H), 3.09 (dd, J=13.1, 5.5, 1H), 3.15 (dd, J=13.4, 9.5, 1H), 3.35 (d, J=12.8, 1H), 3.57 (d, J=12.8, 1H), 3.68 (s, 3H), 5.13 (dd, J=9.5, 3.7, 1H), 7.16 (s, 1H). Mass spec.: 453.30 (MH)$^+$.

(±)-2-Amino-3-(7,7-dimethyl-1,4,6,7-tetrahydro-pyrazolo[4,3-c]pyridin-5-yl)-propionic acid methyl ester

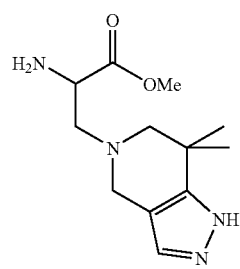

To a solution of 2-(di-tert-butoxycarbonylamino)-3-(7,7-dimethyl-1,4,6,7-tetrahydro-pyrazolo[4,3-c]pyridin-5-yl)-propionic acid methyl ester (0.49 g, 1 equiv) in methylene chloride (5 mL, 0° C.) was added trifluoroacetic acid (1.5 mL). The ice bath was removed and stirring continued for 2 h. The solution was concentrated, redissolved in methanol, and loaded onto a column of strong cation exchange resin. After flushing with methanol, the product was removed from the column by eluting with 2M ammonia in methanol to afford the product as its free base (250 mg, 94%). $^1$H-NMR (CDCl$_3$, 500 MHz) δ 1.27 (s, 3H), 1.28 (s, 3H), 2.41 (d, J=11.3, 1H), 2.50 (d, J=11.3, 1H), 2.69 (dd, J=12.5, 7.9, 1H), 2.82 (dd, J=12.5, 5.2, 1H), 3.45 (d, J=12.8, 1H), 3.52 (d, J=12.8, 1H), 3.67 (m, 1H), 3.69 (s, 3H), 7.19 (s, 1H). Mass spec.: 253.16 (MH)$^+$.

(±)-2-{[4-(2-Oxo-1,4-dihydro-2H-quinazolin-3-yl)-piperidine-1-carbonyl]-amino}-3-(1,4,6,7-tetrahydro-pyrazolo[4,3-c]pyridin-5-yl)-propionic acid methyl ester

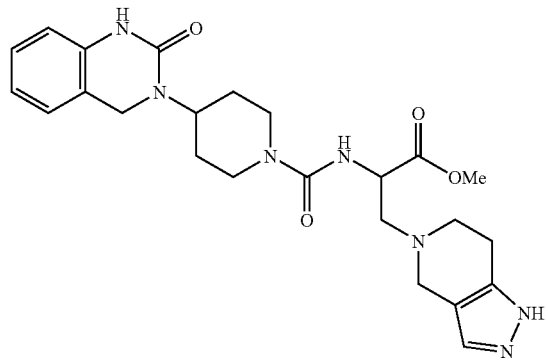

To a solution of 2-amino-3-(1,4,6,7-tetrahydro-pyrazolo[4,3-c]pyridin-5-yl)-propionic acid methyl ester (260 mg, 1- equiv) in methylene chloride (2 mL, 0° C.) was added carbonyl diimidazole (188 mg, 1 equiv). After 15 min, 3-piperidin-4-yl-3,4-dihydro-1H-quinazolin-2-one (295 mg, 1.1 equiv) was added in one portion. The ice bath was removed and stirring continued overnight. The reaction was concentrated and purified by column chromatography to give 118 mg (21%). $^1$H-NMR (CDCl$_3$, 500 MHz) δ 1.60-1.80 (m, 4H), 2.70-3.05 (m, 8H), 3.45 (s, 2H), 3.56 (d, J=13.4, 1H), 3.62 (d, J=13.4, 1H), 3.75 (s, 3H), 4.02 (d, J=13.1, 1H), 4.10 (d, J=12.5, 1H), 4.24 (s, 2H), 4.45-4.57 (m, 2H), 5.79 (bs, 1H), 6.68 (d, J=7.94, 1H), 6.90 (dd, J=7.3, 7.3, 1H), 7.00 (d, J=7.3, 1H), 7.13 (dd, J=7.6, 7.3, 1H), 7.25 (s, 1H), 7.82 (s, 1H). Mass spec.: 482.27 (MH)$^+$.

Example 54

(±)-4-(2-Oxo-1,4-dihydro-2H-quinazolin-3-yl)-piperidine-1-carboxylic acid[2-[1,4']bipiperidinyl-1'-yl-2-oxo-1-(1,4,6,7-tetrahydro-pyrazolo[4,3-c]pyridin-5-ylmethyl)-ethyl]-amide

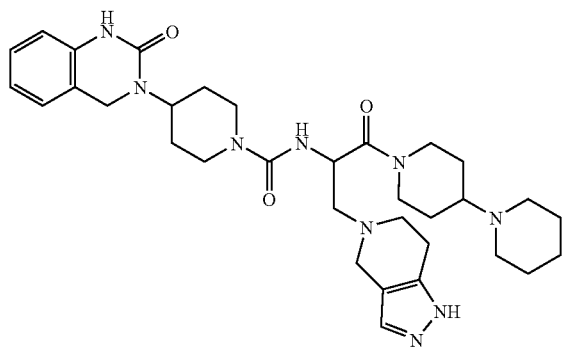

To a solution of 2-{[4-(2-oxo-1,4-dihydro-2H-quinazolin-3-yl)-piperidine-1-carbonyl]-amino}-3-(1,4,6,7-tetrahydro-pyrazolo[4,3-c]pyridin-5-yl)-propionic acid methyl ester (16 mg, 1 equiv) in methanol (0.6 mL) was added lithium hydroxide monohydrate (3 mg, 2.2 equiv) in water (0.1 mL) and stirred for 4 h at room temperature. The solution was cooled to 0° C., treated with aqueous 1 M potassium hydrogen sulfate (60 µl, 1.8 equiv), and concentrated to give the crude acid which was immediately used without purification. The crude acid was dissolved in dimethylformamide (0.3 mL) and sequentially treated with methylene chloride (0.15 mL), 4-piperidyl-piperidine (11 mg, 2 equiv), diisopropylethylamine (12 µL, 2 equiv), and PyBOP® (19 mg, 1.1 equiv). The solution was stirred 30 min and concentrated. The product was purified by column chromatography to give 17.6 mg (85%, 2 steps). $^1$H-NMR (CDCl$_3$, 500 MHz) δ 1.30-1.60 (m, 9H), 1.62-1.78 (m, 5H), 1.81 (bd, J=11.0, 2H), 2.23-2.49 (m, 6H), 2.55-3.10 (m, 11H), 3.59 (d, J=7.3, 2H), 4.00-4.20 (m, 3H), 4.23 (s, 2H), 4.50 (m, 1H), 4.63 (m, 1H), 5.03 (m, 1H), 5.71 (d, J=7.3, 1H), 6.67 (d, J=7.9, 1H), 6.91 (dd, J=7.6, 7.3, 1H), 7.02 (dd, J=7.9, 7.3, 1H), 7.14 (dd, J=7.6, 7.6, 1H), 7.24 (s, 1H), 7.39 (s, 1H), 10.76 (bs, 1H). Mass spec.: 618.34 (MH)$^+$.

Example 55

(±)-3-(7,7-Dimethyl-1,4,6,7-tetrahydro-pyrazolo[4,3-c]pyridin-5-yl)-2-{[4-(2-oxo-1,4-dihydro-2H-quinazolin-3-yl)-piperidine-1-carbonyl]-amino}-propionic acid methyl ester

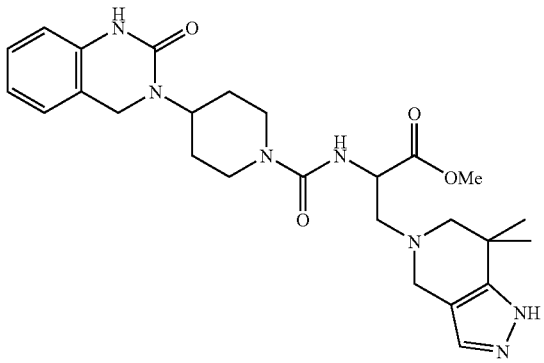

To a solution of 2-amino-3-(7,7-dimethyl-1,4,6,7-tetrahydro-pyrazolo[4,3-c]pyridin-5-yl)-propionic acid methyl ester (250 mg, 1 equiv) in tetrahydrofuran (4 mL, 0° C.) was added carbonyl diimidazole (162 mg, 1 equiv). After 5 min, the ice bath was removed and the reaction stirred at room temperature for 30 min. To this was added 3-piperidin-4-yl-3,4-dihydro-1H-quinazolin-2-one (250 mg, 1.1 equiv) in one portion, and the reaction stirred overnight. The reaction was concentrated and purified by column chromatography to give 228 mg (45%). $^1$H-NMR (CDCl$_3$, 500 MHz) δ 1.30 (s, 3H), 1.31 (s, 3H), 1.60-1.80 (m, 4H), 2.43 (d, J=11.6, 1H), 2.53 (d, J=11.3, 1H), 2.80-2.95 (m, 4H), 3.51 (dd, J=20.4, 13.1, 2H), 3.74 (s, 3H), 4.00 (d, J=13.7, 1H), 4.10 (d, J=12.2, 1H), 4.25 (dd, J=16.2, 14.4, 2H), 4.86 (m, 2H), 6.66 (d, J=7.6, 1H), 6.92 (dd, J=7.6, 7.3, 1H), 7.02 (d, J=7.3, 1H), 7.14 (dd, J=7.6, 7.6, 1H), 7.24 (s, 1H). Mass spec.: 510.27 (MH)$^+$.

Example 56

(±)-4-(2-Oxo-1,4-dihydro-2H-quinazolin-3-yl)-piperidine-1-carboxylic acid[2-[1,4']bipiperidinyl-1'-yl-1-(7,7-dimethyl-1,4,6,7-tetrahydro-pyrazolo[4,3-c]pyridin-5-ylmethyl)-2-oxo-ethyl]-amide

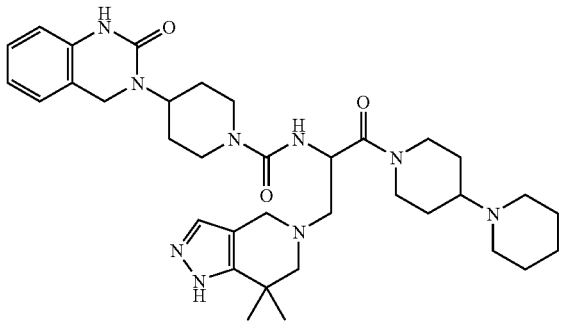

To a solution of 3-(7,7-dimethyl-1,4,6,7-tetrahydro-pyrazolo[4,3-c]pyridin-5-yl)-2-{[4-(2-oxo-1,4-dihydro-2H-quinazolin-3-yl)-piperidine-1-carbonyl]-amino}-propionic acid methyl ester (20 mg, 1.0 equiv) in methanol (0.6 mL) was added lithium hydroxide monohydrate (4 mg, 2.2 equiv) in water (0.1 mL) and stirred for 4 h at room temperature. The solution was cooled to 0° C., treated with aqueous 1M potassium hydrogen sulfate (75 μl, 1.8 equiv), and concentrated to give the crude acid which was immediately used without purification. The crude acid was dissolved in dimethylformamide (0.3 mL) and sequentially treated with methylene chloride (0.15 mL), 4-piperidyl-piperidine (13 mg, 2 equiv), diisopropylethylamine (14 μL, 2 equiv), and PyBOP® (22 mg, 1.1 equiv). The solution was stirred 1.5 h and concentrated. The product was purified by column chromatography to give a product which was tainted with HOBT. The HOBT was removed by passing the product through a plug of basic alumina, eluting with 10% methanol in methylene chloride. Concentration gave 18.3 mg (72%, 2 steps). $^1$H-NMR (CDCl$_3$, 500 MHz) δ 1.25-1.32 (m, 6H), 1.40 (m, 4H), 1.54 (m, 5H), 1.65 (m, 4H), 1.83 (m, 2H), 2.30-2.56 (m, 8H), 2.81 (m, 4H), 3.04 (dt, J=57.1, 12.2, 1H), 3.43-3.60 (m, 2H), 4.00-4.17 (m, 2H), 4.18-4.26 (m, 3H), 4.49 (m, 1H), 4.62 (m, 1H), 5.03 (m, 1H), 5.80 (dd, J=16.8, 9.8, 1H), 6.69 (d, J=7.9, 1H), 6.90 (dd, J=7.3, 7.3, 1H), 6.99 (dd, J=7.6, 7.3, 1H), 7.13 (dd, J=7.6, 7.6, 1H), 7.19 (s, 1H), 7.66 (bd, J=12.8, 1H). Mass spec.: 646.43 (MH)$^+$.

2-Benzyloxycarbonylamino-3-(6-methoxy-pyridin-3-yl)-acrylic acid methyl ester

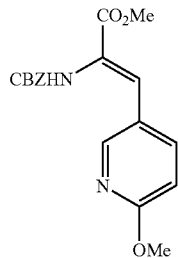

To a suspension of potassium tert-butoxide (1.23 g, 1.5 equiv) in methylene chloride (70 mL, −20° C.) was added a solution of N-benzyloxycarbonyl-α-phosphonoglycine trimethyl ester (3.63 g, 1.5 equiv) in methylene chloride (15 mL). The resulting solution was stirred 5 min and treated with the 6-methoxy-pyridine-3-carbaldehyde (1.0 g, 7.3 mmol) in methylene chloride (15 mL). After stirring for 1.5 h, the reaction was warmed to 0° C. and stirred 1 h. The reaction was quickly poured into a separatory funnel containing ethyl acetate and water. Brine was added to aid in separation of the layers. The aqueous was extracted with ethyl acetate (3×) which were in turn washed with brine, dried over magnesium sulfate, and concentrated to give 2.63 g (quant.) which was used without purification. Mass spec.: 343.08 (MH)$^+$.

(±)-2-Amino-3-(6-methoxy-pyridin-3-yl)-propionic acid methyl ester

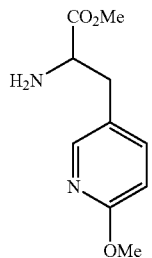

A flask containing 2-benzyloxycarbonylamino-3-(6-methoxy-pyridin-3-yl)-acrylic acid methyl ester (620 mg), palladium on charcoal (10%, 100 mg), ethyl acetate (10 mL) and methanol (20 mL) was flushed with nitrogen, then hydrogen, before finally affixing a balloon of hydrogen. The reaction was allowed to stir overnight. The flask was flushed with nitrogen, filtered through celite, and concentrated to give 390 mg (quant.) which was used without purification. Mass spec.: 211.11 (MH)$^+$.

(±)-3-(6-Methoxy-pyridin-3-yl)-2-{[4-(2-oxo-1,4-dihydro-2H-quinazolin-3-yl)-piperidine-1-carbonyl]-amino}-propionic acid methyl ester

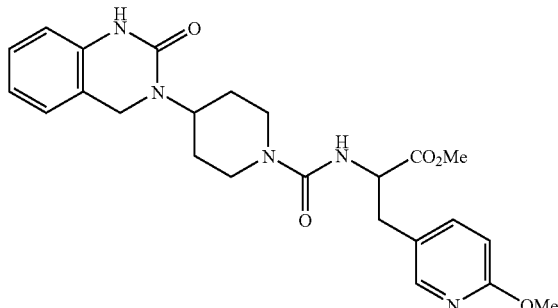

To a solution of 2-amino-3-(6-methoxy-pyridin-3-yl)-propionic acid methyl ester (130 mg) and diisopropylethylamine (0.3 mL) in methylene chloride (2 mL, 0° C.) was added N,N'-disuccinimidyl carbonate (158 mg). After 30 min, 3-piperidin-4-yl-3,4-dihydro-1H-quinazolin-2-one (120 mg) in methylene chloride (1 mL) was added via canula. The reaction was warmed to room temperature and stirred overnight. The reaction was concentrated and purified by prep HPLC to give 160 mg (55%). Mass spec.: 468.19 (MH)$^+$.

Example 57

(±)-4-(2-Oxo-1,4-dihydro-2H-quinazolin-3-yl)-piperidine-1-carboxylic acid[2-[1,4']bipiperidinyl-1'-yl-1-(6-methoxy-pyridin-3-ylmethyl)-2-oxo-ethyl]-amide

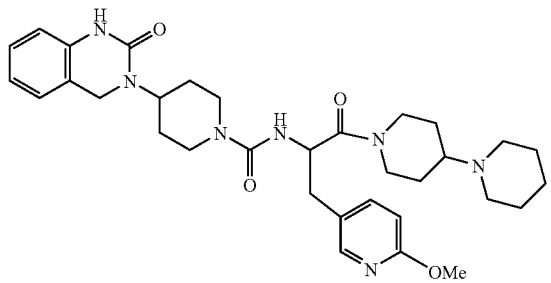

To a solution of 3-(6-methoxy-pyridin-3-yl)-2-{[4-(2-oxo-1,4-dihydro-2H-quinazolin-3-yl)-piperidine-1-carbonyl]-amino}-propionic acid methyl ester (160 mg) in methanol (6 mL) was added a solution of lithium hydroxide monohydrate (29 mg) in water (1 mL). The reaction was stirred at room temperature for 4 h and cooled to 0° C. The reaction was treated with 1N hydrochloric acid (0.6 mL), concentrated. The residue obtained was dissolved in methylene chloride (5 mL), and treated sequentially with 4-piperidyl-piperidine (75 mg), triethylamine (0.14 mL), and bis-2-oxo-3-oxazolidinyl) phosphinic chloride (104 mg). The reaction was stirred overnight, concentrated, and purified by prep HPLC to give 94 mg (45%). LC/MS: t$_R$=1.86 min, 604.51 (MH)$^+$.

2-Benzyloxycarbonylamino-3-(2-methoxy-pyrimidin-5-yl)-acrylic acid methyl ester

To a suspension of potassium t-butoxide (1.23 g) in methylene chloride (70 mL, −30° C.) was added a solution of N-benzyloxycarbonyl-α-phosphonoglycine trimethyl ester (3.63 g) in methylene chloride (15 mL). The resulting solution was stirred 5 min and treated with the 2-methoxy-pyrimidine-5-carbaldehyde (1.0 g) in methylene chloride (15 mL). After stirring for 1.5 h, the reaction was warmed to 0° C. and stirred 1 h. The reaction was quickly poured into a sep funnel containing ethyl acetate and water. Brine was added to aid in separation of the layers. The aqueous was extracted with ethyl acetate (3×) which were in turn washed with brine, dried over magnesium sulfate, and concentrated. The crude product was recrystallized from hot methanol to give 1.4 g of pure material. Mass spec.: 344.10 (MH)+.

(±)-2-Amino-3-(2-methoxy-pyrimidin-5-yl)-propionic acid methyl ester

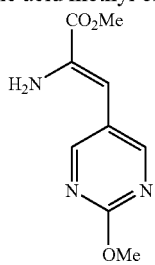

A flask containing amino ester (700 mg), palladium on charcoal (10%, 100 mg) and methanol (20 mL) was flushed with nitrogen, then hydrogen, before finally affixing a balloon of hydrogen. The reaction was allowed to stir overnight. The flask was flushed with nitrogen, filtered through celite, and concentrated to give 379 mg (88%) which was used without purification. Mass spec.: 212.08 (MH)+.

(±)-3-(2-Methoxy-pyrimidin-5-yl)-2-{[4-(2-oxo-1,4-dihydro-2H-quinazolin-3-yl)-piperidine-1-carbonyl]-amino}-propionic acid methyl ester

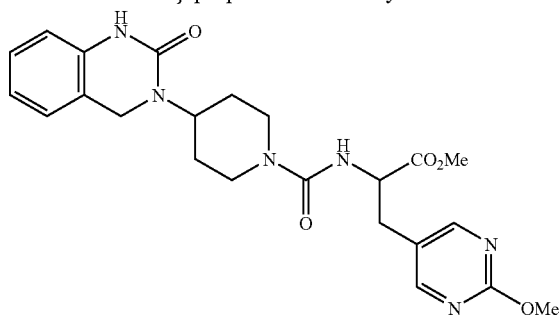

To a solution of 2-Amino-3-(2-methoxy-pyrimidin-5-yl)-propionic acid methyl ester (125 mg) and diisopropylethylamine (0.3 mL) in methylene chloride (2 mL, 0° C.) was added N,N'-disuccinimidyl carbonate (155 mg). After 30 min, 3-piperidin-4-yl-3,4-dihydro-1H-quinazolin-2-one (120 mg) in methylene chloride (2 mL) was added via canula. The reaction was warmed to room temperature and stirred overnight. The reaction was concentrated and purified by prep HPLC to give 99 mg (36%). Mass spec.: 469.10 (MH)+.

Example 58

(±)-4-(2-Oxo-1,4-dihydro-2H-quinazolin-3-yl)-piperidine-1-carboxylic acid[2-[1,4']bipiperidinyl-1'-yl-1-(2-methoxy-pyrimidin-5-ylmethyl)-2-oxo-ethyl]-amide

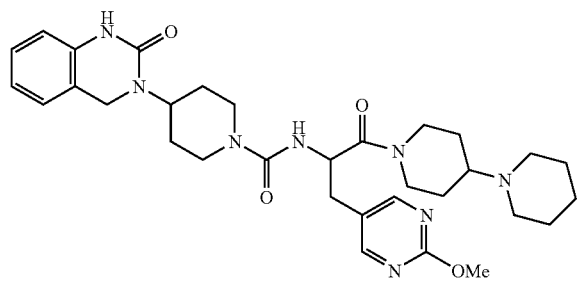

To a solution of 3-(2-methoxy-pyrimidin-5-yl)-2-{[4-(2-oxo-1,4-dihydro-2H-quinazolin-3-yl)-piperidine-1-carbonyl]-amino}-propionic acid methyl ester (99 mg) in methanol (6 mL) was added a solution of lithium hydroxide monohydrate (18 mg) in water (1 mL). The reaction was stirred at room temperature for 4 h and cooled to 0° C. The reaction was treated with 1N hydrochloric acid (0.4 mL), concentrated. The residue obtained was dissolved in methylene chloride (3 mL), and treated sequentially with 4-piperidyl-piperidine (50 mg), triethylamine (88 μL), and bis-2-oxo-3-oxazolidinyl) phosphinic chloride (71 mg). The reaction was stirred overnight, concentrated, and purified by prep HPLC to give 103 mg (45%). LC/MS: $t_R$=1.23 min, 605.54 (MH)+.

2-Benzyloxy-5-bromo-pyridine

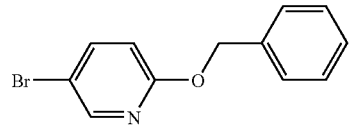

A suspension of 2,5-dibromopyridine (2.0 g, 8.4 mmol), dibenzo-18-crown-6 (0.14 g, 0.05 equiv), benzyl alcohol (1.1 mL, 1.3 equiv), and potassium hydroxide (1.1 g, 2.4 equiv) in toluene (30 mL) were heated at reflux for 3 h in an apparatus fitted with a Dean-Stark trap. The suspension was cooled, concentrated, suspended in water, and extracted into methylene chloride. The combined organic phases were washed with water, then brine, dried over magnesium sulfate, and concentrated to give 1.9 g (85%) which was used without purification. Mass spec.: 264.25 (MH)+.

6-Benzyloxy-pyridine-3-carbaldehyde

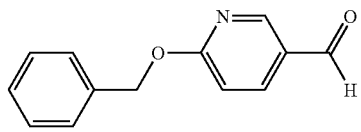

To a solution of 2-benzyloxy-5-bromo-pyridine (1.64 g, 6.2 mmol) in tetrahydrofuran (25 mL, −78° C.) was added n-butyllithium (2.5 M in hexane, 2.61 mL, 1.05 equiv). After 1 h at −78° C., dimethylformamide (0.97 mL, 2 equiv) was added and the mixture stirred for 30 min. The reaction was quickly poured into a stirred solution of 5% aqueous sodium bicarbonate (50 mL) and extracted with diethyl ether (3×). The ethereal was washed with brine, dried over magnesium sulfate, and concentrated to give 1.16 g (quant.) which was used without purification. Mass spec.: 186.34 (MH)$^+$.

2-Benzyloxycarbonylamino-3-(6-benzyloxy-pyridin-3-yl)-acrylic acid methyl ester

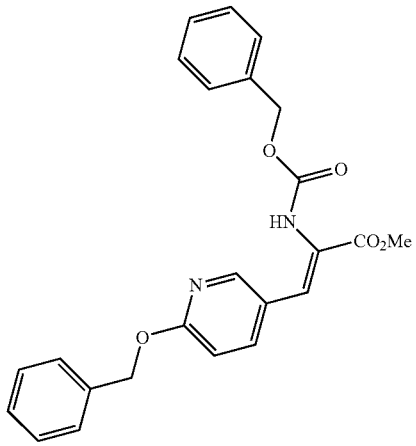

To a stirred suspension of potassium tert-butoxide (0.440 g, 1.7 equiv) in methylene chloride (25 mL) at −20° C. was added N-benzyloxycarbonyl-α-phosphonoglycine trimethyl ester (1.3 g, 1.7 equiv) in methylene chloride (5 mL). The resulting solution was stirred for 5 min and treated with the 6-benzyloxy-pyridine-3-carbaldehyde (0.49 g, 2.28 mmol) in methylene chloride (5 mL). The reaction was stirred at −20° C. for 1 h, allowed to gradually warm to 0° C., and poured into a separatory funnel containing water and diethyl ether. The reaction was extracted with diethyl ether (2×), washed with brine, dried over magnesium sulfate, and concentrated to give 0.98 g (quant.) as an oil which was used without purification. Mass spec.: 419.32 (MH)$^+$.

(±)-2-Benzyloxycarbonylamino-3-(6-benzyloxy-pyridin-3-yl)-propionic acid methyl ester

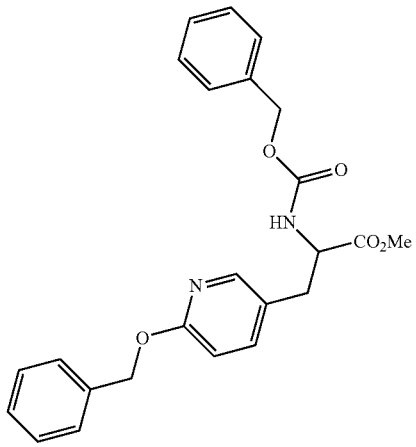

A flask was charged with 2-benzyloxycarbonylamino-3-(6-benzyloxy-pyridin-3-yl)-acrylic acid methyl ester (0.50 g, 1.2 mmol), Wilkinson's catalyst (200 mg, 0.2 equiv), methanol (5 mL), and toluene (3 mL). The flask was flushed with nitrogen, then hydrogen, heated to 35° C., and allowed to stir under an atmosphere of hydrogen for 4 days. The reaction was flushed with nitrogen, diluted with methanol, filtered, and concentrated to afford the crude product which was purified by column chromatography to give 145 mg (29%).

(±)-2-Amino-3-(6-benzyloxy-pyridin-3-yl)-propionic acid methyl ester

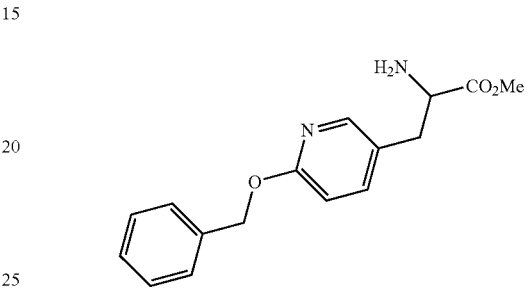

To a stirred solution of 2-benzyloxycarbonylamino-3-(6-benzyloxy-pyridin-3-yl)-propionic acid methyl ester (130 mg, 0.31 mmol) in methylene chloride (5 mL, 0° C.) was added trimethylsilyl iodide (44 μL, 1.0 equiv). The ice bath was removed and stirring continued for 1 h. Reaction was poured into saturated sodium bicarbonate, extracted with ethyl acetate (3×), washed with brine, dried over magnesium sulfate, and concentrated to give 81 mg (91%) which was used without purification. Mass spec.: 287.37 (MH)$^+$.

(±)-3-(6-Benzyloxy-pyridin-3-yl)-2-{[4-(2-oxo-1,4-dihydro-2H-quinazolin-3-yl)-piperidine-1-carbonyl]-amino}-propionic acid methyl ester

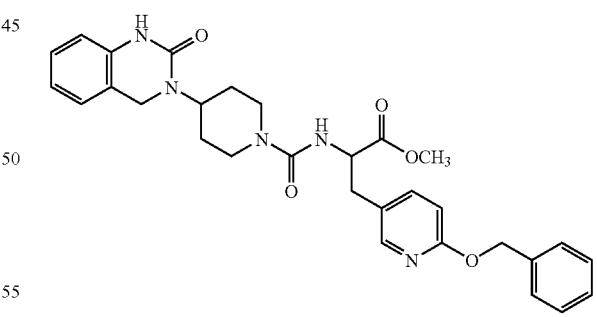

To a stirred solution of 2-amino-3-(6-benzyloxy-pyridin-3-yl)-propionic acid methyl ester (60 mg, 0.21 mmol) in methylene chloride (1 mL, 0° C.) was added carbonyl diimidazole (34 mg, 1.0 equiv.). After 15 min, a solution of 3-piperidin-4-yl-3,4-dihydro-1H-quinazolin-2-one (58 mg, 1.2 equiv.) in methylene chloride (0.5 mL) was added via canula. The ice bath was removed and stirring continued overnight. The reaction was concentrated and purified by column chromatography to give 59 mg (52%). Mass spec.: 544.49 (MH)$^+$.

Example 59

(±)-4-(2-Oxo-1,4-dihydro-2H-quinazolin-3-yl)-piperidine-1-carboxylic acid [1-(6-benzyloxy-pyridin-3-ylmethyl)-2-[1,4']bipiperidinyl-1'-yl-2-oxo-ethyl]-amide

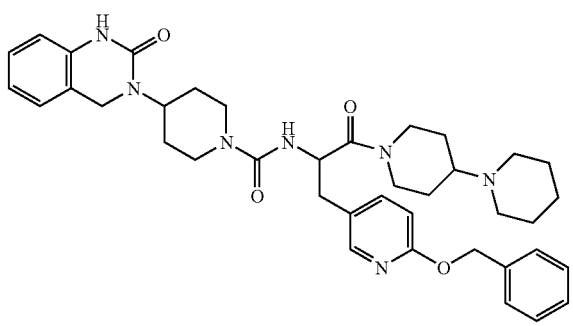

To a stirred solution of 3-(6-benzyloxy-pyridin-3-yl)-2-{[4-(2-oxo-1,4-dihydro-2H-quinazolin-3-yl)-piperidine-1-carbonyl]-amino}-propionic acid methyl ester (59 mg, 0.11 mmol) in methanol (3 mL) was added a solution of lithium hydroxide monohydrate (9.1 mg, 2 equiv) in water (0.5 mL). The reaction was stirred 2 h at room temperature, cooled to 0° C., quenched by addition of 1N hydrochloric acid (0.15 mL), and concentrated. The crude product was used without purification. The crude acid was dissolved in methylene chloride (2 mL, 0° C.), and treated sequentially with 4-piperidinopiperidine (34 mg, 1.8 equiv), triethylamine (35 µL, 2.3 equiv.), and bis-2-oxo-3-oxazolidinyl)phosphinic chloride (34 mg, 1.2 equiv). The ice bath was removed and the reaction allowed to stir overnight. The reaction was concentrated and purified by Prep TLC to give 30.3 mg (41%). LC/MS: $t_R$=1.49 min, 680.29 (MH)$^+$.

Example 60

(±)-4-(2-Oxo-1,4-dihydro-2H-quinazolin-3-yl)-piperidine-1-carboxylic acid[2-[1,4']bipiperidinyl-1'-yl-2-oxo-1-(6-oxo-1,6-dihydro-pyridin-3-ylmethyl)-ethyl]-amide

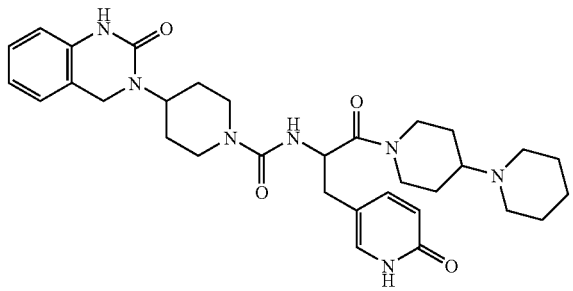

A flask was charged with 4-(2-oxo-1,4-dihydro-2H-quinazolin-3-yl)-piperidine-1-carboxylic acid [1-(6-benzyloxy-pyridin-3-ylmethyl)-2-[1,4']bipiperidinyl-1'-yl-2-oxoethyl]-amide (27 mg, 0.04 mmol), palladium on charcoal (10%, 4 mg), and methanol (1 mL). The flask was flushed with nitrogen, then hydrogen, and allowed to stir under an atmosphere of hydrogen overnight. The flask was flushed with nitrogen, and the reaction filtered through celite to give 22.1 mg (94%). LC/MS: $t_R$=0.93 min, 590.32 (MH)$^+$.

Piperidine-1,4-dicarboxylic acid 1-tert-butyl ester 4-ethyl ester

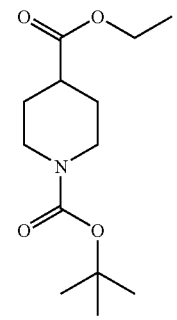

To a solution of ethyl isonipecotate (5.00 g, 0.032 mol) and triethylamine (4.9 mL, 0.035 mmol) in dichloromethane (25 mL) at 0° C. was slowly added a solution of di-tert-butyldicarbonate (7.2 g, 0.033 mol) in dichloromethane (25 mL). The reaction mixture was stirred at room temperature overnight, then washed with potassium hydrogen sulfate three times and with brine once. The organic extract was dried over anhydrous sodium sulfate, filtered and concentrated in vacuum to give the desired product (8.23 g, 100%) as colorless oil. $^1$H NMR (C$_6$D$_6$, 500 MHz) δ 3.88 (q, J=7.5 Hz, 2H), 2.52 (m, 1H), 1.60-1.48 (m, 8H), 1.42 (s, 9H), 0.92 (t, 3H). Mass spec.: 280.44 (M+Na)$^+$.

4-(2-Nitro-benzyl)-piperidine-1,4-dicarboxylic acid 1-tert-butyl ester 4-ethyl ester

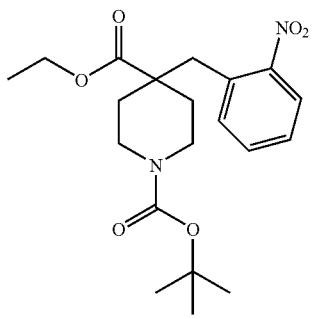

To a solution of piperidine-1,4-dicarboxylic acid 1-tert-butyl ester 4-ethyl ester (8.23 g, 0.032 mol) in tetrahydrofuran (85 mL) was slowly added a solution of sodium bis(trimethylsilyl)amide (44 mL, 0.044 mol). After the resulting mixture had been stirred at −78° C. for 1 h, a solution of 2-nitrobenzyl bromide (8.21 g, 0.038 mol) was added. The reaction mixture was allowed to warm up to room temperature and was stirred overnight. It was then concentrated and the residue was partitioned between water and ethyl acetate. The organic extract was washed with brine, dried over anhydrous magnesium sulfate, filtered, and concentrated under vacuum. The final product was purified from the complex reaction mixture by way of column chromatography on silica gel (eluent-hexanes-ethyl acetate 4:1) to give the desired product (1.61 g, 13%) as brown oil. Mass spec.: 415.38 (M+Na)$^+$.

4-(2-Amino-benzyl)-piperidine-1,4-dicarboxylic acid 1-tert-butyl ester 4-ethyl ester

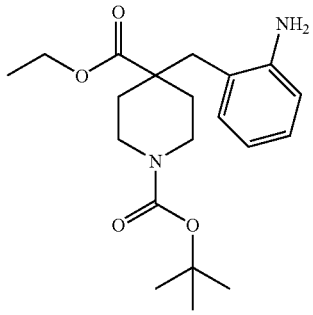

A mixture of 4-(2-nitro-benzyl)-piperidine-1,4-dicarboxylic acid 1-tert-butyl ester 4-ethyl ester (1.61 g, 4.102 mmol) and 10% palladium on charcoal (0.10 g) in ethanol (190 mL) was hydrogenated at 50 psi overnight. The resultant mixture was filtered through a plug of celite, and the filtrate concentrated under vacuum to provide the desired product (1.29 g, 99%) as colorless oil. Mass spec.: 363.45 (MH)+.

4-(2-Amino-benzyl)-piperidine-4-carboxylic acid ethyl ester hydrochloride

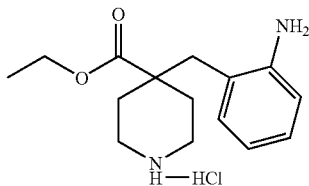

To a solution of 4-(2-amino-benzyl)-piperidine-1,4-dicarboxylic acid 1-tert-butyl ester 4-ethyl ester (1.29 g, 4.102 mmol) in dichloromethane (15 mL) was added a 4.0M solution of hydrogen chloride in dioxane (5 mL). The resulting solution was stirred at room temperature overnight. The concentration of the solution under vacuum provided the title compound (1.23 g, 100%) as white solid, which was used in the next step without purification. Mass spec.: 263.40 (MH)+.

3,4-Benzo-2,9-diazaspiro[5.5]undeca-1-one

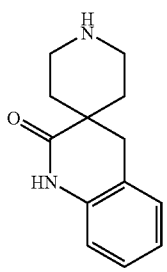

A solution of 4-(2-amino-benzyl)-piperidine-4-carboxylic acid ethyl ester hydrochloride (1.23 g, 4.102 mmol) was dissolved in methanol and the resulting solution was stirred at room temperature overnight. The solution was diluted by half with water and passed through a short plug of the hydroxide form of AG® 1-X2 ion-exchange resin (100-200 mesh), eluting with 50% aqueous methanol. The evaporation of the collected fractions gave the desired product (0.89 g, 100%) as white solid. $^1$H-NMR (CD$_3$OD, 500 MHz) δ 7.23 (m, 2H), 7.05 (d, J=7.5 Hz, 1H), 6.89 (d, J=8.0 Hz, 1H), 3.46-3.41 (m, 2H), 3.34-3.30 (m, 2H), 2.14-2.09 (m, 2H), 1.73-1.67 (m, 4H). Mass spec.: 217.46 (MH)+.

(R)-2-Amino-3-benzo[b]thiophen-3-yl-1-[1,4']bipiperidinyl-1'-yl-propan-1-one, dihydrochloride

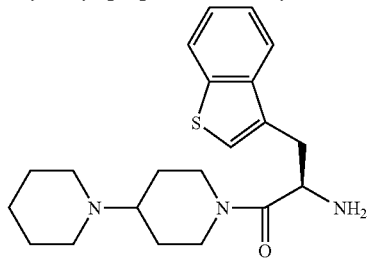

To a well stirred solution of 3-benzo[b]thiophen-3-yl-(2R)-2-tert-butoxycarbonylamino-propionic acid (1.0 g, 3.1 mmol) in methylene chloride (30 mL) at room temp was added 4-piperidinopiperidine (573 mg, 3.4 mmol), triethylamine (1.3 mL, 9.3 mmol) followed by 3-(diethoxyphosphoryloxy)-1,2,3-benzotriazin-4(3H)-one (1.02 g, 3.4 mmol). After 3 h, the reaction mixture was treated with aqueous sodium hydrogencarbonate (15 mL), brine (20 mL) and dried (sodium sulfate). The crude mixture was purified by flash chromatography using 5% methanol in methylene chloride to give (1R)-1-benzo[b]thiophen-3-ylmethyl-2-[1,4']bipiperidinyl-1'-yl-2-oxo-ethyl)-carbamic acid tert-butylester in 82% yield. (1R)-1-Benzo[b]thiophen-3-ylmethyl-2-[1,4']bipiperidinyl-1'-yl-2-oxo-ethyl)-carbamic acid tert-butylester (1.2 g, 2.54 mmol) in methylene chloride (5 mL) was added to a saturated solution of hydrogen chloride in dioxane (20 mL) and stirred for 2 h. The solvents were removed to give (2R)-2-amino-3-benzo[b]thiophen-3-yl-1-[1,4']bipiperidinyl-1'-yl-propan-1-one, dihydrochloride in 98% yield. $^1$H-NMR (500 MHz, CD$_3$OD): δ 7.98-7.88 (m, 2H), 7.55-7.40 (m, 3H), 4.85-4.83 (m, 1H), 3.66-2.68 (m, 9H), 1.92-1.44 (m, 12H). Mass spec.: 372 (MH)+.

Example 61

(R)-1-Oxo-3,4-benzo-2,9-diaza-spiro[5.5]undec-3-ene-9-carboxylic acid (1-benzo[b]thiophen-3-ylmethyl-2-[1,4']bipiperidinyl-1'-yl-2-oxo-ethyl)-amide

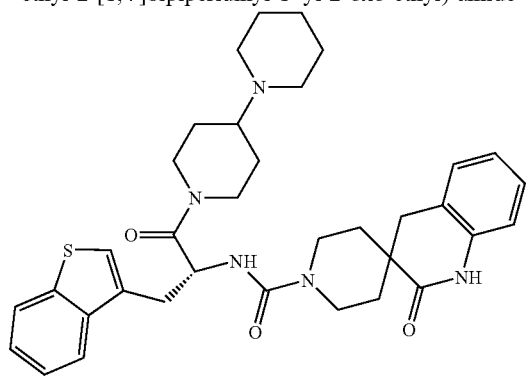

To a solution of 2-amino-3-benzo[b]thiophen-3-yl-1-[1,4']bipiperidinyl-1'-yl-propan-1-one (50.0 mg, 0.135 mmol) in 1,2-dichloroethane (1.5 mL) were added N,N'-disuccinimidyl carbonate (34.6 mg, 0.135 mmol) and diisopropylethylamine (0.09 mL, 0.500 mmol). The resulting solution was stirred for 1 h, at which point 3,4-benzo-2,9-diazaspiro[5.5]undeca-1-one (30.4 mg, 0.140 mmol) was added. The reaction mixture was stirred at room temperature overnight and concentrated. The purification was achieved by way of reversed-phase preparative HPLC to give the desired product (75.5 mg, 77%) as brown oil.

$^1$H-NMR (CD$_3$OD, 500 MHz) δ 7.92-7.85 (m, 2H), 7.44-7.34 (m, 3H), 7.21-7.16 (m, 2H), 7.00 (t, J=7.0 Hz, 1H), 6.86 (t, J=8.5 Hz, 1H), 5.15-5.02 (m, 1H), 4.72-4.45 (m, 1H), 3.95-3.20 (m, 8H), 3.18-2.92 (m, 4H), 2.92-2.75 (m, 2H), 2.75-2.63 (m, 1H), 2.40-2.30 (m, 1H), 2.08-1.64 (m, 8H), 1.58-1.20 (m, 6H). Mass spec.: 614.37 (MH)$^+$.

Example 62

N-[(1R)-1-(Benzo[b]thien-3-ylmethyl)-2-[1,4-bipiperidin]-1-yl-2-oxoethyl]-3',4'-dihydro-2-oxospiro-[piperidine-4,4'(1H)-quinoline]-1-carboxamide

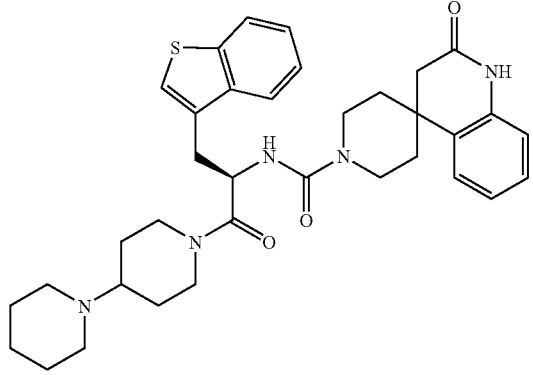

Prepared as described for (R)-1-oxo-3,4-benzo-2,9-diazaspiro[5.5]undec-3-ene-9-carboxylic acid (1-benzo[b]thiophen-3-ylmethyl-2-[1,4']bipiperidinyl-1'-yl-2-oxoethyl)-amide from 3',4'-dihydro-2-oxospiro-[piperidine-4,4'(1H)-quinoline (M. S. Chambers, et al., J. Med. Chem., 1992, 35, 2033-2039; WO-94/13696). $^1$H-NMR (CDCl$_3$, 500 MHz) δ −0.35 (1H, m), 0.79 (1H, m), 1.2-2.1 (12H, m), 2.22 (5H, m), 2.38 (2H, m), 2.74 (2H, ABq), 3.19 (3H, m), 3.33 (2H, m), 3.65 (1H, d), 3.80 (1H, m), 3.93 (1H, t), 4.49 (1H, d), 5.31 (1H, t), 5.96 (1H, t), 6.89 (1H, d), 7.05 (1H, t), 7.18 (1H, d), 7.26 (1H, m), 7.33 (1H, m), 7.40 (1H, m), 7.78 (1H, m), 7.96 (1H, Abq), 9.01 (1H, brs), 9.17 (1H, brs). Mass spec.: 614.36 (MH)$^+$.

Example 63

N-[(1R)-1-(Benzo[b]thien-3-ylmethyl)-2-[1,4-bipiperidin]-1-yl-2-oxoethyl]-2',3'-dihydro-1-oxospiro-[piperidine-4,4'(1H)-isoquinoline]-1-carboxamide

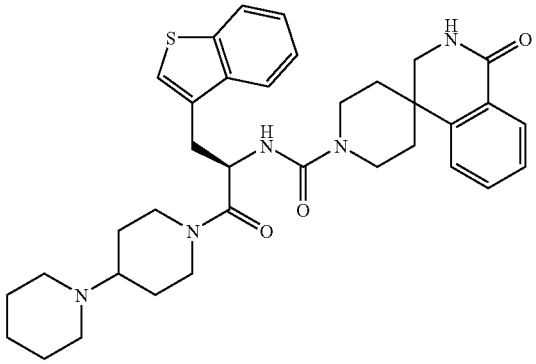

Prepared as described for (R)-1-oxo-3,4-benzo-2,9-diazaspiro[5.5]undec-3-ene-9-carboxylic acid (1-benzo[b]thiophen-3-ylmethyl-2-[1,4']bipiperidinyl-1'-yl-2-oxoethyl)-amide from 2',3'-dihydro-1-oxospiro-[piperidine-4,4'(1H)-isoquinoline (M. S. Chambers, et al., J. Med. Chem., 1992, 35, 2033-2039; WO-94/13696). $^1$H-NMR (CDCl$_3$, 500 MHz) δ 0.01 (1H, m), 0.78 (1H, m), 1.1-2.0 (12H, m), 2.15-2.30 (5H, m), 2.74 (1H, t), 3.0-3.6 (9H), 3.89 (2H, m), 4.46 (1H, d), 5.29 (1H, m), 5.62 (1H, d), 6.47 (1H, brs), 7.38 (5H, m), 7.51 (1H, m), 7.77 (1H, m), 7.85 (1H, m), 8.11 (1H, d). Mass spec.: 614.42 (MH)$^+$.

Example 64

N-[(1R)-1-(Benzo[b]thien-3-ylmethyl)-2-[1,4'-bipiperidin]-1'-yl-2-oxoethyl]-1,2-dihydro-2-oxospiro-[4H-3,1-benzoxazine-4,4'-piperidine]-1'-carboxamide

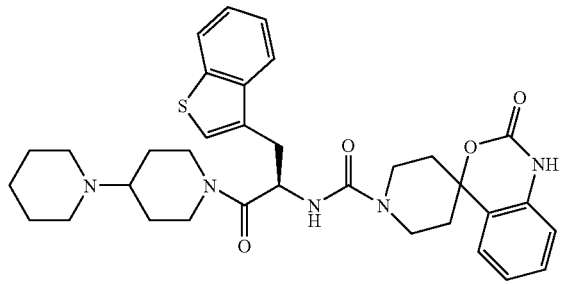

Prepared as described for (R)-1-oxo-3,4-benzo-2,9-diazaspiro[5.5]undec-3-ene-9-carboxylic acid (1-benzo[b]thiophen-3-ylmethyl-2-[1,4']bipiperidinyl-1'-yl-2-oxoethyl)-amide from 1,2-dihydro-2-oxospiro-[4H-3,1-benzoxazine-4,4'-piperidine (prepared as described in Takai, et al.; Chem. Pharm. Bull. 1985, 33, 1129-1139) to give the title compound (76%). Mass spec.: 616 (MH)$^+$. R$_f$=1.42.

Succinate Intermediates and Examples

3-Benzo[b]thiophen-3-yl-acrylic acid

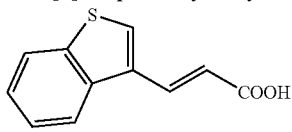

A suspension of 1-benzothiophene-3-carbaldehyde (4.9 g, 0.03 mol), malonic acid (6.6 g, 0.06 mol) and piperidine (1 mL) in 100 mL anhydrous pyridine was heated at 110° C. overnight. The reaction mixture was cooled to room temperature and the solvent was removed in vacuo. The residue was taken up in 100 mL of water and 1 N hydrochloric acid was added to adjust the pH of this solution to ca. 3. The suspension was filtered and the yellow solid was collected, washed with water (3×50 mL) and concentrated in vacuo to give the indicated product with 95% purity (5.65 g, 91%).

3-Benzo[b]thiophen-3-yl-propionic acid

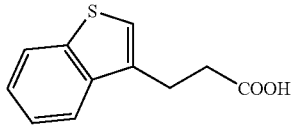

A suspension of 3-benzo[b]thiophen-3-yl-acrylic acid: (5.6 g, 0.027 mol) and 10% Pd/C (600 mg) in 1:1 methanol/ethyl acetate (50 mL) was hydrogenated in a Parr apparatus at 50 psi overnight. The mixture was filtered and concentrated to give the crude product without further purification (ca. 100% conversion). Mass spec.: 205(MH)⁻.

3-(3-Benzo[b]thiophen-3-yl-propionyl)-4(R)-benzyl-oxazolidin-2-one

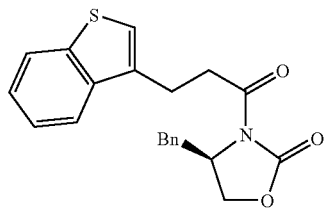

To a solution of 3-benzo[b]thiophen-3-yl-propionic acid (2.1 g, 0.010 mol), triethylamine (4.12 g, 0.040 mol) in anhydrous tetrahydrofuran (100 mL) at 0° C. was added pivaloyl chloride (1.38 mL, 0.011 mol). After stirring for 1.5 h at 0° C., lithium chloride (0.475 g, 0.011 mol) and (R)-4-benzyl-2-oxazolidinone (1.988 g, 0.011 mol) were added. The reaction mixture was allowed to warm up to room temperature and stirred overnight. Then the mixture was washed with water (3×150 mL). The organic layer was separated, dried, and evaporated to give the crude product. The title product was obtained as a brown oil (90%) by flash chromatography on silica gel eluting with 100% methylene chloride. This compound was used immediately in the following procedure.

3 (S)-Benzo[b]thiophen-3-ylmethyl-4-(4-benzyl-2-oxo-oxazolidin-3-yl)-4-oxo butyric acid tert-butyl ester

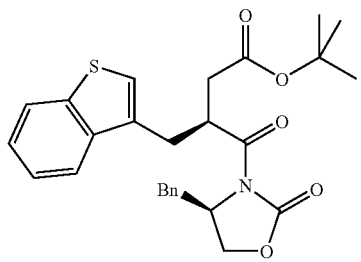

To a solution of 3-(3-benzo[b]thiophen-3-yl-propionyl)-4-benzyl-oxazolidin-2-one (3.35 g, 9.18 mmol) in 100 mL anhydrous tetrahydrofuran at −78° C. was added lithium diisopropyl amide in tetrahydrofuran (6.1 mL, 11.01 mmol) and the reaction mixture was stirred for 30 min Following addition of t-butyl bromoacetate (1.62 mL, 11.01 mmol) at −78° C., the mixture was stirred overnight while it was allowed to warm to room temperature. The solvent was evaporated and the residue diluted with ethyl acetate. The organic layer was washed with water (3×100 mL), dried, filtered, and concentrated to give the crude product. The title product was obtained by filtration through a pad of silica, eluting with methylene chloride (49%).

2(S)-Benzo[b]thiophen-3-ylmethyl-succinic acid, 4-tert-butyl ester

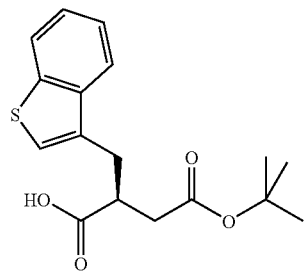

To a stirred solution of 3-benzo[b]thiophen-3-ylmethyl-4-(4-benzyl-2-oxo-oxazolidin-3-yl)-4-oxobutyric acid tert-butyl ester (2.15 g, 4.49 mmol) in tetrahydrofuran (50 mL) and water (30 mL) at 0° C. was added 30% aqueous hydrogen peroxide (1 mL) followed by lithium hydroxide (0.2155 g, 8.98 mmol). The reaction mixture was stirred overnight. Tetrahydrofuran was removed in vacuo and the resulting solution was acidified with 10% citric acid, and extracted with ethyl acetate (3×50 mL). The organic layer was washed with sodium bisulfite solution, dried and concentrated to give the title product.

3 (S)-Benzo[b]thiophen-3-ylmethyl-4-[1,4']bipiperidinyl-1'-yl-4-oxo-butyric acid tert-butyl ester A solution of 2-benzo[b]thiophen-3-ylmethyl-succinic acid 4-tert-butyl ester (1.8420 g, 5.76 mmol), piperidylpiperidine (1.2240 g, 7.28 mmol) and triethylamine (0.7353 g, 7.28 mmol) in 100 mL methylene chloride was treated with 3-(diethoxyphosphoryloxy)-1,2,3-benzotriazin-4(3H)-one (DEPBT, 1.8953 g, 6.34 mmol). The mixture was stirred overnight and then washed with water (3×40 mL). The organic layer was dried, filtered, and concentrated in vacuo to give the crude product. This was further purified by flash chromatography on silica gel, eluting with 0-10% 2 M ammonia in methanol/methylene chloride, to give the desired product. This product was carried on without further purification.

143

3 (S)-Benzo[b]thiophen-3-ylmethyl-4-[1,4']bipiperidinyl-1'-yl-4-oxo-butyric acid

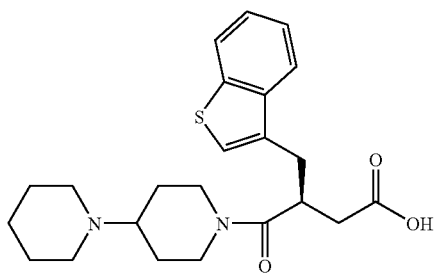

A solution of 3-benzo[b]thiophen-3-ylmethyl-4-[1,4']bipiperidinyl-1'-yl-4-oxo-butyric acid tert-butyl ester in 15 mL methylene chloride was treated with trifluoroacetic acid (3 mL) and the reaction mixture was stirred overnight at room temperature. The solvent was evaporated to give the corresponding trifluoroacetate salt of the title product (99%).

Example 65

1-[1,4']Bipiperidinyl-1'-yl-2-(3 (S)-Benzo[b]thiophen-3-ylmethyl)-4-[1',2'-dihydro-2'-oxospiro-[4H-3',1-benzoxazine-4,4'-piperidinyl]-butane-1,4-dione

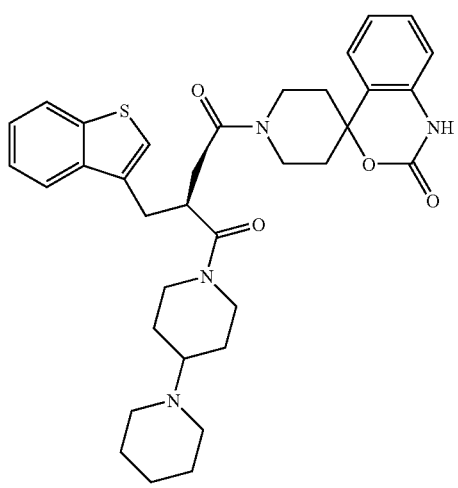

A solution of 3-benzo[b]thiophen-3-ylmethyl-4-[1,4']bipiperidinyl-1'-yl-4-oxo-butyric acid (25.0 mg, 0.060 mmol), 1,2-dihydro-2-oxospiro-4H-3,1-dihydro-benzoxazine-4'4-piperidine (15.7 mg, 0.072 mmol) and triethylamine (7.3 mg, 0.072 mmol) in 5 mL methylene chloride at room temperature was treated with 3-(diethoxyphosphoryloxy)-1,2,3-benzotriazin-4(3H)-one (DEPBT, 21.5 mg, 0.072 mmol). The solution was stirred overnight and then washed with water (3×5 mL). The organic layer was dried, concentrated, and the crude product was purified by flash chromatography on silica gel, eluting with 0-10% 2M ammonia in methanol/methylene chloride, to give the desired product in 60% yield. LC/MS: $t_R$=1.34 min, 615.45 (MH)$^+$.

144

2-(7-Methyl-1H-indazol-5-ylmethylene)-succinic acid 1-methyl ester

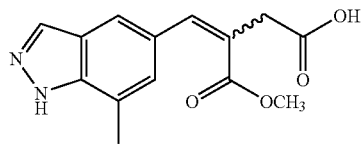

To a mixture of 7-methyl indazole aldehyde (0.2619 g, 1.64 mmol) and DBE-4 dibasic ester (dimethyl succinate) (0.32 mL, 2.45 mmol) in t-butanol (20 mL) was added potassium t-butoxide (0.4036 g, 3.60 mmol). The reaction mixture was heated at 50° C. for 2 h under nitrogen. After a further 16 h at room temperature, the solvent was removed in vacuo and the residue was taken up in water (100 mL) and extracted with ethyl acetate (3×50 mL). The aqueous layer was acidified with 1 N hydrochloric acid to pH 3-4 and extracted with ethyl acetate (3×50 mL). The combined ethyl acetate solution was dried and concentrated in vacuo to give the crude product as a yellow solid (99%, cis/trans isomer approximately 40:60). The crude mixture was carried to next step without further purification. Mass spec.: 275 (MH)$^+$.

(±)-2-(7-Methyl-1H-indazol-5-ylmethyl)-succinic acid 1-methyl ester

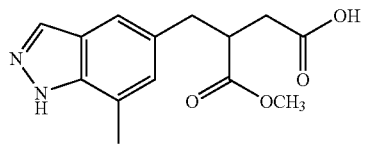

A suspension of 2-(7-methyl-1H-indazol-5-ylmethylene)-succinic acid 1-methyl ester (0.4440 g, 1.62 mmol) and 10% Pd/C (0.04 g) in ethyl acetate (15 mL) and methanol (5 mL) was hydrogenated in a Parr apparatus overnight at 50 psi. The reaction mixture was filtered through a pad of celite and the filtrate evaporated to give the desired product as a yellow solid (100%). Mass spec.: 277 (MH)$^+$.

Example 66

(±)-2-(7-Methyl-1H-indazol-5-ylmethyl)-4-oxo-4-[1',2'-dihydro-2'-oxospiro-[4H-3',1-benzoxazine-4,4'-piperidinyl]-butyric acid methyl ester

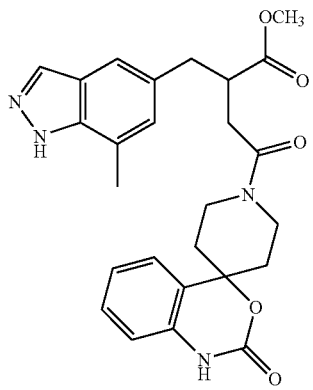

A solution of 2-(7-methyl-1H-indazol-5-ylmethyl)-succinic acid 1-methyl ester (0.2253 g, 0.82 mmol), 1,2-dihydro- 2-oxospiro-4H-3,1-dihydro-benzoxazine-4'4-piperidine (0.1938 g, 0.89 mmol) and triethylamine (0.099 g, 0.98 mmol) in methylene chloride (15 mL) was treated with 3-(diethoxyphosphoryloxy)-1,2,3-benzotriazin-4(3H)-one (DEPBT, 0.2685 g, 0.90 mmol). The mixture was stirred overnight and then washed with water (3×5 mL). The organic layer was dried, and concentrated in vacuo. The residue was purified by flash chromatography on silica gel, eluting with 0-10% 2M ammonia in methanol/methylene chloride, to afford the desired product (53%). LC/MS: $t_R$=1.40 min, 477.28 (MH)$^+$.

Similarly Prepared:

Example 67

(±)-2-(7-Methyl-1H-indazol-5-ylmethyl)-4-oxo-4-[4-(2-oxo-1,4-dihydro-2H-quinazolin-3-yl)-piperidin-1-yl]-butyric acid methyl ester

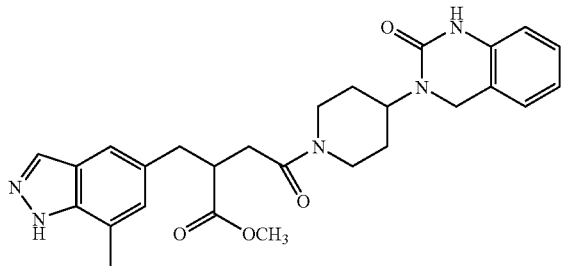

$^1$H-NMR (400 MHz, CDCl$_3$) δ 8.02 (1H, s), 7.98 (1H, m), 7.90 (1H, m), 7.35-6.89 (4H, m), 6.72 (1H, m), 4.71 (1H, m), 4.57 (1H, m), 4.27 (1H, s), 4.22 (1H, m), 3.85 (1H, m), 3.65 (3H, m), 3.30 (1H, m), 3.11 (2H, m), 2.83 (2H, m), 2.81-2.54 (4H, m), 2.35 (1H, m), 1.73-1.67 (4H, m). Mass spec.: 490.32 (MH)$^+$.

(±)-2-(7-Methyl-1H-indazol-5-ylmethyl)-4-oxo-4-[1',2'-dihydro-2'-oxospiro-[4H-3',1-benzoxazine-4,4'-piperidinyl]-butyric acid

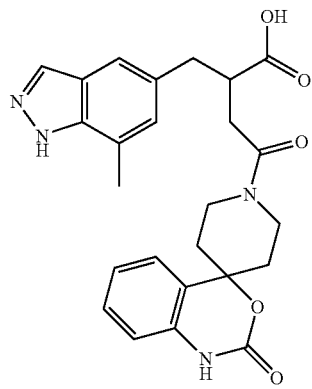

A solution of 2-(7-methyl-1H-indazol-5-ylmethyl)-4-oxo-4-[1',2'-dihydro-2'-oxospiro-[4H-3',1-benzoxazine-4,4'-piperidinyl]-butyric acid methyl ester (0.1911 g, 0.40 mmol) and lithium hydroxide (19.3 mg, 0.80 mmol) in tetrahydrofuran (10 mL) and water (8 mL) was stirred overnight at room temperature. The reaction mixture was acidified with 1N hydrochloric acid to ca. pH 1 and concentrated to remove tetrahydrofuran in vacuo to afford a white solid precipitate which was collected by filtration. The solid was washed twice with small amounts of water and dried in vacuo overnight (100%). Mass spec.: 477 (MH)$^+$.

Example 68

(±)-1-[1,4']Bipiperidinyl-1'-yl-2-(7-methyl-1H-indazol-5-ylmethyl)-4-[1',2'-dihydro-2'-oxospiro-[4H-3',1-benzoxazine-4,4'-piperidinyl]-butane-1,4-dione

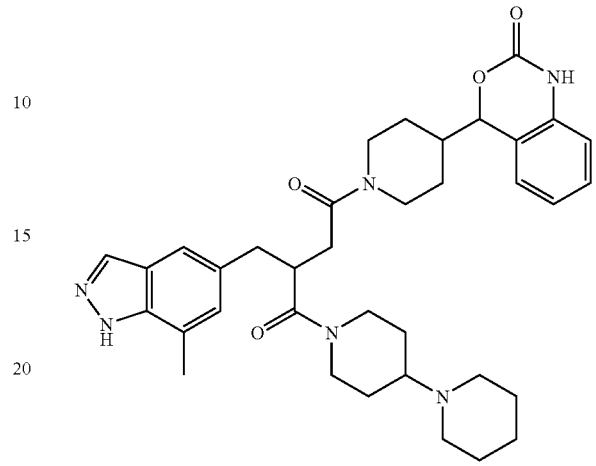

A solution of 2-(7-methyl-1H-indazol-5-ylmethyl)-4-oxo-4-[1',2'-dihydro-2'-oxospiro-[4H-3',1-benzoxazine-4,4'-piperidinyl]-butyric acid (0.020 g, 0.04 mmol), piperidylpiperidine (0.0087 g, 0.05 mmol) and triethylamine (0.09 g, 0.08 mmol) in methylene chloride (5 mL) at room temperature was treated with 3-(diethoxyphosphoryloxy)-1,2,3-benzotriazin-4(3H)-one (DEPBT, 0.0155 g, 0.05 mmol). The mixture was stirred overnight and then washed with water (3×5 mL). The organic layer was dried and the solvents were removed in vacuo. The crude product was purified by preparative TLC on silica gel (10% 2 M ammonium hydroxide/methanol in methylene chloride) to give the desired product (36%). LC/MS: $t_R$=1.18 min, 613.47 (MH)$^+$.

Similarly Prepared:

Example 69

(±)-1-[1,4']Bipiperidinyl-1'-yl-2-(7-methyl-1H-indazol-5-ylmethyl)-4-[4-(2-oxo-1,4-dihydro-2H-quinazolin-3-yl)-piperidin-1-yl]-butane-1,4-dione

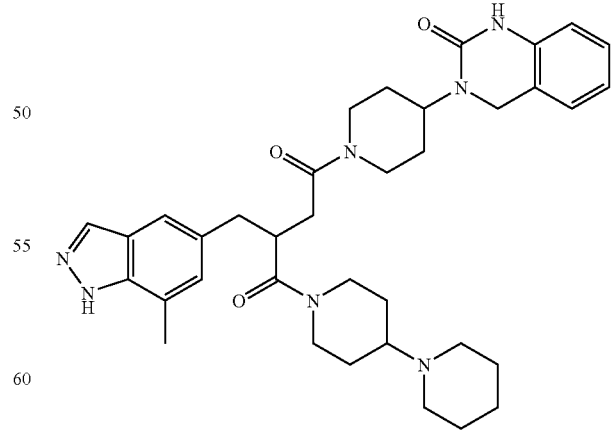

$^1$H-NMR (400 MHz, CDCl$_3$) δ 7.99 (1H, m), 7.62 (1H, m), 7.38 (1H, m), 7.14 (1H, m), 7.04-6.90 (3H, m), 6.70 (2H, d, J=8.0 Hz), 4.70-4.58 (3H, m), 4.24 (2H, m), 4.00 (2H, m), 3.70 (1H, m), 3.18-2.72 (5H, m), 2.64-2.22 (8H, m), 2.18-0.82 (17H, m). Mass spec.: 626.34 (MH)$^+$.

Example 70

(±)-1-(1,4-Dioxa-8-aza-spiro[4.5]dec-8-yl)-2-(7-methyl-1H-indazol-5-ylmethyl)-4-[4-(2-oxo-1,4-dihydro-2H-quinazolin-3-yl)-piperidin-1-yl]-butane-1,4-dione

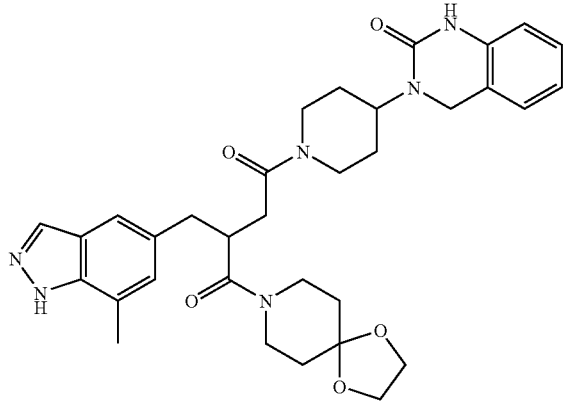

$^1$H-NMR (400 MHz, CDCl$_3$) δ 8.06 (1H, s), 7.75 (1H, m), 7.36 (1H, m), 7.14 (1H, m), 7.01-6.79 (3H, m), 6.70 (1H, m), 4.70-4.49 (2H, m), 4.23 (2H, m), 3.98 (1H, m), 3.87 (3H, m), 3.65-3.44 (4H, m), 3.26 (1H, m), 3.10-2.88 (3H, m), 2.75 (1H, m), 2.51 (3H, s), 2.35 (1H, m), 2.00 (1H, m), 1.70-1.00 (9H, m). Mass spec.: 601.38 (MH)$^+$.

Example 71

(±)-1-(1,4-Dioxa-8-aza-spiro[4.5]dec-8-yl)-2-(7-methyl-1H-indazol-5-ylmethyl)-4-[1',2'-dihydro-2'-oxospiro-[4H-3',1-benzoxazine-4,4'-piperidinyl]-butane-1,4-dione

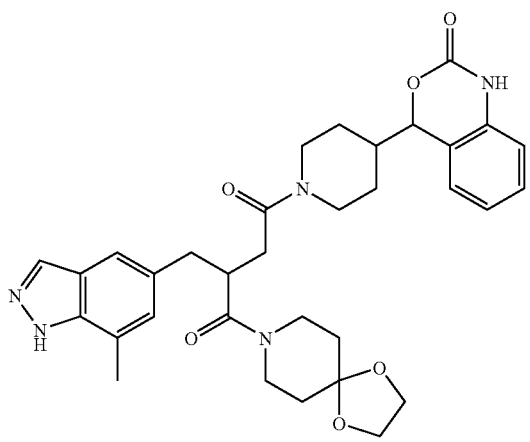

$^1$H-NMR (400 MHz, CDCl$_3$) δ 9.27 (1H, m), 8.00 (1H, s), 7.37 (1H, m), 7.23 (1H, m), 7.10-6.99 (3H, m), 6.87 (1H, m), 4.54 (1H, m), 3.97-3.50 (10H, m), 3.30 (1H, m), 3.16-2.76 (4H, m), 2.53 (3H, s), 2.35 (1H, m), 2.20-1.00 (9H, m). Mass spec.: 588.36 (MH)$^+$.

Example 72

(±)-N,N-Dimethyl-2-(7-methyl-1H-indazol-5-ylmethyl)-4-oxo-4-[4-(2-oxo-1,4-dihydro-2H-quinazolin-3-yl)-piperidin-1-yl]-butyramide

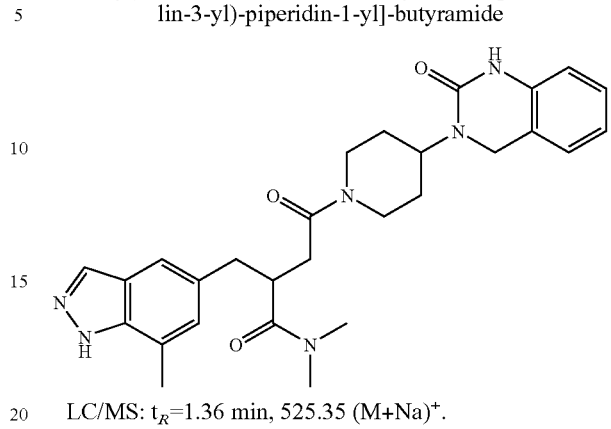

LC/MS: t$_R$=1.36 min, 525.35 (M+Na)$^+$.

Example 73

(±)-1-(2,6-Dimethyl-morpholin-4-yl)-2-(7-methyl-1H-indazol-5-ylmethyl)-4-[4-(2-oxo-1,4-dihydro-2H-quinazolin-3-yl)-piperidin-1-yl]-butane-1,4-dione

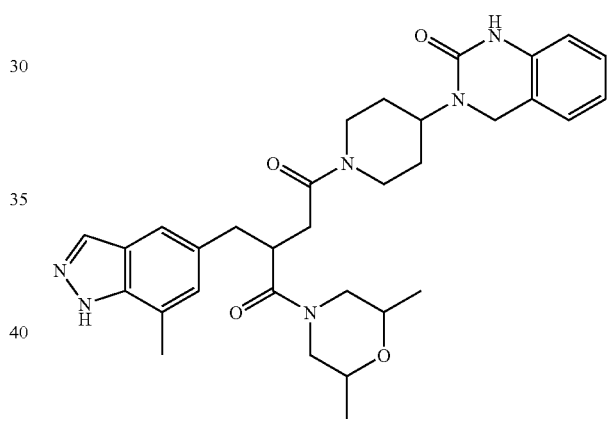

LC/MS: t$_R$=1.41 min, 573.39 (MH)$^+$.

Example 74

(±)-2-(7-Methyl-1H-indazol-5-ylmethyl)-1-(4-methyl-piperidin-1-yl)-4-[4-(2-oxo-1,4-dihydro-2H-quinazolin-3-yl)-piperidin-1-yl]-butane-1,4-dione

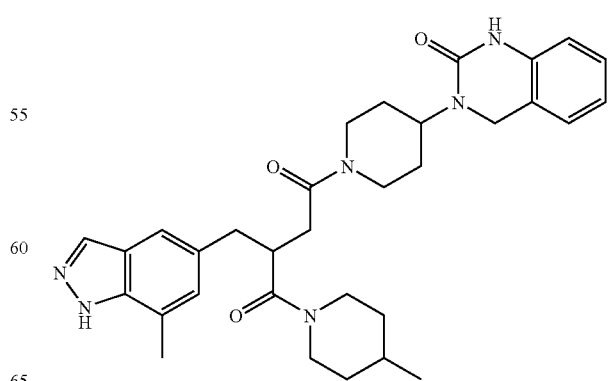

$^1$H-NMR (400 MHz, CDCl$_3$) δ 8.06 (1H, b), 7.60-6.73 (7H, m), 4.71 (1H, m), 4.54 (2H, m), 4.26 (2H, m), 4.05-3.89

(2H, m), 3.65 (1H, m), 3.09-2.81 (4H, m), 2.61 (3H, s), 2.41 (2H, m), 1.76-0.51 (15H, m). Mass spec.: 557.38 (MH)+.

Example 75

(±)-2-(7-Methyl-1H-indazol-5-ylmethyl)-1-morpholin-4-yl-4-[4-(2-oxo-1,4-dihydro-2H-quinazolin-3-yl)-piperidin-1-yl]-butane-1,4-dione

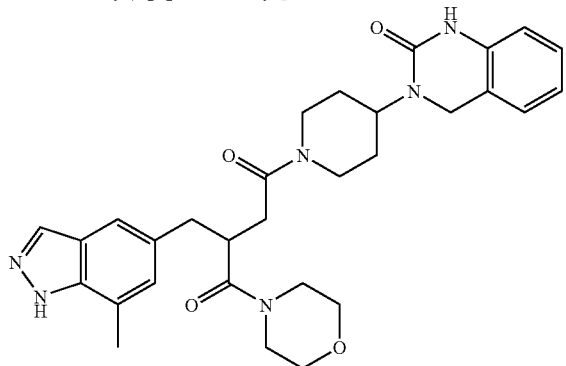

LC/MS: $t_R$=1.32 min, 545.42 (MH)+.

Example 76

(±)—N,N-Dimethyl-2-(7-methyl-1H-indazol-5-ylmethyl)-4-oxo-4-[1',2'-dihydro-2'-oxospiro-[4H-3',1-benzoxazine-4,4'-piperidinyl]-butyramide

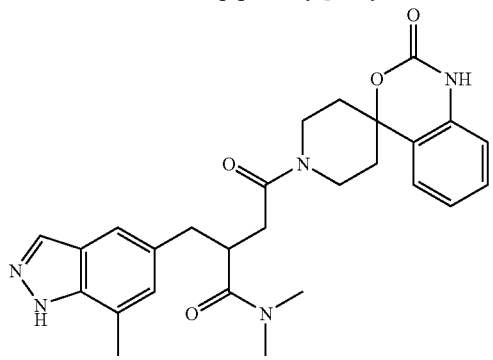

LC/MS: $t_R$=1.27 min, 512.30 (M+Na)+.

Example 77

(±)-2-(7-Methyl-1H-indazol-5-ylmethyl)-1-(piperidin-1-yl)-4-[1',2'-dihydro-2'-oxospiro-[4H-3',1-benzoxazine-4,4'-piperidinyl]-butane-1,4-dione

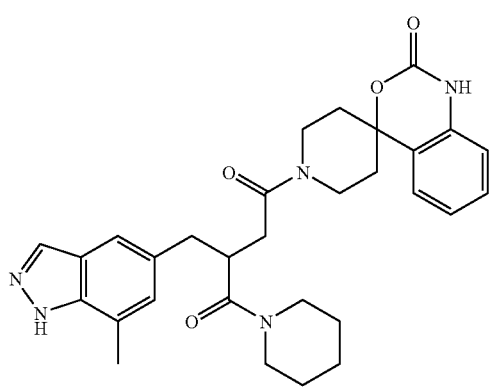

¹H-NMR (400 MHz, CDCl₃) δ 9.26-9.01 (1H, m), 8.09 (1H, s), 7.42-6.89 (7H, m), 4.56 (1H, m), 3.84 (1H, m), 3.65 (3H, m), 3.30 (2H, m), 3.05 (3H, m), 2.81 (1H, m), 2.60 (3H, s), 2.39 (1H, m), 2.09 (2H, m), 1.85 (1H, m), 1.43-0.79 (9H, m). Mass spec.: 530.34 (MH)+.

Example 78

(±)-2-(7-Methyl-1H-indazol-5-ylmethyl)-4-[4-(2-oxo-1,4-dihydro-2H-quinazolin-3-yl)-piperidin-1-yl]-1-piperidin-1-yl-butane-1,4-dione

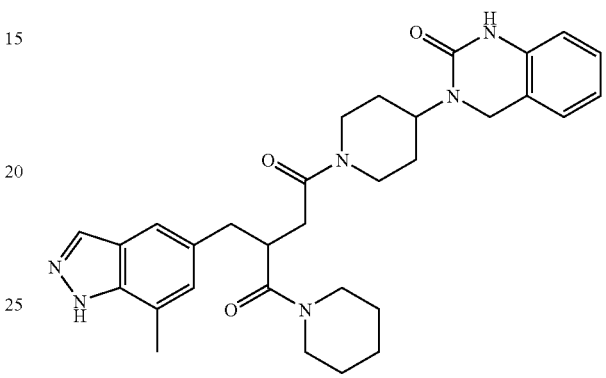

¹H-NMR (400 MHz, CDCl₃) δ 8.02 (1H, s), 7.82 (1H, m), 7.37 (1H, m), 7.14 (1H, m), 7.04-6.90 (3H, m), 6.73 (1H, d, J=8.0 Hz), 4.69 (1H, m), 4.56 (1H, m), 4.24 (2H, d, J=7.2 Hz), 4.02 (1H, m), 3.65 (2H, m), 3.33 (3H, m), 3.07 (3H, m), 2.78 (1H, m), 2.55 (3H, s), 2.36 (1H, m), 1.80-1.50 (4H, m), 1.43 (4H, b), 1.26 (2H, b), 0.81 (2H, b). Mass spec.: 543.40 (MH)+.

Example 79

(±)-1-[1,4']Bipiperidinyl-1'-yl-2-(1H-indazol-5-ylmethyl)-4-[1',2'-dihydro-2'-oxospiro-[4H-3',1-benzoxazine-4,4'-piperidinyl]-butane-1,4-dione

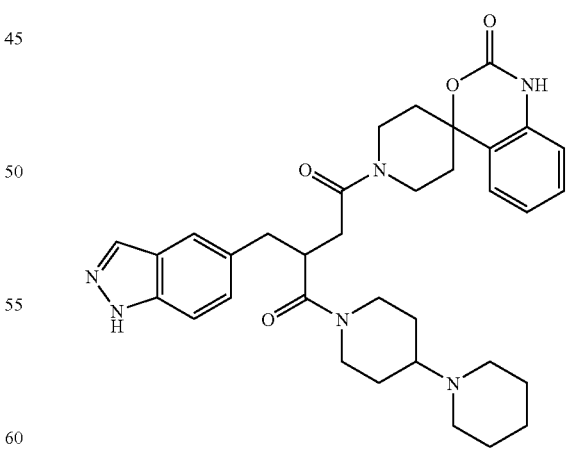

¹H-NMR (400 MHz, CDCl₃) δ 8.86 (1H, m), 7.98 (1H, s), 7.54-6.85 (7H, m), 4.73-4.48 (3H, m), 3.96-0.80 (3H, m), 3.73-3.58 (3H, m), 3.17-2.78 (5H, m), 2.55-2.24 (5H, m), 2.02-1.79 (6H, m), 1.70-0.79 (7H, m). Mass spec.: 599.31 (M+Na)+.

Example 80

(±)-1-(1,4-Dioxa-8-aza-spiro[4.5]dec-8-yl)-2-(1H-indazol-5-ylmethyl)-4-[1',2'-dihydro-2'-oxospiro-[4H-3',1-benzoxazine-4,4'-piperidinyl]-butane-1,4-dione

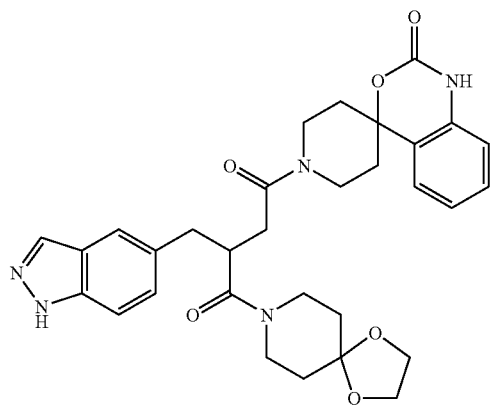

LC/MS: $t_R$=1.25 min, 574.25 (MH)$^+$.

Example 81

(±)-1-(1,4-Dioxa-8-aza-spiro[4.5]dec-8-yl)-2-(1H-indazol-5-ylmethyl)-4-[4-(2-oxo-1,4-dihydro-2H-quinazolin-3-yl)-piperidin-1-yl]-butane-1,4-dione

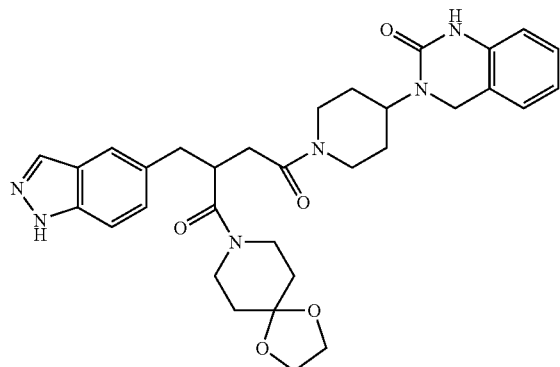

LC/MS: $t_R$=1.34 min, 587.38 (MH)$^+$.

Example 82

(±)-2-(1H-Indazol-5-ylmethyl)-N,N-dimethyl-4-oxo-4-[4-(2-oxo-1,4-dihydro-2H-quinazolin-3-yl)-piperidin-1-yl]-butyramide

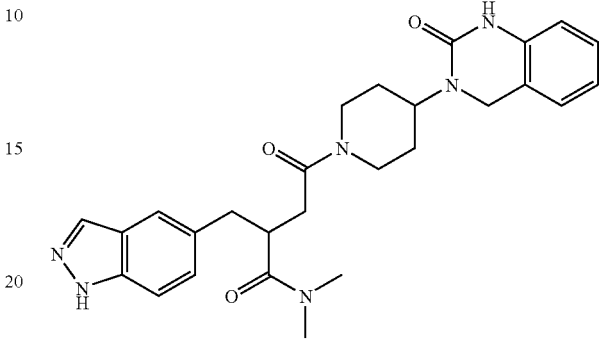

LC/MS: $t_R$=1.28 min, 489.33 (MH)$^+$.

Example 83

(±)-5-{2-([1,4']Bipiperidinyl-1'-carbonyl)-4-oxo-4-[4-(2-oxo-1,4-dihydro-2H-quinazolin-3-yl)-piperidin-1-yl]-butyl}-indazole-1-carboxylic acid tert-butyl ester

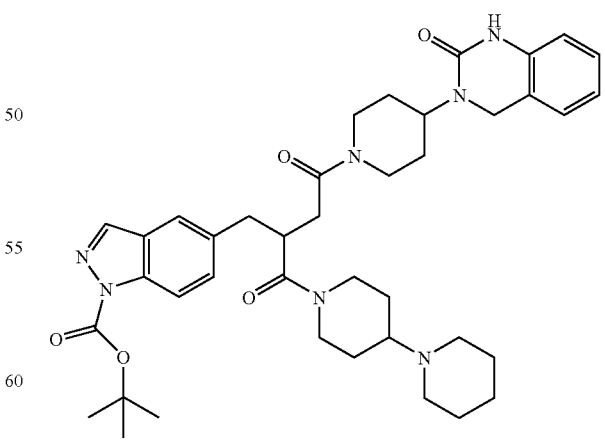

LC/MS: $t_R$=1.47 min, 742.55 (M+Na)$^+$.

Example 84

(±)-2-(7-Methyl-1H-indazol-5-ylmethyl)-4-oxo-4-[4-(2-oxo-1,4-dihydro-2H-quinazolin-3-yl)-piperidin-1-yl]-N-prop-2-ynyl-butyramide

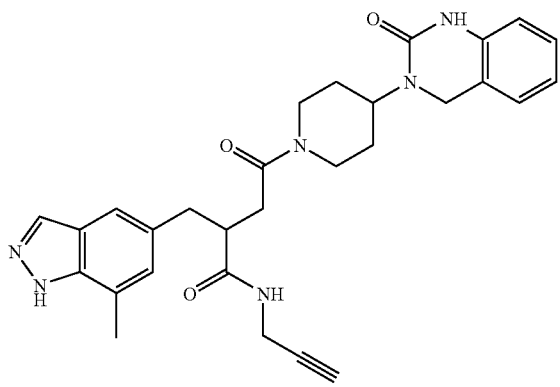

LC/MS: $t_R$=1.33 min, 535.32 (M+Na)$^+$.

Aspartate Intermediates and Examples (L)-2-tert-Butoxycarbonylamino-4-oxo-4-[4-(2-oxo-1,4-dihydro-2H-quinazolin-3-yl)-piperidin-1-yl]-butyric acid benzyl ester

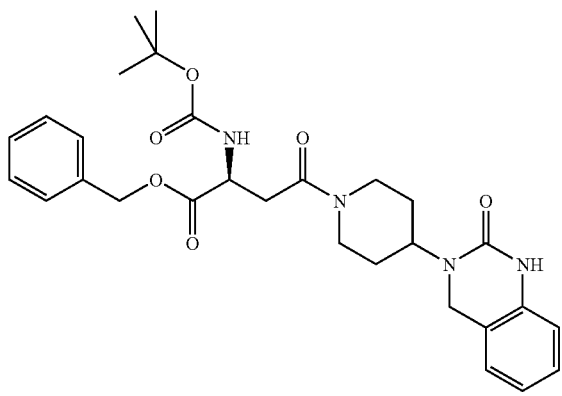

To a stirred solution of N-tert-butyloxycarbonyl-L-aspartic acid-alpha-benzyl ester (1.4 g, 4.33 mmol) and 3,4-dihydro-3-(4-piperidinyl-2(1H)-quinazolinone (1.26 g, 4.33 mmol) in methylene chloride (12 mL) was added 3-(diethoxyphosphoryloxy)-1,2,3-benzotriazin-4(3H)-one (DEPBT, 1.425 g, 4.76 mmol) in one portion followed by dropwise addition of triethylamine (0.724 mL, 5.20 mmol). The resulting suspension gradually became homogeneous with stirring and was stirred at room temperature overnight (15 h). The mixture was diluted with methylene chloride and washed with sodium hydroxide (0.5 N) and water. The layers were separated and the organic layer was dried with sodium sulfate, and concentrated in vacuo to give a light yellow foam. The crude product was purified by flash column chromatography (10% methanol in methylene chloride) to give a colorless oil. Mass spec.: 559 (M+Na)$^+$.

(L)-2-tert-Butoxycarbonylamino-4-oxo-4-[4-(2-oxo-1,4-dihydro-2H-quinazolin-3-yl)-piperidin-1-yl]-butyric acid

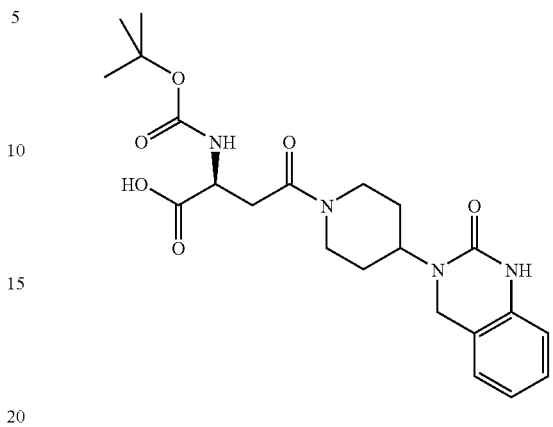

To a solution of 2-tert-butoxycarbonylamino-4-oxo-4-[4-(2-oxo-1,4-dihydro-2H-quinazolin-3-yl)-piperidin-1-yl]-butyric acid benzyl ester (1.48 g, 2.76 mmol) in ethyl acetate/methanol (16 mL, 1:1) in a Parr bottle was added 10% palladized charcoal (150 mg) in one portion. Hydrogenation was carried out with a Parr apparatus at 52 psi for 1 h. TLC (10% methanol in methylene chloride) indicated a quantitative conversion. The mixture was filtered and concentrated in vacuo to afford a glassy colorless solid (1.14 g, 93%).

Example 85

(L)-{1-([1,4']Bipiperidinyl-1'-carbonyl)-3-oxo-3-[4-(2-oxo-1,4-dihydro-2H-quinazolin-3-yl)-piperidin-1-yl]-propyl}-carbamic acid tert-butyl ester

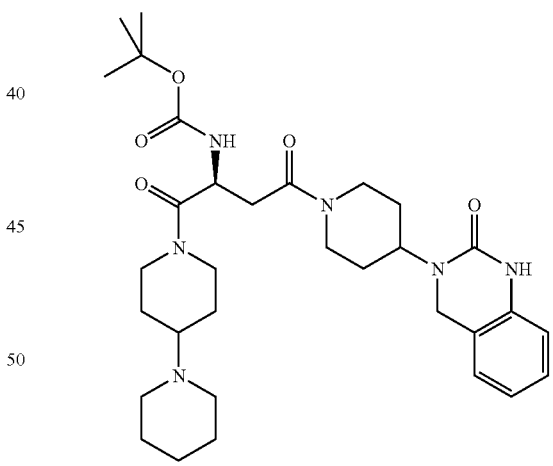

To a stirred solution of 2-tert-butoxycarbonylamino-4-oxo-4-[4-(2-oxo-1,4-dihydro-2H-quinazolin-3-yl)-piperidin-1-yl]-butyric acid (1.14 g, 2.55 mmol) and 4-piperidinyl-piperidine (525 mg, 2.81 mmol) in methylene chloride (20 mL) was added 3-(diethoxyphosphoryloxy)-1,2,3-benzotriazin-4(3H)-one (DEPBT, 840 mg, 2.81 mmol) in one portion followed by dropwise addition of triethylamine (0.427 mL, 3.06 mmol). The resulted mixture was stirred at room temperature overnight (15 h). The mixture was diluted with methylene chloride and washed with sodium hydroxide (0.5 N) solution and water. The layers were separated and the organic layer was dried with sodium sulfate and concentrated in vacuo to give a light yellow foam. The crude product was purified by flash column chromatography (10% (1M ammonia in methanol) in methylene chloride) to give a colorless foam (1.08 g, 71%). $^1$H-NMR (400 MHz, CDCl$_3$) δ 8.86-8.55 (1H, br), 7.05 (1H, br), 6.93 (1H, br), 6.82 (1H, br), 6.72 (1H, d, J=7.6 Hz), 6.10-5.68 (1H, br), 5.20 (1H, m), 54.70-4.40 (2H, br), 4.20 (2H, br), 4.01-3.82 (2H, br.), 3.10-2.88 (3H, br), 2.99 (3H, br), 2.53 (6H, br), 1.90-1.10 (23H, m). Mass spec.: 597 (MH)$^+$.

(L)-2-Amino-1-[1,4']bipiperidinyl-1'-yl-4-[4-(2-oxo-1,4-dihydro-2H-quinazolin-3-yl)-piperidin-1-yl]-butane-1,4-dione

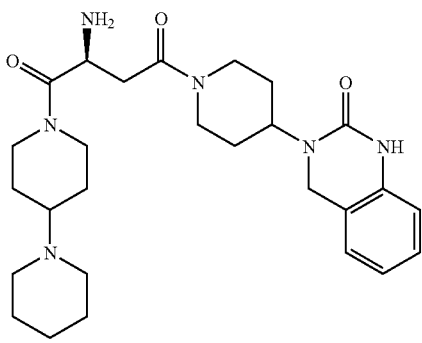

To a stirred solution of {1-([1,4']bipiperidinyl-1'-carbonyl)-3-oxo-3-[4-(2-oxo-1,4-dihydro-2H-quinazolin-3-yl)-piperidin-1-yl]-propyl}-carbamic acid tert-butyl ester (1.05 g, 1.76 mmol) in methylene chloride (12 mL) was added trifluoroacetic acid (2 mL). The mixture was stirred at room temperature until complete conversion (monitored by LCMS, ca. 15 h). The mixture was then diluted with water and sodium hydroxide (1.5 g) was slowly added with stirring. The layers were separated and the aqueous layer was extracted with methylene chloride. The combined organic layers were dried over sodium sulfate and concentrated in vacuo to give a light yellow foam (860 mg, 98%). Mass spec.: 497 (MH)$^+$.

Example 86

(L)-1-[1,4']Bipiperidinyl-1'-yl-2-(1H-indol-5-ylamino)-4-[4-(2-oxo-1,4-dihydro-2H-quinazolin-3-yl)-piperidin-1-yl]-butane-1,4-dione

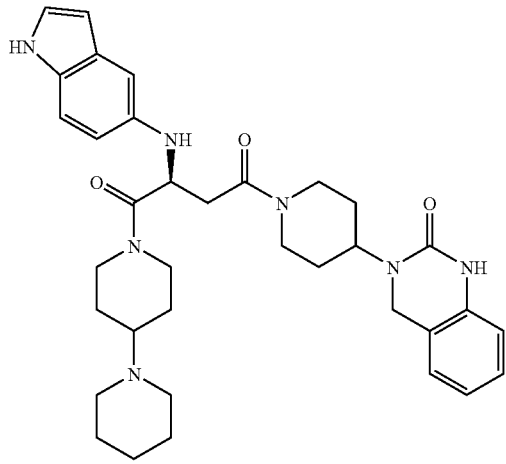

To a solution of 2-amino-1-[1,4']bipiperidinyl-1'-yl-4-[4-(2-oxo-1,4-dihydro-2H-quinazolin-3-yl)-piperidin-1-yl]-butane-1,4-dione (52 mg, 0.105 mmol) and N-tert-BOC-5-bromo-indole (prepared as described in *Tetrahedron* 2000, pp 8473-8482) (31 mg, 0.105 mmol) in tetrahydrofuran (1 mL) in a 5 mL drum vial was added 2-dicyclohexylphosphino-2'-(N,N-dimethylamino)-biphenyl (4.1 mg, 0.0105 mmol), Pd$_2$(dba)$_3$ (4.8 mg, 0.005 mmol), and cesium carbonate (54.6 mg, 0.168 mmol) under nitrogen. The vial was sealed with a Teflon®-lined cap. The deep orange-colored reaction mixture was heated at 80° C. with stirring. The reaction was continued at 80° C. overnight. Conversion reached approximately 50% after 17 h. The solvent was removed in vacuo and the residue dissolved in methylene chloride and filtered. The desired product was purified by preparative TLC (10% methanol in methylene chloride) to afford the tert-butyloxycarbonyl-protected product (11 mg, 15%). Mass spec.: 712 (MH)$^+$. This intermediate (11 mg) was dissolved in 3 mL methylene chloride and treated with trifluoroacetic acid (1.5 mL). The colorless solution turned to a tan color and was stirred at room temperature for 1.5 h. The mixture was concentrated in vacuo and dried under high vacuum to a give tan powder (15 mg, 100%). Mass spec.: 612 (MH)$^+$.

Example 87

(L)-1-[1,4']Bipiperidinyl-1'-yl-2-(5-chloro-2-nitrophenylamino)-4-[4-(2-oxo-1,4-dihydro-2H-quinazolin-3-yl)-piperidin-1-yl]-butane-1,4-dione

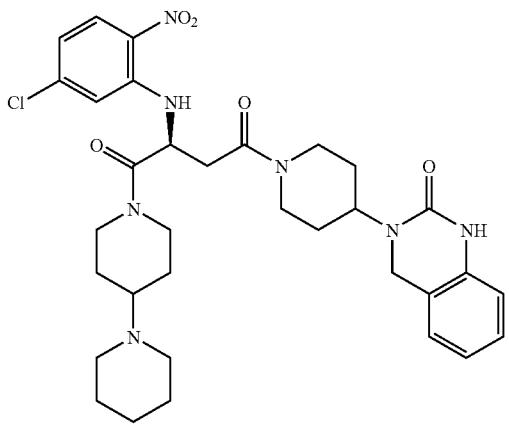

To a stirred solution of 2-amino-1-[1,4']bipiperidinyl-1'-yl-4-[4-(2-oxo-1,4-dihydro-2H-quinazolin-3-yl)-piperidin-1-yl]-butane-1,4-dione (33.7 mg, 0.068 mmol) and 4-chloro-1,2-dinitrobenzene (16.8 mg, 0.075 mmol) in ethanol (0.5 mL) was added a saturated sodium bicarbonate solution (4 drops). The mixture was stirred at room temperature for 70 h to approximately 60% conversion. The product was purified by preparative HPLC to give a yellow solid (17.7 mg, 40%). Mass spec.: 652 (MH)$^+$.

Example 88

(L)-1-[1,4']Bipiperidinyl-1'-yl-2-(6-chloro-pyrimidin-4-ylamino)-4-[4-(2-oxo-1,4-dihydro-2H-quinazolin-3-yl)-piperidin-1-yl]-butane-1,4-dione

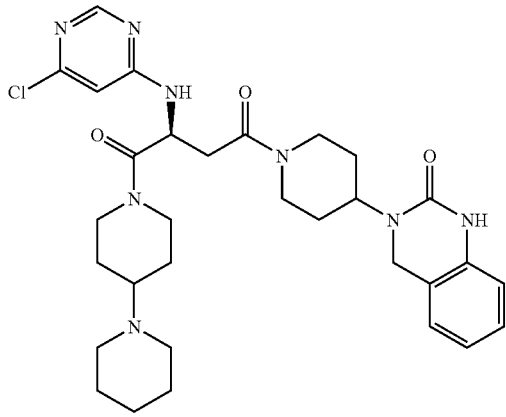

A mixture of 2-amino-1-[1,4']bipiperidinyl-1'-yl-4-[4-(2-oxo-1,4-dihydro-2H-quinazolin-3-yl)-piperidin-1-yl]-butane-1,4-dione (22.3 mg, 0.045 mmol) and 4,6-dichloropyrimidine (16 mg, 0.095 mmol) in 2-propanol (0.5 mL) in a microwavable vial was heated at 130° C. under microwave irradiation for 40 min. LC/MS indicated 90% conversion. The solvent was removed in vacuo and the residue was partitioned between methylene chloride and 1 N sodium hydroxide solution. The organic layer was separated, dried over sodium sulfate, and concentrated in vacuo. The residue was purified by flash column chromatography (10% (1N ammonia in methanol) in methylene chloride) to afford a white solid (23 mg, 84%). $^1$H-NMR (400 MHz, CDCl$_3$) δ 8.36 (1H, d, J=12.8 Hz), 8.04-7.81 (1H, 2s), 7.14 (1H, t, J=7.6 Hz), 7.10-6.80 (2H, m), 6.74 (1H, t, J=8.2 Hz), 6.52-6.42 (1H, m), 5.90-5.50 (1H, br), 4.85-4.40 (3H, m), 4.40-4.05 (3H, m), 4.05-3.82 (1H, m), 3.20-3.00 (2H, m), 3.00-2.68 (2H, m), 2.68-2.30 (8H, m), 2.05-1.90 (2H, m), 1.90-0.70 (12H, m). Mass spec.: 609 (MH)$^+$.

Similarly Prepared:

Example 89

(L)-1-[1,4']Bipiperidinyl-1'-yl-2-(2-chloro-9H-purin-6-ylamino)-4-[4-(2-oxo-1,4-dihydro-2H-quinazolin-3-yl)-piperidin-1-yl]-butane-1,4-dione

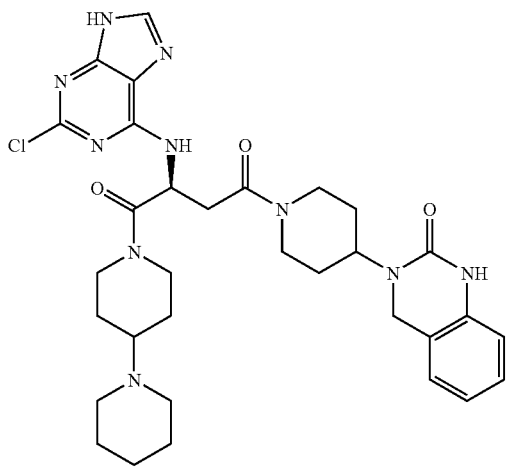

LC/MS: t$_R$=1.10 min, 649 (MH)$^+$.

Example 90

(L)-2-(4-Amino-6-methyl-5-nitro-pyrimidin-2-ylamino)-1-[1,4']bipiperidinyl-1'-yl-4-[4-(2-oxo-1,4-dihydro-2H-quinazolin-3-yl)-piperidin-1-yl]-butane-1,4-dione

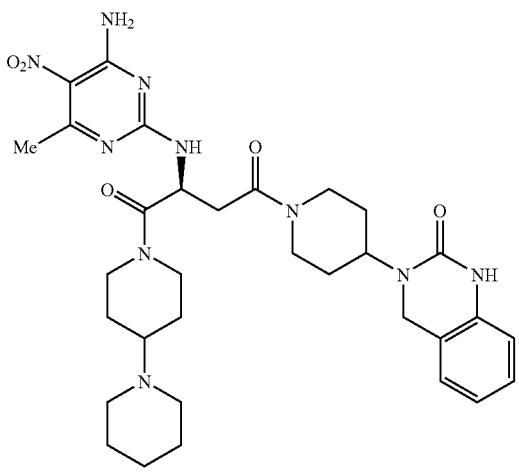

LC/MS: t$_R$=1.12 min, 649 (MH)$^+$.

Example 91

(L)-1-[1,4']Bipiperidinyl-1'-yl-2-(4,5-diamino-6-methyl-pyrimidin-2-ylamino)-4-[4-(2-oxo-1,4-dihydro-2H-quinazolin-3-yl)-piperidin-1-yl]-butane-1,4-dione

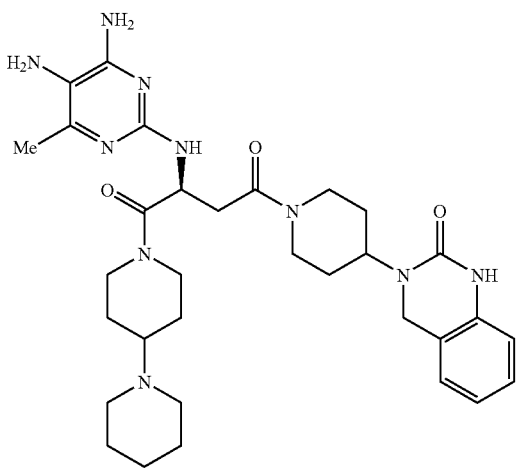

To a solution of 2-(4-amino-6-methyl-5-nitro-pyrimidin-2-ylamino)-1-[1,4']bipiperidinyl-1'-yl-4-[4-(2-oxo-1,4-dihydro-2H-quinazolin-3-yl)-piperidin-1-yl]-butane-1,4-dione in 2:1 methanol/ethyl acetate (6 mL) in a Parr bottle was added 10% palladized charcoal (60 mg). The mixture was shaken under a hydrogen atmosphere at 55 psi for 20 h. The mixture was filtered through celite and the filtrate was concentrated in vacuo to afford a colorless solid (41.2 mg, 49.2% for two steps). LC/MS: t$_R$=0.86 min, 619 (MH)$^+$.

Example 92
(L)-1-[1,4']Bipiperidinyl-1'-yl-2-(7-methyl-1H-[1,2,3]triazolo[4,5-d]pyrimidin-5-ylamino)-4-[4-(2-oxo-1,4-dihydro-2H-quinazolin-3-yl)-piperidin-1-yl]-butane-1,4-dione

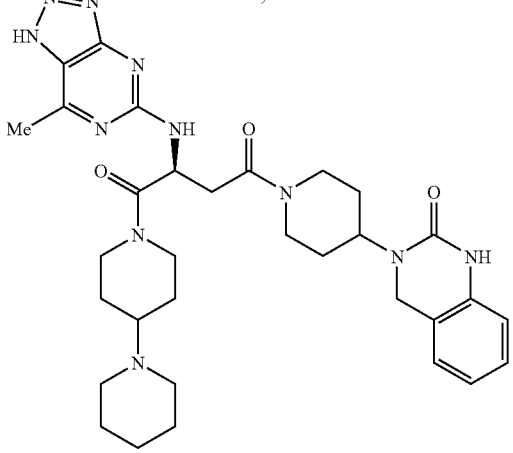

To a stirred solution of 1-[1,4']bipiperidinyl-1'-yl-2-(4,5-diamino-6-methyl-pyrimidin-2-ylamino)-4-[4-(2-oxo-1,4-dihydro-2H-quinazolin-3-yl)-piperidin-1-yl]-butane-1,4-dione (10.6 mg, 0.0125 mmol) in acetic acid (1.5 mL) was added sodium nitrite (24 mg) followed by a few drops of water. The resulting light yellow solution was stirred at room temperature for 6 h. The reaction mixture was diluted with water and methanol and purified by preparative HPLC to afford a colorless oil/solid (3.0 mg, 28%). LC/MS: $t_R$=1.07 min, 630 (MH)$^+$.

General Procedure for the Synthesis of Examples 93-95

A mixture of 2-amino-1-[1,4']bipiperidinyl-1'-yl-4-[4-(2-oxo-1,4-dihydro-2H-quinazolin-3-yl)-piperidin-1-yl]-butane-1,4-dione (0.014 mmol), one of a series of aldehydes (0.07 mmol, 5 equiv) and solid anhydrous magnesium sulfate (0.031 mmol, 2.2 equiv) in 1,2-dichloroethane (3.0 mL) was treated with a catalytic amount of acetic acid and was shaken overnight. Sodium cyanoborohydride (0.07 mmol, 5 eq) was then added in one portion and the suspension was again shaken overnight. Purification was carried out either by filtration through an SCX cartridge or by preparative HPLC.

Example 93
(L)-1-[1,4']Bipiperidinyl-1'-yl-2-((2'-pyridyl)-methyl-amino)-4-[4-(2-oxo-1,4-dihydro-2H-quinazolin-3-yl)-piperidin-1-yl]-butane-1,4-dione

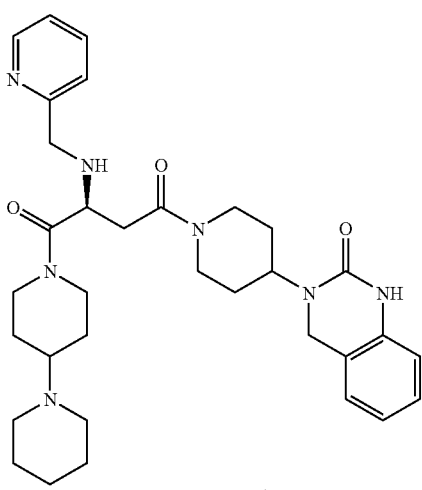

LC/MS: $t_R$=0.87 min, 588 (MH)$^+$.

Example 94
(L)-1-[1,4']Bipiperidinyl-1'-yl-2-((5'-indazolyl)-methyl-amino)-4-[4-(2-oxo-1,4-dihydro-2H-quinazolin-3-yl)-piperidin-1-yl]-butane-1,4-dione

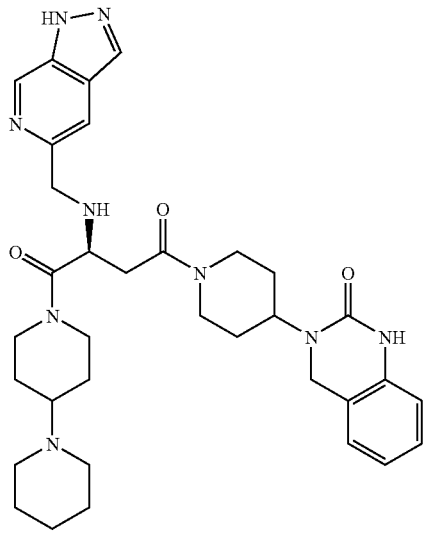

LC/MS: $t_R$=0.92 min, 626 (MH)$^+$.

Example 95
(L)-1-[1,4']Bipiperidinyl-1'-yl-2-((3'-methyl-phenyl)-methyl-amino)-4-[4-(2-oxo-1,4-dihydro-2H-quinazolin-3-yl)-piperidin-1-yl]-butane-1,4-dione

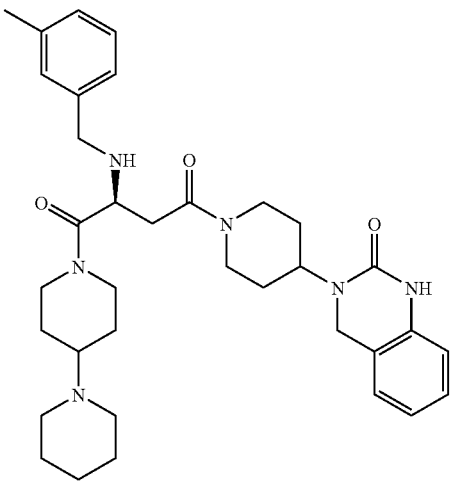

LC/MS: $t_R$=1.08 min, 600 (MH)$^+$.

Example 96

(L)-1-[1,4']Bipiperidinyl-1'-yl-4-[4-(2-oxo-1,4-dihydro-2H-quinazolin-3-yl)-piperidin-1-yl]-2-(pyrimidin-4-ylamino)-butane-1,4-dione

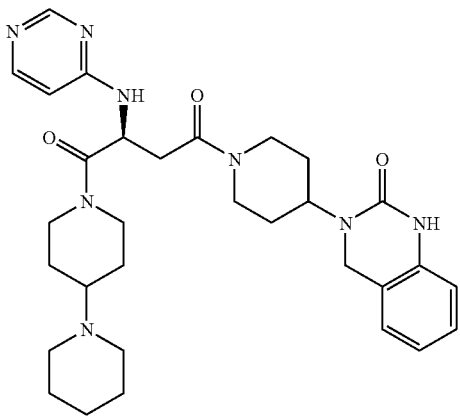

To a solution of 1-[1,4']bipiperidinyl-1'-yl-2-(6-chloro-pyrimidin-4-ylamino)-4-[4-(2-oxo-1,4-dihydro-2H-quinazolin-3-yl)-piperidin-1-yl]-butane-1,4-dione (21 mg) was dissolved in 4 mL ethyl acetate/methanol (1:1) in a Parr bottle was added 10% palladized charcoal (10 mg). Hydrogenation was carried out on a Parr apparatus at 55 psi overnight. The degassed mixture was then filtered and concentrated in vacuo. The residue was purified by preparative HPLC to afford a yellow solid (12.4 mg, 45%). Mass spec.: 575 (MH)$^+$.

Example 97

(L)-1-[1,4']Bipiperidinyl-1'-yl-2-(4-hydroxy-cyclohexylamino)-4-[4-(2-oxo-1,4-dihydro-2H-quinazolin-3-yl)-piperidin-1-yl]-butane-1,4-dione

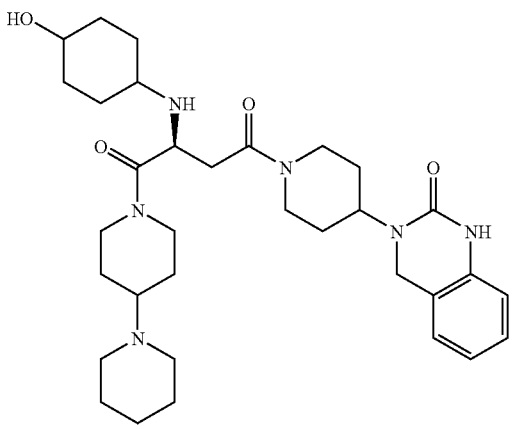

To a stirred mixture of 2-amino-1-[1,4']bipiperidinyl-1'-yl-4-[4-(2-oxo-1,4-dihydro-2H-quinazolin-3-yl)-piperidin-1-yl]-butane-1,4-dione (47.9 mg, 0.096 mmol) and 4-hydroxy-cyclohexanone (Synthesis reported in Can. J. Chem. 1994, 72, 1699-1704) (11 mg, 0.096 mmol) in methanol (1.0 mL) was added excess zinc chloride followed by sodium cyanoborohydride (5 equiv). The suspension was stirred at room temperature for 6 days. The methanol was removed in vacuo and the residue partitioned between methylene chloride and 1 N sodium hydroxide. The aqueous layer was extracted with methylene chloride (3×). The combined methylene chloride solution was passed through a celite cartridge and concentrated in vacuo. The residue was purified by preparative TLC (10% (1N ammonia in methanol) in methylene chloride) to afford the desired product as a white solid (15.3 mg, 27%). Mass spec.: 595 (MH)$^+$.

Example 98

(L)-1-[1,4']Bipiperidinyl-1'-yl-2-[(1H-imidazol-4-ylmethyl)-amino]-4-[4-(2-oxo-1,4-dihydro-2H-quinazolin-3-yl)-piperidin-1-yl]-butane-1,4-dione

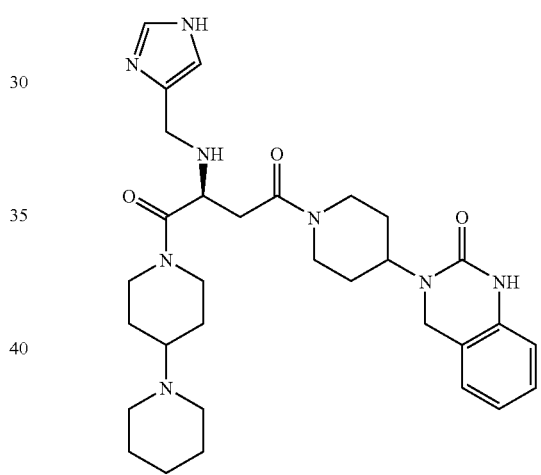

To a stirred solution of 2-amino-1-[1,4']bipiperidinyl-1'-yl-4-[4-(2-oxo-1,4-dihydro-2H-quinazolin-3-yl)-piperidin-1-yl]-butane-1,4-dione (20.6 mg, 0.0415 mmol) and 4-imidazlecarboxyaldehyde (4 mg, 0.0415 mmol) in methylene chloride (1.0 mL) was added sodium cyanoborohydride (8.8 mg, 0.0415 mmol) in one portion. The suspension was stirred at room temperature for 2 days and then partitioned between methylene chloride and 1N sodium hydroxide. The layers were separated and the aqueous layer was extracted with methylene chloride. The combined organic layers were dried over sodium sulfate, and concentrated in vacuo. The residue was purified by preparative TLC (10% (1N ammonia in methanol) in methylene chloride) to afford the desired product as a colorless oil that solidified upon standing (6.1 mg, 26%). $^1$H-NMR (400 MHz, CDCl$_3$) δ 7.61 (1H, d, J=4.8 Hz), 7.16 (1H, t, J=7.6 Hz), 7.10-6.85 (3H, m), 6.67 (1H, d, J=8.0 Hz), 4.85-4.63 (2H, m), 4.63-4.40 (1H, m), 4.40-3.65 (7H, m), 3.25-2.40 (10H, m), 2.15-0.70 (18H, m). Mass spec.: 577 (MH)$^+$.

Example 99

(L)-N-{1-([1,4']Bipiperidinyl-1'-carbonyl)-3-oxo-3-[4-(2-oxo-1,4-dihydro-2H-quinazolin-3-yl)-piperidin-1-yl]-propyl}-4-methoxy-benzamide

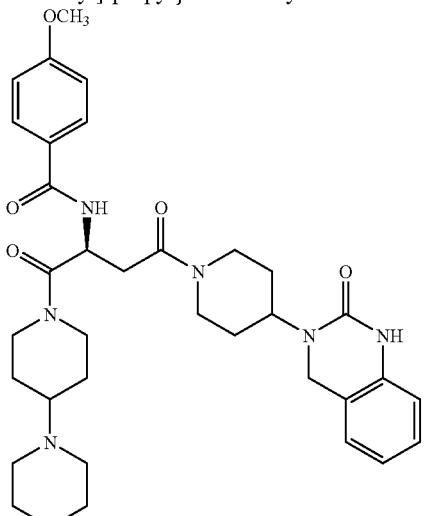

To a stirred mixture of 2-amino-1-[1,4']bipiperidinyl-1'-yl-4-[4-(2-oxo-1,4-dihydro-2H-quinazolin-3-yl)-piperidin-1-yl]-butane-1,4-dione (91.5 mg, 0.184 mmol) and p-anisoyl chloride (34.6 mg, 0.203 mmol) in methylene chloride was added two drops of triethylamine (35 µL). The light yellow solution was stirred at room temperature for 2.5 h to achieve complete conversion. The reaction mixture was washed with sodium hydroxide (1N) and the aqueous layer was then extracted with methylene chloride. The combined organic layers were passed through a celite cartridge and concentrated in vacuo to give a glassy solid. The crude product was purified by flash column chromatography (10% (1N ammonia in methanol) in methylene chloride) to give a glassy solid (92.8 mg, 80%). $^1$H-NMR (400 MHz, CDCl$_3$) δ 8.55-8.47 (1H, d), 8.10-7.78 (3H, m), 7.09 (1H, t, J=7.4 Hz), 6.96-6.74 (4H, m), 5.62-5.44 (1H, br), 4.75-4.40 (3H, m), 4.40-4.05 (3H, m), 4.05-3.82 (1H, br), 3.76 (3H, s), 3.18-2.88 (3H, m), 2.88-2.70 (1H, m), 2.70-2.30 (8H, m), 2.05-1.19 (14H, m). Mass spec.: 631 (MH)$^+$.

Example 100

(L)-N-{1-([1,4']Bipiperidinyl-1'-carbonyl)-3-oxo-3-[4-(2-oxo-1,4-dihydro-2H-quinazolin-3-yl)-piperidin-1-yl]-propyl}-4-hydroxy-benzamide

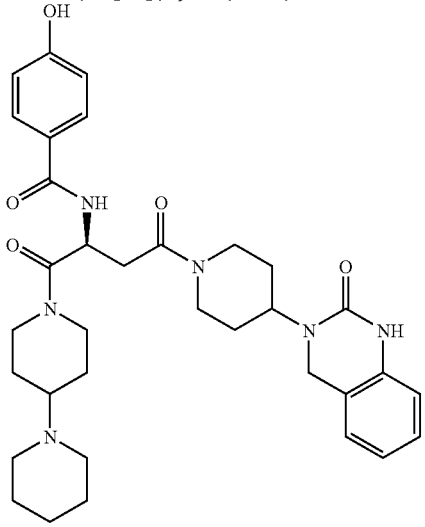

A stirred solution of N-{1-([1,4']bipiperidinyl-1'-carbonyl)-3-oxo-3-[4-(2-oxo-1,4-dihydro-2H-quinazolin-3-yl)-piperidin-1-yl]-propyl}-4-methoxy-benzamide solution in methylene chloride (69 mg) was treated with boron tribromide (1M in methylene chloride, 0.6 mL), dropwise at room temperature. The resulting suspension was stirred at room temperature for 7 h and then the reaction was quenched with excess triethylamine followed by methanol. The solvents were removed in vacuo and the residue was dissolved in methanol and purified by preparative HPLC. LC/MS: t$_R$=1.03 min, 617 (MH)$^+$.

Example 101

(L)-1H-Pyrazole-3-carboxylic acid {1-([1,4']bipiperidinyl-1'-carbonyl)-3-oxo-3-[4-(2-oxo-1,4-dihydro-2H-quinazolin-3-yl)-piperidin-1-yl]-propyl}-amide

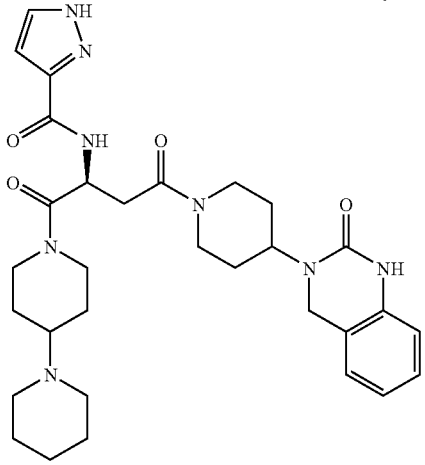

To a stirred solution of pyrrazole-3-carboxylic acid (4 mg, 0.036 mmol) and 2-amino-1-[1,4']bipiperidinyl-1'-yl-4-[4-(2-oxo-1,4-dihydro-2H-quinazolin-3-yl)-piperidin-1-yl]-butane-1,4-dione (13 mg, 0.026 mmol) in methylene chloride (1 mL) was added 3-(diethoxyphosphoryloxy)-1,2,3-benzotriazin-4(3H)-one (DEPBT, 8.6 mg, 0.036 mmol) in one portion followed by one drop of triethylamine. The resulting mixture was stirred at room temperature overnight (15 h). The mixture was then partitioned between sodium hydroxide (0.5 N) and methylene chloride. The layers were separated and the aqueous layer was extracted with methylene chloride (3×). LCMS indicated that the product was remained in the aqueous layer. The product was purified by preparative HPLC to give a yellow oil (17.2 mg, 94%). Mass spec.: 591 (MH)$^+$.

General Procedure for the Synthesis of Examples 102-134:

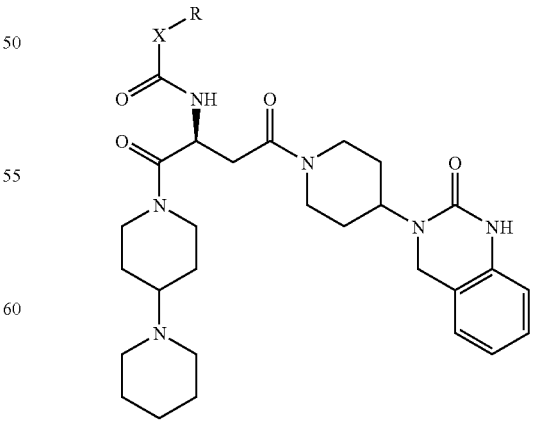

X = C, O

The starting amine, 2-amino-1-[1,4']bipiperidinyl-1'-yl-4-[4-(2-oxo-1,4-dihydro-2H-quinazolin-3-yl)-piperidin-1-yl]- butane-1,4-dione, was dispersed in a 96-well mini-reactor (ca. 10 mg each) in 1 mL dichloroethane. Individual acyl chlorides (ca. 2 equiv.) were added followed by a resin-bound solid-phase piperidine base (4 equiv). The block was shaken overnight. Approximately 4 equivalents of tris-amine resin was added to each well and the mini-reactor was shaken for another 5 h. The reaction mixtures were filtered, and purified by either preparative HPLC or filtration through an SCX cartridge or both. HPLC retention times and mass spectral data for each example are listed in Table 2.

TABLE 2

Amides and Carbamates

| Example | Structure | | HPLC $t_R$ (min) | MS (M+) |
|---|---|---|---|---|
| 102 | 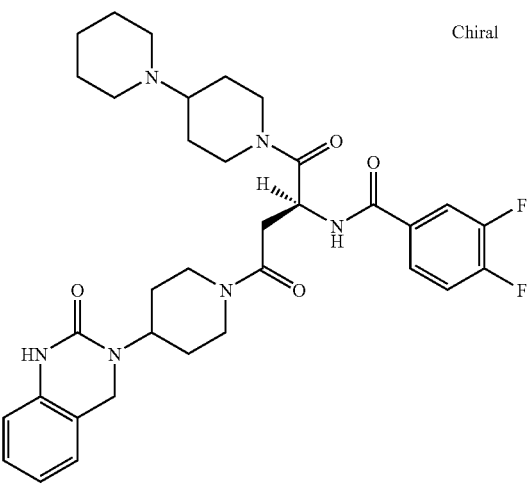 | Chiral | 1.84 | 637.38 |
| 103 | 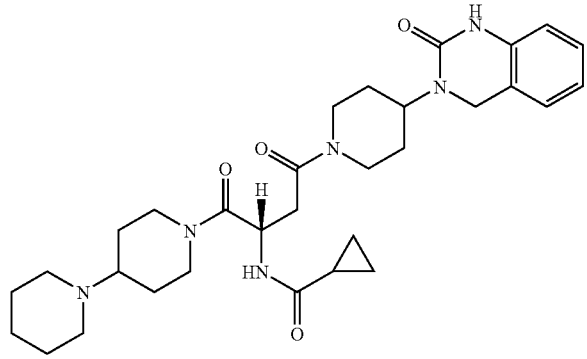 | Chiral | 1.39 | 565.45 |
| 104 | 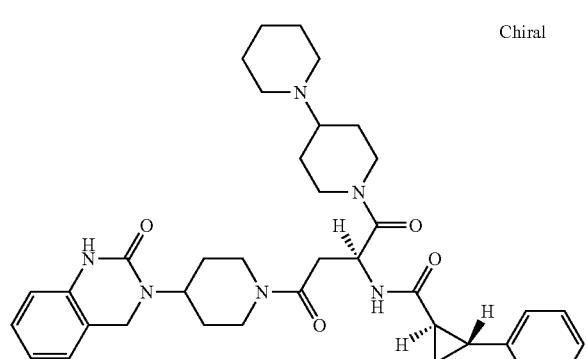 | Chiral | 1.89 | 641.46 |

TABLE 2-continued

Amides and Carbamates

| Example | Structure | | HPLC $t_R$ (min) | MS (M+) |
|---|---|---|---|---|
| 105 | 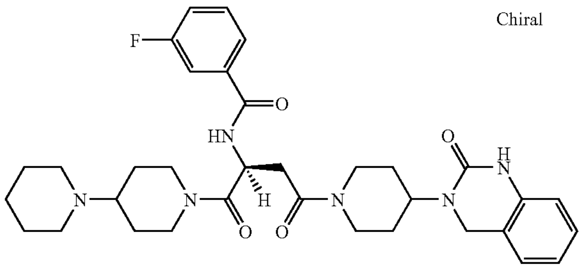 | Chiral | 1.73 | 619.42 |
| 106 | 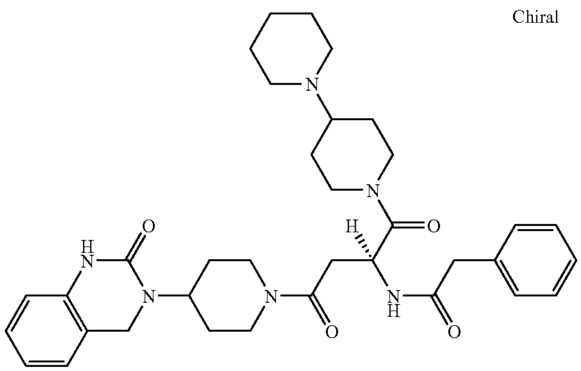 | Chiral | 1.62 | 615.41 |
| 107 | 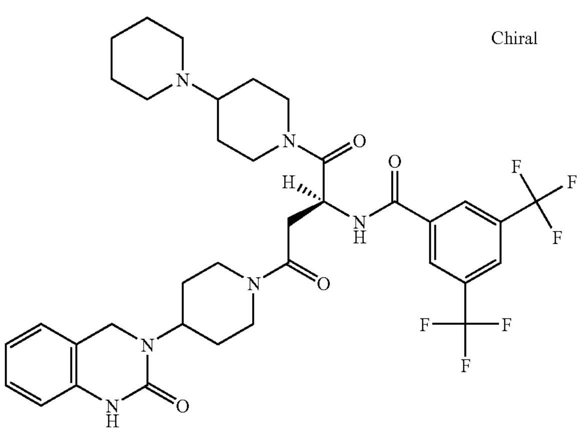 | Chiral | 2.25 | 737.37 |

TABLE 2-continued
Amides and Carbamates
| Example | Structure | HPLC $t_R$ (min) | MS (M+) |
|---|---|---|---|
| 108 | 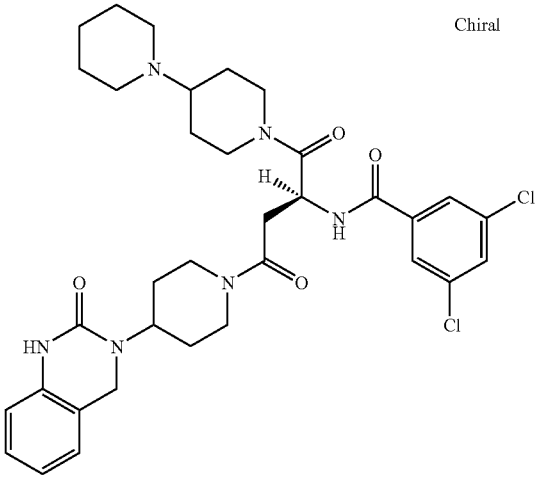 Chiral | 2.12 | 669.3 |
| 109 | 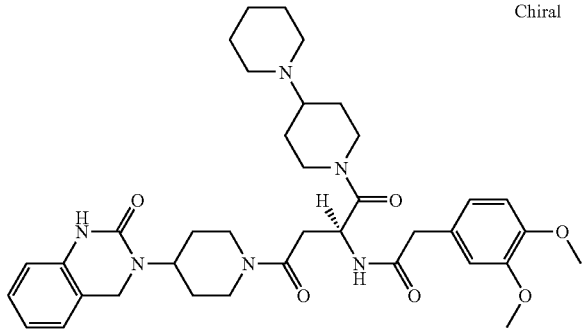 Chiral | 1.59 | 675.46 |
| 110 | 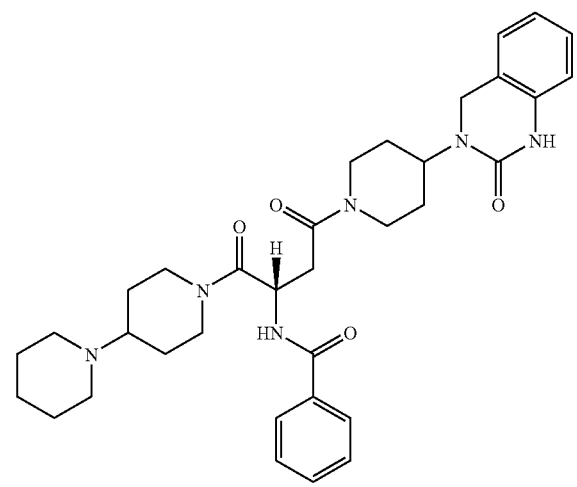 Chiral | 1.62 | 601.43 |

TABLE 2-continued

Amides and Carbamates

| Example | Structure | | HPLC $t_R$ (min) | MS (M+) |
|---|---|---|---|---|
| 111 | 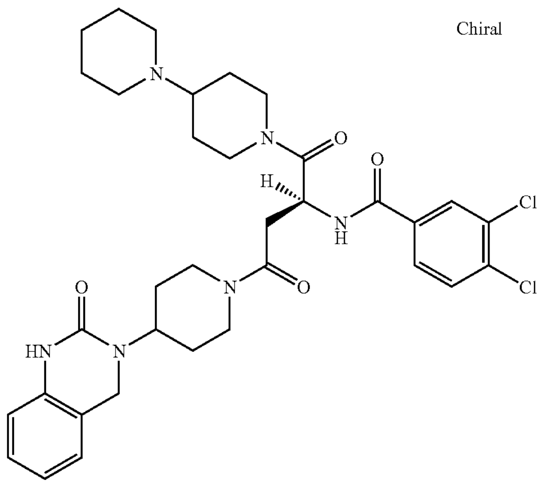 | Chiral | 2.09 | 669.33 |
| 112 | 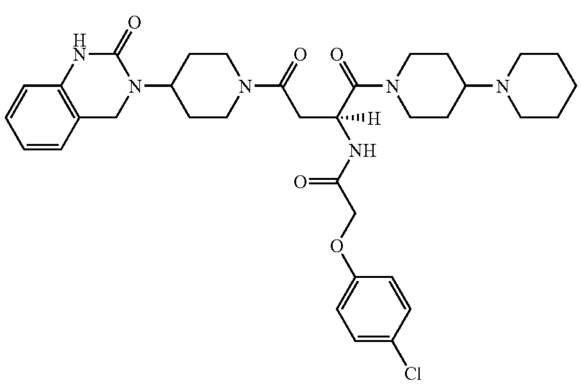 | Chiral | 1.91 | 665.36 |
| 113 | 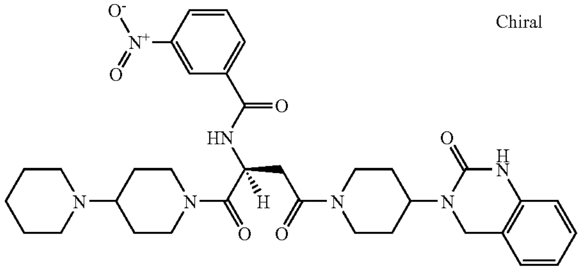 | Chiral | 1.68 | 646.37 |

TABLE 2-continued
Amides and Carbamates
| Example | Structure | HPLC $t_R$ (min) | MS (M+) |
|---|---|---|---|
| 114 | 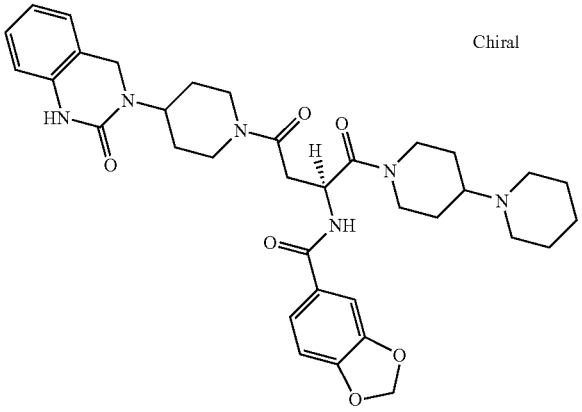 Chiral | 1.66 | 645.4 |
| 115 | 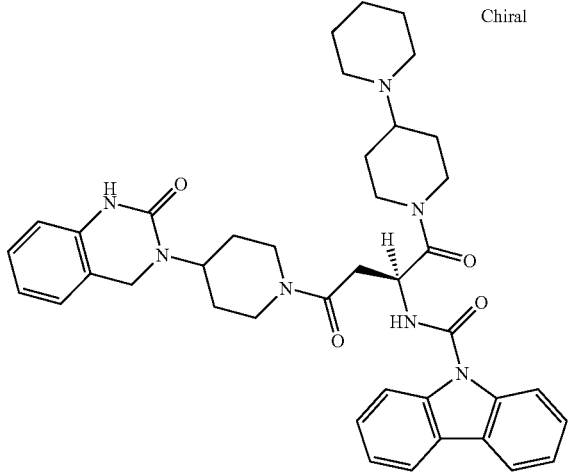 Chiral | 2.14 | 690.45 |
| 116 | 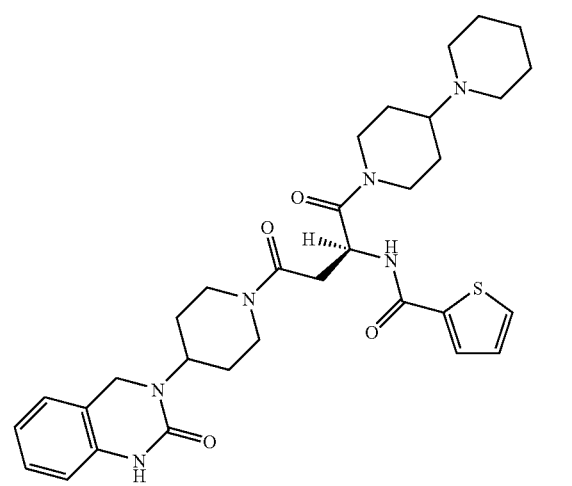 Chiral | 1.59 | 607.39 |

TABLE 2-continued

Amides and Carbamates

| Example | Structure | HPLC $t_R$ (min) | MS (M+) |
|---|---|---|---|
| 117 | Chiral | 1.59 | 621.4 |
| 118 | Chiral | 2.01 | 735.43 |
| 119 | Chiral | 1.92 | 679.32 |

TABLE 2-continued
Amides and Carbamates
| Example | Structure | HPLC $t_R$ (min) | MS (M+) |
|---|---|---|---|
| 120 | 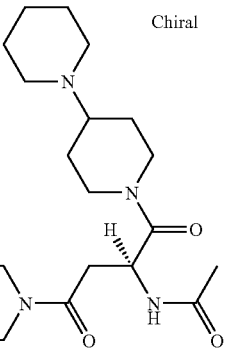 Chiral | 1.22 | 537.4 |
| 121 | 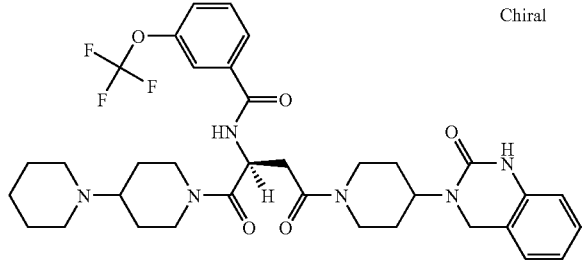 Chiral | 2.03 | 685.4 |
| 122 | 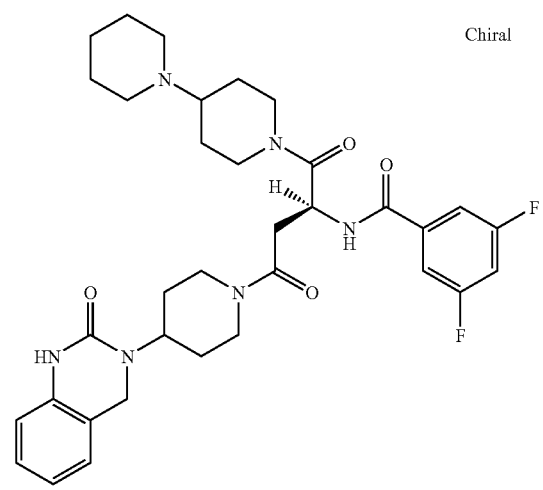 Chiral | 1.79 | 637.38 |

TABLE 2-continued

Amides and Carbamates

| Example | Structure | HPLC $t_R$ (min) | MS (M+) |
|---|---|---|---|
| 123 | Chiral | 1.84 | 669.3 |
| 124 | Chiral | 1.53 | 636.35 |
| 125 | Chiral | 2.04 | 691.35 |

TABLE 2-continued
Amides and Carbamates
| Example | Structure | HPLC $t_R$ (min) | MS (M+) |
|---|---|---|---|
| 126 | 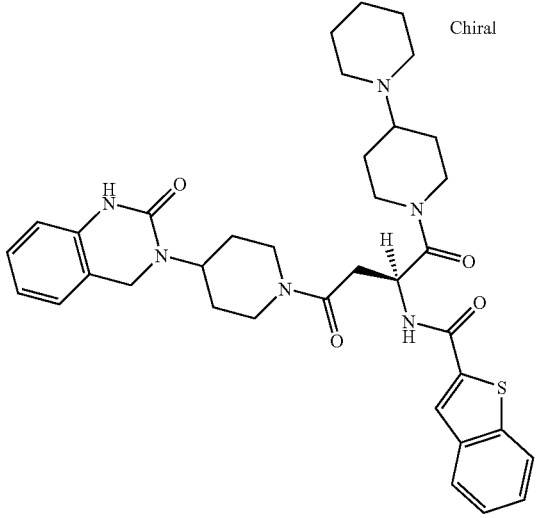 Chiral | 1.89 | 657.35 |
| 127 | 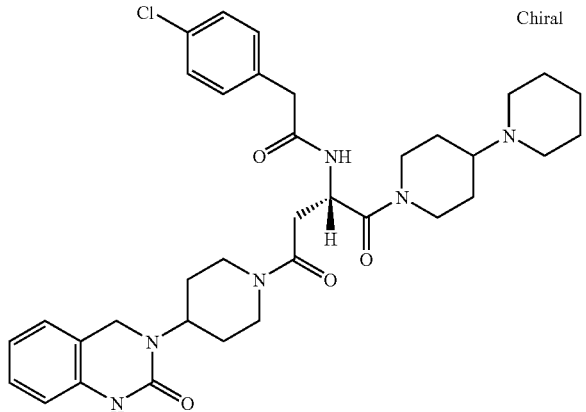 Chiral | 1.86 | 649.39 |

TABLE 2-continued

Amides and Carbamates

| Example | Structure | | HPLC $t_R$ (min) | MS (M+) |
|---|---|---|---|---|
| 128 | 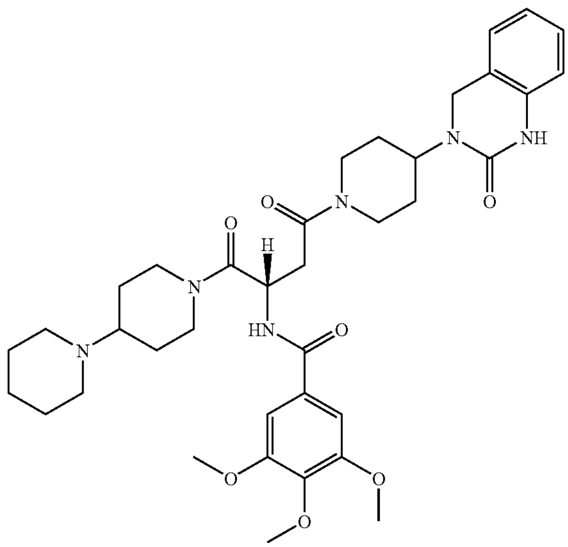 | Chiral | 1.67 | 691.42 |
| 129 | 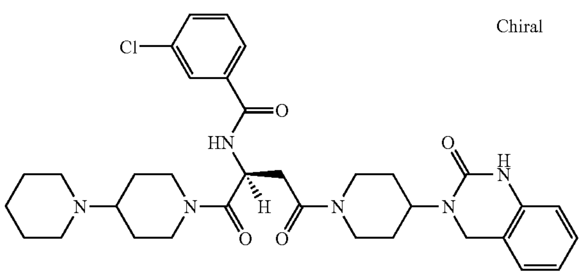 | Chiral | 1.84 | 635.38 |
| 130 | 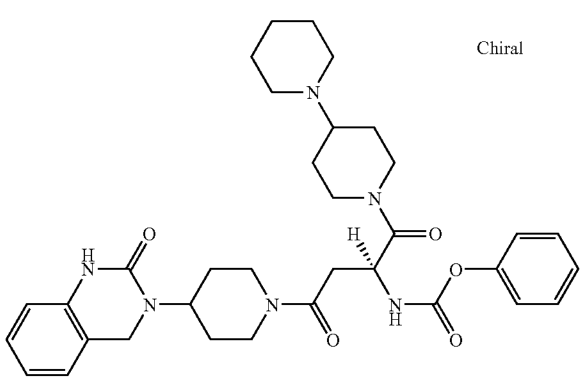 | Chiral | 1.69 | 617.42 |

TABLE 2-continued

Amides and Carbamates

| Example | Structure | | HPLC $t_R$ (min) | MS (M+) |
|---|---|---|---|---|
| 131 | 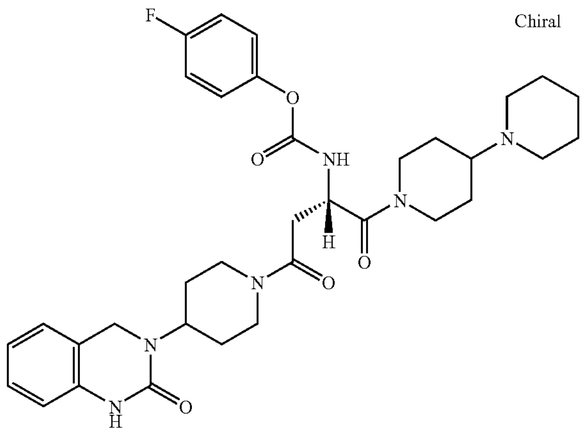 | Chiral | 1.74 | 635.38 |
| 132 | 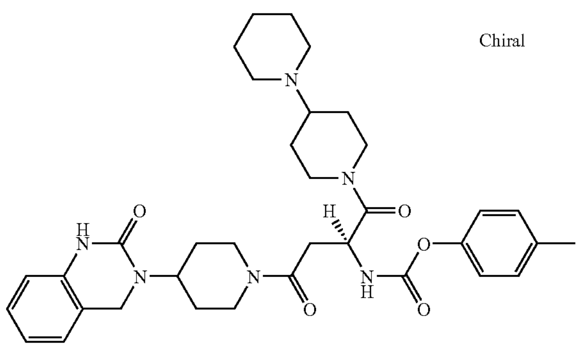 | Chiral | 1.84 | 631.44 |
| 133 | 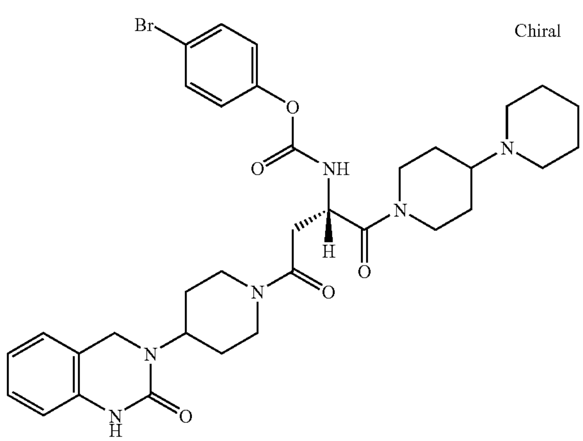 | Chiral | 1.94 | 695.28 |

TABLE 2-continued

Amides and Carbamates

| Example | Structure | HPLC $t_R$ (min) | MS (M+) |
|---|---|---|---|
| 134 | 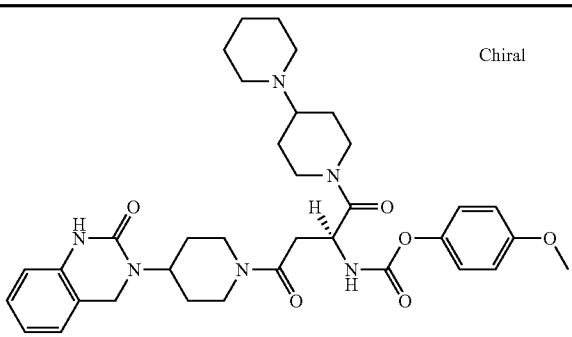 Chiral | 1.7 | 647.41 |

General Procedure for the Synthesis of Examples 135-200:

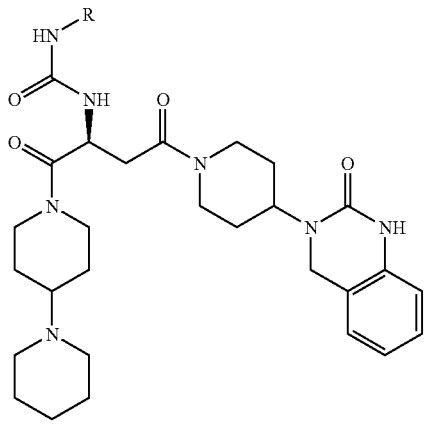

The starting amine, 2-amino-1-[1,4']bipiperidinyl-1'-yl-4-[4-(2-oxo-1,4-dihydro-2H-quinazolin-3-yl)-piperidin-1-yl]-butane-1,4-dione, was dispersed in a 96-well mini-reactor (ca. 10 mg in each well) in dichloroethane (1 mL). Individual isocyanates (ca. 2 equiv) were added to individual wells. The block was shaken for 2 days. Approximately 4 equivalent of tris-amine resin was added to each well and the mini-reactor was shaken for another two days. The reaction mixtures were filtered, and individual product was purified by either preparative HPLC or filtration through an SCX cartridge or both. HPLC retention times and mass spectral data for each example are listed in Table 3.

TABLE 3

Ureas

| Example | Structure | HPLC $t_R$ (min) | MS (MH)+ |
|---|---|---|---|
| 135 | 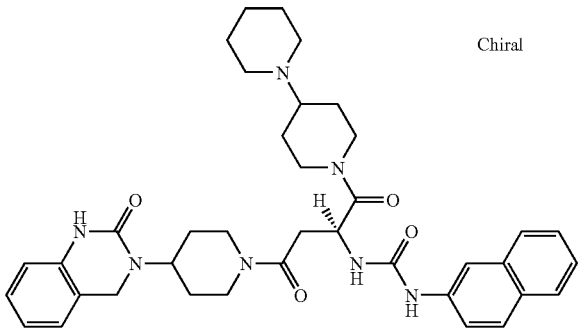 Chiral | 1.43 | 665.84 |

TABLE 3-continued
Ureas
| Example | Structure | HPLC $t_R$ (min) | MS (MH)+ |
|---|---|---|---|
| 136 | 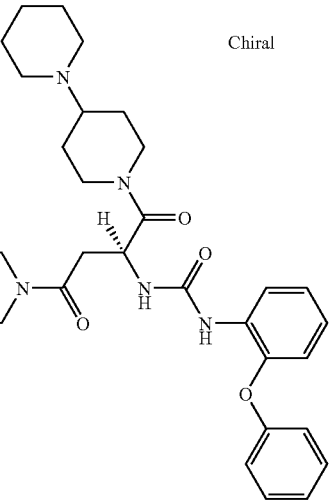 Chiral | 1.56 | 707.88 |
| 137 | 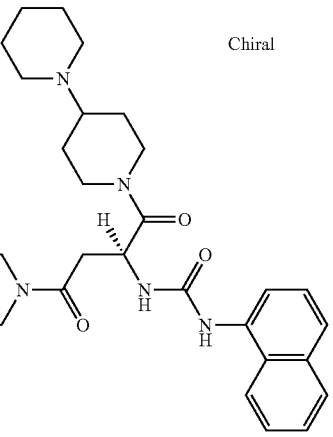 Chiral | 1.39 | 665.84 |
| 138 | 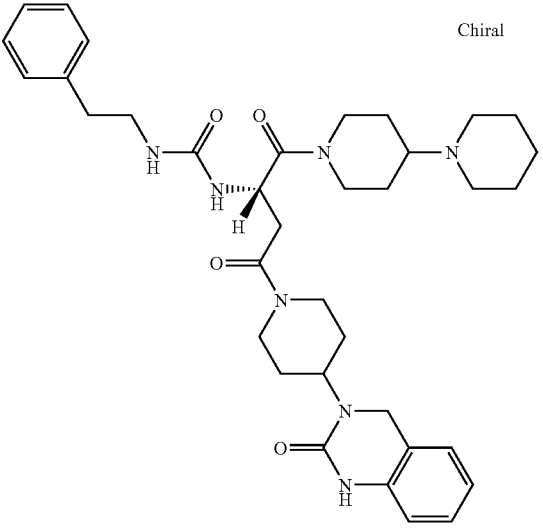 Chiral | 1.3 | 643.83 |

TABLE 3-continued

Ureas

| Example | Structure | HPLC $t_R$ (min) | MS $(MH)^+$ |
|---|---|---|---|
| 139 | Chiral | 1.44 | 657.86 |
| 140 | Chiral | 1.42 | 650.22 |
| 141 | Chiral | 1.26 | 629.81 |

TABLE 3-continued

Ureas

| Example | Structure | HPLC $t_R$ (min) | MS (MH)+ |
|---|---|---|---|
| 142 | Chiral | 1.41 | 643.83 |
| 143 | Chiral | 1.24 | 615.78 |
| 144 | Chiral | 1.53 | 691.88 |
| 145 | Chiral | 1.21 | 629.81 |

TABLE 3-continued
Ureas
| Example | Structure | HPLC $t_R$ (min) | MS $(MH)^+$ |
|---|---|---|---|
| 146 | 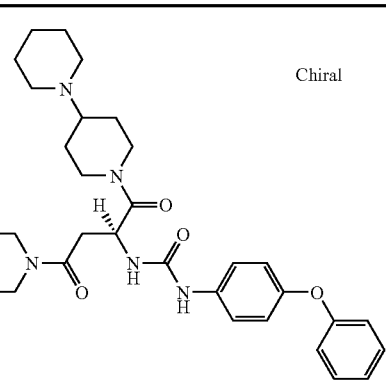 Chiral | 1.52 | 707.88 |
| 147 | 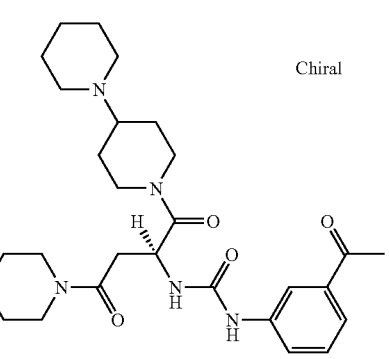 Chiral | 1.19 | 657.82 |
| 148 | 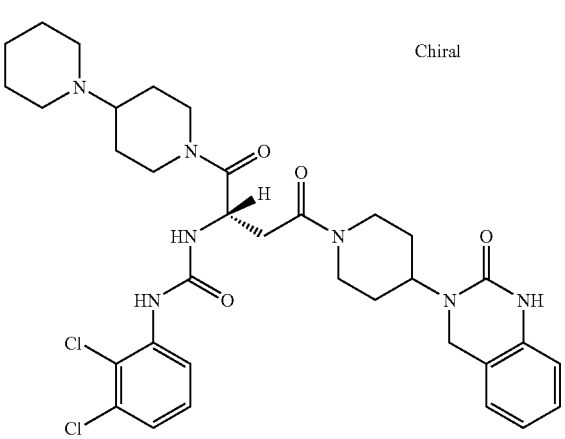 Chiral | 1.44 | 684.67 |

TABLE 3-continued

Ureas

| Example | Structure | HPLC $t_R$ (min) | MS $(MH)^+$ |
|---|---|---|---|
| 149 | Chiral | 1.3 | 645.81 |
| 150 | Chiral | 1.24 | 645.81 |
| 151 | Chiral | 1.33 | 643.83 |

TABLE 3-continued
Ureas
| Example | Structure | HPLC $t_R$ (min) | MS $(MH)^+$ |
|---|---|---|---|
| 152 | 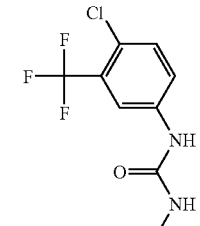 Chiral | 1.56 | 718.22 |
| 153 | 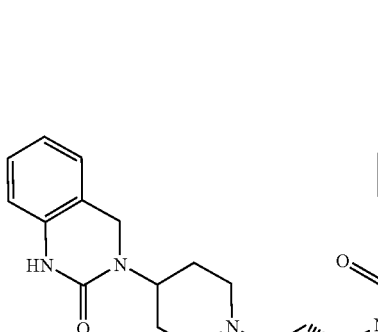 Chiral | 1.55 | 683.78 |
| 154 | 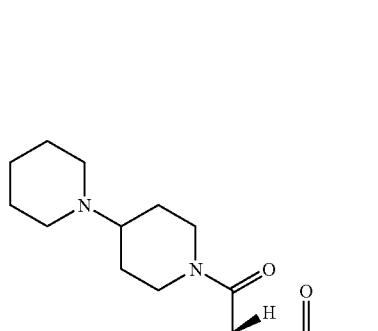 Chiral | 1.37 | 655.84 |

TABLE 3-continued

Ureas

| Example | Structure | HPLC $t_R$ (min) | MS (MH)+ |
|---|---|---|---|
| 155 | Chiral | 1.27 | 675.83 |
| 156 | Chiral | 1.26 | 651.76 |
| 157 | Chiral | 1.39 | 643.83 |

TABLE 3-continued

Ureas

| Example | Structure | HPLC $t_R$ (min) | MS (MH)⁺ |
|---|---|---|---|
| 158 | Chiral | 1.43 | 643.83 |
| 159 | Chiral | 1.57 | 684.67 |
| 160 | Chiral | 1.46 | 683.78 |

TABLE 3-continued

Ureas

| Example | Structure | | HPLC $t_R$ (min) | MS (MH)+ |
|---|---|---|---|---|
| 161 | 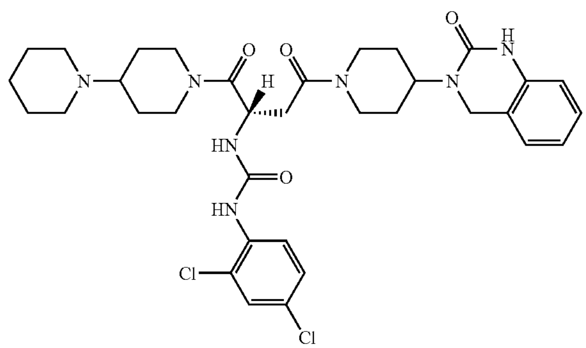 | Chiral | 1.48 | 684.67 |
| 162 | 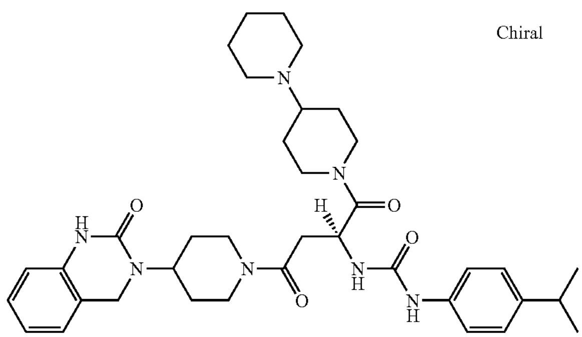 | Chiral | 1.5 | 657.86 |
| 163 | 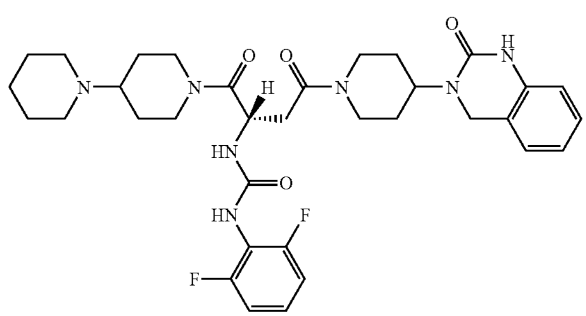 | Chiral | 1.14 | 651.76 |
| 164 | 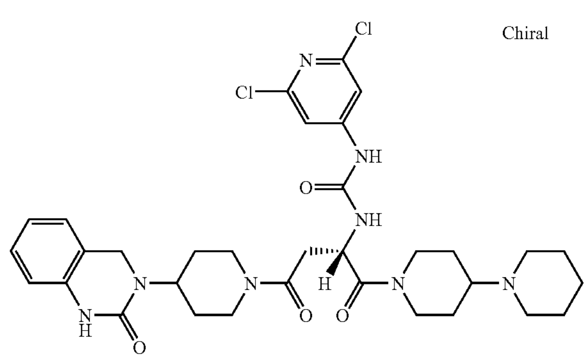 | Chiral | 1.34 | 685.66 |

TABLE 3-continued

Ureas

| Example | Structure | HPLC $t_R$ (min) | MS (MH)+ |
|---|---|---|---|
| 165 | Chiral | 1.26 | 675.83 |
| 166 | Chiral | 1.28 | 701.87 |
| 167 | Chiral | 1.52 | 718.22 |

TABLE 3-continued

Ureas

| Example | Structure | HPLC $t_R$ (min) | MS (MH)+ |
|---|---|---|---|
| 168 | Chiral | 1.35 | 669.75 |
| 169 | Chiral | 1.24 | 649.86 |
| 170 | Chiral | 1.11 | 639.8 |

TABLE 3-continued

Ureas

| Example | Structure | HPLC $t_R$ (min) | MS (MH)$^+$ |
|---|---|---|---|
| 171 | Chiral | 1.31 | 633.77 |
| 172 | Chiral | 1.34 | 650.22 |
| 173 | Chiral | 1.47 | 684.67 |
| 174 | Chiral | 1.27 | 675.83 |

TABLE 3-continued
Ureas
| Example | Structure | HPLC $t_R$ (min) | MS (MH)+ |
|---|---|---|---|
| 175 | Chiral 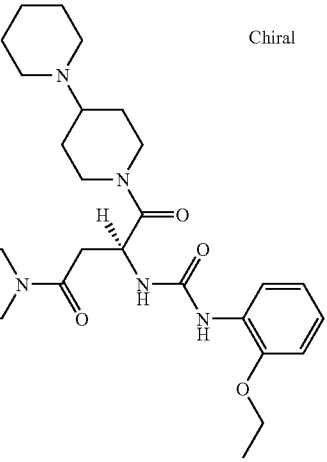 | 1.34 | 659.83 |
| 176 | Chiral 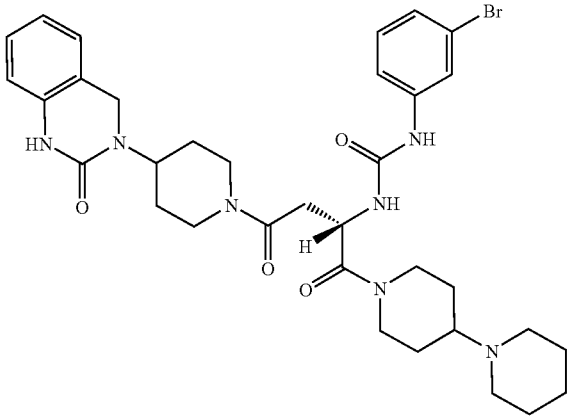 | 1.41 | 694.68 |
| 177 | Chiral 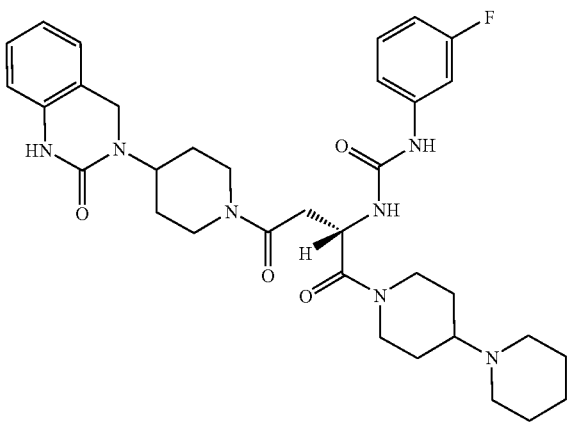 | 1.28 | 633.77 |

TABLE 3-continued
Ureas
| Example | Structure | HPLC $t_R$ (min) | MS $(MH)^+$ |
|---|---|---|---|
| 178 | Chiral 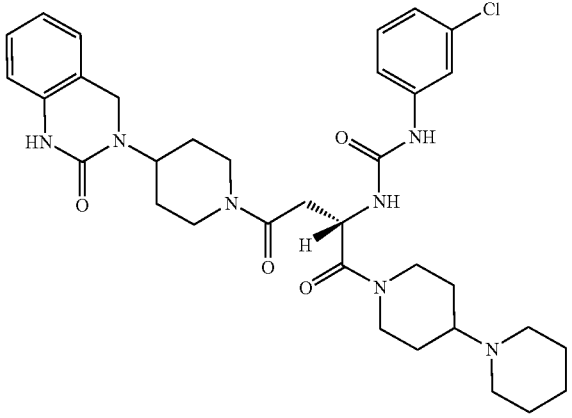 | 1.39 | 650.22 |
| 179 | Chiral 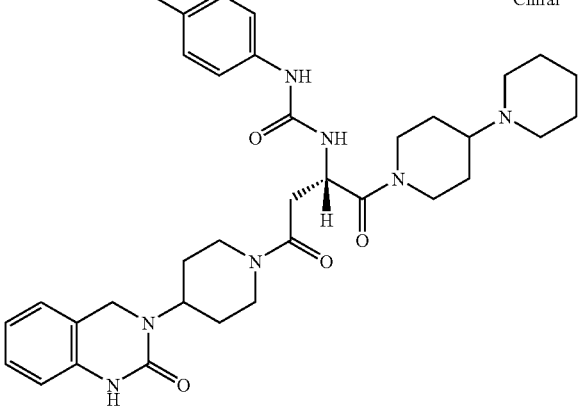 | 1.42 | 694.68 |
| 180 | Chiral 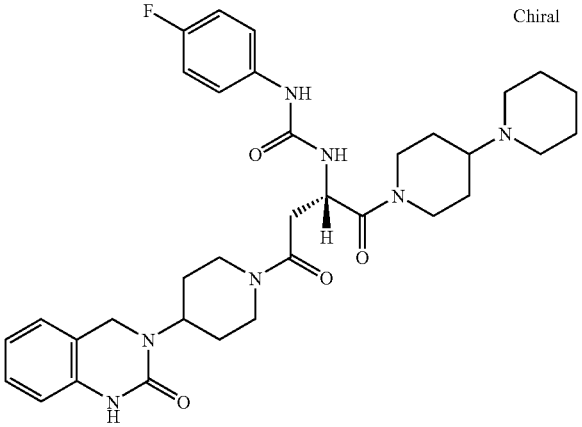 | 1.26 | 633.77 |

TABLE 3-continued

Ureas

| Example | Structure | | HPLC $t_R$ (min) | MS (MH)$^+$ |
|---|---|---|---|---|
| 181 | | Chiral | 1.19 | 645.81 |
| 182 | | Chiral | 1.34 | 687.84 |
| 183 | | Chiral | 1.08 | 581.76 |

TABLE 3-continued

Ureas

| Example | Structure | | HPLC $t_R$ (min) | MS (MH)+ |
|---|---|---|---|---|
| 184 | 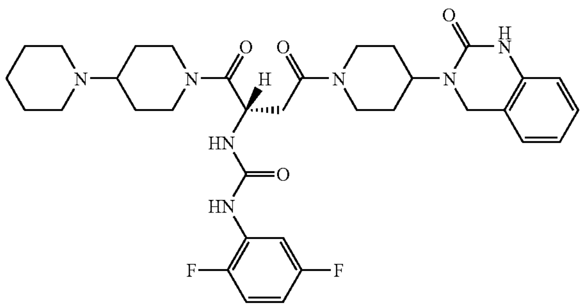 | Chiral | 1.31 | 651.76 |
| 185 | 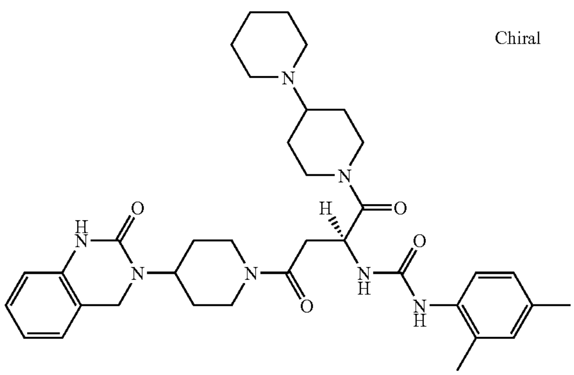 | Chiral | 1.39 | 643.83 |
| 186 | 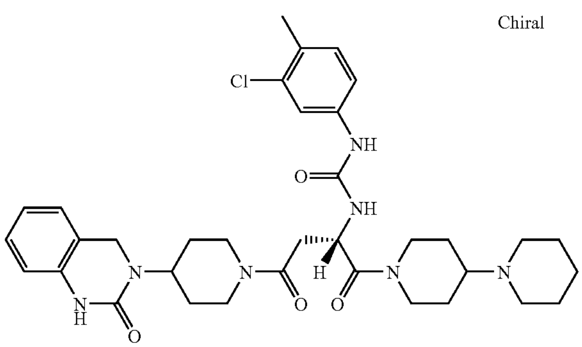 | Chiral | 1.33 | 664.25 |

TABLE 3-continued

Ureas

| Example | Structure | | HPLC $t_R$ (min) | MS (MH)$^+$ |
|---|---|---|---|---|
| 187 | 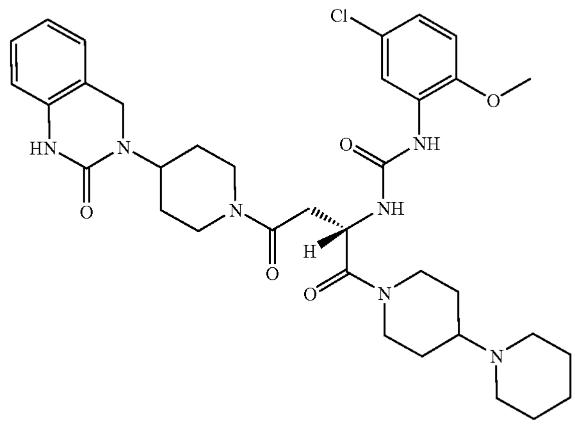 | Chiral | 1.41 | 680.25 |
| 188 | 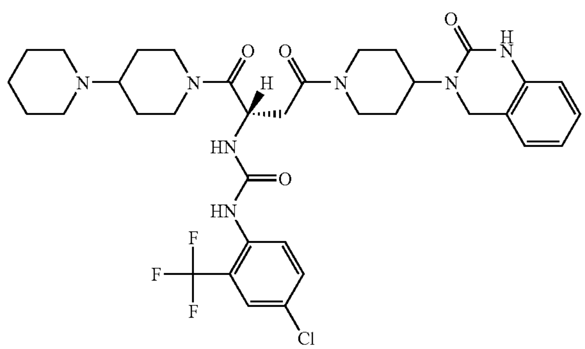 | Chiral | 1.48 | 718.22 |
| 189 | 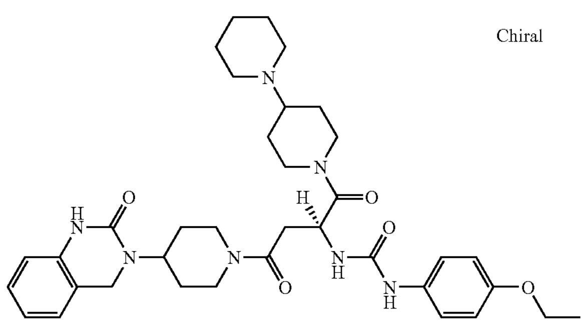 | Chiral | 1.28 | 659.83 |
| 190 | 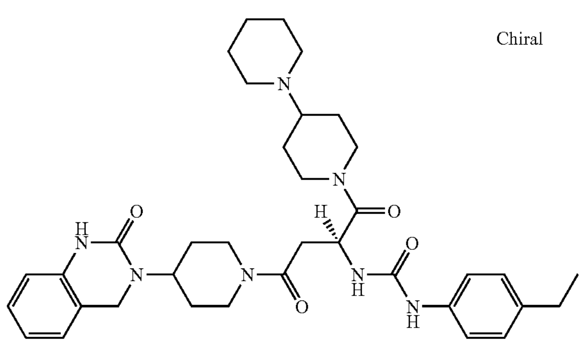 | Chiral | 1.41 | 643.83 |

TABLE 3-continued

Ureas

| Example | Structure | HPLC $t_R$ (min) | MS (MH)+ |
|---|---|---|---|
| 191 | Chiral | 1.41 | 664.25 |
| 192 | Chiral | 1.41 | 664.25 |
| 193 | Chiral | 1.41 | 668.21 |

TABLE 3-continued

Ureas

| Example | Structure | | HPLC t$_R$ (min) | MS (MH)$^+$ |
|---|---|---|---|---|
| 194 | 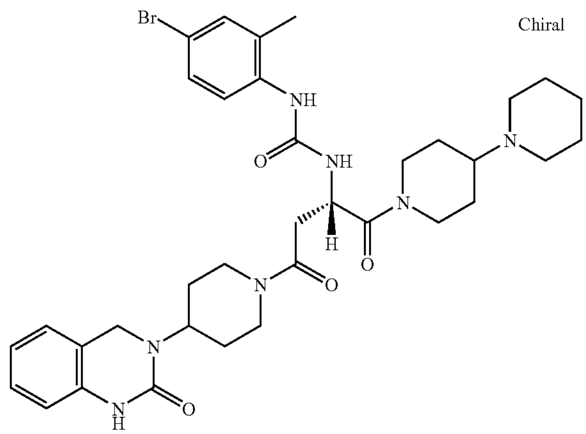 | Chiral | 1.45 | 708.71 |
| 195 | 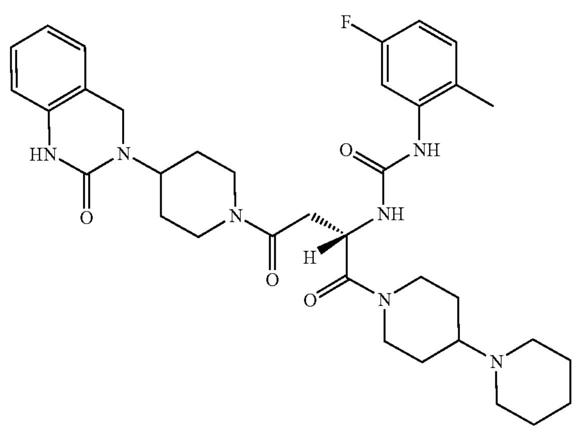 | Chiral | 1.39 | 647.8 |
| 196 | 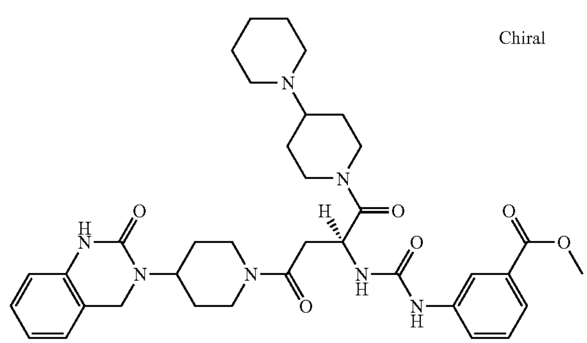 | Chiral | 1.27 | 673.82 |

TABLE 3-continued
Ureas
| Example | Structure | HPLC $t_R$ (min) | MS $(MH)^+$ |
|---|---|---|---|
| 197 | 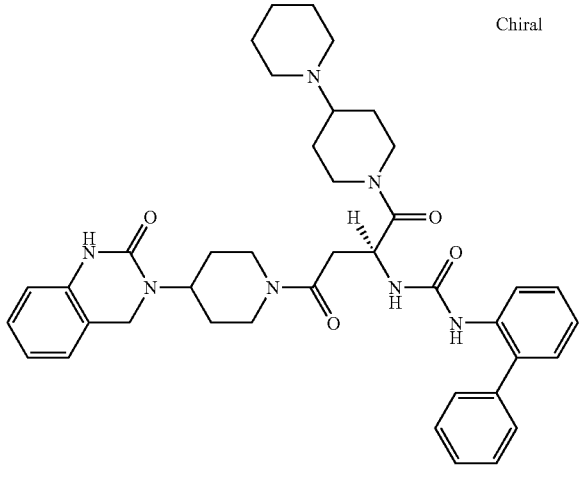 Chiral | 1.45 | 691.88 |
| 198 | 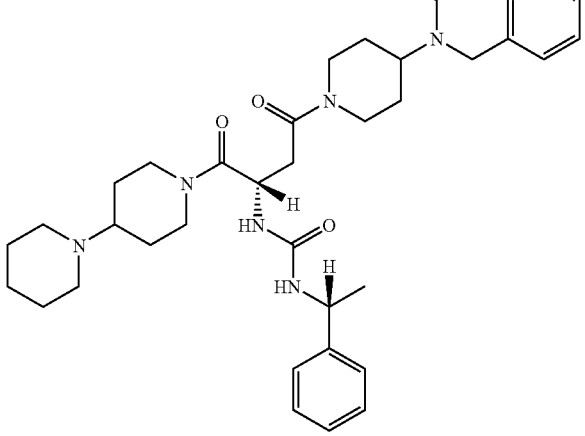 Chiral | 1.26 | 643.83 |

TABLE 3-continued

Ureas

| Example | Structure | HPLC $t_R$ (min) | MS (MH)+ |
|---|---|---|---|
| 199 | Chiral | 1.45 | 693.89 |
| 200 | Chiral | 1.4 | 699.78 |

2-(1H-Indazol-5-ylamino)-succinic acid 4-tert-butyl ester 1-ethyl ester

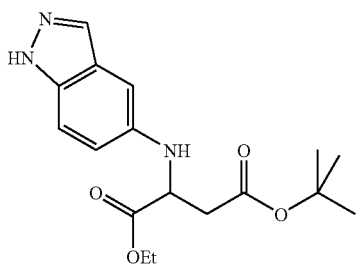

To a solution/suspension of 5-aminoindazole (1.01 g, 7.6 mmol) in tetrahydrofuran (20 mL) was added ethyl glyoxylate solution (ca. 50% in toluene, 1.7 mL, 1.1 equiv) in one portion followed by magnesium sulfate (4.6 g). The mixture was stirred at room temperature overnight (23 h) and then filtered and concentrated in vacuo. The resulting crude imine intermediate (1.3 g, 6 mmol) was dried by azeotroping with anhydrous benzene and further dried under high vacuum. The residue was then dissolved in tetrahydrofuran (20 mL) and cooled at 0° C. A solution of 2-tert-butoxy-2-oxoethylzinc chloride (0.5 M in ether, 24 mL, 2 equiv) was then slowly added. After stirring at 0° C. for 1 h, the mixture was stored at 4° C. overnight. The mixture was then diluted with ethyl acetate and quenched with half-saturated ammonium chloride solution along with a minimum amount of 0.5 N HCl to dissolve the precipitated solids. The layers were separated and the aqueous layer was extracted with ethyl acetate. The combined organic layers were washed with water and saturated sodium bicarbonate solution. The organic layer was dried over sodium sulfate and concentrated in vacuo. The crude product was purified by flash column chromatography on silica gel, eluting with 10% methanol in methylene chloride, to afford the desired product (1.3 g, 65%) as a tan oil. $^1$H-NMR (400 MHz, CDCl$_3$) δ 7.89 (1H, s), 7.40-7.27 (1H, m), 6.98-6.77 (2H, m), 4.42-4.35 (1H, m), 4.30-4.12 (3H, m), 2.80 (2H, d, J=4.4 Hz), 1.43 (9H, s), 1.27-1.17 (4H, m). Mass spec.: 356.24 (M+Na)+, 278.23 (M–tBu)+, $t_R$=1.287 min.

2-(1H-Indazol-5-ylamino)-succinic acid 1-ethyl ester

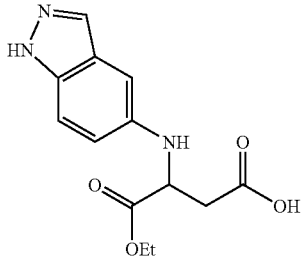

A stirred solution of 2-(1H-indazol-5-ylamino)-succinic acid 4-tert-butyl ester 1-ethyl ester (123.6 mg, 0.37 mmol) in methylene chloride (2 mL) and trifluoroacetic acid (0.5 mL) was stirred at room temperature overnight. The reaction mixture was then diluted with ethyl acetate and washed with saturated ammonium chloride solution, water and brine. The organic layer was dried and concentrated to give a dark green oil: LC/MS: $t_R$=0.643 min, 278.19 (MH)+.

2-(1H-Indazol-5-ylamino)-4-oxo-4-[4-(2-oxo-1,4-dihydro-2H-quinazolin-3-yl)-piperidin-1-yl]-butyric acid ethyl ester

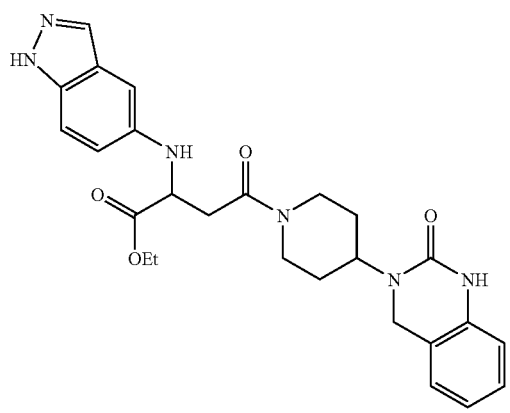

To a stirred solution of 2-(1H-indazol-5-ylamino)-succinic acid 1-ethyl ester (84 mg, 0.215 mmol) in methylene chloride (1 mL) was added the amine (99 mg, 0.429 mmol, 2 equiv) followed by DEPBT (128 mg, 0.43 mmol, 2 equiv.) and triethylamine (70 µL, 0.47 mmol, 2.2 equiv). The mixture was stirred overnight and then diluted with ethyl acetate and washed with half-saturated ammonium chloride solution, water and brine. The organic layer was dried and concentrated to a tan oil. The crude product was purified by flash column chromatography on silica gel, eluting with 10% methanol in methylene chloride, to give the desired product (36.2 mg, 34.5% for two steps) as a reddish oil. 1H-NMR (400 MHz, CDCl3) δ 7.90 (2H, d, J=4.4 Hz), 7.33 (1H, d, J=8.4 Hz), 7.20-7.14 (1H, m), 7.00-6.80 (4H, m), 6.70 (1H, t, J=6.8 Hz), 4.58-4.48 (1H, m), 4.65-4.40 (2H, m), 4.34-4.05 (3H, m), 4.02-3.82 (1H, m), 3.20-2.99 (2H, m), 2.99-2.84 (1H, m), 2.70-2.52 (1H, m), 1.80-1.50 (5H, m), 1.35-1.12 (5H, m). LC/MS: $t_R$=1.130 min, 491.37 (MH)+.

2-(1H-Indazol-5-ylamino)-4-oxo-4-[4-(2-oxo-1,4-dihydro-2H-quinazolin-3-yl)-piperidin-1-yl]-butyric acid

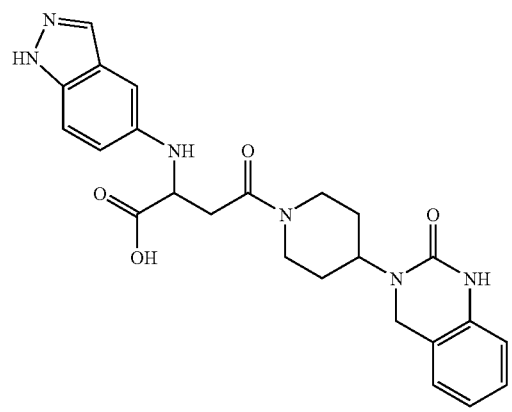

To a solution of the ethyl ester (34 mg, 0.069 mmol) in tetrahydrofuran (0.3 mL) was added lithium hydroxide in water (1M, 280 µL, 4 equiv) and the mixture was stirred at room temperature for 17 h. The solution was dried under a stream of nitrogen. To the residue was added 0.2 mL tetrahydrofuran and 0.2 mL anhydrous benzene and the suspension was blown dry again with a stream of nitrogen. LC/MS: $t_R$=0.900 min, 463.30 (MH)+.

Example 201

(±)-1-[1,4']Bipiperidinyl-1'-yl-2-(1H-indazol-5-ylamino)-4-[4-(2-oxo-1,4-dihydro-2H-quinazolin-3-yl)-piperidin-1-yl]-butane-1,4-dione

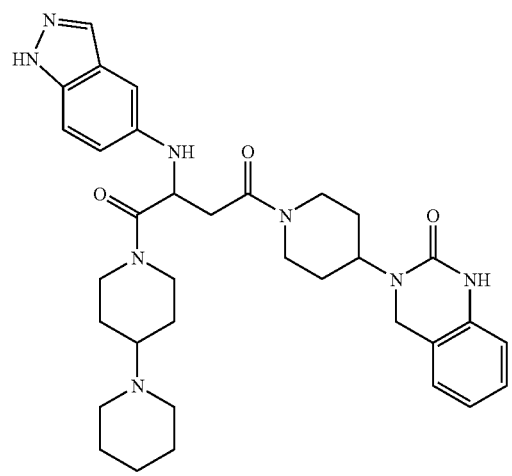

To a solution of 2-(1H-indazol-5-ylamino)-4-oxo-4-[4-(2-oxo-1,4-dihydro-2H-quinazolin-3-yl)-piperidin-1-yl]-butyric acid ethyl ester (0.069 mmol) in dimethylformamide (0.5 mL) in a capped drum vial was added piperidinylpiperidine (14.3 mg, 0.076 mmol, 1.1 equiv), DEPBT (22.8 mg, 1.1 equiv) and triethylamine (8 drops, ca. 160 µL). The mixture was stirred at room temperature overnight. The final product was purified by preparative HPLC to afford the desired product (15 mg, 26% for two steps) as a tan solid. LC/MS: $t_R$=0.917 min, 613.54 (MH)+.

Additional Examples (1-Benzyl-piperidin-4-yl)-(2-nitro-benzyl)-amine

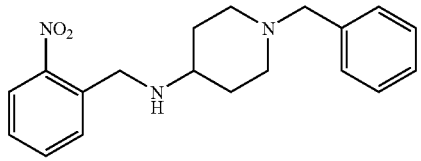

2-Nitrobenzaldehyde (1 g, 6.61 mmol) and 4-amino-1-benzylpiperidine (1.35 mL, 6.61 mmol) were combined in ethanol (20 mL). The resulting suspension was stirred at room temperature for 20 min before a solution of sodium borohydride (0.25 g, 6.61 mmol) in ethanol (5 mL) was added dropwise over 10 min. After the addition was complete, the reaction was stirred for 1 h, cooled to 0° C. and concentrated ammonium chloride was added to the reaction mixture until no bubbling was observed. The solvents were evaporated in vacuo and the resultant crude mixture was dissolved in water (10 mL) and methylene chloride (10 mL). The layers were separated and the organic layer washed with water (2x) and brine (2x), dried over sodium sulfate, filtered, and concentrated to afford 1.5 g (70%) of the desired product. LC/MS: $t_R$=0.7 min, 326.18 (MH)$^+$.

(2-Amino-benzyl)-(1-benzyl-piperidin-4-yl)-amine

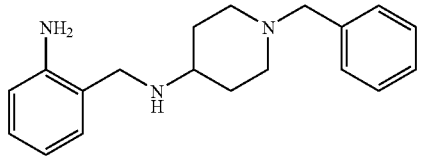

(1-Benzyl-piperidin-4-yl)-(2-nitro-benzyl)-amine (1.2 g, 3.7 mmol) and zinc dust (1 g, excess) were combined in 75% aqueous acetic acid (16 mL) and stirred at 60° C. for 2 h. After cooling to room temperature, the solvents were removed in vacuo and the resultant crude dissolved in water (10 mL), followed by addition of ammonium hydroxide until pH 3 was attained. The solution was extracted with methylene chloride (3x). The organic layers were pooled together washed with water (2x), brine (2x), dried over sodium sulfate, filtered, and concentrated to afford 0.8 g (73%) of the desired product. $^1$H-NMR (CD$_3$OD) δ 2.50 (m, 2H), 3.20 (m, 2H), 3.49 (dd, J=7.0, 7.3, 1H), 3.62 (m, 4H), 4.20 (s, 2H), 4.36 (s, 2H), 7.04 (m, 2H), 7.32 (dd, J=7.3, 7.6, 1H), 7.41 (d, J=7.9, 1H), 7.50 (m, 5H). Mass spec.: 296.40 (MH)$^+$.

3-(1-Benzyl-piperidin-4-yl)-3,4-dihydro-1H-benzo[1,2,6]thiadiazine-2,2-dioxide

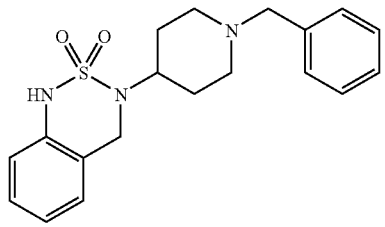

A solution of (2-amino-benzyl)-(1-benzyl-piperidin-4-yl)-amine (1.0 g, 3.39 mmol) and sulfamide (0.64 g, 6.78 mmol) in pyridine was heated at reflux for 14 h. After cooling to room temperature, the solvent was evaporated and the crude product dissolved in water. After being adjusted to pH 9 with 6N sodium hydroxide, the resulting mixture was extracted with methylene chloride (2x). The extracts were washed with water (2x), dried over sodium sulfate, filtered, and concentrated to afford an oily residue which was dissolved in ethyl acetate (4 mL). This solution was mixed with 4N HCl in 1,4-dioxane (2 mL) followed by addition of diethyl ether until precipitation of product occurred. The desired product was obtained by filtration to afford 0.7 g (53%). LC/MS: $t_R$=0.96 min, 358.16 (MH)$^+$.

3-Piperidin-4-yl-3,4-dihydro-1H-benzo[1,2,6]thiadiazine-2,2-dioxide

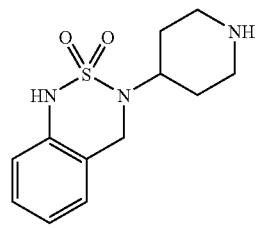

3-(1-Benzyl-piperidin-4-yl)-3,4-dihydro-1H-benzo[1,2,6]thiadiazine-2,2-dioxide (0.46 g, 1.29 mmol) in methanol (10 mL) was flushed with nitrogen, and treated with palladium on charcoal (10%, 46 mg). The flask was flushed with hydrogen and allowed to stir under an atmosphere of hydrogen overnight. The reaction was flushed with nitrogen, filtered through celite, and concentrated. Column chromatography gave 0.26 g (75%) of the desired material. $^1$H-NMR (CD$_3$OD) δ 1.53-1.61 (m, 2H), 1.80 (m, 2H), 2.55 (m, 2H), 2.95-3.05 (m, 2H), 3.30 (m, 2H), 3.70 (m, 2H), 4.65 (s, 2H), 6.70 (d, J=7.9, 1H), 7.40 (dd, J=8.2, 6.7, 1H), 7.10 (m, 2H). Mass spec.: 268.10 (MH)$^+$.

6-Bromo-3-piperidin-4-yl-3,4-dihydro-1H-quinazolin-2-one

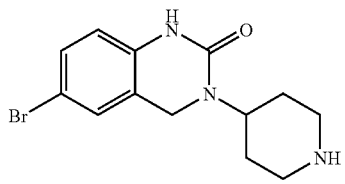

3-Piperidin-4-yl-3,4-dihydro-1H-quinazolin-2-one (0.2 g, 0.87 mmol) was dissolved in acetic acid (2 mL). To this solution was added a solution of bromine (1.8 mL, 35.14 mmol) in acetic acid (0.5 mL) dropwise over 5 min. After stirring for at room temperature for 1 h, the reaction mixture was diluted with methylene chloride, washed with water (2x), brine (2x), dried over sodium sulfate, filtered, and concentrated to afford 0.16 g (59%) which was used immediately without further purification. LC/MS: $t_R$=0.91 min, 310.15 (MH)$^+$.

2-Oxo-3-piperidin-4-yl-1,2,3,4-tetrahydro-quinazoline-6-carbonitrile

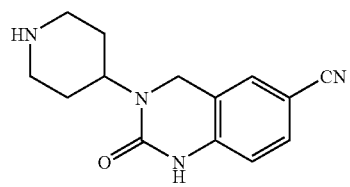

6-Bromo-3-piperidin-4-yl-3,4-dihydro-1H-quinazolin-2-one (0.16 g, 0.52 mmol), zinc cyanide (37 mg, 0.31 mmol) and tetrakis(triphenylphosphine)palladium(0) (60 mg, 0.05 mmol) were combined in dimethylformamide (4 mL). The reaction flask was connected to high vacuum and degassed (3×) by a freeze-thawing method, before being heated at 90° C. with stirring under nitrogen for 1 h. After cooling to room temperature, the solution was evaporated in vacuo and the crude mixture purified by preparative HPLC to afford 50 mg (38%) of the desired nitrile. $^1$H-NMR (CD$_3$OD) δ 1.99 (m, 2H), 2.08-2.23 (m, 2H), 3.15 (m, 2H), 3.50 (bs, 1H), 3.55 (bs, 1H), 4.40 (m, 1H), 4.47 (s, 2H), 6.93 (d, J=8.1, 1H), 4.10 (m, 2H). Mass spec.: 257.13 (MH)$^+$.

N-(1-Benzyl-piperidin-4-yl)-2-(2-nitro-phenyl)-acetamide

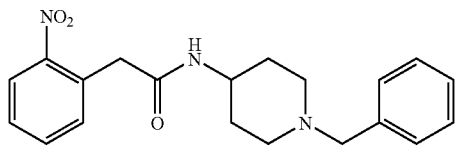

(2-Nitro-phenyl)-acetic acid (2.0 g, 11.04 mmol), 4-amino-1-benzylpiperidine (2.25 mL, 10.03 mmol), 1-hydroxybenzotriazole (1.49 g, 11.04 mmol) and 1-(3-dimethylaminopropyl)-3-ethyl carbodiimide (2.3 g, 12.03 mmol) were combined in ethyl acetate (25 mL). To this solution was added triethylamine (4.2 mL. 30.1 mmol) and the reaction mixture stirred at 40° C. for 2 h. After cooling to room temperature, the mixture was diluted with ethyl acetate and washed with water (2×), 5% sodium bicarbonate, brine (2×), dried over sodium sulfate, and concentrated to afford 3.5 g (98%) of the desired product.
LC/MS: $t_R$=1.24 min, 354.30 (MH)$^+$.

[2-(2-Amino-phenyl)-ethyl]-(1-benzyl-piperidin-4-yl)-amine

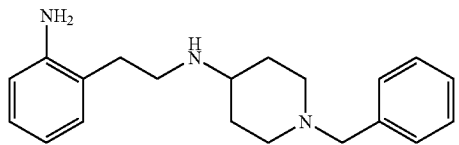

Into a flame dried flask, N-(1-benzyl-piperidin-4-yl)-2-(2-nitro-phenyl)-acetamide (3.2 g, 9.06 mmol) and lithium aluminium hydride (1.0 g, 18.12 mmol) were combined. 1,4-Dioxane (15 mL) was added and the mixture slowly brought to reflux over 1 h and stirred at reflux for 16 h. The reaction mixture was cooled to 0° C. and excess lithium aluminium hydride destroyed by dropwise addition of methanol, followed by careful addition of 20% potassium hydroxide. The aluminum salts were filtered, the filtrate concentrated and used as is for the next reaction.

3-(1-Benzyl-piperidin-4-yl) 1,3,4,5-tetrahydro-benzo[d][1,3]diazepin-2-one

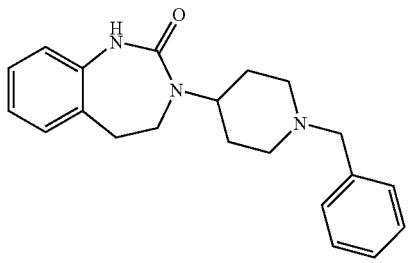

A stirred solution of [2-(2-amino-phenyl)-ethyl]-(1-benzyl-piperidin-4-yl)-amine (0.44 g, 1.42 mmol) in tetrahydrofuran (5 mL) at 0° C. was treated with carbonyl diimidazole (0.23 g, 1.42 mmol). The reaction was stirred for 30 min at 0° C. and at reflux for 1 h. After cooling to room temperature, the solvent was evaporated and the residue purified by column to afford 100 mg (21%) of the desired product. LC/MS: $t_R$=1.29 min, 336.34 (MH)$^+$.

3-Piperidin-4-yl-1,3,4,5-tetrahydro-benzo[d][1,3]diazepin-2-one

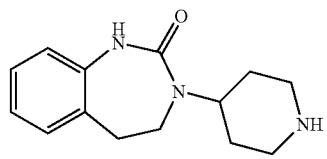

3-(1-Benzyl-piperidin-4-yl) 1,3,4,5-tetrahydro-benzo[d][1,3]diazepin-2-one (100 mg, 0.3 mmol) in methanol (5 mL) was flushed with nitrogen, and treated with palladium on charcoal (10%, 10 mg). The flask was flushed with hydrogen and allowed to stir under an atmosphere of hydrogen overnight. The reaction was flushed with nitrogen, filtered through celite, and concentrated. Column chromatography gave 50 mg (68%) of the desired material. LC/MS: $t_R$=1.07 min, 246.26 (MH)$^+$.

3-[(1-Benzyl-piperidin-4-yl-amino)-methyl]-4-nitrophenol

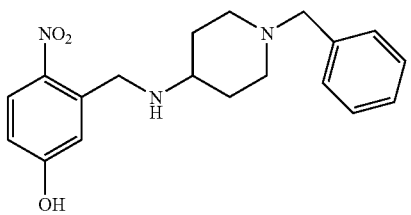

5-Hydroxy-2-nitro-benzaldehyde (5 g, 29.9 mmol) and 4-amino-1-benzylpiperidine (5.6 mL, 29.9 mmol) were combined in ethanol (30 mL). The resulting suspension was stirred at room temperature for 20 min before a solution of sodium borohydride (1.13 g, 29.9 mmol) in ethanol (10 mL) was added dropwise over 10 min. After the addition was complete, the reaction was stirred at room temperature for 1 h, cooled to 0° C. and concentrated ammonium chloride added to the reaction mixture until no bubbling was observed. The solvents were evaporated in vacuo and the resultant crude mixture was dissolved in water (30 mL) and methylene chloride (40 mL). The layers were separated and the organic layer washed with water (2×), brine (2×), dried over sodium sulfate, filtered, and concentrated to afford 5.8 g (57%) of the desired product. LC/MS: $t_R$=0.95 min, 342.27 (MH)$^+$.

4-Amino-3-[(1-benzyl-piperidin-4-yl-amino)-methyl]-phenol

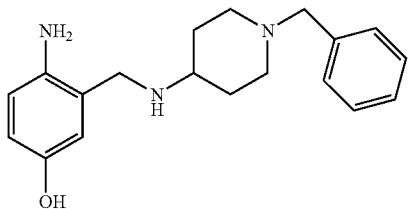

(1-Benzyl-piperidin-4-yl)-(2-nitro-benzyl)-amine (0.25 g, 0.7 mmol) and zinc dust (0.2 g, excess) were combined in 75% aqueous acetic acid (8 mL) and stirred at 60° C. for 2 h. After cooling to room temperature, the solvents were removed in vacuo and the resultant crude mixture dissolved in water (10 mL), followed by addition of ammonium hydroxide until pH 3 was attained. The solution was extracted with methylene chloride (3×). The organic layers were pooled together, washed with water (2×), brine (2×), dried over sodium sulfate, filtered, and concentrated to afford 0.18 g (79%) of the desired product.

3-(1-Benzyl-piperidin-4-yl)-6-hydroxy-3,4-dihydro-1H-quinazolin-2-one

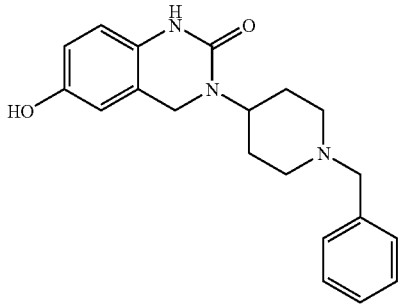

A stirred solution of 4-amino-3-[(1-benzyl-piperidin-4-yl-amino)-methyl]-phenol (0.16 g, 0.51 mmol) in tetrahydrofuran (3 mL) at 0° C. was treated with carbonyl diimidazole (52 mg, 0.51 mmol). The reaction was stirred for 30 min at 0° C. and at reflux for 1 h. After cooling to room temperature, the solvent was evaporated and the residue purified by column to afford 100 mg (57%) of the desired product. LC/MS: $t_R$=1.09 min, 338.28 (MH)$^+$.

6-Hydroxy-3-piperidin-4-yl-3,4-dihydro-1H-quinazolin-2-one

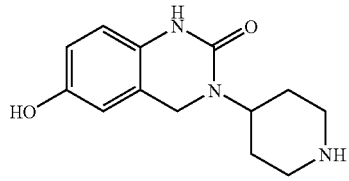

3-(1-Benzyl-piperidin-4-yl)-6-hydroxy-3,4-dihydro-1H-quinazolin-2-one (100 mg, 0.3 mmol) in methanol (5 mL) was flushed with nitrogen, and treated with palladium on charcoal (10%, 10 mg). The flask was flushed with hydrogen and allowed to stir under an atmosphere of hydrogen overnight. The reaction was flushed with nitrogen, filtered through celite, and concentrated. Column chromatography gave 60 mg (81%) of the desired material. LC/MS: $t_R$=0.75 min, 248.22 (MH)$^+$.

N-(1-Benzyl-piperidin-4-yl)-2-methoxy-6-nitro-benzamide

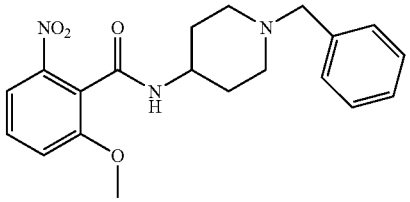

2-Methoxy-6-nitro-benzoic acid (2.0 g, 10.1 mmol), 4-amino-1-benzylpiperidine (1.9 mL, 10.1 mmol), 1-hydroxybenzotriazole (1.43 g, 10.5 mmol) and 1-(3-dimethylaminopropyl)-3-ethyl carbodiimide (1.9 g, 10.1 mmol) were combined in ethyl acetate (25 mL). To this solution was added triethylamine (4.2 mL. 30.3 mmol) and the reaction mixture stirred at 40° C. for 2 h. After cooling to room temperature, the mixture was diluted with ethyl acetate and washed with water (2×), 5% sodium bicarbonate, brine (2×), dried over sodium sulfate, and concentrated to afford 3.2 g (86%) of the desired product.

LC/MS: $t_R$=1.10 min, 370.28 (MH)$^+$.

(2-Amino-6-methoxy-benzyl)-(1-benzyl-piperidin-4-yl)-amine

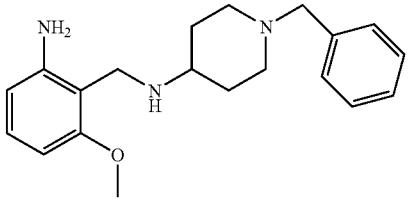

Into a flame dried flask, N-(1-benzyl-piperidin-4-yl)-2-methoxy-6-nitro-benzamide (1.0 g, 2.8 mmol) and lithium aluminium hydride (0.31 g, 8.45 mmol) were combined. To the mixture was added anhydrous 1,4-dioxane (15 mL). The mixture was slowly brought to reflux over 1 h and stirred at reflux for 16 h. The reaction mixture was cooled to 0° C. and excess lithium aluminium hydride destroyed by dropwise addition of methanol, followed by careful addition of 20% potassium hydroxide. The aluminum salts were filtered, the filtrate concentrated and used as is for the next reaction.

3-(1-Benzyl-piperidin-4-yl)-8-methoxy-3,4-dihydro-1H-quinazolin-2-one

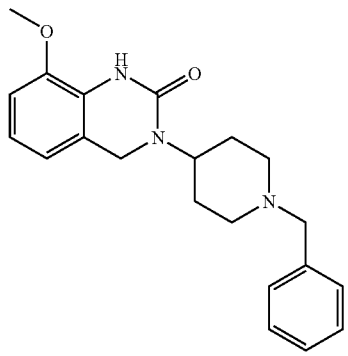

A stirred solution of (2-amino-6-methoxy-benzyl)-(1-benzyl-piperidin-4-yl)-amine (0.2 g, 0.62 mmol) in tetrahydrofuran (3 mL) at 0° C. was treated with carbonyl diimidazole (99 mg, 0.62 mmol). The reaction was stirred for 30 min at 0° C. and at reflux for 1 h. After cooling to room temperature, the solvent was evaporated and the residue purified by column to afford 150 mg (68%) of the desired product. LC/MS: $t_R$=1.41 min, 352.30 (MH)$^+$.

8-Methoxy-3-piperidin-4-yl-3,4-dihydro-1H-quinazolin-2-one

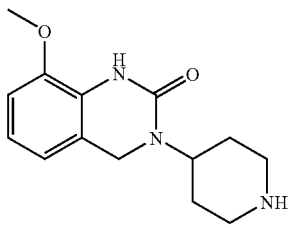

3-(1-Benzyl-piperidin-4-yl)-8-methoxy-3,4-dihydro-1H-quinazolin-2-one (100 mg, 0.28 mmol) in methanol (5 mL) was flushed with nitrogen, and treated with palladium on charcoal (10%, 10 mg). The flask was flushed with hydrogen and allowed to stir under an atmosphere of hydrogen overnight. The reaction was flushed with nitrogen, filtered through celite, and concentrated. Column chromatography gave 68 mg (93%) of the desired material. LC/MS: $t_R$=1.11 min, 262.23 (MH)$^+$.

N-(1-Benzyl-piperidin-4-yl)-2-chloro-6-nitro-benzamide

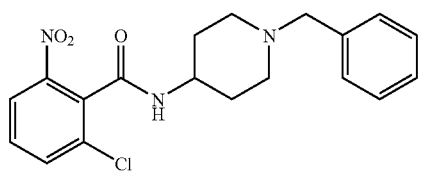

2-Chloro-6-nitro-benzoic acid (1.2 g, 5.97 mmol), 4-amino-1-benzylpiperidine (1.1 mL, 5.97 mmol), 1-hydroxybenzotriazole (0.84 g, 1.05 equiv) and 1-(3-dimethylaminopropyl)-3-ethyl carbodiimide (1.1 g, 1.05 equiv) were combined in ethyl acetate (20 mL). To this solution was added triethylamine (2.5 mL. 3.0 equiv) and the reaction mixture stirred at 40° C. for 2 h. After cooling to room temperature, the mixture was diluted with ethyl acetate and washed with water (2×), 5% sodium bicarbonate, brine (2×), dried over sodium sulfate, and concentrated to afford 1.9 g (85%) of the desired product.

(2-Amino-6-chloro-benzyl)-(1-benzyl-piperidin-4-yl)-amine

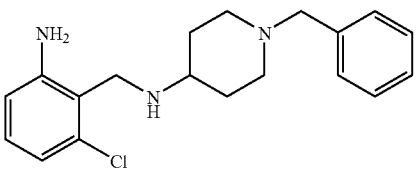

Into a flame dried flask, N-(1-benzyl-piperidin-4-yl)-2-chloro-6-nitro-benzamide (1.67 g, 4.47 mmol) and lithium aluminium hydride (0.51 g, 13.43 mmol) were combined. To this was added anhydrous 1,4-dioxane (15 mL). The mixture was slowly brought to reflux and stirred for 16 h. The reaction mixture was cooled to 0° C. and excess lithium aluminium hydride destroyed by dropwise addition of methanol, followed by careful addition of 20% potassium hydroxide. The aluminum salts were filtered, the filtrate concentrated and used as is for the next reaction.

3-(1-Benzyl-piperidin-4-yl)-8-chloro-3,4-dihydro-1H-quinazolin-2-one

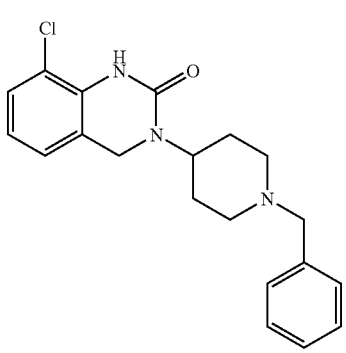

A stirred solution of (2-amino-6-chloro-benzyl)-(1-benzyl-piperidin-4-yl)-amine (0.66 g, 2.0 mmol) in tetrahydrofuran (8 mL) at 0° C. was treated with carbonyl diimidazole (0.36 g, 2.05 mmol). The reaction was stirred for 30 min at 0° C. and at reflux for 1 h. After cooling to room temperature, the solvent was evaporated and the residue purified by column to afford 0.58 g (82%) of the desired product. LC/MS: $t_R$=1.40 min, 356.25 (MH)$^+$.

2-Chloro-3-piperidin-4-yl-3,4-dihydro-1H-quinazolin-2-one

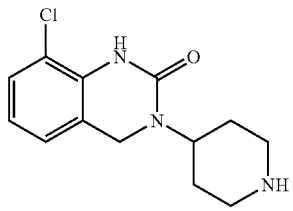

3-(1-Benzyl-piperidin-4-yl)-8-chloro-3,4-dihydro-1H-quinazolin-2-one (0.17 g, 0.48 mmol) in methanol (10 mL) was flushed with nitrogen, and treated with palladium on charcoal (10%, 17 mg). Trifluoroacetic acid (0.2 mL) was added and the mixture flushed with nitrogen then allowed to stir under an atmosphere of hydrogen overnight. The reaction was flushed with nitrogen, filtered through celite, and concentrated. Column chromatography gave 100 mg (79%) of the desired material. LC/MS: $t_R$=0.99 min, 266.08 (MH)$^+$.

5-Bromo-1H-indole-3-carbonitrile

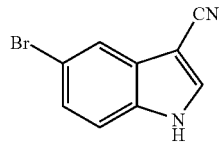

A mixture of 5-bromo-indole-3-carboxaldehyde (5 g, 22.3 mmol), diammonium hydrogen phosphate (15.6 g, 31.8 mmol) in 1-nitropropane (66 mL) and acetic acid (22 mL) were heated at reflux for 16 h. After cooling to room temperature, the solvents were removed under reduced pressure and water added to the dark residue. After a short while, 5-bromo-1H-indole-3-carbonitrile precipitated rapidly. The solid was filtered, washed severally with water and dried for several hours to afford 4.3 g (86%) of the desired product. $^1$H-NMR (CD$_3$OD) δ 7.40 (m, 2H), 7.77 (s, 1H), 7.97 (s, 1H). Mass spec.: 222.95 (MH)$^+$.

5-Formyl-1H-indole-3-carbonitrile

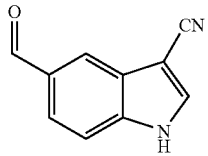

5-Bromo-1H-indole-3-carbonitrile (4.25 g, 19.23 mmol) and sodium hydride (0.51 g, 21.2 mmol) were weighed into a flame-dried round-bottom flask containing a magnetic stir bar. Under a nitrogen atmosphere at room temperature, dry tetrahydrofuran (24 mL) was added. The mixture was stirred at room temperature for 15 min, during which time it became homogeneous. The stirred mixture was cooled to −78° C. and a solution of sec-butyllithium in cyclohexane (1.4M, 30.2 mL, 2.2 equiv) was added over several minutes. After 1 h at −78° C., dimethylformamide (6.0 mL) was slowly added and the mixture allowed to warm to room temperature overnight. The solution was cooled to 0° C. and carefully treated with 1 N hydrochloric acid (45 mL). After a few minutes, solid sodium bicarbonate was added until a pH of 9-10 was attained. The two layers were separated and the aqueous phase washed twice with ethyl acetate. The combined organic layers were washed with water (2×), brine (2×), dried over sodium sulfate, and concentrated. Column chromatography gave 2.4 g (72%) of pure material. LC/MS: $t_R$=0.99 min, 171.07 (MH)$^+$.

2-Benzyloxycarbonylamino-3-(3-cyano-1H-indol-5-yl)-acrylic acid methyl ester

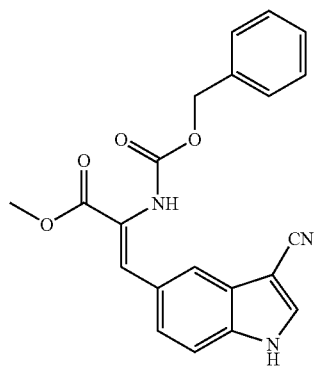

A stirred solution of N-benzyloxycarbonyl-α-phosphonoglycine trimethyl ester (1.68 g, 5.1 mmol) in tetrahydrofuran (10 mL) at room temperature was treated with tetramethylguanidine (0.6 mL, 1.1 equiv). After 10 min, 5-formyl-1H-indole-3-carbonitrile (0.72 g, 4.24 mmol) was added. After stirring at room temperature for 3 days, the solvent was evaporated and the residue washed with water (2×), brine (2×), dried over sodium sulfate, and concentrated. Column chromatography gave 1.3 g (82%) of pure material. LC/MS: $t_R$=1.43 min, 376.22 (MH)$^+$.

(±)-2-Amino-3-(3-cyano-1H-indol-5-yl)-propionic acid methyl ester

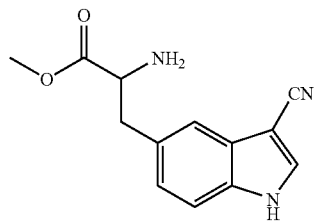

2-Benzyloxycarbonylamino-3-(3-cyano-1H-indol-5-yl)-acrylic acid methyl ester (0.5 g, 1.3 mmol) in methanol (8 mL) was flushed with nitrogen, and treated with palladium on charcoal (10%, 50 mg). The flask was flushed with hydrogen and allowed to stir under an atmosphere of hydrogen overnight. The reaction was flushed with nitrogen, filtered through celite, and concentrated. Column chromatography gave 0.3 g (92%) of the desired material. LC/MS: $t_R$=0.80 min, 244.20 (MH)$^+$.

Example 202

(±)-3-(3-Cyano-1H-indol-5-yl)-2-{[4-(2-oxo-1,4-dihydro-2H-quinazolin-3-yl)-piperidine-1-carbonyl]-amino}-propionic acid methyl ester

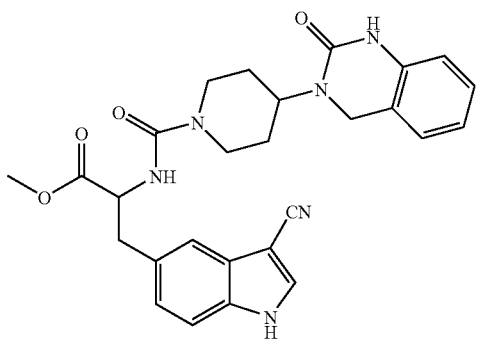

A stirred solution of 2-amino-3-(3-cyano-1H-indol-5-yl)-propionic acid methyl ester (25 mg, 0.11 mmol) in tetrahydrofuran (3 mL) at 0° C. was treated with carbonyl diimidazole (17.5 mg, 1.1 equiv.). The reaction was stirred for 5 min at 0° C., warmed to room temperature, stirred 10 min, and treated with 3-piperidin-4-yl-3,4-dihydro-1H-quinazolin-2-one (25 mg, 1.1 equiv.). The mixture was stirred at room temperature overnight. The solvent was evaporated and the residue purified by column chromatography to give 40 mg (75%) as a white powder. LC/MS: $t_R$=1.37 min, 501.33 $(MH)^+$.

Example 203

(±)-4-(2-Oxo-1,4-dihydro-2H-quinazolin-3-yl)-piperidine-1-carboxylic acid[2-[1,4']bipiperidinyl-1'-yl-1-(3-cyano-1H-indol-5-yl-methyl)-2-oxo-ethyl]-amide

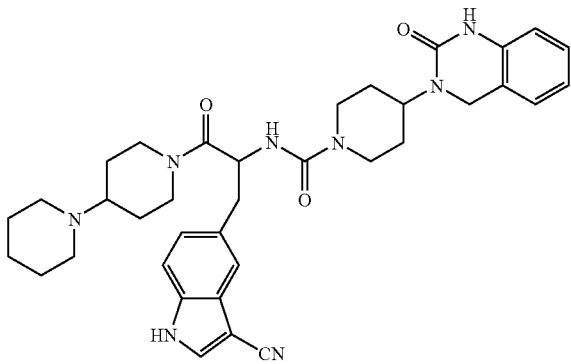

A solution of 3-(3-cyano-1H-indol-5-yl)-2-{[4-(2-oxo-1,4-dihydro-2H-quinazolin-3-yl)-piperidine-1-carbonyl]-amino}-propionic acid methyl ester (15 mg, 0.03 mmol) in methanol (0.6 mL) at room temperature was treated with a solution of lithium hydroxide monohydrate (3.0 mg, 2.5 equiv.) in water (0.1 mL). The solution was stirred at room temperature for 2 h. The solution was cooled to 0° C., and treated with aqueous 1M potassium hydrogen sulfate (60 µL, 2.0 equiv.), and the solvents evaporated to give the crude acid which was used immediately without purification. The crude acid was dissolved in dimethylformamide (0.4 mL) cooled to 0° C., and sequentially treated with methylene chloride (0.2 mL), 4-piperidyl-piperidine (11 mg, 2.2 equiv), N,N-diisopropylethylamine (12 µL, 2.3 equiv) and PyBop (19 mg, 1.2 equiv). The solution was stirred for 15 min at 0° C., warmed to room temperature, stirred 1.5 h, and concentrated. The product was purified by column chromatography to give 10.1 mg (52% 2 steps). $^1$H-NMR (CD$_3$OD) δ 1.60-2.10 (m, 14H), 2.53 (d, J=13.0, 1H), 2.58 (d, J=12.2, 1H), 2.65-3.00 (m, 7H), 3.12 (d, J=7.0, 1H), 3.17 (d, J=7.0, 1H), 3.84 (s, 1H), 3.46 (bs, 1H), 4.08-4.86 (m, 5H), 4.70 (m, 1H), 5.02 (dd, J=8.2, 6.7, 1H), 6.79 (d, J=7.6, 1H), 6.9 (m, 1H), 7.10 (dd, J=7.3, 7.9, 1H), 9.18 (s, 1H), 7.15 (dd, J=7.3, 7.6, 1H), 7.30 (m, 1H), 7.50 (m, 1H), 8.00 (s, 1H). Mass spec.: 647.41 $(MH)^+$.

3-(4-Bromo-2-methyl-phenylamino)-2-methyl-acrylic acid ethyl ester

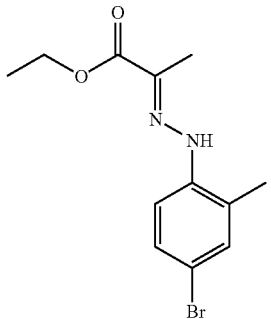

To a solution of 4-bromo-2-methyl aniline (7.0 g, 37.8 mmol) in acetonitrile (80 mL) was added, sequentially, concentrated hydrochloric acid (15 mL), water (40 mL) and a solution of sodium nitrite (2.74 g, 39.7 mmol) in water (40 mL) under ice cooling to give the diazonium salt. The solution was transferred dropwise to a solution of 50% potassium hydroxide (16 mL) and ethyl-2-methyl acetoacetate (5.38 mL, 38 mmol) in ethanol (50 mL) at 0° C. After the addition was complete, the reaction mixture was poured into ice-water (150 mL) and extracted with ethyl acetate. The organic layer was washed with brine (2×), dried over sodium sulfate, filtered, and concentrated to give 7.5 g (66%) of the title compound which was used immediately without purification.

$^1$H-NMR (CD$_3$OD) δ 1.80 (t, J=7.0, 3H), 2.13 (s, 3H), 2.29 (s, 3H), 4.26 (dd, J=5.8, 7.0, 1H), 4.30 (dd, J=5.8, 7.0, 1H), 7.26 (m, 2H), 7.43 (m, 1H). Mass spec.: 323.07 $(MNa)^+$.

5-Bromo-7-methyl-1H-indole-2-carboxylic acid ethyl ester

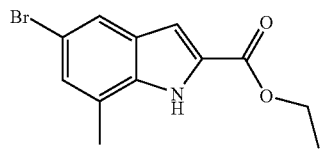

A solution of p-toluenesulfonic acid monohydrate (4.26 g, 75 mmol) in toluene (80 mL) was heated at reflux under a dean-stark water separator for 1.5 h. To this solution was added a solution of 5-bromo-7-methyl-1H-indole-2-carboxylic acid ethyl ester (7.5 g, 25.0 mmol) in toluene (40 mL) and the reaction mixture heated at reflux for 5 h. After cooling to room temperature, the reaction mixture was poured in to ice-water (120 mL) and extracted twice with ethyl acetate. The organic layers were pooled together and washed with sodium bicarbonate (2×), brine (2×), dried over sodium sulfate, filtered, and concentrated. Column chromatography on silica gel afforded 5.5 g (78%) of the title compound.

$^1$H-NMR (CD$_3$OD) δ 1.35 (t, J=7.0, 3H), 2.52 (s, 3H), 4.36 (q, J=7.0, 2H), 7.13 (s, 1H), 7.14 (s, 1H), 7.70 (s, 1H), 11.90 (s, 1H). Mass spec.: 284.09 (MH)$^+$.

5-Bromo-7-methyl-1H-indole

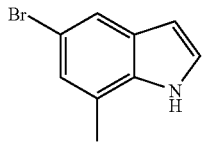

5-Bromo-7-methyl-1H-indole-2-carboxylic acid ethyl ester (5.3 g, 18.7 mmol) was added to a potassium hydroxide solution in 1:1 water/ethanol mixture (20 mL) and heated at reflux for 12 h. After cooling to room temperature, the solvents were removed in vacuo and the resultant residue transferred to a 6N hydrochloric acid solution (20 mL). The white precipitate that formed was filtered, washed severally with water, and dried for several hours. The crude solid was dissolved in quinoline (14 mL) and heated at reflux for 4 h. After cooling to room temperature, the crude mixture was poured into a mixture of ice water (100 mL) and concentrated hydrochloric acid (16 mL), extracted with ethyl acetate (2×), brine (2×), dried over sodium sulfate, and concentrated. Attempts to recrystallize the desired product from isopropanol resulted in significant decomposition. The title compound was obtained by flash chromatography on silica get to afford 1.5 g (38%, 2 steps). LC/MS: $t_R$=1.72 min, 210.05 (MH)$^+$.

5-Bromo-7-methyl-1H-indole-3-carboxaldehyde

5-Bromo-7-methyl-1H-indole (1.2 g, 5.71 mmol) was dissolved in acetonitrile (6 mL) and transferred slowly to a solution of bromomethylene dimethyl ammonium bromide (1.36 g, 6.28 mmol) in acetonitrile (9 mL) at −10° C. to 0° C. The reaction was stirred at 0° C. for 2 h and at room temperature for 30 min. The solvents were evaporated and the crude mixture dissolved in water and stirred at 50° C. for 4 h. After cooling to room temperature, the crude mixture was extracted with ethyl acetate (2×). The organic layers were pooled together and washed with brine (2×), dried over magnesium sulfate, filtered, and concentrated. Purification by flash chromatography on silica gel afforded 0.7 g (52%, 2 steps) of the desired compound. $^1$H-NMR (CD$_3$OD) δ 2.50 (s, 3H), 7.24 (s, 1H), 8.34 (m, 1H), 9.93 (s, 1H). Mass spec.: 238.05 (MH)$^+$ 5-Bromo-7-methyl-1H-indole-3-carbonitrile

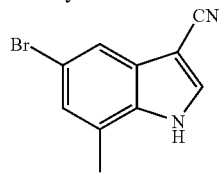

A mixture of 5-bromo-indole-3-carboxaldehyde (0.7 g, 2.94 mmol), diammonium hydrogen phosphate (2.05 g, 15.5 mmol) in 1-nitropropane (9 mL) and acetic acid (3 mL) were heated at reflux for 16 h. After cooling to room temperature, the solvents were removed under reduced pressure and water added to the dark residue. After a short while, 5-bromo-1H-indole-3-carbonitrile precipitated rapidly, was filtered, washed severally with water and dried for several hours to afford 0.6 g (87%) of the desired nitrile. LC/MS: $t_R$=1.71 min, 235.01 (MH)$^+$.

5-Formyl-7-methyl-1H-indole-3-carbonitrile

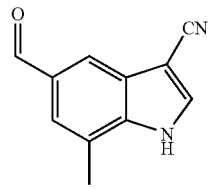

5-Bromo-7-methyl-1H-indole-3-carbonitrile (0.58 g, 2.46 mmol) and sodium hydride (68 mg, 2.7 mmol) were weighed into a flame-dried round-bottom flask containing a magnetic stir bar. Under a nitrogen atmosphere at room temperature, dry tetrahydrofuran (9 mL) was added. The mixture was stirred at room temperature for 15 min, during which time it became homogeneous. The stirred mixture was cooled to −78° C. and a solution of sec-butyllithium in cyclohexane (1.4M, 3.8 mL, 2.2 equiv) was added over several minutes. After 1 h at −78° C., dimethylformamide (0.9 mL) was slowly added and the mixture allowed to warm to room temperature overnight. The solution was cooled to 0° C. and carefully treated with 1N hydrochloric acid. After a few minutes, solid sodium bicarbonate was added until a pH of 9-10 was attained. The two layers were separated and the aqueous phase washed twice with ethyl acetate. The combined organic layers were washed with water (2×), brine (2×), dried over sodium sulfate, and concentrated. Column chromatography gave 60 mg (14%) of desired product and 0.4 g of unreacted starting material. LC/MS: $t_R$=1.21 min, 185.10 (MH)$^+$.

2-Benzyloxycarbonylamino-3-(3-cyano-7-methyl-1H-indol-5-yl)-acrylic acid methyl ester

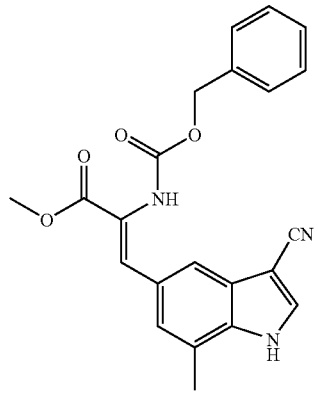

A stirred solution of N-benzyloxycarbonyl-α-phosphonoglycine trimethyl ester (180 mg, 0.54 mmol) in tetrahydrofuran (3 mL) at room temperature was treated with tetramethylguanidine (40 μL, 1.1 equiv). After 10 min, 5-formyl-7-methyl-1H-indole-3-carbonitrile (50 mg, 0.27 mmol) was added. After stirring at room temperature for 3 days, the solvent was evaporated and the residue washed with water (2×), brine (2×), dried over sodium sulfate, and concentrated. Column chromatography gave 100 mg (95%) of pure material. LC/MS: $t_R$=1.59 min, 390.24 (MH)$^+$.

(±)-2-Amino-3-(3-cyano-7-methyl-1H-indol-5-yl)-propionic acid methyl ester

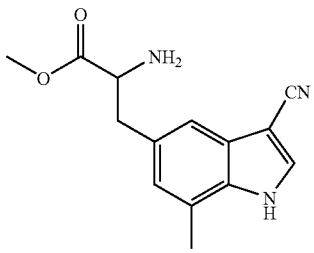

2-Benzyloxycarbonylamino-3-(3-cyano-7-methyl-1H-indol-5-yl)-acrylic acid methyl ester (0.1 g, 0.26 mmol) in methanol (2.5 mL) was flushed with nitrogen, and treated with palladium on charcoal (10%, 10 mg). The flask was flushed with hydrogen and allowed to stir under an atmosphere of hydrogen overnight. The reaction was flushed with nitrogen, filtered through celite, and concentrated. Column chromatography gave 60 mg (90%) of the desired material. LC/MS: $t_R$=0.93 min, 258.22 (MH)$^+$.

Example 204

(±)-4-(2-Oxo-1,4-dihydro-2H-quinazolin-3-yl)-piperidine-1-carboxylic acid[2-[1,4']bipiperidinyl-1'-yl-[(3-cyano-7-methyl-1H-indol-5-yl-methyl)-2-oxo-ethyl]-amide

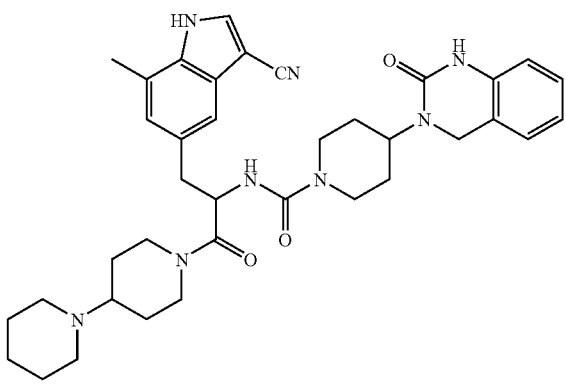

Prepared as describe above for Example 203: $^1$H-NMR (CD$_3$OD) δ 1.55-2.10 (m, 16H), 2.50 (s, 3H), 2.80-3.20 (m, 9H), 4.10-4.40 (m, 7H), 4.90 (m, 3H), 6.72 (d, J=7.9, 1H), 6.93 (dd, J=8.5, 8.5, 1H), 7.40 (s, 1H), 7.88 (s, 1H), 7.90 (s, 1H), 7.99 (s, 1H). Mass spec.: 651.57 (MH)$^+$.

4-Bromo-2-isopropyl-6-methyl-phenylamine

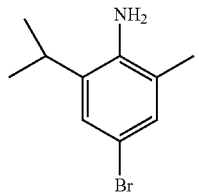

2-Isopropyl-6-methyl-phenylamine (5 g, 33.5 mmol) was dissolved in acetic acid (20 mL). To this solution was added a solution of bromine (1.8 mL, 35.14 mmol) in acetic acid (5 mL) dropwise over 10 min. After stirring for 1 h at room temperature, the reaction mixture was diluted with methylene chloride, washed with water (2×), saturated sodium thiosulfate (2×), saturated sodium bicarbonate (2×), and brine. The organic phase was dried over sodium sulfate, filtered, and concentrated. Purification by flash chromatography on silica gel afforded 7.6 g (quantitative) of the desired product. LC/MS: $t_R$=1.37 min, 230.07 (MH)$^+$.

4-Bromo-2-isopropyl-6-methyl-phenyldiazo-t-butyl sulfide

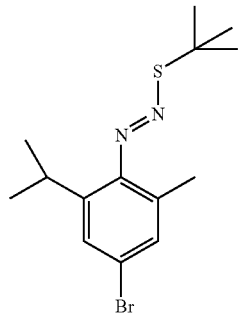

4-Bromo-2-isopropyl-6-methyl-phenylamine (7.6 g, 33.5 mmol) was suspended in 24% hydrochloric acid (15 mL). The stirred mixture was cooled to −20° C. and treated with sodium nitrite (2.4 g, 1.05 equiv.) in water (5 mL), dropwise over 30 min while the temperature was maintained below −5° C. After a further 30 min at −5° C. to −20° C., the mixture was buffered to ca. pH 5 with solid sodium acetate. This mixture (kept at ca. −10° C.) was added in portions to a stirred solution of t-butyl thiol (3.77 mL, 1.0 equiv.) in ethanol (25 mL) at 0° C. over ca. 30 min. Following addition, the mixture was stirred at 0° C. for 30 min and then crushed ice (ca. 50 mL) was added. The resulting light-brown solid was collected by filtration, washed with water, and dried under high vacuum for several hours to afford 7.9 g (72%) of the desired product. $^1$H-NMR (CDCl$_3$) δ 1.15 (t, J=6.7, 3H), 1.58 (s, 9H), 2.00 (s, 3H), 2.54 (m, 1H), 7.20 (s, 1H), 7.28 (s, 1H). Mass spec.: 331.08 (MNa)$^+$.

5-Bromo-7-isopropyl-1H-indazole

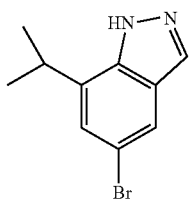

A flame-dried round bottom flask was charged with 4-bromo-2,6-diethylphenyldiazo-t-butyl sulfide (7.94 g, 24 mmol) and potassium t-butoxide (27 g, 10 equiv). A stir bar was added and the mixture placed under nitrogen. To this was added dry dimethylsulfoxide (70 mL). The mixture was stirred vigorously overnight at room temperature. The reaction mixture was carefully poured into a mixture of crushed ice (250 mL) and 10% hydrochloric acid (120 mL). The resulting suspension was collected by filtration and washed severally with water. The solid was collected and dried in vacuo to give 4.2 g (74%) of the desired product. LC/MS: $t_R$=1.73 min, 241.06 (MH)$^+$.

7-Isopropyl-1H-indazole-5-carbaldehyde

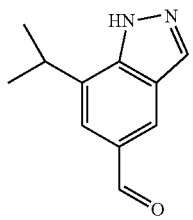

5-Bromo-7-isopropyl-1H-indazole (3.1 g, 12.1 mmol) and sodium hydride (0.34 g, 1.1 equiv.) were weighed into a flame-dried round-bottom flask containing a magnetic stir bar. Under a nitrogen atmosphere at room temperature, dry tetrahydrofuran (18 mL) was added. The mixture was stirred at room temperature for 15 min, during which time it became homogeneous. The stirred mixture was cooled to −78° C. and a solution of sec-butyllithium in cyclohexane (1.4M, 20 mL, 2.2 equiv.) was added over several minutes. After 1 h at −78° C., dimethylformamide (3.0 mL) was slowly added and the mixture allowed to warm to room temperature overnight. The solution was cooled to 0° C. and carefully treated with 1 N hydrochloric acid (35 mL). After a few minutes, solid sodium bicarbonate was added until a pH of 9-10 was attained. The two layers were separated and the aqueous phase washed twice with ethyl acetate. The combined organic layers were washed with water (2×), brine (2×), dried over sodium sulfate, and concentrated. Column chromatography gave 2.1 g (92%) of pure material. LC/MS: $t_R$=1.15 min, 189.12 (MH)$^+$.

2-Benzyloxycarbonylamino-3-(7-isopropyl-1H-indazol-5-yl)acrylic acid methyl ester

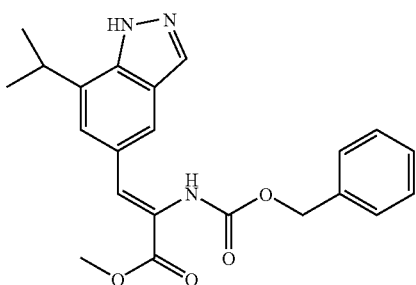

A stirred solution of N-benzyloxycarbonyl-α-phosphonoglycine trimethyl ester (0.39 g, 1.2 equiv) in tetrahydrofuran (5 mL) at room temperature was treated with tetramethylguanidine (0.16 mL, 1.1 equiv.). After 10 min, 7-isopropyl-1H-indazole-5-carbaldehyde (0.2 g, 1.06 mmol) was added.

After stirring at room temperature for 3 days, the solvent was evaporated and the residue purified by flash chromatography on silica gel to give 0.35 g (84%) of product. LC/MS: $t_R$=1.61 min, 394.16 (MH)$^+$.

(±)-2-Amino-3-(7-isopropyl-1H-indazol-5-yl)propionic acid methyl ester

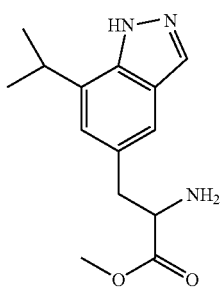

A solution of 2-benzyloxycarbonylamino-3-(7-isopropyl-1H-indazol-5-yl)acrylic acid methyl ester (0.35 g, 0.89 mmol) in methanol (7 mL) was flushed with nitrogen, and treated with palladium on charcoal (10%, 35 mg). The flask was flushed with hydrogen and allowed to stir under an atmosphere of hydrogen overnight. The reaction was flushed with nitrogen, filtered through celite, and concentrated. Column chromatography gave 0.21 g (90%) of the desired material.

Example 205

(±)-3-(7-Isopropyl-1H-indazol-5-yl)-2-{[4-(2-oxo-1,4-dihydro-2H-quinazolin-3-yl)-piperidine-1-carbonyl]-amino}-propionic acid methyl ester

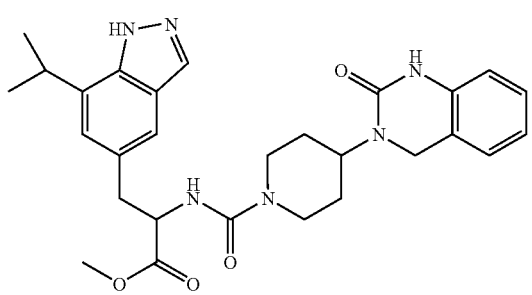

Prepared as described above for 3-(3-cyano-1H-indol-5-yl)-2-{[4-(2-oxo-1,4-dihydro-2H-quinazolin-3-yl)-piperidine-1-carbonyl]-amino}-propionic acid methyl ester. LC/MS: $t_R$=1.49 min, 519.35 (MH)$^+$.

Example 206

(±)-4-(2-Oxo-1,4-dihydro-2H-quinazolin-3-yl)-piperidine-1-carboxylic acid[2-[1,4']bipiperidinyl-1'-yl-[(7-isopropyl-1H-indazol-5-yl-methyl)-2-oxo-ethyl]-amide

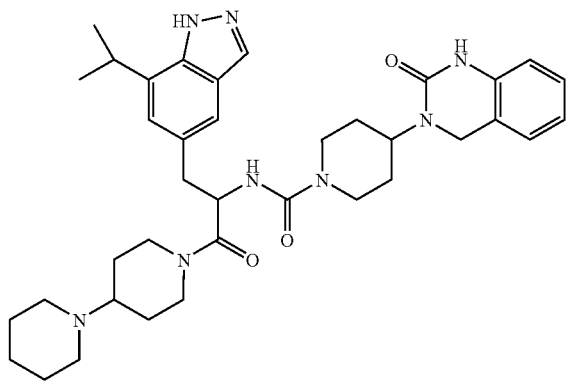

Prepared as described above for Example 203 from 3-(7-isopropyl-1H-indazol-5-yl)-2-{[4-(2-oxo-1,4-dihydro-2H-quinazolin-3-yl)-piperidine-1-carbonyl]-amino}-propionic acid methyl ester: $^1$H-NMR (CD$_3$OD) δ 1.45 (m, 6H), 1.60-2.05 (m, 14H), 2.20-2.50 (m, 4H), 2.73 (d, J=13.7, 1H), 2.90 (m, 4H), 4.05 (d, J=14.0, 1H), 4.20 (m, 2H), 4.35 (s, 1H), 4.65 (dd, J=12.2, 14.3, 1H), 4.95 (m, 2H), 6.79 (d, J=7.9, 1H), 6.92 (dd, J=7.6, 6.1, 1H), 7.13 (m, 1H), 7.80 (s, 1H), 7.45 (s, 1H), 8.05 (s, 1H). Mass spec.: 655.40 (MH)$^+$.

4-Bromo-2,6-diethylphenyldiazo-t-butyl sulfide

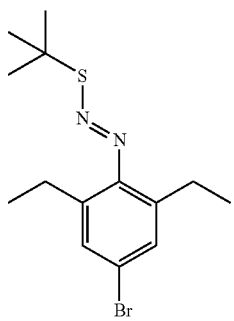

4-Bromo-2,6-diethylaniline (6.3 g, 27.6 mmol) was suspended in 24% hydrochloric acid (15 mL). The stirred mixture was cooled to −20° C. and treated with sodium nitrite (2.0 g, 1.05 equiv.) in water (5 mL), dropwise over 30 min while the temperature was maintained below −5° C. After a further 30 min at −5° C. to −20° C., the mixture was buffered to ca. pH 5 with solid sodium acetate. This mixture (kept at ca. −10° C.) was added in portions to a stirred solution of t-butyl thiol (3.15 mL, 1.0 equiv.) in ethanol (25 mL) at 0° C. over ca. 30 min. Following addition, the mixture was stirred at 0° C. for 30 min and then crushed ice (ca. 50 mL) was added. The resulting light-brown solid was collected by filtration, washed with water, and dried under high vacuum for several hours to afford 6.0 g (66%) of the desired product. $^1$H-NMR (CDCl$_3$) δ 1.15 (t, J=7.6, 6H), 1.50 (s, 9H), 2.27 (m, 4H), 7.21 (s, 2H). Mass spec.: 331.08 (MH)$^+$.

5-Bromo-7-ethyl-3-methylindazole

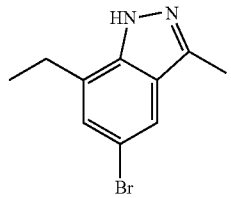

A flame-dried round bottom flask was charged with 4-bromo-2,6-diethylphenyldiazo-t-butyl sulfide (4.0 g, 12.1 mmol) and potassium t-butoxide (13.2 g, 10 equiv). A stir bar was added and the mixture placed under nitrogen. To this was added dry dimethylsulfoxide (35 mL). The mixture was stirred vigorously overnight at room temperature. The reaction mixture was carefully poured into a mixture of crushed ice (130 mL) and 10% hydrochloric acid (60 mL). The resulting suspension was collected by filtration and washed severally with water. The solid was collected and dried in vacuo to give 2.85 g (98%) as a beige solid. $^1$H-NMR (CD$_3$OD) δ 1.32 (t, J=7.6, 3H), 2.50 (s, 3H), 2.88 (m, 2H), 7.25 (s, 1H), 7.68 (s, 1H). Mass spec.: 239.26 (MH)$^+$.

7-Ethyl-3-methylindazole-5-carboxaldehyde

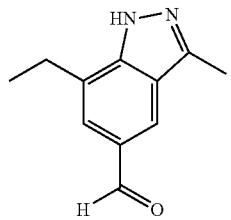

5-Bromo-7-ethyl-3-methylindazole (2.85 g, 11.9 mmol) and sodium hydride (0.31 g, 1.1 equiv.) were weighed into a flame-dried round-bottom flask containing a magnetic stir bar. Under a nitrogen atmosphere at room temperature, dry tetrahydrofuran (15 mL) was added. The mixture was stirred at room temperature for 15 min, during which time it became homogeneous. The stirred mixture was cooled to −78° C. and a solution of tert-butyllithium in pentane (1.4M, 18.7 mL, 2.0 equiv) was added over several minutes. After 1 h at −78° C., dimethylformamide (2.8 mL) was slowly added and the mixture allowed to warm to room temperature overnight. The solution was cooled to 0° C. and carefully treated with 1N hydrochloric acid (30 mL). After a few minutes, solid sodium bicarbonate was added until a pH of 9-10 was attained. The two layers were separated and the aqueous phase washed twice with ethyl acetate. The combined organic layers were washed with water (2×), brine (2×), dried over sodium sulfate, and concentrated. Column chromatography gave 1.5 g (67%) of pure material. LC/MS: t$_R$=1.15 min, 189.12 (MH)$^+$.

253

2-Benzyloxycarbonylamino-3-(7-ethyl-3-methyl-1H-indazol-5-yl)-acrylic acid methyl ester

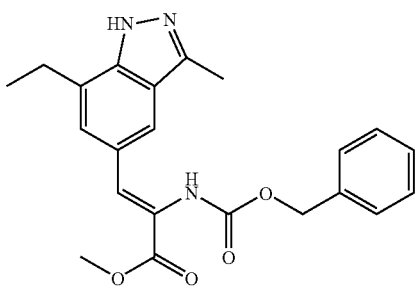

A stirred solution of N-benzyloxycarbonyl-α-phosphonoglycine trimethyl ester (3.17 g, 9.57 mmol, 1.2 equiv.) in tetrahydrofuran (15 mL) at room temperature was treated with tetramethylguanidine (1.1 mL, 1.1 equiv.). After 10 min, 7-ethyl-3-methylindazole-5-carboxaldehyde (1.5 g, 7.98 mmol) was added. After stirring at room temperature for 3 days, the solvent was evaporated and the residue purified by flash chromatography on silica gel to give 2.5 g (80%) of product. LC/MS: $t_R$=1.61 min, 394.16 (MH)$^+$.

(±)-2-Amino-3-(7-ethyl-3 methyl-1H-indazol-5-yl)-propionic acid methyl ester

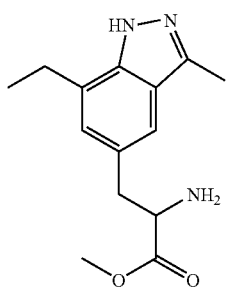

2-Benzyloxycarbonylamino-3-(7-ethyl-3-methyl-1H-indazol-5-yl)-acrylic acid methyl ester (1.0 g, 2.54 mmol) in methanol (15 mL) was flushed with nitrogen, and treated with palladium on charcoal (10%, 100 mg). The flask was flushed with hydrogen and allowed to stir under an atmosphere of hydrogen overnight. The reaction was flushed with nitrogen, filtered through celite, and concentrated. Column chromatography gave 0.6 g (91%) of the desired material. $^1$H-NMR (CD$_3$OD) δ 1.32 (m, 3H), 2.50 (s, 3H), 2.88 (dd, J=7.3, 7.6, 1H), 2.89 (dd, J=7.6, 7.6, 1H), 3.02 (dd, J=6.4, 7.0, 1H), 3.11 (dd, J=7.6, 5.8, 1H), 3.35 (s, 1H), 3.65 (m, 3H), 7.00 (s, 1H), 7.33 (s, 1H). Mass spec.: 262.24 (MH)$^+$.

254

Example 207

(±)-4-(2-Oxo-1,4-dihydro-2H-quinazolin-3-yl)-piperidine-1-carboxylic acid[2-[1,4']bipiperidinyl-1'-yl-[(7-ethyl-1H-indazol-5-yl-methyl)-2-oxo-ethyl]-amide

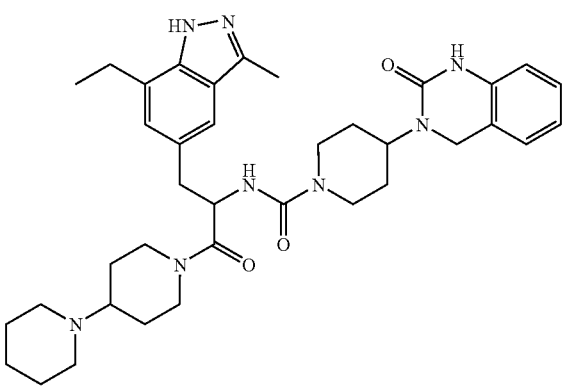

Prepared as described above for Example 203 from (±)-2-amino-3-(7-ethyl-3 methyl-1H-indazol-5-yl)-propionic acid methyl ester. $^1$H-NMR (CD$_3$OD) δ 1.35 (m, 3H), 1.85-2.20 (m, 4H), 2.50 (s, 1H), 2.70 (m, 2H), 2.85 (s, 3H), 2.88-3.25 (m, 7H), 3.35 (s, 1H), 3.47 (dd, J=7.3, 7.3, 1H), 4.00-4.40 (m, 7H), 4.70 (m, 1H), 5.00 (m, 3H), 6.79 (d, J=7.6, 1H), 6.93 (dd, J=7.3, 7.3, 1H), 7.10 (m, 1H), 7.15 (dd, J=7.3, 7.6, 1H), 7.45 (m, 1H). Mass spec.: 655.50 (MH)$^+$.

Example 208

(±)-4-(2,2-Dioxo-1,4-dihydro-2H-2λ$^6$-benzo[1,2,6]thiadiazin-3-yl)-piperidine-1-carboxylic acid[2-[1,4']bipiperidinyl-1'-yl-[(7-methyl-1H-indazol-5-yl-methyl)-2-oxo-ethyl]-amide

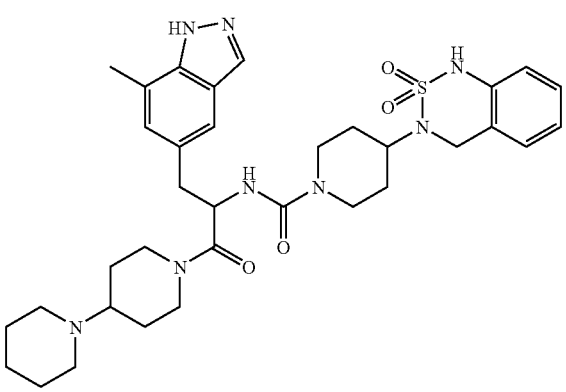

Prepared as described above for Example 203 from 3-piperidin-4-yl-3,4-dihydro-1H-benzo[1,2,6]thiadiazine-2,2-dioxide: $^1$H-NMR (CD$_3$OD) δ 1.20-2.10 (m, 12H), 2.20-2.60 (m, 6H), 2.90 (m, 6H), 3.78-4.11 (m, 4H), 4.60 (s, 3H), 4.90 (m, 1H), 6.70 (d, J=8.1, 1H), 6.79 (dd, J=7.67, 7.3, 1H), 7.44 (s, 1H), 7.10 (m, 1H), 7.13 (m, 3H), 8.03 (s, 1H). Mass spec.: 663.60 (MH)$^+$.

Example 209

(±)-4-(2,2-Dioxo-1,4-dihydro-2H-2λ⁶-benzo[1,2,6]thiadiazin-3-yl)-piperidine-1-carboxylic acid[2-[1,4']bipiperidinyl-1'-yl-1 (7-ethyl-3-methyl-1H-indazol-5-yl-methyl)-2-oxo-ethyl]-amide

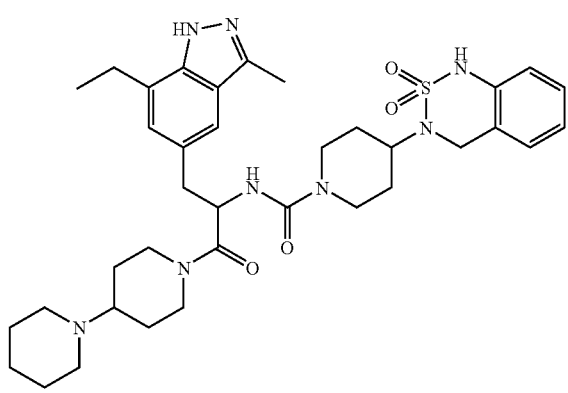

Prepared as described above for Example 203 from 3-piperidin-4-yl-3,4-dihydro-1H-benzo[1,2,6]thiadiazine-2,2-dioxide: $^1$H-NMR (CD$_3$OD) δ 1.35 (m, 3H), 1.42-2.05 (m, 10H), 2.40 (m, 3H), 2.55 (s, 3H), 2.67-3.12 (m, 7H), 3.85 (m, 1H), 3.97 (s, 1H), 4.03 (m, 3H), 4.65 (m, 4H), 4.95 (dd, J=4.9, 5.8, 1H), 6.73 (d, J=7.9, 1H), 6.98 (dd, J=7.3, 6.4, 1H), 7.20 (m, 2H), 7.88 (s, 1H). Mass spec.: 691.51 (MH)$^+$.

Example 210

(±)-2-[4-(6-Cyano-2-oxo-1,4-dihydro-2H-quinazolin-3-yl)-piperidine-1-carbonyl]-amino]-3-(7-methyl-1H-indazol-5-yl)-propionic acid methyl ester

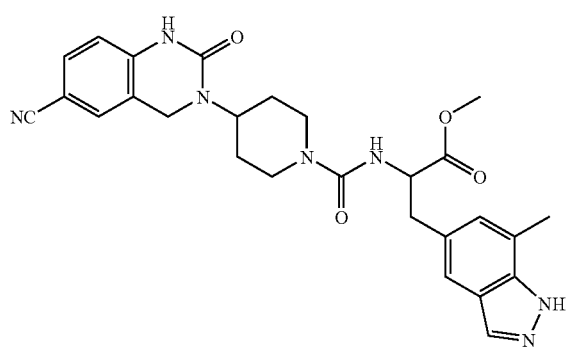

Prepared as described above for 3-(3-cyano-1H-indol-5-yl)-2-{[4-(2-oxo-1,4-dihydro-2H-quinazolin-3-yl)-piperidine-1-carbonyl]-amino}-propionic acid methyl ester: LC/MS: $t_R$=1.34 min, 516.40 (MH)$^+$.

Example 211

(±)-4-(6-Cyano-2-oxo-1,4-dihydro-2H-quinazolin-3-yl)-piperidine-1-carboxylic acid {2-[1,4']bipiperidinyl-1'-yl-1-(7-methyl-1H-indazol-5-yl methyl)-2-oxo-ethyl}-amide

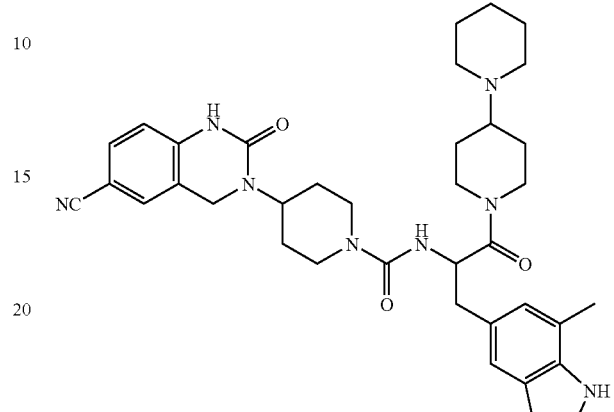

Prepared as described above for Example 203 from 2-oxo-3-piperidin-4-yl-1,2,3,4-tetrahydro-quinazoline-6-carbonitrile: $^1$H-NMR (CD$_3$OD) δ 1.80 (m, 12H), 2.40 (m, 4H), 2.60 (s, 3H), 2.70-3.20 (m, 10H), 4.00-4.30 (m, 6H), 5.00 (m, 1H), 5.50 (s, 2H), 6.90 (d, J=7.8, 1H), 7.21 (s, 1H), 7.50 (m, 4H), 8.05 (s, 1H). Mass spec.: 652.64 (MH)$^+$.

Example 212

(±)-4-(2-Oxo-1,2,4,5-tetrahydro-benzo[d][1,3]diazepin-3-yl-1-carboxylic acid {2-[1,4']bipiperidinyl-1'-yl-1-(7-methyl-1H-indazol-5-yl methyl)-2-oxo-ethyl}-amide

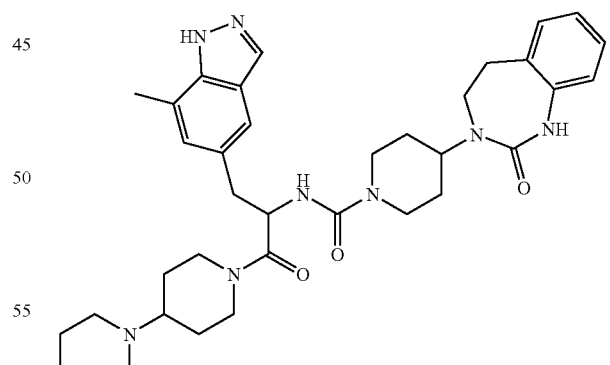

Prepared as described above for Example 203 from 3-piperidin-4-yl-1,3,4,5-tetrahydro-benzo[d][1,3]diazepin-2-one: $^1$H-NMR (CD$_3$OD) δ 1.40-2.00 (m, 12H), 2.30-2.60 (m, 8H), 2.70-3.20 (m, 10H), 3.70 (m, 2H), 3.60 (d, J=9.5, 1H), 4.00-4.30 (m, 4H), 4.70 (m, 1H), 5.00 (m, 1H), 6.90 (m, 2H), 7.10 (m, 3H), 7.20 (s, 1H), 7.50 (s, 1H), 8.05 (s, 1H). Mass spec.: 652.64 (MH)$^+$.

Example 213

(±)-4-(6-Hydroxy-2-oxo-1,4-dihydro-2H-quinazolin-3-yl)-piperidine-1-carboxylic acid {2-[1,4']bipiperidinyl-1'-yl-1-(7-methyl-1H-indazol-5-yl methyl)-2-oxo-ethyl}-amide

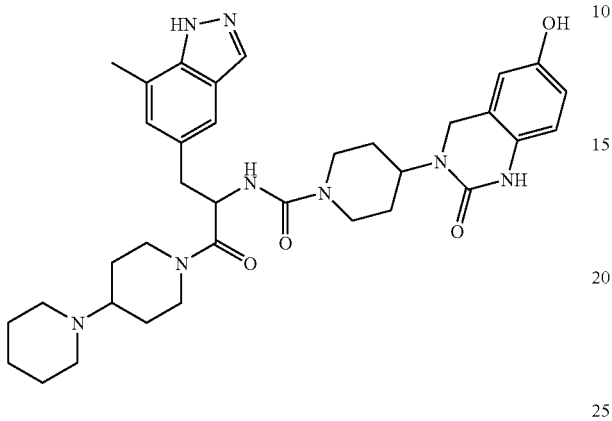

Prepared as described above for Example 203 from 6-hydroxy-3-piperidin-4-yl-3,4-dihydro-1H-quinazolin-2-one: LC/MS: $t_R$=1.24 min, 643.62 (MH)$^+$.

Example 214

(±)-4-(8-Methoxy-2-oxo-1,4-dihydro-2H-quinazolin-3-yl)-piperidine-1-carboxylic acid {2-[1,4']bipiperidinyl-1'-yl-1-(7-methyl-1H-indazol-5-yl methyl)-2-oxo-ethyl}-amide

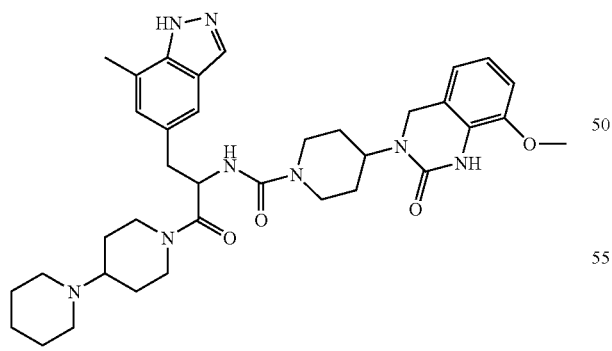

Prepared as described above for Example 203 from 8-methoxy-3-piperidin-4-yl-3,4-dihydro-1H-quinazolin-2-one: $^1$H-NMR (CD$_3$OD) δ 1.40-2.00 (m, 12H), 2.40 (m, 2H), 2.50 (s, 3H), 2.80 (m, 3H), 3.00-3.20 (m, 3H), 3.50 (m, 2H), 4.00-4.60 (m, 6H), 5.00 (m, 2H), 6.70 (dd, J=8.5, 10.1, 1H), 6.85 (m, 2H), 7.10 (m, 1H), 7.20 (s, 1H), 7.47 (s, 1H). Mass spec.: 657.41 (MH)$^+$.

Example 215

(±)-4-(8-Chloro-2-oxo-1,4-dihydro-2H-quinazolin-3-yl)-piperidine-1-carboxylic acid {2-[1,4']bipiperidinyl-1'-yl-1-(7-methyl-1H-indazol-5-yl methyl)-2-oxo-ethyl}-amide

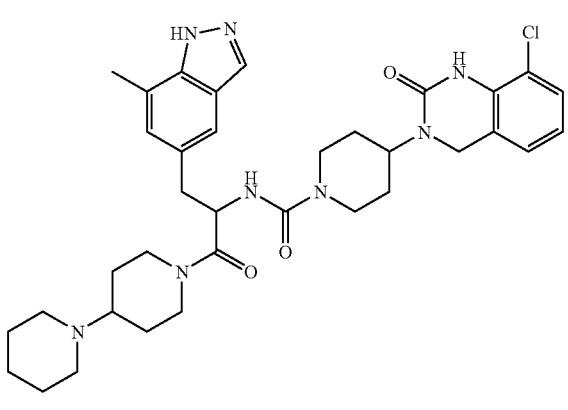

Prepared as described above for Example 203 from 2-chloro-3-piperidin-4-yl-3,4-dihydro-1H-quinazolin-2-one: $^1$H-NMR (CD$_3$OD) δ 1.40-2.00 (m, 14H), 2.30-2.60 (m, 8H), 2.80 (m, 4H), 3.50 (m, 3H), 3.98 (s, 1H), 4.10 (m, 4H), 4.40 (m, 2H), 4.60 (m, 1H), 4.95 (m, 1H), 6.95 (dd, J=7.9, 7.9, 1H), 7.10 (m, 1H), 7.26 (dd, J=6.7, 7.6, 1H), 7.47 (m, 1H), 8.04 (s, 1H). Mass spec.: 661.27 (MH)$^+$.

Example 216

(±)—N-(3-(7-Ethyl-3-methyl-1H-indazol-5-yl)-1-oxo-1-(4-(piperidin-1-yl)piperidin-1-yl)propan-2-yl)-2',3'-dihydro-2'-oxospiro-(piperidine-4,4'-quinazoline)-1-carboxamide

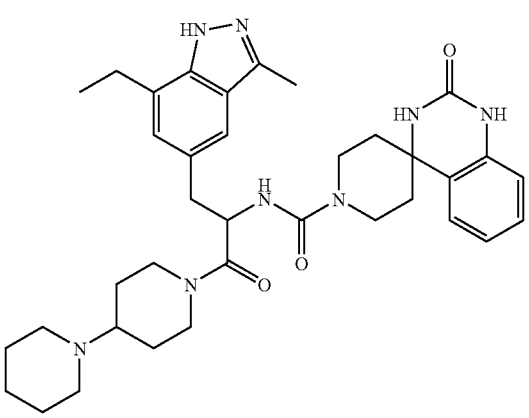

Prepared as described above for Example 203: LC/MS: $t_R$=1.51 min, 641.63 (MH)$^+$.

Example 217

(±)—N-(3-(7-Ethyl-3-methyl 1H-indazol-5-yl)-1-oxo-1-(4-(piperidin-1-yl)piperidin-1-yl)propan-2-yl)-2,4-dihydro-2'-oxospiro-(piperidine-4,4'-1H-benzo[d][1,3]oxazine)-1-carboxamide

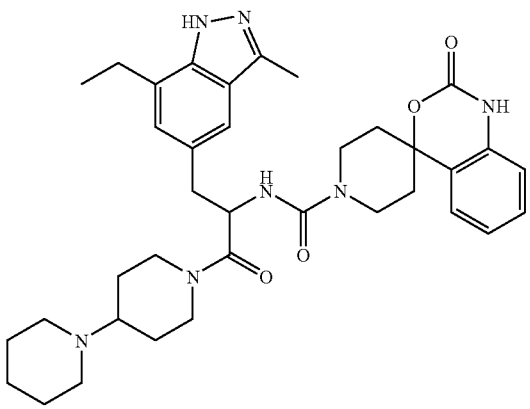

Prepared as described above for Example 203: LC/MS: $t_R$=1.48 min, 642.61 (MH)$^+$.

tert-Butyl 2-fluorophenylcarbamate

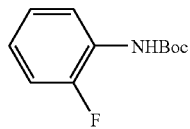

To a solution of di-tert-butyldicarbonate (45.2 g, 207 mmol, 1.0 equiv.) in tetrahydrofuran (210 mL) at room temperature was added 2-fluoroaniline (20.0 mL, 207 mmol). The reaction was heated to reflux and held there for 6 h. It was cooled, concentrated, dissolved in pentane, washed with 5% citric acid, then 1 M potassium bisulfate (2×), then water, then 20% potassium hydroxide, then brine, dried over magnesium sulfate, and concentrated to give 48.0 g (quant.) as an amber oil which was used without purification. $^1$H-NMR (CDCl$_3$, 500 MHz) δ 1.52 (s, 9H), 6.68 (bs, 1H), 6.85-7.20 (m, 3H), 8.07 (dd, J=8.1, 8.1, 1H). Mass spec.: 234.18 (MNa)$^+$.

2-(tert-Butoxycarbonylamino)-3-fluoro-benzoic acid

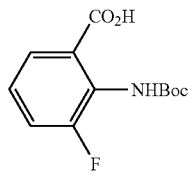

To a solution of tert-butyl 2-fluorophenylcarbamate (44.0 g, 208 mmol) in tetrahydrofuran (660 mL) at −78° C. was added tert-butyllithium in pentane (1.7 M, 306 mL, 2.5 equivx) dropwise. After addition was complete, the reaction was stirred at −78° C. for 30 min. The solution was allowed to gradually reach −20° C. before being recooled to −78° C. and transferred via canula to a slurry of carbon dioxide (excess) and tetrahydrofuran (500 mL). The solution was allowed to slowly warm to room temperature. The reaction mixture was concentrated to remove most of the tetrahydrofuran, and poured into a sep funnel containing water and diethyl ether. The layers were separated, and the aqueous extracted with diethyl ether twice more. The ethereals were discarded. The aqueous was acidified with 5% citric acid, extracted with diethyl ether (3×). The ethereal was dried over magnesium sulfate, and concentrated to give a light yellow solid which was recrystallized from hot toluene to give 37.1 g (70%) as a faint yellow solid.

$^1$H-NMR (CDCl$_3$, 500 MHz) δ 1.50 (s, 9H), 6.25 (bs, 1H), 7.18 (ddd, J=7.9, 7.9, 4.9, 1H), 7.33 (dd, J=9.5, 9.2, 1H), 7.79 (d, J=7.9, 1H), 7.94 (s, 1H). Mass spec.: 278.21 (MNa)$^+$.

tert-Butyl 2-(1-benzylpiperidin-4-ylcarbamoyl)-6-fluorophenylcarbamate

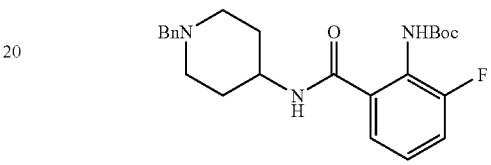

To a solution of 2-(tert-butoxycarbonylamino)-3-fluoro-benzoic acid (37.1 g, 145 mmol), 4-amino-1-benzylpiperidine (35.6 mL, 1.20 equiv.), 1-hydroxybenzotriazole (21.6 g, 1.1 equiv.), and triethylamine (44.1 g, 3.0 equiv.) in ethyl acetate (450 mL) was added 1-(3-dimethylaminopropyl)-3-ethylcarbodiimide hydrochloride (30.7 g, 1.1 equiv.) in one portion. Initially, everything went into solution, but a precipitate formed very rapidly. The reaction was fitted with a reflux condenser and heated at reflux for 5 h. The reaction was diluted with ethyl acetate, washed with water (2×), then 1N sodium hydroxide (2×), then brine, dried over magnesium sulfate, and concentrated to give 67.0 g (quant.) as a white solid which was used without purification. $^1$H-NMR (CDCl$_3$, 500 MHz) δ 1.48 (s, 9H), 1.55 (m, 2H), 1.99 (bd, J=11.0, 2H), 2.17 (dd, J=11.0, 11.0, 2H), 2.84 (bd, J=11.3, 2H), 3.51 (s, 2H), 3.94 (m, 1H), 6.13 (bd, J=7.6, 1H), 7.10-7.28 (m, 4H), 7.31 (m, 4H), 7.59 (s, 1H). Mass spec.: 428.41 (MH)$^+$.

2-Amino-N-(1-benzylpiperidin-4-yl)-3-fluorobenzamide

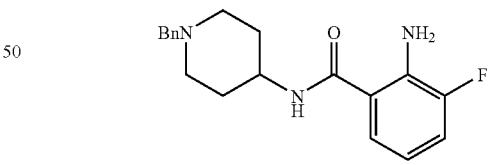

To a solution of tert-butyl 2-(1-benzylpiperidin-4-ylcarbamoyl)-6-fluorophenylcarbamate (67.0 g, 157 mmol) in dichloromethane (700 mL) at 0° C. was added trifluoroacetic acid (100 mL). The ice bath was removed and the reaction stirred at room temperature overnight. The reaction was concentrated and partitioned between ethyl acetate and saturated sodium bicarbonate. The aqueous was extracted with ethyl acetate (2×), which were washed with water (3×), then brine, dried over magnesium sulfate, and concentrated to give 47.6 g (93%) as a white solid which was used without purification. Mass spec.: 328.33 (MH)$^+$.

N-(2-Amino-3-fluorobenzyl)-1-benzylpiperidin-4-amine

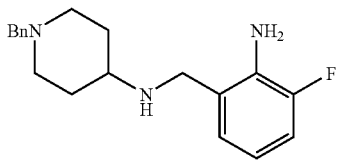

To a refluxing suspension of lithium aluminum hydride (16.1 g, 424 mmol, 3.50 equiv.) in dioxane (800 mL) was added a solution of 2-amino-N-(1-benzylpiperidin-4-yl)-3-fluorobenzamide (39.7 g, 121 mmol) in dioxane (250 mL) at such a rate that gas evolution was limited to a safe flow. Upon completion of the addition, the resulting suspension was heated at reflux for 4 h. The reaction was cooled to 0° C., and quenched by the cautious addition of 20% potassium hydroxide. Upon formation of a white, filterable precipitate, the solid was filtered through a course glass sintered funnel, and the eluent concentrated to give 36.3 g (96%) as a light yellow oil which was used without purification. Mass spec.: 314.29 (MH)$^+$.

3-(1-Benzylpiperidin-4-yl)-8-fluoro-3,4-dihydro-quinazolin-2(1H)-one

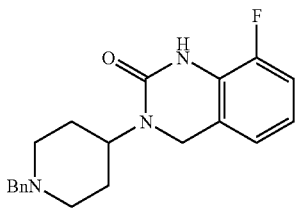

To a solution of N-(2-amino-3-fluorobenzyl)-1-benzylpiperidin-4-amine (36.3 g, 116 mmol) in tetrahydrofuran (600 mL) at room temperature was added carbonyl diimidazole (20.7 g, 1.10 equiv.) in one portion. The reaction was stirred at room temperature for 3 h, heated at reflux for 30 min, and concentrated. The resulting solid was dissolved in 1:1 diethyl ether/ethyl acetate, washed with water (3×), then brine, dried over magnesium sulfate, and concentrated to give the crude product as a wet, yellow solid. The solid was triturated with diethyl ether and filtered to give 30.0 g (76%) as a white powder. $^1$H-NMR (CDCl$_3$, 500 MHz) δ 1.68 (m, 2H), 1.86 (dddd, J=11.9, 11.9, 11.9, 3.4, 2H), 2.14 (dd, J=11.6, 10.1, 2H), 2.98 (d, J=11.6, 2H), 3.51 (s, 2H), 4.34-4.44 (m, 3H), 6.71 (bs, 1H), 6.79-6.89 (m, 2H), 6.94 (dd, J=9.2, 9.2, 1H), 7.21-7.34 (m, 5H). Mass spec.: 340.30 (MH)$^+$.

8-Fluoro-3,4-dihydro-3-(piperidin-4-yl)quinazolin-2(1H)-one

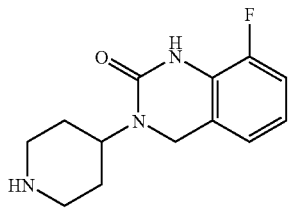

A 250 mL flask was charged with 3-(1-benzylpiperidin-4-yl)-8-fluoro-3,4-dihydroquinazolin-2(1H)-one (1.40 g, 4.12 mmol) and methanol (25.0 mL). The suspension was heated with a heat gun to aid in dissolution. The flask was flushed with nitrogen, treated with palladium on charcoal (141 mg, 0.032 equiv.), flushed with nitrogen, then hydrogen, and vigorously stirred under an atmosphere of hydrogen overnight. The reaction was flushed with nitrogen, filtered through celite, and concentrated to give 0.99 g (97%) as a white solid which was used without purification. $^1$H-NMR (CDCl$_3$, 500 MHz) δ 1.71 (m, 4H), 2.75 (m, 2H), 3.16 (m, 2H), 4.38 (s, 2H), 4.46 (m, 1H), 6.77 (bs, 1H), 6.81-6.89 (m, 2H), 6.95 (m, 1H). Mass spec.: 250.22 (MH)$^+$.

3-(1-Benzylpiperidin-4-yl)-8-fluoroquinazoline-2,4(1H,3H)-dione

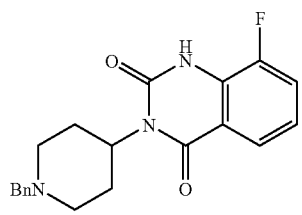

To a solution of 2-amino-N-(1-benzylpiperidin-4-yl)-3-fluorobenzamide (750 mg, 2.29 mmol) in dichloromethane (30.0 mL) at 0° C. was added triphosgene (227 mg, 0.33 equiv.) as a solution in dichloromethane (5 mL). The ice bath was removed and the reaction heated at reflux for 6 h. The reaction was concentrated, dissolved in ethyl acetate, washed with saturated sodium bicarbonate, then water, then brine, dried over magnesium sulfate, and concentrated to give 700 mg of a white solid. The crude product was purified by flash chromatography to give 205 mg (25%) as a white solid. Mass spec.: 354.13 (MH)$^+$.

8-Fluoro-3-(piperidin-4-yl)quinazoline-2,4(1H,3H)-dione

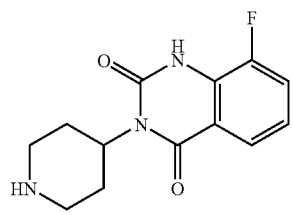

A flask containing a solution of 3-(1-benzylpiperidin-4-yl)-8-fluoroquinazoline-2,4(1H,3H)-dione (75.0 mg, 0.21 mmol) and palladium on charcoal (8.00 mg, 0.035 equiv) in methanol (3.00 mL) was flushed first with nitrogen, then hydrogen. The reaction was stirred under an atmosphere of hydrogen overnight. The reaction was flushed with nitrogen, filtered through celite, and concentrated to give 53 mg (95%) as a white solid which was used without purification. Mass spec.: 264.25 (MH)$^+$.

8'-Fluoro-2',3'-dihydro-2'-oxospiro-(1-phenylmethylpiperidine)-4,4'-quinazoline

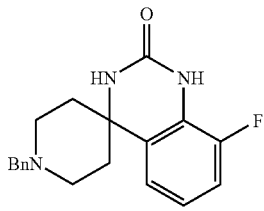

A 500 mL 3-neck flask was charged with polyphosphoric acid (110 mL) and fitted with an overhead stirrer, a nitrogen inlet, and a bubbler. The flask was flushed with nitrogen and heated to 105° C. in an oil bath. To this was added 1-benzyl-4-piperidone (21.0 mL, 115 mmol). To this was added N-(2-Fluorophenyl)urea (21.3 g, 1.2 equiv) in many small portions over 2 h. The reaction was heated to 160° C. with vigorous stirring. After 2 h, the reaction was quenched by pouring over crushed ice and neutralizing with 20% potassium hydroxide. The reaction mixture was extracted with dichloromethane, washed with water, then brine, dried over magnesium sulfate, and concentrated. The whole lot was purified by preparative HPLC (~130 injections) to give a much purer product. The product was repurified by flash chromatography to give a solid which was triturated with diethyl ether and filtered to give 275 mg (0.7%) as a white solid. $^1$H-NMR (CDCl$_3$, 500 MHz) δ 1.91 (dd, J=13.7, 2.1, 2H), 2.10 (ddd, J=13.1, 13.1, 4.3, 2H), 2.27 (ddd, J=12.5, 12.5, 2.1, 2H), 2.86 (m, 2H), 3.57 (s, 2H), 5.40 (bs, 1H), 6.90 (bs, 1H), 6.90-7.05 (m, 3H), 7.27 (m, 1H), 7.32 (m, 4H). Mass spec.: 326.13 (MH)$^+$.

8'-Fluoro-2',3'-dihydro-2'-oxospiro-piperidine-4,4'-quinazoline

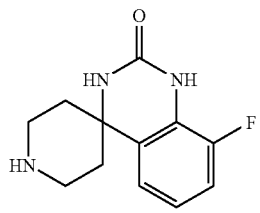

To a solution of 8'-fluoro-2',3'-dihydro-2'-oxospiro-(1-phenylmethylpiperidine)-4,4'-quinazoline (250 mg, 0.77 mmol) in methanol (4 mL) and dichloromethane (4 mL) was added palladium on charcoal (30.0 mg, 0.037 equiv.). The reaction was flushed with hydrogen, and stirred under an atmosphere of hydrogen overnight. The balloon was removed, the reaction flushed with nitrogen, filtered through celite, washed with additional methanol, and concentrated to give 158 mg (87%) as a white solid which was used without purification. $^1$H-NMR (CDCl$_3$/CD$_3$OD, 500 MHz) δ 1.87 (d, J=12.8, 2H), 2.15 (ddd, J=14.0, 14.0, 5.5, 2H), 3.10 (m, 4H), 6.84 (m, 2H), 6.93 (d, J=7.0, 1H). Mass spec.: 236.11 (MH)$^+$.

Example 218

(±)—N-(3-(7-Ethyl-1H-indazol-5-yl)-1-(6,7-dihydro-1H-pyrazolo[4,3-c]pyridin-5(4H)-yl)-1-oxopropan-2-yl)-4-(1,2-dihydro-2-oxoquinazolin-3(4H)-yl)piperidine-1-carboxamide

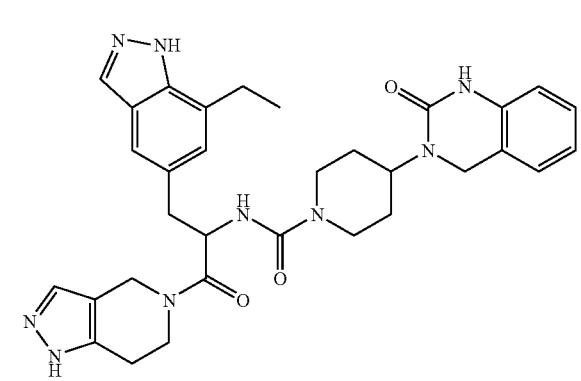

Prepared as described above for Example 203: $^1$H-NMR (CD$_3$OD, 500 MHz) δ 1.24 (m, 2H), 1.55-2.07 (m, 5H), 2.57 (m, 1H), 2.82 (m, 4H), 3.08 (m, 2H), 3.30 (m, 3H), 3.35 (m, 5H), 3.48 (m, 3H), 3.65 (m, 1H), 4.14 (m, 2H), 4.27 (m, 2H), 4.33-4.57 (m, 2H), 5.06 (dd, J=6.7, 6.7, 1H), 5.22 (d, J=1.8, 2H), 6.78 (d, J=7.6, 1H), 6.93 (m, 1H), 7.00-7.18 (m, 3.5H), 7.37 (d, J=9.8, 1H), 7.46 (s, 0.5H), 7.91 (dd, J=10.1, 1.8, 1H). Mass spec.: 596.43 (MH)$^+$.

Example 219

(±)—N-(3-(7-Ethyl-1H-indazol-5-yl)-1-(6,7-dihydro-7,7-dimethyl-1H-pyrazolo[4,3-c]pyridin-5(4H)-yl)-1-oxopropan-2-yl)-4-(1,2-dihydro-2-oxoquinazolin-3(4H)-yl)piperidine-1-carboxamide

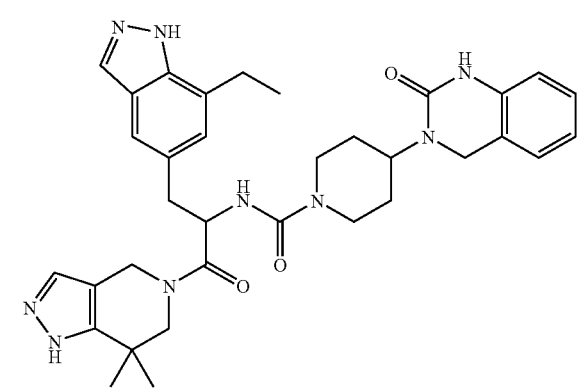

Prepared as described above for Example 203: $^1$H-NMR (CD$_3$OD, 500 MHz) δ 1.11 (m, 3H), 1.50-1.80 (m, 4H), 2.87 (m, 4H), 3.10 (m, 2H), 3.32 (m, 9H), 3.48 (m, 4H), 4.00-4.45 (m, 6H), 5.05-5.25 (m, 2H), 6.77 (d, J=6.1, 1H), 6.93 (m, 1H), 7.13 (m, 3H), 7.30-7.60 (m, 2H), 7.95 (m, 1H). Mass spec.: 624.49 (MH)$^+$.

Example 220

(±)-Methyl 2-(4-(8-fluoro-1,2-dihydro-2-oxo-quinazolin-3(4H)-yl)piperidine-1-carboxamido)-3-(7-methyl-1H-indazol-5-yl)propanoate

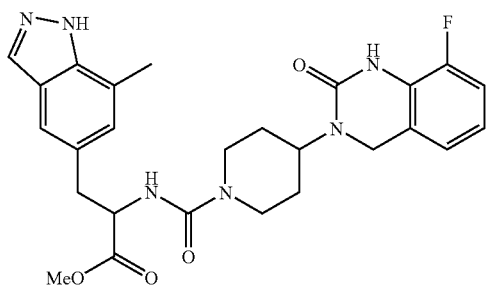

Prepared as described above for 3-(3-cyano-1H-indol-5-yl)-2-{[4-(2-oxo-1,4-dihydro-2H-quinazolin-3-yl)-piperidine-1-carbonyl]-amino}-propionic acid methyl ester: $^1$H-NMR (CDCl$_3$, 500 MHz) δ 1.53-1.68 (m, 4H), 2.48 (s, 3H), 2.82 (m, 2H), 3.05 (m, 6H), 3.09 (dd, $J_{AB}$=13.7, 6.1, 1H), 3.14 (dd, $J_{AB}$=14.0, 6.1, 1H), 3.35 (bs, 1H), 3.68 (s, 3H), 3.88-4.02 (m, 2H), 4.22 (d, $J_{AB}$=15.6, 1H), 4.25 (d, $J_{AB}$=15.3, 1H), 4.44 (m, 1H), 4.71 (dd, J=6.1, 6.1, 1H), 6.78 (d, J=7.3, 1H), 6.84 (ddd, J=7.6, 7.6, 4.9, 1H), 6.88-6.95 (m, 2H), 7.28 (s, 1H), 7.91 (s, 1H). Mass spec.: 509.25 (MH)$^+$.

Example 221

(±)-4-(8-Fluoro-1,2-dihydro-2-oxoquinazolin-3(4H)-yl)-N-(3-(7-methyl-1H-indazol-5-yl)-1-oxo-1-(4-(piperidin-1-yl)piperidin-1-yl)propan-2-yl)piperidine-1-carboxamide

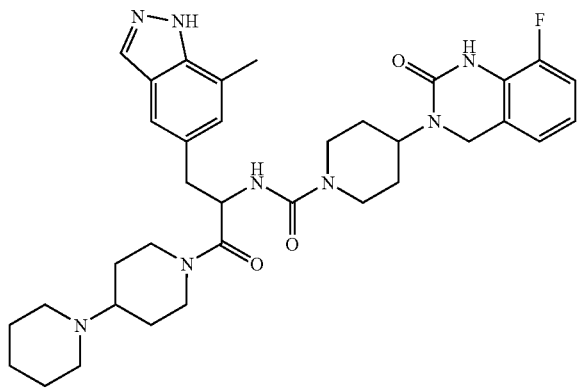

Prepared as described above for Example 203: $^1$H-NMR (CD$_3$OD, 500 MHz) δ −0.25 (m, 1H), 0.82 (m, 1H), 1.25-2.10 (m, 13H), 2.20-2.63 (m, 6H), 2.68-2.98 (m, 4H), 3.00-3.22 (m, 3H), 3.31 (m, 2H), 3.44 (bs, 1H), 4.00-4.50 (m, 6H), 4.64 (m, 1H), 4.96 (m, 1H), 6.85-7.05 (m, 3H), 7.08 (s, 0.4H), 7.20 (s, 0.6H), 7.46 (d, J=7.0, 1H), 7.99 (s, 0.4H), 8.05 (d, J=2.4, 0.6H). Mass spec.: 645.58 (MH)$^+$.

Example 222

(±)-4-(8-Fluoro-1,2-dihydro-2-oxoquinazolin-3(4H)-yl)-N-(3-(7-methyl-1H-indazol-5-yl)-1-oxo-1-(4-phenylpiperazin-1-yl)propan-2-yl)piperidine-1-carboxamide

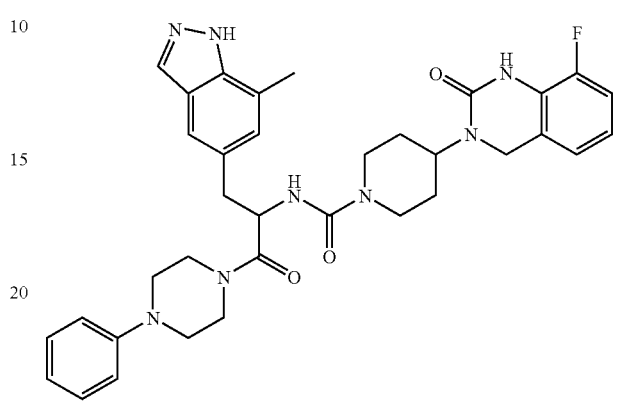

Prepared as described above for Example 203: $^1$H-NMR (CDCl$_3$, 500 MHz) δ 1.73 (m, 4H), 2.49 (m, 4H), 2.80-3.26 (m, 7H), 3.43 (m, 2H), 3.65-3.95 (m, 3H), 4.14 (dd, J=21.7, 14.3, 2H), 4.32 (s, 2H), 4.51 (m, 1H), 5.15 (dd, J=7.9, 6.4, 1H), 5.90 (bs, 1H), 6.80 (d, J=7.3, 1H), 6.83-7.01 (m, 4H), 7.06 (dd, J=7.6, 7.3, 1H), 7.10 (s, 1H), 7.26-7.33 (m, 2H), 7.44 (s, 1H), 7.87 (s, 1H), 8.06 (s, 1H). Mass spec.: 639.36 (MH)$^+$.

Example 223

(±)-4-(8-Fluoro-1,2-dihydro-2-oxoquinazolin-3(4H)-yl)-N-(1-(4-(4-fluorophenyl)piperazin-1-yl)-3-(7-methyl-1H-indazol-5-yl)-1-oxopropan-2-yl)piperidine-1-carboxamide

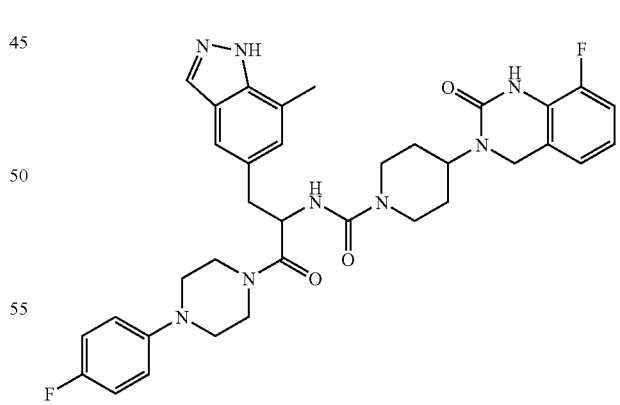

Prepared as described above for Example 203: $^1$H-NMR (CDCl$_3$, 500 MHz) δ 1.73 (m, 4H), 2.26 (dd, J=7.9, 7.6, 1H), 2.49 (s, 3H), 2.75-3.05 (m, 4H), 3.09 (m, 2H), 3.19-3.45 (m, 3H), 3.63 (m, 1H), 3.78 (m, 2H), 4.13 (dd, J=16.5, 15.3, 2H), 4.32 (s, 2H), 4.50 (m, 1H), 5.15 (dd, J=8.2, 6.1, 1H), 5.85 (bs, 1H), 6.70-6.84 (m, 3H), 6.85-7.02 (m, 5H), 7.09 (s, 1H), 7.43 (s, 1H), 7.78 (s, 1H), 8.06 (s, 1H). Mass spec.: 657.35 (MH)$^+$.

Example 224

(±)-4-(8-Fluoro-1,2-dihydro-2-oxoquinazolin-3(4H)-yl)-N-(1-(4-(2-fluorophenyl)piperazin-1-yl)-3-(7-methyl-1H-indazol-5-yl)-1-oxopropan-2-yl)piperidine-1-carboxamide

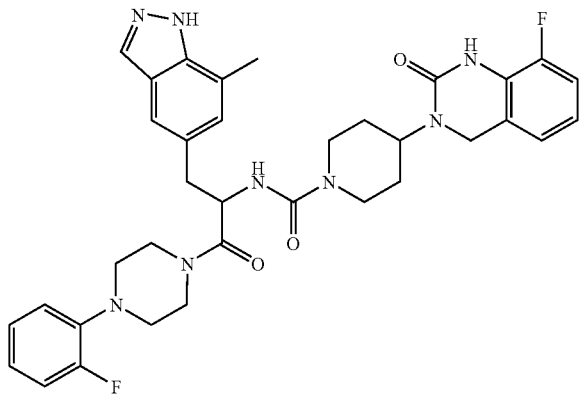

Prepared as described above for Example 203: $^1$H-NMR (CDCl$_3$, 500 MHz) δ 1.62-1.78 (m, 4H), 2.24 (dd, J=7.9, 8.2, 1H), 2.50 (s, 3H), 2.70-2.85 (m, 2H), 2.85-2.96 (m, 2H), 2.00 (m, 1H), 3.08 (dd, J$_{AB}$=13.1, 8.6, 1H), 3.12 (m, 1H), 3.30 (m, 1H), 3.57 (m, 1H), 3.73 (m, 2H), 4.13 (dd, J=19.8, 15.0, 2H), 4.33 (s, 2H), 4.53 (m, 1H), 5.18 (dd, J=8.2, 5.8, 1H), 5.82 (bs, 1H), 6.58 (dd, J=8.2, 8.2, 1H), 6.81 (d, J=7.6, 1H), 6.85-7.05 (m, 5H), 7.09 (s, 1H), 7.44 (s, 1H), 7.58 (s, 1H), 8.05 (s, 1H). Mass spec.: 657.37 (MH)$^+$.

Example 225

(±)-4-(8-Fluoro-1,2-dihydro-2-oxoquinazolin-3(4H)-yl)-N-(3-(7-methyl-1H-indazol-5-yl)-1-oxo-1-(4-o-tolylpiperazin-1-yl)propan-2-yl)piperidine-1-carboxamide

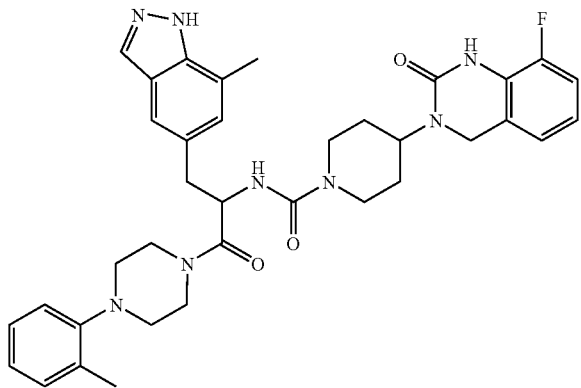

Prepared as described above for Example 203: $^1$H-NMR (CDCl$_3$, 500 MHz) δ 1.60-1.79 (m, 4H), 2.03 (dd, J=8.5, 8.2, 1H), 2.22 (s, 3H), 2.49 (s, 3H), 2.54 (dd, J=8.6, 8.5, 1H), 2.65 (m, 1H), 2.81 (m, 1H), 2.85-2.97 (m, 2H), 3.05-3.22 (m, 3H), 3.38 (m, 1H), 3.50-3.65 (m, 2H), 3.83 (m, 1H), 4.15 (dd, J=15.9, 15.3, 2H), 4.31 (s, 2H), 4.53 (m, 1H), 5.19 (dd, J=7.9, 5.8, 1H), 5.84 (bs, 1H), 6.54 (d, J=7.6, 1H), 6.81 (d, J=7.6, 1H), 6.89 (ddd, J=7.6, 7.6, 5.2, 1H), 6.96 (m, 2H), 7.00-7.23 (m, 4H), 7.39 (s, 1H), 7.43 (s, 1H), 8.04 (s, 1H). Mass spec.: 653.38 (MH)$^+$.

Example 226

(±)-Methyl 2-(4-(8-fluoro-1,2-dihydro-2-oxoquinazolin-3(4H)-yl)piperidine-1-carboxamido)-3-(7-ethyl-3-methyl-1H-indazol-5-yl)propanoate

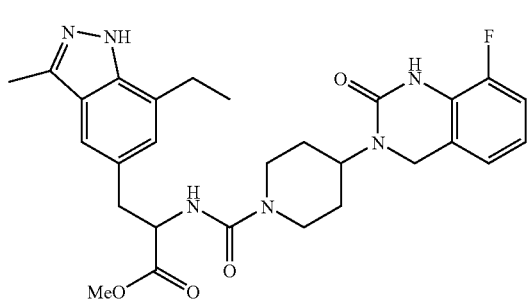

Prepared as described above for 3-(3-cyano-1H-indol-5-yl)-2-{[4-(2-oxo-1,4-dihydro-2H-quinazolin-3-yl)-piperidine-1-carbonyl]-amino}-propionic acid methyl ester: $^1$H-NMR (CD$_3$OD, 500 MHz) δ 1.33 (m, 3H), 1.39-1.72 (m, 4H), 2.70-2.95 (m, 3H), 3.06 (m, 1H), 3.25 (m, 1H), 3.70 (m, 3H), 3.95-4.30 (m 4H), 4.38 (m, 1H), 4.57 (m, 1H), 6.80-7.05 (m, 3H), 7.08 (s, 1H), 7.38 (s, 1H). Mass spec.: 537.47 (MH)$^+$.

Example 227

(±)—N-(3-(7-Ethyl-3-methyl-1H-indazol-5-yl)-1-oxo-1-(4-(piperidin-1-yl)piperidin-1-yl)propan-2-yl)-4-(8-fluoro-1,2-dihydro-2-oxoquinazolin-3(4H)-yl)piperidine-1-carboxamide

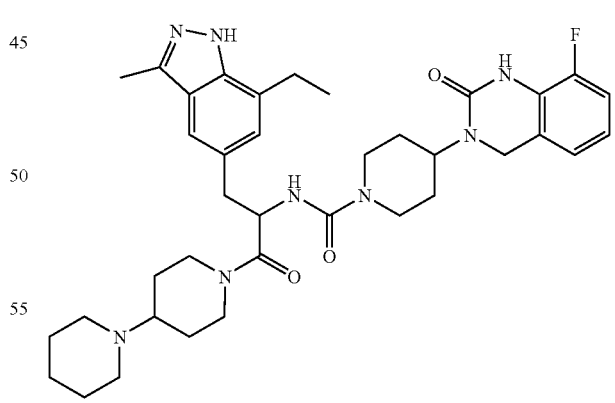

Prepared as described above for Example 203: $^1$H-NMR (CD$_3$OD, 500 MHz) δ −0.36 (m, 1H), 0.70 (m, 1H), 1.21 (bd, J=11.9, 1H), 1.28-2.00 (m, 19H), 2.31 (dd, J=11.6, 11.3, 1H), 2.40 (dd, J=13.1, 11.6, 1H), 2.79-3.16 (m, 7H), 3.72 (m, 1H), 3.85-4.03 (m, 1H), 4.10-4.48 (m, 5H), 4.53 (bd, J=11.0, 1H), 5.05 (m, 1H), 6.85-7.03 (m, 3H), 7.08 (s, 0.2H), 7.18 (s, 0.8H), 7.37 (s, 1H). Mass spec.: 673.42 (MH)$^+$.

Example 228

(R)—N—((R)-3-(2-Oxo-2,3-dihydro-benzooxazol-6-yl)-1-oxo-1-(4-(piperidin-1-yl)piperidin-1-yl)propan-2-yl)-4-(8-fluoro-1,2-dihydro-2-oxoquinazolin-3(4H)-yl)piperidine-1-carboxamide

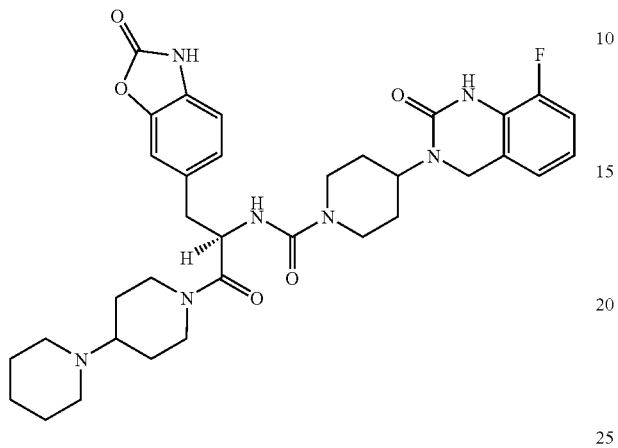

Prepared as described above for Example 203: $^1$H-NMR (CD$_3$OD, 500 MHz) δ 0.71 (m, 1H), 1.26 (m, 1H), 1.40-2.15 (m, 13H), 2.50-3.29 (m, 9H), 3.32-3.64 (m, 3H), 4.14 (d, J$_{AB}$=12.8, 1H), 4.17 (d, J$_{AB}$=11.6, 1H), 4.32-4.45 (m, 3H), 4.68 (bd, J=13.4, 1H), 4.92 (m, 1H), 6.87-7.22 (m, 6H). Mass spec.: 648.47 (MH)$^+$.

Example 229

(±)—N-(3-(7-Methyl-1H-indazol-5-yl)-1-oxo-1-(4-(piperidin-1-yl)piperidin-1-yl)propan-2-yl)-8'-fluoro-2',3'-dihydro-2'-oxospiro-(piperidine-4,4'-quinazoline)-1-carboxamide

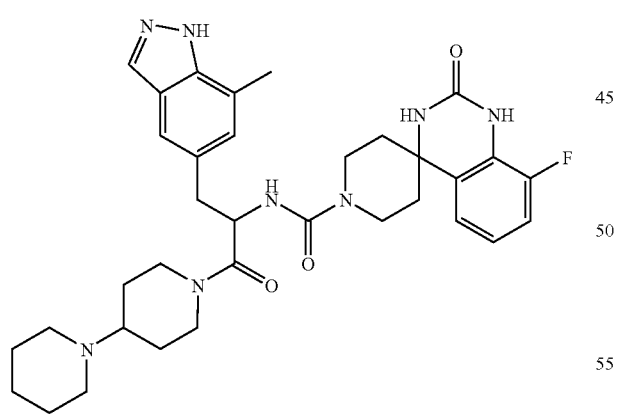

Prepared as described above for Example 203: $^1$H-NMR (CD$_3$OD, 500 MHz) δ −0.23 (m, 1H), 0.85 (m, 1H), 1.20-2.10 (m, 22H), 2.25-2.55 (m, 7H), 2.58 (s, 3H), 2.74 (d, J=11.3, 1H), 2.94 (dd, J=12.5, 12.2, 2H), 3.00-3.20 (m, 5H), 3.40-3.65 (m, 2H), 3.80-4.15 (m, 4H), 4.55-4.73 (m, 2H), 4.96 (dd, J=7.9, 7.6, 1H), 5.01 (dd, J=10.4, 5.8, 1H), 6.65-7.15 (m, 5H), 7.21 (s, 1H), 7.47 (s, 1H), 7.96 (m, 1H), 8.04 (s, 1H). Mass spec.: 631.29 (MH)$^+$.

Example 230

(±)-4-(8-Fluoro-1,2-dihydro-2,4-dioxoquinazolin-3(4H)-yl)-N-(3-(7-methyl-1H-indazol-5-yl)-1-oxo-1-(4-(piperidin-1-yl)piperidin-1-yl)propan-2-yl)piperidine-1-carboxamide Prepared as described above for Example 203: $^1$H-NMR (CD$_3$OD, 500 MHz) δ −0.26 (m, 1H), 0.81 (m, 1H), 1.20-2.10 (m, 11H), 2.20-2.80 (m, 9H), 2.90 (m, 3H), 3.10 (m, 3H), 3.34 (m, 1H), 3.44 (m, 1H), 4.06 (bd, J=13.4, 1H), 4.17 (d, J$_{AB}$=15.9, 1H), 4.22 (d, J$_{AB}$=13.1, 1H), 4.64 (dd, J=24.4, 13.1, 1H), 4.91-5.13 (m, 2H), 7.00-7.25 (m, 2H), 7.44 (m, 2H), 7.81 (m, 1H), 7.92-8.08 (m, 1H). Mass spec.: 659.59 (MH)$^+$.

(R)-Methyl 2-amino-3-(2-(trifluoromethyl)-1H-benzo[d]imidazol-5-yl)propanoate

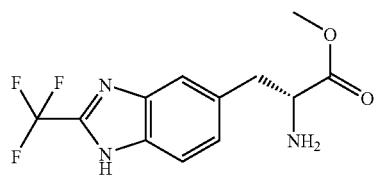

A mixture of (R)-2-benzyloxycarbonylamino-3-(3,4-diamino-phenyl)-propionic acid methyl ester (500 mg, 1.20 mmol) and trifluoroacetic acid (6 mL) was heated at 80° C. for 16 h. The reaction mixture was poured into ice water (75 mL), neutralized to pH 7 with aqueous saturated sodium bicarbonate, and extracted with ethyl acetate (2×250 mL). The organic extracts were dried over sodium sulfate, filtered and evaporated to give the title compound as the trifluoroacetic acid salt (459 mg, 84% yield). $^1$H-NMR (CDCl$_3$, 300 MHz) δ 7.37 (bs, 1H) 7.35 (bs, 1H), 7.17 (d, J=8.4 Hz, 1H), 4.70 (s, 2H), 3.85 (dd, J=8.4, 4.8 Hz, 1H), 3.77 (s, 3H), 3.30 (dd, J=13.9, 4.8 Hz, 1H), 2.97 (dd, J=13.5, 8.4 Hz, 1H). Mass spec.: 288 (MH)$^+$.

(R)-Methyl 2-(4-(1,2-dihydro-2-oxoquinazolin-3 (4H)-yl)piperidine-1-carboxamido)-3-(2-(trifluoromethyl)-1H-benzo[d]imidazol-5-yl)propanoate

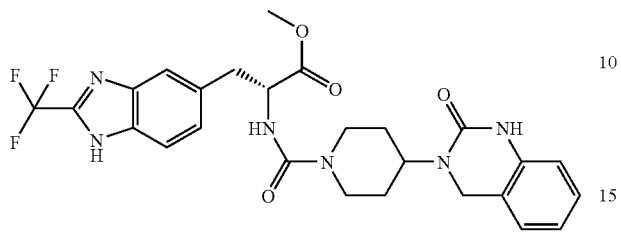

A solution of the amino ester (R)-methyl 2-amino-3-(2-(trifluoromethyl)-1H-benzo[d]imidazol-5-yl)propanoate (230 mg, 0.51 mmol), diisopropylethylamine (262 mg, 2.03 mmol), and disuccinimidyl carbonate (129 mg, 0.51 mmol) in a mixture of methylene chloride/dimethylformamide (15:1 ratio) was stirred at room temperature for 30 min. To the solution was added 4-(2-keto-1-benzimidazolinyl)piperidine and the reaction mixture was allowed to stir at room temperature for 16 h. The reaction mixture was filtered to remove any solids and was then purified by flash column chromatography (95:3:2 methylene chloride/methanol/triethylamine) to give the title compound (215 mg, 77% yield) as a tan solid. $^1$H-NMR (CDCl$_3$, 300 MHz) δ 7.67 (d, J=8.4 Hz, 1H), 7.39 (s, 1H), 7.21-7.16 (m, 1H), 7.05-6.94 (m, 3H), 6.70-6.68 (m, 2H), 5.11 (d, J=7.3 Hz, 1H), 4.78 (dd, J=12.1, 5.5 Hz, 1H), 4.42 (d, J=4.4 Hz, 2H), 4.29 (d, J=12.1 Hz, 1H), 3.82-3.72 (m, 2H), 3.74 (s, 3H), 3.44 (dd, J=13.9, 5.5 Hz, 1H), 3.22 (dd, J=13.9, 5.5 Hz), 2.95-2.83 (m, 3H), 2.18-2.03 (m, 2H), 1.79-1.68 (m, 2H). Mass spec.: 545 (MH)$^+$.

(R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid

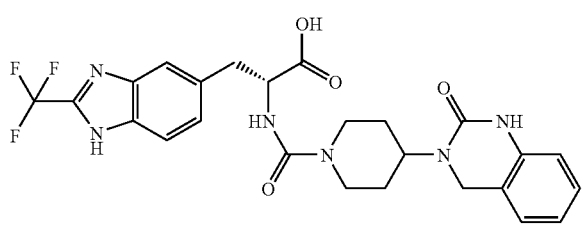

To a solution of the ester (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl)propanoate (220 mg, 0.40 mmol) in tetrahydrofuran and methanol (1:1 mixture, 20 mL) at 0° C. was added lithium hydroxide (36 mg, 1.51 mmol) in water (10 mL). The mixture was stirred at 0° C. for 2 h and then stored at −15° C. for 16 h. The organic solvents were evaporated. The aqueous solution was extracted with ethyl acetate while adjusting the pH to 4 with 1N HCl (3 mL). The organic extracts were dried over sodium sulfate, filtered, and evaporated to give the title compound (176 mg, 82% yield). LC/MS: t$_R$=2.01 min, 531 (MH)$^+$.

Example 231

N—((R)-3-(2-(trifluoromethyl)-1H-benzo[d]imidazol-5-yl)-1-oxo-1-(4-(piperidin-1-yl)piperidin-1-yl) propan-2-yl)-4-(1,2-dihydro-2-oxoquinazolin-3(4H)-yl)piperidine-1-carboxamide

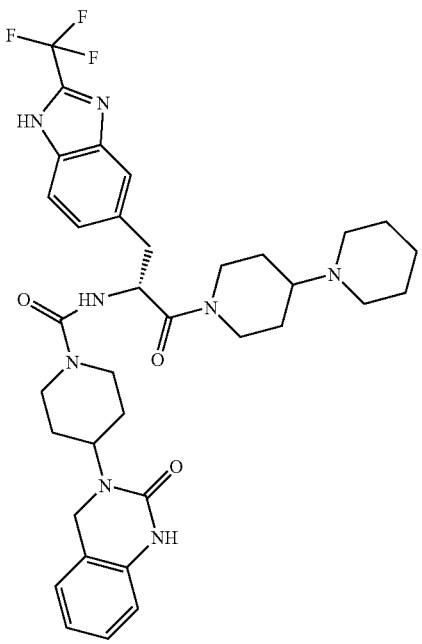

To a stirred solution of the acid (R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid (33 mg, 0.06 mmol) and diisopropylethylamine (33 mg, 0.25 mmol) in methylene chloride (2 mL) was added a solution of PyBOP (33 mg, 0.06 mmol) and 4-piperidinopiperidine (12 mg, 0.07 mmol) in methylene chloride (1 mL). The reaction mixture was stirred at room temperature for 16 h and was subjected to preparative thin layer chromatography for purification (1:10 2M ammonia in methanol/methylene chloride) to give the title compound (4.6 mg, 12% yield). $^1$H-NMR (CD$_3$OD, 500 MHz) δ 7.73-7.71 (m, 1H), 7.62 (bs, 1H), 7.39-7.36 (m, 1H), 7.19-7.11 (m, 2H), 6.96 (t, J=7.2 Hz, 1H), 6.81 (d, J=7.9 Hz, 1H), 5.06-5.02 (m, 1H), 4.67-4.58 (m, 1H), 4.49-4.40 (m, 1H), 4.38 (s, 1H), 4.33 (bs, 1H), 4.25-4.16 (m, 2H), 4.10-4.03 (m, 1H), 3.22-3.14 (m, 3H), 3.04-2.87 (m, 4H), 2.79-2.71 (m, 1H), 2.58-2.48 (m, 1H), 2.44-2.33 (m, 1H), 2.31-2.22 (m, 1H), 2.04-1.92 (m, 1H), 1.86-1.43 (m, 11H), 1.33-1.29 (m, 1H), 0.94-0.84 (m, 1H), −0.04-−0.12 (m, 1H). LC/MS: t$_R$=1.97 min, 681 (MH)$^+$.

Example 232

N—((R)-1-(dimethylcarbamoyl)-2-(2-(trifluoromethyl)-1H-benzo [d]imidazol-5-yl)ethyl)-4-(1,2-dihydro-2-oxoquinazolin-3(4H)-yl)piperidine-1-carboxamide

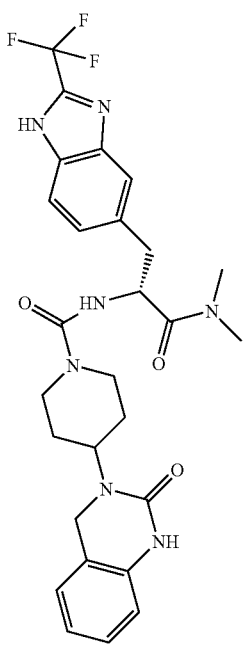

Prepared as described above for Example 231. ¹H-NMR (CD₃OD, 300 MHz) δ 7.69-7.56 (m, 2H), 7.34 (d, J=7.7 Hz, 1H), 7.17-7.08 (m, 2H), 6.92 (t, J=7.7 Hz, 1H), 6.77 (d, J=8.4 Hz, 1H), 6.56 (d, J=7.7 Hz, 1H), 5.02-4.97 (m, 1H), 4.46-4.35 (m, 1H), 4.29 (s, 2H), 4.15 (d, J=12.8 Hz, 1H), 3.26-3.11 (m, 5H), 2.87 (s, 6H), 1.86-1.68 (m, 2H), 1.66-1.59 (m, 2H). LC/MS: $t_R$=2.37 min, 558 (MH)⁺.

Benzyl (R)-1-(methoxycarbonyl)-2-(2,3-dihydro-2-oxo-1H-benzo[d]imidazol-6-yl)ethylcarbamate

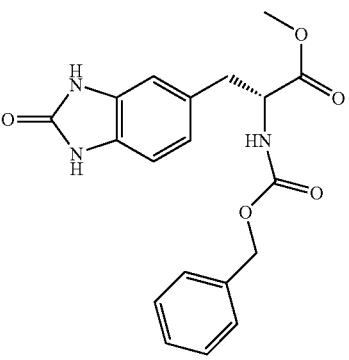

To a dilute solution of (R)-2-benzyloxycarbonylamino-3-(3,4-diamino-phenyl)-propionic acid methyl ester (600 mg, 1.44 mmol) in tetrahydrofuran (125 mL) was added triethylamine (320 mg, 3.17 mmol) followed by 1,1'-carbonyldiimidazole (280 mg, 1.73 mmol). The reaction mixture was stirred at room temperature for 16 h and then filtered to remove solid. The filtrate was evaporated and subjected to flash column chromatography (1:12 methanol/methylene chloride) to give the title compound (313 mg, 59% yield).

¹H-NMR (CD₃OD, 300 MHz) δ 7.28-7.21 (m, 5H), 6.94-6.83 (m, 3H), 5.06-4.95 (m, 2H), 4.46-4.41 (m, 1H), 3.68 (s, 3H), 3.17-3.11 (m, 1H), 2.95-2.88 (m, 1H). LC/MS: $t_R$=2.11 min, 370 (MH)⁺.

(R)-methyl 2-amino-3-(2,3-dihydro-2-oxo-1H-benzo[d]imidazol-6-yl)propanoate

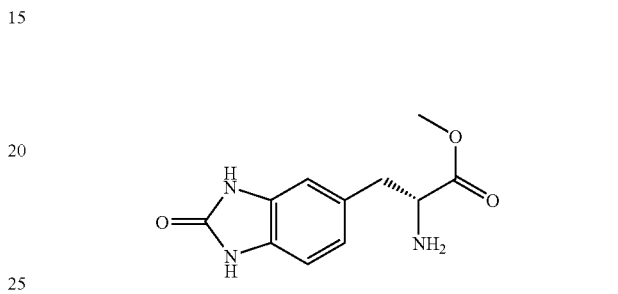

Benzyl (R)-1-(methoxycarbonyl)-2-(2,3-dihydro-2-oxo-1H-benzo[d]imidazol-6-yl)ethylcarbamate (265 mg, 0.72 mmol) and 10% palladium on carbon (30 mg) in methanol (15 mL) were agitated for 1.5 h under 50 psi hydrogen using a Parr apparatus. The reaction mixture was purged with 3 vacuum/nitrogen purge cycles. The reaction mixture was then filtered through a pad of Celite® and the pad was rinsed with several portions of methanol. The methanol filtrate was evaporated to give the title compound (168 mg, quantitative yield). ¹H-NMR (CD₃OD, 300 MHz) δ 6.97 (d, J=8.1 Hz, 1H), 6.87 (s, 1H), 6.86 (d, J=8.2 Hz, 1H), 3.71-3.64 (m, 1H), 3.67 (s, 3H), 3.04-2.89 (m, 2H). LC/MS: $t_R$=0.87 min, 236 (MH)⁺.

Example 233

(R)-methyl 2-(4-(1,2-dihydro-2-oxoquinazolin-3(4H)-yl)piperidine-1-carboxamido)-3-(2,3-dihydro-2-oxo-1H-benzo[d]imidazol-6-yl)propanoate

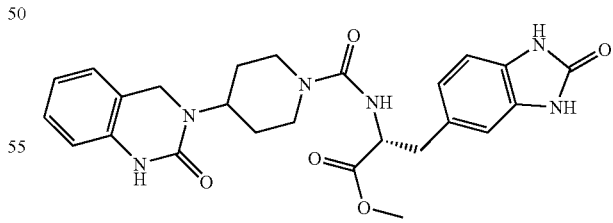

Prepared as described above for (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl)propanoate. ¹H-NMR (CD₃OD, 300 MHz) δ 7.16-7.08 (m, 2H), 6.98-6.90 (m, 4H), 6.76 (d, J=8.1 Hz, 1H), 4.52-4.47 (m, 1H), 4.39-4.35 (m, 1H), 4.27 (s, 2H), 4.13-4.05 (m, 2H), 3.70 (s, 3H), 3.21-3.14 (m, 1H), 3.04-2.96 (m, 1H), 2.89-2.74 (m, 2H), 1.78-1.59 (m, 4H). LC/MS: $t_R$=1.77 min, 493 (MH)⁺.

(R)-2-(4-(1,2-dihydro-2-oxoquinazolin-3(4H)-yl)
piperidine-1-carboxamido)-3-(2,3-dihydro-2-oxo-
1H-benzo[d]imidazol-6-yl)propanoic acid

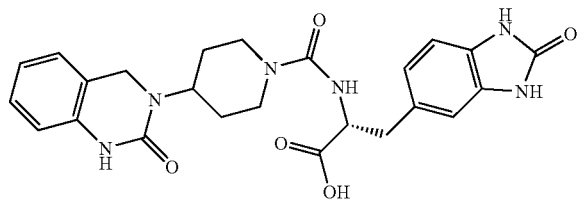

Prepared as described above for (R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid. $^1$H-NMR (CD$_3$OD, 300 MHz) δ 7.16-7.09 (m, 2H), 6.99-6.90 (m, 4H), 6.76 (d, J=7.3 Hz, 1H), 4.53-4.48 (m, 1H), 4.28 (s, 2H), 4.13-4.03 (m, 2H), 3.07-2.97 (m, 1H), 2.89-2.77 (m, 2H), 1.79-1.60 (m, 4H), 1.28-1.21 (m, 1H). LC/MS: $t_R$=1.83 min, 479 (MH)$^+$.

Example 234

N—((R)-3-(2,3-dihydro-2-oxo-1H-benzo[d]imida-
zol-6-yl)-1-oxo-1(4-piperidin-1-yl)piperidine-1-yl)
propan-2-yl)-4-(1,2-dihydro-2-oxoquinazolin-3(4H)-
yl)piperidine-1-carboxamide

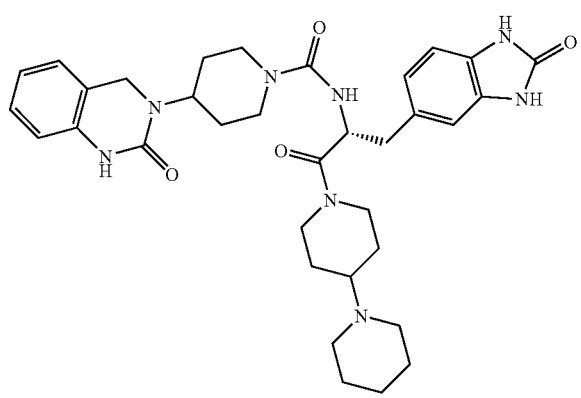

Prepared as described above for Example 231. $^1$H-NMR (CD$_3$OD, 300 MHz) δ 7.17-7.10 (m, 2H), 7.01 (s, 1H), 6.95-6.90 (m, 3H), 6.78 (d, J=8.1 Hz, 1H), 4.98-4.93 (m, 1H), 4.62-4.55 (m, 1H), 4.41-4.33 (m, 2H), 4.20-4.16 (m, 2H), 4.04-3.96 (m, 1H), 3.05-2.85 (m, 7H), 2.71-2.57 (m, 1H), 2.53-2.32 (m, 1H), 1.86-1.76 (m, 2H), 1.70-1.61 (m, 8H), 1.50-1.41 (m, 2H), 1.03-0.89 (m, 1H), 0.10--0.02 (m, 1H). Mass spec.: 629.22 (MH)$^+$.

Example 235

N—((R)-1-(dimethylcarbamoyl)-2-(2,3-dihydro-2-
oxo-1H-benzo [d]imidazol-6-yl)ethyl)-4-(1,2-dihy-
dro-2-oxoquinazolin-3(4H)-yl)piperidine-1-carboxa-
mide

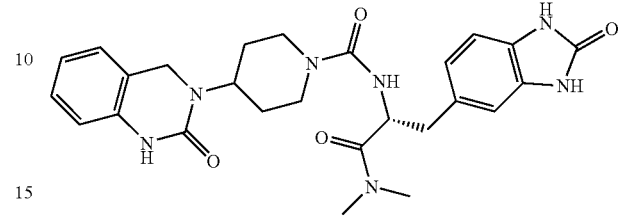

Prepared as described above for Example 231. LC/MS: $t_R$=1.96 min, 506 (MH)$^+$.

(R)-Methyl 2-[2',3'-dihydro-2'-oxospiro-(piperidine-
4,4'-(1H)-quinazoline)carbonylamino]-3-2,3-dihy-
dro-2-oxo-1H-benzo[d]imidazol-6-yl)propanoate

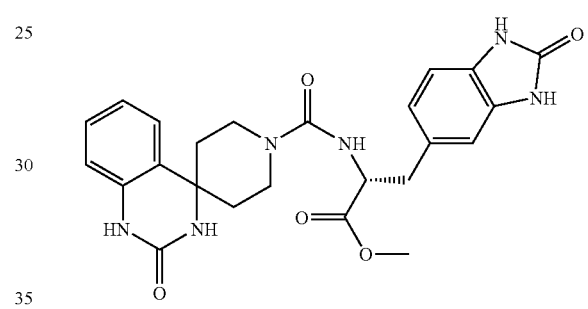

Prepared as described above for (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl)propanoate. $^1$H-NMR (DMSO-d6, 500 MHz) δ 10.54 (s, 1H), 10.50 (s, 1H), 9.22 (s, 1H), 7.21 (s, 1H), 7.13-7.10 (m, 1H), 6.96-6.79 (m, 7H), 4.29-4.25 (m, 1H), 3.82-3.78 (m, 2H), 3.60 (s, 3H), 3.32-3.23 (m, 1H), 3.16-3.14 (m, 1H), 3.00-2.90 (m, 2H), 2.08 (s, 1H), 1.67-1.55 (m, 4H). LC/MS: $t_R$=1.62 min, 479 (MH)$^+$.

(R)-2-[2',3'-dihydro-2'-oxospiro-(piperidine-4,4'-
(1H)-quinazoline)carbonylamino]-3-2,3-dihydro-2-
oxo-1H-benzo[d]imidazol-6-yl)propanoic acid

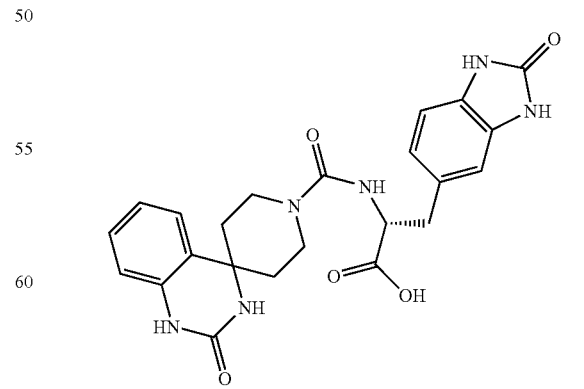

Prepared as described above for (R)-2-(4-(1,2-dihydro-2-oxoquinazolin-3(4 μl)-yl)piperidine-1-carboxamido)-3-(2-

(trifluoromethyl)-1H-benzo[d]imidazol-5-yl)propanoic acid. $^1$H-NMR (CD$_3$OD, 300 MHz) δ 7.19-7.14 (m, 1H), 7.05-6.95 (m, 5H), 6.81 (d, J=7.7 Hz, 1H), 5.04-4.90 (m, 1H), 4.57-4.52 (m, 1H), 3.96-3.84 (m, 2H), 3.24-3.14 (m, 2H), 3.07-2.95 (m, 1H), 1.94-1.73 (m, 4H). LC/MS: $t_R$=1.67 min, 465 (MH)$^+$ Example 236

N—((R)-3-(2,3-dihydro-2-oxo-1H-benzo[d]imidazol-6-yl)-1-oxo-1(4-piperidin-1-yl)piperidine-1-yl)propan-2-yl)-4-(2',3'-dihydro-2'-oxospiro(piperidine-4,4'-(1H)-quinazoline)carboxamide

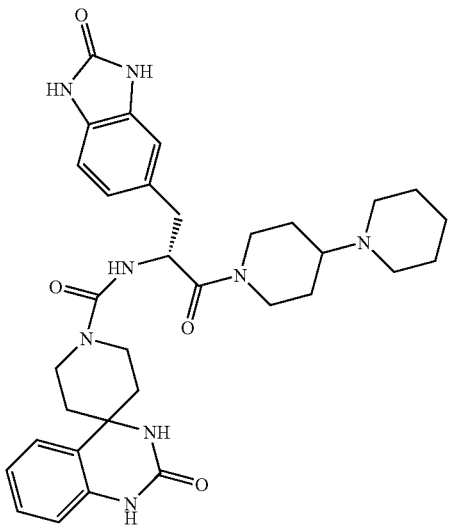

Prepared as described above for Example 231. LC/MS: $t_R$=1.55 min, 615 (MH)$^+$.

4-Acetamido-3-methylbenzoic acid

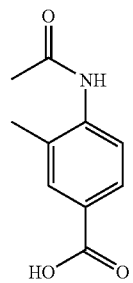

To a suspension of 4-amino-3-methylbenzoic acid (60 g, 0.40 mol) in methylene chloride (800 mL) was added triethylamine (121 g, 1.19 mol). The solution became clear. Then, acetic anhydride (81 g, 0.79 mol) was added and the reaction mixture was stirred for 60 h at room temperature. The solvent was evaporated. The residue was diluted with water (400 mL) and extracted with ethyl acetate (3×600 mL). The combined organic extracts were dried over magnesium sulfate, filtered and evaporated to give the title compound as a tan solid (43 g, 56% yield). $^1$H-NMR (d$_6$-DMSO, 300 MHz) δ 9.36 (s, 1H), 7.77 (s, 1H), 7.10 (s, 2H), 2.27 (s, 3H), 2.10 (s, 3H). LC/MS: $t_R$=1.22 min, 194 (MH)$^+$.

4-Acetamido-3-methyl-5-nitrobenzoic acid

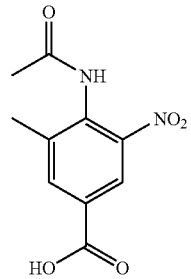

To a solution of 60% nitric acid in sulfuric acid (410 mL) was added 4-acetamido-3-methylbenzoic acid (43 g, 0.22 mol) in small portions over 40 min while cooling with an ice bath. After addition of all amide was complete, the reaction mixture was stirred for 1 h at 0° C. and then very slowly poured over 1500 mL of ice. The yellow solid was collected by filtration and washed with ice cold water to give the title compound (38 g, 72% yield). $^1$H-NMR (CD$_3$OD, 300 MHz) δ 8.29 (s, 1H), 8.18 (s, 1H), 2.39 (s, 3H), 2.16 (s, 3H). Mass spec.: 237 (MH)$^+$.

4-Amino-3-methyl-5-nitrobenzoic acid

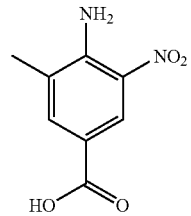

A suspension of 4-acetamido-3-methyl-5-nitrobenzoic acid (38 g, 0.16 mol) in 3N hydrochloric acid (800 mL) was heated at reflux for 8 h and then stirred at room temperature for 8 h. The yellow solid was collected by filtration and transferred to a 2 L flask with a mixture of methylene chloride and methanol. The solvent was evaporated under high vacuum to give the title compound (23 g, 74% yield). $^1$H-NMR (DMSO-d6, 300 MHz) δ 12.79 (bs, 1H), 8.46 (s, 1H), 7.79 (s, 1H), 7.61 (s, 2H), 2.34 (s, 3H). $^{13}$C-NMR (d$_6$-DMSO, 75 MHz) δ 166.0, 147.0, 135.1, 130.0, 126.4, 125.9, 116.7, 17.9. LC/MS: $t_R$=1.23 min, 195 (MH)$^-$ 3-Methyl-4,5-dinitrobenzoic acid

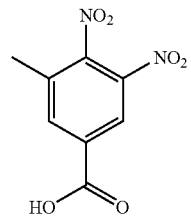

To a suspension of 4-amino-3-methyl-5-nitrobenzoic acid (5.0 g, 25.5 mmol) in trifluoroacetic acid (200 mL) was added hydrogen peroxide (50 wt-%, 15 mL). The reaction mixture was heated at 50° C. for 2 h and the solution eventually went from a dark orange clear solution to a pale yellow clear solution. The reaction mixture was slowly poured into ice water (800 mL). The solid was collected by filtration and dried under vacuum to give the title compound as an off-white solid (4.0 g, 70% yield). $^1$H-NMR (CD$_3$OD, 300 MHz) δ 8.59 (s, 1H), 8.40 (s, 1H), 2.45 (s, 3H). $^{13}$C-NMR (CD$_3$OD, 75 MHz) δ 165.8, 147.4, 142.0, 139.3, 134.8, 134.6, 125.4, 17.2. Mass spec.: 225.14 (MH)$^-$.

(3-Methyl-4,5-dinitrophenyl)methanol

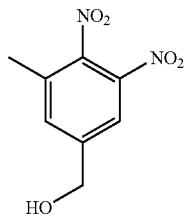

A solution of 3-methyl-4,5-dinitrobenzoic acid (4.0 g, 17.7 mmol) in tetrahydrofuran (200 mL) was cooled to −70° C. with a dry ice/acetone bath. To this solution was added borane-tetrahydrofuran (1M in tetrahydrofuran, 35.4 mL). The reaction mixture was allowed to slowly warm to room temperature and was stirred for 16 h. The reaction was incomplete, was again cooled to −50° C. and additional borane-tetrahydrofuran (1M in tetrahydrofuran, 35.4 mL) was added. Again, the reaction mixture was allowed to slowly warm to room temperature overnight. The reaction was quenched with a mixture of acetic acid and water (1:1, 30 mL) while cooling at 0° C. After stirring for 30 min, all organic solvent was evaporated and the aqueous material was neutralized by pouring into ice cold saturated sodium bicarbonate (350 mL) in small portions. The aqueous layer was extracted with ethyl acetate. The extracts were washed with brine, dried over magnesium sulfate, filtered and evaporated. The residue was subjected to flash column chromatography (1:2 hexanes/ethyl acetate) to give the title compound (3.2 g, 86% yield). $^1$H-NMR (CDCl$_3$, 300 MHz) δ 8.00 (s, 1H), 7.62 (s, 1H), 4.82 (s, 2H), 2.41 (s, 3H). $^{13}$C-NMR (CDCl$_3$, 75 MHz) δ 144.5, 143.3, 140.9, 134.3, 132.9, 120.8, 63.0, 17.4.

3-Methyl-4,5-dinitrobenzaldehyde

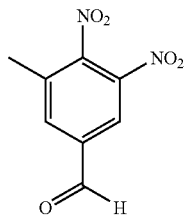

In a flame-dried flask, manganese (IV) oxide (36.0 g, 414 mmol) was azeotropically dried with toluene. Then, a solution of (3-methyl-4,5-dinitrophenyl)methanol (3.2 g, 15 mmol) in chloroform (100 mL) was transferred to the flask containing the manganese dioxide. The reaction mixture was heated at 50° C. with stirring for 3 h. Upon completion of the reaction, the reaction mixture was filtered through a pad of Celite® to remove manganese dioxide and the Celite was washed with chloroform several time. The filtrate was evaporated to give the title compound (1.4 g, 44% yield). $^1$H-NMR (CDCl$_3$, 300 MHz) δ 10.09 (s, 1H), 8.51 (s, 1H), 8.16 (s, 1H), 2.51 (s, 3H).

Benzyl (Z)-1-(methoxycarbonyl)-2-(3-methyl-4,5-dinitrophenyl)vinylcarbamate

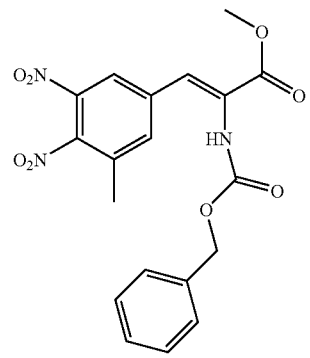

To a solution of N-(benzyloxycarbonyl)-α-phophonoglycine trimethyl ester (2.4 g, 7.3 mmol) in tetrahydrofuran (40 mL) at −78° C. was added 1,1,3,3-tetramethylguanidine (729 mg, 6.33 mmol) and the mixture was stirred for 1 h at −78° C. To this mixture was added a solution of 3-methyl-4,5-dinitrobenzaldehyde (1.4 g, 6.7 mmol) in tetrahydrofuran (15 mL). The reaction mixture was allowed to slowly warm to room temperature and was then stirred for 16 h at room temperature. The solvent was evaporated and the residue subjected to flash column chromatography (gradient, 1:2 to 1:1 ethyl acetate/hexanes). The product was then recrystallized from ethyl acetate/hexanes (1:1) to give the title compound (1.7 g, 62% yield). $^1$H-NMR (CDCl$_3$, 300 MHz) δ 8.01 (s, 1H), 7.55 (s, 1H), 7.33-7.22 (m, 6H), 6.94 (bs, 1H), 5.06 (s, 2H), 3.89 (s, 3H), 2.29 (s, 3H). $^{13}$C-NMR (CDCl$_3$, 75 MHz) δ 164.7, 152.5, 143.1, 140.6, 137.7, 137.0, 135.3, 132.5, 128.8, 128.7, 128.6, 127.1, 123.5, 123.2, 68.3, 53.5, 17.4. Mass spec.: 414.20 (MH)$^-$.

Benzyl (R)-1-(methoxycarbonyl)-2-(3-methyl-4,5-dinitrophenyl)ethylcarbamate

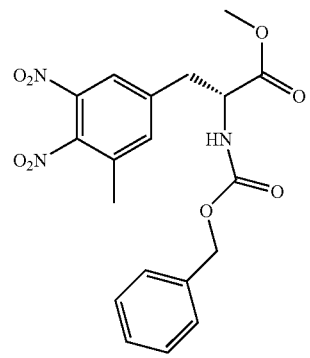

In a glove bag that was subjected to 3 vacuum/nitrogen purge cycles, an AIRFREE® (Schlenk) reaction flask equipped with stir bar was charged with (−)-1,2-bis((2R,5R)-2,5-diethylphospholano)benzene(cyclooctadiene) rhodium (I) trifluoromethylsulfonate (125 g, 0.173 mmol, 4 mol %), sealed with a rubber septum, and removed from the glove bag. The benzyl (Z)-1-(methoxycarbonyl)-2-(3-methyl-4,5-dinitrophenyl)vinylcarbamate (1.65 g, 3.97 mmol) was weighed into a second AIRFREE® (Schlenk) reaction flask equipped with stir bar and sealed with a rubber septum. After 3 vacuum/nitrogen purge cycles, it was dissolved in a mixture of anhydrous methylene chloride (40 mL). The solvent was deoxygenated prior to addition by sparging with nitrogen for at least 1 h. Once in solution, the mixture was again subjected to 3 vacuum/nitrogen purge cycles. The dehydroamino acid solution was introduced into the AIRFREE® (Schlenk) reaction flask containing the catalyst via cannula. The reaction mixture was subjected to 5 vacuum/hydrogen purge cycles before opening the flask to 1 atmosphere of hydrogen. After 16 h, the reaction mixture was purged with 3 vacuum/nitrogen purge cycles. The solvent was evaporated and the residue was subjected to column chromatography (1:1 ethyl acetate/hexanes) to give the title compound (1.58 g, 95%). $^1$H-NMR (CDCl$_3$, 300 MHz) δ 7.75 (s, 1H), 7.39-7.33 (m, 6H), 5.37 (d, J=7.0 Hz, 1H), 5.15-5.04 (m, 2H), 4.70-4.46 (m, 1H), 3.77 (s, 3H), 3.30 (dd, J=13.9, 5.5 Hz, 1H), 3.12 (dd, J=13.9, 6.2 Hz, 1H), 2.33 (s, 3H). LC/MS: $t_R$=2.71 min, 418 (MH)$^+$.

Benzyl (R)-1-(methoxycarbonyl)-2-(3,4-diamino-5-methylphenyl)ethylcarbamate

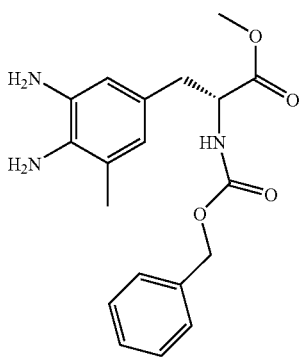

Solid ammonium formate (755 mg, 11.9 mmol) was added in small portions at 0° C. to suspension of benzyl (R)-1-(methoxycarbonyl)-2-(3-methyl-4,5-dinitrophenyl)ethylcarbamate (500 mg, 1.20 mmol) and zinc powder (470 mg, 7.19 mmol) in methanol (20 mL, degassed with nitrogen for 2 h). The resulting mixture was stirred at room temperature for 60 h. Reaction was incomplete. The reaction mixture was again cooled to 0° C. and additional zinc powder (470 mg, 7.19 mmol) was added. The reaction was stirred for 4 h at which time the reaction was complete. The reaction mixture was filtered to remove zinc. The filtrate was evaporated. A mixture of toluene and ethyl acetate (1:1) were added, followed by acetic acid (2 mL). The mixture was further diluted until all organic solids dissolved, then it was washed with water, brine, dried over sodium sulfate, and evaporated. The residue was then redissolved in ethyl acetate and 4N hydrogen chloride in dioxane (4 mL) was added. The solvent was evaporated to give the title compound as the dihydrochloride salt (515 mg, quantitative yield).

$^1$H-NMR (CD$_3$OD, 300 MHz) δ 7.35-7.30 (m, 5H), 6.94-6.93 (m, 2H), 5.03 (s, 2H), 4.42-4.37 (m, 1H), 3.70 (s, 3H), 3.09-3.03 (m, 1H), 2.87-2.79 (m, 1H), 2.25 (s, 3H). LC/MS: $t_R$=1.79 min, 358 (MH)$^+$.

Benzyl (R)-1-(methoxycarbonyl)-2-(7-methyl-1H-benzo[d][1,2,3]triazol-5-yl)ethylcarbamate

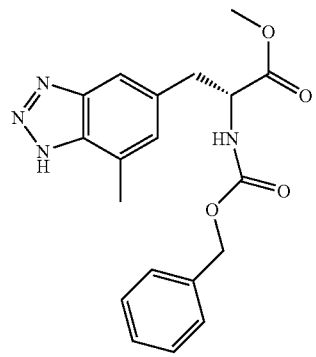

To a solution of benzyl (R)-1-(methoxycarbonyl)-2-(3,4-diamino-5-methylphenyl)ethylcarbamate (250 mg, 0.58 mmol) in acetic acid (6 mL) and water (10 mL) was added a solution of sodium nitrite (40 mg, 0.58 mmol) in water (1 mL), dropwise over several minutes at room temperature. The resulting mixture was stirred at room temperature for 30 min, then cooled to 0° C. A mixture of ammonium hydroxide and water (1:1, 15 mL) was added to adjust pH to 11. The mixture was extracted with ethyl acetate twice. The organic layers washed with brine and dried over sodium sulfate. After filtration, solvents were removed in vacuo and the residue was purified by flash column chromatography (1:1 ethyl acetate/hexanes) on silica gel to afford the title compound as a tan solid (155 mg, 72% yield). $^1$H-NMR (CDCl$_3$, 300 MHz) δ 7.34 (s, 1H), 7.32-7.28 (m, 6H), 6.93 (s, 1H), 5.40 (d, J=8.1 Hz, 1H), 5.13-5.02 (m, 2H), 4.76-4.69 (m, 1H), 3.73 (s, 3H), 3.28 (dd, J=13.9, 5.5 Hz, 1H), 3.16 (dd, J=13.9, 6.2 Hz, 1H), 2.64 (s, 3H). LC/MS: $t_R$=2.30 min, 369 (MH)$^+$.

(R)-Methyl 2-amino-3-(7-methyl-1H-benzo[d][1,2,3]triazol-5-yl)propanoate

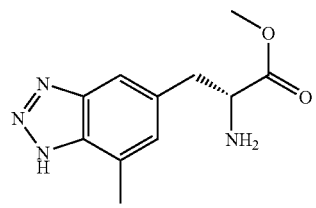

Benzyl (R)-1-(methoxycarbonyl)-2-(7-methyl-1H-benzo[d][1,2,3]triazol-5-yl)ethylcarbamate (146 mg, 0.40 mmol) was dissolved in 12 mL of a solution of 4.4% formic acid in methanol. The reaction flask containing this solution was equipped with a magnetic stirbar and then flushed with nitrogen over several minutes. To the solution was added palladium on carbon (10%, 200 mg) and the reaction was stirred for 16 h at room temperature under nitrogen atmosphere. The reaction mixture was filtered through a pad of Celite® washing the pad several times with methanol. The filtrate was evaporated to give the title compound (quantitative yield). $^1$H-NMR (CDCl$_3$, 300 MHz) δ 8.40 (bs, 1H), 7.55 (s, 1H), 7.14 (s, 1H), 4.29-4.24 (m, 1H), 3.78 (s, 3H), 3.39-3.19 (m, 2H), 2.69 (s, 3H). LC/MS: $t_R$=1.18 min, 235 (MH)$^+$.

283

(R)-methyl 2-(4-(1,2-dihydro-2-oxoquinazolin-3 (4H)-yl)piperidine-1-carboxamido)-3-(7-methyl-1H-benzo[d][1,2,3]triazol-5-yl)propanoate

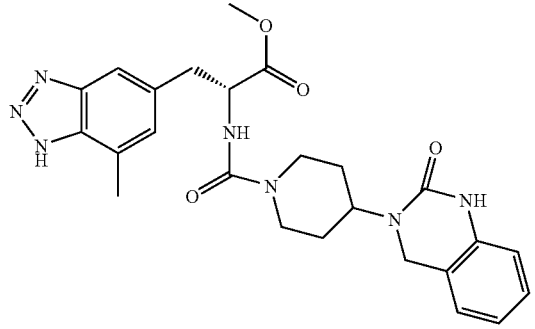

Prepared as described above for (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl)propanoate. LC/MS: $t_R$=2.17 min, 492 (MH)$^+$.

(R)-2-(4-(1,2-dihydro-2,4-dioxoquinazolin-3(4H)-yl)piperidine-1-carboxamido)-3-(7-methyl-1H-benzo[d][1,2,3]triazol-5-yl)propanoic acid

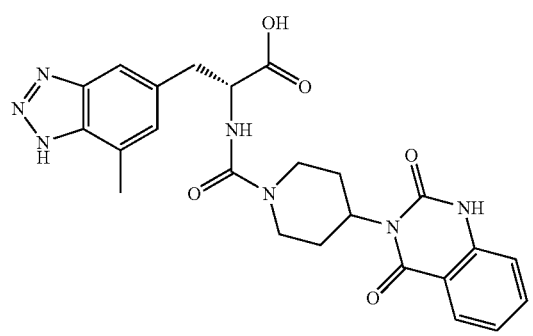

Prepared as described above for (R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid. LC/MS: $t_R$=2.11 min, 492 (MH)$^+$.

Example 237

4-(1,2-dihydro-2,4-dioxoquinazolin-3(4H)-yl)-N—((R)-3-(7-methyl-1H-benzo[d][1,2,3]triazol-5-yl)-1-oxo-1-(4-(piperidin-1-yl)piperidin-1-yl)propan-2-yl)piperidine-1-carboxamide

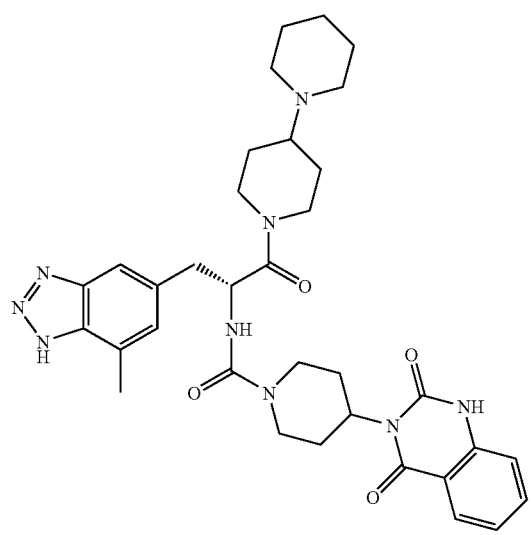

284

Prepared as described above for Example 231. $^1$H-NMR (CD$_3$OD, 300 MHz) δ 8.01 (d, J=8.1 Hz, 1H), 7.63 (t, J=7.5 Hz, 1H), 7.28-7.11 (m, 4H), 5.06-5.00 (m, 1H), 4.70-4.60 (m, 1H), 4.31-4.17 (m, 2H), 3.50-3.44 (m, 1H), 3.20-2.82 (m, 7H), 2.75-2.47 (m, 6H), 2.12-2.02 (m, 2H), 1.93-1.67 (m, 11H), 1.37-1.28 (m, 2H, 0.97-0.79 (m, 2H), 0.23-0.09 (m, 1H). Mass spec.: 642 (MH)$^+$.

(R)-2-Benzyloxycarbonylamino-3-(4-chloro-2-oxo-2,3-dihydro-benzooxazol-6-yl)-propionic acid methyl ester

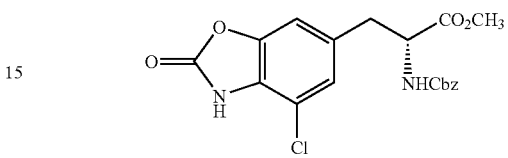

A mixture of (R)-2-benzyloxycarbonylamino-3-(2-oxo-2,3-dihydro-benzooxazol-6-yl)-propionic acid methyl ester (373 mg, 1.01 mmol), N-chlorosuccinimide (168 mg, 1.26 mmol), silica gel (EM Scientific, 230-400 mesh, 3.73 g) in dichloroethane (20 mL) was heated at 90° C. for 16 h. After cooling down to room temperature, the solvents were removed in vacuo. The residue was subjected to silica gel chromatography using ethyl acetate/hexanes (1:2) as eluent to afford the title compound (40 mg, 9.8%), also 2-benzyloxycarbonylamino-3-(5-chloro-2-oxo-2,3-dihydro-benzooxazol-6-yl)-propionic acid methyl ester (78 mg, 19%). The structure was confirmed by 2D NMR and by comparison with that of 2-benzyloxycarbonylamino-3-(5-chloro-2-oxo-2,3-dihydro-benzooxazol-6-yl)-propionic acid methyl ester prepared by the reaction shown below. $^1$H-NMR (CD$_3$COCD$_3$, 500 MHz) δ 7.37-7.27 (m, 5H), 7.18 (d, J=1.0 Hz, 1H), 7.16 (s, 1H), 6.76 (d, J=8.5 hz, 1H), 5.06 (d, J=12.5 Hz, 1H), 5.02 (d, J=12.5 Hz, 1H), 4.55-4.51 (m, 1H), 3.72 (s, 3H), 3.26 (dd, J=14.0, 5.0 Hz, 1H), 3.04 (dd, J=14.0, 9.5 Hz, 1H); $^{13}$C-NMR (CD$_3$COCD$_3$, 125 MHz) δ 172.2, 156.4, 154.0, 144.8, 137.6, 133.3, 128.7, 128.2, 128.0, 127.9, 125.0, 66.3, 55.9, 52.0, 37.3; Mass spec. 405 (MH$^+$).

(R)-2-Benzyloxycarbonylamino-3-(5-chloro-2-oxo-2,3-dihydro-benzooxazol-6-yl)-propionic acid methyl ester

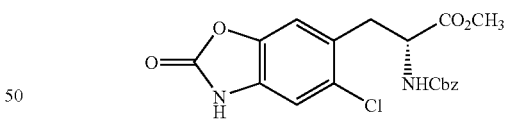

N-Chlorosuccinimide (315 mg, 2.36 mmol) was added to a solution of (R)-2-benzyloxycarbonylamino-3-(2-oxo-2,3-dihydro-benzooxazol-6-yl)-propionic acid methyl ester (700 mg, 1.89 mmol) in acetic acid (50 mL) at room temperature. The mixture was heated at 100° C. for 16 h. After it was cooled down to room temperature, solvents were removed in vacuo. The residue was subjected to silica gel chromatography using ethyl acetate/hexanes (4:6) then (1:1) as eluent to afford the title compound as an off-yellow solid (242 mg, 32%). The structure of the product was confirmed by 2D NMR. $^1$H-NMR (CD$_3$COCD$_3$, 500 MHz) δ 10.47 (s, 1H), 7.36-7.28 (m, 6H), 7.20 (s, 1H), 6.80 (d, J=8.5 Hz, 1H), 5.05 (d, J=12.5 Hz, 1H), 5.00 (d, J=12.5 Hz, 1H), 4.65-4.60 (m, 1H), 3.73 (s, 3H), 3.43 (dd, J=14.0, 5.0 Hz, 1H), 3.08 (dd, J=14.0, 10.5 Hz, 1H); $^{13}$C-NMR (CD$_3$COCD$_3$, 125 MHz) δ

172.2, 156.5, 154.5, 143.1, 137.5, 130.8, 129.0, 128.9, 128.7, 128.2, 128.0, 112.8, 110.9, 66.3, 54.3, 52.1, 35.8; Mass spec. 405 (MH$^+$).

(R)-2-Benzyloxycarbonylamino-3-(4-bromo-2-oxo-2,3-dihydro-benzooxazol-6-yl)-propionic acid methyl ester

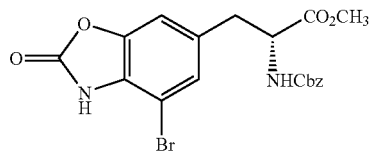

A mixture of (R)-2-benzyloxycarbonylamino-3-(2-oxo-2,3-dihydro-benzooxazol-6-yl)-propionic acid methyl ester (418 mg, 1.13 mmol), N-bromosuccinimide (221 mg, 1.24 mmol), silica gel (EM Scientific, 230-400 mesh, 2.51 g) and methylene chloride (70 mL) was stirred at room temperature for 16 h. Solvents were removed in vacuo and the residue was subjected to silica gel chromatography using ethyl acetate/hexanes (2:3) as eluent to afford the title compound. $^1$H-NMR (CD$_3$COCD$_3$, 500 MHz) δ 10.71 (s, 1H), 7.35-7.28 (m, 6H), 7.21 (s, 1H), 6.75 (d, J=7.5 Hz, 1H), 5.06 (d, 12.5 Hz, 1H), 5.02 (d, J=12.5 Hz, 1H), 4.56-4.51 (m, 1H), 3.73 (s, 3H), 3.26 (dd, J=14.0, 5.0 Hz, 1H), 3.03 (dd, J=14.0, 10.0 Hz, 1H); $^{13}$C-NMR (CD$_3$COCD$_3$, 125 MHz) δ 172.2, 156.4, 153.8, 144.4, 137.6, 133.7, 129.8, 128.7, 128.2, 128.0, 127.8, 110.1, 100.9, 66.3, 55.9, 52.0, 37.3; Mass spec. 448.03 (MH$^+$).

(R)-2-Benzyloxycarbonylamino-3-(5-bromo-2-oxo-2,3-dihydro-benzooxazol-6-yl)-propionic acid methyl ester

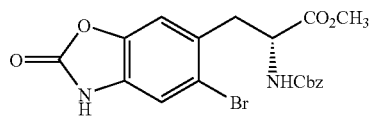

A mixture of (R)-2-benzyloxycarbonylamino-3-(2-oxo-2,3-dihydro-benzooxazol-6-yl)-propionic acid methyl ester (1.07 g, 2.89 mmol), N-bromosuccinimide (643 mg, 3.61 mmol), and acetic acid (150 mL) was heated at 105° C. for 14 h. After cooling to room temperature, the solvents were removed in vacuo. The residue was subjected to silica gel chromatography using ethyl acetate/hexanes (2:3), then (1:1) as eluent to afford the title compound (446 mg, 34%). The structure of the title compound was confirmed by 2D NMR. $^1$H-NMR (CD$_3$COCD$_3$, 500 MHz) δ 10.46 (s, 1H), 7.36-7.28 (m, 7H), 6.82 (d, J=8.5 Hz, 1H), 5.05 (d, J=12.5 Hz, 1H), 5.00 (d, J=12.5 Hz, 1H), 4.67-4.62 (m, 1H), 3.73 (s, 3H), 3.43 (dd, J=14.0, 5.0 Hz, 1H), 3.10 (dd, J=14.0, 10.5 Hz, 1H); $^{13}$C-NMR (CD$_3$COCD$_3$, 125 MHz) δ 172.2, 156.4, 154.2, 143.7, 137.6, 131.1, 130.6, 128.7, 128.2, 128.0, 118.2, 113.9, 112.9, 66.2, 54.3, 52.1, 38.3; Mass spec. 448.03 (MH$^+$).

(R)-2-Benzyloxycarbonylamino-3-(4-iodo-2-oxo-2,3-dihydro-benzooxazol-6-yl)-propionic acid methyl ester

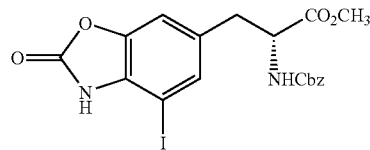

A mixture of (R)-2-benzyloxycarbonylamino-3-(2-oxo-2,3-dihydro-benzooxazol-6-yl)-propionic acid methyl ester (324 mg, 0.87 mmol), I(PyH)$_2$BF$_4$ (409 mg, 1.08 mmol), silica gel (EM Scientific, 230-400 mesh, 3.24 g) and dichloroethane (20 mL) was heated at 90° C. for 6 h. After cooling to room temperature the solvents were removed in vacuo. The residue was subjected to silica gel chromatography using ethyl acetate/hexanes (1:2) as eluent to afford the title compound (175 mg, 40%). The structure of the title compound was confirmed by 2D NMR. $^1$H-NMR (CD$_3$COCD$_3$, 500 MHz) δ 10.47 (s, 1H), 7.46 (s, 1H), 7.37-7.29 (m, 5H), 7.22 (s, 1H), 6.74 (d, J=8.5 Hz, 1H), 5.07 (d, J=12.5 Hz, 1H), 5.02 (d, J=12.5 Hz, 1H), 4.54-4.49 (m, 1H), 3.72 (s, 3H), 3.23 (dd, J=14.0, 5.0 Hz, 1H), 3.01 (dd, J=14.0, 9.5 Hz, 1H); $^{13}$C-NMR (CD$_3$COCD$_3$, 125 MHz) δ 172.2, 156.4, 153.4, 143.3, 137.6, 134.1, 133.64, 133.60, 128.7, 128.2, 128.0, 110.7, 71.1, 66.3, 56.0, 52.0, 37.1; Mass spec. 496.01 (MH$^+$).

(R)-2-Amino-3-(5-bromo-2-oxo-2,3-dihydro-benzooxazol-6-yl)-propionic acid methyl ester

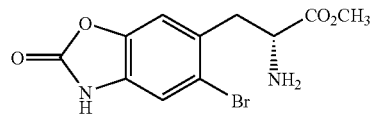

Trimethylsilyliodide (73 mL, 0.73 mmol) was added to a solution of azotropically dried (R)-2-benzyloxycarbonylamino-3-(5-bromo-2-oxo-2,3-dihydro-benzooxazol-6-yl)-propionic acid methyl ester (146 mg, 0.33 mmol) in acetonitrile (10 mL) at room temperature, and the resulting mixture was stirred at room temperature for 2 h. Triethylamine (0.12 mL) was added and the mixture was stirred at room temperature for 15 min. The solvents were removed in vacuo, and the residue was extracted with ethyl acetate. The combined organics were washed with sodium bicarbonate and brine, dried over sodium sulfate and filtered. Solvents were removed and the residue was used directly in the next step. Mass spec. 315.10 (MH)$^+$.

(R)-2-Amino-3-(4-bromo-2-oxo-2,3-dihydro-benzooxazol-6-yl)-propionic acid methyl ester

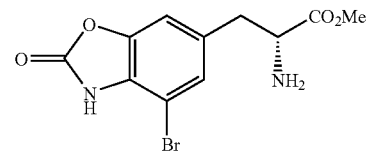

Prepared as described above for (R)-2-amino-3-(5-bromo-2-oxo-2,3-dihydro-benzooxazol-6-yl)-propionic acid methyl ester. Mass spec. 315.06 (MH)$^+$.

287

(R)-2-Amino-3-(5-chloro-2-oxo-2,3-dihydro-benzooxazol-6-yl)-propionic acid methyl ester

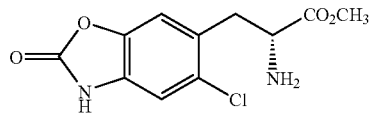

Prepared as described above for (R)-2-amino-3-(5-bromo-2-oxo-2,3-dihydro-benzooxazol-6-yl)-propionic acid methyl ester. Mass spec. 271.10 (MH)$^+$.

(R)-2-Amino-3-(4-chloro-2-oxo-2,3-dihydro-benzooxazol-6-yl)-propionic acid methyl ester

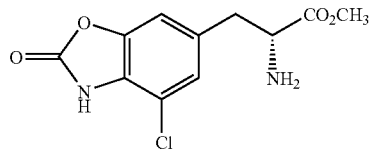

Prepared as described above for (R)-2-amino-3-(5-bromo-2-oxo-2,3-dihydro-benzooxazol-6-yl)-propionic acid methyl ester. Mass spec. 271.16 (MH)$^+$.

(R)-2-Amino-3-(4-iodo-2-oxo-2,3-dihydro-benzooxazol-6-yl)-propionic acid methyl ester

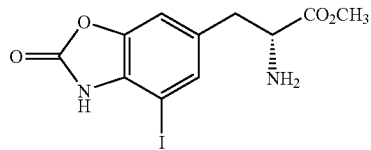

Prepared as described above for (R)-2-Amino-3-(5-bromo-2-oxo-2,3-dihydro-benzooxazol-6-yl)-propionic acid methyl ester. Mass spec. 363.04 (MH)$^+$.

(R)-3-(2-Oxo-2,3-dihydro-benzooxazol-6-yl)-2-{[2,4-dihydro-2'-oxospiro-(piperidine-4,4'-1H-benzo[d][1,3]oxazine)-1-carbonyl]-amino}-propionic acid methyl ester

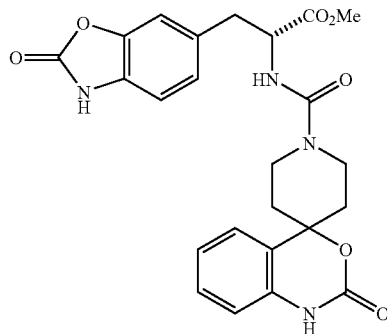

Prepared as described above for (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl)propanoate. Mass spec. 481.20 (MH)$^+$.

288

(R)-3-(2-Oxo-2,3-dihydro-benzooxazol-6-yl)-2-{[2,4-dihydro-2'-oxospiro-(piperidine-4,4'-1H-quinazoline)-1-carbonyl]-amino}-propionic acid methyl ester

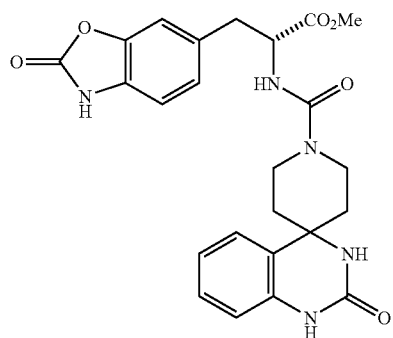

Prepared as described above for (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl) propanoate. Mass spec. 480.24 (MH)$^+$.

(R)-3-(4-Chloro-2-oxo-2,3-dihydro-benzooxazol-6-yl)-2-{[4-(2-oxo-1,4-dihydro-2H-quinazolin-3-yl)-piperidine-1-carbonyl]-amino}-propionic acid methyl ester

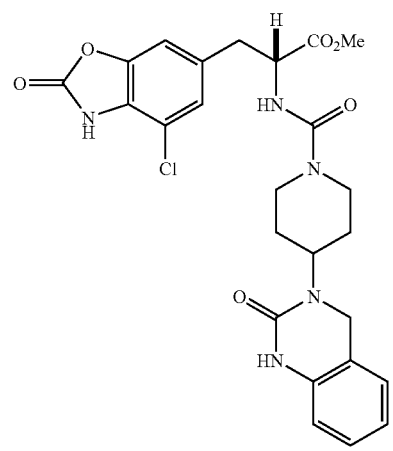

Prepared as described above for (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl)propanoate. Mass spec. 528.16 (MH)$^+$.

289

(R)-3-(5-Chloro-2-oxo-2,3-dihydro-benzooxazol-6-yl)-2-{[4-(2-oxo-1,4-dihydro-2H-quinazolin-3-yl)-piperidine-1-carbonyl]-amino}-propionic acid methyl ester

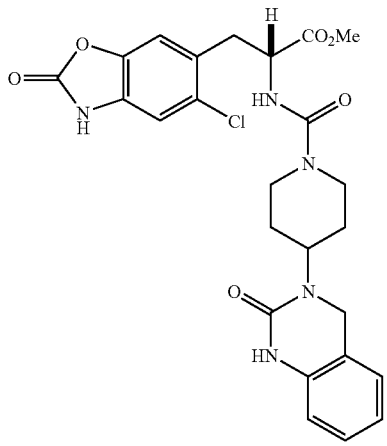

Prepared as described above for (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl)propanoate. Mass spec. 528.20 (MH)+.

290

(R)-3-(5-Bromo-2-oxo-2,3-dihydro-benzooxazol-6-yl)-2-{[4-(2-oxo-1,4-dihydro-2H-quinazolin-3-yl)-piperidine-1-carbonyl]-amino}-propionic acid methyl ester

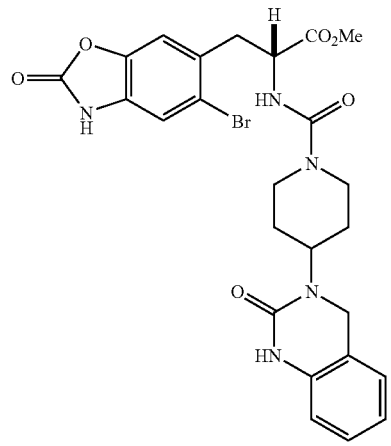

Prepared as described above for (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl)propanoate. Mass spec. 572.15 (MH)+.

(R)-3-(4-Bromo-2-oxo-2,3-dihydro-benzooxazol-6-yl)-2-{[4-(2-oxo-1,4-dihydro-2H-quinazolin-3-yl)-piperidine-1-carbonyl]-amino}-propionic acid methyl ester

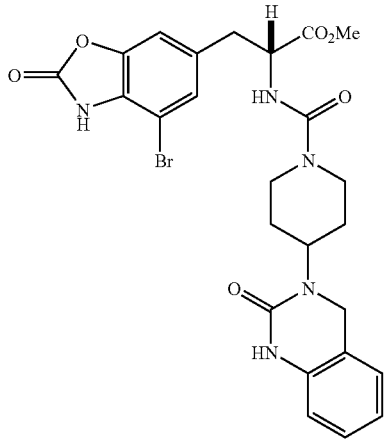

Prepared as described above for (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl)propanoate. Mass spec. 572.20 (MH)+.

(R)-3-(4-Iodo-2-oxo-2,3-dihydro-benzooxazol-6-yl)-2-{[4-(2-oxo-1,4-dihydro-2H-quinazolin-3-yl)-piperidine-1-carbonyl]-amino}-propionic acid methyl ester Prepared as described above for (R)-methyl 2-(4-(1,2-dihydro-2-oxoquinazolin-3(4H)-yl)piperidine-1-carboxamido)-3-(2-(trifluoromethyl)-1H-benzo[d]imidazol-5-yl)propanoate. Mass spec. 620.20 (MH)+.

291

(R)-3-(2-Oxo-2,3-dihydro-benzooxazol-6-yl)-2-{[2,4-dihydro-2'-oxospiro-(piperidine-4,4'-1H-benzo[d][1,3]oxazine)-1-carbonyl]-amino}-propionic acid

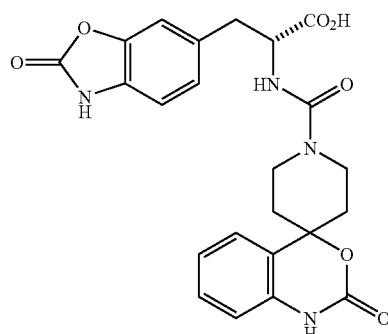

Prepared as described above for (R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid. Mass spec. 467.18 (MH)$^+$.

292

(R)-3-(4-Chloro-2-oxo-2,3-dihydro-benzooxazol-6-yl)-2-{[4-(2-oxo-1,4-dihydro-2H-quinazolin-3-yl)-piperidine-1-carbonyl]-amino}-propionic acid

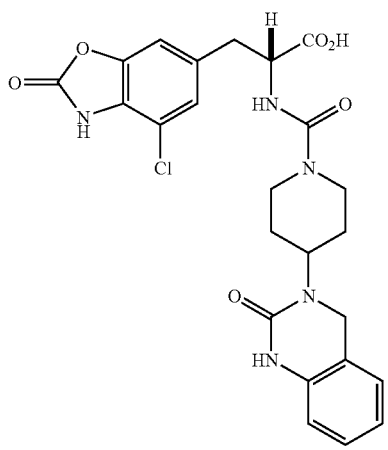

Prepared as described above for (R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid. Mass spec. 514.20 (MH)$^+$.

(R)-3-(2-Oxo-2,3-dihydro-benzooxazol-6-yl)-2-{[2,4-dihydro-2'-oxospiro-(piperidine-4,4'-1H-quinazoline)-1-carbonyl]-amino}-propionic acid

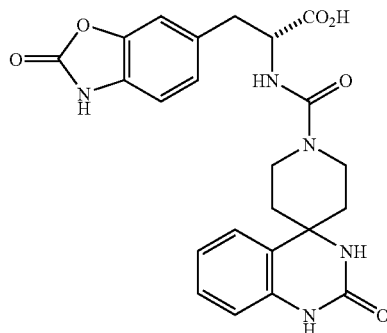

(R)-3-(5-Chloro-2-oxo-2,3-dihydro-benzooxazol-6-yl)-2-{[4-(2-oxo-1,4-dihydro-2H-quinazolin-3-yl)-piperidine-1-carbonyl]-amino}-propionic acid

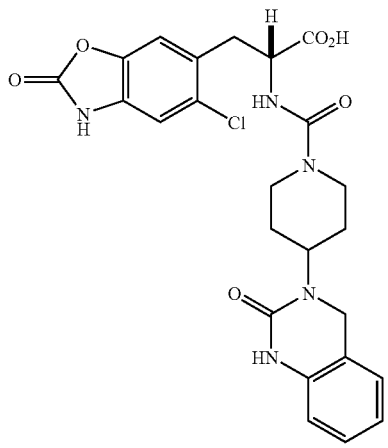

Prepared as described above for (R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid. Mass spec. 466.20 (MH)$^+$.

Prepared as described above for (R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid. Mass spec. 514.24 (MH)$^+$.

293

(R)-3-(4-Bromo-2-oxo-2,3-dihydro-benzooxazol-6-yl)-2-{[4-(2-oxo-1,4-dihydro-2H-quinazolin-3-yl)-piperidine-1-carbonyl]-amino}-propionic acid

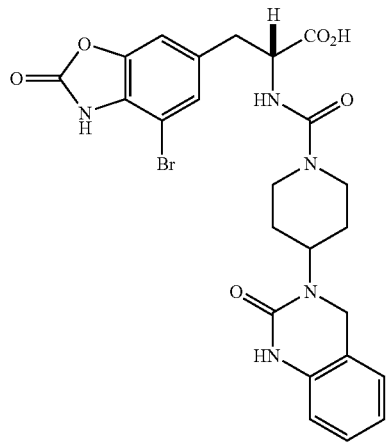

Prepared as described above for (R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid. Mass spec. 558.30 (MH)⁺.

(R)-3-(5-Bromo-2-oxo-2,3-dihydro-benzooxazol-6-yl)-2-{[4-(2-oxo-1,4-dihydro-2H-quinazolin-3-yl)-piperidine-1-carbonyl]-amino}-propionic acid

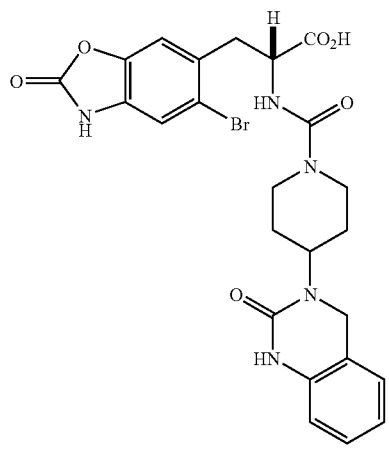

Prepared as described above for (R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid. Mass spec. 558.25 (MH)⁺.

294

(R)-3-(4-Iodo-2-oxo-2,3-dihydro-benzooxazol-6-yl)-2-{[4-(2-oxo-1,4-dihydro-2H-quinazolin-3-yl)-piperidine-1-carbonyl]-amino}-propionic acid

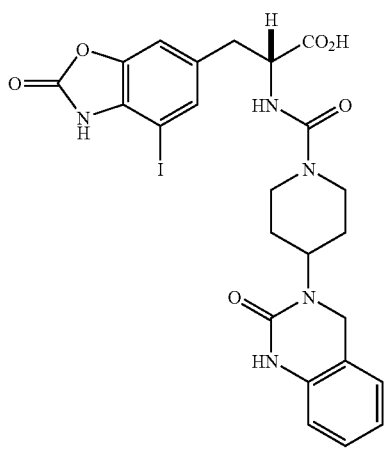

Prepared as described above for (R)-2-(4-(1,2-dihydro-2-oxoquinazolin-3(4H)-yl)piperidine-1-carboxamido)-3-(2-(trifluoromethyl)-1H-benzo[d]imidazol-5-yl)propanoic acid. Mass spec. 606.10 (MH)⁺.

Example 238

(R)-4-(2-Oxo-1,4-dihydro-2H-quinazolin-3-yl)-piperidine-1-carboxylic acid [2-(4-cyclohexyl-piperazin-1-yl)-2-oxo-1-(2-oxo-2,3-dihydro-benzooxazol-6-ylmethyl)-ethyl]-amide

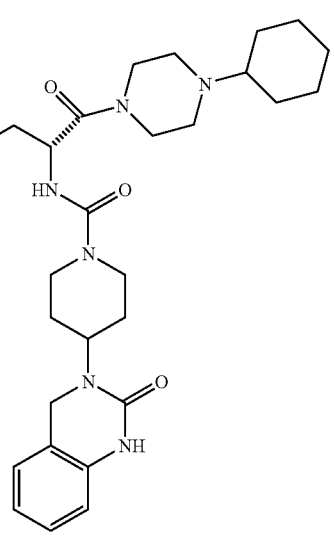

Prepared as described above for Example 231. LC/MS: $t_R$=1.80 min, 630.37 (MH)⁺.

Example 239

(R)-4-(2-Oxo-1,4-dihydro-2H-quinazolin-3-yl)-piperidine-1-carboxylic acid [2-(4-isopropyl-piperazin-1-yl)-2-oxo-1-(2-oxo-2,3-dihydro-benzooxazol-6-ylmethyl)-ethyl]-amide

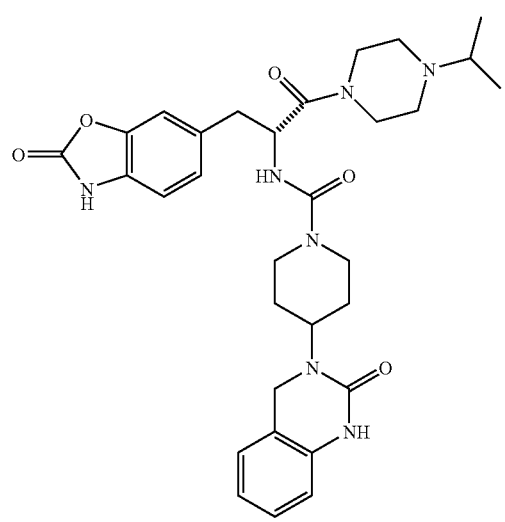

Prepared as described above for Example 231. LC/MS: $t_R$=1.71 min, 590.34 (MH)$^+$.

Example 240

(R)—N—((R)-3-(2-Oxo-2,3-dihydro-benzooxazol-6-yl)-1-oxo-1-(4-(piperidin-1-yl)piperidin-1-yl)propan-2-yl)-2,4-dihydro-2'-oxospiro-(piperidine-4,4'-1H-benzo[d][1,3]oxazine)-1-carboxamide

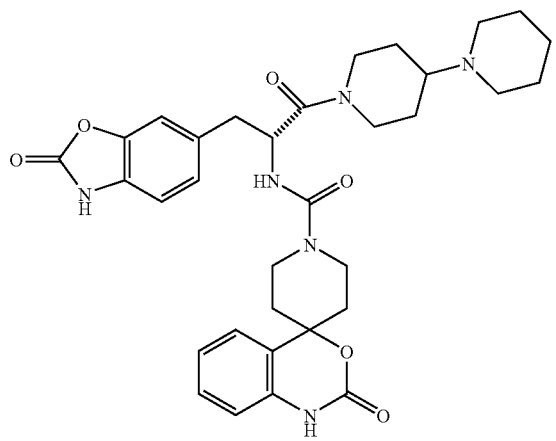

Prepared as described above for Example 231. LC/MS: $t_R$=1.64 min, 617.34 (MH)$^+$.

Example 241

(R)—N—((R)-3-(2-Oxo-2,3-dihydro-benzooxazol-6-yl)-1-oxo-1-(4-(cyclohex-1-yl)piperazin-1-yl)propan-2-yl)-2,4-dihydro-2'-oxospiro-(piperidine-4,4'-1H-benzo[d][1,3]oxazine)-1-carboxamide

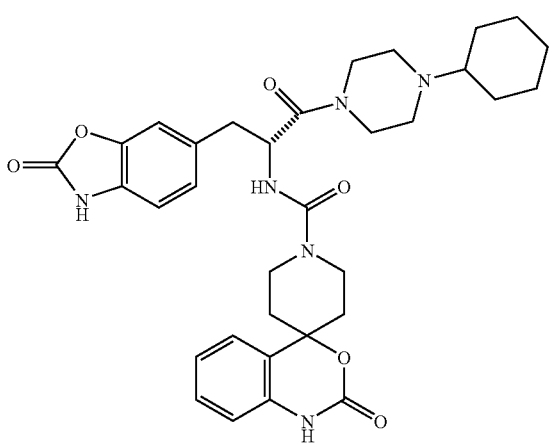

Prepared as described above for Example 231. LC/MS: $t_R$=1.69 min, 617.35 (MH)$^+$.

Example 242

(R)—N—((R)-3-(2-Oxo-2,3-dihydro-benzooxazol-6-yl)-1-oxo-1-(4-(prop-2-yl)piperazin-1-yl)propan-2-yl)-2,4-dihydro-2'-oxospiro-(piperidine-4,4'-1H-benzo[d][1,3]oxazine)-1-carboxamide

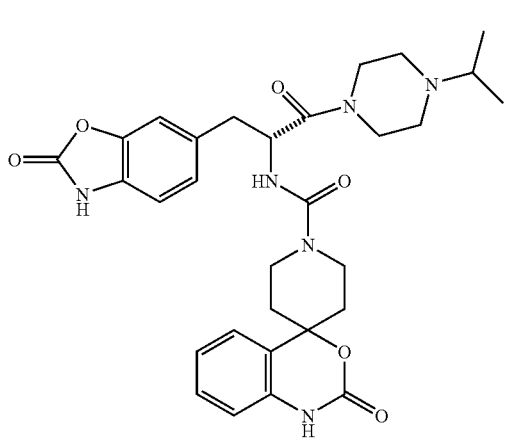

Prepared as described above for Example 231. LC/MS: $t_R$=1.57 min, 577.32 (MH)$^+$.

Example 243

(R)—N—((R)-3-(2-Oxo-2,3-dihydro-benzooxazol-6-yl)-1-oxo-1-(4-(piperidin-1-yl)piperidin-1-yl)propan-2-yl)-2,4-dihydro-2'-oxospiro-(piperidine-4,4'-1H-quinazoline)-1-carboxamide

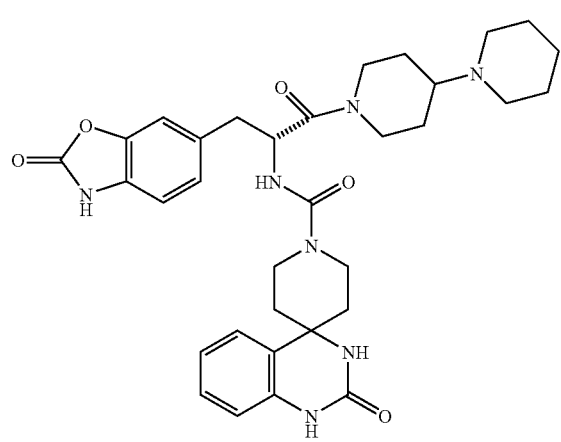

Prepared as described above for Example 231. LC/MS: $t_R$=1.74 min, 616.37 (MH)$^+$.

Example 244

(R)—N—((R)-3-(2-Oxo-2,3-dihydro-benzooxazol-6-yl)-1-oxo-1-(4-(cyclohex-1-yl)piperazin-1-yl)propan-2-yl)-2,4-dihydro-2'-oxospiro-(piperidine-4,4'-1H-quinazoline)-1-carboxamide

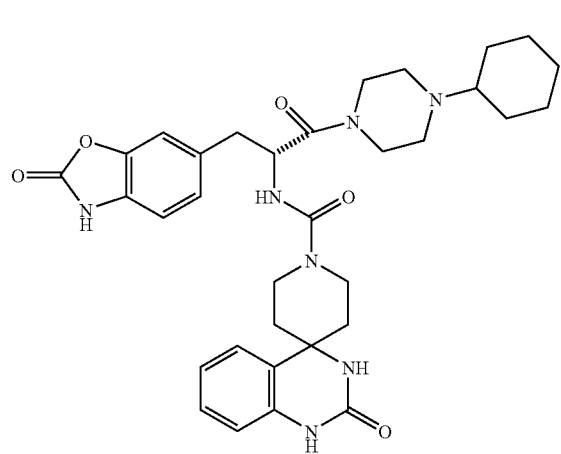

Prepared as above. LC/MS: $t_R$=1.79 min, 616.36 (MH)$^+$.

Example 245

(R)—N—((R)-3-(2-Oxo-2,3-dihydro-benzooxazol-6-yl)-1-oxo-1-(4-(prop-2-yl)piperazin-1-yl)propan-2-yl)-2,4-dihydro-2'-oxospiro-(piperidine-4,4'-1H-quinazoline)-1-carboxamide

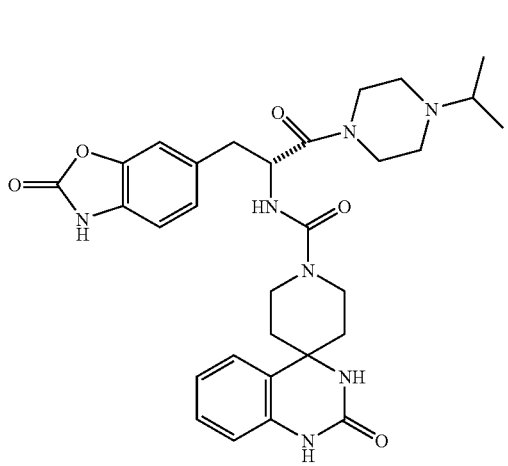

Prepared as described above for Example 231. LC/MS: $t_R$=1.67 min, 576.34 (MH)$^+$.

Example 246

(R)-4-(2-Oxo-1,4-dihydro-2H-quinazolin-3-yl)-piperidine-1-carboxylic acid[2-[1,4']bipiperidinyl-1'-yl-1-(4-chloro-2-oxo-2,3-dihydro-benzooxazol-6-ylmethyl)-2-oxo-ethyl]-amide

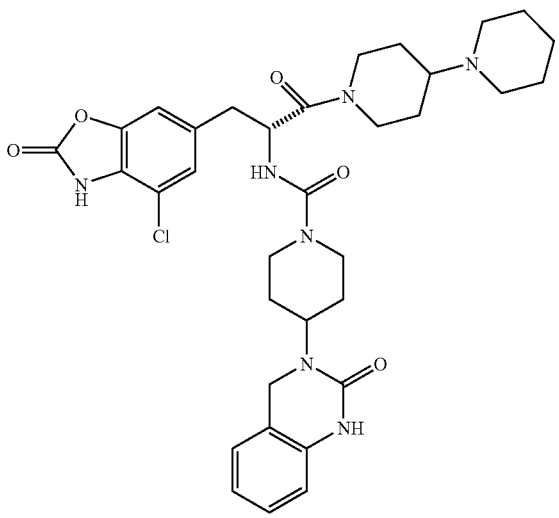

Prepared as described above for Example 231. LC/MS: $t_R$=1.91 min, 664.35 (MH)$^+$.

Example 247

(R)-4-(2-Oxo-1,4-dihydro-2H-quinazolin-3-yl)-piperidine-1-carboxylic acid[2-[1,4']bipiperidinyl-1'-yl-1-(5-chloro-2-oxo-2,3-dihydro-benzooxazol-6-ylmethyl)-2-oxo-ethyl]-amide

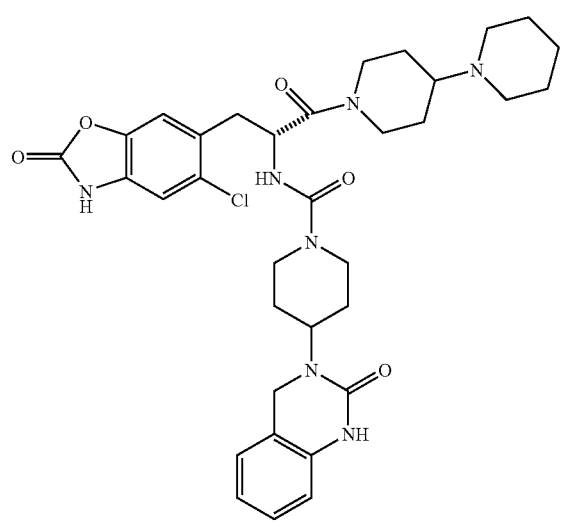

Prepared as described above for Example 231. LC/MS: $t_R$=1.91 min, 664.34 (MH)$^+$.

Example 248

(R)-4-(2-Oxo-1,4-dihydro-2H-quinazolin-3-yl)-piperidine-1-carboxylic acid[2-[1,4']bipiperidinyl-1'-yl-1-(4-bromo-2-oxo-2,3-dihydro-benzooxazol-6-ylmethyl)-2-oxo-ethyl]-amide

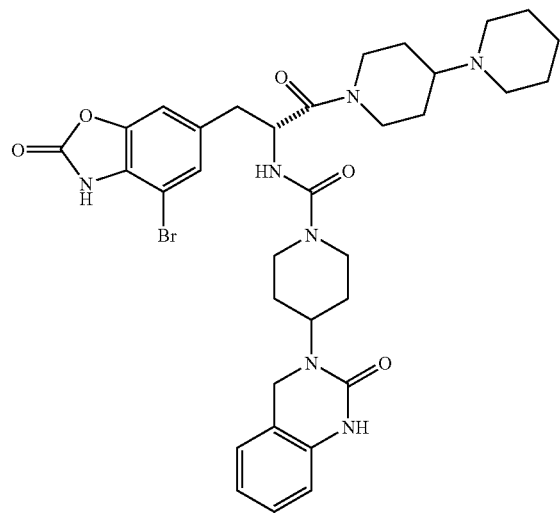

Prepared as described above for Example 231. LC/MS: $t_R$=1.96 min, 708.31 (MH)$^+$.

Example 249

(R)-4-(2-Oxo-1,4-dihydro-2H-quinazolin-3-yl)-piperidine-1-carboxylic acid[2-[1,4']bipiperidinyl-1'-yl-1-(5-bromo-2-oxo-2,3-dihydro-benzooxazol-6-ylmethyl)-2-oxo-ethyl]-amide

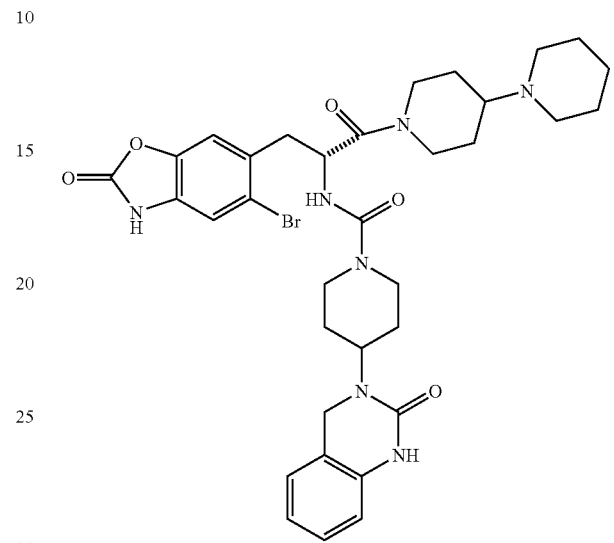

Prepared as described above for Example 231. LC/MS: $t_R$=1.96 min, 708.31 (MH)$^+$.

Example 250

(R)-4-(2-Oxo-1,4-dihydro-2H-quinazolin-3-yl)-piperidine-1-carboxylic acid[2-[1,4']bipiperidinyl-1'-yl-1-(4-iodo-2-oxo-2,3-dihydro-benzooxazol-6-ylmethyl)-2-oxo-ethyl]-amide

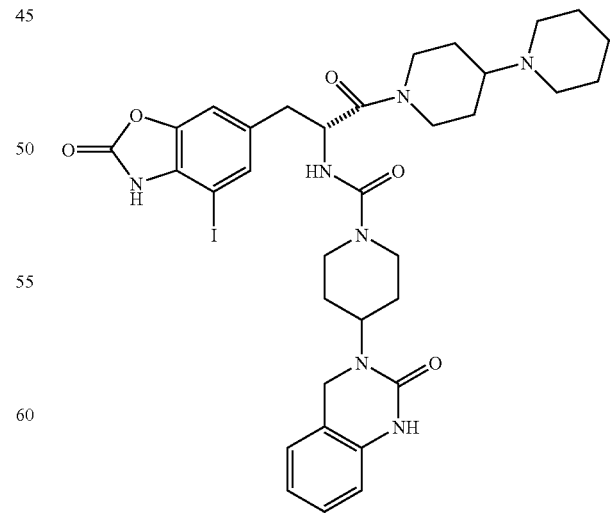

Prepared as described above for Example 231. LC/MS: $t_R$=1.97 min, 756.36 (MH$^+$).

Example 251

(±)—N-(1-Benzyl-2-hydroxy-ethyl)-2-(7-methyl-1H-indazol-5-ylmethyl)-4-oxo-4-[1',2'-dihydro-2'-oxospiro-[4H-3',1-benzoxazine-4,4'-piperidinyl]-butyramide

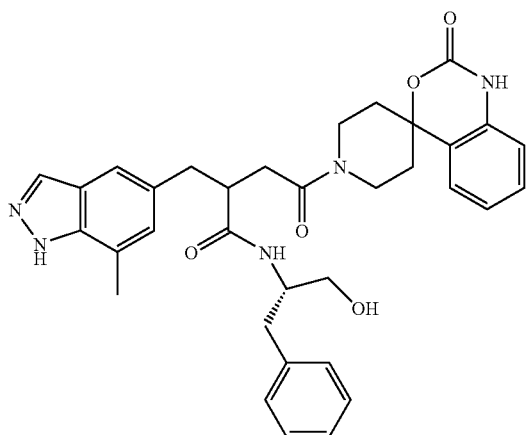

Prepared as described above for (±)-1-[1,4']bipiperidinyl-1'-yl-2-(7-methyl-1H-indazol-5-ylmethyl)-4-[1',2'-dihydro-2'-oxospiro-[4H-3',1-benzoxazine-4,4'-piperidinyl]-butane-1,4-dione. LC/MS: $t_R$=1.38 min, 596 (MH)$^+$.

Example 252

(±)—N-(1-Benzyl-2-hydroxy-ethyl)-2-(7-methyl-1H-indazol-5-ylmethyl)-4-oxo-4-[4-(2-oxo-1,4-dihydro-2H-quinazolin-3-yl)-piperidin-1-yl]-butyramide

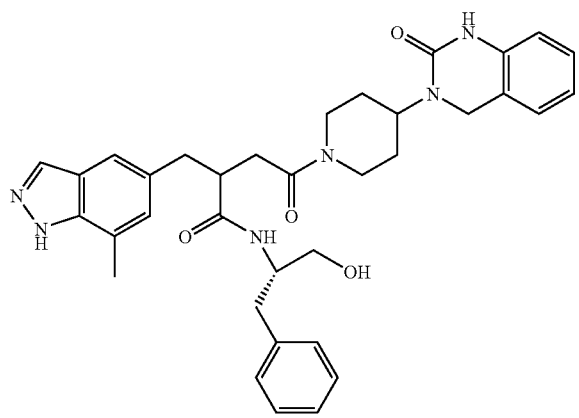

Prepared as described above for (±)-1-[1,4']bipiperidinyl-1'-yl-2-(7-methyl-1H-indazol-5-ylmethyl)-4-[1',2'-dihydro-2'-oxospiro-[4H-3',1-benzoxazine-4,4'-piperidinyl]-butane-1,4-dione. LC/MS: $t_R$=1.50 min, 609 (MH)$^+$. $^1$H NMR (400 MHz, CD$_3$OD) δ 7.90 (1H, s), 7.64-7.84 (1H, m), 6.71-7.42 (11H, m), 4.58 (1H, m), 3.82-4.50 (6H, m), 2.21-3.52 (13H, m), 1.42-1.87 (4H, m).

Example 253

(±)-Phenyl-acetic acid N'-{2-(7-methyl-1H-indazol-5-ylmethyl)-4-oxo-4-[4-(2-oxo-1,4-dihydro-2H-quinazolin-3-yl)-piperidin-1-yl]-butyryl}-hydrazide

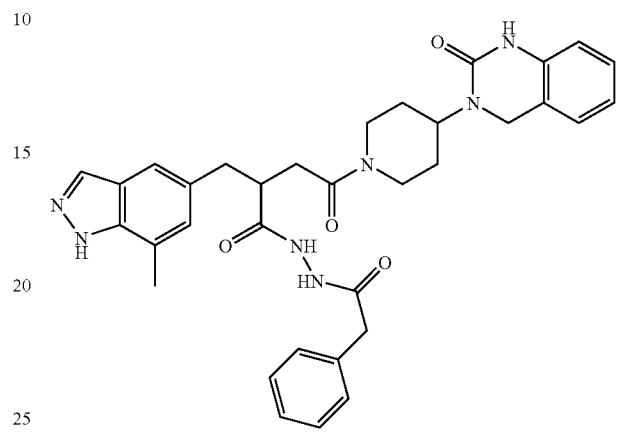

Prepared as described above for (±)-1-[1,4']bipiperidinyl-1'-yl-2-(7-methyl-1H-indazol-5-ylmethyl)-4-[1',2'-dihydro-2'-oxospiro-[4H-3',1-benzoxazine-4,4'-piperidinyl]-butane-1,4-dione. LC/MS: $t_R$=1.43 min, 630 (M+Na)$^+$.

Example 254

(±)-1-[1,4']Bipiperidinyl-1'-yl-4-[4-(8-fluoro-2-oxo-1,4-dihydro-2H-quinazolin-3-yl)-piperidin-1-yl]-2-(7-methyl-1H-indazol-5-ylmethyl)-butane-1,4-dione

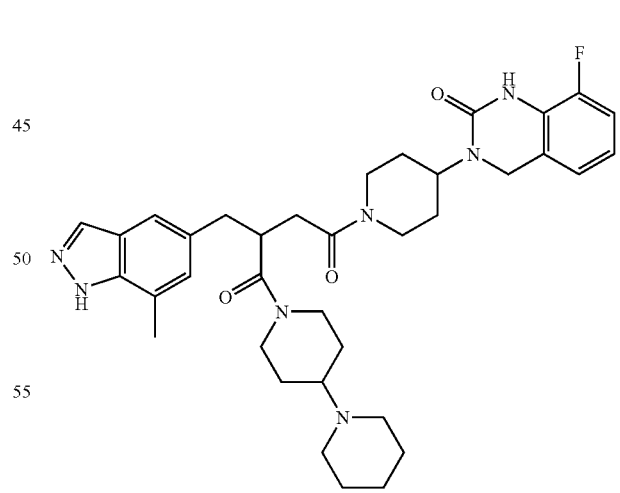

Prepared as described above for (±)-1-[1,4']bipiperidinyl-1'-yl-2-(7-methyl-1H-indazol-5-ylmethyl)-4-[1',2'-dihydro-2'-oxospiro-[4H-3',1-benzoxazine-4,4'-piperidinyl]-butane-1,4-dione. LC/MS: $t_R$=1.18 min, 644 (MH)$^+$. $^1$H NMR (400 MHz, CDCl$_3$) δ 8.00 (1H, s), 6.82-7.40 (6H, m), 4.48-4.70 (3H, m), 4.31 (2H, s), 3.85-4.11 (2H, m), 3.65 (1H, m), 2.70-3.16 (5H, m), 2.53 (3H, s), 0.72-2.52 (23H, m).

Example 255

(±)-1-[1,4']Bipiperidinyl-1'-yl-2-(7-methyl-1H-indazol-5-ylmethyl)-4-[2',3'-dihydro-2'-oxospiro-(piperidine-4,4'-quinazoline]-butane-1,4-dione

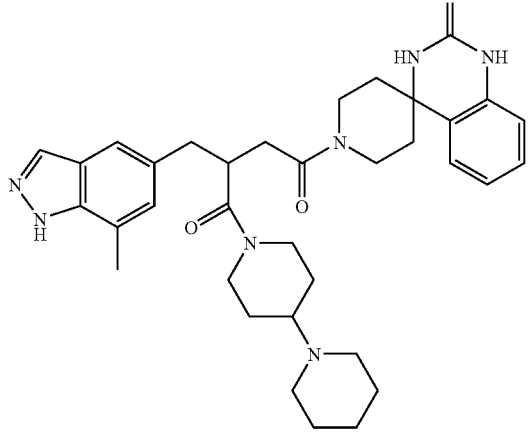

Prepared as described above for (±)-1-[1,4']bipiperidinyl-1'-yl-2-(7-methyl-1H-indazol-5-ylmethyl)-4-[1',2'-dihydro-2'-oxospiro-[4H-3',1-benzoxazine-4,4'-piperidinyl]-butane-1,4-dione. LC/MS: $t_R$=1.09 min, 612 (MH)$^+$.

2-Oxo-2,3-dihydro-benzooxazole-6-carbaldehyde

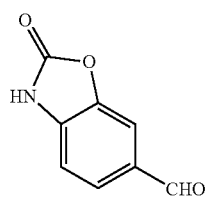

A solution of 6-bromo-3H-benzooxazol-2-one (0.9236 g, 4.31 micromoles) in anhydrous tetrahydrofuran (25 mL) and dimethylformamide (3 mL) under nitrogen was cooled to −78° C. before addition of n-butyllithium (2.5M in hexane) (3.8 mL, 2.2 equiv). After stirring for 10 min at −78° C., 24 mL of sec-butyllithium (1.4 M in cyclohexane, 8 equiv) was added. The reaction was stirred while slowly warming to −40° C. When this temperature was reached, the reaction was quenched by addition of methanol. The reaction mixture was concentrated in vacuo and water was added. The aqueous layer was acidified with 1N HCl (ca. pH 5) and extracted with ethyl acetate (3×50 mL), dried over sodium sulfate, filtered and concentrated to give the product, 0.6402 g (91%). MS (ESI) 164 (MH)$^+$. $^1$H NMR (400 MHz, DMSO-d6) δ 9.90 (1H, s), 7.79 (1H, d, J=8.0 Hz), 7.74 (1H, s), 7.28 (1H, d, J=8.0 Hz).

3-(2-Oxo-2,3-dihydro-benzooxazol-6-ylmethylene)-pentanedioic acid monomethyl ester

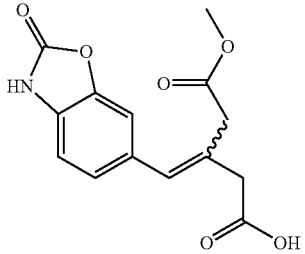

Prepared as described above for 2-(7-methyl-1H-indazol-5-ylmethylene)-succinic acid 1-methyl ester (1.4 g, 90% yield). MS (ESI) 300 (M+Na)$^+$.

(±)-3-(2-Oxo-2,3-dihydro-benzooxazol-6-ylmethyl)-pentanedioic acid monomethyl ester

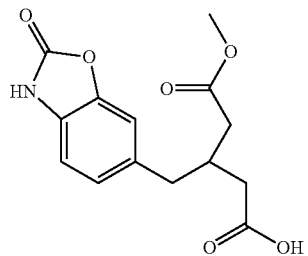

Prepared as described above for (±)-2-(7-methyl-1H-indazol-5-ylmethyl)-succinic acid 1-methyl ester (1.4 g, 99% yield). MS (ESI) 302 (M+Na)$^+$.

(±)-4-Oxo-2-(2-oxo-2,3-dihydro-benzooxazol-6-ylmethyl)-4-[4-(2-oxo-1,4-dihydro-2H-quinazolin-3-yl)-piperidin-1-yl]-butyric acid methyl ester

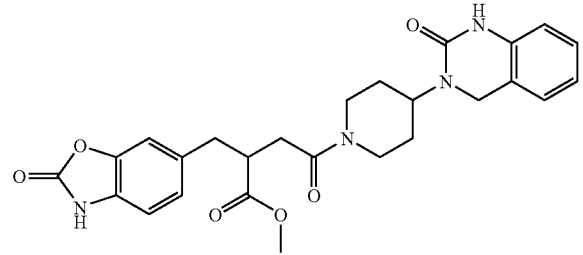

Prepared as described above for (±)-2-(7-methyl-1H-indazol-5-ylmethyl)-4-oxo-4-[1',2'-dihydro-2'-oxospiro-[4H-3',1-benzoxazine-4,4'-piperidinyl]-butyric acid methyl ester. MS (ESI) 493 (MH)$^+$.

(±)-4-Oxo-2-(2-oxo-2,3-dihydro-benzooxazol-6-ylmethyl)-4-[2',3'-dihydro-2'-oxospiro-(piperidine-4,4'-quinazoline)]-butyric acid methyl ester

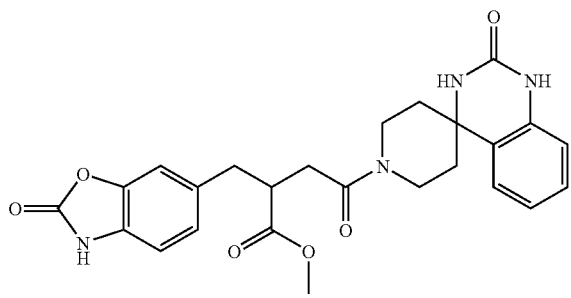

Prepared as described above for (±)-2-(7-methyl-1H-indazol-5-ylmethyl)-4-oxo-4-[1',2'-dihydro-2'-oxospiro-[4H-3',1-benzoxazine-4,4'-piperidinyl]-butyric acid methyl ester. MS (ESI) 479 (MH)$^+$.

(±)-4-Oxo-2-(2-oxo-2,3-dihydro-benzooxazol-6-ylmethyl)-4-[2',3'-dihydro-2'-oxospiro-(piperidine-4,4'-quinazoline)]-butyric acid

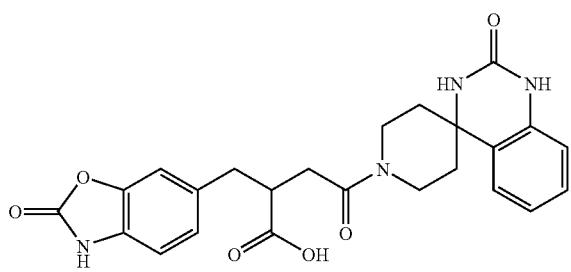

Prepared as described above for (±)-2-(7-methyl-1H-indazol-5-ylmethyl)-4-oxo-4-[1',2'-dihydro-2'-oxospiro-[4H-3',1-benzoxazine-4,4'-piperidinyl]-butyric acid. MS (ESI) 465 (MH)$^+$.

(±)-4-Oxo-2-(2-oxo-2,3-dihydro-benzooxazol-6-ylmethyl)-4-[4-(2-oxo-1,4-dihydro-2H-quinazolin-3-yl)-piperidin-1-yl]-butyric acid

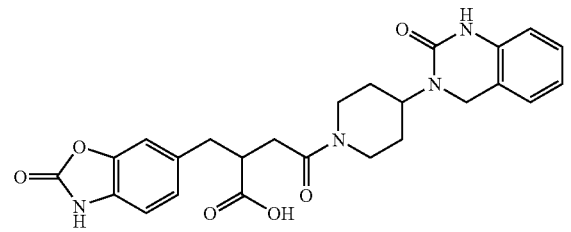

Prepared as described above for (±)-2-(7-methyl-1H-indazol-5-ylmethyl)-4-oxo-4-[1',2'-dihydro-2'-oxospiro-[4H-3',1-benzoxazine-4,4'-piperidinyl]-butyric acid. MS (ESI) 479 (MH)$^+$.

Example 256

(±)-1-(4-Cyclohexyl-piperazin-1-yl)-2-(2-oxo-2,3-dihydro-benzooxazol-6-ylmethyl)-4-[4-(2-oxo-1,4-dihydro-2H-quinazolin-3-yl)-piperidin-1-yl]-butane-1,4-dione

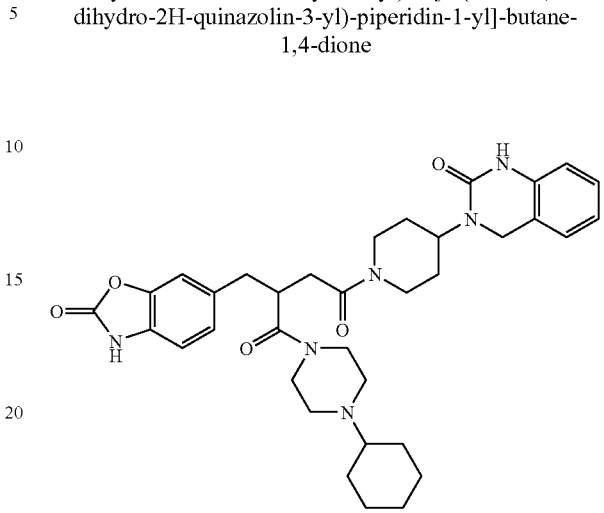

Prepared as described above for (±)-1-[1,4']bipiperidinyl-1'-yl-2-(7-methyl-1H-indazol-5-ylmethyl)-4-[1',2'-dihydro-2'-oxospiro-[4H-3',1-benzoxazine-4,4'-piperidinyl]-butane-1,4-dione. LC/MS: $t_R$=1.10 min, 629 (MH)$^+$.

Example 257

(±)-1-[1,4']Bipiperidinyl-1'-yl-2-(2-oxo-2,3-dihydro-benzooxazol-6-ylmethyl)-4-[4-(2-oxo-1,4-dihydro-2H-quinazolin-3-yl)-piperidin-1-yl]-butane-1,4-dione

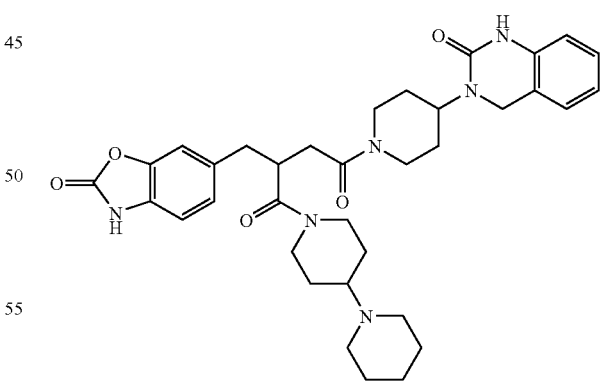

Prepared as described above for (±)-1-[1,4']bipiperidinyl-1'-yl-2-(7-methyl-1H-indazol-5-ylmethyl)-4-[1',2'-dihydro-2'-oxospiro-[4H-3',1-benzoxazine-4,4'-piperidinyl]-butane-1,4-dione. LC/MS: $t_R$=1.08 min, 629 (MH)$^+$. $^1$H NMR (400 MHz, CDCl$_3$) δ 9.89 (1H, s), 8.28 (1H, d, J=11.2 Hz), 6.90-7.25 (5H, m), 6.75 (1H, d, J=8.0 Hz), 4.40-4.79 (3H, m), 4.35 (2H, s), 2.27-3.98 (19H, m), 1.46-2.10 (9H, m), 1.36 (1H, m), 1.08 (1H, m), 0.12 (1H, m).

Example 258

(±)-1-[1,4']Bipiperidinyl-1'-yl-2-(2-oxo-2,3-dihydro-benzooxazol-6-ylmethyl)-4-[2',3'-dihydro-2'-oxospiro-(piperidine-4,4'-quinazoline)]-butane-1,4-dione

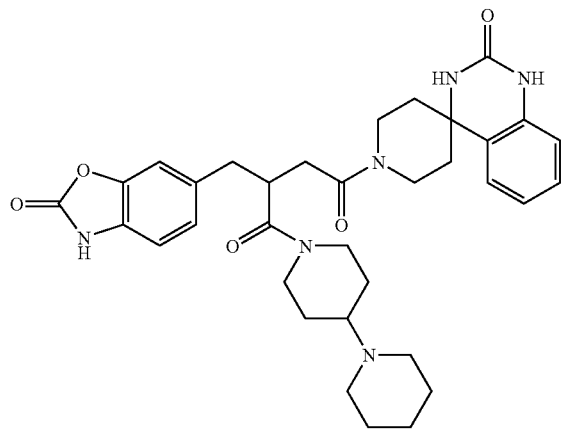

Prepared as described above for (±)-1-[1,4']bipiperidinyl-1'-yl-2-(7-methyl-1H-indazol-5-ylmethyl)-4-[1',2'-dihydro-2'-oxospiro-[4H-3',1-benzoxazine-4,4'-piperidinyl]-butane-1,4-dione. LC/MS: $t_R$=1.02 min, 615 (MH)$^+$.

Example 259

(±)-1-(4-cyclohexyl-piperazin-1-yl)-2-(2-oxo-2,3-dihydro-benzooxazol-6-ylmethyl)-4-[2',3'-dihydro-2'-oxospiro-(piperidine-4,4'-quinazoline)]-butane-1,4-dione

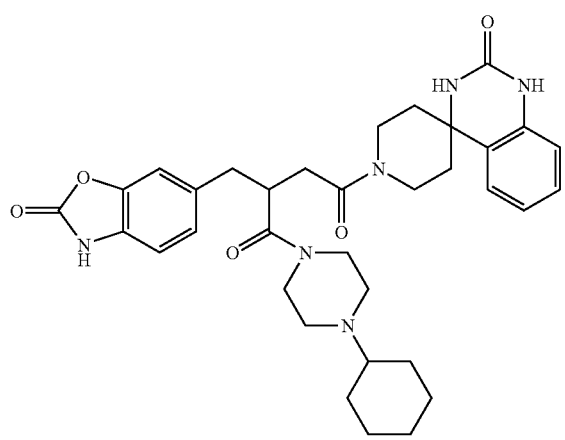

Prepared as described above for (±)-1-[1,4']bipiperidinyl-1'-yl-2-(7-methyl-1H-indazol-5-ylmethyl)-4-[1',2'-dihydro-2'-oxospiro-[4H-3',1-benzoxazine-4,4'-piperidinyl]-butane-1,4-dione. LC/MS: $t_R$=1.04 min, 615 (MH)$^+$.

Example 260

(±)-4-(2-Oxo-1,4-dihydro-2H-quinazolin-3-yl)-piperidine-1-carboxylic acid [2-(4-cyclohexyl-piperazin-1-yl)-1-(7-methyl-1H-indazol-5-ylmethyl)-2-oxo-ethyl]-amide

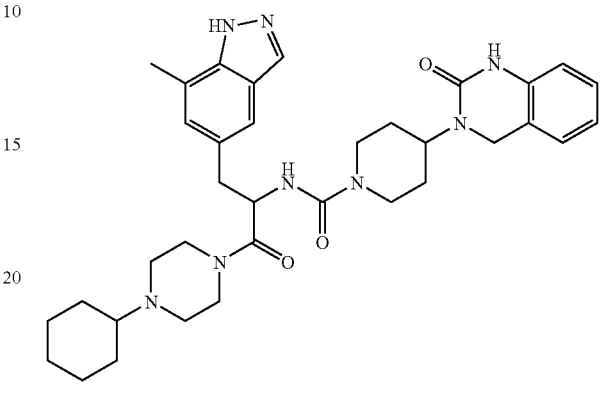

Prepared as described above for Example 16. $^1$H-NMR (CD$_3$OD, 500 MHz) δ 0.81 (1H, m), 0.89 (1H, m), 1.02 (1H, m), 1.1-2.0 (12H, m), 2.23 (1H, d), 2.47 (1H, d), 2.61 (3H, s), 2.90 (4H, t), 3.08 (4H, m), 3.2-3.5 (4H, m), 3.82 (1H, m), 4.14 (2H, d), 4.29 (2H, s), 4.40 (1H, t), 6.80 (1H, d), 6.95 (1H, t), 7.12 (3H, m), 7.47 (1H, s), 8.01 (1H, s). Mass spec.: 627.47 (MH)$^+$.

Example 261

(±)-4-(2-Oxo-1,4-dihydro-2H-quinazolin-3-yl)-piperidine-1-carboxylic acid[2-[4-(4-fluoro-phenyl)-piperazin-1-yl]-1-(7-methyl-1H-indazol-5-ylmethyl)-2-oxo-ethyl]-amide

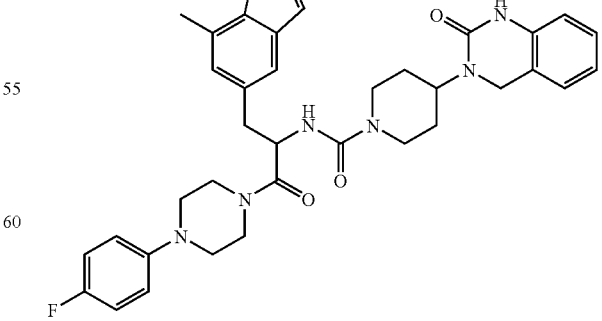

Prepared as described above for Example 16. LC/MS: $t_R$=2.34 min, 621.42 (MH)$^+$.

Example 262

(±)-3-(7-Methyl-1H-indazol-5-yl)-2-{[4-(2-oxo-1,4-dihydro-2H-quinazolin-3-yl)-piperidine-1-carbonyl]-amino}-propionic acid tert-butyl ester

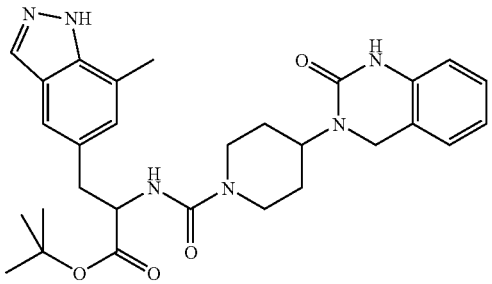

A solution of (±)-3-(7-methyl-1H-indazol-5-yl)-2-{[4-(2-oxo-1,4-dihydro-2H-quinazolin-3-yl)-piperidine-1-carbonyl]-amino}-propionic acid (50 mg, 0.105 mmol) and dicyclohexylcarbodiimide (25 mg, 0.12 mmol) in dimethylformamide was stirred for 30 min at room temperature, and then pentafluorophenol (26 mg, 1.3 mmol) was added. Stirring was continued at room temperature overnight, and then the solvent was removed, the residue was dried under high vacuum for 4 h. The crude pentafluorophenyl ester was used without further purification in the next step.

To a solution of tert-butyl alcohol (10 equiv.) in tetrahydrofuran at −78° C. under nitrogen was added 1.4M sec-butyllithium in cyclohexane (10 equiv.). After 10-15 min, a solution of pentafluorophenol ester (1 equiv.) in tetrahydrofuran was added. The reaction mixture was stirred at room temperature overnight. The solvents were removed in vacuo, and the residue was purified by preparative-HPLC to give the desired compound. $^1$H-NMR(CD$_3$OD) δ 1.40 (s, 9H) 1.56 (m, 4H), 2.54 (s, 3H) 2.85 (m, 2H) 3.05 (m, 1H) 3.19 (m, 1H) 4.14 (m, 4H) 4.44 (m, 2H) 6.76 (d, J=7.68 Hz, 1H) 6.93 (t, J=7.5 Hz, 1H) 7.10 (m, 3H) 7.14 (s, 1H) 7.97 (s, 1H). LC/MS: $t_R$=2.19 min, 533.36 (MH)$^+$.

Example 263

(±)-3-(7-Methyl-1H-indazol-5-yl)-2-{[4-(2-oxo-1,4-dihydro-2H-quinazolin-3-yl)-piperidine-1-carbonyl]-amino}-propionic acid 1-methyl cyclohexyl ester

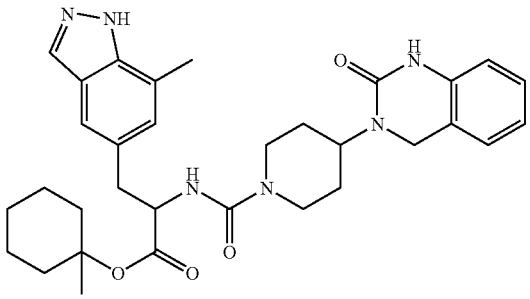

Prepared as described above for (±)-3-(7-methyl-1H-indazol-5-yl)-2-{[4-(2-oxo-1,4-dihydro-2H-quinazolin-3-yl)-piperidine-1-carbonyl]-amino}-propionic acid tert-butyl ester. LC/MS: $t_R$=2.47 min, 574.39 (MH)$^+$.

Example 264

(±)-3-(7-Methyl-1H-indazol-5-yl)-2-{[4-(2-oxo-1,4-dihydro-2H-quinazolin-3-yl)-piperidine-1-carbonyl]-amino}-propionic acid 1-aza-bicyclo[2.2.2]oct-3-yl ester

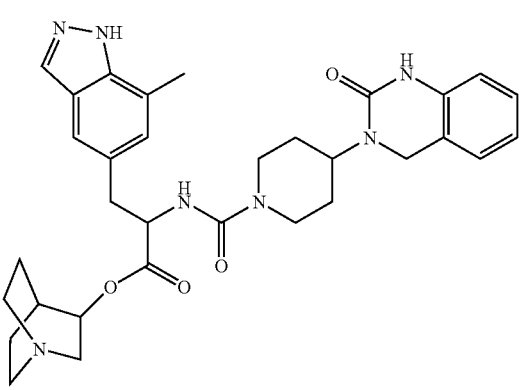

To a solution of (±)-3-(7-methyl-1H-indazol-5-yl)-2-{[4-(2-oxo-1,4-dihydro-2H-quinazolin-3-yl)-piperidine-1-carbonyl]-amino}-propionic acid (50 mg, 0.105 mmol), EDCI (100 mg), and 4-dimethylaminopyridine (0.2 equiv.) in dimethylformamide was added aza-bicyclo[2.2.2]oct-3-yl alcohol (0.525 mmol, 5 equiv.). The mixture was stirred at room temperature overnight. The solvent was removed in vacuo and the residue was dissolved in ethyl acetate, washed with brine, dried over magnesium sulfate, and purified by preparative HPLC to yield the desired compound. LC/MS: $t_R$=1.62 min, 586.41 (MH)$^+$.

Example 265

(±)-3-(7-Methyl-1H-indazol-5-yl)-2-{[4-(2-oxo-1,4-dihydro-2H-quinazolin-3-yl)-piperidine-1-carbonyl]-amino}-propionic acid piperidin-4-yl ester

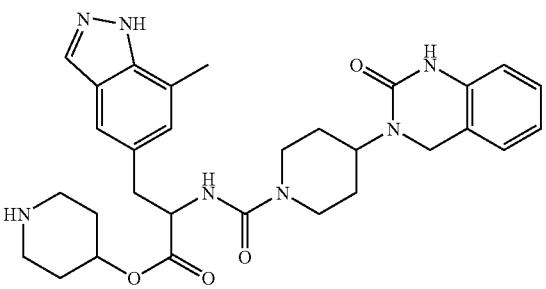

Prepared as described above for (±)-3-(7-methyl-1H-indazol-5-yl)-2-{[4-(2-oxo-1,4-dihydro-2H-quinazolin-3-yl)-piperidine-1-carbonyl]-amino}-propionic acid 1-aza-bicyclo[2.2.2]oct-3-yl ester. LC/MS: $t_R$=1.58 min, 560.37 (MH)$^+$.

311

Example 266

(±)-4-(3-(7-Methyl-1H-indazol-5-yl)-2-{[4-(2-oxo-1,4-dihydro-2H-quinazolin-3-yl)-piperidine-1-carbonyl]-amino}-propionyloxy)-piperidine-1-carboxylic acid tert-butyl ester

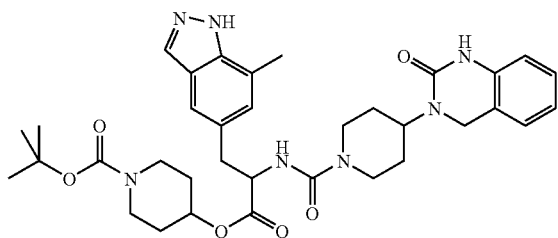

Prepared as described above for (±)-3-(7-methyl-1H-indazol-5-yl)-2-{[4-(2-oxo-1,4-dihydro-2H-quinazolin-3-yl)-piperidine-1-carbonyl]-amino}-propionic acid 1-aza-bicyclo[2.2.2]oct-3-yl ester. LC/MS: $t_R$=2.38 min, 660.42 $(MH)^+$.

Example 267

(±)-3-(7-Methyl-1H-indazol-5-yl)-2-{[4-(2-oxo-1,4-dihydro-2H-quinazolin-3-yl)-piperidine-1-carbonyl]-amino}-propionic acid 3,4,5,6-tetrahydro-2H-[1,4']bipyridinyl-4-yl ester

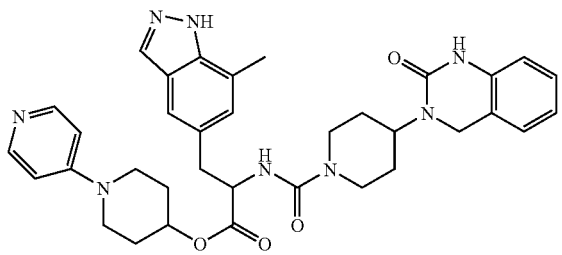

Prepared as described above for (±)-3-(7-methyl-1H-indazol-5-yl)-2-{[4-(2-oxo-1,4-dihydro-2H-quinazolin-3-yl)-piperidine-1-carbonyl]-amino}-propionic acid 1-aza-bicyclo[2.2.2]oct-3-yl ester. LC/MS: $t_R$=1.67 min, 637.43 $(MH)^+$.

Example 268

(±)-3-(7-Methyl-1H-indazol-5-yl)-2-{[4-(2-oxo-1,4-dihydro-2H-quinazolin-3-yl)-piperidine-1-carbonyl]-amino}-propionic acid 1-diethylamino-1-methyl-ethyl ester

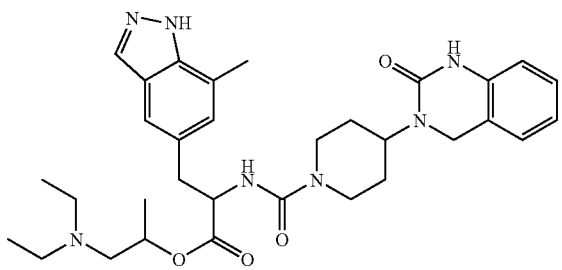

Prepared as described above for (±)-3-(7-methyl-1H-indazol-5-yl)-2-{[4-(2-oxo-1,4-dihydro-2H-quinazolin-3-yl)-piperidine-1-carbonyl]-amino}-propionic acid 1-aza-bicyclo[2.2.2]oct-3-yl ester. LC/MS: $t_R$=1.66 min, 590.44 $(MH)^+$.

312

Example 269

(±)-3-(7-Methyl-1H-indazol-5-yl)-2-{[4-(2-oxo-1,4-dihydro-2H-quinazolin-3-yl)-piperidine-1-carbonyl]-amino}-propionic acid 1,1-dimethyl-2-phenyl-ethyl ester

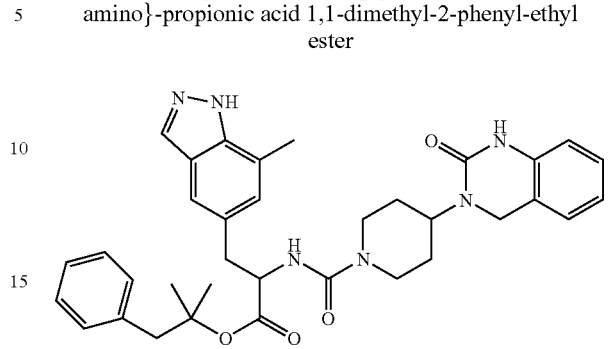

Prepared as described above for (±)-3-(7-methyl-1H-indazol-5-yl)-2-{[4-(2-oxo-1,4-dihydro-2H-quinazolin-3-yl)-piperidine-1-carbonyl]-amino}-propionic acid t-butyl ester. LC/MS: $t_R$=2.52 min, 609.46 $(MH)^+$.

Example 270

(±)-3-(7-Methyl-1H-indazol-5-yl)-2-{[4-(2-oxo-1,4-dihydro-2H-quinazolin-3-yl)-piperidine-1-carbonyl]-amino}-propionic acid 1,1-dimethyl-3-phenyl-propyl ester

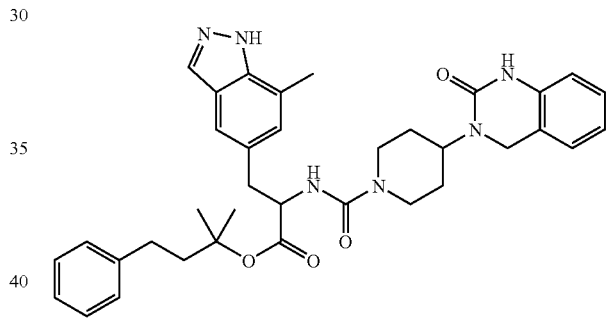

Prepared as described above for (±)-3-(7-methyl-1H-indazol-5-yl)-2-{[4-(2-oxo-1,4-dihydro-2H-quinazolin-3-yl)-piperidine-1-carbonyl]-amino}-propionic acid t-butyl ester. LC/MS: $t_R$=2.61 min, 623.48 $(MH)^+$.

Example 271

(±)-3-(7-Methyl-1H-indazol-5-yl)-2-{[4-(2-oxo-1,4-dihydro-2H-quinazolin-3-yl)-piperidine-1-carbonyl]-amino}-propionic acid ethyl ester

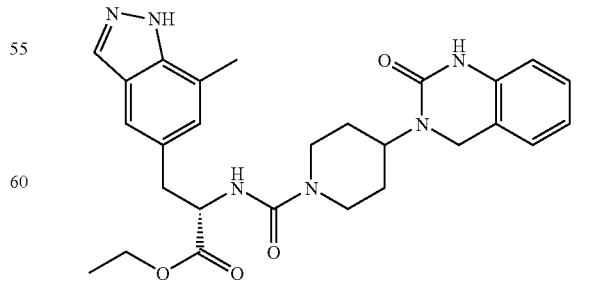

Prepared as described above for (±)-3-(7-methyl-1H-indazol-5-yl)-2-{[4-(2-oxo-1,4-dihydro-2H-quinazolin-3-yl)-piperidine-1-carbonyl]-amino}-propionic acid t-butyl ester. LC/MS: $t_R$=1.98 min, 505.32 (MH)⁺.

Example 272

(±)-1-(7-Methyl-1H-indazol-5-ylmethyl)-2-[1-pyridin-4-yl-methyl]-2-oxoethyl]-2',3'-dihydro-2'-oxospiro-[piperidine-4,4'-(1H)-quinazoline]-1-carboxamide

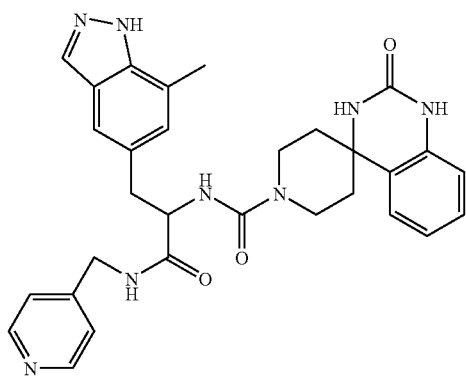

Prepared as described above for Example 16. LC/MS: $t_R$=1.49 min, 553.12 (MH)⁺.

Example 273

(±)-1-(7-Methyl-1H-indazol-5-ylmethyl)-2-[1-pyridin-4-yl-piperazinyl]-2-oxoethyl]-2',3'-dihydro-2'-oxospiro-[piperidine-4,4'-(1H)-quinazoline]-1-carboxamide

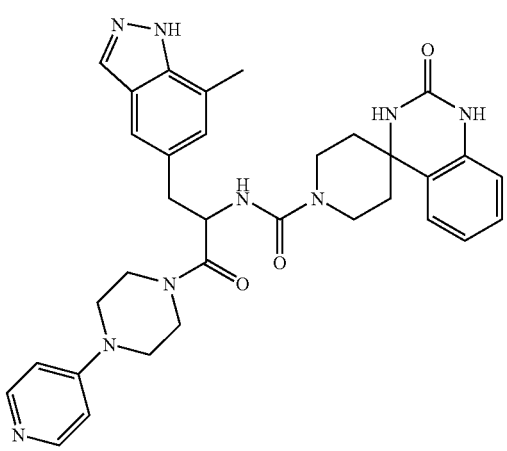

Prepared as described above for Example 16. LC/MS: $t_R$=1.56 min, 608.18 (MH)⁺.

Example 274

(±)-1-(7-Methyl-1H-indazol-5-ylmethyl)-2-[(2-dimethylamino-ethyl-ethyl carbamoyl)-2-oxoethyl]-2',3'-dihydro-2'-oxospiro-[piperidine-4,4'-(1H)-quinazoline]-1-carboxamide

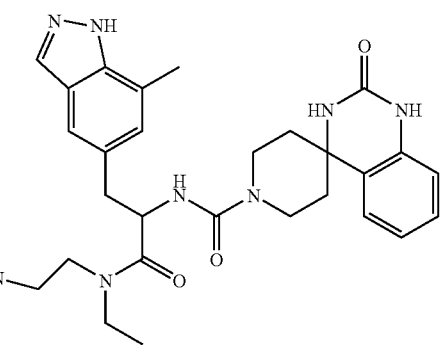

Prepared as described above for Example 16. LC/MS: $t_R$=1.58 min, 561.20 (MH)⁺.

Example 275

(±)-1-(7-Methyl-1H-indazol-5-ylmethyl)-2-[1-pyridin-4-yl-piperazinyl]-11',2'-dihydro-2'-oxospiro-[4H-3' 1-benzoxazine-4,4'-piperidine]-1-carboxamide

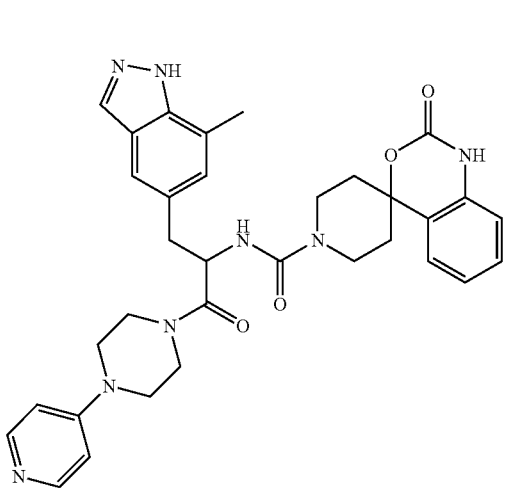

Prepared as described above for Example 16. LC/MS: $t_R$=1.56 min, 609.14 (MH)⁺.

Example 276

(±)-1-(7-Methyl-1H-indazol-5-ylmethyl)-2-[1-pyridin-2-yl-piperazinyl]-2-oxoethyl]-1',2'-dihydro-2'-oxospiro-[4H-3',1-benzoxazine-4,4'-piperidine]-1-carboxamide

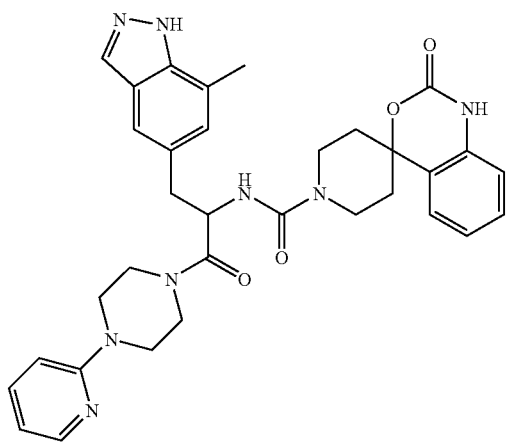

Prepared as described above for Example 16. LC/MS: $t_R$=1.57 min, 609.17 (MH)$^+$.

Example 277

(R)-4-(2-Oxo-1,4-dihydro-2H-quinazolin-3yl)-piperidine-1d-carboxylic acid[2-[1,4']bipiperidinyl-1'-yl-1-(7-methyl-1H-indazol-5-ylmethyl)-2-oxo-ethyl]amide

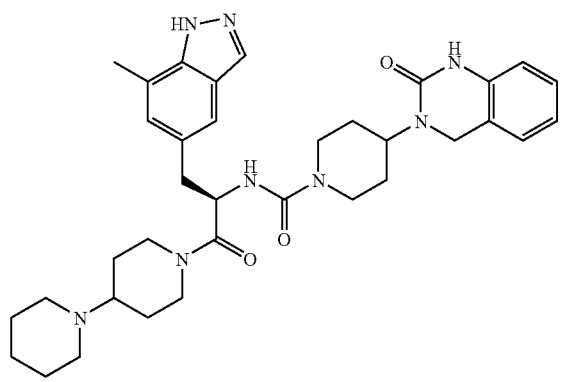

Prepared as described above for Example 16. $^1$H-NMR (CD$_3$OD, 500 MHz) δ −0.27 (1H, m), 0.75 (1H, m), 1.1-2.0 (12H, m), 2.10 (2H, m), 2.4-2.5 (3H, m), 2.57 (3H, s), 2.68 (2H, m), 2.92 (4H, m), 3.10 (4H, m), 3.9-5.1 (4H, several m), 6.82 (1H, d), 6.96 (1H, t), 7.18 (3H, m), 7.50 (1H, s), 8.05 (1H, s). LC/MS: $t_R$=1.68 min, 627.42 (MH)$^+$.

Example 278

(R)-1-(7-Methyl-1H-indazol-5-ylmethyl)-2-[1,4-bipiperidin]-1-yl-2-oxoethyl]-2',3'-dihydro-2'-oxospiro-[piperidine-4,4'-(1H)-quinazoline]-1-carboxamide

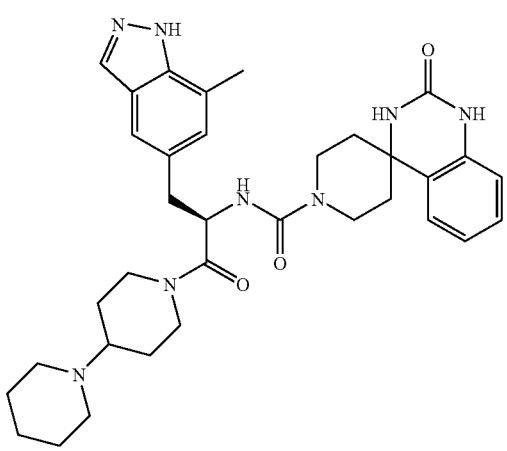

Prepared as described above for Example 16. LC/MS: $t_R$=1.63 min, 613.36 (MH)$^+$.

Among other compounds envisaged within the present invention and capable of being made according to the description provided herein or those methods known to those skilled in the art include the following prophetic examples:

4-(2-Oxo-1,4-dihydro-2H-quinazolin-3-yl)-piperidine-1-carboxylic acid[2-[1,4']bipiperidinyl-1'-yl-1-(7-bromo-1H-indazol-5-ylmethyl)-2-oxo-ethyl]-amide

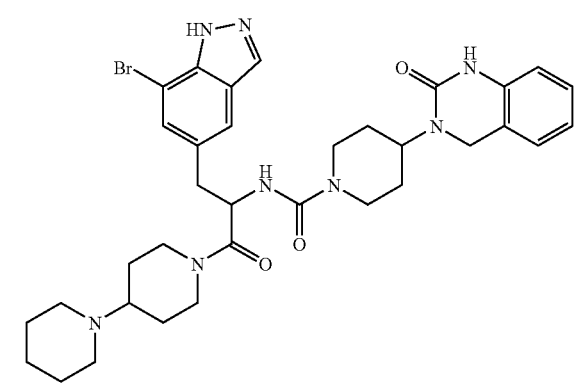

317

4-(2-Oxo-1,4-dihydro-2H-quinazolin-3-yl)-piperidine-1-carboxylic acid [2-oxo-1-(2-oxo-2,3-dihydro-benzooxazol-6-ylmethyl)-2-(4-pyridin-4-yl-piperazin-1-yl)-ethyl]-amide

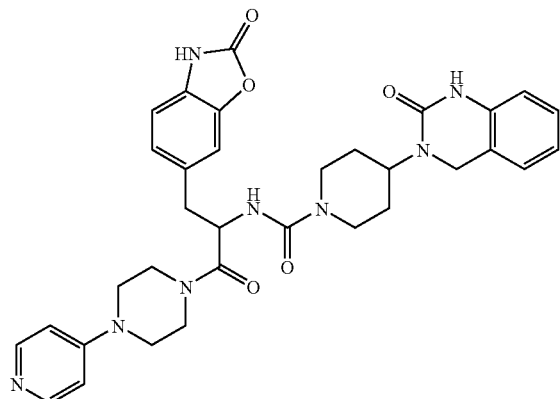

4-(2-Oxo-1,4-dihydro-2H-quinazolin-3-yl)-piperidine-1-carboxylic acid [2-oxo-1-(2-oxo-2,3-dihydro-benzooxazol-6-ylmethyl)-2-piperidin-1-yl-ethyl]-amide

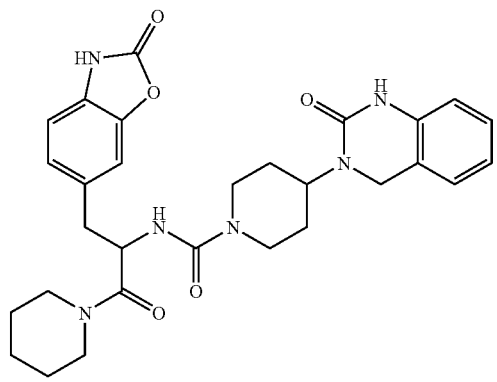

4-(2-Oxo-1,4-dihydro-2H-quinazolin-3-yl)-piperidine-1-carboxylic acid [2-(4-methyl-piperazin-1-yl)-2-oxo-1-(2-oxo-2,3-dihydro-benzooxazol-6-ylmethyl)-ethyl]-amide

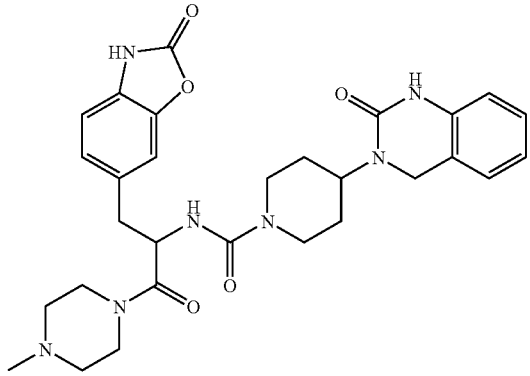

318

4-(2-Oxo-1,4-dihydro-2H-quinazolin-3-yl)-piperidine-1-carboxylic acid[2-[1,4']bipiperidinyl-1'-yl-1-(4-methyl-2-oxo-2,3-dihydro-benzooxazol-6-ylmethyl)-2-oxo-ethyl]-amide

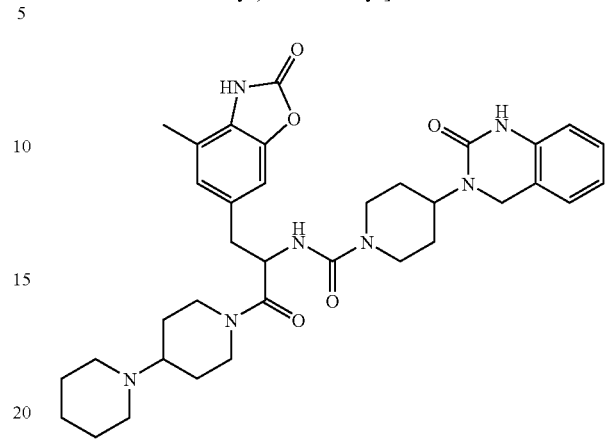

4-(2-Oxo-1,4-dihydro-2H-quinazolin-3-yl)-piperidine-1-carboxylic acid [1-(4-methyl-2-oxo-2,3-dihydro-benzooxazol-6-ylmethyl)-2-oxo-2-piperidin-1-yl-ethyl]-amide

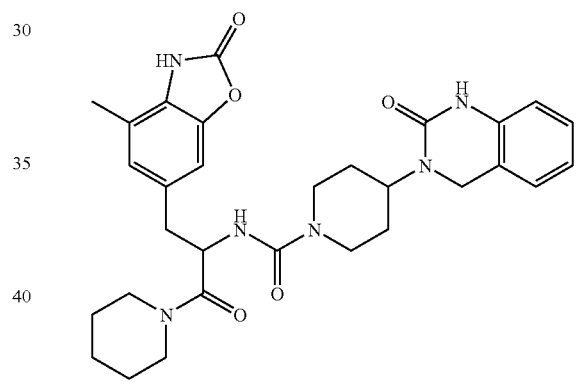

4-(2-Oxo-1,4-dihydro-2H-quinazolin-3-yl)-piperidine-1-carboxylic acid [1-(4-chloro-2-oxo-2,3-dihydro-benzooxazol-6-ylmethyl)-2-oxo-2-piperidin-1-yl-ethyl]-amide

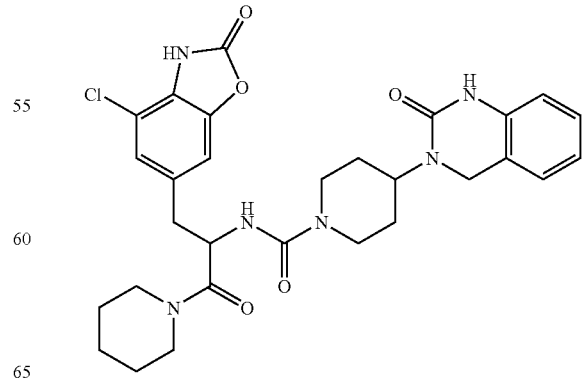

319

4-(2-Oxo-1,4-dihydro-2H-quinazolin-3-yl)-piperidine-1-carboxylic acid [1-dimethylcarbamoyl-2-(4-methyl-2-oxo-2,3-dihydro-benzooxazol-6-yl)-ethyl]-amide

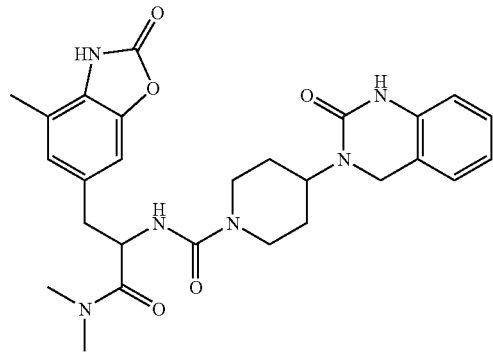

4-(2-Oxo-1,4-dihydro-2H-quinazolin-3-yl)-piperidine-1-carboxylic acid [2-(4-chloro-2-oxo-2,3-dihydro-benzooxazol-6-yl)-1-dimethylcarbamoyl-ethyl]-amide

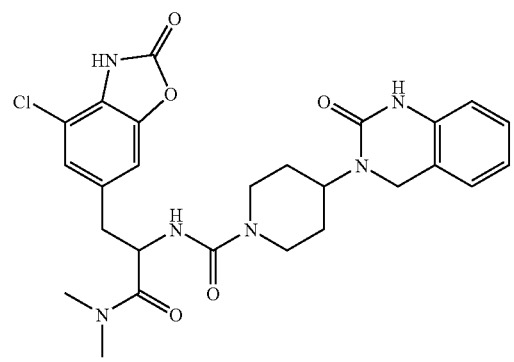

4-(2-Oxo-1,4-dihydro-2H-quinazolin-3-yl)-piperidine-1-carboxylic acid [1-(4-methyl-2-oxo-2,3-dihydro-benzooxazol-6-ylmethyl)-2-oxo-2-(4-pyridin-4-yl-piperazin-1-yl)-ethyl]-amide

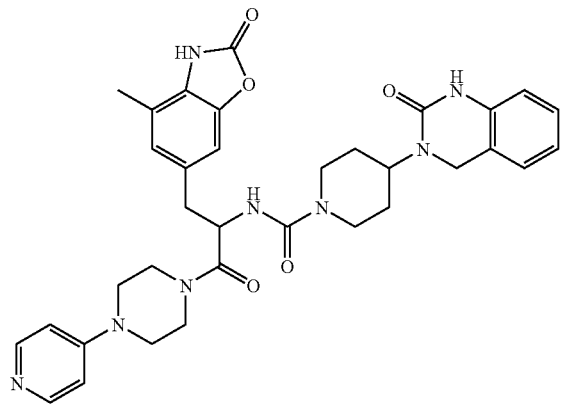

320

4-(2-Oxo-1,4-dihydro-2H-quinazolin-3-yl)-piperidine-1-carboxylic acid [1-(4-chloro-2-oxo-2,3-dihydro-benzooxazol-6-ylmethyl)-2-oxo-2-(4-pyridin-4-yl-piperazin-1-yl)-ethyl]-amide

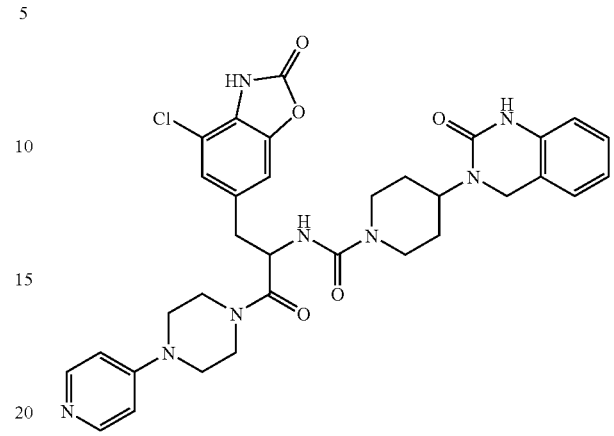

4-(2-Oxo-1,4-dihydro-2H-quinazolin-3-yl)-piperidine-1-carboxylic acid[2-[1,4']bipiperidinyl-1'-yl-1-(4-ethyl-2-oxo-2,3-dihydro-benzooxazol-6-ylmethyl)-2-oxo-ethyl]-amide

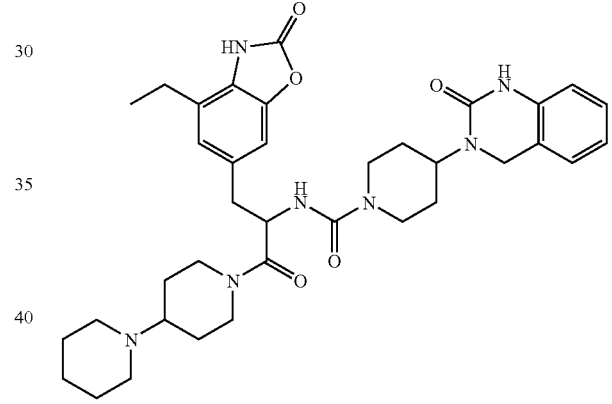

4-(2-Oxo-1,4-dihydro-2H-quinazolin-3-yl)-piperidine-1-carboxylic acid[2-[1,4']bipiperidinyl-1'-yl-1-(7-methyl-2-oxo-2,3-dihydro-1H-benzoimidazol-5-ylmethyl)-2-oxo-ethyl]-amide

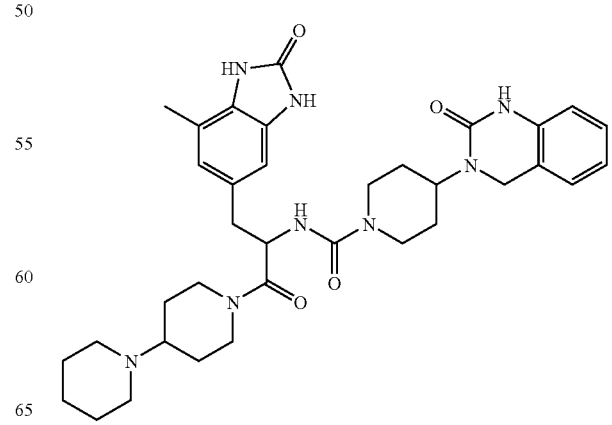

321

4-(2-Oxo-1,4-dihydro-2H-quinazolin-3-yl)-piperidine-1-carboxylic acid[2-[1,4']bipiperidinyl-1'-yl-1-(7-chloro-2-oxo-2,3-dihydro-1H-benzoimidazol-5-ylmethyl)-2-oxo-ethyl]-amide

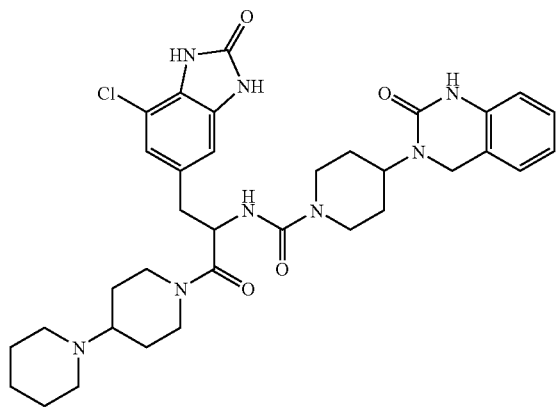

4-(2-Oxo-1,4-dihydro-2H-quinazolin-3-yl)-piperidine-1-carboxylic acid[2-[1,4']bipiperidinyl-1'-yl-1-(7-ethyl-2-oxo-2,3-dihydro-1H-benzoimidazol-5-ylmethyl)-2-oxo-ethyl]-amide

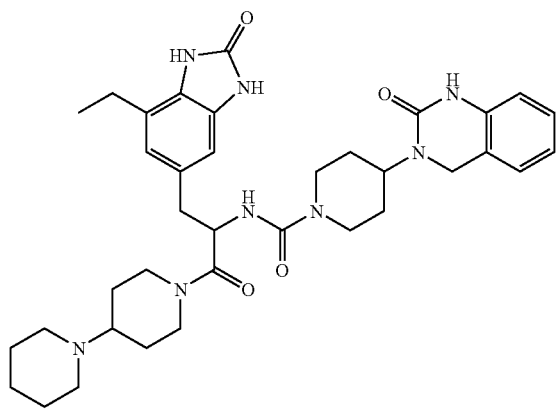

4-(2-Oxo-1,4-dihydro-2H-quinazolin-3-yl)-piperidine-1-carboxylic acid[2-[1,4']bipiperidinyl-1'-yl-1-(3-methyl-2-oxo-2,3-dihydro-1H-benzoimidazol-5-ylmethyl)-2-oxo-ethyl]-amide

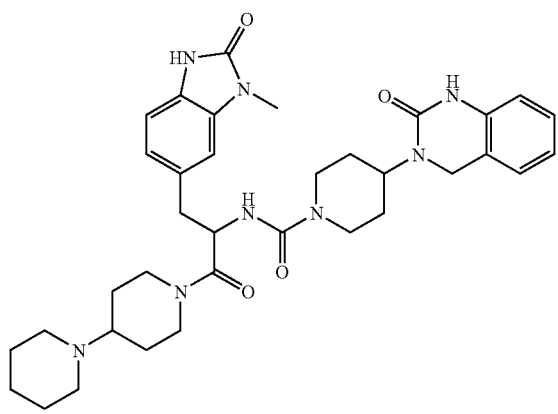

322

4-(2-Oxo-1,4-dihydro-2H-quinazolin-3-yl)-piperidine-1-carboxylic acid[2-[1,4']bipiperidinyl-1'-yl-1-(3,7-dimethyl-2-oxo-2,3-dihydro-1H-benzoimidazol-5-ylmethyl)-2-oxo-ethyl]-amide

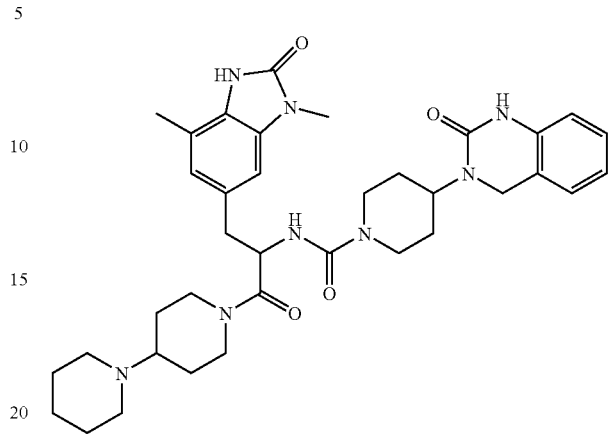

4-(2-Oxo-1,4-dihydro-2H-quinazolin-3-yl)-piperidine-1-carboxylic acid[2-[1,4']bipiperidinyl-1'-yl-1-(7-chloro-3-methyl-2-oxo-2,3-dihydro-1H-benzoimidazol-5-ylmethyl)-2-oxo-ethyl]-amide

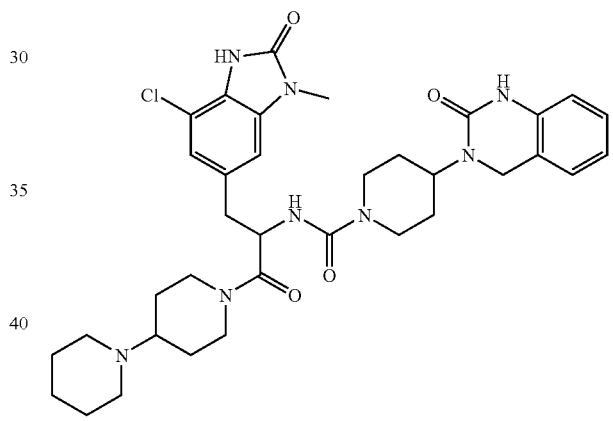

4-(2-Oxo-1,4-dihydro-2H-quinazolin-3-yl)-piperidine-1-carboxylic acid[2-[1,4']bipiperidinyl-1'-yl-1-(7-ethyl-3-methyl-2-oxo-2,3-dihydro-1H-benzoimidazol-5-ylmethyl)-2-oxo-ethyl]-amide

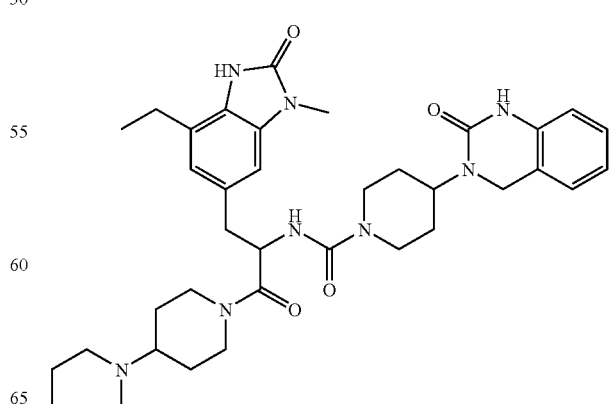

323

3-(7-Methyl-1H-indazol-5-yl)-2-{[4-(2-oxo-1,4-dihydro-2H-quinazolin-3-yl)-piperidine-1-carbonyl]-amino}-propionic acid isopropyl ester

324

3-(7-Ethyl-1H-indazol-5-yl)-2-{[4-(2-oxo-1,4-dihydro-2H-quinazolin-3-yl)-piperidine-1-carbonyl]-amino}-propionic acid tert-butyl ester

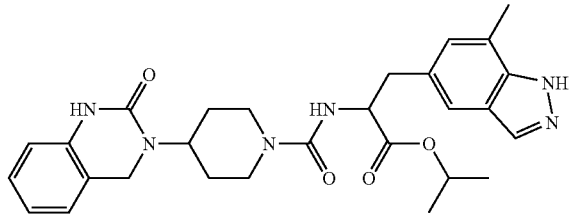

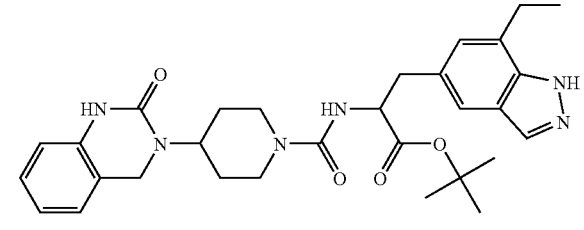

3-(7-Chloro-1H-indazol-5-yl)-2-{[4-(2-oxo-1,4-dihydro-2H-quinazolin-3-yl)-piperidine-1-carbonyl]-amino}-propionic acid isopropyl ester 3-(7-Chloro-1H-indazol-5-yl)-2-{[4-(2-oxo-1,4-dihydro-2H-quinazolin-3-yl)-piperidine-1-carbonyl]-amino}-propionic acid cyclohexyl ester

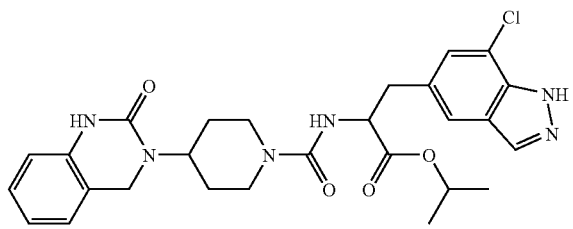

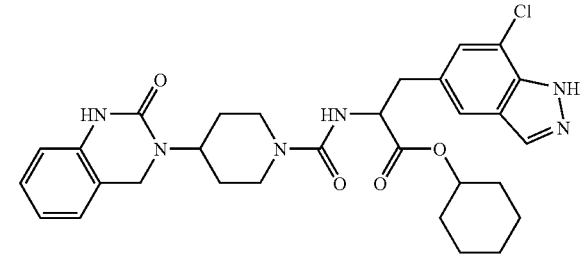

3-(7-Ethyl-1H-indazol-5-yl)-2-{[4-(2-oxo-1,4-dihydro-2H-quinazolin-3-yl)-piperidine-1-carbonyl]-amino}-propionic acid isopropyl ester 3-(7-Ethyl-1H-indazol-5-yl)-2-{[4-(2-oxo-1,4-dihydro-2H-quinazolin-3-yl)-piperidine-1-carbonyl]-amino}-propionic acid cyclohexyl ester

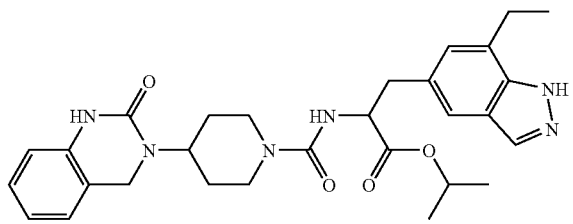

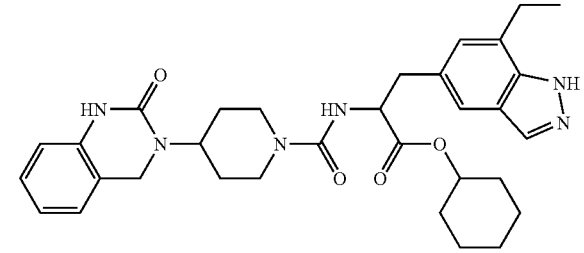

3-(7-Chloro-1H-indazol-5-yl)-2-{[4-(2-oxo-1,4-dihydro-2H-quinazolin-3-yl)-piperidine-1-carbonyl]-amino}-propionic acid tert-butyl ester 3-(7-Chloro-1H-indazol-5-yl)-2-{[4-(2-oxo-1,4-dihydro-2H-quinazolin-3-yl)-piperidine-1-carbonyl]-amino}-propionic acid 1-methyl-piperidin-4-yl ester

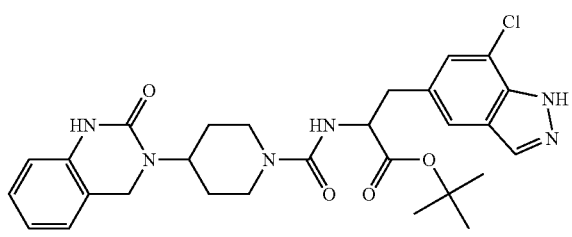

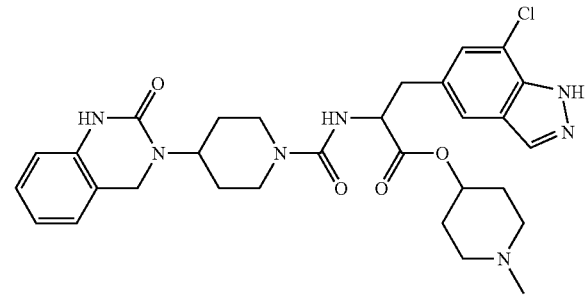

325

3-(7-Ethyl-1H-indazol-5-yl)-2-{[4-(2-oxo-1,4-dihydro-2H-quinazolin-3-yl)-piperidine-1-carbonyl]-amino}-propionic acid 1-methyl-piperidin-4-yl ester

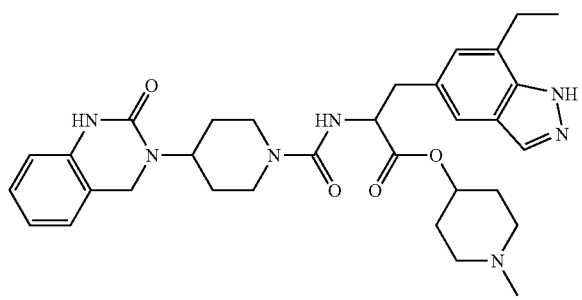

3-(7-Chloro-1H-indazol-5-yl)-2-{[4-(2-oxo-1,4-dihydro-2H-quinazolin-3-yl)-piperidine-1-carbonyl]-amino}-propionic acid 1-methyl-cyclohexyl ester

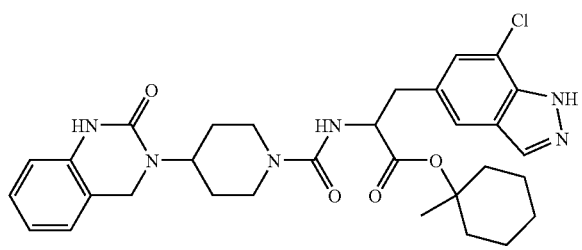

3-(7-Ethyl-1H-indazol-5-yl)-2-{[4-(2-oxo-1,4-dihydro-2H-quinazolin-3-yl)-piperidine-1-carbonyl]-amino}-propionic acid 1-methyl-cyclohexyl ester

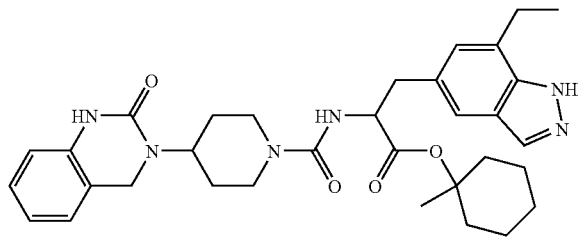

3-(7-Chloro-1H-indazol-5-yl)-2-{[4-(2-oxo-1,4-dihydro-2H-quinazolin-3-yl)-piperidine-1-carbonyl]-amino}-propionic acid 4-phenyl-cyclohexyl ester

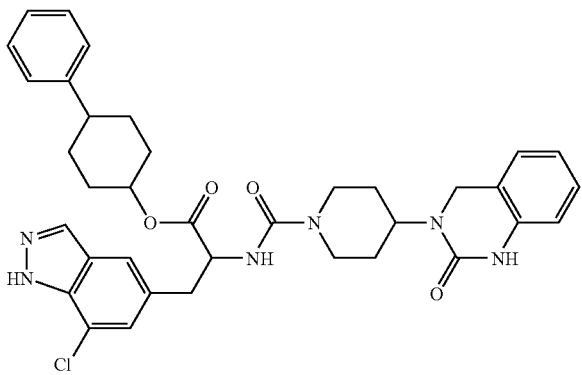

326

3(7-Ethyl-1H-indazol-5-yl)-2-{[4-(2-oxo-1,4-dihydro-2H-quinazolin-3-yl)-piperidine-1-carbonyl]-amino}-propionic acid 4-phenyl-cyclohexyl ester

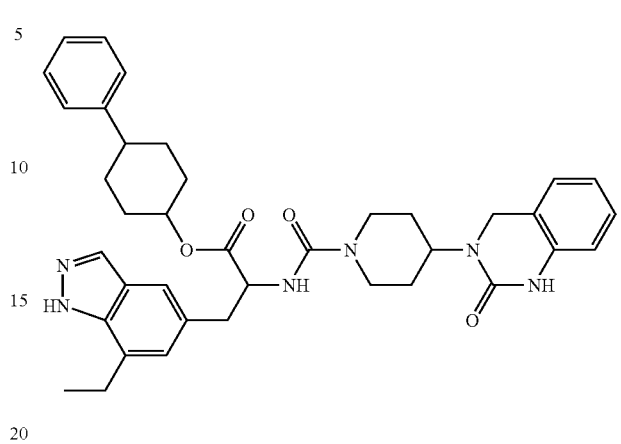

CGRP Binding Assay

Tissue Culture. SK-N-MC cells were grown at 37° C. in 5% $CO_2$ as a monolayer in medium consisting of MEM with Earle's salts and L-glutamine (Gibco) supplemented with 10% fetal bovine serum (Gibco).

Cell Pellets. The cells were rinsed twice with phosphate-buffered saline (155 mM NaCl, 3.3 mM $Na_2HPO_4$, 1.1 mM $KH_2PO_4$, pH 7.4), and incubated for 5-10 min. at 4° C. in hypotonic lysis buffer consisting of 10 mM Tris (pH 7.4) and 5 mM EDTA. The cells were transferred from plates to polypropylene tubes (16×100 mm) and homogenized using a polytron. Homogenates were centrifuged at 32,000×g for 30 min. The pellets were resuspended in cold hypotonic lysis buffer with 0.1% mammalian protease inhibitor cocktail (Sigma) and assayed for protein concentration. The SK-N-MC homogenate was then aliquoted and stored at −80° C. until needed.

Radioligand Binding Assay. The compounds of invention were solubilized and carried through serial dilutions using 100% DMSO. Aliquots from the compound serial dilutions were further diluted 25 fold into assay buffer (50 mM Tris-Cl pH 7.5, 5 mM $MgCl_2$, 0.005% Triton X-100) and transferred (volume 50 µl) into 96 well assay plates. [$^{125}$I]-CGRP (Amersham Biosciences) was diluted to 60 µM in assay buffer and a volume of 50 µl was added to each well. SK-N-MC pellets were thawed, diluted in assay buffer with fresh 0.1% mammalian protease inhibitor cocktail (Sigma), and homogenized again. SK-N-MC homogenate (5 µg/well) was added in a volume of 100 µl. The assay plates were then incubated at room temperature for 2 h. Assays were stopped by addition of excess cold wash buffer (20 mM Tris-Cl pH 7.5, 0.1% BSA) immediately followed by filtration over glass fiber filters (Whatman GF/B) previously soaked in 0.5% PEI. Non-specific binding was defined with 1 µM beta-CGRP. Protein bound radioactivity was determined using a gamma or scintillation counter. The $IC_{50}$ was defined as the concentration of a compound of invention required to displace 50% of radioligand binding.

In the table below, results are denoted as follows: A≦10 nM; 10 nM<B≦100 nM; 100 nM<C≦1000 nM; D>1000 nM.

TABLE 4

CGRP Binding, cAMP Function and Ex Vivo Human Cerebral Artery Data

| Example # | CGRP binding[1] IC$_{50}$ (nM) | cAMP Function[2] IC$_{50}$ (nM) | Cerebral Artery[3] EC$_{50}$ (nM) |
|---|---|---|---|
| 1 | C | * | * |
| 2 | A | A | A |
| 3 | B | B | B |
| 4 | B | B | * |
| 5 | A | A | * |
| 6 | A | A | A |
| 7 | C | C | * |
| 8 | C | C | * |
| 9 | B | B | * |
| 10 | C | B | * |
| 11 | B | B | * |
| 12 | B | C | * |
| 13 | C | * | * |
| 14 | D | * | * |
| 15 | C | C | * |
| 16 | A | A | A |
| 17 | A | A | A |
| 18 | A | B | A |
| 19 | A | A | A |
| 20 | A | A | A |
| 21 | A | A | A |
| 22 | A | A | * |
| 23 | A | A | A |
| 24 | B | B | * |
| 25 | A | A | A |
| 26 | B | B | * |
| 27 | B | C | * |
| 28 | C | * | * |
| 29 | A | * | * |
| 30 | B | * | * |
| 31 | A | A | * |
| 32 | C | * | * |
| 33 | C | * | * |
| 34 | A | A | * |
| 35 | B | B | * |
| 36 | B | B | * |
| 37 | A | B | * |
| 38 | B | B | * |
| 39 | C | C | * |
| 40a | A | A | * |
| 40b | B | * | * |
| 40c | D | * | * |
| 40d | C | * | * |
| 40e | D | * | * |
| 40f | D | * | * |
| 40g | D | * | * |
| 40h | D | * | * |
| 40i | B | * | * |
| 40j | D | * | * |
| 40k | D | * | * |
| 41a | B | * | * |
| 41b | A | * | * |
| 41c | A | * | * |
| 41d | B | * | * |
| 41e | A | * | * |
| 41f | B | * | * |
| 42 | C | * | * |
| 43 | A | A | A |
| 44 | C | * | * |
| 45 | A | * | * |
| 46 | B | B | * |
| 47 | A | A | A |
| 48 | D | * | * |
| 49 | A | * | * |
| 50 | A | * | * |
| 51 | D | * | * |
| 52 | D | * | * |
| 53 | D | * | * |
| 54 | B | C | A |
| 55 | C | * | * |
| 56 | A | A | * |
| 57 | C | * | * |
| 58 | D | * | * |
| 59 | C | * | * |
| 60 | C | * | * |
| 61 | C | C | * |
| 62 | B | B | * |
| 63 | C | C | * |
| 64 | B | * | B |
| 65 | A | B | B |
| 66 | C | * | * |
| 67 | B | C | B |
| 68 | A | A | A |
| 69 | A | A | A |
| 70 | A | A | A |
| 71 | A | A | A |
| 72 | A | A | A |
| 73 | B | B | * |
| 74 | A | A | A |
| 75 | A | B | * |
| 76 | B | B | A |
| 77 | B | B | * |
| 78 | A | A | * |
| 79 | B | C | * |
| 80 | C | * | * |
| 81 | B | C | * |
| 82 | B | C | * |
| 83 | B | C | * |
| 84 | B | B | * |
| 85 | C | * | * |
| 86 | C | B | C |
| 87 | B | B | * |
| 88 | C | B | * |
| 89 | C | B | * |
| 90 | B | * | * |
| 91 | C | * | * |
| 92 | B | C | * |
| 93 | C | * | * |
| 94 | C | C | * |
| 95 | C | * | * |
| 96 | D | * | * |
| 97 | D | * | * |
| 98 | D | * | * |
| 99 | D | D | * |
| 100 | C | * | * |
| 101 | D | * | * |
| 102 | C | * | * |
| 103 | C | * | * |
| 104 | C | * | * |
| 105 | C | * | * |
| 106 | C | * | * |
| 107 | C | * | * |
| 108 | C | * | * |
| 109 | C | * | * |
| 110 | C | * | * |
| 111 | C | * | * |
| 112 | C | * | * |
| 113 | C | * | * |
| 114 | C | * | * |
| 115 | C | * | * |
| 116 | C | * | * |
| 117 | C | * | * |
| 118 | C | * | * |
| 119 | C | * | * |
| 120 | C | * | * |
| 121 | C | * | * |
| 122 | C | * | * |
| 123 | B | * | * |
| 124 | C | * | * |
| 125 | C | * | * |
| 126 | C | * | * |
| 127 | C | * | * |
| 128 | C | * | * |
| 129 | C | * | * |

TABLE 4-continued

CGRP Binding, cAMP Function and Ex Vivo Human Cerebral Artery Data

| Example # | CGRP binding[1] IC$_{50}$ (nM) | cAMP Function[2] IC$_{50}$ (nM) | Cerebral Artery[3] EC$_{50}$ (nM) |
|---|---|---|---|
| 130 | C | * | * |
| 131 | C | * | * |
| 132 | C | * | * |
| 133 | C | * | * |
| 134 | C | * | * |
| 135 | C | * | * |
| 136 | C | * | * |
| 137 | C | * | * |
| 138 | C | * | * |
| 139 | C | * | * |
| 140 | B | * | * |
| 141 | C | * | * |
| 142 | C | * | * |
| 143 | C | * | * |
| 144 | C | * | * |
| 145 | C | * | * |
| 146 | B | * | * |
| 147 | C | * | * |
| 148 | B | * | * |
| 149 | B | * | * |
| 150 | B | * | * |
| 151 | C | * | * |
| 152 | C | * | * |
| 153 | C | * | * |
| 154 | C | * | * |
| 155 | C | * | * |
| 156 | C | * | * |
| 157 | C | * | * |
| 158 | B | * | * |
| 159 | B | * | * |
| 160 | C | * | * |
| 161 | B | * | * |
| 162 | C | * | * |
| 163 | C | * | * |
| 164 | C | * | * |
| 165 | C | * | * |
| 166 | C | * | * |
| 167 | C | * | * |
| 168 | C | * | * |
| 169 | C | * | * |
| 170 | C | * | * |
| 171 | B | * | * |
| 172 | B | * | * |
| 173 | C | * | * |
| 174 | C | * | * |
| 175 | C | * | * |
| 176 | B | * | * |
| 177 | B | * | * |
| 178 | B | * | * |
| 179 | C | * | * |
| 180 | C | * | * |
| 181 | C | * | * |
| 182 | C | * | * |
| 183 | C | * | * |
| 184 | B | * | * |
| 185 | C | * | * |
| 186 | C | * | * |
| 187 | C | * | * |
| 188 | C | * | * |
| 189 | C | * | * |
| 190 | C | * | * |
| 191 | C | * | * |
| 192 | C | * | * |
| 193 | B | * | * |
| 194 | C | * | * |
| 195 | C | * | * |
| 196 | B | * | * |
| 197 | C | * | * |
| 198 | C | * | * |
| 199 | B | * | * |
| 200 | B | * | * |
| 201 | C | * | * |

Cyclic AMP Assay

Functional Antagonism. Antagonism of the compounds of invention was determined by measuring the formation of cyclic AMP (adenosine 3'5'-cyclic monophosphate) in SK-N-MC cells that endogenously express the human CGRP receptor. CGRP receptor complex is coupled with Gs protein and CGRP binding to this complex leads to the cyclic AMP production via Gs-dependent activation of an adenylate cyclase (Juaneda C et al., TiPS, 2000; 21:432-438; incorporated by reference herein). Consequently, CGRP receptor antagonists inhibit CGRP-induced cyclic AMP formation in SK-N-MC cells (Doods H et al., Br J Pharmacol, 2000; 129(3):420-423); incorporated by reference herein). For cyclic AMP measurements SK-N-MC cells were incubated with 0.3 nM CGRP alone or in the presence of various concentrations of the compounds of invention for 30 min at room temperature. Compounds of invention were pre-incubated with SK-N-MC cells for 15 min before the addition of CGRP to allow receptor occupancy (Edvinsson et al., Eur J Pharmacol, 2001, 415:39-44; incorporated by reference herein). Cyclic AMP was extracted using the lysis reagent and its concentration was determined by radioimmunoassay using RPA559 cAMP SPA Direct Screening Assay Kit (Amersham Pharmacia Biotech). IC50 values were calculated using Excel fit. The tested compounds of invention were determined to be antagonists as they exhibited a dose-dependent inhibition of the CGRP-induced cyclic AMP production. See Table 3 for summary of results.

Schild Analysis. Schild analysis can be used to characterize the nature of antagonism of the compounds of invention. The dose response of CGRP stimulated cAMP production was generated either with CGRP alone, or in the presence of various concentrations of compounds of invention. The antagonist dose is plotted as X against the dose ratio (defined as IC50 of agonist with the presence of the compounds divided by the IC50 of the agonist alone) minus 1 as Y. Linear regression was then performed with both X and Y axis log-transformed. A slope that does not differ significantly from unity (1) indicates competitive antagonism. $K_b$ is the dissociation constant of the antagonist.

TABLE 5

Schild Analysis

| Example # | $K_b$(nM) | slope |
|---|---|---|
| 2 | 0.16 | 0.94 |
| 3 | 55 | 0.96 |
| 5 | 3 | 0.92 |
| 6 | 0.36 | 0.93 |
| 16 |  | 1.3 |
| 17 | 1.1 | 0.92 |
| 18 | 1 | 0.8 |
| 21 | 0.018 | 0.89 |
| 43 | 0.018 | 1.2 |
| 45 |  | 1.4 |

TABLE 5-continued

Schild Analysis

| Example # | $K_b$(nM) | slope |
|---|---|---|
| 47 | 0.1 | 0.93 |
| 69 | 0.016 | 1 |
| 70 |  | 0.71 |
| 71 | 2 | 0.87 |

See FIG. 1. Schild Analysis.

Ex Vivo Human Cerebral Artery Assay

Rationale and Overview. To provided direct evidence of the ability for novel compounds to reverse CGRP-induced dilation in human cerebral vessels, an ex vivo assay was designed. Briefly, isolated vessel rings were mounted in a tissue bath where vessels were pre-contracted with potassium chloride (KCl) and fully dilated with hCGRP, then this relaxation was reversed by the cumulative addition of CGRP-receptor antagonists (complete details follow).

Tissue Samples. Autopsy samples of human arteries were obtained from vendors (ABS Inc. or NDRI). All vessels were transported on ice-cold HEPES buffer (composition in mM: NaCl 130, KCl 4, KH2PO4 1.2, MgSO4 1.2, CaCl2 1.8, Glucose 6, NaHCO3 4, HEPES 10, EDTA 0.025). Upon receipt, the vessels were placed in cold Kreb's buffer (composition in mM: NaCl 118.4, KCl 4.7, KH2PO4 1.2, MgSO4 1.2, CaCl2 1.8, Glucose 10.1, NaHCO3 25) saturated with carbogen (5% CO2 and 95% oxygen).

Isolated Tissue Baths. The vessels were cleaned of connective tissues and cut into cylindrical segments of 4-5 mm in length. The vessels were then mounted in tissue baths between two stainless steel hooks; one of which is fixed and the other of which was connected to a force displacement transducer. The vessel tension was continuously recorded using a data acquisition system (Powerlab, ADInstruments, Mountain View, Calif.) connected to the transducer. The tissue baths containing Krebs buffer and mounted vessels were temperature (37° C.) and pH (7.4) controlled with continuous bubbling of carbogen. The artery segments were allowed to equilibrate for about 30-45 min until a stable resting tone was achieved. Prior to the assay, vessels were primed (conditioned) with 100 mM KCl and subsequently washed. The vessels were pre-contracted with 10 mM KCl and fully dilated with 1 nM hCGRP. Concentration-response curves to CGRP-receptor antagonists were performed by the cumulative addition of drugs in half log units in fully dilated vessels. At each concentration, the effects of the drugs were expressed as % reversal of CGRP-induced relaxation in each vessel. The actual assay and data analysis were performed for each vessel individually, fitting the concentration-response data to a four parameter logistic function by non-linear regression analysis, to estimate the EC50 values. A summary of results is provided in Table 3.

Non-Terminal Method for Assessing In Vivo Efficacy of Small Molecule CGRP-Receptor Antagonists in Mammals Overview. Blocking cerebral artery dilation induced by calcitonin gene-related peptide (CGRP) has been proposed as a treatment for migraine headache, however, novel small molecule CGRP-receptor antagonists have shown species-specific differences with relatively poor activity in rodents (Mallee et al. J Biol Chem 2002 277:14294) requiring new models for assessment of in vivo efficacy. Non-human primates (e.g., marmosets) are the only animals known to have human-like CGRP receptor pharmacology conferred by the presence of the specific amino acid residue (Trp74) in their RAMP1 sequence which is responsible for the phenotype of the human receptor (Mallee et al. J Biol Chem 2002 277:14294). Since current migraine models primarily use rats (Escott et al. Brain Res 1995 669:93; Williamson et al. Cephalalgia 1997 17:525), or are invasive, terminal procedures in primates (Doods et al. Br J Pharmacol 2000 129:420), a novel non-invasive, survival model in non-human primates for in vivo efficacy assessment of CGRP-receptor antagonists as in the present invention is a significant contribution. While it is known that trigeminal activation increases both cerebral (Goadsby & Edvinsson, 1993) and facial blood flow (Doods et al., 2000), demonstration of a direct relationship between facial blood flow and cerebral artery dilation conducted in the same animals was not known. Therefore, before initiating studies in non-human primates, laser Doppler measurement of facial blood flow was directly validated in the rat as a surrogate for cerebral artery dilation in terminal studies that measured both cerebral artery diameter and changes in facial blood flow in the same animals (see FIG. 2. Direct Validation of Facial Blood Flow as Surrogate for Cerebral Artery Dilation in the Rat). In both measures, comparable increases were induced by i.v. CGRP and blocked by the peptide antagonist hαCGRP(8-37). Next, the method of i.v. CGRP-induced changes in facial blood flow was validated as a recovery model in isoflurane anesthetized rats using hαCGRP(8-37). The survival method was then established in non-human primates and a dose-response study characterizing i.v. CGRP activity was completed (see FIG. 3. Dose-Response for hαCGRP in Non-Human-Primate Laser Doppler Facial Blood Flow). Peptide and small-molecule CGRP-receptor antagonists were used to validate the non-human primate model. Pre-treatment with small molecule antagonists or hαCGRP(8-37) dose-dependently inhibited i.v. CGRP-stimulated increases in primate facial blood flow (see FIG. 4. Inhibition of CGRP-Induced Changes in Non-Human Primate Facial Blood Flow), without altering blood pressure (see FIG. 5. Effect of CGRP Antagonist on Non-Human Primate Blood Pressure). Post-treatment of antagonists also reversed CGRP-induced increases in facial blood flow (not shown). This survival model provides a novel, non-invasive recovery procedure for evaluating prophylactic and abortive effects of CGRP-receptor antagonists in non-human primates, or in transgenic animals with humanized RAMP1 (Trp74) which have similar CGRP receptor pharmacology, as a surrogate marker for activity in cerebral vessel diameter.

Animals. Adult male and female common marmosets (Callithrix jacchus) purchased from Harlan and weighing 350-550 g served as subjects. Other mammals endogenously expressing RAMP1 having Trp 74 or transgenic mammals with humanized RAMP1 having Trp 74 can also be employed in the method described herein.

Anesthesia & Surgical Preparation. Animals are anesthetized by isoflurane inhalation in an induction chamber (4-5% rapid induction, maintained with 1-2.5%; Solomon et al., 1999). Anesthesia is maintained by delivering a constant supply of air:oxygen (50:50) and isoflurane via face mask, or by intubation and ventilation (with blood gas monitoring). Body temperature is maintained at 38±0.5° C. by placement on an automated temperature controlled surface with rectal probe. A small area of fur (approx. 1.5 cm square) is removed from one or both sides of the face by application of a depilatory cream and/or shaving. Surgical areas are clipped and prepared with betadine. An i.v. line is placed in any accessible vein for the administration of test compounds and CGRP-receptor agonist and, if needed, withdrawal of blood samples (max 2.5 ml, 10%) for blood gas monitoring and content analysis. A solution of 5% dextrose is administered i.v. in order to maintain blood sugar levels. Anesthesia depth is monitored by measuring blood pressure and heart rate using a non-invasive arm cuff method and a pulse oximeter, respectively. Guanethidine 5-10 mg/kg i.v., supplemented with 5 mg/kg i.v. as needed, may be given to stabilize the peak flux in facial blood flow seen with repeated stimulation-induced changes in blood flow (Escott et al., 1999; incorporated by reference herein). Microvascular blood flow is monitored by attaching a self adhesive laser Doppler flow probe to the facial skin.

Compound Administration Test compounds may be administered i.v. (0.01-5 ml/kg), i.m. (0.01-0.5 ml/kg), s.c. (0.01-5 ml/kg) or p.o. (0.1-10 ml/kg) (Diehl et al., 2001; incorporated by reference herein). CGRP-receptor agonists may be delivered i.v. (0.01-5 ml/kg), i.d. (10-100 µl/site) or s.c. (10-100 µl/site).

Laser Doppler Flowmetry A control increase in facial blood flow is induced by administration of a vasodilator, such as CGRP (0.05-100 µg/kg i.v.) or 2-20 pmol/site i.d) or adrenomedullin (ADM, 0.05-5 mg/kg i.v. or 10-100 pmol/site i.d.). Test compound or vehicle is administered either before (pre-treatment) or after (post-treatment) subsequent repeat administration of the vasodilating agent, providing the ability to assess prophylactic or therapeutic actions. Blood pressure is monitored continuously to ensure adequate depth of anesthesia, and anesthetic is adjusted to maintain stable levels that match pre-treatment values. During collection of laser Doppler flowmetry data, isoflurane may be reduced to 0.25-0.75% as previous electrophysiologic studies in marmosets found that recordings were sensitive to isoflurane concentration (Solomon, 1999; incorporated by reference herein). To reduce the number of animals used, the effect of test compound on i.v. vasodilator-induced changes in blood flow may be repeated up to 6 times in a single session.

Recovery Animals are returned to the transport cage which is placed on a temperature controlled surface to keep the animals warm until fully awake and ambulatory. Animals may be tested again after 7-14 days rest, and may be tested repeatedly at 7-14 day intervals depending on the health of the animal.

See Diehl K H, Hull R, Morton D, Pfister R, Rabemampianina Y, Smith D, Vidal J M, van de Vorstenbosch C. A good practice guide to the administration of substances and removal of blood, including routes and volumes. J Appl Toxicol. 2001 January-February; 21(1):15-23; Doods H, Hallermayer G, Wu D, Entzeroth M, Rudolf K, Engel W, Eberlein W. Pharmacological profile of BIBN4096BS, the first selective small molecule CGRP-receptor antagonist. Br J Pharmacol. 2000 February; 129(3):420-3; Edvinsson L. Calcitonin gene-related peptide (CGRP) and the pathophysiology of headache: therapeutic implications. CNS Drugs 2001; 15(10):745-53; Escott K J, Beattie D T, Connor H E, Brain S D. Trigeminal ganglion stimulation increases facial skin blood flow in the rat: a major role for calcitonin gene-related peptide. Brain Res. 1995 Jan. 9; 669(1):93-9; Goadsby P J, Edvinsson L. The trigeminovascular system and migraine: studies characterizing cerebrovascular and neuropeptide changes seen in humans and cats. Ann Neurol. 1993 January; 33(1):48-56; Lassen L H, Haderslev P A, Jacobsen V B, Iversen H K, Sperling B, Olsen J. CGRP may play a causative role in migraine. Cephalalgia, 2002, 22, 54-61; Mallee J J, Salvatore C A, LeBourdelles B, Oliver K R, Longmore J, Koblan K S, Kane S A. RAMP1 determines the species selectivity of non-peptide CGRP receptor antagonists. J Biol Chem. 2002 Feb. 14 [epub ahead of print]; Solomon S G, White A J, Martin P R. Temporal contrast sensitivity in the lateral geniculate nucleus of a New World monkey, the marmoset Callithrix jacchus. J Physiol. 1999 Jun. 15; 517 (Pt 3):907-17; all incorporated by reference herein.

Departures from Other Migraine Models. This invention represents a novel migraine model and is remarkably distinct from other migraine models. Some of the distinguishing characteristics of the method of the present invention include: (i) the only survival model of migraine in any species; (ii) the only model to demonstrate the abortive (post-treatment) effects of CGRP antagonists on active induced increases in blood flow; (iii) the only demonstration of a direct relationship between facial blood flow and intracranial artery dilation carried out in the same animals; (iv) the only model to use non-invasive surgical techniques, and does not require catheter placement, intubation, or neuromuscular blockade; (v) the only primate model to use exogenous CGRP as the stimulus and demonstrate pretreatment blockade by CGRP antagonism and post-treatment reversal by CGRP antagonism; (vi) the only migraine model to use isoflurane anesthesia in spontaneously breathing animals. The models described in Williamson et al., Sumatriptan inhibits neurogenic vasodilation of dural blood vessels in the anaesthetized rat-intravital microscope studies. Cephalalgia. 1997 June; 17(4):525-31; Williamson D J, Hargreaves R J, Hill R G, Shepheard S L. Intravital microscope studies on the effects of neurokinin agonists and calcitonin gene-related peptide on dural vessel diameter in the anaesthetized rat. Cephalalgia. 1997 June; 17(4):518-24; Escott K J et al., Trigeminal ganglion stimulation increases facial skin blood flow in the rat: a major role for calcitonin gene-related peptide. Brain Res. 1995 Jan. 9; 669(1):93-9; Chu D Q et al., The calcitonin gene-related peptide (CGRP) antagonist CGRP(8-37) blocks vasodilatation in inflamed rat skin: involvement of adrenomedullin in addition to CGRP. Neurosci Lett. 2001 Sep. 14; 310(2-3):169-72; Escott K J, Brain S D. Effect of a calcitonin gene-related peptide antagonist (CGRP8-37) on skin vasodilatation and oedema induced by stimulation of the rat saphenous nerve. Br J Pharmacol. 1993 October; 110(2):772-6; Hall J M, Siney L, Lippton H, Hyman A, Kang-Chang J, Brain S D. Interaction of human adrenomedullin 13-52 with calcitonin gene-related peptide receptors in the microvasculature of the rat and hamster. Br J Pharmacol. 1995 February; 114(3):592-7; Hall J M, Brain S D. Interaction of amylin with calcitonin gene-related peptide receptors in the microvasculature of the hamster cheek pouch in vivo. Br J Pharmacol. 1999 January; 126(1):280-4; and Doods H, Hallermayer G, Wu D, Entzeroth M, Rudolf K, Engel W, Eberlein W. Pharmacological profile of BIBN4096BS, the first selective small molecule CGRP-receptor antagonist. Br J Pharmacol. 2000 February; 129(3):420-3 fail to possess the remarkable features of the method of the present invention.

In the table below, results are denoted as follows: $W \leq 25\%$; $25\% < X \leq 50\%$; $50\% < Y \leq 75\%$; $Z > 75\%$.

TABLE 6

Inhibition of CGRP-Induced Increase in Laser Doppler Facial Blood Flow in the Non-Human Primate (e.g., Common Marmoset)

| Example # | Non-Human Primate (% Inhibition) of CGRP-induced (10 µg/kg, iv) increase in laser Doppler facial blood flow | | | | |
|---|---|---|---|---|---|
| | 0.01 mg/kg, iv | 0.03 mg/kg, iv | 0.1 mg/kg, iv | 0.3 mg/kg, iv | 1 mg/kg, iv |
| 2 | W | X | X | Y | Z |
| 6 | | | | | Z |
| 16 | | Y | | | |
| 69 | | Y | Z | | |
| hαCGRP (8-37) | | | | | Z |

$W \leq 25\%; 25\% < X \leq 50\%; 50\% < Y \leq 75\%; Z > 75\%$.

See FIG. 5. Effect of CGRP Antagonist on Non-Human Primate Blood Pressure.

What is claimed is:

1. A compound according to Formula (I)

$$\text{(I)}$$

or a pharmaceutically acceptable salt thereof
wherein
V is $-N(R^1)(R^2)$ or $OR^4$;
  $R^4$ is H, $C_{1-6}$alkyl, $C_{1-4}$haloalkyl or $(C_{1-4}$alkylene$)_{0-1}R^{4'}$
  $R^{4'}$ is $C_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl; and
    $R^{4'}$ is optionally substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, $(C_{1-3}$alkyl$)_{0-2}$ureido, phenyl and benzyl; and
    $R^{4'}$ optionally contains 1 or 2 carbonyls wherein the carbon atom of said carbonyl is a member of the ring structure of $R^{4'}$;
  $R^1$ and $R^2$ are each independently $L^1$, wherein $L^1$ is selected from the group consisting of H, $C_{1-6}$alkyl, $C_{2-6}$alkenyl, $C_{2-6}$ alkynyl, $-C_{1-6}$alkylene-amino $(C_{1-3}$ alkyl$)_2$, $C_{3-7}$cycloalkyl, phenyl, azetidinyl, adamantyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and
    $R^1$ and $R^2$ are each optionally and independently substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, $(C_{1-3}$alkyl$)_{0-2}$ureido, phenyl and benzyl;
    $R^1$ and $R^2$ optionally and independently contain 1 or 2 carbonyls wherein the carbon atom of said carbonyl is a member of the heterocycles comprising $R^1$ and $R^2$;
  $R^1$ and $R^2$ together with the nitrogen to which they are attached form X,
    wherein X is azetidinyl, pyrrolyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;
    wherein X is optionally substituted with Y, wherein Y is dioxolanyl, $C_{1-9}$alkyl, $C_{2-9}$alkenyl, $C_{2-9}$ alkynyl, $C_{1-4}$alkylamino, $C_{1-4}$dialkylamino, $C_{1-4}$alkoxy, $C_{3-7}$cycloalkyl, phenyl, azetidinyl, furanyl, thienyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;
Q is Q' or Q";
  wherein
    Q' is $(S^y)_sR^3$; and
    Q" is $NH(S^y)_sR^3$, $NHC(O)(S^y)_sR^3$, $NHC(O)O(S^y)_sR^3$, $NHC(O)NH(S^y)_sR^3$, $O(S^y)_sR^3$, $(S^y)_sNHR^3$, $(S^y)_sNHC(O)R^3$, $(S^y)_sNHC(O)OR^3$, $(S^y)_sNHC(O)NHR^3$ or $(S^y)_sOR^3$;
    wherein $S^y$ is $C_{1-3}$alkylene or $C_{1-3}$alkylidene and s is 0 or 1;
U is $CH_2$ or NH;
provided that if Q is Q", then U is $CH_2$;
$R^3$ is $R^{3a}$ or $R^{3b}$
  wherein
    $R^{3a}$ is
      (i) a heterocycle having two fused rings with 5 to 7 members in each of said rings, said heterocycle containing one to five of the same or different heteroatoms selected from the group consisting of O, N and S and said heterocycle optionally containing 1 or 2 carbonyls wherein the carbon atom of said carbonyl is a member of said fused rings;
      (ii) a 4 to 6 membered heterocycle containing one to three of the same or different heteroatoms selected from the group consisting of O, N and S, optionally containing 1 to 2 carbonyls, wherein the carbon atom of said carbonyl is a member of said 4 to 6 membered heterocycle;
      (iii) $C_{3-7}$cycloalkyl;
      (iv) carbazolyl, fluorenyl, phenyl, —O-phenyl, —O—$C_{1-4}$ alkylene-phenyl, or napthyl; or
      (v) $C_{1-8}$alkyl, $C_{2-7}$alkenyl, —C(O)$R^{3'}$, CHC(O)O—$R^{3'}$, CH(CH$_3$)C(O)O—$R^{3'}$, —C(O)O—$R^{3'}$ or $C_{2-7}$alkynyl; and
    wherein $R^{3a}$ is optionally substituted with 1 to 3 of the same or different substituents selected from the group consisting of benzyl, phenyl, —O-phenyl, —O—$C_{1-3}$alkylenephenyl, —$C_{1-3}$alkylene-OC(O)-phenyl, cyano, amino, nitro, halo, $C_{1-6}$alkyl, $C_{1-3}$mono-bi-tri-haloalkyl, $C_{1-3}$mono-bi-tri-haloalkyloxy, $(C_{1-3}$ alkyl$)_{1-2}$-amine, —OR$^{3'}$, —C(O)R$^{3'}$, —C(O)O—R$^{3'}$, —O—C(O)R$^{3'}$, —N(R$^{3'}$)$_2$, —C(O)N(R$^{3'}$)$_2$, —N(R$^{3'}$)C(O)(R$^{3'}$)$_2$, —N(R$^{3'}$)C(O)N(R$^{3'}$)$_2$, —N(R$^{3'}$)C(O)OR$^{3'}$, —O—C(O)N(R$^{3'}$)$_2$, —N(R$^{3'}$)SO$_2$R$^{3'}$, —SO$_2$N(R$^{3'}$)$_2$ and —SO$_2$R$^{3'}$;

R$^{3'}$ is H or —C$_{1-6}$alkyl;

provided that if R$^{3a}$ is, —C(O)R$^{3'}$, CHC(O)O—R$^{3'}$, CH(CH$_3$)C(O)O—R$^{3'}$ or —C(O)O—R$^{3'}$, then said —C(O)R$^{3'}$, CHC(O)O—R$^{3'}$, CH(CH$_3$)C(O)O—R$^{3'}$ or —C(O)O—R$^{3'}$ are unsubstituted;

R$^{3b}$ is R$^{3a}$ but is not phenyl, 1-naphthyl, 2-naphthyl, 1,2,3,4-tetrahydro-1-naphthyl, 1H-indol-3-yl, 1-methyl-1H-indol-3-yl, 1-formyl-1H-indol-3-yl, 1-(1,1-dimethylethoxycarbonyl)-1H-indol-3-yl, 4-imidazolyl, 1-methyl-4-imidazolyl, 2-thienyl, 3-thienyl, thiazolyl, 1H-indazol-3-yl, 1-methyl-1H-indazol-3-yl, benzo[b]fur-3-yl, benzo[b]thien-3-yl, pyridinyl, quinolinyl or isoquinolinyl; optionally substituted in the carbon skeleton with mono-, di- or trisubstituted by fluorine, chlorine or bromine atoms or by branched or unbranched alkyl groups, C$_{3-8}$-cycloalkyl groups, phenylalkyl groups, alkenyl, alkoxy, phenyl, phenylalkoxy, trifluoromethyl, alkoxycarbonylalkyl, carboxyalkyl, alkoxycarbonyl, carboxy, dialkylaminoalkyl, dialkylaminoalkoxy, hydroxy, nitro, amino, acetylamino, propionylamino, benzoyl, benzoylamino, benzoylmethylamino, methylsulphonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulphinyl- or trifluoromethylsulphonyl groups;

wherein said substituents may be the same or different and the above-mentioned benzoyl, benzoylamino- and benzoylmethylamino groups may in turn additionally be substituted in the phenyl moiety by a fluorine, chlorine or bromine atom, or by an alkyl, trifluoromethyl, amino or acetylamino group;

D is O, NCN or NSO$_2$C$_{1-3}$alkyl;

A is C;

m and n are each 1;

p is 0 such that G and J are each attached to A, then G, J, and A form a spirocyclic ring system with said rings of said system containing A and wherein G, J, and A together are GJA' wherein GJA' is A$^y$;

A$^y$ is a 4 to 6 membered heterocycle containing one to three heteroatoms selected from the group consisting of O, N and S; and optionally containing 1 to 2 carbonyls, wherein the carbon atom of said carbonyl is a member of said 4 to 6 membered heterocycle;

wherein A$^y$ are optionally substituted with C$_{1-4}$alkyl, C$_{1-4}$alkoxy, C$_{1-4}$haloalkyl, cyano, C$_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino;

provided that

A$^y$ is not a 1,3-diaza-heterocycle; and and further provided that if Q is Q", then R$^3$ is R$^{3a}$; and if Q is Q', then
R$^3$ is R$^{3b}$.

2. A compound according to claim 1, or a pharmaceutically acceptable salt thereof, wherein Q is Q' and R$^3$ is R$^{3b}$.

3. A compound according to claim 1, or a pharmaceutically acceptable salt thereof, wherein Q is Q".

4. A compound according to claim 3, or a pharmaceutically acceptable salt thereof, wherein Q" is NH(S$^y$)$_s$R$^3$.

5. A compound according to claim 3, or a pharmaceutically acceptable salt thereof, wherein Q" is NHC(O)(S$^y$)$_s$R$^3$.

6. A compound according to claim 3, or a pharmaceutically acceptable salt thereof, wherein Q" is NHC(O)O(S$^y$)$_s$R$^3$.

7. A compound according to claim 3, or a pharmaceutically acceptable salt thereof, wherein Q" is NHC(O)NH(S$^y$)$_s$R$^3$.

8. A compound according to claim 3, or a pharmaceutically acceptable salt thereof, wherein Q" is O(S$^y$)$_s$R$^3$.

9. A compound according to claim 3, or a pharmaceutically acceptable salt thereof, wherein Q" is (S$^y$)$_s$NHR$^3$.

10. A compound according to claim 3, or a pharmaceutically acceptable salt thereof, wherein Q" is (S$^y$)$_s$NHC(O)R$^3$.

11. A compound according to claim 3, or a pharmaceutically acceptable salt thereof, wherein Q" is (S$^y$)$_s$NHC(O)OR$^3$.

12. A compound according to claim 3, or a pharmaceutically acceptable salt thereof, wherein Q" is (S$^y$)$_s$NHC(O)NHR$^3$.

13. A compound according to claim 3, or a pharmaceutically acceptable salt thereof, wherein Q" is (S$^y$)$_s$OR$^3$.

14. A compound according to claim 1, or a pharmaceutically acceptable salt thereof, wherein V is OR$^4$.

15. A compound according to claim 1, or a pharmaceutically acceptable salt thereof, wherein V is —N(R$^1$)(R$^2$).

16. A compound according to claim 1, or a pharmaceutically acceptable salt thereof, wherein R$^4$ is H, C$_{1-6}$alkyl or (C$_{1-4}$alkylene)$_{0-1}$R$^{4'}$ and R$^{4'}$ is C$_{3-7}$cycloalkyl.

17. A compound according to claim 1, or a pharmaceutically acceptable salt thereof, wherein V is —N(R$^1$)(R$^2$) and
R$^1$ and R$^2$ are each independently L$^1$, wherein L$^1$ is selected from the group consisting of H, C$_{1-6}$alkyl, —C$_{1-6}$alkylene-amino(C$_{1-3}$alkyl)$_2$, C$_{3-7}$cycloalkyl, phenyl, azetidinyl, adamantyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; or
R$^1$ and R$^2$ together with the nitrogen to which they are attached form X, wherein X is azetidinyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;

wherein X is substituted with Y, wherein Y is dioxolanyl, C$_{1-4}$alkyl, C$_{1-4}$alkoxy, C$_{3-7}$ cycloalkyl, phenyl, azetidinyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino.

18. A compound according to claim 1, or a pharmaceutically acceptable salt thereof, wherein V is —N(R$^1$)(R$^2$), and R$^1$ and R$^2$ are each independently L$^1$, wherein L$^1$ is selected from the group consisting of H, C$_{1-6}$alkyl, or R$^1$ and R$^2$ together with the nitrogen to which they are attached form X,
wherein X is piperidinyl or morpholino;
wherein X is substituted with Y, wherein Y is dioxolanyl, C$_{1-4}$alkyl or piperidinyl.

19. A compound according to claim 1, or a pharmaceutically acceptable salt thereof, wherein V is —N(R$^1$)(R$^2$) and wherein R$^1$ and R$^2$ are each independently L$^1$, wherein L$^1$ is selected from the group consisting of H, C$_{1-6}$alkyl.

20. A compound according to claim 1, or a pharmaceutically acceptable salt thereof, wherein V is —N(R$^1$)(R$^2$) and wherein
R$^2$ and R$^2$ together with the nitrogen to which they are attached form X,
wherein X is piperidinyl or morpholino;
wherein X is substituted with Y, wherein Y is dioxolanyl, C$_{1-4}$alkyl or piperidinyl.

21. A compound according to claim 1, or a pharmaceutically acceptable salt thereof, wherein V is —N(R$^1$)(R$^2$) and wherein
R$^1$ and R$^2$ together with the nitrogen to which they are attached form X,
wherein X is piperidinyl;
wherein X is substituted with Y, wherein Y is piperidinyl.

22. A compound according to claim 1, or a pharmaceutically acceptable salt thereof, wherein V is —N(R$^1$)(R$^2$) and wherein
R$^1$ and R$^2$ together with the nitrogen to which they are attached form X,
wherein X is morpholino;
wherein X is substituted with Y, wherein Y is C$_{1-4}$ alkyl.

23. A compound according to claim 1, or a pharmaceutically acceptable salt thereof, wherein V is —N(R$^1$)(R$^2$) and wherein
R$^1$ and R$^2$ together with the nitrogen to which they are attached form X, wherein X is piperidinyl;
wherein X is substituted with Y, wherein Y is C$_{1-4}$ alkyl.

24. A compound according to claim 1, or a pharmaceutically acceptable salt thereof, wherein R$^3$ is R$^{3a}$ and R$^{3a}$ is substituted or unsubstituted phenyl, hydroxyphenyl, azetidinyl, napthyl, C$_{1-6}$alkyl, C$_{2-6}$alkenyl, C$_{2-6}$alkynl, dihydroquinolinonyl, hydroquinolinonyl, quinolinyl, dihydroisoquinolinonyl, hydroisoquinolinonyl, isoquinolinyl, dihydroquinazolinonyl, hydroquinazolinonyl, quinazolinyl, dihydroquinoxalinonyl, hydroquinoxalinonyl, quinoxalinyl, benzimidazolyl, indazolyl, dihydrobenzimidazolonyl, hydrobenzimidazolonyl, benzimidazolinyl, dihydro-benzthiazolonyl, hydrobenzthiazolonyl, benzthiazolyl, dihydrobenzoxazolyl, benzotriazolyl, dihydrobenzothiophenonyl, hydrobenzothiophenonyl, benzothienyl, dihydrobenzofuranonyl, hydrobenzofuranonyl, benzofuranyl, benzdioxolanyl, dihydroindolonyl, hydroindolonyl, indolyl, indolizinyl, isoindolyl, indolinyl, indazolyl, pyrazolyl, pyrazolinyl, pyrazolidinyl, furanyl, thienyl, pyrrolyl, pyrrolinyl, pyrrolidinyl, imidazolyl, imidazolinyl, imidazolidinyl, pyridyl, purinyl, carbazolyl, pyrimidinyl, piperidinyl, triazolopyrimidinyl, tetrahydropyrazolopyridinyl, piperazinyl or morpholino.

25. A compound according to claim 1, or a pharmaceutically acceptable salt thereof, wherein R$^3$ is R$^{3b}$ and R$^{3b}$ is substituted or unsubstituted dihydrobenzimidazolonyl, hydrobenzimidazolonyl, benzimidazolinyl, dihydro-benzthiazolonyl, hydrobenzthiazolonyl, benzthiazolyl, dihydrobenzothiophenonyl, hydrobenzothiophenonyl, dihydrobenzofuranonyl, hydrobenzofuranonyl, 1H-indazol-5-yl, benzdioxolanyl, dihydrobenzoxazolyl, benzotriazolyl, dihydroindolonyl, hydroindolonyl, indolizinyl, isoindolyl, indolinyl, pyrazolyl, pyrazolinyl, pyrazolidinyl, furanyl, pyrrolyl, pyrrolinyl, pyrrolidinyl, imidazolinyl, imidazolidinyl, purinyl, carbazolyl, pyrimidinyl, piperidinyl, piperazinyl or morpholino.

26. A compound according to claim 1, or a pharmaceutically acceptable salt thereof, wherein D is O and m and n are each 1.

27. A compound according to claim 1 wherein R$^3$ is R$^{3b}$ and R$^{3b}$ is

1H-Indol-5-yl

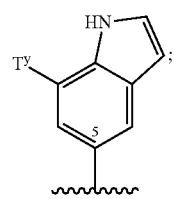

1H-Indazol-5-yl

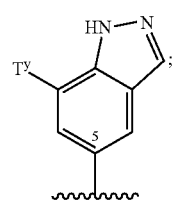

1H-Benzotriazol-5-yl

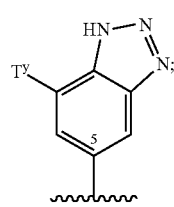

1,3-Dihydro-indol-2-on-5-yl

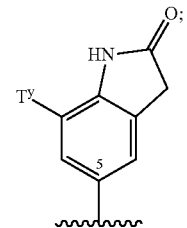

3H-Benzooxazol-2-on-6-yl

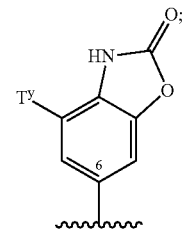

-continued
1,3 Dihydro-benzoimidazol-2-on-5-yl

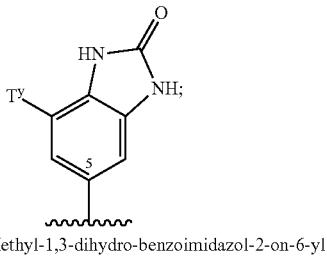

1-Methyl-1,3-dihydro-benzoimidazol-2-on-6-yl

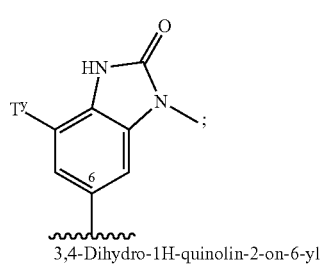

3,4-Dihydro-1H-quinolin-2-on-6-yl

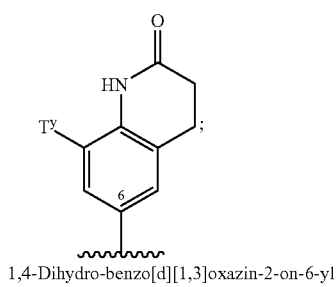

1,4-Dihydro-benzo[d][1,3]oxazin-2-on-6-yl

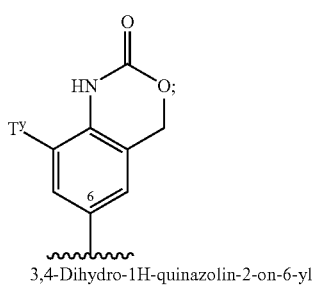

3,4-Dihydro-1H-quinazolin-2-on-6-yl

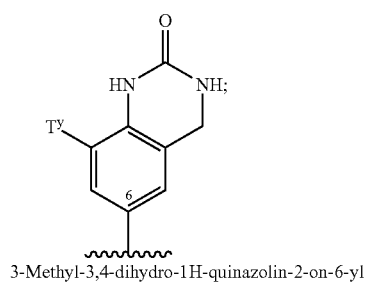

3-Methyl-3,4-dihydro-1H-quinazolin-2-on-6-yl

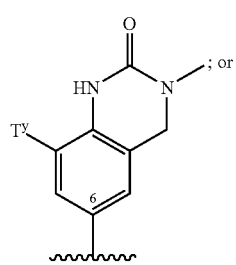

-continued
4H-Benzo[1,4]oxazin-3-on-7-yl

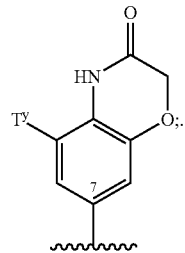

wherein $T^y$ is H, $C_{1-4}$alkyl, F, Cl, Br or nitrile.

28. A compound according to claim 1, or a pharmaceutically acceptable salt thereof, wherein
V is —N(R$^1$)(R$^2$);
R$^1$ and R$^2$ are each independently L$^1$, wherein L$^1$ is selected from the group consisting of H, $C_{1-6}$alkyl, $C_{2-6}$alkenyl, $C_{2-6}$ alkynyl, —$C_{1-6}$alkylene-amino ($C_{1-3}$ alkyl)$_2$, $C_{3-7}$cycloalkyl, phenyl, azetidinyl, adamantyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and
R$^1$ and R$^2$ are each optionally and independently substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, ($C_{1-3}$alkyl)$_{0-2}$ureido, phenyl and benzyl;
R$^1$ and R$^2$ optionally and independently contain 1 or 2 carbonyls wherein the carbon atom of said carbonyl is a member of the heterocycles comprising R$^1$ and R$^2$;
R$^1$ and R$^2$ together with the nitrogen to which they are attached form X, wherein X is piperidinyl;
wherein X is optionally substituted with Y, wherein Y is piperidinyl;
Q is Q'';
wherein
Q' is (S$^y$)$_s$R$^3$;
wherein S$^y$ is $C_{1-3}$alkylene or $C_{1-3}$alkylidene and s is 0 or 1;
U is CH$_2$ or NH;
R$^3$ is R$^{3a}$
wherein
R$^{3a}$ is
(i) a heterocycle having two fused rings with 5 to 7 members in each of said rings, said heterocycle containing one to five of the same or different heteroatoms selected from the group consisting of O, N and S and said heterocycle optionally containing 1 or 2 carbonyls wherein the carbon atom of said carbonyl is a member of said fused rings;
wherein R$^{3a}$ is optionally substituted with 1 to 3 of the same or different substituents selected from the group consisting of $C_{1-6}$alkyl
D is O;
A is C;

m and n are each 1;

p is 0;

G and J are each attached to A and together form the spirocyclic ring system $A^y$ wherein $A^y$ is a 4 to 6 membered heterocycle containing one to three heteroatoms selected from the group consisting of O, N and S; and optionally containing 1 to 2 carbonyls, wherein the carbon atom of said carbonyl is a member of said 4 to 6 membered heterocycle;

wherein $A^y$ are optionally substituted with $C_{1-4}$alkyl, $C_{1-4}$alkoxy, $C_{1-4}$haloalkyl, cyano, $C_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino; and wherein provided that $A^y$ is not a 1,3-diaza-heterocycle.

29. A compound selected from the group consisting of (±)-4-Oxo-2-phenyl-1,3,8-triaza-spiro[4,5]dec-1-ene-8-carboxylic acid{1-7-methyl-1H-indazol-5-yl methyl)-2-[1,4]bi-piperidinyl-1'-yl-2-oxo-ethyl}-amide; (±)-4-Oxo-2-phenyl-1,3,8-triaza-spiro[4,5]dec-1-ene-8-carboxylic acid {1-(7-methyl-1H-indazol-5-yl methyl)-2-[1-piperidinylyl]-2-oxo-ethyl}-amide and (±)-4-Oxo-2-phenyl-1,3,8-triaza-spiro[4,5]dec-1-ene-8-carboxylic acid[1-dimethylcarbamoyl-2-(7-methyl-1H-indazol-5-yl)-ethyl]amide or a pharmaceutically acceptable salt thereof.

30. A pharmaceutical composition comprising a compound according to claim 1 or a pharmaceutically acceptable salt thereof and a pharmaceutically acceptable carrier.

31. A method of treating headache, circulatory shock, pain, flushing associated with menopause or airway inflammatory diseases by the administration to a patient in need thereof an effective amount of a pharmaceutical composition comprising a compound according to claim 1.

32. A method according to claim 31, wherein said headache is migraine and said airway inflammatory disease is asthma.

* * * * *

UNITED STATES PATENT AND TRADEMARK OFFICE
CERTIFICATE OF CORRECTION

PATENT NO. : 7,754,732 B2
APPLICATION NO. : 11/620253
DATED : July 13, 2010
INVENTOR(S) : Prasad V. Chaturvedula et al.

It is certified that error appears in the above-identified patent and that said Letters Patent is hereby corrected as shown below:

Column 5, line 57, change "napthyl" to -- naphthyl --.

Column 14, line 27, change "napthyl" to -- naphthyl --.

Column 14, line 32, change "napthyl" to -- naphthyl --.

Column 15, line 3, change "napthyl" to -- naphthyl --.

Column 15, line 26, change "napthyl" to -- naphthyl --.

Column 27, line 37, change "napthyl" to -- naphthyl --.

Claim 1:

Column 336, line 11, after "$R^2$;" insert -- or --.

Column 336, line 32, change "$NH(S^y)_sR^3$" to -- $NH(S^y)_sR^3$ --.

Column 336, line 58, change "alklylene-phenyl, or napthyl" to -- alkylene-phenyl, or naphthyl --.

Column 338, line 1, before "further", delete "and".

Claim 18:

Column 339, line 2, after "$N(R^1)(R^2)$", delete ",".

Claim 23:

Column 339, line 41, change "$R^2$together" to -- $R^2$ together --.

Claim 24:

Column 339, line 47 change "napthyl" to -- naphthyl --.

Claim 28:

Column 342, line 43, after "$R^2$;" insert -- or --.

Signed and Sealed this
Fifteenth Day of November, 2011

David J. Kappos
*Director of the United States Patent and Trademark Office*

CERTIFICATE OF CORRECTION (continued)
U.S. Pat. No. 7,754,732 B2

Claim 29:

Column 343, line 20, change "{1-7" to -- {1-(7 --.